US010975161B2

(12) United States Patent
Balloi et al.

(10) Patent No.: US 10,975,161 B2
(45) Date of Patent: Apr. 13, 2021

(54) MOLECULES THAT BIND PROSTATE SPECIFIC MEMBRANE ANTIGEN (PSMA)

(71) Applicant: CRESCENDO BIOLOGICS LIMITED, Cambridge (GB)

(72) Inventors: Eleanora Balloi, Cambridge (GB); Normann Goodwin, Cambridge (GB); Brian McGuinness, Cambridge (GB); Chris Rossant, Cambridge (GB); Thomas Sandal, Cambridge (GB); Lorraine Thompson, Cambridge (GB)

(73) Assignee: CRESCENDO BIOLOGICS LIMITED, Cambridge (GB)

(*) Notice: Subject to any disclaimer, the term of this patent is extended or adjusted under 35 U.S.C. 154(b) by 201 days.

(21) Appl. No.: 16/069,495

(22) PCT Filed: Jan. 12, 2017

(86) PCT No.: PCT/GB2017/050075
§ 371 (c)(1),
(2) Date: Jul. 11, 2018

(87) PCT Pub. No.: WO2017/122018
PCT Pub. Date: Jul. 20, 2017

(65) Prior Publication Data
US 2019/0023807 A1 Jan. 24, 2019

(30) Foreign Application Priority Data

Jan. 12, 2016 (GB) .................................. 1600559
Apr. 4, 2016 (GB) .................................. 1605763
Apr. 4, 2016 (GB) .................................. 1605770

(51) Int. Cl.
| | |
|---|---|
| *A61P 35/00* | (2006.01) |
| *C07K 16/30* | (2006.01) |
| *G01N 33/574* | (2006.01) |
| *A61K 47/68* | (2017.01) |
| *A61K 47/64* | (2017.01) |

(52) U.S. Cl.
CPC ........ *C07K 16/3069* (2013.01); *A61K 47/643* (2017.08); *A61K 47/644* (2017.08); *A61K 47/6415* (2017.08); *A61K 47/6425* (2017.08); *A61K 47/6811* (2017.08); *A61K 47/6869* (2017.08); *A61K 47/6889* (2017.08); *A61P 35/00* (2018.01); *G01N 33/57434* (2013.01); *C07K 2317/21* (2013.01); *C07K 2317/35* (2013.01); *C07K 2317/569* (2013.01); *C07K 2317/77* (2013.01); *C07K 2317/92* (2013.01); *C07K 2317/94* (2013.01)

(58) Field of Classification Search
CPC .............................. C07K 16/3069; A61P 35/00
USPC .................................................... 424/138.1
See application file for complete search history.

(56) References Cited

U.S. PATENT DOCUMENTS

2010/0122358 A1 5/2010 Bruggemann et al.

FOREIGN PATENT DOCUMENTS

| | | |
|---|---|---|
| CN | 105384825 | 3/2016 |
| WO | WO 2007/117264 A2 * | 10/2007 |
| WO | 2014/141192 | 9/2014 |
| WO | 2015/142675 | 9/2015 |
| WO | 2015143079 A1 | 9/2015 |
| WO | 2016/025880 | 2/2016 |
| WO | 2017/122018 | 7/2017 |
| WO | 2017122019 A1 | 7/2017 |
| WO | 2017/191476 | 11/2017 |

OTHER PUBLICATIONS

Zare et al (Int J Biol Markers, 2014, 29(2): e169-e179).*
Bander et al (Semin Oncol, 2003, 30: 667-677).*
Fan, Xiaozhu et al. Ultrasonic Nanobubbles Carrying Anti-PSMA Nanobody: Construction and Application in Prostate Cancer-Targeted Imaging. PLOS ONE. Jun. 25, 2015. p. 1-13.
Evazalipour, Mehdi et al. "Camel Heavy Chain Antibodies Against Prostate-Specific Membrane Antigen" Hybridoma. vol. 31, No. 6, 2012. p. 424-429.
Hamed, Production of Nanobodies Against Prostate-Specific Membrane Antigen (PSMA) Recognizing LnCaP Cells. Research Gate. The International Journal of Biological Markers. Jan. 2014.
Bayachou, Mekki et al. "Catalytic Two-Electron Reductions of N2) and N3 by Myglobin in Surfactant Films" Inorg. Chem. 2000, 39, 289-293.
Chatalic, Kristell et al. "A Novel In-Labeled Anti-Prostate-Specific Membrane Antigen Nanobody for Targeted SPECT/CT Imaging of Prostate Cancer" The Journal of Nuclear Medicine. vol. 56, No. 7, Jul. 2015. p. 1094-1099.
Barve et al., J Control Release. Aug. 10, 2014; 0: 118-132.
International Search Report for PCT/GB2017/050075, Received at International Bureau: Mar. 23, 2017.
Cizeau et al.: "Engineering and characterization of anti-PSMA humabody-deBouganin fusion proteins", Proceedings of the American Association for Cancer Research Annual Meeting 2018; Apr. 2018 (Apr. 2018), Retrieved from the Internet: URL:http://cancerres. aacrjournals.org/content/78/13_Supplement/5770 (Abstract).
Holt L J et al: "Domain antibodies: proteins for therapy", Trends in Biotechnology, Elsevier Publications, Cambridge, GB, vol. 21, No. 11, Nov. 1, 2003 (Nov. 1, 2003), pp. 484-490.
International Search Report and Written Opinion corresponding to International Application No. PCT/GB2017/050074 dated May 30, 2017.
International Search Report and Written Opinion corresponding to International Application No. PCT/GB2018/051941 dated Sep. 14, 2018.
Matthias Di Huyvetter et al: "Radiolabeled nanobodies as theranostic tools in targeted radionuclide therapy of cancer", Expert Opinion on Drug Delivery, vol. 1-6, 49-8111, No. 12, Jul. 18, 2014 (Jul. 18, 2014), pp. 1939-1954.

(Continued)

*Primary Examiner* — Sean E Aeder
(74) *Attorney, Agent, or Firm* — Myers Bigel, P.A.

(57) ABSTRACT

The disclosure relates to binding molecules that bind specifically to prostate specific membrane antigen (PSMA), in particular, single human variable heavy chain domain antibodies and related methods for treatment of cancer.

17 Claims, 34 Drawing Sheets

Figure 16B:
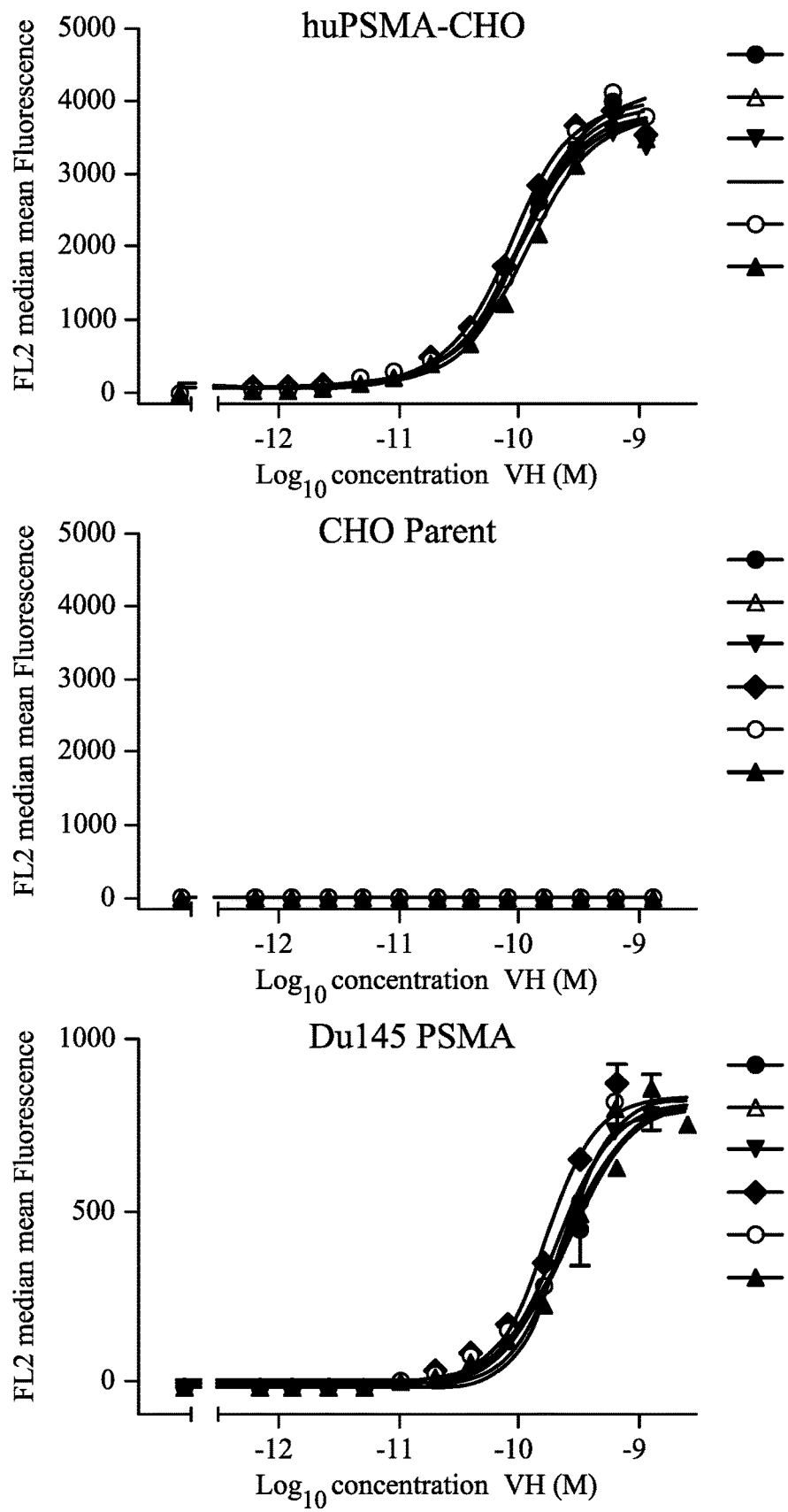
Figure 16B:
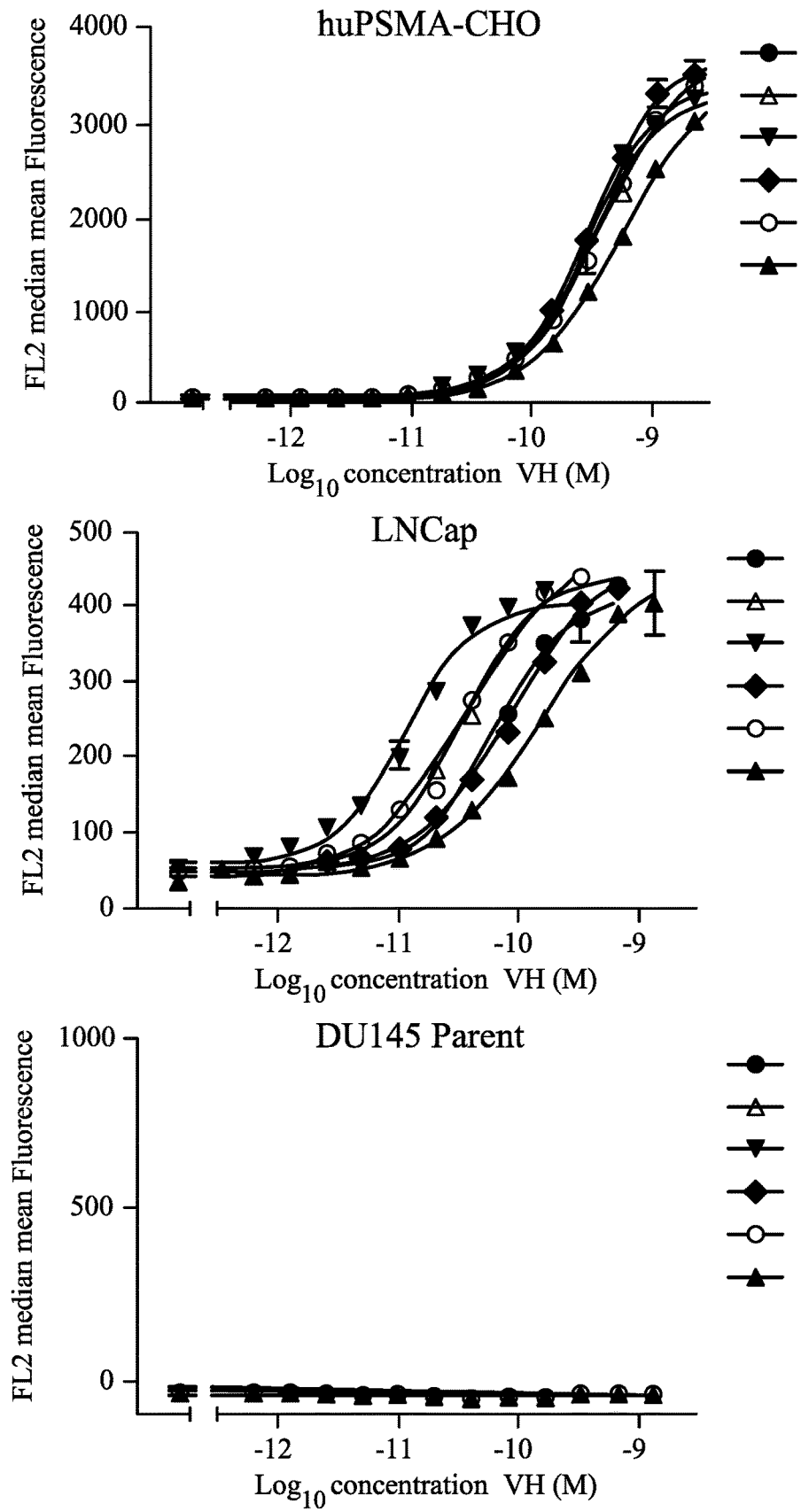

Specification includes a Sequence Listing.

(56) References Cited

OTHER PUBLICATIONS

McGuiness et al: "Multifunctional biologics for targeted T-cell therapy based on in vivo matured fully human VH domains", Proceedings of the American Association for Cancer Research Annual Meeting 2018; Apr. 2018 Retrieved from the Internet: URL:http://cancerres.aacrjournals.org/content/78/13_Supplement/5766 (Abstract).

Rob C. Roovers et al: "A biparatopic anti-EGFR nanobody efficiently inhibits solid tumour growth", International Journal of Cancer, vol. 129, No. 8, Oct. 15, 2011 (Oct. 15, 2011), pp. 2013-2024

International Preliminary Report on Patentability corresponding to International Application No. PCT/GB2017/050074 dated Jul. 26, 2018.

International Preliminary Report on Patentability corresponding to International Application No. PCT/GB2017/050075 dated Jul. 26, 2018.

International Preliminary Report on Patentability corresponding to International Application No. PCT/GB2017/051272 dated Nov. 15, 2018.

International Preliminary Report on Patentability corresponding to International Application No. PCT/GB2018/051941 dated Jan. 23, 2020.

International Search Report and Written Opinion corresponding to International Application No. PCT/GB2017/051272 dated Sep. 11, 2017.

Fatemeh Rahimi Jamnani et al. "T cells expressing VHH-directed oligoclonal chimeric HER2 antigen receptors: Towards tumor-directed oligoclonal T cell therapy", Biochimica Et Biophysica Acta (BB) General Subjects 1840 (1):378-386 (2014).

Evazalipour et al. "Generation and characterization of nanobodies targeting PSMA for molecular imaging of prostate cancer", Contrast Media & Molecular Imaging 9(3):211-220 (2014).

Examination Report corresponding to European Application No. 17701006.3 dated Jun. 5, 2019.

""Humabody Fragments: Small and Perfectly Formed" Crescendo Biologics. BioPharrna Dealmakers. p. 812-813. published Nov. 10, 2015".

"Examination Report corresponding to European Application No. 17700734.1 dated Jul. 24, 2020".

Bruggemann, et al., ""A Repertoire of Monoclonal Antibodies With Human Heavy Chains From Transgenic Mice", Proceedings of the National Academy Sciences, National Academy of Sciences, vol. 86, No. 17, Sep. 1, 1989 (Sep. 1, 1989 ), pp. 6709-6713".

"Office Action corresponding to Japanese Application No. 2018-537519 dated Feb. 5. 2021".

"Office Action corresponding to Japanese Application No. 2018-537533 dated Feb. 16, 2021".

Conrath, Katja Els, et al., "Camel Single-Domain Antibodies as Modular Building Units in Bispecific and Bivalent Antibody Constructs", The Journal of Biological Chemistry 276(10):7346-7350 (Mar. 2001).

Vincke, Cecile, et al., "General strategy to Humanize a Camelid Single-domain Antibody and Identification of a Universal Humanized Nanobody Scaffold", The Journal of Biological Chemistry 284(5):3273-3284 (Jan. 30, 2009).

* cited by examiner 1.1
EVQLLESGGGLVQPGGSLRLSCAASGFSFSSYAMSWVRQAPGKGLEWVSSIGENDGTTDYADSVKGRFTISRD
NSKSMLYLQMNSLRVEDTAVYYCVKDGVHWGQGTLVTVSS
1.2
EVQLVESGGGLVQPGGSLRLSCAASGFTFSSYAMSWVRQAPGKGLEWVSSIGDNNNSTEYADSVKGRFTISR
DNSKSTLYLQMNSLSAEDTAVYYCVKDGVHWGQGTLVTVSS
1.3
EVQLVESGGGLVQPGGSLRLSCAASGFSFSSYAMSWVRQAPGKGLEWVSSIGDNNNSTDYADSVKGRFTISR
DNSKSTLYLQMNSLRAEDTAVYYCVKDGVHWGQGTLVTVSS
1.4
EVQLVESGGGLVQPGGSLRLSCAASGFTFSSYAMSWVRQAPGKGLEWVSSIGDGTTYYADSVKGRFTISRDNS
KSTLYLQMNSLRAEDTAVYYCAKDGVHWGQGTLVTVSS
1.5
EVQLVESGGGLVQPGGSLRLSCAASGFTFSTYAMSWVRQAPGKGLEWVSSIGENDRTTYYVDSVKGRFTISRD
NSKSTLYLQMNSLRAEDTAVYYCAKDGVHWGQGTLVTVSS
1.6
QVQLVESGGGLVQPGGSLRLSCAASGFTFSSYAMSWVRQAPGKGLEWVSSIGDNNRTTYYADSVKGRFTISR
DNSKSTLYLQMNSLRAEDTAVYYCAKDGVHWGQGTLVTVSS
1.7
EVQLVESGGGLVQPGGSLRLSCAASGFTFSSYAMSWVRQAPGKGLEWVSSIGDGTTYYADSVKGRFTISRDNS
KSTLYLQMNSLRAEDTAVYYCAKDGVHWGQGTLVTVSS
1.8
EVQLLESGGGLVQPGGSLRLSCAASGFSFSSYAMSWVRQAPGKGLEWVSSIGENDGTTDYADSVKGRFTISRD
NSKNTLYLQMNSLRVEDTAVYYCVKDGVHWGQGTLVTVSS
1.9
EVQLLESGGGLVQPGGSLRLSCAASGFSFSSYALSWVRQAPGKGLEWVSSIGENDGTTDYADSVKGRFTISRD
NSKNTLYLQMNSLRVEDTAVYYCVKDGVHWGQGTLVTVSS
1.10
EVQLLESGGGLVQPGGSLRLSCAASGFSFSSYALSWVRQAPGKGLEWVSSIGENNATTDYADFVKGRFTISRDN
SKNTLYLQMNSLRVEDTAVYYCVKDGVHWGQGTLVTVSS
1.11
EVQLLESGGGLVQPGGSLRLSCAASGFSFSSYALSWVRQAPGKGLEWVSSIGENNDTTDYADNVKGRFTISRD
NSKNTLYLQMNSLRVEDTAVYYCVKDGVHWGQGTLVTVSS
1.12
EVQLLESGGGLVQPGGSLRLSCAASGFSFSSYALSWVRQAPGKGLEWVSSIGENNATTDYADAVKGRFTISRD
NSKNTLYLQMNSLRVEDTAVYYCVKDGVHWGQGTLVTVSS
1.13
EVQLLESGGGLVQPGGSLRLSCAASGFSFSSYALSWVRQAPGKGLEWVSSIGENNHTTDYAADVKGRFTISRD
NSKNTLYLQMNSLRVEDTAVYYCVKDGVHWGQGTLVTVSS
1.14
EVQLLESGGGLVQPGGSLRLSCAASGFSFSSYALSWVRQAPGKGLEWVSSIGENNATTDYADVVKGRFTISRD
NSKNTLYLQMNSLRVEDTAVYYCVKDGVHWGQGTLVTVSS
1.15
EVQLLESGGGLVQPGGSLRLSCAASGFSFSSYALSWVRQAPGKGLEWVSSIGENNHTTDYAAFVKGRFTISRDN
SKNTLYLQMNSLRVEDTAVYYCVKDGVHWGQGTLVTVSS
1.16
EVQLLESGGGLVQPGGSLRLSCAASGFSFSSYALSWVRQAPGKGLEWVSSIGENNHTTDYADTVKGRFTISRD
NSKNTLYLQMNSLRVEDTAVYYCVKDGVHWGQGTLVTVSS
1.17
EVQLLESGGGLVQPGGSLRLSCAASGFSFSSYALSWVRQAPGKGLEWVSSIGENNDTTDYADAVKGRFTISRD
NSKNTLYLQMNSLRVEDTAVYYCVKDGVHWGQGTLVTVSS

Figure 1

1.18
EVQLLESGGGLVQPGGSLRLSCAASGFSFSSYALSWVRQAPGKGLEWVSSIGENNATTDYAASVKGRFTISRDN
SKNTLYLQMNSLRVEDTAVYYCVKDGVHWGQGTLVTVSS 1.19
EVQLLESGGGLVQPGGSLRLSCAASGFSFSSYALSWVRQAPGKGLEWVSSIGENNDTTDYAAYVKGRFTISRD
NSKNTLYLQMNSLRVEDTAVYYCVKDGVHWGQGTLVTVSS 1.20
EVQLLESGGGLVQPGGSLRLSCAASGFSFSSYALSWVRQAPGKGLEWVSSIGENNHTTDYAATVKGRFTISRD
NSKNTLYLQMNSLRVEDTAVYYCVKDGVHWGQGTLVTVSS

Figure 1 Continued 2.1
EVQLVESGGGVVQPGRSLRLSCAASGFSFSGYGMHWVRQAPGKGLEWVAYISYDGSNKYYADSVKGRFTISRDN
SKNTLYLQMNSLRAEDTAVYYCAKDPAWGLRLGESSSYDFDIWGQGTMVTVSS 2.2
EVQLVESGGGVVQPGRSLRLSCAASGFSFSGYGMHWVRQAPGKGLEWVAYISYDGSNKYYADSVKGRFTISRDN
SKNTLYLQMNSLRAEDTAVYYCAKDPAWGLRLGESSSYDFDIWGQGTMVTVSS 2.3
EVQLVESGGGVVQPGRSLRLSCAASGFSFSGYGMHWVRQAPGKGLEWVAHISYDGSNRYYAESVKGRFTISREN
SKNTLSLQMNSLRAEDTAVYYCAKDPAWGLRLGELSSYDFDIWGQGTMVTVSS 2.4
QVTLKESGGGVVQPGRSLKLSCAASGFSFSGYGMHWVRQAPGKGLEWVAVISYDGSNRYYADSVKGRFTISRD
NSKNTLSLQMNSLRAEDTAVYYCARDPAWGLRLGELSSYDFEIWGQGTMVTVSS 2.5
QVQLVESGGGVVQPGRSLRLSCAASGFSFSGYGMHWVRQAPGKGLEWVAVISYDGSNRYYADSVKGRFTISRD
NSKNTLSLQMNSLRAEDTAVYYCAKDPAWGLRLGELSSYDFEIWGQGTMVTVSS 2.6
EVQLVESGGGVVQPGRSLRLSCAASGFSFSGYGMHWVRQAPGKGLEWVAVISYDGSNKYYADSVKGRFTISRD
NSKNTLYLQMNSLRAEDTAVYYCAKDPAWGLRLGELSSYKFEIWGQGTMVTVSS 2.7
EVQLVESGGGVVQPGRSLRLSCAASGFSFSGYGMHWVRQAPGKGLEWVALISYDGSNKYYADSVKGRFTISRDN
SKNTLYLQMNSLRAEDTAVYYCAKDPAWGLRLGEQSSYAFDIWGQGTMVTVSS 2.8
QVQLVESGGGVVQPGRSLRLSCAASGFSFSGYGMHWVRQAPGKGLEWVSVISYDGSNKYYADSVKGRFTISRD
NSKNTLYLQMNSLRTEDTAVYYCAKDPAWGLRLGEQSSYAFEIWGQGTMVTVSS 2.9
EVQLLESGGGVVQPGRSLRLSCAASGFSFSGYGMHWVRQAPGKGLEWVAVISYDGSNKYYADSVKGRFTISRDN
SKNTLYLQMNSLRVEDTAVYYCAKDPAWGLRLGEQSSYAFEIRGQGTTVTVSS 2.10
EVQLVESGGGVVQPGRSLRLSCAASGFTFSGYGMHWVRQAPGKGLEWVAYISYDGSNRYYADSVKGRFTISRD
NSKKTLSLQMNSLRAEDTAVYYCAKDPAWGLRLGESSSYDFDIWGQGTMVTVSS

Figure 2

2.11
EVQLVESGGGVVQPGRSLRLSCAASGFSFSGYGLHWVRQAPGKGLEWVAYISYDESNKYYAPSVKGRFTISRDNS
KNTLYLQMNSLRAEDTAVYYCAKDPAWGLRLGESSSYDFDIWGQGTMVTVSS 2.12
EVQLVESGGGVVQPGRSLRLSCAASGFSFSGYGMHWVRQAPGKGLEWVAYISYDKSNKYYADKVKGRFTISRDN
SKNTLYLQMNSLRAEDTAVYYCAKDPAWGLRLGESSSYDFDIWGQGTMVTVSS 2.13
EVQLVESGGGVVQPGRSLRLSCAASGFSFSGYGLHWVRQAPGKGLEWVAYISYDASNKYYADNVKGRFTISRDN
SKNTLYLQMNSLRAEDTAVYYCAKDPAWGLRLGESSSYDFDIWGQGTMVTVSS 2.14
EVQLVESGGGVVQPGRSLRLSCAASGFSFSGYGVHWVRQAPGKGLEWVAYISYDASNKYYADNVKGRFTISRDN
SKNTLYLQMNSLRAEDTAVYYCAKDPAWGLRLGESSSYDFDIWGQGTMVTVSS 2.15
EVQLVESGGGVVQPGRSLRLSCAASGFSFSGYGLHWVRQAPGKGLEWVAYISYDKSNKYYADKVKGRFTISRDNS
KNTLYLQMNSLRAEDTAVYYCAKDPAWGLRLGESSSYDFDIWGQGTMVTVSS 2.16
EVQLVESGGGVVQPGRSLRLSCAASGFSFSGYGAHWVRQAPGKGLEWVAYISYDKSNKYYADKVKGRFTISRDN
SKNTLYLQMNSLRAEDTAVYYCAKDPAWGLRLGESSSYDFDIWGQGTMVTVSS 2.17
EVQLVESGGGVVQPGRSLRLSCAASGFSFSGYGMHWVRQAPGKGLEWVAYISYDASNKYYADNVKGRFTISRD
NSKNTLYLQMNSLRAEDTAVYYCAKDPAWGLRLGESSSYDFDIWGQGTMVTVSS 2.18
EVQLVESGGGVVQPGRSLRLSCAASGFSFSGYGQHWVRQAPGKGLEWVAYISYDASNKYYADNVKGRFTISRDN
SKNTLYLQMNSLRAEDTAVYYCAKDPAWGLRLGESSSYDFDIWGQGTMVTVSS 2.19
EVQLVESGGGVVQPGRSLRLSCAASGFSFSGYGFHWVRQAPGKGLEWVAYISYDASNKYYADNVKGRFTISRDN
SKNTLYLQMNSLRAEDTAVYYCAKDPAWGLRLGESSSYDFDIWGQGTMVTVSS 2.20
EVQLVESGGGVVQPGRSLRLSCAASGFSFSGYGMHWVRQAPGKGLEWVAISYDGSNRYYADSVKGRFTISRDN
SKNTLSLQMNSLRAEDTAVYYCAKDPAWGLRLGESSSYDFEIWGQGTMVTVSS 2.21
QVQLVESGGGVVQPGRSLKLSCAASGFSFSGYGMHWVRQAPGKGLEWVAVISYDGSNRYYADSVKGRFTISRD
NSKNTLSLQMNSLRAEDTAVYYCAKDPAWGLRLGKLSSYDFEIWGQGTMVTVSS 2.22
EVQLVESGGGVVQPGRSLRLSCAASGFSFSGYGTHWVRQAPGKGLEWVAYISYDGSNKYYAAPVKGRFTISRDN
SKNTLYLQMNSLRAEDTAVYYCAKDAAWGLRLGESSSYDFDIWGQGTMVTVSS 2.23
EVQLVESGGGVVQPGRSLRLSCAASGFSFSGYGTHWVRQAPGKGLEWVAYISYDESNKYYASSVKGRFTISRDNS
KNTLYLQMNSLRAEDTAVYYCAKDRAWGLRLGESSSYDFDIWGQGTMVTVSS 2.24
EVQLVESGGGVVQPGRSLRLSCAASGFSFSGYGMHWVRQAPGKGLEWVAYISYDESNKYYARLVKGRFTISRDN
SKNTLYLQMNSLRAEDTAVYYCAKDTAWGLRLGESSSYDFDIWGQGTMVTVSS 2.25
EVQLVESGGGVVQPGRSLRLSCAASGFSFSGYGLHWVRQAPGKGLEWVAYISYDLSNKYYARGVKGRFTISRDNS
KNTLYLQMNSLRAEDTAVYYCAKDVAWGLRLGESSSYDFDIWGQGTMVTVSS

Figure 2 Continued 3.1

EVQLVESGGGVVQPGRSLRLSCAASGFPLISYGMHWVRQAPGKGLEWVAFMTYDGSNRYYADSVKGRFTISRD
NSKNTLYLQMNSLRDEDTALYYCARDRIVGGRVPDAFDIWGQGTMVTVSS 3.2

EVQLVESGGGVVQPGRSLRLSCAASGFPLISYGMNWVRQAPGKGLDWVAFISYDGSNKYYADSVKGRFTISKDN
SKNTLYLQMNSLRAEDTAVYYCAKDRIVGARVPDAFDIWGQGTMVTVSS 3.3

EVQLVESGGGVVQPGRSLRLSCAASGFPLISYGMNWVRQAPGKGLEWVAFISYDGSNRYYADSVKGRFTISRDN
SKNTLYLQMNSLRAEDTAVYYCAKDRIVGARVPDAFDIWGQGTMVTVSS 3.4

EVQLVESGGGAVQPGRSLRLSCAASGFPLISYGMNWVRQAPGKGLDWVAFITYDGSNRYYADSVKGRFTISRDN
SKNTLYLQMNSLRPEDTAVYYCAKDRIVGARVPDAYDIWGQGTMVTVSS 3.5

QVQLVESGGGVVQPGRSLRLSCAASGFPLISYGMNWVRQAPGKGLDWVAFITYDGSNRYYADSVKGRFTISRDN
SKNTLYLQMNSLRPEDTAVYYCAKDRIVGARVPDAYDIWGQGTMVTVSS 3.6

EVQLLESGGGVVQPGRSLRLSCAASGFPLISYGMNWVRQAPGKGLDWVAFITYDGSNRYYADSVKGRFTISRDN
SKNTLYLQMNSLRPEDTAVYYCAKDRIVGARVPDAYDIWGQGTMVTVSS 3.7

QVQLVESGGGLVQPGGSLRLSCAASGFPLISYGMNWVRQAPGKGLDWVAFITYDGSNRYYADSVKGRFTISRDN
SKNTLHLQMDSLRPEDTAVYYCAKDRIVGARVPDAYDIWGQGTMVTVSS 3.8

EVQLVESGGGVVQPGRSLRLSCAASGFPLISYGMNWVRQAPGKGLDWVAFITYDGSNRYYADSVKGRFTISRDN
SKNTLYLQMNSLRPEDTAVYYCAKDRIVGARVPDAYDIWGQGTLVTVSS 3.9

QVQLVESGGGVVQPGRSLRLSCAASGFPLISYGMNWVRQAPGKGLEWVAFISYDGSNRYYADSVKGRFTISRDN
SKNTLYLQMNSLRPEDTAVYYCAKDRIVGARVPDAYDIWGQGTMVTVSS 3.10

QVQLVESGGGVVQPGRSLRLSCAASGFPLISYGMNWVRQAPGKGLDWVAFITYDGSNRYYADSVKGRFTISRDN
SKNTLHLQMNSLRPEDTAVYYCAKDRIVGARVPDAYDIWGQGTMVTVSS 3.11

EVQLVESGGGVVQPGRSLRLSCAASGFPLISYGMNWVRQAPGKGLDWVAFITYDGSNRYYADSVKGRFTISRDN
SKNTLHLQMNSLRPEDTAVYYCAKDRIVGARVPDAYDIWGQGTMVTVSS 3.12

EVQLVESGGGVVQPGRSLRLSCAASGFPLISYGMNWVRQAPGKGLDWVAFITYDGSNRYYADSVKGRFTISRDN
SKNTLYLQMNSLRPEDTAVYYCAKDRIVGARVPDAYDIWGQGTMVTVSS

Figure 3

3.13

QVQLVESGGGVVQPGRSLRLSCAASGFPLISYGMNWVRQAPGKGLDWVAFITYDGSNRYYADSVKGRFTISRDN
SKNTLYLQMNSLRPEDTAVYYCAKDRIVGARVPDAYDIWGQGTMVTVSS 3.14

EVQLVESGGGVVRPGGSLRLSCAASGFPLISYGMNWVRQAPGKGLDWVAFITYDGSNRYYADSVKGRFTISRDN
SKNTLHLQMNSLRPEDTAVYYCAKDRIVGARVPDAYDIWGQGTMVTVSS 3.15

EVQLVESGGGLVQPGGSLRLSCAASGFPLISYGMNWVRQAPGKGLDWVAFITYDGSNRYYADSVKGRFTISRDN
SKNTLHLQMNSLRPEDTAVYYCAKDRIVGARVPDAYDIWGQGTMVTVSS 3.16

EVQLLESGGGVVQPGRSLRLSCAASGFPLISYGMNWVRQAPGKGLDWVAFITYDGSNRYYADSVKGRFTISRDN
SKNTLHLQMNSLRPEDTAVYYCAKDRIVGARVPDAYDIWGQGTMVTVSS 3.17

EVQLLESGGGVVQPGRSLRLSCAASGFPLISYGMNWVRQAPGKGLDWVAFITYDGSNRYYADSVKGRFTISRDN
SKNTLYLQMNSLKPEDTAVYYCAKDRIVGARVPDAYDIWGQGTMVTVSS 3.18

EVQLVESGGGVVQPGRSLRLSCAASGFPLISYGMNWVRQAPGKGLDWVAFITYDGSNRYYADSVKGRFTISRDN
SKNTLYLQMNSLKPEDTAVYYCAKDRIVGARVPDAYDIWGQGTMVTVSS 3.19

QVQLVESGGGVVQPGRSLRLSCAASGFPLISYGMHWVRQAPGKGLEWVAFMTYDGSNRYYADAVKGRFTISRD
NSKNTLYLQMNSLRAEDTAVYYCARDRIVGGRVPDAFDIWGQGTMVTVSS 3.20

QVQLVESGGGVVQPGRSLRLSCAASGFPLISYGMHWVRQAPGKGLEWVAFQTYDGSNRYYADAVKGRFTISRD
NSKNTLYLQMNSLRAEDTAVYYCARDRIVGGRVPDAFDIWGQGTMVTVSS 3.21

QVQLVESGGGVVQPGRSLRLSCAASGFPLISYGMHWVRQAPGKGLEWVAFQTYDGSNRYYADSVKGRFTISRD
NSKNTLYLQMNSLRAEDTAVYYCARDRIVGGRVPDAFDIWGQGTMVTVSS 3.22

QVQLVESGGGVVQPGRSLRLSCAASGFPLISYGMHWVRQAPGKGLEWVAFQTYDASNRYYADSVKGRFTISRD
NSKNTLYLQMNSLRAEDTAVYYCARDRIVGGRVPDAFDIWGQGTMVTVSS 3.23

QVQLVESGGGVVQPGRSLRLSCAASGFPLISYGMHWVRQAPGKGLEWVAFQTYDASNRYYADAVKGRFTISRD
NSKNTLYLQMNSLRAEDTAVYYCARDRIVGGRVPDAFDIWGQGTMVTVSS 3.24

QVQLVESGGGVVQPGRSLRLSCAASGFPLISYGMNWVRQAPGKGLEWVAFITYDGSNRYYADSVKGRFTISRDN
SKNTLYLQMNSLRAEDTAVYYCAKDRIVGARVPDAYDIWGQGTMVTVSS

Figure 3 Continued 4.1

QVQLVESGGGVVQPGRSLRLSCVASGFPFSYGMHWVRQAPGKGREWVAVISYDGSNRYYADSVKGRFTISRD
NSKNTLYLQMNSLRPEDTAVYYCAKERIFGVLTPDDFDIWGQGTTVTVSS 4.2

QVQLVESGGGVVQPGRSLRLSCAASGFPFSYGMHWVRQAPGKGLEWVAVISYDGSNRYYADSVKGRFTISRDN
SKNTLYLQMNSLRPEDTAVYYCAKERIFGVLTPDDFDIWGQGTTVTVSS 4.3

EVQLLESGGGVVQPGRSLRLSCAASGFPFSYGMHWVRQAPGKGLEWVAVISYDGANRYYADSVKGRFTISRDN
SKNTLYLQMNSLRPEDTAVYYCAKERIFGVLTPDDFEIWGQGTTVTVSS 4.4

EVQLVESGGGVVQPGRSLRLSCAASGFTFTSYGMHWVRQAPGKGLEWVAVISYDGSNRYYADSVKGRFTISRDN
SKNTLYLQMNSLRPEDTAVYYCAKERIFGALTPDDFDIWGQGTTVTVSS

Figure 4

5.1

QVQLVESGGGVVQPGRSLRLSCAASGFTFNNYGMHWVRQAPGKGLEWVAIISYDGNTKYYTDSVKGRFTISRD
NSKNTLYLQMNSLRVEDTAVYYCAKGLWPSDVWGQGTTVTVSS 5.2

EVQLVESGGGVVQPGRSLRLSCAASGFTFNNYGMHWVRQAPGKGLEWVAIISYDGNSKYYTDSVKGRFTISRDN
SKNTLYLQMNSLRVEDTAVYYCAKGLWPSDVWGQGTTVTVSS

Figure 5

6.1

QVQLQESGPGLVKPSQTLSLTCTVSGGSISNSGYYWSWVRQHPGKDLEWIGFIYYNGSIHYNPSLKSRVISVDTSK
NQFSLKMNSVTAADTAVYYCARDGDDYGDYLRGQGTLVTVSS 6.2

QVQLQESGPGLVKPSQTLSLTCTVSGGSISNSGYYWSWIRQHPGKGLEWIGFIYYNGSIHYNPSLKSRVISVDTSK
NQFSLKMSSVTAADTAVYYCARDGDDYGDYLRGQGTLVTVSS 6.3

QVQLQESGPGLVKPSQTLSLTCTVSGGSISNSGYYWSWVRQHPGKGLEWIGFIYYNGSIHYNPSLKSRVISVDTSK
NQFSLKLNSVTAADTAVYYCARDGDDYGDYLRGQGTLVTVSS 6.4

QVQLQESGPGLVKPSQTLSLTCTVSGGSISNSGYYWSWIRQHPGKGLEWIGFIYYNGSIHYNPSLKSRVISVDTSK
NQFSLKLSSVTAADTAVYYCARDGDDYGDYLRGQGTLVTVSS 6.5

QVQLQESGPGLVKPSQTLSLTCTVSGGSISNSGYYWSWVRQHPGKGLEWIGFIYYNGSIHYNPSLKSRVTSVDTS
KNQFSLKMSSVTAADTAVYYCARDGDDYGDYLRGQGTLVTVSS 6.6

QVQLQESGPGLVKPSQTLSLTCTVSGGSISNSGYYWSWVRQHPGKGLEWIGFIYYNGSIHYNPSLKSRVTSVDTS
KNQFSLKLNSVTAADTAVYYCARDGDDYGDYLRGQGTLVTVSS 6.7

QVQLQESGPGLVKPSQTLSLTCTVSGGSISNSGYYWSWVRQHPGKGLEWIGFIYYNGSIHYNPSLKSRVTSVDTS
KNQFSLKLSSVTAADTAVYYCARDGDDYGDYLRGQGTLVTVSS

Figure 6

7.1

EVQLVESGGGLVQPGGSLRLSCAASGFTFSSYWMYWVRQAPGKGLEWVANINHDGSEKYYVDSVKGRFTISRD
NAKNSLYLQMNSLRAEDTAVYYCARDSLIVGERGYWGQGTLVTVSS 7.2

EVQLVESGGGLVQPGGSLRLSCAASGFTFSSYWMYWVRQAPGKGLEWVANINHDGSEKYYVDSVKGRFTISRD
NAKNSLYLQMNSLRAEDTAVYYCARDNLIVGERGYWGQGTLVTVSS 7.3

EVQLVESGGGLVQPGGSLRLSCAASGFTFSSYWMYWVRQAPGKGLEWVANINHGGSEKYYVDSVKGRFTISRD
NAKNSLYLQMNSLRAEDTAVYYCARDSLIVGERGYWGQGTLVTVSS 7.4

EVQLVESGGGLVQPGGSLRLSCAASGFTFSSYWMYWVRQAPGKGLEWVANINHQGSEKYYVDSVKGRFTISRD
NAKNSLYLQMNSLRAEDTAVYYCARDSLIVGERGYWGQGTLVTVSS 7.5

EVQLVESGGGLVQPGGSLRLSCAASGFTFSSYWMYWVRQAPGKGLEWVANINHPGSEKYYVDSVKGRFTISRD
NAKNSLYLQMNSLRAEDTAVYYCARDSLIVGERGYWGQGTLVTVSS 7.6

EVQLVESGGGLVQPGGSLRLSCAASGFTFSSYWMYWVRQAPGKGLEWVANINHEGSEKYYVDSVKGRFTISRD
NAKNSLYLQMNSLRAEDTAVYYCARDSLIVGERGYWGQGTLVTVSS 7.7

EVQLVESGGGLVQPGGSLRLSCAASGFTFSSYWMYWVRQAPGKGLEWVANINHIGSEKYYVDSVKGRFTISRDN
AKNSLYLQMNSLRAEDTAVYYCARDSLIVGERGYWGQGTLVTVSS 7.8

EVQLVESGGGLVQPGGSLRLSCAASGFTFSSYWMYWVRQAPGKGLEWVANINHDGSEKYYVDSVKGRFTISRD
NAKNSLYLQMNSLRAEDTAVYYCARDTLIVGERGYWGQGTLVTVSS

Figure 7

8.1

QVQLQQWGAGLLKPSETLSLTCAVYGGSFSGYYWSWIRQPPGKGLEWIGEINHSGSTNYNPSLKSRVTISVDTSKNQFSLKLSSVTAADTAVYYCARGPIPATAIPDAFDWGQGTMVTVSS

Figure 8

9.1

QVQLQQWGAGLLKPSETLSLTCAVYGGSFSGHYWSWIRQPPGKGLEWIGDINHSGSTNYNPSLKSRVTISVDTSKNQFSLKLSSVTAADTAVYYCVRDYGDSRSLFDYWGQGTLVTVSS

Figure 9

10.1

QVQLVESGGGLVQPGGSLRLSCAASGFTFSSYGMHWVRQAPGKGLEWVAFMSYDGSNKYYVDSVKGRFTISRDNSKNTLYLQMNSLRAEDTAVYYCAKGDYDFWSGYPDYDMDVWGQGTTVTVSS

Figure 10

11.1

EVQLVESGGGLVKPGGSLRLSCAASGFNLSYGMYWVRQAPGKGLEWVAVISYDGSNKNYADSVKGRFTISRDNSKNTLFLQMNSLRVEDTAVYYCAKGGNALYSSGWPDDGFDIRGQGTMVTVSS

Figure 11

QVQLVESGGGVVQPGRSLRLSCAASGFTFSNFGMHWARQAPGKGLEWVAVISYDGNSKYYADTVKGRFTISRDNSKNTLYLEMNSLRADDTAVYYCAKGLWPPMDVRGQGTTVTVSS

Figure 12

13.1

EVQLVESGGGSVQPGGSLRLSCAASGFTFSDYWMTWVRQVPGKGLEWVANIKQDGSEKYYVDSVKGRFTISRDNAKNSLYLQMNSLRAEDTAVYYCARDRGGAVALYHNGMDMGGQGTTVTVSS

Figure 13

14.1

KCSWWSLGEVKKPGASVKVSCKASGYTFTSYDINWVRQATGQGLEWMGWMNPNSGNTGYAQKFQGRVTMTRNTSISTAYMELSSLRSEDTAVYYCARGNGPGITGTTDYWGQGTLVTVSS

Figure 14

15.1

EVQLVESGGGVVRPGGSLRLSCAASGFTFDDYGMSWVRQAPGKGLEWVSGINWNGDRTGYADSVKGRFTISRDNAKNSLYLQMNSLRAEDTALYYCGRENVIVPAATYWGQGTLVTVSS

Figure 15

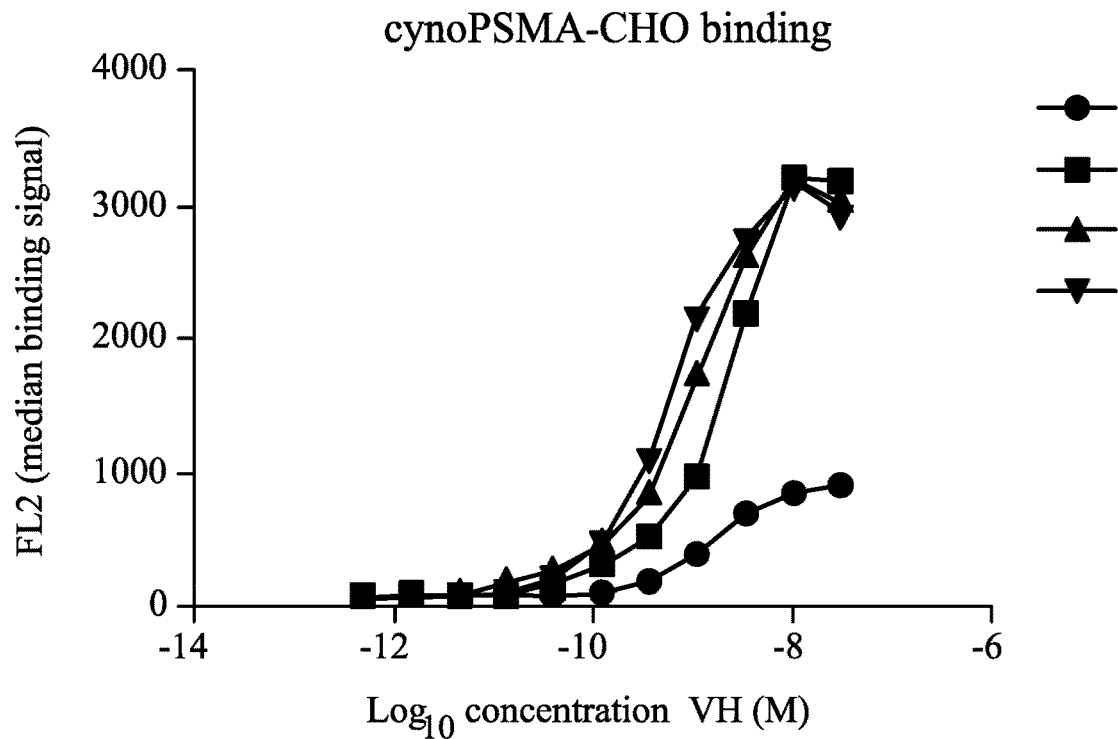
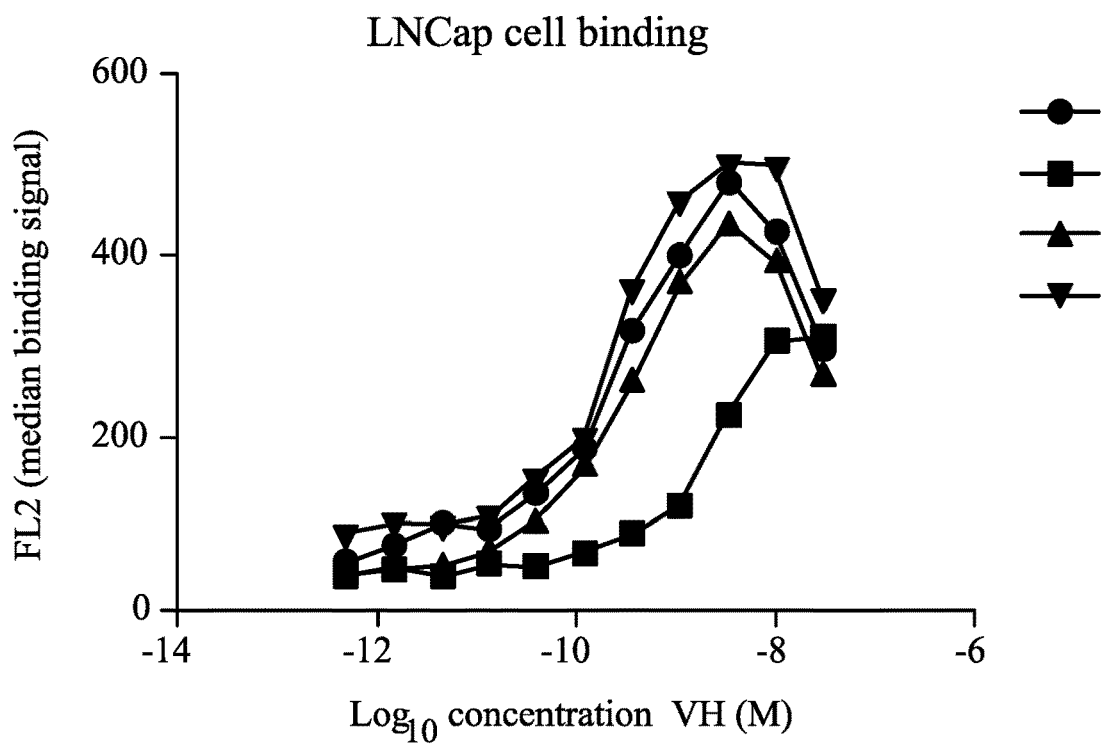
Figure 16a

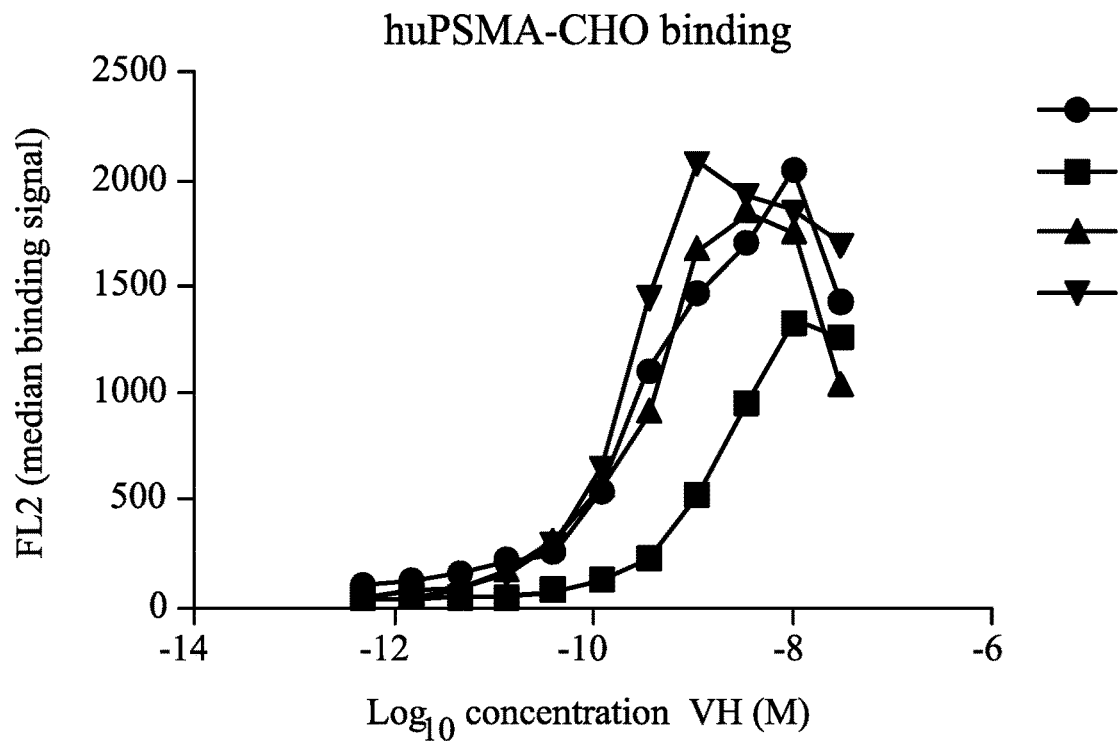
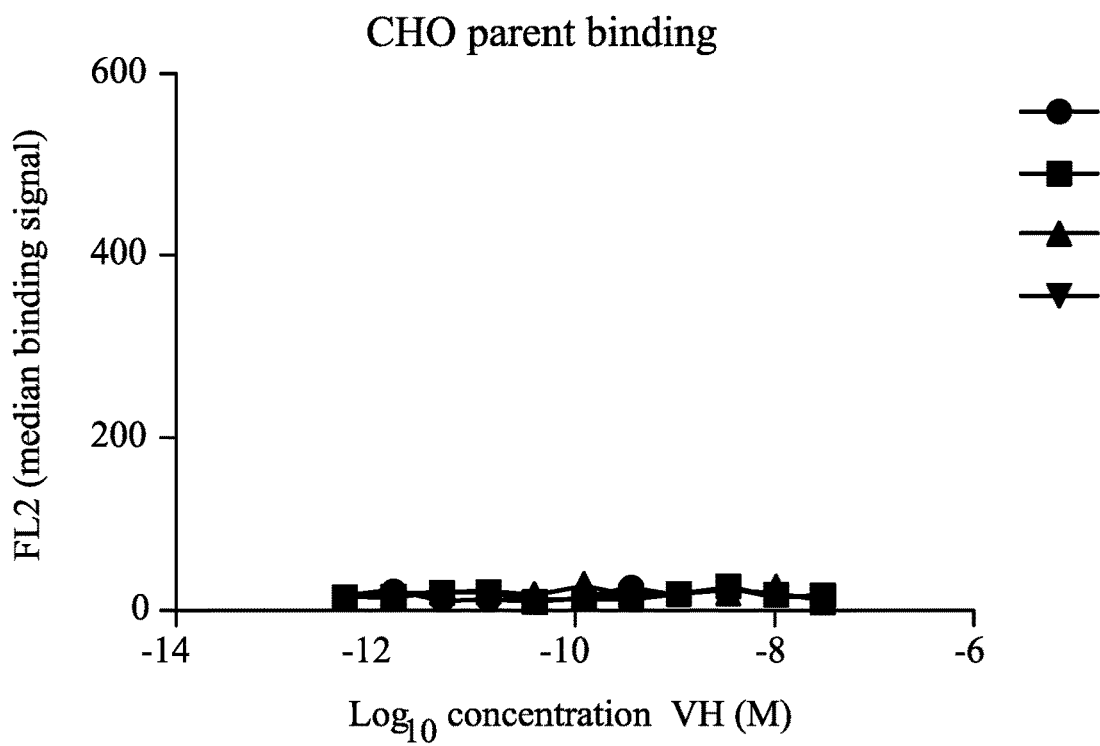
Figure 16a Continued

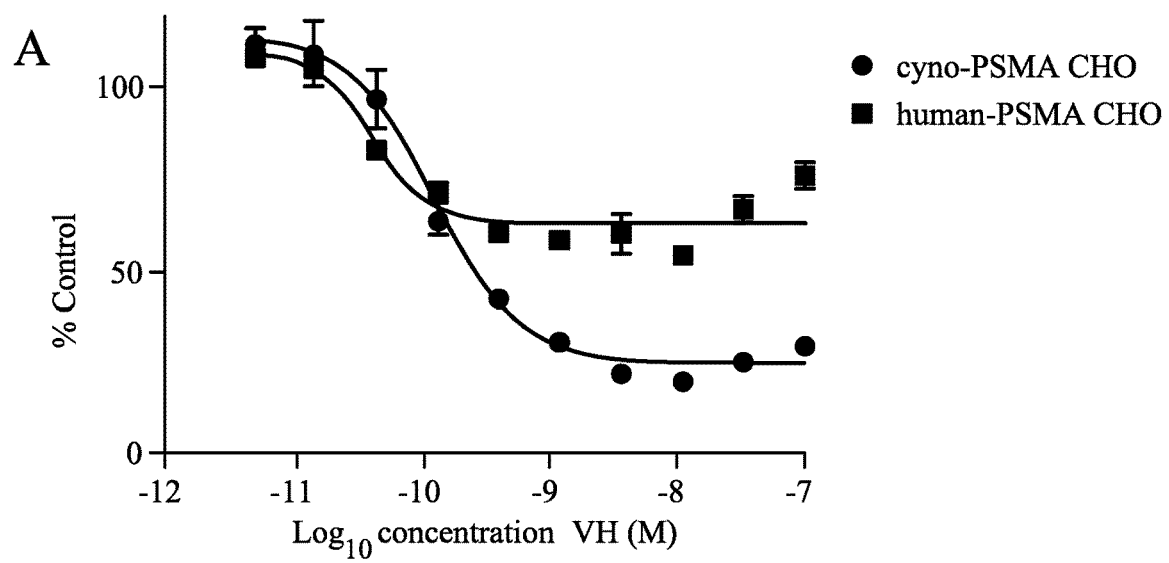
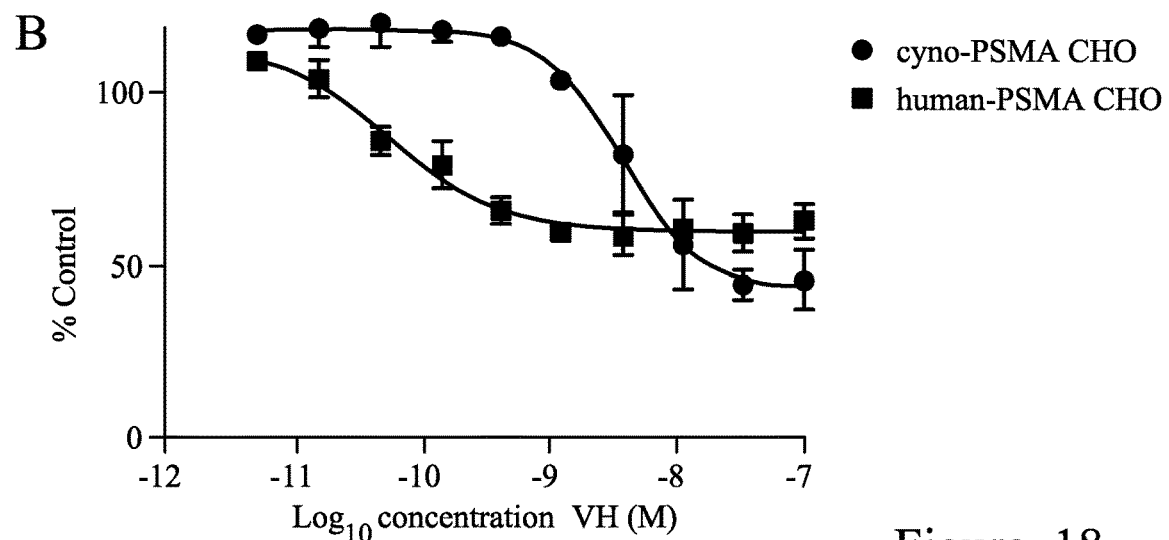
Figure 18
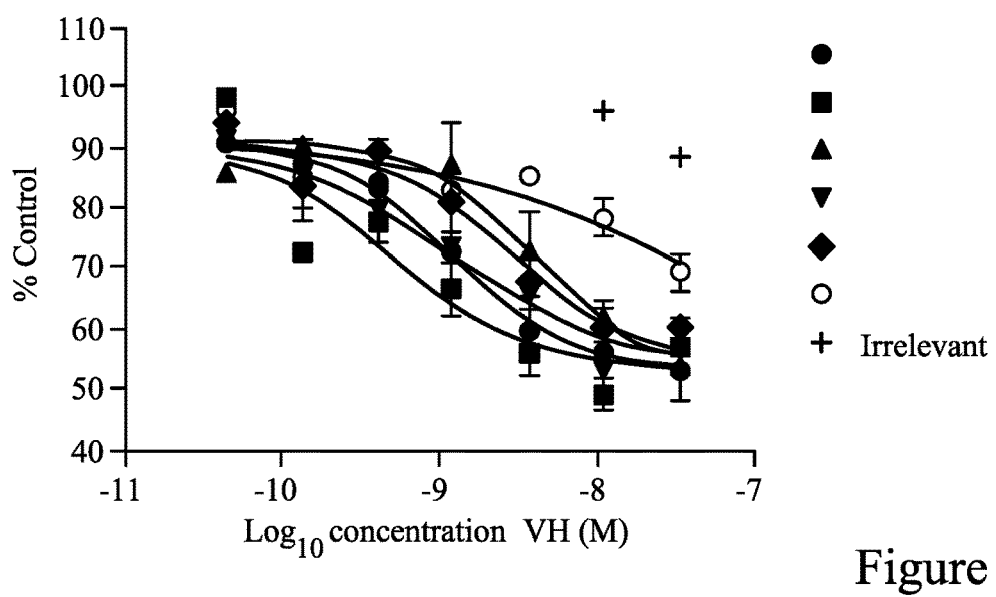
Figure 19

Figure 26:
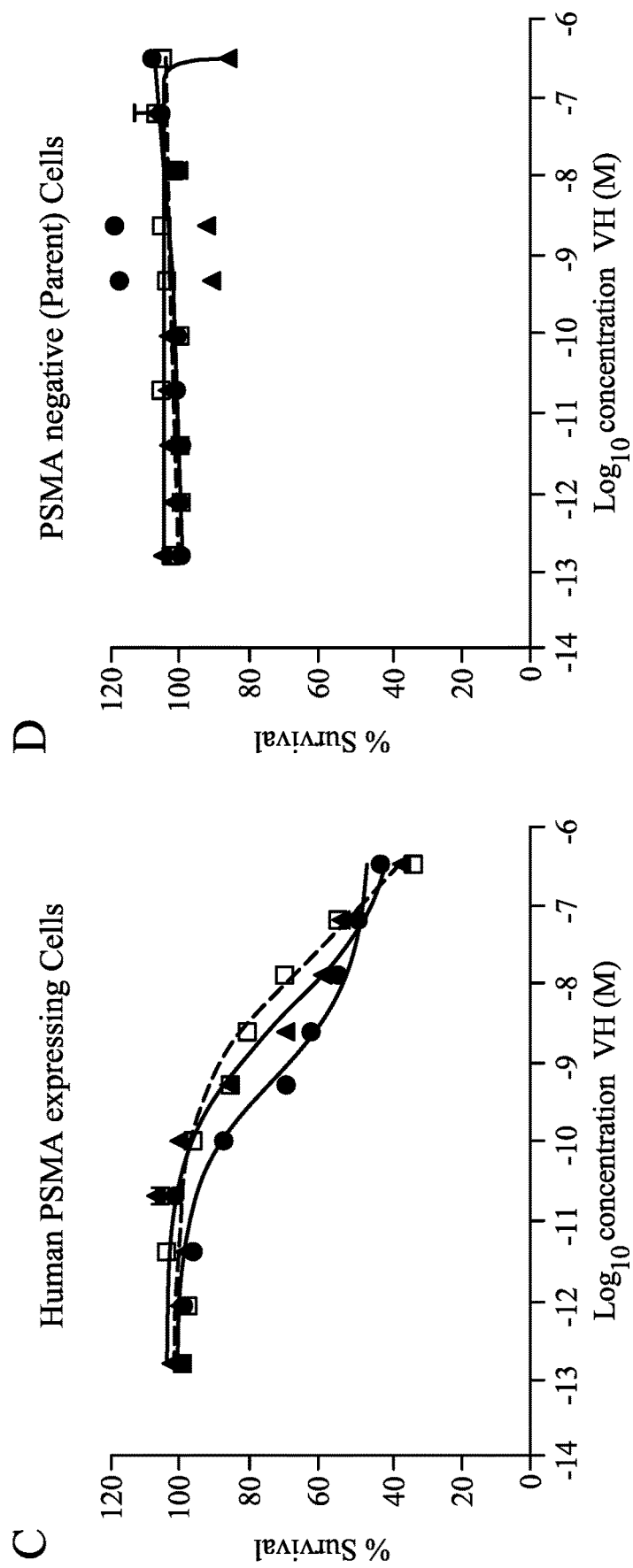
Figure 26:
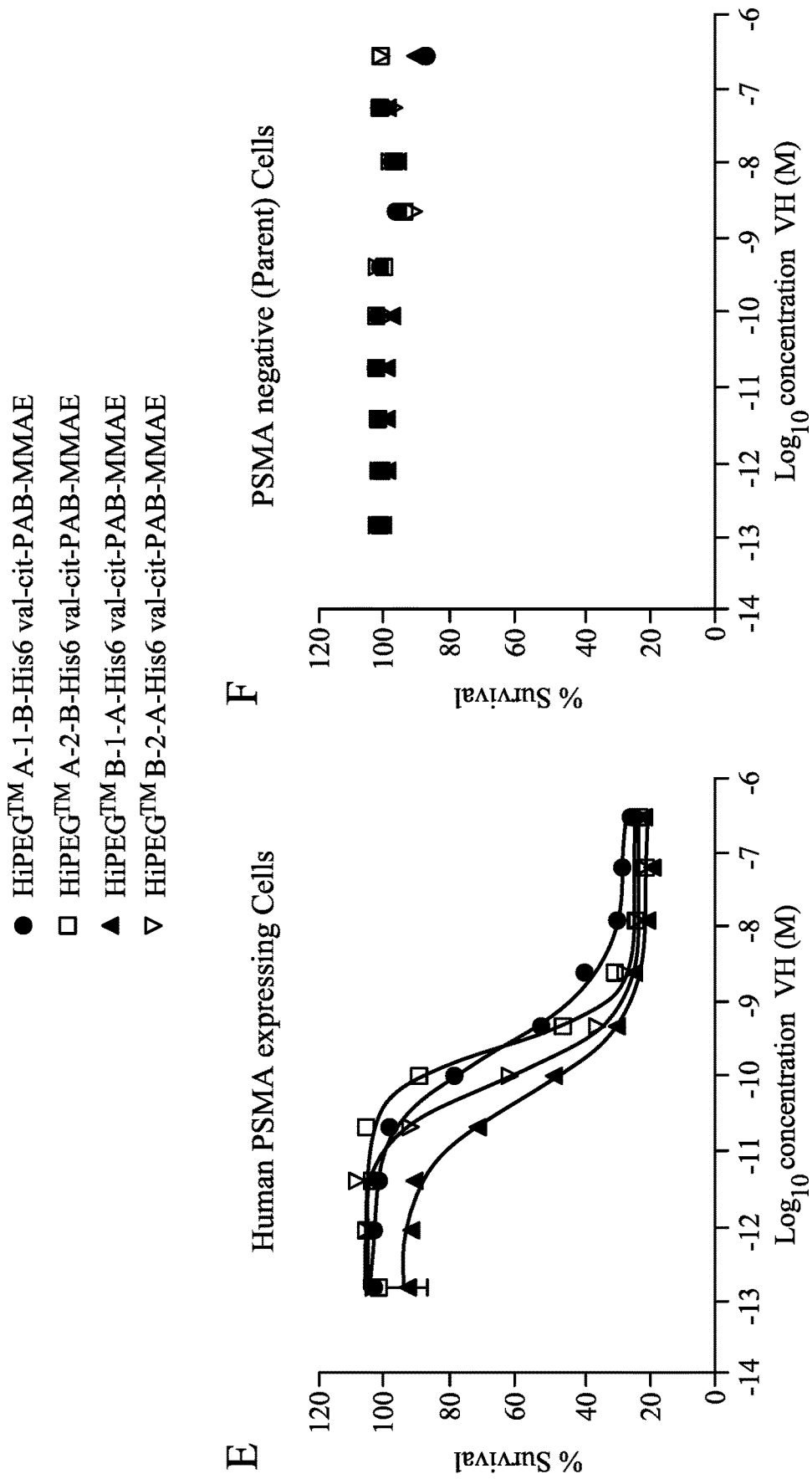

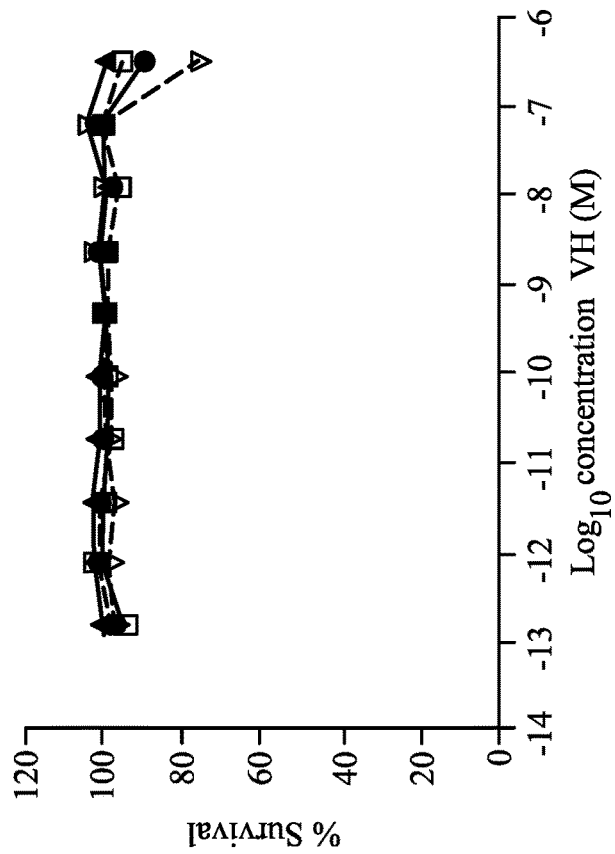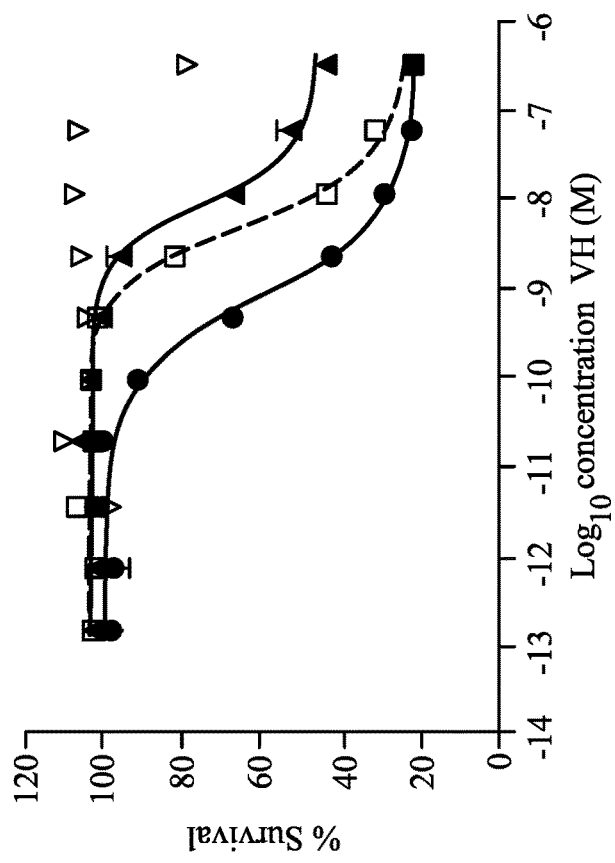
Figure 26

MOLECULES THAT BIND PROSTATE SPECIFIC MEMBRANE ANTIGEN (PSMA)

FIELD OF THE INVENTION

The invention relates to prostate specific membrane antigen (PSMA) binding molecules, and the use of such binding molecules in the treatment of disease.

INTRODUCTION

Prostate cancer is the most commonly diagnosed non-skin-related malignancy in males in developed countries. It is estimated that one in six males will be diagnosed with prostate cancer.

Current treatments for prostate cancer include surgery, radiation, and adjuvant hormonal therapy. Although these therapies are relatively effective in the early stages of disease, the majority of patients initially diagnosed with localized prostate cancer ultimately relapse. Whilst chemotherapy is one of the most widely used approaches in combating advanced prostate cancer, its therapeutic efficacy is usually insufficient due to lack of specificity and associated toxicity. Lack of targeted delivery to prostate cancer cells is one of the primary obstacles in achieving feasible therapeutic effect. Consequently, there remains a critical need for strategies to increase the selectivity of anti-prostate cancer agents (Barve et al., *J Control Release*. 2014 Aug. 10; 0: 118-132).

The diagnosis of prostate cancer has greatly improved following the use of serum-based markers such as the prostate specific antigen (PSA). In addition, prostate tumour-associated antigens offer targets for tumour imaging, diagnosis, and targeted therapies. The prostate specific membrane antigen (PSMA), a prostate tumour associated marker, is such a target.

PSMA is a 750-residue type II transmembrane glycoprotein highly restricted to prostate secretory epithelial cell membranes. It is highly expressed in prostate cancer cells and in nonprostatic solid tumor neovasculature and expressed at lower levels in other tissues, including healthy prostate, kidney, liver, small intestine, and brain. PSMA expression increases with prostate disease progression and metastasis and its expression level has thus been correlated with tumour aggressiveness. Various immunohistological studies have demonstrated increased PSMA levels in virtually all cases of prostatic carcinoma compared to those levels in benign prostate epithelial cells. Intense PSMA staining is found in all stages of the disease, including prostatic intraepithelial neoplasia, late stage androgen-independent prostate cancer and secondary prostate tumours localized to lymph nodes, bone, soft tissue, and lungs. PSMA is thus widely used as a biomarker for prostate cancer cells.

PSMA has a 3-part structure: a 19-amino-acid internal portion, a 24-amino-acid transmembrane portion, and a 707-amino-acid external portion. It forms a noncovalent homodimer that possesses glutamate carboxypeptidase activity based on its ability to process the neuropeptide N-acetylaspartylglutamate and glutamate-conjugated folate derivatives. PSMA is rapidly and efficiently internalized by an endocytic pathway and rapidly recycles back to the membrane.

Antibody-based therapeutics have emerged as important components of therapies for an increasing number of human malignancies in such fields as oncology, inflammatory and infectious diseases. In most cases, the basis of the therapeutic function is the high degree of specificity and affinity the antibody-based drug has for its target antigen. Arming monoclonal antibodies (mAbs) with drugs, toxins, or radionuclides is yet another strategy by which mAbs may induce a therapeutic effect. By combining the targeting specificity of an antibody with the tumour killing power of toxic effector molecules, immunoconjugates permit sensitive discrimination between target and normal tissue thereby resulting in fewer side effects than most conventional chemotherapeutic drugs.

Due to their size and other physical properties, however, mAbs have to be administered either intravenously (iv) or subcutaneously (sc) and therefore have a high systemic exposure. Thus, their route of delivery can often be suboptimal, resulting either in antibody binding to target antigen at non-disease locations (potentially compromising the healthy function of normal, non-disease tissue) or resulting in suboptimal PK/PD characteristics. Either outcome may result in a loss of efficacy and/or a compromised safety profile by virtue of the suboptimal route of administration.

The first PSMA-specific mAb reported, murine mAb 7E11, was subsequently developed and commercialized as a diagnostic agent for tumour imaging (ProstaScint, Cytogen, Princeton, N.J.). However, this antibody recognizes an intracellular epitope of PSMA exposed upon cell death which limits its usefulness as an imaging agent for the detection of PSMA. More recently, mAbs such as J591 that recognize the extracellular portion of PSMA have been identified.

The aim of the present invention is to address the need of alternative antibody-based treatments for use in the treatment of prostate cancer.

SUMMARY OF THE INVENTION

The invention relates to binding molecules that bind human PSMA. In particular, the invention relates to multivalent/multiparatopic binding molecules that bind human PSMA comprising two or more single human heavy chain variable ($V_H$) domain antibodies. In particular, the binding is to human PSMA in its native form. In preferred embodiments, the single $V_H$ domain is generated from a heavy chain only antibody produced in a transgenic rodent expressing human V gene loci and immunised with a PSMA antigen. Single domain antibodies used in the binding molecules of the invention bind a target in monovalent form. Single domain antibodies are smaller than conventional monoclonal antibody formats and the inventors have shown that such molecules facilitate high levels of specific tumor targeting, fast penetration and high accumulation in the tumor compared to a monoclonal antibody benchmark. As shown herein, the binding molecules have improved properties compared to monovalent single domain antibodies, in particular they demonstrate improved cell internalisation. They also show different properties compared to a monoclonal benchmark antibody. The inventors have also shown that the single domain antibodies bind human PSMA with high affinity, are very stable and expressed to high level. Furthermore, single $V_H$ domain antibodies of the invention are less immunogenic than murine antibodies and no humanization is required. These properties make the compounds of the invention particularly useful in different formats, for example in multivalent/multiparatopic formats and conjugated to a toxin or half-life extending moiety. The compounds are thus useful in treating disease, in particular cancer. In one aspect, the invention provides an immunoconjugate comprising more than one single $V_H$ domain antibody described herein. Aspects of the invention are further summarised below.

In one aspect, the invention thus relates to a binding molecule comprising a first single human heavy chain variable immunoglobulin ($V_H$) domain antibody capable of binding human PSMA and a second single $V_H$ domain antibody capable of binding human PSMA.

In one embodiment, said first $V_H$ domain and said second $V_H$ domain bind to the same epitope on human PSMA.

In one embodiment, said first single $V_H$ domain antibody binds to a first epitope on PSMA and said second single $V_H$ domain antibody binds to a second epitope on PSMA wherein said first and said second epitope are not identical.

The invention also relates to a binding molecule according to a preceding claim wherein said first or second single $V_H$ domain antibody comprises a CDR3 sequence comprising SEQ ID NO. 3 or a sequence with at least 70%, at least 80%, at least 90% or at least 95% homology thereto.

The invention also relates to a binding molecule wherein said first or second single $V_H$ domain antibody comprises a CDR3 sequence comprising SEQ ID NO. 83 or a sequence with at least 70%, at least 80%, at least 90% or at least 95% homology thereto.

The invention also relates to a binding molecule wherein said first or second $V_H$ domain comprises a CDR3 sequence comprising SEQ ID NO. 183 or a sequence with at least 70%, at least 80%, at least 90% or at least 95% homology thereto.

The invention also relates to a binding molecule wherein said first or second $V_H$ domain comprises a CDR3 sequence comprising SEQ ID NO. 279 or a sequence with at least 70%, at least 80%, at least 90% or at least 95% homology thereto.

The invention also relates to a binding molecule wherein said first or second $V_H$ domain comprises a CDR3 sequence comprising SEQ ID NO. 295 or a sequence with at least 70%, at least 80%, at least 90% or at least 95% homology thereto.

The invention also relates to a binding molecule wherein said first or second $V_H$ domain comprises a CDR3 sequence comprising SEQ ID NO. 303 or a sequence with at least 70%, at least 80%, at least 90% or at least 95% homology thereto.

The invention also relates to a binding molecule wherein said first or second $V_H$ domain comprises a CDR3 sequence comprising SEQ ID NO. 331 or a sequence with at least 70%, at least 80%, at least 90% or at least 95% homology thereto.

The invention also relates to a binding molecule wherein said first or second $V_H$ domain comprises a CDR3 sequence comprising SEQ ID NO. 363 or a sequence with at least 70%, at least 80%, at least 90% or at least 95% homology thereto.

The invention also relates to a binding molecule wherein said first or second $V_H$ domain comprises a CDR3 sequence comprising SEQ ID NO. 367 or a sequence with at least 70%, at least 80%, at least 90% or at least 95% homology thereto.

The invention also relates to a binding molecule wherein said first and/or second $V_H$ domain comprises a CDR3 sequence comprising SEQ ID NO. 371 or a sequence with at least 70%, at least 80%, at least 90% or at least 95% homology thereto.

The invention also relates to a binding molecule wherein said first and/or second $V_H$ domain comprises a CDR3 sequence comprising SEQ ID NO. 375 or a sequence with at least 70%, at least 80%, at least 90% or at least 95% homology thereto.

The invention also relates to a binding molecule wherein said first or second $V_H$ domain comprises a CDR3 sequence comprising SEQ ID NO. 379 or a sequence with at least 70%, at least 80%, at least 90% or at least 95% homology thereto.

The invention also relates to a binding molecule wherein said first or second $V_H$ domain comprises a CDR3 sequence comprising SEQ ID NO. 383 or a sequence with at least 70%, at least 80%, at least 90% or at least 95% homology thereto.

The invention also relates to a binding molecule wherein said first or second $V_H$ domain comprises a CDR3 sequence comprising SEQ ID NO. 387 or a sequence with at least 70%, at least 80%, at least 90% or at least 95% homology thereto.

The invention also relates to a binding molecule wherein said first or second $V_H$ domain comprises a CDR3 sequence comprising SEQ ID NO. 391 or a sequence with at least 70%, at least 80%, at least 90% or at least 95% homology thereto.

The invention also relates to a binding molecule according to claim 3 in which a) the first single $V_H$ domain antibody is selected from a single $V_H$ domain antibody of family 2, 3, 4, 7, 9, 10, 11 or 14 and in which b) the second single$_H$ domain antibody is selected from family 1, 5, 6, 12 or 13.

The invention also relates to a binding molecule in which a) the first single $V_H$ domain antibody is selected from a single $V_H$ domain antibody of family 2, in which b) the second single $V_H$ domain antibody is selected from a single $V_H$ domain antibody of family 1. Said first single $V_H$ domain antibody is located either C or N terminally so that either direction is within the scope of the invention.

The invention also relates to a binding molecule in which a) the first $V_H$ domain can compete with a Humabody® comprising SEQ ID NO: 4 for binding to PSMA and/or can cross-block the binding of a Humabody® comprising SEQ ID NO: 4 to PSMA and in which b) the second $V_H$ domain can compete with a Humabody® comprising SEQ ID NO: 76 for binding to PSMA and/or can cross-block the binding of a Humabody® comprising SEQ ID NO:76 to PSMA.

In another aspect, the invention relates to a pharmaceutical composition comprising a binding molecule described herein and a pharmaceutical carrier.

In another aspect, the invention relates to a method for treating prostate cancer or a prostatic disorder comprising administering a therapeutically-effective amount of a binding molecule or a pharmaceutical composition described herein.

In another aspect, the invention relates to a binding molecule or a pharmaceutical composition described herein for use as medicament.

In another aspect, the invention relates to a binding molecule or a pharmaceutical composition described herein for use in the treatment of prostate cancer or a prostatic disorder.

In another aspect, the invention relates to the use of a binding molecule or a pharmaceutical composition described herein in the manufacture of a medicament for the treatment of prostate cancer or a prostatic disorder.

In another aspect, the invention relates to an in vivo or in vitro method for reducing human PSMA activity comprising contacting human PSMA with a binding molecule described herein.

In another aspect, the invention relates to a method for determining the presence of PSMA in a test sample by an immunoassay comprising contacting said sample with a binding molecule described herein and at least one detectable label.

In another aspect, the invention relates to a nucleic acid construct comprising a nucleic acid according described herein.

In another aspect, the invention relates to a host cell comprising a nucleic acid or a construct described herein.

In another aspect, the invention relates to a method for producing a binding molecule described herein comprising expressing a nucleic acid encoding said binding molecule in a host cell and isolating the binding molecule from the host cell culture.

In another aspect, the invention relates to a kit comprising a binding molecule or a pharmaceutical composition described herein.

In another aspect, the invention relates to a biparatopic, bivalent or multispecific binding molecule comprising one or more single domain antibody described herein.

DRAWINGS

FIG. 1. Family 1 sequences. This Figure shows the full length VH sequence for single domain antibodies in family 1 (SEQ ID NOS: 4, 8, 12, 16, 20, 24, 28, 32, 36, 40, 44, 48, 52, 56, 60, 64, 68, 72, 76, 80). Framework (FR) and complementarity determining regions (CDR) are labelled. CDR1, CDR2 and CDR3 are highlighted in bold.

FIG. 2. Family 2 sequences. This Figure shows the full length VH sequence for single domain antibodies in family 2 (SEQ ID NOS: 84, 88, 92, 96, 100, 104, 108, 112, 116, 120, 124, 128, 132, 136, 140, 144, 148, 152, 156, 160, 164, 168, 172, 176, 180). Framework (FR) and complementarity determining regions (CDR) are labelled. CDR1, CDR2 and CDR3 are highlighted in bold.

FIG. 3. Family 3 sequences. This Figure shows the full length VH sequence for single domain antibodies in family 3 (SEQ ID NOS: 184, 188, 192, 196, 200, 204, 208, 212, 216, 220, 224, 228, 232, 236, 240, 244, 248, 252, 256, 260, 264, 268, 272, 276). Framework (FR) and complementarity determining regions (CDR) are labelled. CDR1, CDR2 and CDR3 are highlighted in bold.

FIG. 4. Family 4 sequences. This Figure shows the full length VH sequence for single domain antibodies in family 4 (SEQ ID NOS: 280, 284, 288, 292). Framework (FR) and complementarity determining regions (CDR) are labelled. CDR1, CDR2 and CDR3 are highlighted in bold.

FIG. 5. Family 5 sequences. This Figure shows the full length VH sequence for single domain antibodies in family 5 (SEQ ID NOS: 296, 300). Framework (FR) and complementarity determining regions (CDR) are labelled. CDR1, CDR2 and CDR3 are highlighted in bold.

FIG. 6. Family 6 sequences. This Figure shows the full length VH sequence for single domain antibodies in family 6 (SEQ ID NOS: 304, 308, 312, 316, 320, 324, 328). Framework (FR) and complementarity determining regions (CDR) are labelled. CDR1, CDR2 and CDR3 are highlighted in bold.

FIG. 7. Family 7 sequences. This Figure shows the full length VH sequence for single domain antibodies in family 7 (SEQ ID NOS: 332, 336, 340, 344, 348, 352, 356, 360). Framework (FR) and complementarity determining regions (CDR) are labelled. CDR1, CDR2 and CDR3 are highlighted in bold.

FIG. 8. Family 8 sequences. This Figure shows the full length VH sequence for single domain antibodies in family 8 (SEQ ID NO: 364). Framework (FR) and complementarity determining regions (CDR) are labelled. CDR1, CDR2 and CDR3 are highlighted in bold.

FIG. 9. Family 9 sequences. This Figure shows the full length VH sequence for single domain antibodies in family 9 (SEQ ID NO: 368). Framework (FR) and complementanty determining regions (CDR) are labelled. CDR1, CDR2 and CDR3 are highlighted in bold.

FIG. 10. Family 10 sequences. This Figure shows the full length VH sequence for single domain antibodies in family 10 (SEQ ID NO: 372). Framework (FR) and complementarity determining regions (CDR) are labelled. CDR1, CDR2 and CDR3 are highlighted in bold.

FIG. 11. Family 11 sequences. This Figure shows the full length VH sequence for single domain antibodies in family 11 (SEQ ID NO: 376). Framework (FR) and complementarity determining regions (CDR) are labelled. CDR1, CDR2 and CDR3 are highlighted in bold.

FIG. 12. Family 12 sequences. This Figure shows the full length VH sequence for single domain antibodies in family 12 (SEQ ID NO: 380). Framework (FR) and complementarity determining regions (CDR) are labelled. CDR1, CDR2 and CDR3 are highlighted in bold.

FIG. 13. Family 13 sequences. This Figure shows the full length VH sequence for single domain antibodies in family 13 (SEQ ID NO: 384). Framework (FR) and complementarity determining regions (CDR) are labelled. CDR1, CDR2 and CDR3 are highlighted in bold.

FIG. 14. Family 14 sequences. This Figure shows the full length VH sequence for single domain antibodies in family 14 (SEQ ID NO: 388). Framework (FR) and complementarity determining regions (CDR) are labelled. CDR1, CDR2 and CDR3 are highlighted in bold.

FIG. 15. Family 15 sequences. This Figure shows the full length VH sequence for single domain antibodies in family 15 (SEQ ID NO: 392,). Framework (FR) and complementarity determining regions (CDR) are labelled. CDR1, CDR2 and CDR3 are highlighted in bold.

FIG. 16. Binding of purified anti-PSMA $V_H$ in FMAT Mirrorball Assay. 16a •1.1, ■3.1, ▲2.10, ▼2.1, 16b •2.1, ▲2.13, ▼2.17 ◊2.15, ○2.12 ∆2.22 16c single domain antibodies tested as shown by symbols from top to bottom •1.8, ■1.10, ▲1.11, ▼1.12, 1.13, ○1.14, 1.16, ∆ 1.17, 1.18 d) biparatopic binding molecules tested as shown by symbols from top to bottom: L=(G4S)$_6$ 1.1-L-2.1; 1.16-L-2.1; 1.11-L-2.1, 1.18-L-2.1, 1.17-2.1, 1.1-2.17, 1.16-L-2.17, 1.11-L-2.17, 1.18-L-2.17, 1.17-L-2.17; e) 1.1-L-2.15, 1.16-L-2.15, 1.11-L-2.15, 1.18-L-2.15, 1.17-L-2.15, 1.1-L-2.22, 1.16-L-2.22, 1.11-L-2.22, 1.11-L-2.22, 1.18-L-2.22, 1.17-L-L2.22

Figure 17:
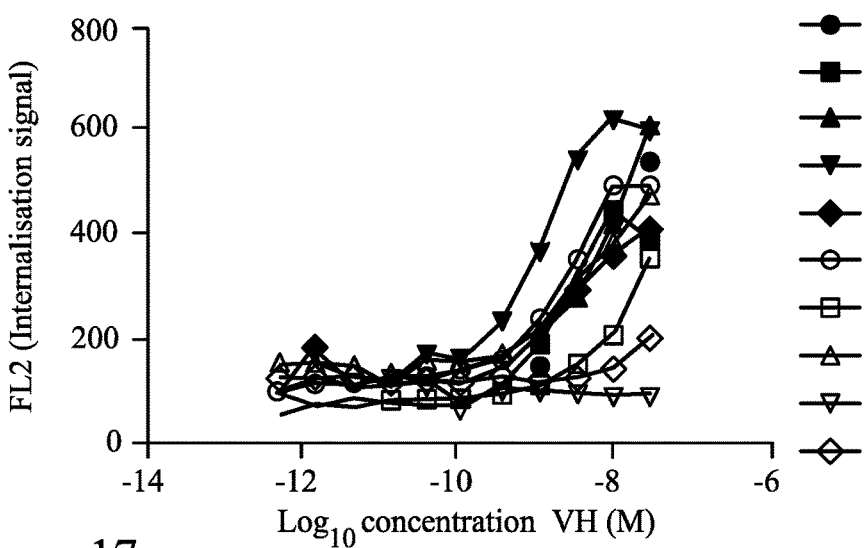

FIG. 17. pHrodo® Green internalisation of purified anti-PSMA single domain antibodies. Single domain antibodies used (symbols in legend from top to bottom): 2.20, 12.1, 3.1, 3.2, 4.1, 5.1, 9.1, 14.1, 10.1, 7.1.

FIG. 18. Killing of cynoPSMA and human PSMA CHO with anti-PSMA single domain antibodies A. 2.1 B. 1.1.

FIG. 19. Killing of LNCap with anti-PSMA single domain antibodies. Single domain antibodies used (symbols in legend from top to bottom): 1.1, 2.1, 7.1, 3.1, 12.1, 4.1.

Figure 20A:
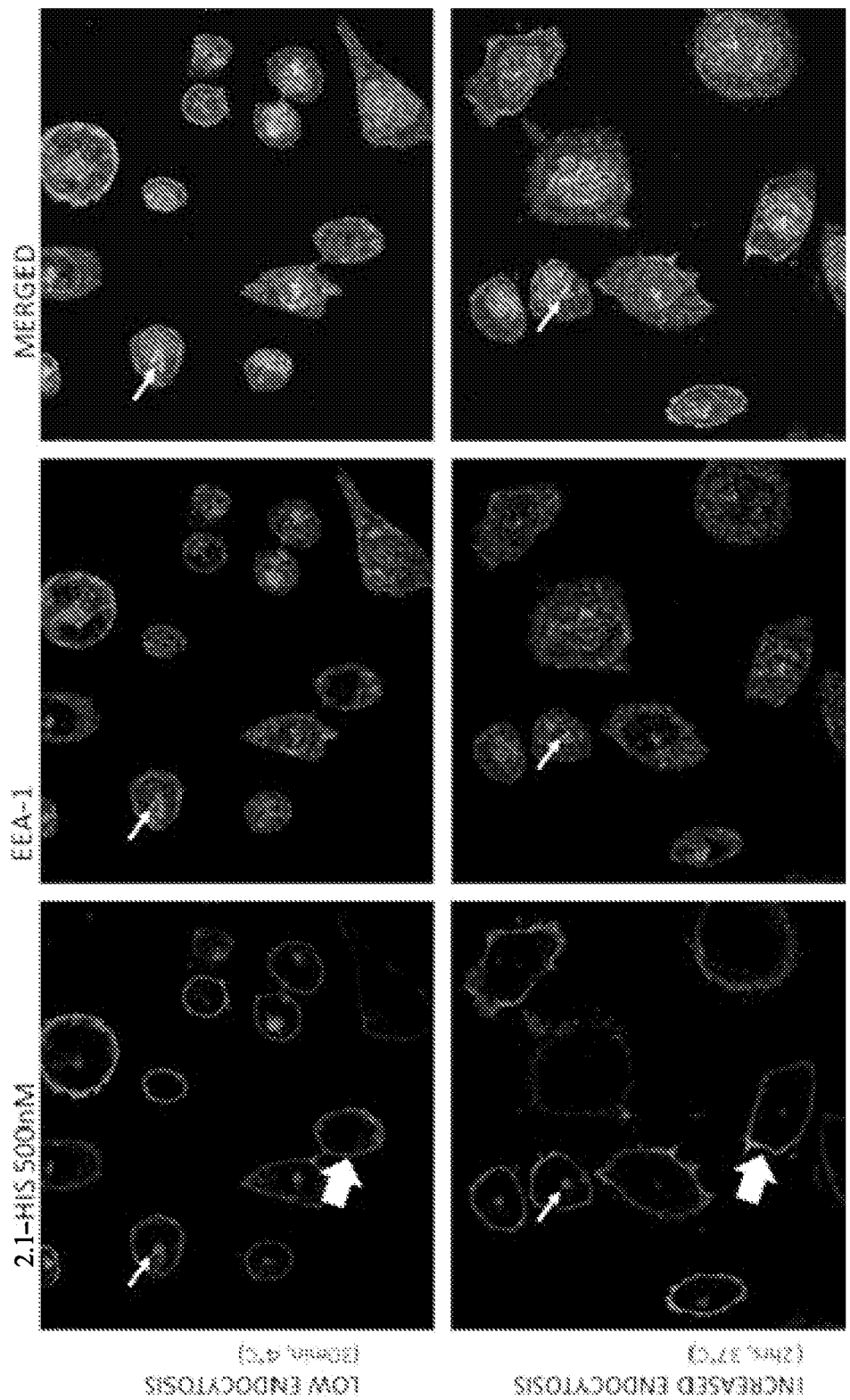
Figure 20B:
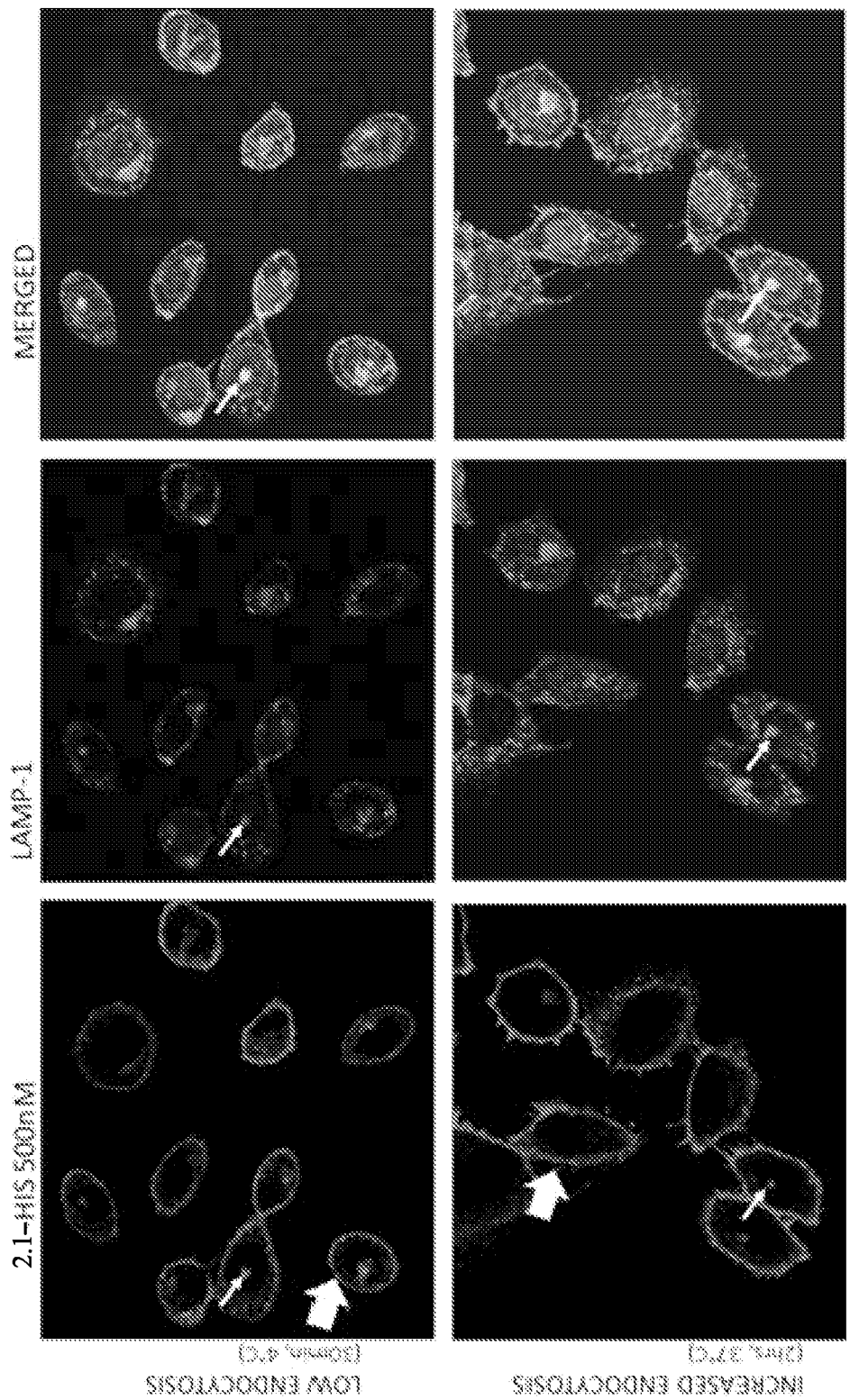

FIG. 20. Localisation studies using $V_H$ 2.1-HIS. $V_H$ staining is localized mainly on the cell membrane (indicated by the large arrow), but some internalization can also be observed (thin arrow) at both 4° C. and 37° C. in the form of a single central cluster localizing with both LAMP-1 (b) and EEA-1 (a).

Figure 21A:
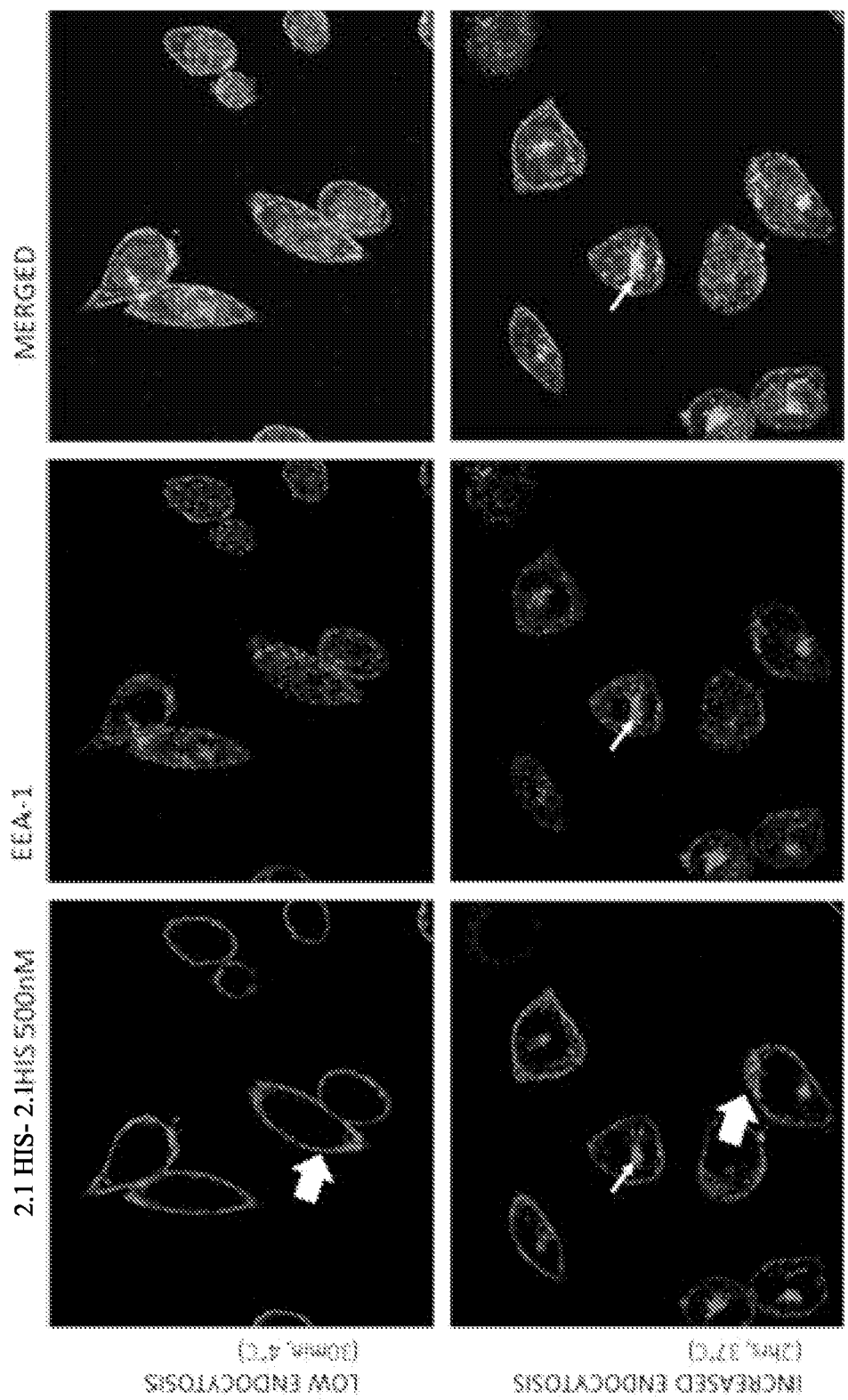
Figure 21B:
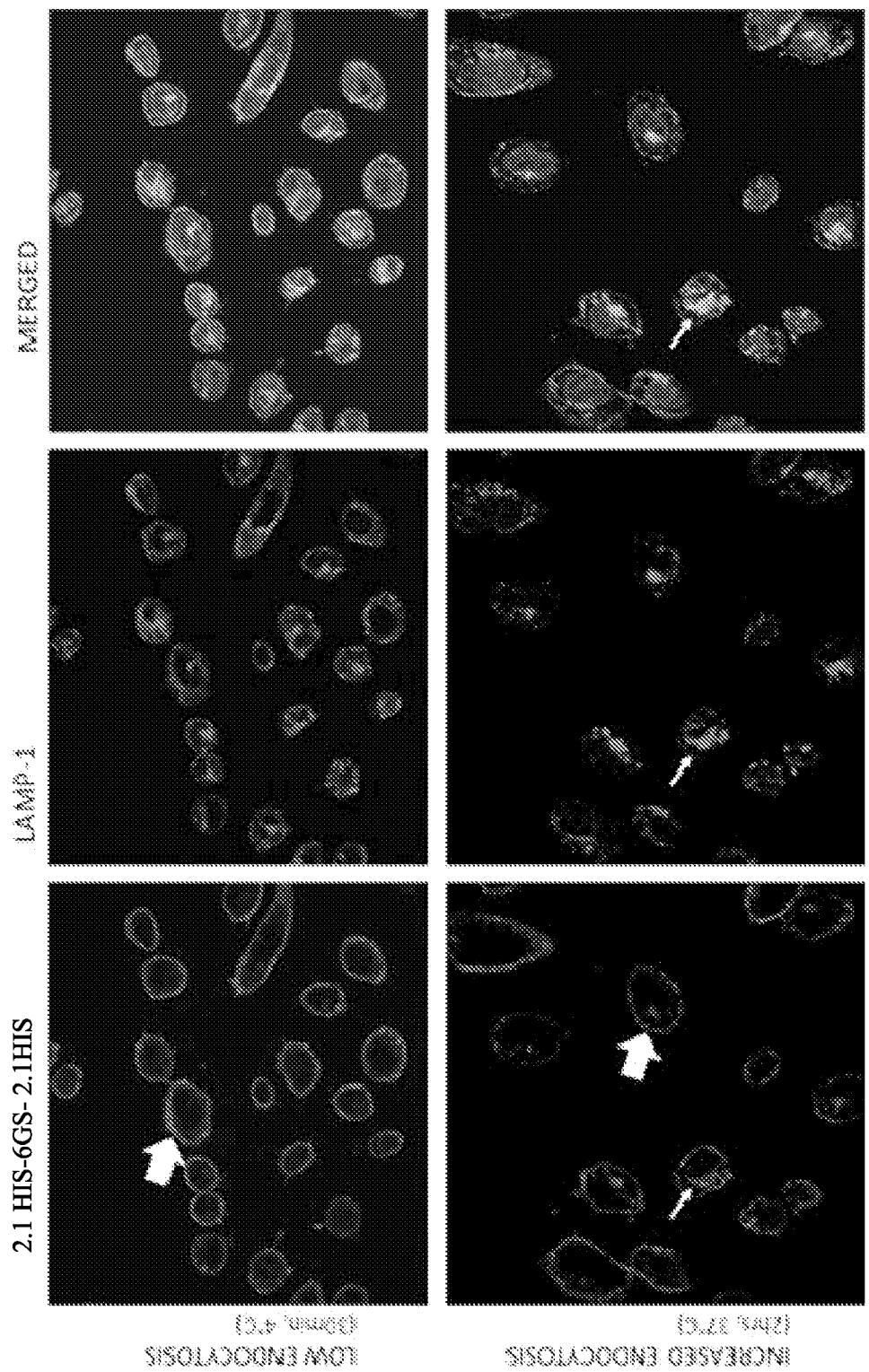

FIG. 21. Localisation studies using bivalent $V_H$ construct 2.1-6GS-2.1-HIS. At 4° C., $V_H$ staining is localized mainly on the cell membrane (large arrows). After 2 hrs at 37° C. the membrane staining appears more punctuated (large arrow), and internalization is shown by the presence of small $V_H$ clusters inside the cell localizing with both LAMP-1 (a) and EEA-1 (b) (thin arrows).

Figure 22A:
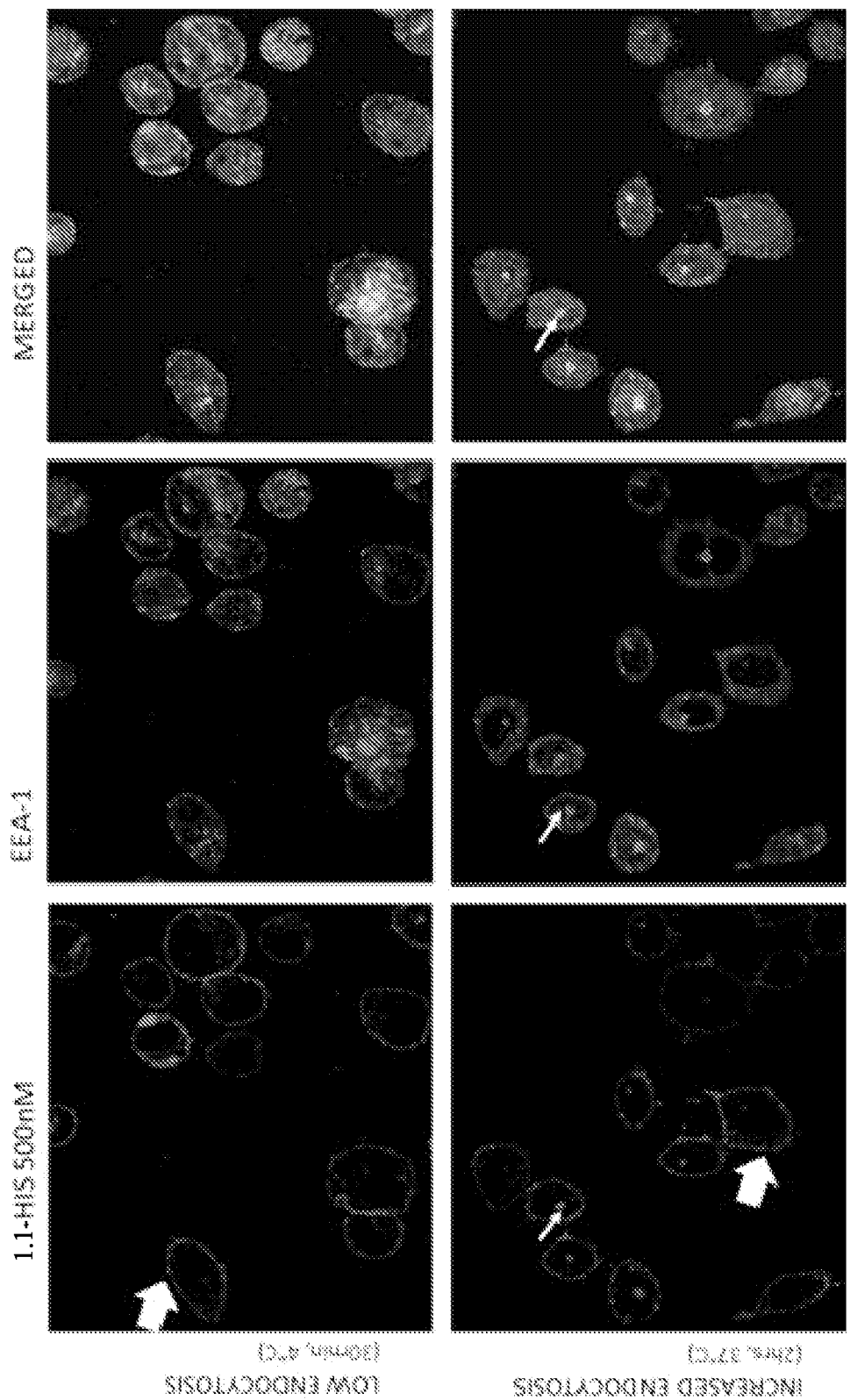
Figure 22B:
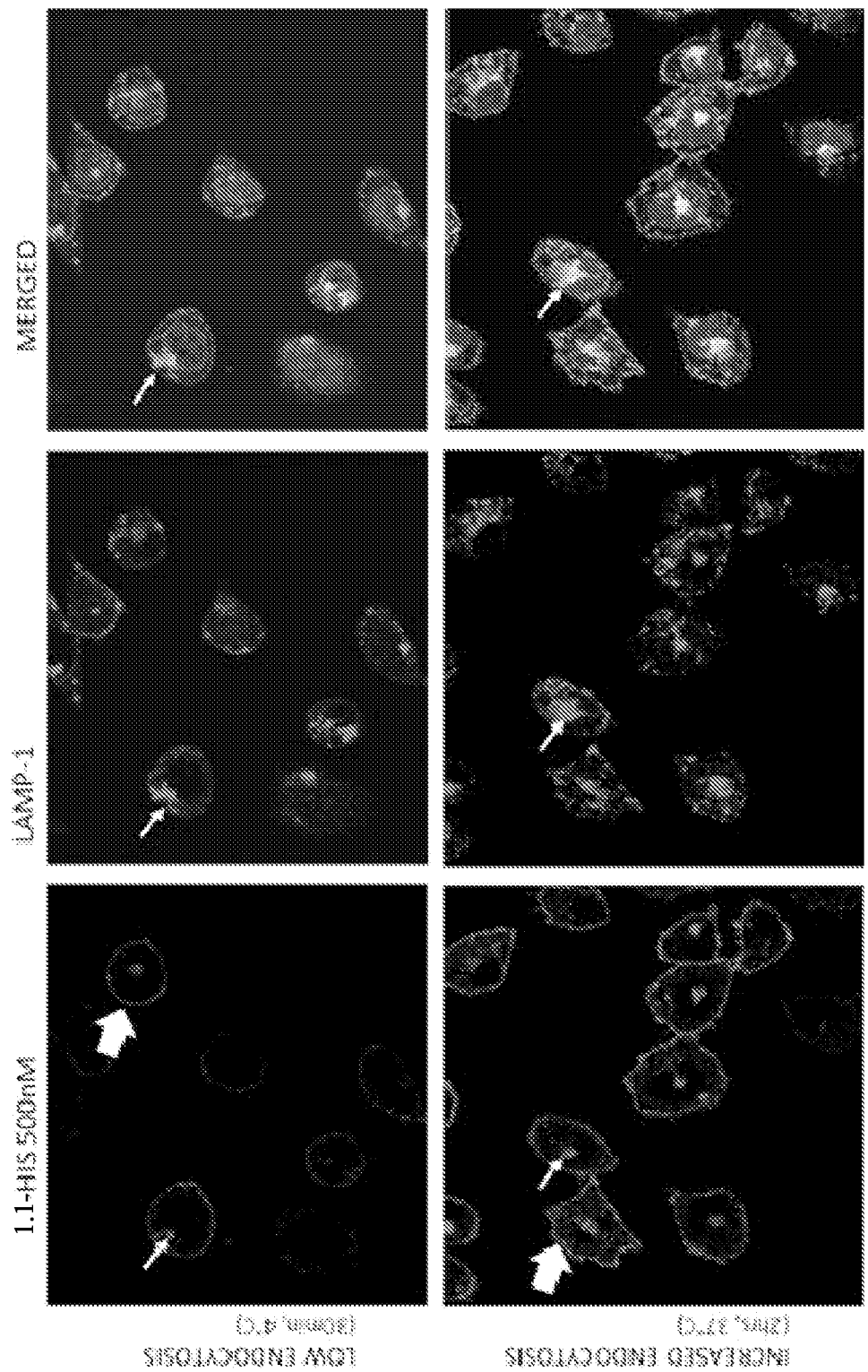

FIG. 22. Localisation studies using $V_H$ 1.1-HIS. $V_H$ staining is localized mainly on the cell membrane (indicated by the large arrow), but some internalization is present (thin arrow) at both 4° C. and 37° C. in the form of a single central cluster localizing with both LAMP-1 (b) and EEA-1 (a).

Figure 23A:
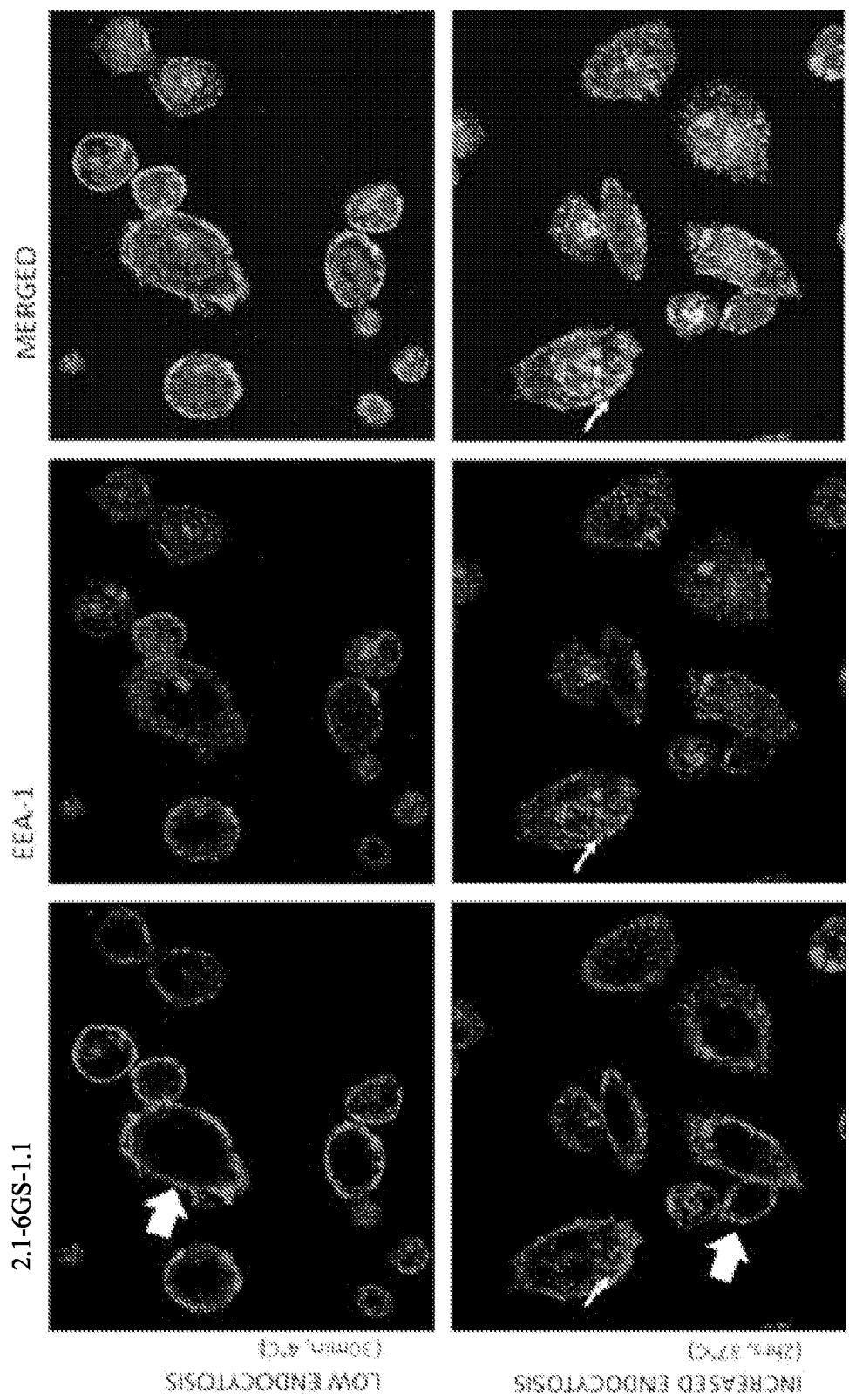
Figure 23B:
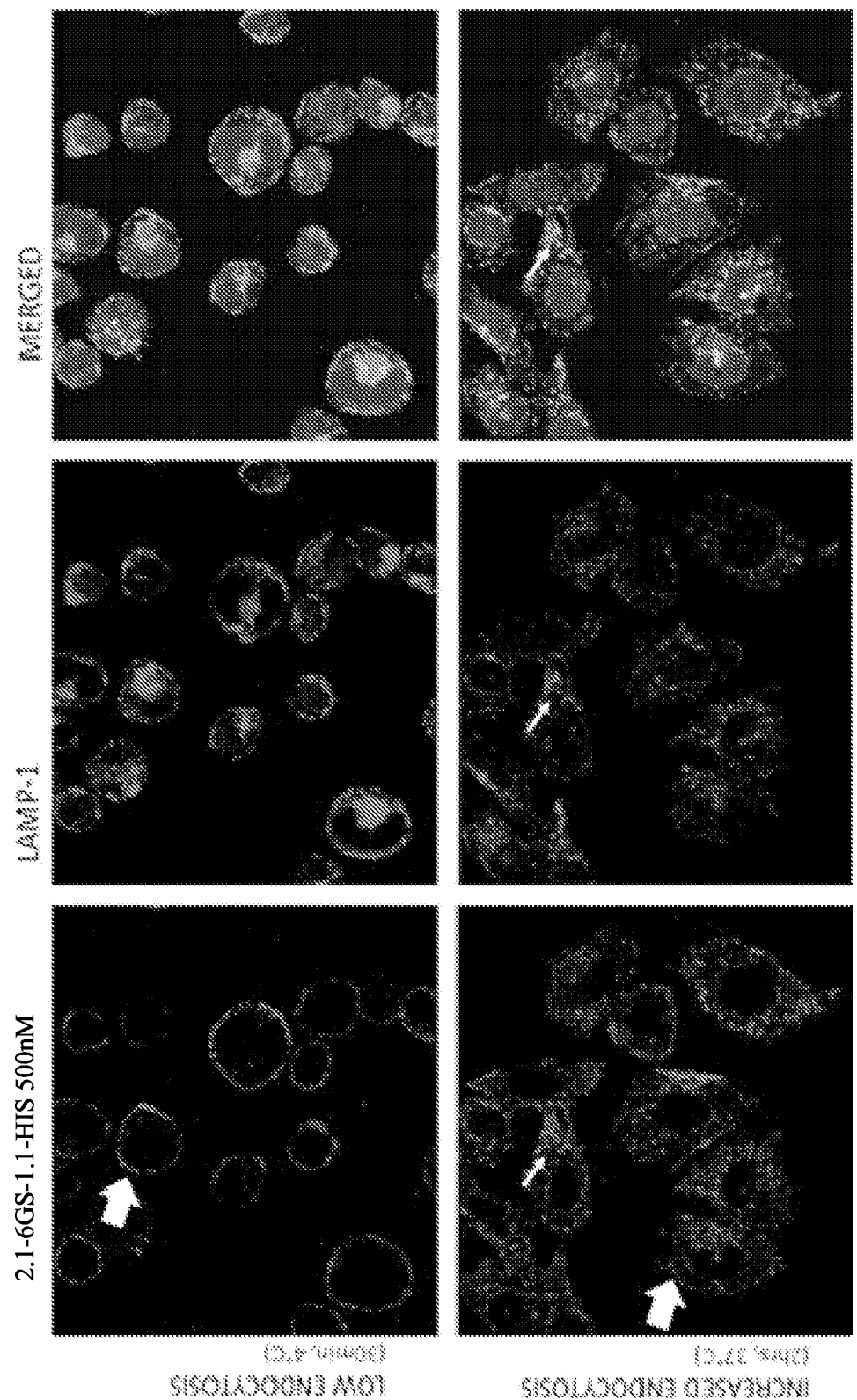

FIG. 23. Localisation studies using biparatopic $V_H$ construct 2.1-6GS-1.1-HIS. At 4° C., $V_H$ staining is localized mainly on the cell membrane (large arrows). After 2 hrs at 37° C. the membrane staining has almost disappeared (large arrow), and $V_H$ is internalized as shown by the punctuated staining inside the cell localizing with both LAMP-1 (b) and EEA-1 (a) (thin arrows).

Figure 24A:
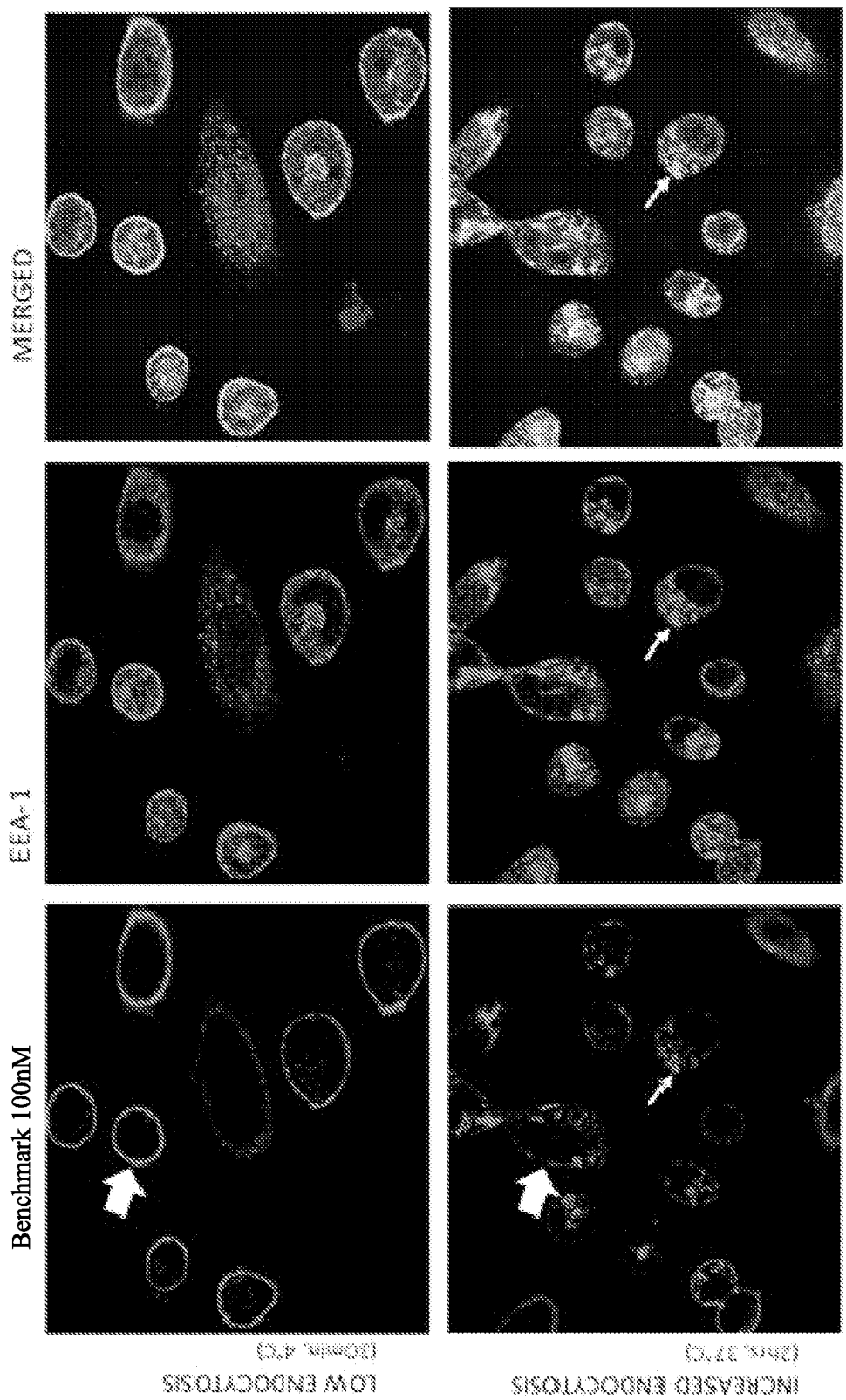
Figure 24B:
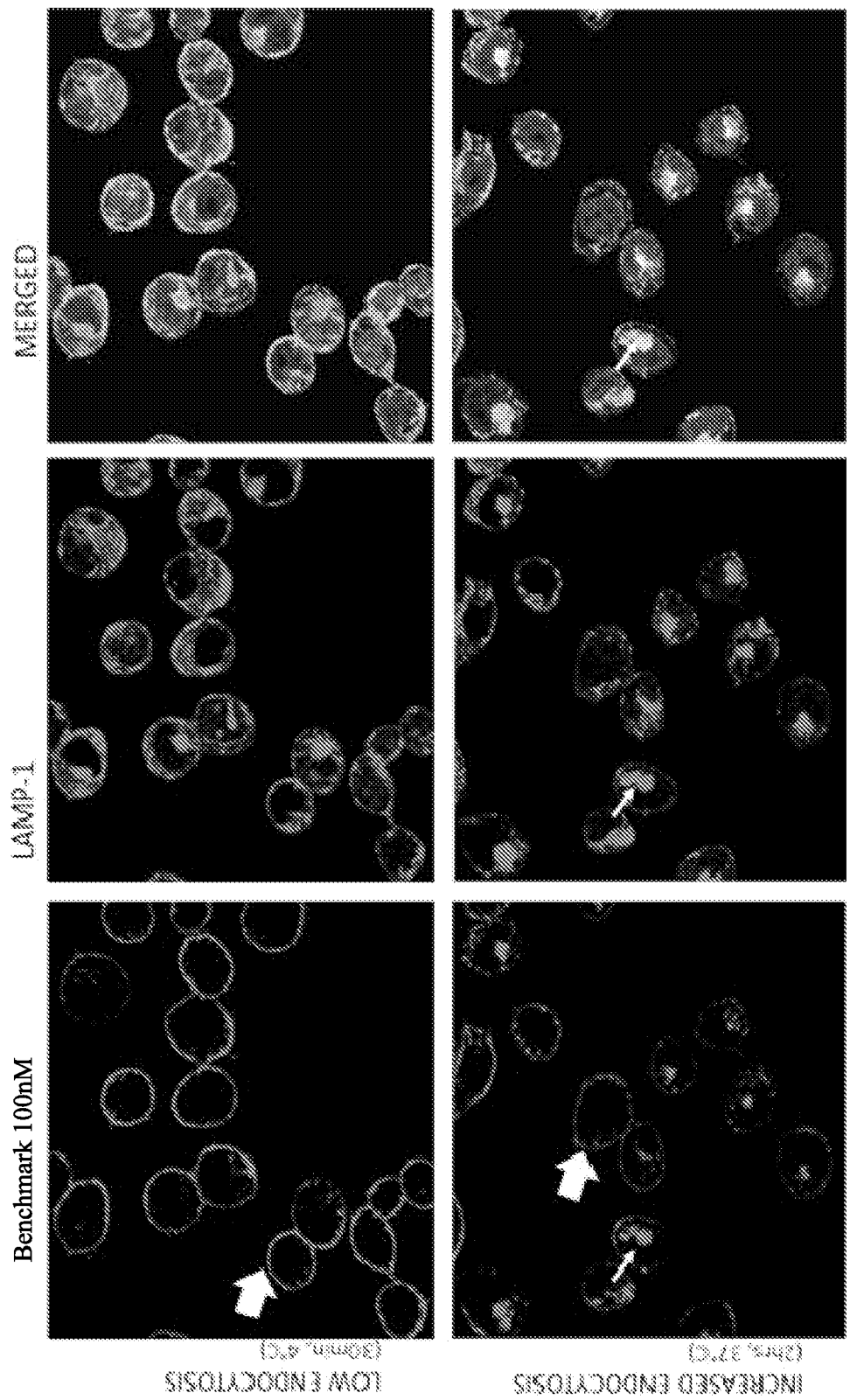

FIG. 24. Localisation studies using benchmark anti-PSMA IgG. At 4° C., $V_H$ staining is localized mainly on the cell membrane (large arrows). After 2 hrs at 37° C., the membrane staining is thinner (large arrow), and most of the $V_H$ is internalized as shown by the presence of clusters inside the cell localizing with both LAMP-1 (b) and EEA-1 (a) (thin arrows).

Figure 25:
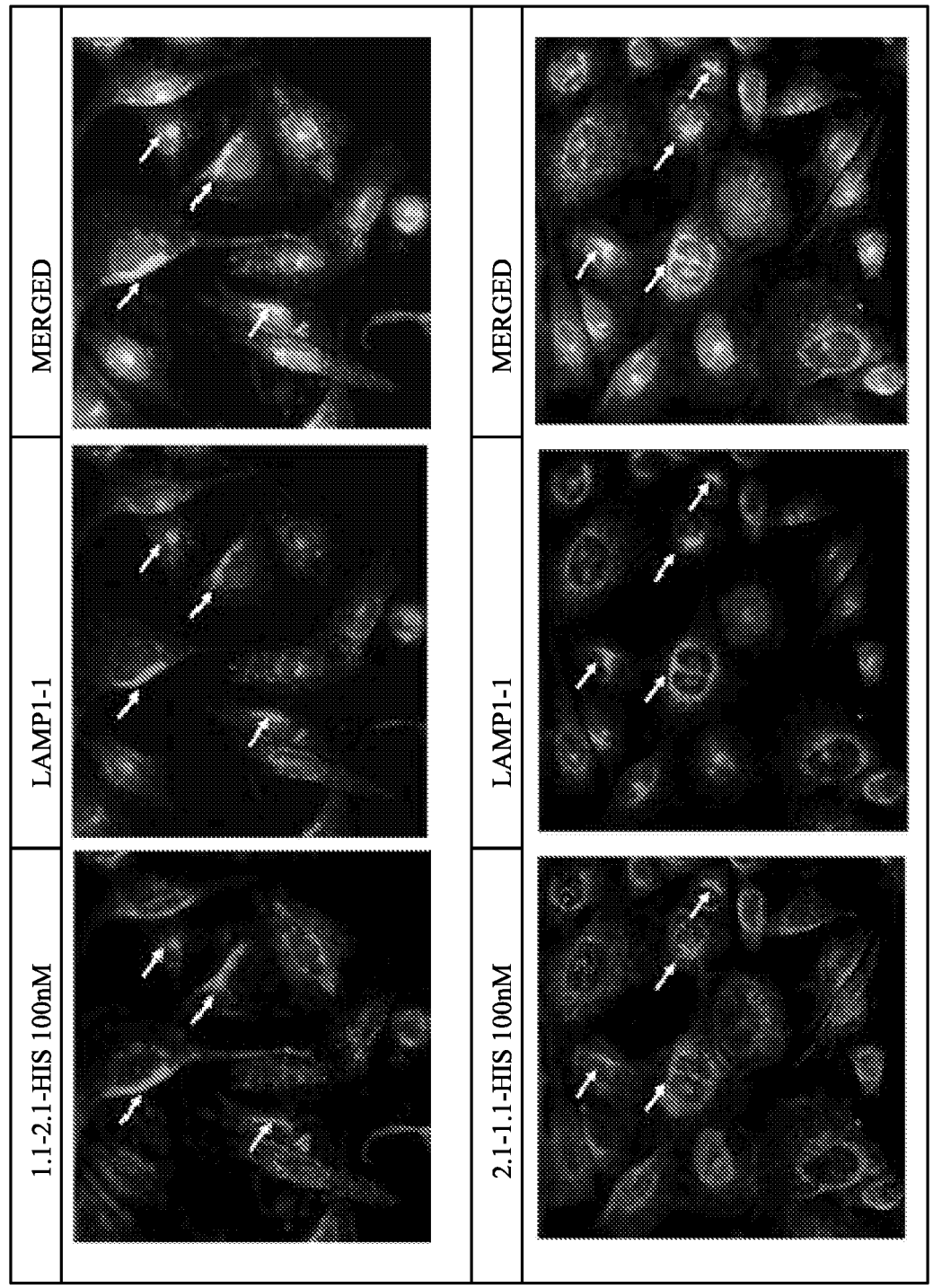

FIG. 25. Localisation studies using CHO cells expressing human PSMA using 1.1-6GS-2.1-HIS (top panel) and 2.1-6GS-1.1-HIS (bottom panel).

FIG. 26. shows in vitro cytotoxicity of monomeric MMAE-conjugated $V_H$ (A and B), bivalent $V_H$ (C and D) and biparatopic VH (E and F) on human cells stably expressing human PSMA protein and matched parental cells (PSMA negative) at a 48 hour incubation time point.

Figure 27:
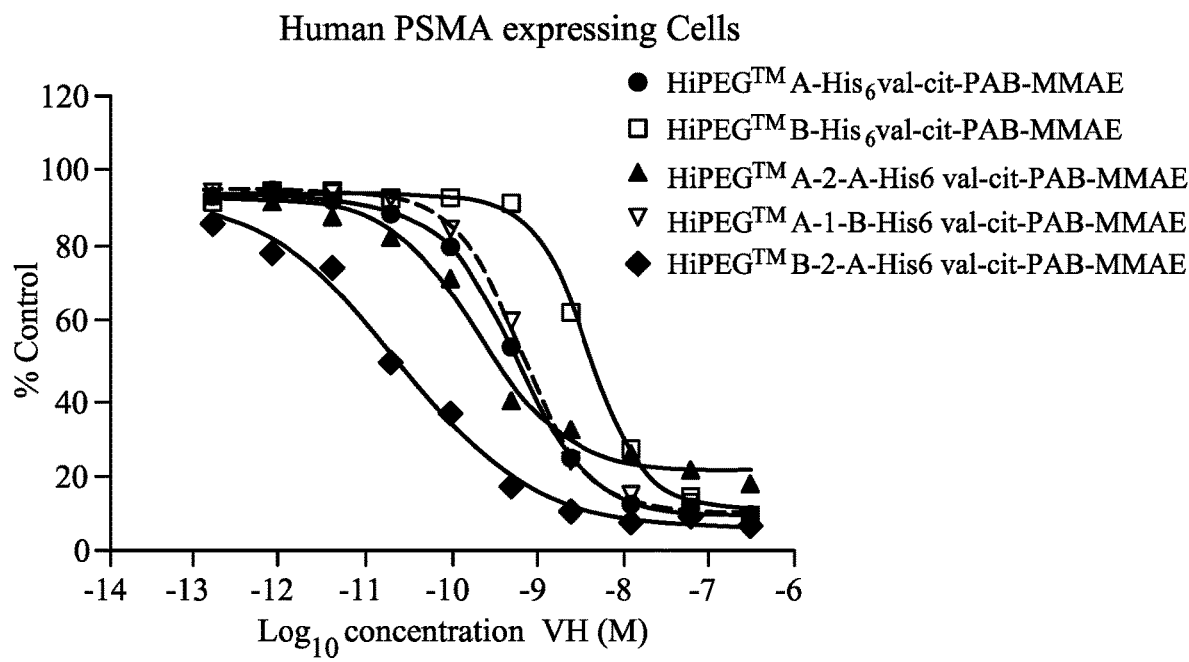

FIG. 27. shows in vitro cytotoxicity of MMAE-conjugated $V_H$ on human cells stably expressing human PSMA protein at a 72 hour incubation time point.

Figure 28:
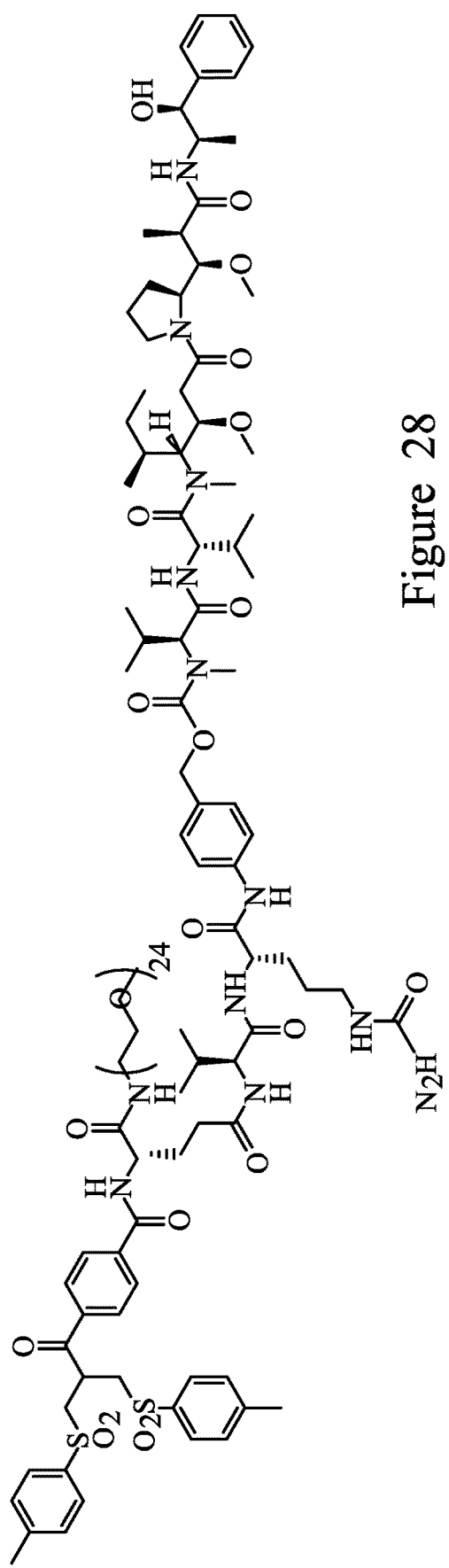

FIG. 28. shows the HiPEG™ val-cit-PAB-MMAE reagent (MW=2805 g/mol) used to prepare Humabody™ drug conjugates (HDCs).

Figure 29:
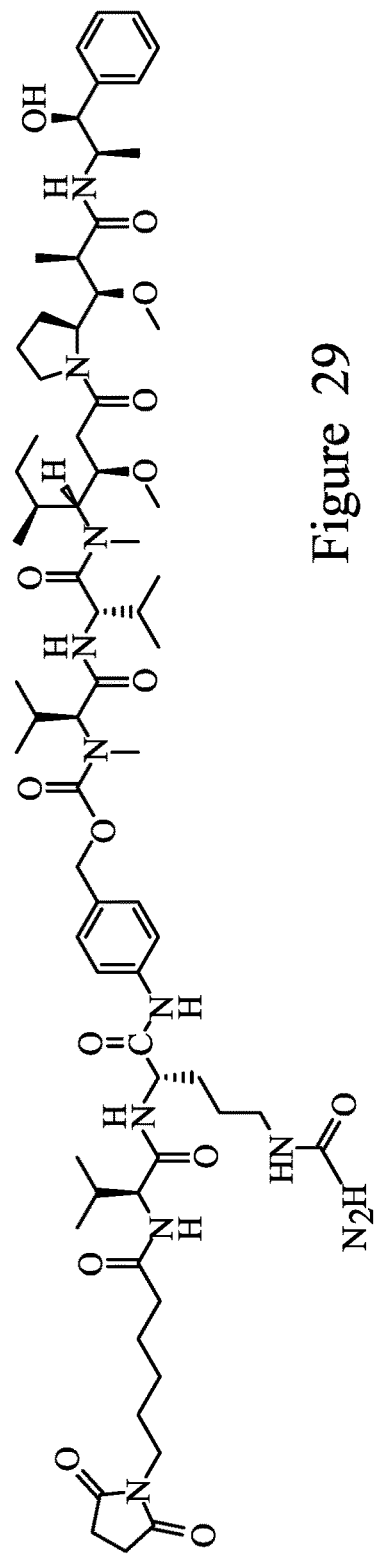

FIG. 29. shows the Maleimidocaproyl-valine-citrulline-p-aminobenzoyloxycarbonyl-monomethyl auristatin E (mc-val-cit-PAB-MMAE) conjugation reagent (MW=1317 g/mol) used to produce the Pro_006 control antibody drug conjugates (ADC).

Figure 30:
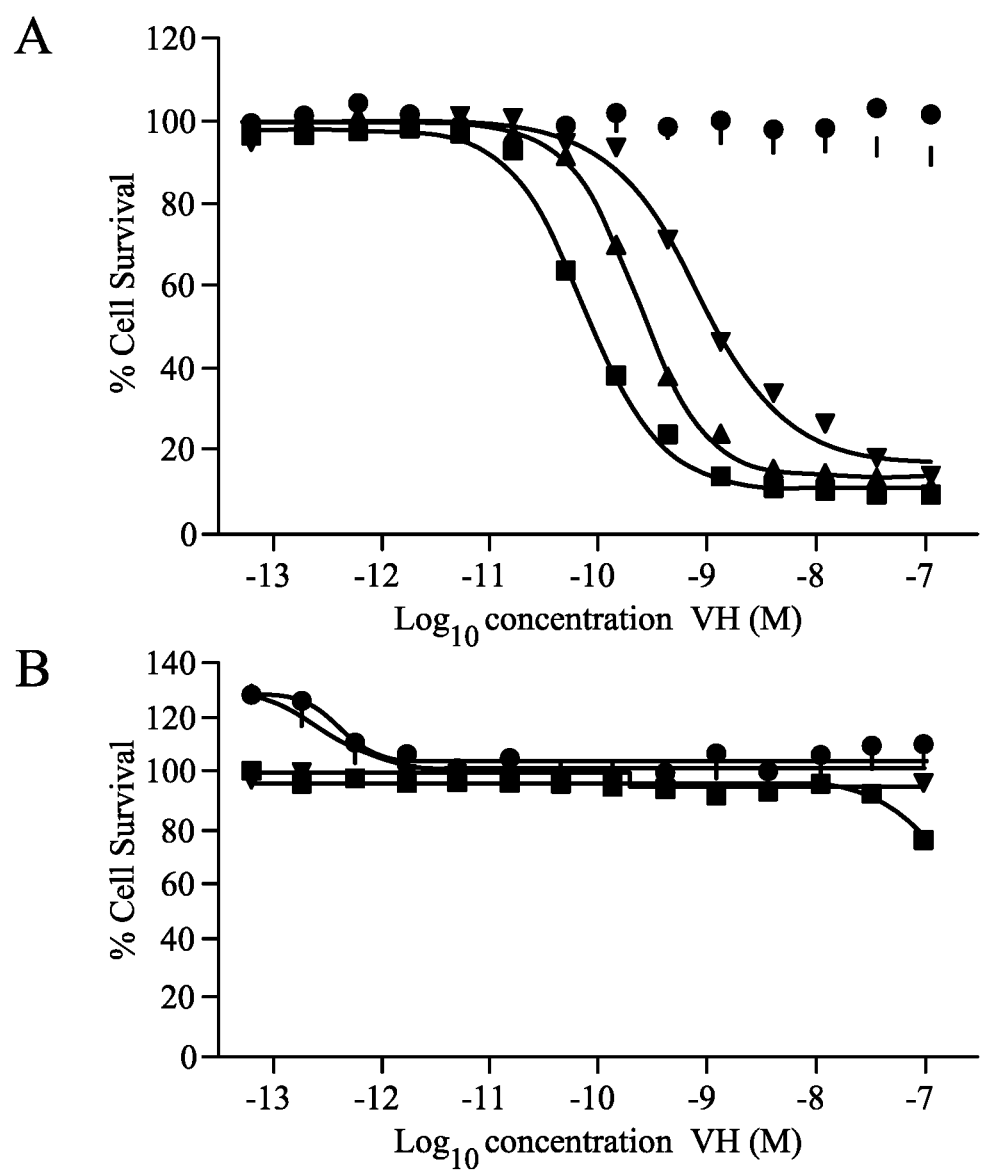

FIG. 30. A & B show $IC_{50}$ values in the PSMA-DU145 cytotoxicity assay (72 h) for: Control ADC mAb-MMAE (■), 2.1 6G4S-1.1-MMAE biparatopic (▲), 2.1 6GS-1.1-MMAE-HLE half-life extended biparatopic (▼), HEL4-MMAE Monovalent (•) and HEL4-HLE-MMAE Monovalent half-life extended (I), for (A) DU145 cells expressing PSMA and (B) DU145 parental cells that have not been modified to express PSMA.

DETAILED DESCRIPTION

The present invention will now be further described. In the following passages, different aspects of the invention are defined in more detail. Each aspect so defined may be combined with any other aspect or aspects unless clearly indicated to the contrary. In particular, any feature indicated as being preferred or advantageous may be combined with any other feature or features indicated as being preferred or advantageous.

Generally, nomenclatures used in connection with, and techniques of, cell and tissue culture, pathology, oncology, molecular biology, immunology, microbiology, genetics and protein and nucleic acid chemistry and hybridization described herein are those well-known and commonly used in the art. The methods and techniques of the present disclosure are generally performed according to conventional methods well-known in the art and as described in various general and more specific references that are cited and discussed throughout the present specification unless otherwise indicated. See, e.g., Sambrook et al., Molecular Cloning: A Laboratory Manual (2d ed., Cold Spring Harbor Laboratory Press, Cold Spring Harbor, N.Y. (1989)). Enzymatic reactions and purification techniques are performed according to manufacturer's specifications, as commonly accomplished in the art or as described herein. The nomenclatures used in connection with, and the laboratory procedures and techniques of, analytical chemistry, synthetic organic chemistry, and medicinal and pharmaceutical chemistry described herein are those well-known and commonly used in the art. Standard techniques are used for chemical syntheses, chemical analyses, pharmaceutical preparation, formulation, and delivery, and treatment of patients.

The invention provides isolated formatted binding molecules that bind to human PSMA, in particular those comprising at least two single $V_H$ domain antibodies that bind human PSMA, pharmaceutical compositions comprising such binding molecules, as well as isolated nucleic acid constructs, recombinant expression vectors and isolated host cells for making such binding proteins and fragments. Also provided are methods of using the binding proteins disclosed herein to detect human PSMA, to inhibit human PSMA either in vitro or in vivo, and methods of treating disease. One aspect of the invention provides isolated human anti-human PSMA binding molecules, specifically those comprising, or consisting of, more than one single $V_H$ domain antibody that binds to human PSMA with high affinity and a slow off rate.

The PSMA binding molecules of the invention bind to wild type human PSMA (accession NO. Q04609). The sequence for the monomer is shown below (SEQ ID No. 529).

```
  1 MWNLLHETDS AVATARRPRW LCAGALVLAG GFFLLGFLFG WFIKSSNEAT NITPKHNMKA

61 FLDELKAENI KKFLYNFTQI PHLAGTEQNF QLAKQIQSQW KEFGLDSVEL AHYDVLLSYP

121 NKTHPNYISI INEDGNEIFN TSLFEPPPPG YENVSDIVPP FSAFSPQGMP EGDLVYVNYA

181 RTEDFFKLER DMKINCSGKI VIARYGKVFR GNKVKNAQLA GAKGVILYSD PADYFAPGVK

241 SYPDGWNLPG GGVQRGNILN LNGAGDPLTP GYPANEYAYR RGIAEAVGLP SIPVHPIGY

301 DAQKLLEKMG GSAPPDSSWR GSLKVPYNVG PGFTGNFSTQ KVKMHIHSTN EVTRIYNVIG

361 TLRGAVEPDR YVILGGHRDS WVFGGIDPQS GAAVVHEIVR SFGTLKKEGW RPRRTILFAS
```

```
421 WDAEEFGLLG STEWAEENSR LLQERGVAYI NADSSIEGNY TLRVDCTPLM YSLVHNLTKE

481 LKSPDEGFEG KSLYESWTKK SPSPEFSGMP RISKLGSGND FEVFFQRLGI ASGRARYTKN

541 WETNKFSGYP LYHSVYETYE LVEKFYDPMF KYHLTVAQVR GGMVFELANS IVLPFDCRDY

601 AVVLRKYADK IYSISMKHPQ EMKTYSVSFD SLFSAVKNFT EIASKFSERL QDFDKSNPIV

661 LRMMNDQLMF LERAFIDPLG LPDRPFYRHV IYAPSSHNKY AGESFPGIYD ALFDIESKVD

721 PSKAWGEVKR QIYVAAFTVQ AAAETLSEVA
```

In one embodiment, the PSMA binding molecules of the invention bind to wild type human PSMA and/or cyno PSMA. The terms "PSMA binding molecule", "PSMA binding protein" "anti-PSMA single domain antibody" or "anti-PSMA antibody" as used herein all refer to a molecule capable of binding to the human PSMA antigen. The term "PSMA binding molecule" includes a PSMA binding protein. The binding reaction may be shown by standard methods (qualitative assays) including, for example, a binding assay, competition assay or a bioassay for determining the inhibition of PSMA binding to its receptor or any kind of binding assays, with reference to a negative control test in which an antibody of unrelated specificity. Suitable assays are shown in the examples.

An antibody or binding molecule of the invention, including a single domain antibody and multivalent or multispecific binding agent described herein, "which binds" or is "capable of binding" an antigen of interest, e.g. PSMA, is one that binds the PSMA antigen with sufficient affinity such that it is useful in therapy in targeting a cell or tissue expressing the antigen.

Binding molecules of the invention bind specifically to human PSMA. In other words, binding to the PSMA antigen is measurably different from a non-specific interaction. Preferably, the single domain antibodies used in the binding molecules of the invention bind to human PSMA and also bind to cyno PSMA. The term "specific binding" or "specifically binds to" or is "specific for" a particular polypeptide or an epitope on a particular polypeptide target as used herein can be exhibited, for example, by a molecule having a KD for the target of at least about $10^{-4}$ M, alternatively at least about $10^{-5}$ M, alternatively at least about $10^{-6}$ M, alternatively at least about $10^{-7}$ M, alternatively at least about $10^{-8}$ M, alternatively at least about $10^{-9}$ M, alternatively at least about $10^{-10}$ M, alternatively at least about $10^{-11}$ M, alternatively at least about $10^{-12}$ M, or greater. In one embodiment, the term "specific binding" refers to binding where a molecule binds to a particular polypeptide or epitope on a particular polypeptide without substantially binding to any other polypeptide or polypeptide epitope.

In one aspect, the invention relates to a binding molecule comprising a first single $V_H$ domain antibody capable of binding human PSMA and a second moiety capable of binding human PSMA. The single $V_H$ domain antibody and the second moiety are preferably covalently linked, for example via a peptide linker. The second moiety may be an antibody, a heavy chain only antibody (HCAb), a fragment thereof or an antibody mimetic.

In one aspect, the invention relates to a binding molecule comprising a first single $V_H$ domain antibody capable of binding human PSMA and a second single $V_H$ domain antibody capable of binding human PSMA. The single $V_H$ domain antibodies are preferably covalently linked, for example via a peptide linker.

In one aspect, the invention relates to a binding molecule comprising a HCAb comprising a $V_H$ domain as described herein capable of binding human PSMA and a second HCAb capable of binding human PSMA. The HCAbs are preferably covalently linked, for example via a peptide linker.

In one embodiment, the heavy chain only antibody comprises human variable regions. In one embodiment, the HCAb lacks the $C_H1$ domain. In one embodiment, the HCAb comprises murine C regions. In one embodiment, the binding molecule comprises at least one single $V_H$ domain antibody.

In one aspect, the invention relates to multivalent/multiparatopic isolated binding molecules capable of binding to human PSMA comprising a heavy chain variable immunoglobulin domain ($V_H$) comprising a CDR3 sequence as shown in any of FIGS. 1 to 15 with reference to Tables 1 to 15 or a sequence with at least 60%, 70%, 80%, 90%, 95% or more sequence identity thereto. In one embodiment, the binding molecule comprises a set of CDR1, 2 and 3 sequences selected from the sets of CDR1, 2 and 3 sequences as shown for the any of the clones of any of FIGS. 1 to 15 with reference to Tables 1 to 15. In one embodiment, the binding molecule comprises a $V_H$ domain with a set of CDR1, 2 and 3 sequences selected from the sets of CDR1, 2 and 3 sequences as shown for the any of the clones of any of FIGS. 1 to 15 with reference to Tables 1 to 15. The binding molecules of the invention comprise more than one single $V_H$ domain antibody.

The terms "single domain antibody, variable single domain or immunoglobulin single variable domain (ISV)" are all well known in the art and describe the single variable fragment of an antibody that binds to a target antigen. These terms are used interchangeably herein. As explained below, preferred embodiments of the various aspects of the invention relate to single heavy chain variable domain antibodies/ immunoglobulin heavy chain single variable domains which bind a PSMA antigen in the absence of light chain. Fragments of the single domain antibody, variable single domain or immunoglobulin single variable domain that bind to human PSMA are also within the scope of the invention. Single heavy chain variable domain antibodies ($V_H$) do not comprise an immunoglobulin light chain. Human heavy chain single variable ($V_H$) domain antibodies are particularly preferred. Human heavy chain single variable $V_H$ are commonly abbreviated as $V_H$ domains. Single $V_H$ domain antibodies are also termed Humabody® herein. Humabody® is a registered trademark of Crescendo Biologics Ltd.

Thus, in some preferred embodiments, the isolated binding agents/molecules of the invention comprise at least two single $V_H$ domain antibodies wherein said domain is preferably a human heavy chain variable domain. Thus, in one aspect, the binding agents of the invention comprise at least two human immunoglobulin single variable heavy chain domain; they are devoid of $V_L$ domains.

Each single $V_H$ domain antibody comprises three CDRs and four FRs, arranged from amino-terminus to carboxy-terminus in the following order: FR1-CDR1-FR2-CDR2-FR3-CDR3-FR4. Thus, in one embodiment of the invention, the domain is a human variable heavy chain ($V_H$) domain with the following formula FR1-CDR1-FR2-CDR2-FR3-CDR3-FR4.

The term "isolated" single domain antibody refers to a single domain antibody that is substantially free of other single domain antibodies, antibodies or antibody fragments having different antigenic specificities. Moreover, an isolated single domain antibody may be substantially free of other cellular material and/or chemicals.

In one embodiment, said first or second single $V_H$ domain antibody comprises a CDR3 sequence as shown in any of FIGS. 1 to 15 with reference to Tables 1 to 15 or a sequence with at least 60%, 70%, 80%, 90%, 95% or more sequence identity thereto. In one embodiment, said first or second single $V_H$ domain comprises a set of CDR1, 2 and 3 sequences selected from the sets of CDR1, 2 and 3 sequences as shown for the any of the clones of any of FIGS. 1 to 15 with reference to Tables 1 to 15. In one embodiment, the first or second single $V_H$ domain antibody comprises a set of CDR1, 2 and 3 sequences selected from the sets of CDR1, 2 and 3 sequences as shown for the any of the clones of any of FIGS. 1 to 15 and Tables 1 to 15. In one embodiment, the binding molecule is a heavy-chain-only antibody (HCAb).

In one embodiment, the first or second single $V_H$ domain antibody comprises a CDR3 sequence as shown in any of FIGS. 1 to 15 and Tables 1 to 15 or a sequence with at least 60%, 70%, 80%, 90%, 95% or more sequence identity thereto.

In one embodiment, the first or second single $V_H$ domain antibody comprises a set of CDRs1, 2 and 3 sequences selected from the sets of CDR1, 2 and 3 sequences as shown for any of the sdAbs of any of FIGS. 1 to 15 and 1 to 15. In another embodiment, the first or second single $V_H$ domain antibody is selected from any of the following single $V_H$ domain antibodies 1.1 to 1.20, 2.1 to 2.25, 3.1 to 3.24, 4.1 to 4.4, 5.1-5.2, 6.1 to 6.7, 7.1 to 7.8, 8.1, 9.1, 10.1, 11.1, 12.1, 13.1, 14.1 or 15.1.

In one embodiment, said sequence homology or identity is at least 60%, 61%, 62%, 63%, 64%, 65%, 66%, 67%, 68%, 69%, 70%, 71%, 72%, 73%, 74%, 75%, 76%, 77%, 78%, 79%, 80%, 81%, 82%, 83%, 84%, 85%, 86%, 87%, 88%, 89%, 90%, 91%, 92%, 93%, 94%, 95%, 96%, 97%, 98% or 99%.

"Homology" generally refers to the percentage of amino acid residues in the candidate sequence that are identical with the residues of the polypeptide with which it is compared, after aligning the sequences and in some embodiments after introducing gaps, if necessary, to achieve the maximum percent homology, and not considering any conservative substitutions as part of the sequence identity. Thus, the percent homology between two amino acid sequences is equivalent to the percent identity between the two sequences. Neither N- or C-terminal extensions, tags or insertions shall be construed as reducing identity or homology. Methods and computer programs for the alignment are well known.

The term "antibody", broadly refers to any immunoglobulin (Ig) molecule, or antigen binding portion thereof, comprised of four polypeptide chains, two heavy (H) chains and two light (L) chains, or any functional fragment, mutant, variant, or derivation thereof, which retains the essential epitope binding features of an Ig molecule. Such mutant, variant, or derivative antibody formats are known in the art. In a full-length antibody, each heavy chain is comprised of a heavy chain variable region (abbreviated herein as HCVR or $V_H$) and a heavy chain constant region. The heavy chain constant region is comprised of three domains, $C_H1$, $C_H2$ and $C_H3$. Each light chain is comprised of a light chain variable region (abbreviated herein as LCVR or $V_L$) and a light chain constant region. The light chain constant region is comprised of one domain, CL. The $V_H$ and $V_L$ regions can be further subdivided into regions of hypervariability, termed complementarity determining regions (CDR), interspersed with regions that are more conserved, termed framework regions (FR). Each $V_H$ and $V_L$ is composed of three CDRs and four FRs, arranged from amino-terminus to carboxy-terminus in the following order: FR1, CDR1, FR2, CDR2, FR3, CDR3, FR4. Immunoglobulin molecules can be of any type (e.g., IgG, IgE, IgM, IgD, IgA and IgY), class (e.g., IgG 1, IgG2, IgG 3, IgG4, IgA1 and IgA2) or subclass.

An antibody fragment is a portion of an antibody, for example as F(ab')$_2$, Fab, Fv, sFv and the like. Functional fragments of a full length antibody retain the target specificity of a full length antibody. Recombinant functional antibody fragments, such as Fab (Fragment, antibody), scFv (single chain variable chain fragments) and single domain antibodies (dAbs) have therefore been used to develop therapeutics as an alternative to therapeutics based on mAbs. scFv fragments (~25 kDa) consist of the two variable domains, $V_H$ and $V_L$. Naturally, $V_H$ and $V_L$ domain are non-covalently associated via hydrophobic interaction and tend to dissociate. However, stable fragments can be engineered by linking the domains with a hydrophilic flexible linker to create a single chain Fv (scFv). The smallest antigen binding fragment is the single variable fragment, namely the $V_H$ or $V_L$ domain. Binding to a light chain/heavy chain partner respectively is not required for target binding. Such fragments are used in single domain antibodies. A single domain antibody (~12 to 15 kDa) therefore has either the $V_H$ or $V_L$ domain.

Thus, in some preferred embodiments of the invention, the binding molecule does not comprise a light chain. In some embodiments, the binding molecule does not comprise heavy chain domains $C_H2$ and $C_H3$. In some embodiments, the binding molecule does not comprise a hinge region and heavy chain domains $C_H2$ and $C_H3$. In some embodiments, the binding molecule does not comprise heavy chain domains $C_H1$, $C_H2$, and $C_H3$. In some embodiments the binding molecule does not comprise heavy chain domain $C_H1$, a hinge region heavy chain domain $C_H2$ and heavy chain domain $C_H3$. In some embodiments the binding molecule does not comprise a light chain, a heavy chain domain $C_H1$, a hinge region heavy chain domain $C_H2$ and heavy chain domain $C_H3$.

Each $V_H$ domain comprises three CDRs and four FRs, arranged from amino-terminus to carboxy-terminus in the following order: FR1, CDR1, FR2, CDR2, FR3, CDR3, FR4. Modifications to the $V_H$ framework may be made to improve binding properties. For example, the $V_H$ domain may comprise C or N-terminal extensions. In one embodiment, the $V_H$ domain comprises C-terminal extensions of from 1 to 10, for example 1, 2, 3, 4, 5, 6, 7, 8, 9 or 10 additional amino acids. In one embodiment, the $V_H$ domain comprises C-terminal extensions of from 1 to 12 amino acid residues, for example 1, 2, 3, 4, 5, 6, 7, 8, 9 or 10 additional amino acids of the $C_H1$ domain. In one embodiment, said extension comprises at least 1 alanine residue, for example a single alanine residue, a pair of alanine residues or a triplet of alanine residues. Such extended $V_H$ domains are within the scope of the invention. Also within the scope of the invention are binding molecules that comprise $V_H$ domains that comprise additional C or N-terminal residues, for example linker residues and/or His tags, e.g., hexa-His (HHHHHH, SEQ ID No. 530) or myc tags. Additional residues of the vector may also be present, for example in addition to tags. Binding molecules used may have the additional residues LEGGGSEQKLISEED-LNHHHHHHGS (SEQ ID No. 531).

According to the various aspects and embodiments of the invention, the variable domain of the single domain antibodies is preferably a human variable domain ($V_H$). As used herein, a human $V_H$ domain includes a fully human or substantially fully human $V_H$ domain. As used herein, the term human $V_H$ domain also includes $V_H$ domains that are isolated from heavy chain only antibodies made by transgenic mice expressing fully human immunoglobulin heavy chain loci, in particular in response to an immunisation with an antigen of interest, for example as described in WO2016/062990 and in the examples. In one embodiment, a human $V_H$ domain can also include a $V_H$ domain that is derived from or based on a human $V_H$ domain amino acid or nucleic acid sequence encoding such $V_H$ domain. Thus, the term includes variable heavy chain regions derived from or encoded by human germline immunoglobulin sequences. A substantially human $V_H$ domain or $V_H$ domain that is derived from or based on a human $V_H$ domain may include amino acid residues not encoded by human germline immunoglobulin sequences (e.g., mutations introduced in vitro, e.g. by random or site-specific mutagenesis, or introduced by somatic mutation in vivo). The term "human $V_H$ domain" therefore also includes a substantially human $V_H$ domain wherein one or more amino acid residue has been modified. For example, a substantially human $V_H$ domain the $V_H$ domain may include up to 10, for example 1, 2, 3, 4 or 5 amino acid modifications compared to a fully human sequence. However, the term "human $V_H$ domain" or "substantially human $V_H$ domain", as used herein, is not intended to include antibodies in which CDR sequences derived from the germline of another mammalian species, such as a mouse, have been grafted onto human framework sequences. Preferably, the term "human $V_H$ domain", as used herein, is also not intended to include camelized $V_H$ domains, that is human $V_H$ domains that have been specifically modified, for example in vitro by conventional mutagenesis methods to select predetermined positions in the $V_H$ domains sequence and introduce one or more point mutation at the predetermined position to change one or more predetermined residue to a specific residue that can be found in a camelid $V_{HH}$ domain.

As used herein, the term $V_H$ or "variable domain" refers to immunoglobulin variable domains defined by Kabat et al., Sequences of Immunological Interest, $5^{th}$ ed., U.S. Dept. Health & Human Services, Washington, D.C. (1991). The numbering and positioning of CDR amino acid residues within the variable domains is in accordance with the well-known Kabat numbering convention.

More particularly, the invention provides a single $V_H$ domain antibody or a binding molecule single $V_H$ domain antibody wherein said single $V_H$ domain antibody binds to human PSMA with an affinity, a Kon-rate, a Koff rate, KD and/or KA, EC50 and IC50 values as further described herein, in particular in the examples. Assays suitable for measuring these values are also shown in the examples.

A binding molecule of the invention comprises or consists of an amino acid sequence and preferred sequences and/or parts thereof, such as CDRs, as defined herein.

The term "CDR" refers to the complementarity-determining region within antibody variable sequences. There are three CDRs in each of the variable regions of the heavy chain and the light chain, which are designated CDR1, CDR2 and CDR3, for each of the variable regions.

The term "CDR set" refers to a group of three CDRs that occur in a single variable region capable of binding the antigen. The exact boundaries of these CDRs have been defined differently according to different systems. The system described by Kabat is used herein. The terms "Kabat numbering", "Kabat definitions" and "Kabat labeling" are used interchangeably herein. These terms, which are recognized in the art, refer to a system of numbering amino acid residues which are more variable (i.e., hypervariable) than other amino acid residues in the heavy and light chain variable regions of an antibody, or an antigen binding portion thereof (Kabat et al., (1971) Ann. NY Acad. Sci. 190:382-391 and Kabat, et al., (1991) Sequences of Proteins of Immunological Interest, Fifth Edition, U.S. Department of Health and Human Services, NIH Publication No. 91-3242).

The binding molecule may be multivalent, for example bivalent, or multiparatopic, for example biparatopic. Thus, the binding molecule may have the following formula: $V_H(A)$-$V_H(B)$. Each $V_H$ comprises CDR and FR regions. Thus, the binding molecule may have the following formula: FR1(A)-CDR1(A)-FR2(A)-CDR2(A)-FR3(A)-CDR3(A)-FR4(A)-FR1(B)-CDR1(B)-FR2(B)-CDR2(BA)-FR3(B)-CDR3(B)-FR4(B). The order of the immunoglobulin single variable domains A (first single $V_H$ domain antibody) and B (second single $V_H$ domain antibody) is not particularly limited, so that, within a polypeptide of the invention, immunoglobulin single variable domain A may be located N-terminally and immunoglobulin single variable domain B may be located C-terminally, or vice versa. The $V_H$ domains may be connected via a linker.

In one embodiment, the binding molecule is biparatopic. In a biparatopic binding molecule, the two binding moieties bind to different epitopes on a target molecule. Preferred biparatopic binding molecules comprise two different single $V_H$ domain antibodies that bind to the target protein PSMA, but on different sites. These sites may be overlapping. Complete or partial blocking can be assessed in epitope binning studies.

The term "epitope" or "antigenic determinant" refers to a site on the surface of an antigen (e.g., PSMA) to which an immunoglobulin, antibody or antibody fragment, including a VH single domain antibody specifically binds. Generally, an antigen has several or many different epitopes and reacts with many different antibodies. The term specifically includes linear epitopes and conformational epitopes. Epitopes within protein antigens can be formed both from contiguous amino acids (usually a linear epitope) or non-contiguous amino acids juxtaposed by tertiary folding of the protein (usually a conformational epitope). Epitopes formed from contiguous amino acids are typically, but not always, retained on exposure to denaturing solvents, whereas epitopes formed by tertiary folding are typically lost on treatment with denaturing solvents. An epitope typically includes at least 3, 4, 5, 6, 7, 8, 9, 10, 11, 12, 13, 14 or 15 amino acids in a unique spatial conformation. Methods for determining what epitopes are bound by a given antibody or antibody fragment (i.e., epitope mapping) are well known in the art and include, for example, immunoblotting and immunoprecipitation assays, wherein overlapping or contiguous peptides from are tested for reactivity with a given antibody or antibody fragment. An antibody binds "essentially the same epitope" as a reference antibody, when the two antibodies recognize identical or sterically overlapping epitopes. The most widely used and rapid methods for determining whether two epitopes bind to identical or sterically overlapping epitopes are competition assays, which can be configured in different formats, using either labelled antigen or labelled antibody.

In one embodiment, the binding molecule is bivalent. Bivalent binding molecules comprise two Humabody® $V_H$ that bind to the same target protein (PSMA) at the same sites. In one embodiment, such molecules may comprise the same Humabody® $V_H$. In another embodiment, such molecules may comprise two Humabody® $V_H$ that are part of the same Humabody® $V_H$ family. In another embodiment, such molecules may comprise two Humabody® $V_H$ that are not part of the same Humabody® $V_H$ but bind to the same site. Biparatopic and bivalent binding molecules of the present invention can be constructed using methods known in the art.

As described in more detail in the experimental part, single $V_H$ domain antibodies that can be used in the multiparatopic or multivalent binding molecules of the invention were isolated and grouped into 15 families based on sequence homology in the CDR3 sequence. Through a process of optimization, a panel of variant single $V_H$ domain antibodies with a CDR sequence derived from a parent CDR sequence were also generated to improve affinities to PSMA and/or improve potencies compared to the parent molecule. Each single $V_H$ domain antibody has a set of CDR sequences (CDR1, 2 and 3) as shown in FIGS. 1 to 15. Epitope binning studies were conducted to assess epitope binding as demonstrated in example 11. For example, it was demonstrated that the single $V_H$ domain antibodies in family 1 bind to a different epitope than those in family 2. Combinations of a family 1 single $V_H$ domain antibody and a family 2 single $V_H$ domain antibody are thus one embodiment of the biparatopic binding molecule of the invention. Family 1 single $V_H$ domain antibody can be located at the C or N terminus. In a preferred embodiment, it is located at the N terminus.

In some embodiments, the first or second single $V_H$ domain antibody is a variant $V_H$ single domain antibodies of a parent molecules, in particular of a parent $V_H$ single domain antibody selected from sdAb 1.1, 2.1, 3.1, 4.1, 5.1, 6.1, 7.1, 8.1, 9.1, 10.1, 11.1, 12.1, 13.1, 14.1 or 15.1 having one or more amino acid substitutions, deletions, insertions or other modifications, and which retains a biological function of the single domain antibody. Thus, a variant $V_H$ single domain antibody can be sequence engineered. Modifications may include one or more substitution, deletion or insertion of one or more codons encoding the single domain antibody or polypeptide that results in a change in the amino acid sequence as compared with the native sequence $V_H$ single domain antibody or polypeptide. Amino acid substitutions can be the result of replacing one amino acid with another amino acid having similar structural and/or chemical properties, such as the replacement of a leucine with a serine, i.e., conservative amino acid replacements. Insertions or deletions may optionally be in the range of about 1 to 5 amino acids. The variation allowed may be determined by systematically making insertions, deletions or substitutions of amino acids in the sequence and testing the resulting variants for activity exhibited by the full-length or mature native sequence. A variant of a $V_H$ single domain antibody described herein has at least 75%, 76%, 77%, 78%, 79%, 80%, 81%, 82%, 83%, 84%, 85%, 86%, 87%, 88%, 89%, 90%, 91%, 92%, 93%, 94%, 95%, 96%, 97%, 98% or 99% sequence homology to the non-variant molecule, preferably at least 90%, 91%, 92%, 93%, 94%, 95%, 96%, 97%, 98% or 99% sequence homology.

In one embodiment, the modification is a conservative sequence modification. As used herein, the term "conservative sequence modifications" is intended to refer to amino acid modifications that do not significantly affect or alter the binding characteristics of the antibody containing the amino acid sequence. Such conservative modifications include amino acid substitutions, additions and deletions. Modifications can be introduced into binding molecule of the invention by standard techniques known in the art, such as site-directed mutagenesis and PCR-mediated mutagenesis. Conservative amino acid substitutions are ones in which the amino acid residue is replaced with an amino acid residue having a similar side chain. Families of amino acid residues having similar side chains have been defined in the art. These families include amino acids with basic side chains (e.g., lysine, arginine, histidine), acidic side chains (e.g., aspartic acid, glutamic acid), uncharged polar side chains (e.g., glycine, asparagine, glutamine, serine, threonine, tyrosine, cysteine, tryptophan), nonpolar side chains (e.g., alanine, valine, leucine, isoleucine, proline, phenylalanine, methionine), beta-branched side chains (e.g., threonine, valine, isoleucine) and aromatic side chains (e.g., tyrosine, phenylalanine, tryptophan, histidine). Thus, one or more amino acid residues within the CDR regions of a single domain antibody can be replaced with other amino acid residues from the same side chain family and the altered antibody can be tested for retained function (i.e., the functions set forth in (c) through (I) above) using the functional assays described herein.

In some embodiments, the $V_H$ single domain antibody that is a variant of a single domain antibody selected from those shown in Tables 1 to 15 that comprises one or more sequence modification and has improvements in one or more of a property such as binding affinity, specificity, thermostability, expression level, effector function, glycosylation, reduced immunogenicity, or solubility as compared to the unmodified single domain antibody.

A skilled person will know that there are different ways to identify, obtain and optimise the antigen binding molecules as described herein, including in vitro and in vivo expression libraries. This is further described in the examples. Optimisation techniques known in the art, such as display (e.g., ribosome and/or phage display) and/or mutagenesis (e.g., error-prone mutagenesis) can be used. The invention therefore also comprises sequence optimised variants of the single domain antibodies described herein.

In one embodiment, modifications can be made to decrease the immunogenicity of the single domain antibody. For example, one approach is to revert one or more framework residues to the corresponding human germline sequence. More specifically, a single domain antibody that has undergone somatic mutation may contain framework residues that differ from the germline sequence from which the single domain antibody is derived. Such residues can be identified by comparing the single domain antibody framework sequences to the germline sequences from which the single domain antibody is derived. To return one or more of the amino acid residues in the framework region sequences to their germline configuration, the somatic mutations can be "backmutated" to the germline sequence by, for example, site-directed mutagenesis or PCR-mediated mutagenesis.

Another type of framework modification involves mutating one or more residues within the framework region, or even within one or more CDR regions, to remove T cell epitopes to thereby reduce the potential immunogenicity of the antibody. In still another embodiment, the glycosylation of an antibody is modified. For example, an aglycoslated antibody can be made (i.e., the antibody lacks glycosylation). Glycosylation can be altered to, for example, increase the affinity of the antibody for antigen. Such carbohydrate modifications can be accomplished by, for example, altering one or more sites of glycosylation within the antibody sequence. For example, one or more amino acid substitutions can be made that result in elimination of one or more variable region framework glycosylation sites to thereby eliminate glycosylation at that site. Such aglycosylation may increase the affinity of the antibody for antigen.

In one aspect, the binding molecule comprises a single $V_H$ domain antibody comprising a family 1 or a family-1 like sequence. In one embodiment, two $V_H$ domains comprising a family 1 or a family-1 like sequence may be combined for a bivalent binding molecule. In another embodiment, a first $V_H$ domain comprising a family 1 or a family-1 like sequence may be combined with a second $V_H$ domain as described herein that binds to the same a epitope, part, domain, subunit or confirmation of PSMA for a bivalent binding molecule. The second $V_H$ domain may be selected from family 1, 5, 6, 12 or 13 or family 1, 5, 6, 12 or 13-like sequence. In one embodiment, the first $V_H$ domain comprises SEQ ID No:4 and the second $V_H$ domain comprises SEQ ID NO:4.

In one embodiment, a first $V_H$ domain comprising a family 1 or a family-1 like sequence may be combined with a second $V_H$ domain as described herein that binds to a different epitope, part, domain, subunit or confirmation of PSMA for a biparatopic binding molecule. The second $V_H$ domain may be selected from a family 2, 3, 4, 7, 9, 10, 11 or 14 or a family 2, 3, 4, 7, 9, 10, 11 or 14-like sequence. In one embodiment, the first $V_H$ domain comprises SEQ ID No:4 and the second $V_H$ domain comprises SEQ ID NO:84.

A single $V_H$ domain antibody of family 1 may include the sequence of the parent (1.1; SEQ ID NO. 4) or a part thereof, for example a CDR3 sequence, and sequences that are derived from the parent 1.1 through a process of optimization, for example sequences as shown as shown in FIG. 1. CDR sequences and full length $V_H$ sequences in family 1 are numbered according to Table 1 as shown below.

TABLE 1

This shows SEQ ID NOs. of family 1 CDR sequences and of family 1 full length $V_H$ sequences that are within the scope of the invention. Corresponding sequences are shown in FIG. 1. Family 1-like sequences are variants that have certain percentage sequence identity with family 1 sequences as set out herein.

| Name | CDR1 | CDR2 | CDR3 | $V_H$ Full length sequence |
|---|---|---|---|---|
| 1.1 | SEQ ID NO. 1 SYAMS | SEQ ID NO. 2 SIGENDGTTDYADSVKG | SEQ ID NO. 3 DGVH | SEQ ID NO. 4 EVQLLESGGGLVQPGGSLRLSCAASGFSFSSYAMSWVRQAPGKGLEWVSSIGENDGTTDYADSVKGRFTISRDNSKSMLYLQMNSLRVEDTAVYYCVKDGVHWGQGTLVTVSS |
| 1.2 | SEQ ID NO. 5 SYAMS | SEQ ID NO. 6 SIGDNNNSTEYADSVKG | SEQ ID NO. 7 DGVH | SEQ ID NO. 8 EVQLVESGGGLVQPGGSLRLSCAASGFTFSSYAMSWVRQAPGKGLEWVSSIGDNNNSTEYADSVKGRFTISRDNSKSTLYLQMNSLSAEDTAVYYCVKDGVHWGQGTLVTVSS |
| 1.3 | SEQ ID NO. 9 SYAMS | SEQ ID NO. 10 IGDNNNSTDYADSVKG | SEQ ID NO. 11 DGVH | SEQ ID NO. 12 EVQLVESGGGLVQPGGSLRLSCAASGFSFSSYAMSWVRQAPGKGLEWVSSIGDNNNSTDYADSVKGRFTISRDNSKSTLYLQMNSLRAEDTAVYYCVKDGVHWGQGTLVTVSS |
| 1.4 | SEQ ID NO. 13 SYAMS | SEQ ID NO. 14 IGDGTTYYADSVKG | SEQ ID NO. 15 DGVH | SEQ ID NO. 16 EVQLVESGGGLVQPGGSLRLSCAASGFTFSSYAMSWVRQAPGKGLEWVSSIGDGTTYYADSVKGRFTISRDNSKSTLYLQMNSLRAEDTAVYYCAKDGVHWGQGTLVTVSS |
| 1.5 | SEQ ID NO. 17 TYAMS | SEQ ID NO. 18 SIGENDRTTYYVDSVKG | SEQ ID NO. 19 DGVH | SEQ ID NO. 20 EVQLVESGGGLVQPGGSLRLSCAASGFTFSTYAMSWVRQAPGKGLEWVSSIGENDRTTYYVDSVKGRFTISRDNSKSTLYLQMNSLRAEDTAVYYCAKDGVHWGQGTLVTVSS |
| 1.6 | SEQ ID NO. 21 SYAMS | SEQ ID NO. 22 SIGDNNRTTYYADSVKG | SEQ ID NO. 23 DGVH | SEQ ID NO. 24 QVQLVESGGGLVQPGGSLRLSCAASGFTFSSYAMSWVRQAPGKGLEWVSSIGDNNRTTYYADSVKGRFTISRDNSKSTLYLQMNSLRAEDTAVYYCAKDGVHWGQGTLVTVSS |
| 1.7 | SEQ ID NO. 25 SYAMS | SEQ ID NO. 26 SIGDGTTYYADSVKG | SEQ ID NO. 27 DGVH | SEQ ID NO. 28 EVQLVESGGGLVQPGGSLRLSCAASGFTFSSYAMSWVRQAPGKGLEWVSSIGDGTTYYADSVKGRFTISRDNSKSTLYLQMNSLRAEDTAVYYCAKDGVHWGQGTLVTVSS |

TABLE 1-continued

This shows SEQ ID NOs. of family 1 CDR sequences and of family 1 full length $V_H$ sequences that are within the scope of the invention. Corresponding sequences are shown in FIG. 1. Family 1-like sequences are variants that have certain percentage sequence identity with family 1 sequences as set out herein.

| Name | CDR1 | CDR2 | CDR3 | $V_H$ Full length sequence |
|---|---|---|---|---|
| 1.8 | SEQ ID NO. 29 SYAMS | SEQ ID NO. 30 SIGENDGTTDYADSVKG | SEQ ID NO. 31 DGVH | SEQ ID NO. 32 EVQLLESGGGLVQPGGSLRLSCAASGFSFSSYAMSWVRQAPGKGLEWVSSIGENDGTTDYADSVKGRFTISRDNSKNTLYLQMNSLRVEDTAVYYCVKDGVHWGQGTLVTVSS |
| 1.9 | SEQ ID NO. 33 SYALS | SEQ ID NO. 34 SIGENDGTTDYADSVKG | SEQ ID NO. 35 DGVH | SEQ ID NO. 36 EVQLLESGGGLVQPGGSLRLSCAASGFSFSSYALSWVRQAPGKGLEWVSSIGENDGTTDYADSVKGRFTISRDNSKNTLYLQMNSLRVEDTAVYYCVKDGVHWGQGTLVTVSS |
| 1.10 | SEQ ID NO. 37 SYALS | SEQ ID NO. 38 SIGENNATTDYADFVKG | SEQ ID NO. 39 DGVH | SEQ ID NO. 40 EVQLLESGGGLVQPGGSLRLSCAASGFSFSSYALSWVRQAPGKGLEWVSSIGENNATTDYADFVKGRFTISRDNSKNTLYLQMNSLRVEDTAVYYCVKDGVHWGQGTLVTVSS |
| 1.11 | SEQ ID NO. 41 SYALS | SEQ ID NO. 42 SIGENNDTTDYADNVKG | SEQ ID NO. 43 DGVH | SEQ ID NO. 44 EVQLLESGGGLVQPGGSLRLSCAASGFSFSSYALSWVRQAPGKGLEWVSSIGENNDTTDYADNVKGRFTISRDNSKNTLYLQMNSLRVEDTAVYYCVKDGVHWGQGTLVTVSS |
| 1.12 | SEQ ID NO. 45 SYALS | SEQ ID NO. 46 SIGENNATTDYADAVKG | SEQ ID NO. 47 DGVH | SEQ ID NO. 48 EVQLLESGGGLVQPGGSLRLSCAASGFSFSSYALSWVRQAPGKGLEWVSSIGENNATTDYADAVKGRFTISRDNSKNTLYLQMNSLRVEDTAVYYCVKDGVHWGQGTLVTVSS |
| 1.13 | SEQ ID NO. 49 SYALS | SEQ ID NO. 50 SIGENNHTTDYAADVKG | SEQ ID NO. 51 DGVH | SEQ ID NO. 52 EVQLLESGGGLVQPGGSLRLSCAASGFSFSSYALSWVRQAPGKGLEWVSSIGENNHTTDYAADVKGRFTISRDNSKNTLYLQMNSLRVEDTAVYYCVKDGVHWGQGTLVTVSS |
| 1.14 | SEQ ID NO. 53 SYALS | SEQ ID NO. 54 SIGENNATTDYADVVKG | SEQ ID NO. 55 DGVH | SEQ ID NO. 56 EVQLLESGGGLVQPGGSLRLSCAASGFSFSSYALSWVRQAPGKGLEWVSSIGENNATTDYADVVKGRFTISRDNSKNTLYLQMNSLRVEDTAVYYCVKDGVHWGQGTLVTVSS |
| 1.15 | SEQ ID NO. 57 SYALS | SEQ ID NO. 58 SIGENNHTTDYAAFVKG | SEQ ID NO. 59 DGVH | SEQ ID NO. 60 EVQLLESGGGLVQPGGSLRLSCAASGFSFSSYALSWVRQAPGKGLEWVSSIGENNHTTDYAAFVKGRFTISRDNSKNTLYLQMNSLRVEDTAVYYCVKDGVHWGQGTLVTVSS |
| 1.16 | SEQ ID NO. 61 SYALS | SEQ ID NO. 62 SIGENNHTTDYADTVKG | SEQ ID NO. 63 DGVH | SEQ ID NO. 64 EVQLLESGGGLVQPGGSLRLSCAASGFSFSSYALSWVRQAPGKGLEWVSSIGENNHTTDYADTVKGRFTISRDNSKNTLYLQMNSLRVEDTAVYYCVKDGVHWGQGTLVTVSS |
| 1.17 | SEQ ID NO. 65 SYALS | SEQ ID NO. 66 SIGENNDTTDYADAVKG | SEQ ID NO. 67 DGVH | SEQ ID NO. 68 EVQLLESGGGLVQPGGSLRLSCAASGFSFSSYALSWVRQAPGKGLEWVSSIGENNDTTDYADAVKGRFTISRDNSKNTLYLQMNSLRVEDTAVYYCVKDGVHWGQGTLVTVSS |
| 1.18 | SEQ ID NO. 69 SYALS | SEQ ID NO. 70 SIGENNATTDYAASVKG | SEQ ID NO. 71 DGVH | SEQ ID NO. 72 EVQLLESGGGLVQPGGSLRLSCAASGFSFSSYALSWVRQAPGKGLEWVSSIGENNATTDYAASVKGRFTISRDNSKNTLYLQMNSLRVEDTAVYYCVKDGVHWGQGTLVTVSS |

TABLE 1-continued

This shows SEQ ID NOs. of family 1 CDR sequences and of family 1 full length V$_H$ sequences that are within the scope of the invention. Corresponding sequences are shown in FIG. 1. Family 1-like sequences are variants that have certain percentage sequence identity with family 1 sequences as set out herein.

| Name | CDR1 | CDR2 | CDR3 | V$_H$ Full length sequence |
|---|---|---|---|---|
| 1.19 | SEQ ID NO. 73 SYALS | SEQ ID NO. 74 SIGENNDT TDYAAYV KG | SEQ ID NO. 75 DGVH | SEQ ID NO. 76 EVQLLESGGGLVQPGGSLRLSCAASGFS FSSYALSWVRQAPGKGLEWVSSIGENND TDYAAYVKGRFTISRDNSKNTLYLQMNS LRVEDTAVYYCVKDGVHWGQGTLVTVSS |
| 1.20 | SEQ ID NO. 77 SYALS | SEQ ID NO. 78 SIGENNHT TDYAATVKG | SEQ ID NO. 79 DGVH | SEQ ID NO. 80 EVQLLESGGGLVQPGGSLRLSCAASGFS FSSYALSWVRQAPGKGLEWVSSIGENNH TDYAATVKGRFTISRDNSKNTLYLQMNS LRVEDTAVYYCVKDGVHWGQGTLVTVSS |

In one aspect, the V$_H$ domain comprises a CDR3 sequence comprising SEQ ID NO. 3 or a sequence having at least 70%, at least 80%, at least 90%, or at least 95% homology to SEQ ID NO. 3.

In one embodiment, the V$_H$ domain comprises a CDR3 sequence comprising or consisting of an amino acid sequence selected from SEQ ID NO. 3, 7, 11, 15, 19, 23, 27, 31, 35, 39, 43, 47, 51, 55, 59, 63, 67, 71, 75 or 79.

In one embodiment, the V$_H$ domain comprises hypervariable regions CDR1, CDR2 and CDR3, said CDR1 comprises the amino acid sequence SEQ ID NO. 1 or a sequence with at least 70%, at least 80%, at least 90%, or at least 95% homology thereto, said CDR2 comprising the amino acid sequence SEQ ID NO. 2 or a sequence with at least 70%, at least 80%, at least 90%, or at least 95% homology thereto, and said CDR3 comprising the amino acid sequence SEQ ID NO. 3 or a sequence with at least 70%, at least 80%, at least 90%, or at least 95% homology thereto. For example, the CDR may be a CDR selected from those shown in FIG. 1.

In one embodiment, said CDR1 comprises or consists of the amino acid sequence SEQ ID NO. 1 or a sequence with at least at least 70%, 71%, 72%, 73%, 74%, 75%, 76%, 77%, 78%, 79%, 80%, 81%, 82%, 83%, 84%, 85%, 86%, 87%, 88%, 89%, 90%, 91%, 92%, 93%, 94%, 95% 96%, 97%, 98% or 99% homology thereto. In one embodiment, said CDR2 comprises or consists of the amino acid sequence SEQ ID NO. 2 or a sequence with at least 70%, 71%, 72%, 73%, 74%, 75%, 76%, 77%, 78%, 79%, 80%, 81%, 82%, 83%, 84%, 85%, 86%, 87%, 88%, 89%, 90%, 91%, 92%, 93%, 94%, 95% 96%, 97%, 98% or 99% homology thereto. In one embodiment, said CDR3 comprises or consists of the amino acid sequence SEQ ID NO. 3 or a sequence with at least 70%, 71%, 72%, 73%, 74%, 75%, 76%, 77%, 78%, 79%, 80%, 81%, 82%, 83%, 84%, 85%, 86%, 87%, 88%, 89%, 90%, 91%, 92%, 93%, 94%, 95% 96%, 97%, 98% or 99% homology thereto.

In one embodiment, the CDR sequences of the V$_H$ domain are as shown for single V$_H$ domain antibodies 1.1 to 1.20 as in FIG. 1 or combinations thereof. In one embodiment, CDR1 comprises or consists of the amino acid sequence SEQ ID NO. 1, 5, 9, 13, 17, 21, 25, 29, 33, 37, 41, 45, 49, 53, 57, 61, 65, 69, 73 or 77, CDR2 comprises or consists of the amino acid sequence SEQ ID NO. 2, 6, 10, 14, 18, 22, 26, 30, 34, 38, 42, 46, 50, 54, 58, 62, 66, 70, 74 or 78 and CDR3 comprises or consists of the amino acid sequence SEQ ID NO. 3, 7, 11, 15, 19, 23, 27, 31, 35, 39, 43, 47, 51, 55, 59, 63, 67, 71, 75 or 79. IN one embodiment, CDR is SEQ ID NO. 33.

In one aspect, the single V$_H$ domain antibody has combinations of CDR1, CDR2 and CDR3 as shown for clones 1.1 to 1.20 in FIG. 1. Thus, in one embodiment, the single V$_H$ domain antibody comprises CDR1, 2 and 3 sequences wherein CDR1 is SEQ ID NO. 1, CDR2 is SEQ ID NO. 2 and CDR3 is SEQ ID NO. 3. In another embodiment, CDR1 is SEQ ID NO. 5, CDR2 is SEQ ID NO. 6 and CDR3 is SEQ ID NO. 7. In another embodiment, CDR1 is SEQ ID NO. 9, CDR2 is SEQ ID NO. 10 and CDR3 is SEQ ID NO. 11. In another embodiment, CDR1 is SEQ ID NO. 13, CDR2 is SEQ ID NO. 14 and CDR3 is SEQ ID NO. 15. In another embodiment, CDR1 is SEQ ID NO. 17, CDR2 is SEQ ID NO. 18 and CDR3 is SEQ ID NO. 19. In another embodiment, CDR1 is SEQ ID NO. 21, CDR2 is SEQ ID NO. 22 and CDR3 is SEQ ID NO. 23. In another embodiment, CDR1 is SEQ ID NO. 25, CDR2 is SEQ ID NO. 26 and CDR3 is SEQ ID NO. 27. In another embodiment, CDR1 is SEQ ID NO. 29, CDR2 is SEQ ID NO. 30 and CDR3 is SEQ ID NO. 31. In another embodiment, CDR1 is SEQ ID NO. 33, CDR2 is SEQ ID NO. 34 and CDR3 is SEQ ID NO. 35. In another embodiment, CDR1 is SEQ ID NO. 37, CDR2 is SEQ ID NO. 38 and CDR3 is SEQ ID NO. 39. In another embodiment, CDR1 is SEQ ID NO. 41, CDR2 is SEQ ID NO. 42 and CDR3 is SEQ ID NO. 43. In another embodiment, CDR1 is SEQ ID NO. 45, CDR2 is SEQ ID NO. 46 and CDR3 is SEQ ID NO. 47. In another embodiment, CDR1 is SEQ ID NO. 49, CDR2 is SEQ ID NO. 50 and CDR3 is SEQ ID NO. 51. In another embodiment, CDR1 is SEQ ID NO. 53, CDR2 is SEQ ID NO. 54 and CDR3 is SEQ ID NO. 55. In another embodiment, CDR1 is SEQ ID NO. 57, CDR2 is SEQ ID NO. 58 and CDR3 is SEQ ID NO. 59. In another embodiment, CDR1 is SEQ ID NO. 61, CDR2 is SEQ ID NO. 62 and CDR3 is SEQ ID NO. 63. In another embodiment, CDR1 is SEQ ID NO. 65, CDR2 is SEQ ID NO. 66 and CDR3 is SEQ ID NO. 67. In another embodiment, CDR1 is SEQ ID NO. 69, CDR2 is SEQ ID NO. 70 and CDR3 is SEQ ID NO. 71. In another embodiment, CDR1 is SEQ ID NO. 73, CDR2 is SEQ ID NO. 74 and CDR3 is SEQ ID NO. 75. In another embodiment, CDR1 is SEQ ID NO. 77, CDR2 is SEQ ID NO. 78 and CDR3 is SEQ ID NO. 79.

In one embodiment, the single $V_H$ domain antibody has a $V_H$ domain that comprises or consists of SEQ ID NO. 4 or a sequence with at least 40%, 50%, 60%, 70%, 80%, 81%, 82%, 83%, 84%, 85%, 86%, 87%, 88%, 89%, 90%, 91%, 92%, 93%, 94%, 95% 96%, 97%, 98% or 99% homology thereto. CDR sequences of such sequences are shown in FIG. 1. For example, the $V_H$ domain comprises or consists of SEQ ID NO. 4, 8, 12, 16, 20, 24, 28, 32, 36, 40, 44, 48, 52, 56, 60, 64, 68, 72 76 or 80. In another embodiment, the $V_H$ domain is selected from one of the sequences above, for example SEQ ID NO. 4, but comprises one or more amino acid substitutions, for example 1, 2, 3, 4, 5, 6, 7, 8, 9 or 10 amino acid substitutions. In one embodiment, the one or more amino acid substitution is in one or more of the framework areas. In another embodiment, the one or more amino acid substitution is in one or more of the CDRs. In one embodiment, the amino acid substitutions are in the framework and CDR sequences. In one embodiment, the $V_H$ domain comprises or consists of SEQ ID NO. 4 or a sequence which comprises one or more amino acid substitutions, for example 1, 2, 3, 4, 5, 6, 7, 8, 9 or 10 amino acid substitutions in the framework regions as compared to SEQ ID NO. 4. In one embodiment, the $V_H$ domain comprises or consists of SEQ ID NO. 32.

Thus, in one embodiment, the invention relates to a binding molecule comprising or consisting of at least one immunoglobulin single domain antibody capable of binding PSMA wherein said domain is a human $V_H$ domain and wherein said $V_H$ domain comprises or consists of SEQ ID NO. 4, 8, 12, 16, 20, 24, 28, 32, 36, 40, 44, 48, 52, 56, 60, 64, 68, 72, 76 or 80 or a sequence with at least 40%, 50%, 60%, 70%, 80%, 81%, 82%, 83%, 84%, 85%, 86%, 87%, 88%, 89%, 90%, 91%, 92%, 93%, 94%, 95%, 96%, 97%, 98% or 99% homology thereto.

In one embodiment, the single $V_H$ domain antibody comprises a $V_H$ domain as shown in SEQ ID NO. 4 or a variant thereof wherein in said variant, residue 33 is T, 36 is L, residue 57 is D, residue 59 is N, R, A, D, H, residue 63 D, Y, residue 65 is V, residue 66 is A, and/or residue 67 is F, N, A, D, V, T, S, Y.

In one embodiment, the $V_H$ domain is as shown in SEQ ID NO. 4 or a variant thereof wherein said variant includes the following changes compared to SEQ ID NO. 4
S77→N and M78→T (as shown for 1.8)
M34→L, D55→N, G56→H, D62→A, S63→T and optionally S77→N and M78→T (as shown for 1.20)
M34→L, D55→N, G56→A, S63→F and optionally S77→N and M78→T (as shown for 1.10)
M34→L, D55→N, G56→D, S63→F and optionally S77→N and M78→T (as shown for 1.11)
M34→L, D55→N, G56→A, S63→A and optionally S77→N and M78→T (as shown for 1.12)
M34→L, D55→N, G56→N, D62→A, S63→D and optionally S77→N and M78→T (as shown for 1.13)
M34→L, D55→, G56→A, S63→V and optionally S77→N and M78→T (as shown for 1.14)
M34→L, D55→N, G56→H, D62→A, S63→F and optionally S77→N and M78→T (as shown for 1.15)
M34→L, D55→N, G56→H, S63→T and optionally S77→N and M78→T (as shown for 1.16)
M34→L, D55→N, G56→H, S63→T and optionally S77→N and M78→T (as shown for 1.17)
M34→L, D55→N, G56→D, D62→A, S63→S and optionally S77→N and M78→T (as shown for 1.18)
M34→L, D55→N, G56→A, D62→A, S63→Y and optionally S77→N and M78→T (as shown for 1.19).

In one embodiment, additional changes may be included. In another embodiment, the variants listed above do not include additional changes.

The single $V_H$ domain antibody in family 1 has KD, Koff, KA, Kd, $EC_{50}$ and $IC_{50}$ values as further described herein and as shown in the examples. The term "KD" as used in this application refers to the "equilibrium dissociation constant" and refers to the value obtained in a titration measurement at equilibrium, or by dividing the dissociation rate constant (Koff) by the association rate constant (Kon). "KA" as used in this application refers to the affinity constant. The association rate constant, the dissociation rate constant and the equilibrium dissociation constant are used to represent the binding affinity of an antibody to an antigen. Methods for determining association and dissociation rate constants are well known in the art. Using fluorescence-based techniques offers high sensitivity and the ability to examine samples in physiological buffers at equilibrium. Other experimental approaches and instruments such as a BIAcore® (biomolecular interaction analysis) assay and assays described in the examples can be used to test the binding molecules of the invention.

In one aspect, the binding molecule of the invention comprises one or more human $V_H$ domain comprising a family 2 or family-2 like sequence. Thus, in one embodiment, the binding molecule comprises or consists of at least two single $V_H$ domain antibody capable of binding PSMA, preferably human PSMA, of family 2. In another embodiment, one $V_H$ domain comprising a family 2 or a family-2 like sequence may be combined with a second $V_H$ domain as described herein that binds to the same a epitope, part, domain, subunit or confirmation of PSMA for a bivalent binding molecule. The second $V_H$ domain may be selected from a family 2, 3, 4, 7, 9, 10, 11 or a family 2, 3, 4, 7, 9, 10, 11-like sequence.

In one embodiment, one $V_H$ domain comprising a family 2 or a family-2 like sequence may be combined with a second $V_H$ domain as described herein that binds to a different epitope, part, domain, subunit or confirmation of PSMA for a biparatopic binding molecule. The second $V_H$ domain may be selected from a family 1, 5, 6, 12 or 13 or a family 1, 5, 6, 12 or 13-like sequence.

The family 2 single $V_H$ domain antibody may include sequences that are derived from the parent (2.1; SEQ ID NO. 84) or a part thereof, for example a CDR3 sequence, and $V_H$ sequences or parts thereof that are derived from the parent 2.1 through a process of optimization, for example as shown in FIG. 2. CDR sequences and full length sequences of clones in family 2 are numbered according to Table 2 as shown below.

TABLE 2

This shows SEQ ID NOs of family 2 CDR sequences and of family 2 full length V$_H$ sequences that are within the scope of the invention. Corresponding sequences are shown in FIG. 2. Family 2-like sequences are variants that have certain percentage sequence identity with Family 2 sequences as set out herein.

| Name | CDR1 | CDR2 | CDR3 | V$_H$ Full length sequence |
|---|---|---|---|---|
| 2.1 | SEQ ID NO. 81 GYGMH | SEQ ID NO. 82 YISYDGSNKYYADSVKG | SEQ ID NO. 83 DPAWGLRLGESSSYDFDI | SEQ ID NO. 84 EVQLVESGGGVVQPGRSLRLSCAASGFSFSGYGMHWVRQAPGKGLEWVAYISYDGSNKYYADSVKGRFTISRDNSKNTLYLQMNSLRAEDTAVYYCAKDPAWGLRLGESSSYDFDIWGQGTMVTVSS |
| 2.2 | SEQ ID NO. 85 GYGMH | SEQ ID NO. 86 YISYDGSNKYYADSVKG | SEQ ID NO. 87 DPAWGLRLGESSSYDFDI | SEQ ID NO. 88 EVQLVESGGGVVQPGRSLRLSCAASGFSFSGYGMHWVRQAPGKGLEWVAYISYDGSNKYYADSVKGRFTISRDNSKNTLYLQMNSLRAEDTAVYYCAKDPAWGLRLGESSSYDFDIWGQGTMVTVSS |
| 2.3 | SEQ ID NO. 89 GYGMH | SEQ ID NO. 90 HISYDGSNRYYAESVKG | SEQ ID NO. 91 DPAWGLRLGELSSYDFDI | SEQ ID NO. 92 EVQLVESGGGVVQPGRSLRLSCAASGFSFSGYGMHWVRQAPGKGLEWVAHISYDGSNRYYAESVKGRFTISRENSKNTLSLQMNSLRAEDTAVYYCAKDPAWGLRLGELSSYDFDIWGQGTMVTVSS |
| 2.4 | SEQ ID NO. 93 GYGMH | SEQ ID NO. 94 VISYDGSNRYYADSVKG | SEQ ID NO. 95 DPAWGLRLGELSSYDFEI | SEQ ID NO. 96 QVTLKESGGGVVQPGRSLKLSCAASGFSFSGYGMHWVRQAPGKGLEWVAVISYDGSNRYYADSVKGRFTISRDNSKNTLSLQMNSLRAEDTAVYYCARDPAWGLRLGELSSYDFEIWGQGTMVTVSS |
| 2.5 | SEQ ID NO. 97 GYGMH | SEQ ID NO. 98 VISYDGSNRYYADSVKG | SEQ ID NO. 99 DPAWGLRLGELSSYDFEI | SEQ ID NO. 100 QVQLVESGGGVVQPGRSLRLSCAASGFSFSGYGMHWVRQAPGKGLEWVAVISYDGSNRYYADSVKGRFTISRDNSKNTLSLQMNSLRAEDTAVYYCAKDPAWGLRLGELSSYDFEIWGQGTMVTVSS |
| 2.6 | SEQ ID NO. 101 GYGMH | SEQ ID NO. 102 VISYDGSNKYYADSVKG | SEQ ID NO. 103 DPAWGLRLGELSSYKFEI | SEQ ID NO. 104 EVQLVESGGGVVQPGRSLRLSCAASGFSFSGYGMHWVRQAPGKGLEWVAVISYDGSNKYYADSVKGRFTISRDNSKNTLYLQMNSLRAEDTAVYYCAKDPAWGLRLGELSSYKFEIWGQGTMVTVSS |
| 2.7 | SEQ ID NO. 105 GYGMH | SEQ ID NO. 106 LISYDGSNKYYADSVKG | SEQ ID NO. 107 DPAWGLRLGEQSSYAFDI | SEQ ID NO. 108 EVQLVESGGGVVQPGRSLRLSCAASGFSFSGYGMHWVRQAPGKGLEWVALISYDGSNKYYADSVKGRFTISRDNSKNTLYLQMNSLRAEDTAVYYCAKDPAWGLRLGEQSSYAFDIWGQGTMVTVSS |
| 2.8 | SEQ ID NO. 109 GYGMH | SEQ ID NO. 110 VISYDGSNKYYADSVKG | SEQ ID NO. 111 DPAWGLRLGEQSSYAFE | SEQ ID NO. 112 QVQLVESGGGVVQPGRSLRLSCAASGFSFSGYGMHWVRQAPGKGLEWVSVISYDGSNKYYADSVKGRFTISRDNSKNTLYLQMNSLRTEDTAVYYCAKDPAWGLRLGEQSSYAFEIWGQGTMVTVSS |
| 2.9 | SEQ ID NO. 113 GYGMH | SEQ ID NO. 114 VISYDGSNKYYADSVKG | SEQ ID NO. 115 DPAWGLRLGEQSSYAFEI | SEQ ID NO. 116 EVQLLESGGGVVQPGRSLRLSCAASGFSFSGYGMHWVRQAPGKGLEWVAVISYDGSNKYYADSVKGRFTISRDNSKNTLYLQMNSLRVEDTAVYYCAKDPAWGLRLGEQSSYAFEIRGQGTTVTVSS |
| 2.10 | SEQ ID NO. 117 GYGMH | SEQ ID NO. 118 YISYDGSNRYYADSVKG | SEQ ID NO. 119 DPAWGLRLGESSSYDF | SEQ ID NO. 120 EVQLVESGGGVVQPGRSLRLSCAASGFTFSGYGMHWVRQAPGKGLEWVAYISYDGSNRYYADSVKGRFTISRDNSKKTLSLQMNSLRAE |

TABLE 2-continued

This shows SEQ ID NOs of family 2 CDR sequences and of family 2 full length $V_H$ sequences that are within the scope of the invention. Corresponding sequences are shown in FIG. 2. Family 2-like sequences are variants that have certain percentage sequence identity with Family 2 sequences as set out herein.

| Name | CDR1 | CDR2 | CDR3 | $V_H$ Full length sequence |
|---|---|---|---|---|
| | | GSNRY YADSV KG | DI | DTAVYYCAKDPAWGLRLGESSSYDFDIWG QGTMVTVSS |
| 2.11 | SEQ ID NO. 121 GYGLH | SEQ ID NO. 122 YISYD ESNKY YAPSV KG | SEQ ID NO. 123 DPAWGLRL GESSSYDF DI | SEQ ID NO. 124 EVQLVESGGGVVQPGRSLRLSCAASGFSFS GYGLHWVRQAPGKGLEWVAYISYDESNKY YAPSVKGRFTISRDNSKNTLYLQMNSLRAE DTAVYYCAKDPAWGLRLGESSSYDFDIWG QGTMVTVSS |
| 2.12 | SEQ ID NO. 125 GYGMH | SEQ ID NO. 126 YISYD KSNKY YADKV KG | SEQ ID NO. 127 DPAWGLRL GESSSYDF DI | SEQ ID NO. 128 EVQLVESGGGVVQPGRSLRLSCAASGFSFS GYGMHWVRQAPGKGLEWVAYISYDKSNKY YADKVKGRFTISRDNSKNTLYLQMNSLRAE DTAVYYCAKDPAWGLRLGESSSYDFDIWG QGTMVTVSS |
| 2.13 | SEQ ID NO. 129 GYGLH | SEQ ID NO. 130 YISYD ASNKY YADNV KG | SEQ ID NO. 131 DPAWGLRL GESSSYDF DI | SEQ ID NO. 132 EVQLVESGGGVVQPGRSLRLSCAASGFSFS GYGLHWVRQAPGKGLEWVAYISYDASNKY YADNVKGRFTISRDNSKNTLYLQMNSLRAE DTAVYYCAKDPAWGLRLGESSSYDFDIWG QGTMVTVSS |
| 2.14 | SEQ ID NO. 133 GYGVH | SEQ ID NO. 134 YISYD ASNKY YADNV KG | SEQ ID NO. 135 DPAWGLRL GESSSYDF DI | SEQ ID NO. 136 EVQLVESGGGVVQPGRSLRLSCAASGFSFS GYGVHWVRQAPGKGLEWVAYISYDASNKY YADNVKGRFTISRDNSKNTLYLQMNSLRAE DTAVYYCAKDPAWGLRLGESSSYDFDIWG QGTMVTVSS |
| 2.15 | SEQ ID NO. 137 GYGLH | SEQ ID NO. 138 YISYD KSNKY YADKV KG | SEQ ID NO. 139 DPAWGLRL GESSSYDF DI | SEQ ID NO. 140 EVQLVESGGGVVQPGRSLRLSCAASGFSFS GYGLHWVRQAPGKGLEWVAYISYDKSNKY YADKVKGRFTISRDNSKNTLYLQMNSLRAE DTAVYYCAKDPAWGLRLGESSSYDFDIWG QGTMVTVSS |
| 2.16 | SEQ ID NO. 141 GYGAH | SEQ ID NO. 142 YISYD KSNKY YADKV KG | SEQ ID NO. 143 DPAWGLRL GESSSYDF DI | SEQ ID NO. 144 EVQLVESGGGVVQPGRSLRLSCAASGFSFS GYGAHWVRQAPGKGLEWVAYISYDKSNKY YADKVKGRFTISRDNSKNTLYLQMNSLRAE DTAVYYCAKDPAWGLRLGESSSYDFDIWG QGTMVTVSS |
| 2.17 | SEQ ID NO. 145 GYGMH | SEQ ID NO. 146 YISYD ASNKY YADNV KG | SEQ ID NO. 147 DPAWGLRL GESSSYDF DI | SEQ ID NO. 148 EVQLVESGGGVVQPGRSLRLSCAASGFSFS GYGMHWVRQAPGKGLEWVAYISYDASNKY YADNVKGRFTISRDNSKNTLYLQMNSLRAE DTAVYYCAKDPAWGLRLGESSSYDFDIWG QGTMVTVSS |
| 2.18 | SEQ ID NO. 149 GYGQH | SEQ ID NO. 150 YISYD ASNKY YADNV KG | SEQ ID NO. 151 DPAWGLRL GESSSYDFD | SEQ ID NO. 152 EVQLVESGGGVVQPGRSLRLSCAASGFSFS GYGQHWVRQAPGKGLEWVAYISYDASNKY YADNVKGRFTISRDNSKNTLYLQMNSLRAE DTAVYYCAKDPAWGLRLGESSSYDFDIWG QGTMVTVSS |
| 2.19 | SEQ ID NO. 153 GYGFH | SEQ ID NO. 154 | SEQ ID NO. 155 DPAWGLRL | SEQ ID NO. 156 EVQLVESGGGVVQPGRSLRLSCAASGFSFS GYGFHWVRQAPGKGLEWVAYISYDASNKY |

TABLE 2-continued

This shows SEQ ID NOs of family 2 CDR sequences and of family 2 full length V$_H$ sequences that are within the scope of the invention. Corresponding sequences are shown in FIG. 2. Family 2-like sequences are variants that have certain percentage sequence identity with Family 2 sequences as set out herein.

| Name | CDR1 | CDR2 | CDR3 | V$_H$ Full length sequence |
|---|---|---|---|---|
| | | YISYD ASNKY YADNV KG | GESSSYDF DI | YADNVKGRFTISRDNSKNTLYLQMNSLRAE DTAVYYCAKDPAWGLRLGESSSYDFDIWG QGTMVTVSS |
| 2.20 | SEQ ID NO. 157 GYGMH | SEQ ID NO. 158 IISYDG SNRYY ADSVKG | SEQ ID NO. 159 DPAWGLRL GESSSYDF EI | SEQ ID NO. 160 EVQLVESGGGVVQPGRSLRLSCAASGFSFS GYGMHWVRQAPGKGLEWVAIISYDGSNRY YADSVKGRFTISRDNSKNTLSLQMNSLRAE DTAVYYCAKDPAWGLRLGESSSYDFEIWGQ GTMVTVSS |
| 2.21 | SEQ ID NO. 161 GYGMH | SEQ ID NO. 162 VISYD GSNRY YADSV KG | SEQ ID NO. 163 DPAWGLRL GKLSSYDF EI | SEQ ID NO. 164 QVQLVESGGGVVQPGRSLKLSCAASGFSFS GYGMHWVRQAPGKGLEWVAVISYDGSNRY YADSVKGRFTISRDNSKNTLSLQMNSLRAE DTAVYYCAKDPAWGLRLGKLSSYDFEIWGQ GTMVTVSS |
| 2.22 | SEQ ID NO. 165 GYGTH | SEQ ID NO. 166 YISYD GSNKY YAAPV KG | SEQ ID NO. 167 DAAWGLRL GESSSYDF DI | SEQ ID NO. 168 EVQLVESGGGVVQPGRSLRLSCAASGFSFS GYGTHWVRQAPGKGLEWVAYISYDGSNKY YAAPVKGRFTISRDNSKNTLYLQMNSLRAE DTAVYYCAKDAAWGLRLGESSSYDFDIWG QGTMVTVSS |
| 2.23 | SEQ ID NO. 169 GYGTH | SEQ ID NO. 170 YISYD ESNKY YASSV KG | SEQ ID NO. 171 DRAWGLRL GESSSYDF DI | SEQ ID NO. 172 EVQLVESGGGVVQPGRSLRLSCAASGFSFS GYGTHWVRQAPGKGLEWVAYISYDESNKY YASSVKGRFTISRDNSKNTLYLQMNSLRAE DTAVYYCAKDRAWGLRLGESSSYDFDIWG QGTMVTVSS |
| 2.24 | SEQ ID NO. 173 GYGMH | SEQ ID NO. 174 YISYD ESNKY YARLV KG | SEQ ID NO. 175 DTAWGLRL GESSSYDF DI | SEQ ID NO. 176 EVQLVESGGGVVQPGRSLRLSCAASGFSFS GYGMHWVRQAPGKGLEWVAYISYDESNKY YARLVKGRFTISRDNSKNTLYLQMNSLRAED TAVYYCAKDTAWGLRLGESSSYDFDIWGQ GTMVTVSS |
| 2.25 | SEQ ID NO. 177 GYGLH | SEQ ID NO. 178 YISYDL SNKYY ARGVKG | SEQ ID NO. 179 DVAWGLRL GESSSYDF DI | SEQ ID NO. 180 EVQLVESGGGVVQPGRSLRLSCAASGFSFS GYGLHWVRQAPGKGLEWVAYISYDLSNKY YARGVKGRFTISRDNSKNTLYLQMNSLRAE DTAVYYCAKDVAWGLRLGESSSYDFDIWG QGTMVTVSS |

In one aspect, the V$_H$ domain comprising a CDR3 sequence comprising SEQ ID NO. 83 or a sequence having at least 70%, at least 80%, at least 90%, or at least 95% homology to SEQ ID NO. 83. In one embodiment, the V$_H$ domain comprises a CDR3 selected from SEQ ID NO. 83, 87, 91, 95, 99, 103, 107, 111, 115, 119, 123, 127, 131, 135, 139, 143, 147, 151, 155, 159, 163, 167, 171, 175 or 179.

In one embodiment, the V$_H$ domain comprises at least one antigen binding site comprising CDR3 said CDR3 having the amino acid sequence SEQ ID NO. 75 or a sequence having at least 70%, at least 80%, at least 90%, or at least 95% homology thereto. In one embodiment, the family 2 family 2-like sequence comprises a binding molecule comprising or consisting of at least one immunoglobulin single domain antibody capable of binding PSMA wherein said domain is a human V$_H$ domain comprising hypervariable regions CDR1, CDR2 and CDR3, said CDR1 comprises or consists of the amino acid sequence SEQ ID NO. 81 or a sequence with at least 70%, at least 80%, at least 90%, or at least 95% homology thereto, said CDR2 comprises or consists of the amino acid sequence SEQ ID NO. 82 or a sequence with at least 70%, at least 80%, at least 90%, or at least 95% homology thereto, and said CDR3 comprises or consists of the amino acid sequence SEQ ID NO. 83 or a sequence with at least 70%, at least 80%, at least 90%, or at least 95% homology thereto.

In one embodiment, said CDR1 comprises or consists of the amino acid sequence SEQ ID NO. 81 or a sequence with at least 70%, 71%, 72%, 73%, 74%, 75%, 76%, 77%, 78%, 79%, 80%, 81%, 82%, 83%, 84%, 85%, 86%, 87%, 88%, 89%, 90%, 91%, 92%, 93%, 94%, 95% 96%, 97%, 98% or 99% homology thereto. In one embodiment, said CDR2 comprises or consists of the amino acid sequence SEQ ID NO. 82 or a sequence with at least 70%, 71%, 72%, 73%, 74%, 75%, 76%, 77%, 78%, 79%, 80%, 81%, 82%, 83%, 84%, 85%, 86%, 87%, 88%, 89%, 90%, 91%, 92%, 93%, 94%, 95% 96%, 97%, 98% or 99% homology thereto. In one embodiment, said CDR3 comprises or consists of the amino acid sequence SEQ ID NO. 83 or a sequence with at least 70%, 71%, 72%, 73%, 74%, 75%, 76%, 77%, 78%, 79%, 80%, 81%, 82%, 83%, 84%, 85%, 86%, 87%, 88%, 89%, 90%, 91%, 92%, 93%, 94%, 95% 96%, 97%, 98% or 99% homology thereto.

In one embodiment, the CDR sequences of the $V_H$ domain are as shown for sdAbs 2.1 to 2.25 as in FIG. 2 or combinations thereof. In one embodiment, CDR1 comprises or consists of the amino acid sequence SEQ ID NO. 81, 85, 89, 93, 97, 101, 105, 109, 113, 117, 121, 125, 129, 133, 137, 141, 145, 149, 153, 157, 161, 165, 169, 173 or 177, CDR2 comprises or consists of the amino acid sequence SEQ ID NO. 82, 86, 90, 94, 98, 102, 106, 110, 114, 118, 122, 126, 130, 134, 138, 142, 146, 150, 154, 158, 162, 166, 170, 174 or 178 and CDR3 comprises or consists of the amino acid sequence SEQ ID NO. SEQ ID NO. 783, 87, 91, 95, 99, 103, 107, 111, 115, 119, 123, 127, 131, 135, 139, 143, 147, 151, 155, 159, 163, 167, 171, 175 or 179.

In one aspect, the single $V_H$ domain antibody has combinations of CDR1, CDR2 and CDR3 as shown for 2.1 to 2.25 in FIG. 2. In another embodiment, CDR1 is SEQ ID NO. 81, CDR2 is SEQ ID NO. 82 and CDR3 is SEQ ID NO. 83. In another embodiment, CDR1 is SEQ ID NO. 85, CDR2 is SEQ ID NO. 86 and CDR3 is SEQ ID NO. 87. In another embodiment, CDR1 is SEQ ID NO. 89, CDR2 is SEQ ID NO. 90 and CDR3 is SEQ ID NO. 91. In another embodiment, CDR1 is SEQ ID NO. 93, CDR2 is SEQ ID NO. 94 and CDR3 is SEQ ID NO. 95. In another embodiment, CDR1 is SEQ ID NO. 97, CDR2 is SEQ ID NO. 98 and CDR3 is SEQ ID NO. 99. In another embodiment, CDR1 is SEQ ID NO. 101, CDR2 is SEQ ID NO. 102 and CDR3 is SEQ ID NO. 103. In another embodiment, CDR1 is SEQ ID NO. 104, CDR2 is SEQ ID NO. 105 and CDR3 is SEQ ID NO. 106. In another embodiment, CDR1 is SEQ ID NO. 108, CDR2 is SEQ ID NO. 109 and CDR3 is SEQ ID NO. 110. In another embodiment, CDR1 is SEQ ID NO. 112, CDR2 is SEQ ID NO. 113 and CDR3 is SEQ ID NO. 115. In another embodiment, CDR1 is SEQ ID NO. 117, CDR2 is SEQ ID NO. 118 and CDR3 is SEQ ID NO. 119. In another embodiment, CDR1 is SEQ ID NO. 121, CDR2 is SEQ ID NO. 122 and CDR3 is SEQ ID NO. 123. In another embodiment, CDR1 is SEQ ID NO. 125, CDR2 is SEQ ID NO. 127 and CDR3 is SEQ ID NO. 127. In another embodiment, CDR1 is SEQ ID NO. 129, CDR2 is SEQ ID NO. 130 and CDR3 is SEQ ID NO. 131. In another embodiment, CDR1 is SEQ ID NO. 133, CDR2 is SEQ ID NO. 134 and CDR3 is SEQ ID NO. 135. In another embodiment, CDR1 is SEQ ID NO. 137, CDR2 is SEQ ID NO. 138 and CDR3 is SEQ ID NO. 139. In another embodiment, CDR1 is SEQ ID NO. 140, CDR2 is SEQ ID NO. 141 and CDR3 is SEQ ID NO. 142. In another embodiment, CDR1 is SEQ ID NO. 144, CDR2 is SEQ ID NO. 145 and CDR3 is SEQ ID NO. 146. In another embodiment, CDR1 is SEQ ID NO. 148, CDR2 is SEQ ID NO. 149 and CDR3 is SEQ ID NO. 150. In another embodiment, CDR1 is SEQ ID NO. 152, CDR2 is SEQ ID NO. 153 and CDR3 is SEQ ID NO. 154. In another embodiment, CDR1 is SEQ ID NO. 157, CDR2 is SEQ ID NO. 158 and CDR3 is SEQ ID NO. 159. In another embodiment, CDR1 is SEQ ID NO. 161, CDR2 is SEQ ID NO. 162 and CDR3 is SEQ ID NO. 163. In another embodiment, CDR1 is SEQ ID NO. 165, CDR2 is SEQ ID NO. 166 and CDR3 is SEQ ID NO. 167. In another embodiment CDR1 is SEQ ID NO. 169, CDR2 is SEQ ID NO. 170 and CDR3 is SEQ ID NO. 171. In another embodiment, CDR1 is SEQ ID NO. 173, CDR2 is SEQ ID NO. 174 and CDR3 is SEQ ID NO. 175. In another embodiment, CDR1 is SEQ ID NO. 177, CDR2 is SEQ ID NO. 178 and CDR3 is SEQ ID NO. 179.

In one embodiment, the single $V_H$ domain antibody comprises or consists of SEQ ID NO. 84 or a sequence with at least 40%, 50%, 60%, 70%, 80%, 81%, 82%, 83%, 84%, 85%, 86%, 87%, 88%, 89%, 90%, 91%, 92%, 93%, 94%, 95% 96%, 97%, 98% or 99% homology thereto. In one embodiment, homology is at least 70%, 80%, 81%, 82%, 83%, 84%, 85%, 86%, 87%, 88%, 89%, 90%, 91%, 92%, 93%, 94%, 95%, 96%, 97%, 98% or 99%. CDR sequences of such sequences are shown in FIG. 2. For example, the single $V_H$ domain antibody comprises or consists of SEQ ID NO. 84, 88, 92, 96, 100, 104, 108, 112, 116, 120, 124, 128, 132, 136, 140, 144, 148, 152, 156, 160, 164, 168, 172, 176 or 180.

In another embodiment, the $V_H$ domain is selected from one of the sequences above, for example SEQ ID NO. 84, but comprises one or more amino acid substitutions, for example 1, 2, 3, 4, 5, 6, 7, 8, 9 or 10 amino acid substitutions. In one embodiment, the one or more amino acid substitution is in one or more of the framework areas. In another embodiment, the one or more amino acid substitution is in one or more of the CDRs. In one embodiment, the amino acid substitutions are in the framework and CDR sequences.

In one embodiment, the single $V_H$ domain antibody comprises SEQ ID NO. 84 or a variant thereof wherein the variant has the following amino acid substitutions compared to SEQ ID NO. 76: residue 34 is L, V, M, Q, T, F, residue 50 is H, V, L, I, residue 55 is E, K, A, L, residue 58 is R, residue 62 is E, P, R, S, A, residue 63 is E, residue 64 is N, K, P, L, G, S, residue 79 is K, residue is L, Q, residue 84 is K, A, residue is D.

In one embodiment, the single $V_H$ domain antibody comprises or consists of a $V_H$ as shown in SEQ ID NO. 4 or a variant thereof wherein said variant includes the following changes compared to SEQ ID NO. 84:
1) M34→L34, G55→A55 and S63→N63 (as shown for 2.13),
2) G55→A55, G55→A55 and S63→N63 (as shown for 2.17),
3) M34→L34, G55→K55 and S63→K63 (as shown for 2.15),
4) G55→K55, and S63→K63 (as shown for 2.15) or
5) M34→L34, G55→E55 and D62→S62 (as shown for 2.11).

In one embodiment, additional changes may be included. In another embodiment, the variants listed above do not include additional changes. In one embodiment, the variant does not include a combination of the following changes: G55→A55, S63→N63, D99→N99 together with P100→T100; G34→L34, G55→K55 together with S63→K63; G55→T55, S63→R63, D99→G99 together with P100→R100.

The family 2 or family 2-like binding molecules have KD, Koff, KA, Kd, $EC_{50}$ and $IC_{50}$ values as further described herein and as shown in the examples.

In one aspect, the binding molecule capable of binding human PSMA comprises a human $V_H$ domain comprising a family 3 or family-3 like sequence.

In one embodiment, two $V_H$ domains comprising a family 3 or a family-3 like sequence may be combined for a bivalent binding molecule. In another embodiment, one $V_H$ domain comprising a family 3 or a family-3 like sequence may be combined with a second $V_H$ domain as described herein that binds to the same a epitope, part, domain, subunit or confirmation of PSMA for a bivalent binding molecule. The second $V_H$ domain may be selected from a family 2, 3, 4, 7, 9, 10, 11 or a family 2, 3, 4, 7, 9, 10, 11-like sequence.

In one embodiment, one $V_H$ domain comprising a family 3 or a family-3 like sequence may be combined with a second $V_H$ domain as described herein that binds to a different epitope, part, domain, subunit or confirmation of PSMA for a biparatopic binding molecule. The second $V_H$ domain may be selected from a family 1, 5, 6, 12 or 13 or a family 1, 5, 6, 12 or 13-like sequence.

A family 3 or family 3-like single $V_H$ domain antibody includes the parent sequence and sequences of that are derived from the parent (3.1; SEQ ID NO. 184) or a part thereof, for example a CDR3 sequence, and $V_H$ sequences or parts thereof that are derived from the parent 3.1 through a process of optimization, for example as shown in FIG. 3. CDR sequences and full-length sequences of clones in family 3 are numbered according to Table 3 as shown below.

TABLE 3

This shows SEQ ID NOs of family 3 CDR sequences and of family 3 full-length $V_H$ sequences that are within the scope of the invention. Corresponding sequences are shown in FIG. 3. Family 3-like sequences are variants that have certain percentage sequence identity with Family 3 sequences as set out herein.

| Name | CDR1 | CDR2 | CDR3 | $V_H$ Full length sequence |
|---|---|---|---|---|
| 3.1 | SEQ ID NO. 181 SYGMH | SEQ ID NO. 182 FMTYDGSNRYADSVKG | SEQ ID NO. 183 DRIVGGRVPDAFDI | SEQ ID NO. 184 EVQLVESGGGVVQPGRSLRLSCAASGFPLISYGMHWVRQAPGKGLEWVAFMTYDGSNRYYADSVKGRFTISRDNSKNTLYLQMNSLRDEDTALYYCARDRIVGGRVPDAFDIWGQGTMVTVSS |
| 3.2 | SEQ ID NO. 185 SYGMN | SEQ ID NO. 186 FISYDGSNKYYADSVKG | SEQ ID NO. 187 DRIVGARVPDAFDI | SEQ ID NO. 188 EVQLVESGGGVVQPGRSLRLSCAASGFPLISYGMNWVRQAPGKGLDWVAFISYDGSNKYYADSVKGRFTISKDNSKNTLYLQMNSLRAEDTAVYYCAKDRIVGARVPDAFDIWGQGTMVTVSS |
| 3.3 | SEQ ID NO. 189 SYGMN | SEQ ID NO. 190 FISYDGSNRYYADSVKG | SEQ ID NO. 191 DRIVGARVPDAFDI | SEQ ID NO. 192 EVQLVESGGGVVQPGRSLRLSCAASGFPLISYGMNWVRQAPGKGLEWVAFISYDGSNRYYADSVKGRFTISRDNSKNTLYLQMNSLRAEDTAVYYCAKDRIVGARVPDAFDIWGQGTMVTVSS |
| 3.4 | SEQ ID NO. 193 SYGMN | SEQ ID NO. 194 FITYDGSNRYYADSVKG | SEQ ID NO. 195 DRIVGARVPDAYDI | SEQ ID NO. 196 EVQLVESGGGAVQPGRSLRLSCAASGFPLISYGMNWVRQAPGKGLDWVAFITYDGSNRYYADSVKGRFTISRDNSKNTLYLQMNSLRPEDTAVYYCAKDRIVGARVPDAYDIWGQGTMVTVSS |
| 3.5 | SEQ ID NO. 197 SYGMN | SEQ ID NO. 198 FITYDGSNRYYADSVKG | SEQ ID NO. 199 DRIVGARVPDAYDI | SEQ ID NO. 200 QVQLVESGGGVVQPGRSLRLSCAASGFPLISYGMNWVRQAPGKGLDWVAFITYDGSNRYYADSVKGRFTISRDNSKNTLYLQMNSLRPEDTAVYYCAKDRIVGARVPDAYDIWGQGTMVTVSS |
| 3.6 | SEQ ID NO. 201 SYGMN | SEQ ID NO. 202 FITYDGSNRYYADSVKG | SEQ ID NO. 203 DRIVGARVPDAYDI | SEQ ID NO. 204 EVQLLESGGGVVQPGRSLRLSCAASGFPLISYGMNWVRQAPGKGLDWVAFITYDGSNRYYADSVKGRFTISRDNSKNTLYLQMNSLRPEDTAVYYCAKDRIVGARVPDAYDIWGQGTMVTVSS |
| 3.7 | SEQ ID NO. 205 SYGMN | SEQ ID NO. 206 FITYDGSNRYYADSVKG | SEQ ID NO. 207 DRIVGARVPDAYDI | SEQ ID NO. 208 QVQLVESGGGLVQPGGSLRLSCAASGFPLISYGMNWVRQAPGKGLDWVAFITYDGSNRYYADSVKGRFTISRDNSKNTLHLQMDSLRPEDTAVYYCAKDRIVGARVPDAYDIWGQGTMVTVSS |

TABLE 3-continued

This shows SEQ ID NOs of family 3 CDR sequences and of family 3 full-length V$_H$ sequences that are within the scope of the invention. Corresponding sequences are shown in FIG. 3. Family 3-like sequences are variants that have certain percentage sequence identity with Family 3 sequences as set out herein.

| Name | CDR1 | CDR2 | CDR3 | V$_H$ Full length sequence |
|---|---|---|---|---|
| 3.8 | SEQ ID NO. 209 SYGMN | SEQ ID NO. 210 FITYD GSNRY YADSV KG | SEQ ID NO. 211 DRIVGARV PDAYDI | SEQ ID NO. 212 EVQLVESGGGVVQPGRSLRLSCAASGFPLI SYGMNWVRQAPGKGLDWVAFITYDGSNRY YADSVKGRFTISRDNSKNTLYLQMNSLRPE DTAVYYCAKDRIVGARVPDAYDIWGQGTLV TVSS |
| 3.9 | SEQ ID NO. 213 SYGMN | SEQ ID NO. 214 FISYD GSNRY YADSV KG | SEQ ID NO. 215 DRIVGARV PDAYDI | SEQ ID NO. 216 QVQLVESGGGVVQPGRSLRLSCAASGFPLI SYGMNWVRQAPGKGLEWVAFISYDGSNRY YADSVKGRFTISRDNSKNTLYLQMNSLRPE DTAVYYCAKDRIVGARVPDAYDIWGQGTMV TVSS |
| 3.10 | SEQ ID NO. 217 SYGMN | SEQ ID NO. 218 FITYD GSNRY YADSV KG | SEQ ID NO. 219 DRIVGARV PDAYDI | SEQ ID NO. 220 QVQLVESGGGVVQPGRSLRLSCAASGFPLI SYGMNWVRQAPGKGLDWVAFITYDGSNRY YADSVKGRFTISRDNSKNTLHLQMNSLRPE DTAVYYCAKDRIVGARVPDAYDIWGQGTMV TVSS |
| 3.11 | SEQ ID NO. 221 SYGMN | SEQ ID NO. 222 FITYD GSNRY YADSV KG | SEQ ID NO. 223 DRIVGARV PDAYDI | SEQ ID NO. 224 EVQLVESGGGVVQPGRSLRLSCAASGFPLI SYGMNWVRQAPGKGLDWVAFITYDGSNRY YADSVKGRFTISRDNSKNTLHLQMNSLRPE DTAVYYCAKDRIVGARVPDAYDIWGQGTMV TVSS |
| 3.12 | SEQ ID NO. 225 SYGMN | SEQ ID NO. 226 FITYD GSNRY YADSV KG | SEQ ID NO. 227 DRIVGARV PDAYDI | SEQ ID NO. 228 EVQLVESGGGVVQPGRSLRLSCAASGFPLI SYGMNWVRQAPGKGLDWVAFITYDGSNRY YADSVKGRFTISRDNSKNTLYLQMNSLRPE DTAVYYCAKDRIVGARVPDAYDIWGQGTMV TVSS |
| 3.13 | SEQ ID NO. 229 SYGMN | SEQ ID NO. 230 FITYD GSNRY YADSV KG | SEQ ID NO. 231 DRIVGARV PDAYDI | SEQ ID NO. 232 QVQLVESGGGVVQPGRSLRLSCAASGFPLI SYGMNWVRQAPGKGLDWVAFITYDGSNRY YADSVKGRFTISRDNSKNTLYLQMNSLRPE DTAVYYCAKDRIVGARVPDAYDIWGQGTMV TVSS |
| 3.14 | SEQ ID NO. 233 SYGMN | SEQ ID NO. 234 FITYD GSNRY YADSV KG | SEQ ID NO. 235 DRIVGARV PDAYDI | SEQ ID NO. 236 EVQLVESGGGVVRPGGSLRLSCAASGFPLI SYGMNWVRQAPGKGLDWVAFITYDGSNRY YADSVKGRFTISRDNSKNTLHLQMNSLRPE DTAVYYCAKDRIVGARVPDAYDIWGQGTMV TVSS |
| 3.15 | SEQ ID NO. 237 SYGMN | SEQ ID NO. 238 FITYD GSNRY YADSV KG | SEQ ID NO. 239 DRIVGARV PDAYDI | SEQ ID NO. 240 EVQLVESGGGLVQPGGSLRLSCAASGFPLI SYGMNWVRQAPGKGLDWVAFITYDGSNRY YADSVKGRFTISRDNSKNTLHLQMNSLRPE DTAVYYCAKDRIVGARVPDAYDIWGQGTMV TVSS |
| 3.16 | SEQ ID NO. 241 SYGMN | SEQ ID NO. 242 FITYD GSNRY YADSV KG | SEQ ID NO. 243 DRIVGARV PDAYDI | SEQ ID NO. 244 EVQLLESGGGVVQPGRSLRLSCAASGFPLI SYGMNWVRQAPGKGLDWVAFITYDGSNRY YADSVKGRFTISRDNSKNTLHLQMNSLRPE DTAVYYCAKDRIVGARVPDAYDIWGQGTMV TVSS |

TABLE 3-continued

This shows SEQ ID NOs of family 3 CDR sequences and of family 3 full-length V$_H$ sequences that are within the scope of the invention. Corresponding sequences are shown in FIG. 3. Family 3-like sequences are variants that have certain percentage sequence identity with Family 3 sequences as set out herein.

| Name | CDR1 | CDR2 | CDR3 | V$_H$ Full length sequence |
|---|---|---|---|---|
| 3.17 | SEQ ID NO. 245 SYGMN | SEQ ID NO. 246 FITYD GSNRY YADSV KG | SEQ ID NO. 247 DRIVGARV PDAYDI | SEQ ID NO. 248 EVQLLESGGGVVQPGRSLRLSCAASGFPLI SYGMNWVRQAPGKGLDWVAFITYDGSNRY YADSVKGRFTISRDNSKNTLYLQMNSLKPE DTAVYYCAKDRIVGARVPDAYDIWGQGTMV TVSS |
| 3.18 | SEQ ID NO. 249 SYGMN | SEQ ID NO. 250 FITYD GSNRY YADSV KG | SEQ ID NO. 251 DRIVGARV PDAYDI | SEQ ID NO. 252 EVQLVESGGGVVQPGRSLRLSCAASGFPLI SYGMNWVRQAPGKGLDWVAFITYDGSNRY YADSVKGRFTISRDNSKNTLYLQMNSLKPE DTAVYYCAKDRIVGARVPDAYDIWGQGTMV TVSS |
| 3.19 | SEQ ID NO. 253 SYGMH | SEQ ID NO. 254 FMTYD GSNRY YADAV KG | SEQ ID NO. 255 DRIVGGRV PDAFDI | SEQ ID NO. 256 QVQLVESGGGVVQPGRSLRLSCAASGFPLI SYGMHWVRQAPGKGLEWVAFMTYDGSNR YYADAVKGRFTISRDNSKNTLYLQMNSLRA EDTAVYYCARDRIVGGRVPDAFDIWGQGTM VTVSS |
| 3.20 | SEQ ID NO. 257 SYGMH | SEQ ID NO. 258 FQTYD GSNRY YADAV KG | SEQ ID NO. 259 DRIVGGRV PDAFDI | SEQ ID NO. 260 QVQLVESGGGVVQPGRSLRLSCAASGFPLI SYGMHWVRQAPGKGLEWVAFQTYDGSNR YYADAVKGRFTISRDNSKNTLYLQMNSLRA EDTAVYYCARDRIVGGRVPDAFDIWGQGTM VTVSS |
| 3.21 | SEQ ID NO. 261 SYGMH | SEQ ID NO. 262 FQTYD GSNRY YADSV KG | SEQ ID NO. 263 DRIVGGRV PDAFDI | SEQ ID NO. 264 QVQLVESGGGVVQPGRSLRLSCAASGFPLI SYGMHWVRQAPGKGLEWVAFQTYDGSNR YYADSVKGRFTISRDNSKNTLYLQMNSLRA EDTAVYYCARDRIVGGRVPDAFDIWGQGTM VTVSS |
| 3.22 | SEQ ID NO. 265 SYGMH | SEQ ID NO. 266 FQTYD ASNRY YADSV KG | SEQ ID NO. 267 DRIVGGRV PDAFDI | SEQ ID NO. 268 QVQLVESGGGVVQPGRSLRLSCAASGFPLI SYGMHWVRQAPGKGLEWVAFQTYDASNR YYADSVKGRFTISRDNSKNTLYLQMNSLRA EDTAVYYCARDRIVGGRVPDAFDIWGQGTM VTVSS |
| 3.23 | SEQ ID NO. 269 SYGMH | SEQ ID NO. 270 FQTYD ASNRY YADAV KG | SEQ ID NO. 271 DRIVGGRV PDAFDI | SEQ ID NO. 272 QVQLVESGGGVVQPGRSLRLSCAASGFPLI SYGMHWVRQAPGKGLEWVAFQTYDASNR YYADAVKGRFTISRDNSKNTLYLQMNSLRA EDTAVYYCARDRIVGGRVPDAFDIWGQGTM VTVSS |
| 3.24 | SEQ ID NO. 273 SYGMN | SEQ ID NO. 274 FITYD GSNRY YADSV KG | SEQ ID NO. 275 DRIVGARV PDAYDI | SEQ ID NO. 276 QVQLVESGGGVVQPGRSLRLSCAASGFPLI SYGMNWVRQAPGKGLEWVAFITYDGSNRY YADSVKGRFTISRDNSKNTLYLQMNSLRAE DTAVYYCAKDRIVGARVPDAYDIWGQGTMV TVSS |

In one aspect, the invention relates to a family 3 or family 3-like binding molecule comprising a human V$_H$ domain comprising a CDR3 sequence comprising SEQ ID NO. 183 or a sequence having at least 70%, at least 80%, at least 90%, or at least 95% homology to SEQ ID NO. 183.

In one embodiment, the V$_H$ domain comprises at least one antigen binding site comprising a CDR3 sequence comprising SEQ ID NO. 183 or a sequence having at least 70%, at least 80%, at least 90%, or at least 95% homology to SEQ ID NO. 183. In one embodiment, homology is at least 90%.

In one embodiment, the single $V_H$ domain antibody comprises the amino acid sequence SEQ ID NO. 183 or a sequence having at least 70%, at least 80%, at least 90%, or at least 95% homology thereto. In one embodiment, the family 3 or family 3-like sequence comprises a binding molecule comprising or consisting of at least one immunoglobulin single domain antibody capable of binding PSMA wherein said domain is a human $V_H$ domain and wherein said PSMA binding molecule comprises at least one antigen binding site comprising hypervariable regions CDR1, CDR2 and CDR3, said CDR1 comprises or consists of the amino acid sequence SEQ ID NO. 181 or a sequence with at least 70%, at least 80%, at least 90%, or at least 95% homology thereto, said CDR2 comprises or consists of the amino acid sequence SEQ ID NO. 182 or a sequence with at least 70%, at least 80%, at least 90%, or at least 95% homology thereto, and said CDR3 comprises or consists of the amino acid sequence SEQ ID NO. 183 or a sequence with at least 70%, at least 80%, at least 90%, or at least 95% homology thereto.

In one embodiment, said CDR1 comprises or consists of the amino acid sequence SEQ ID NO. 181 or a sequence with at least 70%, 71%, 72%, 73%, 74%, 75%, 76%, 77%, 78%, 79%, 80%, 81%, 82%, 83%, 84%, 85%, 86%, 87%, 88%, 89%, 90%, 91%, 92%, 93%, 94%, 95%, 96%, 97%, 98% or 99% homology thereto. In one embodiment, said CDR2 comprises or consists of the amino acid sequence SEQ ID NO. 182 or a sequence with at least 70%, 71%, 72%, 73%, 74%, 75%, 76%, 77%, 78%, 79%, 80%, 81%, 82%, 83%, 84%, 85%, 86%, 87%, 88%, 89%, 90%, 91%, 92%, 93%, 94%, 95%, 96%, 97%, 98% or 99% homology thereto. In one embodiment, said CDR3 comprises or consists of the amino acid sequence SEQ ID NO. 183 or a sequence with at least 70%, 71%, 72%, 73%, 74%, 75%, 76%, 77%, 78%, 79%, 80%, 81%, 82%, 83%, 84%, 85%, 86%, 87%, 88%, 89%, 90%, 91%, 92%, 93%, 94%, 95%, 96%, 97%, 98% or 99% homology thereto.

In one embodiment, the CDR sequences of the $V_H$ domain are as shown for sdAbs 3.1 to 3.24 as in FIG. 3 or combinations thereof. In one embodiment, CDR1 comprises or consists of the amino acid sequence SEQ ID NO. 181, 185, 189, 193, 197, 201, 205, 209, 213, 217, 221, 225, 229, 233, 237, 241, 245, 249, 253, 257, 261, 265, 269 or 273, CDR2 comprises or consists of the amino acid sequence SEQ ID NO. 182, 186, 190, 194, 198, 202, 206, 210, 214, 218, 222, 226, 230, 234, 238, 242, 246, 250, 254, 258, 262, 266, 270 or 274 and CDR3 comprises or consists of the amino acid sequence SEQ ID NO. 183, 187, 191, 195, 199, 203, 207, 211, 215, 219, 223, 227, 231, 235, 239, 243 or 247, 251, 255, 259, 263, 267, 271 or 275.

In one aspect, the invention relates to a single $V_H$ domain antibody which has combinations of CDR1, CDR2 and CDR3 as shown for 3.1 to 3.24 in FIG. 3. In one embodiment, CDR1 is SEQ ID NO. 181, CDR2 is SEQ ID NO. 182 and CDR3 is SEQ ID NO. 183. In one embodiment, CDR1 is SEQ ID NO. 185, CDR2 is SEQ ID NO. 186 and CDR3 is SEQ ID NO. 187. In one embodiment, CDR1 is SEQ ID NO. 189, CDR2 is SEQ ID NO. 190 and CDR3 is SEQ ID NO. 191. In one embodiment, CDR1 is SEQ ID NO. 193, CDR2 is SEQ ID NO. 194 and CDR3 is SEQ ID NO. 195. In one embodiment, CDR1 is SEQ ID NO. 197, CDR2 is SEQ ID NO. 198 and CDR3 is SEQ ID NO. 199. In one embodiment, CDR1 is SEQ ID NO. 201, CDR2 is SEQ ID NO. 202 and CDR3 is SEQ ID NO. 203. In one embodiment, CDR1 is SEQ ID NO. 205, CDR2 is SEQ ID NO. 206 and CDR3 is SEQ ID NO. 207. In one embodiment, CDR1 is SEQ ID NO. 209, CDR2 is SEQ ID NO. 210 and CDR3 is SEQ ID NO. 211. In one embodiment, CDR1 is SEQ ID NO. 213, CDR2 is SEQ ID NO. 214 and CDR3 is SEQ ID NO. 215. In one embodiment, CDR1 is SEQ ID NO. 217, CDR2 is SEQ ID NO. 218 and CDR3 is SEQ ID NO. 219. In one embodiment, CDR1 is SEQ ID NO. 221, CDR2 is SEQ ID NO. 222 and CDR3 is SEQ ID NO. 223. In one embodiment, CDR1 is SEQ ID NO. 225, CDR2 is SEQ ID NO. 226 and CDR3 is SEQ ID NO. 227. In one embodiment, CDR1 is SEQ ID NO. 229, CDR2 is SEQ ID NO. 230 and CDR3 is SEQ ID NO. 231. In one embodiment, CDR1 is SEQ ID NO. 233, CDR2 is SEQ ID NO. 234 and CDR3 is SEQ ID NO. 235. In one embodiment, CDR1 is SEQ ID NO. 237, CDR2 is SEQ ID NO. 238 and CDR3 is SEQ ID NO. 239. In one embodiment, CDR1 is SEQ ID NO. 241, CDR2 is SEQ ID NO. 242 and CDR3 is SEQ ID NO. 243. In one embodiment, CDR1 is SEQ ID NO. 245, CDR2 is SEQ ID NO. 246 and CDR3 is SEQ ID NO. 247. In one embodiment, CDR1 is SEQ ID NO. 249, CDR2 is SEQ ID NO. 250 and CDR3 is SEQ ID NO. 251. In one embodiment, CDR1 is SEQ ID NO. 253, CDR2 is SEQ ID NO. 254 and CDR3 is SEQ ID NO. 255. In one embodiment, CDR1 is SEQ ID NO. 257, CDR2 is SEQ ID NO. 258 and CDR3 is SEQ ID NO. 259. In one embodiment, CDR1 is SEQ ID NO. 261, CDR2 is SEQ ID NO. 262 and CDR3 is SEQ ID NO. 263. In one embodiment, CDR1 is SEQ ID NO. 265, CDR2 is SEQ ID NO. 266 and CDR3 is SEQ ID NO. 267. In one embodiment, CDR1 is SEQ ID NO. 269, CDR2 is SEQ ID NO. 270 and CDR3 is SEQ ID NO. 271. In one embodiment, CDR1 is SEQ ID NO. 273, CDR2 is SEQ ID NO. 274 and CDR3 is SEQ ID NO. 275.

In one embodiment, the single $V_H$ domain antibody comprises or consists of SEQ ID NO. 180 or a sequence with at least 40%, 50%, 60%, 70%, 80%, 81%, 82%, 83%, 84%, 85%, 86%, 87%, 88%, 89%, 90%, 91%, 92%, 93%, 94%, 95%, 96%, 97%, 98% or 99% homology thereto. In one embodiment, homology is at least 70%, 80%, 81%, 82%, 83%, 84%, 85%, 86%, 87%, 88%, 89%, 90%, 91%, 92%, 93%, 94%, 95%, 96%, 97%, 98% or 99%. CDR sequences of such sequences are shown in FIG. 3. For example, the $V_H$ domain comprises or consists of SEQ ID NO. 184, 188, 192, 196, 200, 204, 208, 212, 216, 220, 224, 228, 232, 236, 240, 244, 248, 252, 256, 260, 264, 268, 272 or 276.

In one embodiment, the $V_H$ domain comprises or consists of SEQ ID NO. 184, 188, 192, 196, 200, 204, 208, 212, 216, 220, 224, 228, 232, 236, 240, 244, 248, 252, 256, 260, 264, 268, 272 or 276, or a sequence with at least 70%, 80%, 81%, 82%, 83%, 84%, 85%, 86%, 87%, 88%, 89%, 90%, 91%, 92%, 93%, 94%, 95%, 96%, 97%, 98% or 99% homology thereto. CDR sequences of such sequences are listed below.

In another embodiment, the $V_H$ domain is selected from one of the sequences above, but comprises one or more amino acid substitutions, for example 1, 2, 3, 4, 5, 6, 7, 8, 9 or 10 amino acid substitutions. In one embodiment, the one or more amino acid substitution is in one or more of the framework areas. In another embodiment, the one or more amino acid substitution is in one or more of the CDRs. In one embodiment, the amino acid substitutions are in the framework and CDR sequences.

The family 3 or family 3-like binding molecules have KD, Koff, KA, Kd, $EC_{50}$ and $IC_{50}$ values as further described herein and as shown in the examples.

In one aspect, the binding molecule capable of binding human PSMA comprises a human $V_H$ domain comprising a family 4 or family 4-like sequence.

In one embodiment, two $V_H$ domains comprising a family 4 or a family-4 like sequence may be combined for a bivalent binding molecule. In another embodiment, one $V_H$ domain comprising a family 4 or a family-4 like sequence may be combined with a second V$_H$ domain as described herein that binds to the same a epitope, part, domain, subunit or confirmation of PSMA for a bivalent binding molecule. The second V$_H$ domain may be selected from a family 2, 3, 4, 7, 9, 10, 11 or a family 2, 3, 4, 7, 9, 10, 11-like sequence. In one embodiment, one V$_H$ domain comprising a family 4 or a family-4 like sequence may be combined with a second V$_H$ domain as described herein that binds to a different epitope, part, domain, subunit or confirmation of PSMA for a biparatopic binding molecule. The second V$_H$ domain may be selected from a family 1, 5, 6, 12 or 13 or a family 1, 5, 6, 12 or 13-like sequence.

Family 4 single V$_H$ domain antibodies include the parent sequence and sequences of that are derived from the parent (4.1, SEQ ID NO. 279) or a part thereof, for example a CDR3 sequence, and V$_H$ sequences or parts thereof that are derived from the parent 4.1 through a process of optimization, for example as shown in FIG. 4. CDR sequences and full length sequences in family 4 are numbered according to Table 4 as shown below.

sisting of at least one immunoglobulin single domain antibody capable of binding PSMA wherein said domain is a human V$_H$ domain and wherein said PSMA binding molecule comprises at least one antigen binding site comprising hypervariable regions CDR1, CDR2 and CDR3, said CDR1 comprises or consists of the amino acid sequence SEQ ID NO. 277 or a sequence with at least 70%, at least 80%, at least 90%, or at least 95% homology thereto, said CDR2 comprises or consists of the amino acid sequence SEQ ID NO. 278 or a sequence with at least 70%, at least 80%, at least 90%, or at least 95% homology thereto, and said CDR3 comprises or consists of the amino acid sequence SEQ ID NO. 279 or a sequence with at least 70%, at least 80%, at least 90%, or at least 95% homology thereto.

In one embodiment, said CDR1 comprises or consists of the amino acid sequence SEQ ID NO. 277 or a sequence with at least 70%, 71%, 72%, 73%, 74%, 75%, 76%, 77%, 78%, 79%, 80%, 81%, 82%, 83%, 84%, 85%, 86%, 87%, 88%, 89%, 90%, 91%, 92%, 93%, 94%, 95%, 96%, 97%, 98% or 99% homology thereto. In one embodiment, said

TABLE 4

This shows SEQ ID NOs of family 4 CDR sequences and of family 4 full-length V$_H$ sequences that are within the scope of the invention. Corresponding sequences are shown in FIG. 4. Family 4-like sequences are variants that have certain percentage sequence identity with Family 4 sequences as set out herein.

| Name | CDR1 | CDR2 | CDR3 | V$_H$ Full length sequence |
|---|---|---|---|---|
| 4.1 | SEQ ID NO. 277 SYGMH | SEQ ID NO. 278 VISYDGSNRYYADSVKG | SEQ ID NO. 279 ERIFGVLTPDDFDI | SEQ ID NO. 280 QVQLVESGGGVVQPGRSLRLSCVASGFPFISYGMHWVRQAPGKGREWVAVISYDGSNRYYADSVKGRFTISRDNSKNTLYLQMNSLRPEDTAVYYCAKERIFGVLTPDDFDIWGQGTTVTVSS |
| 4.2 | SEQ ID NO. 281 SYGMH | SEQ ID NO. 282 VISYDGSNRYYADSVKG | SEQ ID NO. 283 ERIFGVLTPDDFDI | SEQ ID NO. 284 QVQLVESGGGVVQPGRSLRLSCAASGFPFISYGMHWVRQAPGKGLEWVAVISYDGSNRYYADSVKGRFTISRDNSKNTLYLQMNSLRPEDTAVYYCAKERIFGVLTPDDFDIWGQGTTVTVSS |
| 4.3 | SEQ ID NO. 285 SYGMH | SEQ ID NO. 286 VISYDGANRYYADSVKG | SEQ ID NO. 287 ERIFGVLTPDDFEI | SEQ ID NO. 288 EVQLLESGGGVVQPGRSLRLSCAASGFPFISYGMHWVRQAPGKGLEWVAVISYDGANRYYADSVKGRFTISRDNSKNTLYLQMNSLRPEDTAVYYCAKERIFGVLTPDDFEIWGQGTTVTVSS |
| 4.4 | SEQ ID NO. 289 SYGMH | SEQ ID NO. 290 VISYDGSNRYYADSVKG | SEQ ID NO. 291 ERIFGALTPDDFDI | SEQ ID NO. 292 EVQLVESGGGVVQPGRSLRLSCAASGFTFTSYGMHWVRQAPGKGLEWVAVISYDGSNRYYADSVKGRFTISRDNSKNTLYLQMNSLRPEDTAVYYCAKERIFGALTPDDFDIWGQGTTVTVSS |

In one aspect, the invention relates to a family 4 or family 4-like binding molecule comprising a human V$_H$ domain comprising a CDR3 sequence comprising SEQ ID NO. 279 or a sequence having at least 70%, at least 80%, at least 90%, or at least 95% homology to SEQ ID NO. 279.

In one embodiment, the V$_H$ domain comprises a CDR3 selected from SEQ ID NOs. 279, 282, 287 or 291.

In one embodiment, the single V$_H$ domain antibody comprises at least one antigen binding site comprising hypervariable region CDR3 said CDR3 having the amino acid sequence SEQ ID NO. 279 or a sequence having at least 70%, at least 80%, at least 90%, or at least 95% homology thereto. In one embodiment, the family 4 or family 4-like sequence comprises a binding molecule comprising or con- CDR2 comprises or consists of the amino acid sequence SEQ ID NO. 278 or a sequence with at least 70%, 71%, 72%, 73%, 74%, 75%, 76%, 77%, 78%, 79%, 80%, 81%, 82%, 83%, 84%, 85%, 86%, 87%, 88%, 89%, 90%, 91%, 92%, 93%, 94%, 95%, 96%, 97%, 98% or 99% homology thereto. In one embodiment, said CDR3 comprises or consists of the amino acid sequence SEQ ID NO. 279 or a sequence with at least 70%, 71%, 72%, 73%, 74%, 75%, 76%, 77%, 78%, 79%, 80%, 81%, 82%, 83%, 84%, 85%, 86%, 87%, 88%, 89%, 90%, 91%, 92%, 93%, 94%, 95%, 96%, 97%, 98% or 99% homology thereto.

In one embodiment, the CDR sequences of the V$_H$ domain are as shown for clones 4.1 to 4.4 as in FIG. 4 or combinations thereof. In one embodiment, CDR1 comprises or consists of the amino acid sequence SEQ ID NO. 277, 281, 285 or 289; CDR2 comprises or consists of the amino acid sequence SEQ ID NO. 278, 282, 286 or 290 and CDR3 comprises or consists of the amino acid sequence SEQ ID NO. 279, 283, 287 or 291.

In one aspect, the single $V_H$ domain antibody has combinations of CDR1, CDR2 and CDR3 as shown for 4.1 to 4.4 in FIG. 4. Thus, in one embodiment, CDR1 is SEQ ID NO. 277, CDR2 is SEQ ID NO. 278 and CDR3 is SEQ ID NO. 279. Thus, CDR1 is SEQ ID NO. 281, CDR2 is SEQ ID NO. 282 and CDR3 is SEQ ID NO. 283. In one embodiment, CDR1 is SEQ ID NO. 285, CDR2 is SEQ ID NO. 286 and CDR3 is SEQ ID NO. 287. In one embodiment, CDR1 is SEQ ID NO. 289, CDR2 is SEQ ID NO. 290 and CDR3 is SEQ ID NO. 291.

In one embodiment, the $V_H$ domain comprises or consists of SEQ ID NO. 280 or a sequence with at least 40%, 50%, 60%, 70%, 80%, 81%, 82%, 83%, 84%, 85%, 86%, 87%, 88%, 89%, 90%, 91%, 92%, 93%, 94%, 95%, 96%, 97%, 98%, or 99% homology thereto. In one embodiment, homology is at least 70%, 80%, 81%, 82%, 83%, 84%, 85%, 86%, 87%, 88%, 89%, 90%, 91%, 92%, 93%, 94%, 95%, 96%, 97%, 98% or 99%. CDR sequences of such sequences are shown in FIG. 4. For example, the $V_H$ domain comprises or consists of SEQ ID NO. 280, 284, 288 or 290.

In one embodiment, the $V_H$ domain comprises or consists of SEQ ID NO. 280, 284, 288 or 290, or a sequence with at least 70%, 80%, 81%, 82%, 83%, 84%, 85%, 86%, 87%, 88%, 89%, 90%, 91%, 92%, 93%, 94%, 95%, 96%, 97%, 98% or 99% homology thereto. CDR sequences of such sequences are listed below.

In one embodiment, the binding molecule comprises or consists of a binding molecule comprising or consisting of at least one immunoglobulin single domain antibody capable of binding PSMA, preferably human PSMA, wherein said domain is a human $V_H$ domain and wherein said PSMA binding molecule comprises a family 5 or family-5 sequence. In one embodiment, two $V_H$ domains comprising a family 5 or a family-5 like sequence may be combined for a bivalent binding molecule. In another embodiment, one $V_H$ domain comprising a family 5 or a family-5 like sequence may be combined with a second $V_H$ domain as described herein that binds to the same a epitope, part, domain, subunit or confirmation of PSMA for a bivalent binding molecule. The second $V_H$ domain may be selected from family 1, 5, 6, 12 or 13 or family 1, 5, 6, 12 or 13-like sequence.

In one embodiment, one $V_H$ domain comprising a family 5 or a family-5 like sequence may be combined with a second $V_H$ domain as described herein that binds to a different epitope, part, domain, subunit or confirmation of PSMA for a biparatopic binding molecule. The second $V_H$ domain may be selected from a family 2, 3, 4, 7, 9, 10, 11 or 14 or a family 2, 3, 4, 7, 9, 10, 11 or 14-like sequence.

A single $V_H$ domain antibody of family 5 includes sequences that are derived from the parent (5.1; SEQ ID NO. 292) or a part thereof, for example a CDR3 sequence, and to $V_H$ sequences or parts thereof that are derived from the parent 5.1 through a process of optimization, for example as shown in FIG. 5. CDR sequences and full length sequences in family 5 are numbered according to Table 5 as shown below.

TABLE 5

This shows SEQ ID NOs of family 5 CDR sequences and of family 5 length $V_H$ sequences that are within the scope of the invention. Corresponding sequences are shown in FIG. 5. Family 5-like sequences are variants that have certain percentage sequence identity with Family 5-like sequences as set out herein.

| Name | CDR1 | CDR2 | CDR3 | $V_H$ Full length sequence |
|---|---|---|---|---|
| 5.1 | SEQ ID NO. 293 NYGMH | SEQ ID NO. 294 IISYDG NTKYYT DSVKG | SEQ ID NO. 295 GLWPSDV | SEQ ID NO. 296 QVQLVESGGGVVQPGRSLRLSCAASGFTF NNYGMHWVRQAPGKGLEWVAIISYDGNTK YYTDSVKGRFTISRDNSKNTLYLQMNSLRV EDTAVYYCAKGLWPSDVWGQGTTVTVSS |
| 5.2 | SEQ ID NO. 297 NYGMH | SEQ ID NO. 298 IISYDG NSKYYT DSVKG | SEQ ID NO. 299 GLWPSDV | SEQ ID NO. 300 EVQLVESGGGVVQPGRSLRLSCAASGFTF NNYGMHWVRQAPGKGLEWVAIISYDGNSK YYTDSVKGRFTISRDNSKNTLYLQMNSLRV EDTAVYYCAKGLWPSDVWGQGTTVTVSS |

In another embodiment, the $V_H$ domain is selected from one of the sequences above, but comprises one or more amino acid substitutions, for example 1, 2, 3, 4, 5, 6, 7, 8, 9 or 10 amino acid substitutions. In one embodiment, the one or more amino acid substitution is in one or more of the framework areas. In another embodiment, the one or more amino acid substitution is in one or more of the CDRs. In one embodiment, the amino acid substitutions are in the framework and CDR sequences.

The family 4 or family 4-like binding molecules have KD, Koff, KA, Kd, $EC_{50}$ and $IC_{50}$ values as further described herein and as shown in the examples.

In one aspect, the invention relates to a binding molecule capable of binding human PSMA comprising a human $V_H$ domain comprising a family 5 or family-5 like sequence.

In one aspect, the invention relates to a family 5 or family 5-like binding molecule comprising a human $V_H$ domain comprising a CDR3 sequence comprising SEQ ID NO. 295 or a sequence having at least 70%, at least 80%, at least 90%, or at least 95% homology to SEQ ID NO. 295.

In one embodiment, the $V_H$ domain comprises a CDR3 selected from SEQ ID NO. 295 and 299.

In one embodiment, the single $V_H$ domain antibody comprises at least one antigen binding site comprising hypervariable region CDR3 said CDR3 having the amino acid sequence of SEQ ID NO. 295 or a sequence having at least 70%, at least 80%, at least 90%, or at least 95% homology thereto. In one embodiment, the family 5 or family-5 sequence comprises a binding molecule comprising or consisting of at least one immunoglobulin single domain antibody capable of binding PSMA wherein said domain is a human V$_H$ domain and wherein said PSMA binding molecule comprises at least one antigen binding site comprising hypervariable regions CDR1, CDR2 and CDR3, said CDR1 comprises or consists of the amino acid sequence SEQ ID NO. 293 or a sequence with at least 70%, at least 80%, at least 90%, or at least 95% homology thereto, said CDR2 comprises or consists of the amino acid sequence SEQ ID NO. 294 or a sequence with at least 70%, at least 80%, at least 90%, or at least 95% homology thereto, and said CDR3 comprises or consists of the amino acid sequence SEQ ID NO. 295 or a sequence with at least 70%, at least 80%, at least 90%, or at least 95% homology thereto.

In one embodiment, said CDR1 comprises or consists of the amino acid sequence SEQ ID NO. 293 or a sequence with at least 70%, 71%, 72%, 73%, 74%, 75%, 76%, 77%, 78%, 79%, 80%, 81%, 82%, 83%, 84%, 85%, 86%, 87%, 88%, 89%, 90%, 91%, 92%, 93%, 94%, 95%, 96%, 97%, 98% or 99% homology thereto. In one embodiment, said CDR2 comprises or consists of the amino acid sequence SEQ ID NO. 294 or a sequence with at least 70%, 71%, 72%, 73%, 74%, 75%, 76%, 77%, 78%, 79%, 80%, 81%, 82%, 83%, 84%, 85%, 86%, 87%, 88%, 89%, 90%, 91%, 92%, 93%, 94%, 95%, 96%, 97%, 98% or 99% homology thereto. In one embodiment, said CDR3 comprises or consists of the amino acid sequence SEQ ID NO. 295 or a sequence with at least 70%, 71%, 72%, 73%, 74%, 75%, 76%, 77%, 78%, 79%, 80%, 81%, 82%, 83%, 84%, 85%, 86%, 87%, 88%, 89%, 90%, 91%, 92%, 93%, 94%, 95%, 96%, 97%, 98% or 99% homology thereto.

In one embodiment, the CDR sequences of the V$_H$ domain are as shown for clones 5.1 and 5.2 as in FIG. 5 or combinations thereof. In one embodiment, CDR1 comprises or consists of the amino acid sequence SEQ ID NO. 293 or 297, CDR2 comprises or consists of the amino acid sequence SEQ ID NO. 294 or 2984 and CDR3 comprises or consists of the amino acid sequence SEQ ID NO. 295 or 299.

In one aspect, the invention relates to a V$_H$ domain which has combinations of CDR1, CDR2 and CDR3 as shown for 5.1 to 5.2 in FIG. 5. Thus, in one embodiment, CDR1 is SEQ ID NO. 293, CDR2 is SEQ ID NO. 294 and CDR3 is SEQ ID NO. 295. In one embodiment, CDR1 is SEQ ID NO. 297, CDR2 is SEQ ID NO. 298 and CDR3 is SEQ ID NO. 299.

In one embodiment, the V$_H$ domain comprises or consists of SEQ ID NO. 296 or 300 or a sequence with at least 40%, 50%, 60%, 70%, 80%, 81%, 82%, 83%, 84%, 85%, 86%, 87%, 88%, 89%, 90%, 91%, 92%, 93%, 94%, 95%, 96%, 97%, 98% or 99% homology thereto. In one embodiment, homology is at least 70%, 80%, 81%, 82%, 83%, 84%, 85%, 86%, 87%, 88%, 89%, 90%, 91%, 92%, 93%, 94%, 95%, 96%, 97%, 98% or 99%. CDR sequences of such sequences are shown in FIG. 5. For example, the V$_H$ domain comprises or consists of SEQ ID NO. 296 or 300.

In another embodiment, the V$_H$ domain is selected from one of the sequences above, but comprises one or more amino acid substitutions, for example 1, 2, 3, 4, 5, 6, 7, 8, 9 or 10 amino acid substitutions. In one embodiment, the one or more amino acid substitution is in one or more of the framework areas. In another embodiment, the one or more amino acid substitution is in one or more of the CDRs. In one embodiment, the amino acid substitutions are in the framework and CDR sequences.

The family 5 or family-5 binding molecules have KD, Koff, KA, Kd, EC$_{50}$ and IC$_{50}$ values as further described herein and as shown in the examples.

In one aspect, the invention relates to a binding molecule capable of binding human PSMA comprising a human V$_H$ domain comprising a family 6 or family 6-like sequence.

In one aspect, the binding molecule capable of binding human PSMA comprises a human V$_H$ domain comprising a family 6 or family 6-like sequence. In one embodiment, two V$_H$ domains comprising a family 6 or a family-6 like sequence may be combined for a bivalent binding molecule. In another embodiment, one V$_H$ domain comprising a family 6 or a family-6 like sequence may be combined with a second V$_H$ domain as described herein that binds to the same a epitope, part, domain, subunit or confirmation of PSMA for a bivalent binding molecule. The second V$_H$ domain may be selected from family 1, 5, 6, 12 or 13 or family 1, 5, 6, 12 or 13-like sequence.

In one embodiment, one V$_H$ domain comprising a family 6 or a family-6 like sequence may be combined with a second V$_H$ domain as described herein that binds to a different epitope, part, domain, subunit or confirmation of PSMA for a biparatopic binding molecule. The second V$_H$ domain may be selected from a family 2, 3, 4, 7, 9, 10, 11 or 14 or a family 2, 3, 4, 7, 9, 10, 11 or 14-like sequence.

A family 6 single V$_H$ domain antibody includes the parent (6.1; SEQ ID NO. 304) or a part thereof, for example a CDR3 sequence, and to V$_H$ sequences or parts thereof that are derived from the parent 6.1 through a process of optimization, for example as shown in FIG. 3. CDR sequences and full length sequences in family 6 are numbered according to Table 6 as shown below.

TABLE 6

This shows SEQ ID NOs of family 6 CDR sequences and of family 6 full-length V$_H$ sequences that are within the scope of the invention. Corresponding sequences are shown in FIG. 6. Family 6-like sequences are variants that have certain percentage sequence identity with Family 6 sequences as set out herein.

| Name | CDR1 | CDR2 | CDR3 | V$_H$ Full length sequence |
|---|---|---|---|---|
| 6.1 | SEQ ID NO. 301 NSGYYWS | SEQ ID NO. 302 FIYYNGSIHYNPSLKS | SEQ ID NO. 303 DGDDYGDY | SEQ ID NO. 304 QVQLQESGPGLVKPSQTLSLTCTVSGGSIS NSGYYWSWVRQHPGKDLEWIGFIYYNGSI HYNPSLKSRVIISVDTSKNQFSLKMNSVTAA DTAVYYCARDGDDYGDYLRGQGTLVTVSS |
| 6.2 | SEQ ID NO. 305 NSGYYWS | SEQ ID NO. 306 FIYYNGSIHYNPSLKS | SEQ ID NO. 307 DGDDYGDY | SEQ ID NO. 308 QVQLQESGPGLVKPSQTLSLTCTVSGGSIS NSGYYWSWIRQHPGKGLEWIGFIYYNGSIH YNPSLKSRVIISVDTSKNQFSLKMSSVTAAD TAVYYCARDGDDYGDYLRGQGTLVTVSS |

TABLE 6-continued

This shows SEQ ID NOs of family 6 CDR sequences and of family 6 full-length $V_H$ sequences that are within the scope of the invention. Corresponding sequences are shown in FIG. 6. Family 6-like sequences are variants that have certain percentage sequence identity with Family 6 sequences as set out herein.

| Name | CDR1 | CDR2 | CDR3 | $V_H$ Full length sequence |
|---|---|---|---|---|
| 6.3 | SEQ ID NO. 309 NSGYYWS | SEQ ID NO. 310 FIYYNGSIHYNPSLKS | SEQ ID NO. 311 DGDDYGDY | SEQ ID NO. 312 QVQLQESGPGLVKPSQTLSLTCTVSGGSIS NSGYYWSWVRQHPGKGLEWIGFIYYNGSI HYNPSLKSRVIISVDTSKNQFSLKLNSVTAA DTAVYYCARDGDDYGDYLRGQGTLVTVSS |
| 6.4 | SEQ ID NO. 313 NSGYYWS | SEQ ID NO. 314 FIYYNGSIHYNPSLKS | SEQ ID NO. 315 DGDDYGDY | SEQ ID NO. 316 QVQLQESGPGLVKPSQTLSLTCTVSGGSIS NSGYYWSWIRQHPGKGLEWIGFIYYNGSIH YNPSLKSRVIISVDTSKNQFSLKLSSVTAAD TAVYYCARDGDDYGDYLRGQGTLVTVSS |
| 6.5 | SEQ ID NO. 317 NSGYYWS | SEQ ID NO. 318 FIYYNGSIHYNPSLKS | SEQ ID NO. 319 DGDDYGDY | SEQ ID NO. 320 QVQLQESGPGLVKPSQTLSLTCTVSGGSIS NSGYYWSWVRQHPGKGLEWIGFIYYNGSI HYNPSLKSRVTISVDTSKNQFSLKMSSVTA ADTAVYYCARDGDDYGDYLRGQGTLVTVSS |
| 6.6 | SEQ ID NO. 321 NSGYYWS | SEQ ID NO. 322 FIYYNGSIHYNPSLKS | SEQ ID NO. 323 DGDDYGDY | SEQ ID NO. 324 QVQLQESGPGLVKPSQTLSLTCTVSGGSIS NSGYYWSWVRQHPGKGLEWIGFIYYNGSI HYNPSLKSRVTISVDTSKNQFSLKLNSVTAA DTAVYYCARDGDDYGDYLRGQGTLVTVSS |
| 6.7 | SEQ ID NO. 325 NSGYYWS | SEQ ID NO. 326 FIYYNGSIHYNPSLKS | SEQ ID NO. 327 DGDDYGDY | SEQ ID NO. 328 QVQLQESGPGLVKPSQTLSLTCTVSGGSIS NSGYYWSWVRQHPGKGLEWIGFIYYNGSI HYNPSLKSRVTISVDTSKNQFSLKLSSVTAA DTAVYYCARDGDDYGDYLRGQGTLVTVSS |

In one aspect, the invention relates to a family 6 or family 6-like binding molecule comprising a human $V_H$ domain comprising a CDR3 sequence comprising SEQ ID NO. 303 or a sequence having at least 70%, at least 80%, at least 90%, or at least 95% homology to SEQ ID NO. 303.

In one embodiment, homology is at least 90%. In one embodiment, the $V_H$ domain comprises a CDR3 selected from SEQ ID NO. 303, 307, 311, 315, 319, 323 or 327.

In one embodiment, the single $V_H$ domain antibody comprises at least one antigen binding site comprising hypervariable region CDR3 said CDR3 having the amino acid sequence SEQ ID NO. 303 or a sequence having at least 70%, at least 80%, at least 90%, or at least 95% homology thereto. In one embodiment, the family 6 or family 6-like sequence comprises a binding molecule comprising or consisting of at least one immunoglobulin single domain antibody capable of binding PSMA wherein said domain is a human $V_H$ domain and wherein said PSMA binding molecule comprises at least one antigen binding site comprising hypervariable regions CDR1, CDR2 and CDR3, said CDR1 comprises or consists of the amino acid sequence SEQ ID NO. 301 or a sequence with at least 70%, at least 80%, at least 90%, or at least 95% homology thereto, said CDR2 comprises or consists of the amino acid sequence SEQ ID NO. 302 or a sequence with at least 70%, at least 80%, at least 90%, or at least 95% homology thereto, and said CDR3 comprises or consists of the amino acid sequence SEQ ID NO. 303 or a sequence with at least 70%, at least 80%, at least 90%, or at least 95% homology thereto.

In one embodiment, said CDR1 comprises or consists of the amino acid sequence SEQ ID NO. 301 or a sequence with at least 70%, 71%, 72%, 73%, 74%, 75%, 76%, 77%, 78%, 79%, 80%, 81%, 82%, 83%, 84%, 85%, 86%, 87%, 88%, 89%, 90%, 91%, 92%, 93%, 94%, 95%, 96%, 97%, 98% or 99% homology thereto. In one embodiment, said CDR2 comprises or consists of the amino acid sequence SEQ ID NO.302 or a sequence with at least 70%, 71%, 72%, 73%, 74%, 75%, 76%, 77%, 78%, 79%, 80%, 81%, 82%, 83%, 84%, 85%, 86%, 87%, 88%, 89%, 90%, 91%, 92%, 93%, 94%, 95%, 96%, 97%, 98% or 99% homology thereto. In one embodiment, said CDR3 comprises or consists of the amino acid sequence SEQ ID NO. 303 or a sequence with at least 70%, 71%, 72%, 73%, 74%, 75%, 76%, 77%, 78%, 79%, 80%, 81%, 82%, 83%, 84%, 85%, 86%, 87%, 88%, 89%, 90%, 91%, 92%, 93%, 94%, 95%, 96%, 97%, 98% or 99% homology thereto.

In one embodiment, the CDR sequences of the $V_H$ domain are as shown for clones 6.1 to 6.7 as in FIG. 6 or combinations thereof. In one embodiment, CDR1 comprises or consists of the amino acid sequence SEQ ID NO. 301, 305, 309, 313, 317, 321, 325, CDR2 comprises or consists of the amino acid sequence SEQ ID NO. 302, 306, 310, 314, 318, 322, 326 and CDR3 comprises or consists of the amino acid sequence SEQ ID NO. 303, 307, 311, 315, 319, 323, 327.

In one aspect, single $V_H$ domain antibody which has combinations of CDR1, CDR2 and CDR3 as shown for 6.1 to 6.7 in FIG. 6. Thus, in one embodiment, CDR1 is SEQ ID NO. 301, CDR2 is SEQ ID NO. 302 and CDR3 is SEQ ID NO. 303. Thus, in one embodiment, CDR1 is SEQ ID NO. 305, CDR2 is SEQ ID NO. 306 and CDR3 is SEQ ID NO. 307. In one embodiment, CDR1 is SEQ ID NO. 309, CDR2 is SEQ ID NO. 310 and CDR3 is SEQ ID NO. 311. In one embodiment, CDR1 is SEQ ID NO. 313, CDR2 is SEQ ID NO. 314 and CDR3 is SEQ ID NO. 315. In one embodiment, CDR1 is SEQ ID NO. 317, CDR2 is SEQ ID NO. 318 and CDR3 is SEQ ID NO. 319. In one embodiment, CDR1 is SEQ ID NO. 321, CDR2 is SEQ ID NO. 322 and CDR3 is SEQ ID NO. 323. In one embodiment, CDR1 is SEQ ID NO. 325, CDR2 is SEQ ID NO. 326 and CDR3 is SEQ ID NO. 327.

In one embodiment, the $V_H$ domain comprises or consists of SEQ ID NO. 304 or a sequence with at least 40%, 50%, 60%, 70%, 80%, 81%, 82%, 83%, 84%, 85%, 86%, 87%, 88%, 89%, 90%, 91%, 92%, 93%, 94%, 95%, 96%, 97%, 98% or 99% homology thereto. In one embodiment, homology is at least 70%, 80%, 81%, 82%, 83%, 84%, 85%, 86%, 87%, 88%, 89%, 90%, 91%, 92%, 93%, 94%, 95%, 96%, 97%, 98% or 99%. CDR sequences of such sequences are shown in FIG. 6. For example, the $V_H$ domain comprises or consists of SEQ ID NO. 304, 308, 312, 316, 320, 324 or 328.

In one embodiment, the $V_H$ domain comprises or consists of SEQ ID NO. 304, 308, 312, 316, 320, 324 or 328 or a sequence with at least 70%, 80%, 81%, 82%, 83%, 84%, 85%, 86%, 87%, 88%, 89%, 90%, 91%, 92%, 93%, 94%, 95%, 96%, 97%, 98% or 99% homology thereto.

In another embodiment, the $V_H$ domain is selected from one of the sequences above, but comprises one or more amino acid substitutions, for example 1, 2, 3, 4, 5, 6, 7, 8, 9 or 10 amino acid substitutions. In one embodiment, the one or more amino acid substitution is in one or more of the framework areas. In another embodiment, the one or more amino acid substitution is in one or more of the CDRs. In one embodiment, the amino acid substitutions are in the framework and CDR sequences.

The family 6 or family 6-like binding molecules have KD, Koff, KA, Kd, $EC_{50}$ and $IC_{50}$ values as further described herein and as shown in the examples.

In one aspect, the invention relates to a binding molecule capable of binding human PSMA comprising a human $V_H$ domain comprising a family 7 or family 7-like sequence.

In one aspect, the binding molecule capable of binding human PSMA comprises a human $V_H$ domain comprising a family 7 or family 7-like sequence. In one embodiment, two $V_H$ domains comprising a family 7 or a family-7 like sequence may be combined for a bivalent binding molecule. In another embodiment, one $V_H$ domain comprising a family 7 or a family-7 like sequence may be combined with a second $V_H$ domain as described herein that binds to the same a epitope, part, domain, subunit or confirmation of PSMA for a bivalent binding molecule. The second $V_H$ domain may be selected from a family 2, 3, 4, 7, 9, 10, 11 or a family 2, 3, 4, 7, 9, 10, 11-like sequence.

In one embodiment, one $V_H$ domain comprising a family 7 or a family-7 like sequence may be combined with a second $V_H$ domain as described herein that binds to a different epitope, part, domain, subunit or confirmation of PSMA for a biparatopic binding molecule. The second $V_H$ domain may be selected from a family 1, 5, 6, 12 or 13 or a family 1, 5, 6, 12 or 13-like sequence.

A family 7 or family 7-like sequence includes the parent sequence and sequences of clones that are derived from the parent (7.1) or a part thereof, for example a CDR3 sequence, and to $V_H$ sequences or parts thereof that are derived from the parent 7.1 through a process of optimization, for example as shown in FIG. 7. CDR sequences and full length sequences in family 7 are numbered according to Table 7 as shown below.

TABLE 7

This shows SEQ ID NOs of family 7 CDR sequences and of family 7 full-length $V_H$ sequences that are within the scope of the invention. Corresponding sequences are shown in FIG. 7. Family 7-like sequences are variants that have certain percentage sequence identity with Family 7 sequences as set out herein.

| Name | CDR1 | CDR2 | CDR3 | $V_H$ Full length sequence |
|---|---|---|---|---|
| 7.1 | SEQ ID NO. 329 SYWMY | SEQ ID NO. 330 NINHDGSEKYYV DSVKG | SEQ ID NO. 331 DSLIVGERGY | SEQ ID NO. 332 EVQLVESGGGLVQPG GSLRLSCAASGFTFSS YWMYWVRQAPGKGL EWVANINHDGSEKYY VDSVKGRFTISRDNAK NSLYLQMNSLRAEDTA VYYCARDSLIVGERGY WGQGTLVTVSS |
| 7.2 | SEQ ID NO. 333 SYWMY | SEQ ID NO. 334 NINHDGSEKYYV DSVKG | SEQ ID NO. 335 DNLIVGERGY | SEQ ID NO. 336 EVQLVESGGGLVQPG GSLRLSCAASGFTFSS YWMYWVRQAPGKGL EWVANINHDGSEKYY VDSVKGRFTISRDNAK NSLYLQMNSLRAEDTA VYYCARDNLIVGERGY WGQGTLVTVSS |
| 7.3 | SEQ ID NO. 337 SYWMY | SEQ ID NO. 338 NINHGGSEKYYV DSVKG | SEQ ID NO. 339 DSLIVGERGY | SEQ ID NO. 340 EVQLVESGGGLVQPG GSLRLSCAASGFTFSS YWMYWVRQAPGKGL EWVANINHGGSEKYY VDSVKGRFTISRDNAK NSLYLQMNSLRAEDTA VYYCARDSLIVGERGY WGQGTLVTVSS |

TABLE 7-continued

This shows SEQ ID NOs of family 7 CDR sequences and of family 7 full-length V$_H$ sequences that are within the scope of the invention. Corresponding sequences are shown in FIG. 7. Family 7-like sequences are variants that have certain percentage sequence identity with Family 7 sequences as set out herein.

| Name | CDR1 | CDR2 | CDR3 | V$_H$ Full length sequence |
|---|---|---|---|---|
| 7.4 | SEQ ID NO. 341 SYWMY | SEQ ID NO. 342 NINHQGSEKYYV DSVKG | SEQ ID NO. 343 DSLIVGERGY | SEQ ID NO. 344 EVQLVESGGGLVQPG GSLRLSCAASGFTFSS YWMYWVRQAPGKGL EWVANINHQGSEKYY VDSVKGRFTISRDNAK NSLYLQMNSLRAEDTA VYYCARDSLIVGERGY WGQGTLVTVSS |
| 7.5 | SEQ ID NO. 345 SYWMY | SEQ ID NO. 346 NINHPGSEKYYV DSVKG | SEQ ID NO. 347 DSLIVGERGY | SEQ ID NO. 348 EVQLVESGGGLVQPG GSLRLSCAASGFTFSS YWMYWVRQAPGKGL EWVANINHPGSEKYYV DSVKGRFTISRDNAKN SLYLQMNSLRAEDTAV YYCARDSLIVGERGY WGQGTLVTVSS |
| 7.6 | SEQ ID NO. 349 SYWMY | SEQ ID NO. 350 NINHEGSEKYYV DSVKG | SEQ ID NO. 351 DSLIVGERGY | SEQ ID NO. 352 EVQLVESGGGLVQPG GSLRLSCAASGFTFSS YWMYWVRQAPGKGL EWVANINHEGSEKYYV DSVKGRFTISRDNAKN SLYLQMNSLRAEDTAV YYCARDSLIVGERGY WGQGTLVTVSS |
| 7.7 | SEQ ID NO. 353 SYWMY | SEQ ID NO. 354 NINHIGSEKYYVD SVKG | SEQ ID NO. 355 DSLIVGERGY | SEQ ID NO. 356 EVQLVESGGGLVQPG GSLRLSCAASGFTFSS YWMYWVRQAPGKGL EWVANINHIGSEKYYV DSVKGRFTISRDNAKN SLYLQMNSLRAEDTAV YYCARDSLIVGERGY WGQGTLVTVSS |
| 7.8 | SEQ ID NO. 357 SYWMY | SEQ ID NO. 358 NINHDGSEKYYV DSVKG | SEQ ID NO. 359 DTLIVGERGY | SEQ ID NO. 360 EVQLVESGGGLVQPG GSLRLSCAASGFTFSS YWMYWVRQAPGKGL EWVANINHDGSEKYY VDSVKGRFTISRDNAK NSLYLQMNSLRAEDTA VYYCARDTLIVGERGY WGQGTLVTVSS |

In one aspect, the invention relates to a family 7 or family 7-like binding molecule comprising a human V$_H$ domain comprising a CDR3 sequence comprising SEQ ID NO. 331 or a sequence having at least 70%, at least 80%, at least 90%, or at least 95% homology to SEQ ID NO. 331.

In one embodiment, homology is at least 90%. In one embodiment, the V$_H$ domain comprises a CDR3 selected from SEQ ID NO. 331, 335, 339, 343, 347, 351, 355 or 359.

In one embodiment, the single V$_H$ domain antibody comprises at least one antigen binding site comprising hypervariable region CDR3 said CDR3 having the amino acid sequence SEQ ID NO. 331 or a sequence having at least 70%, at least 80%, at least 90%, or at least 95% homology thereto. In one embodiment, the family 7 or family 7-like sequence comprises a binding molecule comprising or consisting of at least one immunoglobulin single domain antibody capable of binding PSMA wherein said domain is a human V$_H$ domain and wherein said PSMA binding molecule comprises at least one antigen binding site comprising hypervariable regions CDR1, CDR2 and CDR3, said CDR1 comprises or consists of the amino acid sequence SEQ ID NO. 329 or a sequence with at least 70%, at least 80%, at least 90%, or at least 95% homology thereto, said CDR2 comprises or consists of the amino acid sequence SEQ ID NO. 330 or a sequence with at least 70%, at least 80%, at least 90%, or at least 95% homology thereto, and said CDR3 comprises or consists of the amino acid sequence SEQ ID NO. 331 or a sequence with at least 70%, at least 80%, at least 90%, or at least 95% homology thereto.

In one embodiment, said CDR1 comprises or consists of the amino acid sequence SEQ ID NO. 329 or a sequence with at least 70%, 71%, 72%, 73%, 74%, 75%, 76%, 77%, 78%, 79%, 80%, 81%, 82%, 83%, 84%, 85%, 86%, 87%, 88%, 89%, 90%, 91%, 92%, 93%, 94%, 95%, 96%, 97%, 98% or 99% homology thereto. In one embodiment, said CDR2 comprises or consists of the amino acid sequence SEQ ID NO. 330 or a sequence with at least 70%, 71%, 72%, 73%, 74%, 75%, 76%, 77%, 78%, 79%, 80%, 81%, 82%, 83%, 84%, 85%, 86%, 87%, 88%, 89%, 90%, 91%, 92%, 93%, 94%, 95%, 96%, 97%, 98% or 99% homology thereto. In one embodiment, said CDR3 comprises or consists of the amino acid sequence SEQ ID NO. 331 or a sequence with at least 70%, 71%, 72%, 73%, 74%, 75%, 76%, 77%, 78%, 79%, 80%, 81%, 82%, 83%, 84%, 85%, 86%, 87%, 88%, 89%, 90%, 91%, 92%, 93%, 94%, 95%, 96%, 97%, 98% or 99% homology thereto.

In one embodiment, the CDR sequences of the $V_H$ domain are as shown for clones 7.1 to 7.8 as in FIG. 7 or combinations thereof. In one embodiment, CDR1 comprises or consists of the amino acid sequence SEQ ID NO. 329, 333, 337, 341, 345, 349, 353 or 357, CDR2 comprises or consists of the amino acid sequence SEQ ID NO. 330, 334, 338, 342, 346, 350, 354 or 358 and CDR3 comprises or consists of the amino acid sequence SEQ ID NO. 331, 335, 339, 343, 347, 351, 355 or 359.

In one aspect, the single $V_H$ domain antibody has combinations of CDR1, CDR2 and CDR3 as shown for 7.1 to 7.8 in FIG. 7. Thus, in one embodiment, CDR1 is SEQ ID NO. 329, CDR2 is SEQ ID NO. 330 and CDR3 is SEQ ID NO. 331. Thus, in one embodiment, CDR1 is SEQ ID NO. 333, CDR2 is SEQ ID NO. 334 and CDR3 is SEQ ID NO. 335. In one embodiment, CDR1 is SEQ ID NO. 337, CDR2 is SEQ ID NO. 338 and CDR3 is SEQ ID NO. 339. In one embodiment, n CDR1 is SEQ ID NO. 341, CDR2 is SEQ ID NO. 342 and CDR3 is SEQ ID NO. 343. In one embodiment, CDR1 is SEQ ID NO. 345, CDR2 is SEQ ID NO. 346 and CDR3 is SEQ ID NO. 347. In one embodiment, CDR1 is SEQ ID NO. 349, CDR2 is SEQ ID NO. 350 and CDR3 is SEQ ID NO.351. In one embodiment, CDR1 is SEQ ID NO. 353, CDR2 is SEQ ID NO. 354 and CDR3 is SEQ ID NO. 355. In one embodiment, CDR1 is SEQ ID NO. 357, CDR2 is SEQ ID NO. 358 and CDR3 is SEQ ID NO. 359.

In one embodiment, the $V_H$ domain comprises or consists of SEQ ID NO. 332 or a sequence with at least 40%, 50%, 60%, 70%, 80%, 81%, 82%, 83%, 84%, 85%, 86%, 87%, 88%, 89%, 90%, 91%, 92%, 93%, 94%, 95%, 96%, 97%, 98% or 99% homology thereto. In one embodiment, homology is at least 70%, 80%, 81%, 82%, 83%, 84%, 85%, 86%, 87%, 88%, 89%, 90%, 91%, 92%, 93%, 94%, 95%, 96%, 97%, 98% or 99%. CDR sequences of such sequences are shown in FIG. 2. For example, the $V_H$ domain comprises or consists of SEQ ID NO. 332, 336, 340, 344, 348, 352, 356 or 360.

In one embodiment, the $V_H$ domain comprises or consists of SEQ ID NO. 332, 336, 340, 344, 348, 352, 356, 360 or a sequence with at least 70%, 80%, 81%, 82%, 83%, 84%, 85%, 86%, 87%, 88%, 89%, 90%, 91%, 92%, 93%, 94%, 95%, 96%, 97%, 98% or 99% homology thereto.

In another embodiment, the $V_H$ domain is selected from one of the sequences above, but comprises one or more amino acid substitutions, for example 1, 2, 3, 4, 5, 6, 7, 8, 9 or 10 amino acid substitutions. In one embodiment, the one or more amino acid substitution is in one or more of the framework areas. In another embodiment, the one or more amino acid substitution is in one or more of the CDRs. In one embodiment, the amino acid substitutions are in the framework and CDR sequences.

The family 7 or family 7-like binding molecules have KD, Koff, KA, Kd, $EC_{50}$ and $IC_{50}$ values as further described herein and as shown in the examples.

In one aspect, the invention relates to a binding molecule capable of binding human PSMA comprising a human $V_H$ domain comprising a family 8 or family 8-like sequence.

A family 8 or family 8-like sequence includes the parent sequence and sequences of clones that are derived from the parent (8.1, SEQ ID NO. 36) or a part thereof, for example a CDR3 sequence, and $V_H$ sequences or parts thereof that are derived from the parent 8.1 through a process of optimization, CDR sequences and full length sequences of 8.1 in are numbered according to Table 8 as shown below.

TABLE 8

This shows SEQ ID NOs of family 8 CDR sequences and of family 8 full-length $V_H$ sequences that are within the scope of the invention. Corresponding sequences are shown in FIG. 8. Family 8-like sequences are variants that have certain percentage sequence identity with Family 8 sequences as set out herein.

| Name | CDR1 | CDR2 | CDR3 | $V_H$ Full length sequence |
|---|---|---|---|---|
| 8.1 | SEQ ID NO. 361 GYYWS | SEQ ID NO. 362 EINHSGSTNYNPSLKS | SEQ ID NO. 363 GPIPATAIPDAFD | SEQ ID NO. 364 QVQLQQWGAGLLKPS ETLSLTCAVYGGSFSG YYWSWIRQPPGKGLE WIGEINHSGSTNYNPS LKSRVTISVDTSKNQF SLKLSSVTAADTAVYY CARGPIPATAIPDAFDI WGQGTMVTVSS |

In one aspect, the invention relates to a family 8 or family 8-like binding molecule comprising a human $V_H$ domain comprising a CDR3 sequence comprising SEQ ID NO. 363 or a sequence having at least 70%, at least 80%, at least 90%, or at least 95% homology to SEQ ID NO. 363.

In one embodiment, homology is at least 90%. In one embodiment, the $V_H$ domain comprises a CDR3 of SEQ ID NO. 363.

In one embodiment, the single $V_H$ domain antibody comprises at least one antigen binding site comprising hypervariable region CDR3 said CDR3 having the amino acid sequence SEQ ID NO. 363 or a sequence having at least 70%, at least 80%, at least 90%, or at least 95% homology thereto. In one embodiment, the family 8 or family 8-like sequence comprises a binding molecule comprising or consisting of at least one immunoglobulin single domain antibody capable of binding PSMA wherein said domain is a human $V_H$ domain and wherein said PSMA binding molecule comprises at least one antigen binding site comprising hypervariable regions CDR1, CDR2 and CDR3, said CDR1 comprises or consists of the amino acid sequence SEQ ID NO. 361 or a sequence with at least 70%, at least 80%, at least 90%, or at least 95% homology thereto, said CDR2 comprises or consists of the amino acid sequence SEQ ID NO. 362 or a sequence with at least 70%, at least 80%, at least 90%, or at least 95% homology thereto, and said CDR3 comprises or consists of the amino acid sequence SEQ ID NO. 363 or a sequence with at least 70%, at least 80%, at least 90%, or at least 95% homology thereto.

In one embodiment, said CDR1 comprises or consists of the amino acid sequence SEQ ID NO. 361 or a sequence with at least 70%, 71%, 72%, 73%, 74%, 75%, 76%, 77%, 78%, 79%, 80%, 81%, 82%, 83%, 84%, 85%, 86%, 87%, 88%, 89%, 90%, 91%, 92%, 93%, 94%, 95%, 96%, 97%, 98% or 99% homology thereto. In one embodiment, said CDR2 comprises or consists of the amino acid sequence SEQ ID NO. 362 or a sequence with at least 70%, 71%, 72%, 73%, 74%, 75%, 76%, 77%, 78%, 79%, 80%, 81%, 82%, 83%, 84%, 85%, 86%, 87%, 88%, 89%, 90%, 91%, 92%, 93%, 94%, 95%, 96%, 97%, 98% or 99% homology thereto. In one embodiment, said CDR3 comprises or consists of the amino acid sequence SEQ ID NO. 363 or a sequence with at least 70%, 71%, 72%, 73%, 74%, 75%, 76%, 77%, 78%, 79%, 80%, 81%, 82%, 83%, 84%, 85%, 86%, 87%, 88%, 89%, 90%, 91%, 92%, 93%, 94%, 95%, 96%, 97%, 98% or 99% homology thereto. In one embodiment, the CDR sequences of the $V_H$ domain are as shown for sdAb 8.1 as in FIG. 8.

In one embodiment, the $V_H$ domain comprises or consists of SEQ ID NO. 364 or a sequence with at least 40%, 50%, 60%, 70%, 80%, 81%, 82%, 83%, 84%, 85%, 86%, 87%, 88%, 89%, 90%, 91%, 92%, 93%, 94%, 95%, 96%, 97%, 98% or 99% homology thereto.

In another embodiment, the $V_H$ domain is selected from one of the sequences above, but comprises one or more amino acid substitutions, for example 1, 2, 3, 4, 5, 6, 7, 8, 9 or 10 amino acid substitutions. In one embodiment, the one or more amino acid substitution is in one or more of the framework areas. In another embodiment, the one or more amino acid substitution is in one or more of the CDRs. In one embodiment, the amino acid substitutions are in the framework and CDR sequences.

The family 8 or family 8-like binding molecules have KD, Koff, KA, Kd, $EC_{50}$ and $IC_{50}$ values as further described herein and as shown in the examples.

In one aspect, the invention relates to a binding molecule capable of binding human PSMA comprising a human $V_H$ domain comprising a family 9 or family 9-like sequence.

In one aspect, the invention relates to a binding molecule capable of binding human PSMA comprising a human $V_H$ domain comprising a family 9 or family 9-like sequence. In one embodiment, two $V_H$ domains comprising a family 9 or a family-9 like sequence may be combined for a bivalent binding molecule. In another embodiment, one $V_H$ domain comprising a family 9 or a family-9 like sequence may be combined with a second $V_H$ domain as described herein that binds to the same a epitope, part, domain, subunit or confirmation of PSMA for a bivalent binding molecule. The second $V_H$ domain may be selected from a family 2, 3, 4, 7, 9, 10, 11 or a family 2, 3, 4, 7, 9, 10, 11-like sequence.

In one embodiment, one $V_H$ domain comprising a family 9 or a family-9 like sequence may be combined with a second $V_H$ domain as described herein that binds to a different epitope, part, domain, subunit or confirmation of PSMA for a biparatopic binding molecule. The second $V_H$ domain may be selected from a family 1, 5, 6, 12 or 13 or a family 1, 5, 6, 12 or 13-like sequence.

A family 9 or family 9 sequence includes the parent sequence and sequences that are derived from the parent (9.1; SEQ ID NO. 368) or a part thereof, for example a CDR3 sequence, and $V_H$ sequences or parts thereof that are derived from the parent 9.1 through a process of optimization, CDR sequences and full-length sequences of 9.1 in are numbered according to Table 9 as shown below.

TABLE 9

This shows SEQ ID NOs of family 9 CDR sequences and of family 9 full-length $V_H$ sequences that are within the scope of the invention. Corresponding sequences are shown in FIG. 9. Family 9-like sequences are variants that have certain percentage sequence identity with Family 9 sequences as set out herein.

| Name | CDR1 | CDR2 | CDR3 | VH Full length sequence |
|---|---|---|---|---|
| 9.1 | SEQ ID NO. 365 GHYWS | SEQ ID NO. 366 DINHSGSTNYN PSLKS | SEQ ID NO. 367 DYGDSRSLFDY | SEQ ID NO. 368 QVQLQQWGAGLLKPSETL SLTCAVYGGSFSGHYWSW IRQPPGKGLEWIGDINHSG STNYNPSLKSRVTISVDTS KNQFSLKLSSVTAADTAVY YCVRDYGDSRSLFDYWGQ GTLVTVSS |

In one aspect, the invention relates to a family 9 or family 9-like binding molecule comprising a human $V_H$ domain comprising a CDR3 sequence comprising SEQ ID NO. 367 or a sequence having at least 70%, at least 80%, at least 90%, or at least 95% homology to SEQ ID NO. 367.

In one embodiment, the binding molecule comprises at least one immunoglobulin single domain antibody capable of binding PSMA wherein said domain is a human $V_H$ domain and wherein said human $V_H$ domain comprises at least one antigen binding site comprising a CDR3 sequence comprising SEQ ID NO. 367 or a sequence having at least 70%, at least 80%, at least 90%, or at least 95% homology to SEQ ID NO. 367. In one embodiment, homology is at least 90%. In one embodiment, the $V_H$ domain comprises a CDR3 of SEQ ID NO. 367.

In one embodiment, the single $V_H$ domain antibody comprises a CDR3 said CDR3 having the amino acid sequence SEQ ID NO. 363 or a sequence having at least 70%, at least 80%, at least 90%, or at least 95% homology thereto. In one embodiment, the family 9 or family 9-like sequence comprises a binding molecule comprising or consisting of at least one immunoglobulin single domain antibody capable of binding PSMA wherein said domain is a human $V_H$ domain and wherein said PSMA binding molecule comprises at least one antigen binding site comprising hypervariable regions CDR1, CDR2 and CDR3, said CDR1 comprises or consists of the amino acid sequence SEQ ID NO. 365 or a sequence with at least 70%, at least 80%, at least 90%, or at least 95% homology thereto, said CDR2 comprises or consists of the amino acid sequence SEQ ID NO. 366 or a sequence with at least 70%, at least 80%, at least 90%, or at least 95% homology thereto, and said CDR3 comprises or consists of the amino acid sequence SEQ ID NO. 367 or a sequence with at least 70%, at least 80%, at least 90%, or at least 95% homology thereto.

In one embodiment, said CDR1 comprises or consists of the amino acid sequence SEQ ID NO. 365 or a sequence with at least 70%, 71%, 72%, 73%, 74%, 75%, 76%, 77%, 78%, 79%, 80%, 81%, 82%, 83%, 84%, 85%, 86%, 87%, 88%, 89%, 90%, 91%, 92%, 93%, 94%, 95%, 96%, 97%, 98% or 99% homology thereto. In one embodiment, said CDR2 comprises or consists of the amino acid sequence SEQ ID NO. 366 or a sequence with at least 70%, 71%, 72%, 73%, 74%, 75%, 76%, 77%, 78%, 79%, 80%, 81%, 82%, 83%, 84%, 85%, 86%, 87%, 88%, 89%, 90%, 91%, 92%, 93%, 94%, 95%, 96%, 97%, 98% or 99% homology thereto. In one embodiment, said CDR3 comprises or consists of the amino acid sequence SEQ ID NO. 367 or a sequence with at least 70%, 71%, 72%, 73%, 74%, 75%, 76%, 77%, 78%, 79%, 80%, 81%, 82%, 83%, 84%, 85%, 86%, 87%, 88%, 89%, 90%, 91%, 92%, 93%, 94%, 95%, 96%, 97%, 98% or 99% homology thereto. In one embodiment, the CDR sequences of the $V_H$ domain are as shown for clone 9.1 as in FIG. 9.

In one embodiment, the $V_H$ domain comprises or consists of SEQ ID NO. 368 or a sequence with at least 40%, 50%, 60%, 70%, 80%, 81%, 82%, 83%, 84%, 85%, 86%, 87%, 88%, 89%, 90%, 91%, 92%, 93%, 94%, 95%, 96%, 97%, 98% or 99% homology thereto.

In another embodiment, the $V_H$ domain is selected from one of the sequences above, but comprises one or more amino acid substitutions, for example 1, 2, 3, 4, 5, 6, 7, 8, 9 or 10 amino acid substitutions. In one embodiment, the one or more amino acid substitution is in one or more of the framework areas. In another embodiment, the one or more amino acid substitution is in one or more of the CDRs. In one embodiment, the amino acid substitutions are in the framework and CDR sequences.

The family 9 or family 9-like binding molecules have KD, Koff, KA, Kd, $EC_{50}$ and $IC_{50}$ values as further described herein and as shown in the examples.

In one aspect, the invention relates to a binding molecule capable of binding human PSMA comprising a human $V_H$ domain comprising a family 10 or family 10-like sequence.

In one embodiment, two $V_H$ domains comprising a family 10 or a family-10 like sequence may be combined for a bivalent binding molecule. In another embodiment, one $V_H$ domain comprising a family 10 or a family-10 like sequence may be combined with a second $V_H$ domain as described herein that binds to the same a epitope, part, domain, subunit or confirmation of PSMA for a bivalent binding molecule. The second $V_H$ domain may be selected from a family 2, 3, 4, 7, 9, 10, 11 or a family 2, 3, 4, 7, 9, 10, 11-like sequence.

In one embodiment, one $V_H$ domain comprising a family 10 or a family-10 like sequence may be combined with a second $V_H$ domain as described herein that binds to a different epitope, part, domain, subunit or confirmation of PSMA for a biparatopic binding molecule. The second $V_H$ domain may be selected from a family 1, 5, 6, 12 or 13 or a family 1, 5, 6, 12 or 13-like sequence. A family 10 or family 10 sequence includes the parent sequence and sequences that are derived from the parent (10.1) or a part thereof, for example a CDR3 sequence, and $V_H$ sequences of or parts thereof that are derived from the parent 10.1 through a process of optimization, CDR sequences and full length sequences of 10.1 in are numbered according to Table 10 as shown below.

TABLE 10

This shows SEQ ID NOs of family 10 CDR sequences and of family 10 full-length $V_H$ sequences that are within the scope of the invention. Corresponding sequences are shown in FIG. 10. Family 10-like sequences are variants that have certain percentage sequence identity with Family 10 sequences as set out herein.

| Name | CDR1 | CDR2 | CDR3 | $V_H$ Full length sequence |
|---|---|---|---|---|
| 10.1 | SEQ ID NO. 369 SYGMY | SEQ ID NO. 370 FMSYDGSNKY YVDSVKG | SEQ ID NO. 371 GDYDFWSGY PDYD | SEQ ID NO. 372 QVQLVESGGGLVQPGG SLRLSCAASGFTFSSYG MHWVRQAPGKGLEWV AFMSYDGSNKYYVDSV KGRFTISRDNSKNTLYL QMNSLRAEDTAVYYCA KGDYDFWSGYPDYDM DVWGQGTTVTVSS |

In one aspect, the invention relates to a family 10 or family 10-like binding molecule comprising a human $V_H$ domain comprising a CDR3 sequence comprising SEQ ID NO. 371 or a sequence having at least 70%, at least 80%, at least 90%, or at least 95% homology to SEQ ID NO. 371.

In one embodiment, the family 10 or family 10-like binding molecule comprises at least one immunoglobulin single domain antibody capable of binding PSMA wherein said domain is a human $V_H$ domain and wherein said human $V_H$ domain comprises at least one antigen binding site comprising a CDR3 sequence comprising SEQ ID NO. 371 or a sequence having at least 70%, at least 80%, at least 90%, or at least 95% homology to SEQ ID NO. 371. In one embodiment, homology is at least 90%. In one embodiment, the $V_H$ domain comprises a CDR3 of SEQ ID NO. 371.

In one embodiment, said V$_H$ domain and wherein said PSMA binding molecule comprises at least one antigen binding site comprising hypervariable regions CDR1, CDR2 and CDR3, said CDR1 comprises or consists of the amino acid sequence SEQ ID NO. 369 or a sequence with at least 70%, at least 80%, at least 90%, or at least 95% homology thereto, said CDR2 comprises or consists of the amino acid sequence SEQ ID NO. 370 or a sequence with at least 70%, at least 80%, at least 90%, or at least 95% homology thereto, and said CDR3 comprises or consists of the amino acid sequence SEQ ID NO. 371 or a sequence with at least 70%, at least 80%, at least 90%, or at least 95% homology thereto.

In one embodiment, said CDR1 comprises or consists of the amino acid sequence SEQ ID NO. 369 or a sequence with at least 70%, 71%, 72%, 73%, 74%, 75%, 76%, 77%, 78%, 79%, 80%, 81%, 82%, 83%, 84%, 85%, 86%, 87%, 88%, 89%, 90%, 91%, 92%, 93%, 94%, 95%, 96%, 97%, 98% or 99% homology thereto. In one embodiment, said CDR2 comprises or consists of the amino acid sequence SEQ ID NO. 370 or a sequence with at least 70%, 71%, 72%, 73%, 74%, 75%, 76%, 77%, 78%, 79%, 80%, 81%, 82%, 83%, 84%, 85%, 86%, 87%, 88%, 89%, 90%, 91%, 92%, 93%, 94%, 95%, 96%, 97%, 98% or 99% homology thereto. In one embodiment, said CDR3 comprises or consists of the amino acid sequence SEQ ID NO. 371 or a sequence with at least 70%, 71%, 72%, 73%, 74%, 75%, 76%, 77%, 78%, 79%, 80%, 81%, 82%, 83%, 84%, 85%, 86%, 87%, 88%, 89%, 90%, 91%, 92%, 93%, 94%, 95%, 96%, 97%, 98% or 99% homology thereto. In one embodiment, the CDR sequences of the V$_H$ domain are as shown for clone 10.1 as in FIG. 10.

In one embodiment, the V$_H$ domain comprises or consists of SEQ ID NO. 372 or a sequence with at least 40%, 50%, 60%, 70%, 80%, 81%, 82%, 83%, 84%, 85%, 86%, 87%, 88%, 89%, 90%, 91%, 92%, 93%, 94%, 95%, 96%, 97%, 98% or 99% homology thereto.

In another embodiment, the V$_H$ domain is selected from one of the sequences above, but comprises one or more amino acid substitutions, for example 1, 2, 3, 4, 5, 6, 7, 8, 9 or 10 amino acid substitutions. In one embodiment, the one or more amino acid substitution is in one or more of the framework areas. In another embodiment, the one or more amino acid substitution is in one or more of the CDRs. In one embodiment, the amino acid substitutions are in the framework and CDR sequences.

The family 10 or family 10-like binding molecules have KD, Koff, KA, Kd, EC$_{50}$ and IC$_{50}$ values as further described herein and as shown in the examples.

In one aspect, the invention relates to a binding molecule capable of binding human PSMA comprising a V$_H$ domain comprising a family 11 or family 11-like sequence. In one embodiment, two V$_H$ domains comprising a family 11 or a family-11 like sequence may be combined for a bivalent binding molecule. In another embodiment, one V$_H$ domain comprising a family 11 or a family-11 like sequence may be combined with a second V$_H$ domain as described herein that binds to the same a epitope, part, domain, subunit or confirmation of PSMA for a bivalent binding molecule. The second V$_H$ domain may be selected from a family 2, 3, 4, 7, 9, 10, 11 or a family 2, 3, 4, 7, 9, 10, 11-like sequence.

In one embodiment, one V$_H$ domain comprising a family 11 or a family-11 like sequence may be combined with a second V$_H$ domain as described herein that binds to a different epitope, part, domain, subunit or confirmation of PSMA for a biparatopic binding molecule. The second V$_H$ domain may be selected from a family 1, 5, 6, 12 or 13 or a family 1, 5, 6, 12 or 13-like sequence.

A family 11 or family 11 sequence includes the parent sequence and sequences that are derived from the parent (11.1, SEQ ID NO. 376) or a part thereof, for example a CDR3 sequence, and V$_H$ sequences or parts thereof that are derived from the parent 11.1 through a process of optimization, CDR sequences and full-length sequences of 11.1 in are numbered according to Table 11 as shown below.

TABLE 11

This shows SEQ ID NOs of family 11 CDR sequences and of family 11 full-length V$_H$ sequences that are within the scope of the invention. Corresponding sequences are shown in FIG. 11. Family 11-like sequences are variants that have certain percentage sequence identity with Family 11 sequences as set out herein.

| Name | CDR1 | CDR2 | CDR3 | V$_H$ Full length sequence |
|---|---|---|---|---|
| 11.1 | SEQ ID NO. 373 SYGMY | SEQ ID NO. 374 VISYDGSNKNY ADSVKG | SEQ ID NO. 375 GGNALYSSG WPDD | SEQ ID NO. 376 EVQLVESGGGLVKPGGS LRLSCAASGFNLISYGMY WVRQAPGKGLEWVAVIS YDGSNKNYADSVKGRFTI SRDNSKNTLFLQMNSLRV EDTAVYYCAKGGNALYS SGWPDDGFDIRGQGTMV TVSS |

In one embodiment, the V$_H$ domain comprises at least one antigen binding site comprising a CDR3 sequence comprising SEQ ID NO. 375 or a sequence having at least 70%, at least 80%, at least 90%, or at least 95% homology to SEQ ID NO. 375. In one embodiment, homology is at least 90%. In one embodiment, the V$_H$ domain comprises a CDR3 of SEQ ID NO. 375.

In one embodiment, the single V$_H$ domain antibody comprises at least one antigen binding site comprising hypervariable region CDR3 said CDR3 having the amino acid sequence SEQ ID NO. 375 or a sequence having at least 70%, at least 80%, at least 90%, or at least 95% homology thereto. In one embodiment, the family 11 or family 11-like sequence comprises a binding molecule comprising or consisting of at least one immunoglobulin single domain antibody capable of binding PSMA wherein said domain is a human V$_H$ domain and wherein said PSMA binding molecule comprises at least one antigen binding site comprising hypervariable regions CDR1, CDR2 and CDR3, said CDR1 comprises or consists of the amino acid sequence SEQ ID NO. 373 or a sequence with at least 70%, at least 80%, at least 90%, or at least 95% homology thereto, said CDR2 comprises or consists of the amino acid sequence SEQ ID NO. 374 or a sequence with at least 70%, at least 80%, at least 90%, or at least 95% homology thereto, and said CDR3 comprises or consists of the amino acid sequence SEQ ID NO. 375 or a sequence with at least 70%, at least 80%, at least 90%, or at least 95% homology thereto.

In one embodiment, said CDR1 comprises or consists of the amino acid sequence SEQ ID NO. 373 or a sequence with at least 70%, 71%, 72%, 73%, 74%, 75%, 76%, 77%, 78%, 79%, 80%, 81%, 82%, 83%, 84%, 85%, 86%, 87%, 88%, 89%, 90%, 91%, 92%, 93%, 94%, 95%, 96%, 97%, 98% or 99% homology thereto. In one embodiment, said CDR2 comprises or consists of the amino acid sequence SEQ ID NO. 374 or a sequence with at least 70%, 71%, 72%, 73%, 74%, 75%, 76%, 77%, 78%, 79%, 80%, 81%, 82%, 83%, 84%, 85%, 86%, 87%, 88%, 89%, 90%, 91%, 92%, 93%, 94%, 95%, 96%, 97%, 98% or 99% homology thereto. In one embodiment, said CDR3 comprises or consists of the amino acid sequence SEQ ID NO. 375 or a sequence with at least 70%, 71%, 72%, 73%, 74%, 75%, 76%, 77%, 78%, 79%, 80%, 81%, 82%, 83%, 84%, 85%, comprising a family 12 or a family-12 like sequence may be combined with a second $V_H$ domain as described herein that binds to the same a epitope, part, domain, subunit or confirmation of PSMA for a bivalent binding molecule. The second $V_H$ domain may be selected from family 1, 5, 6, 12 or 13 or family 1, 5, 6, 12 or 13-like sequence.

In one embodiment, one $V_H$ domain comprising a family 12 or a family-12 like sequence may be combined with a second $V_H$ domain as described herein that binds to a different epitope, part, domain, subunit or confirmation of PSMA for a biparatopic binding molecule. The second $V_H$ domain may be selected from a family 2, 3, 4, 7, 9, 10, 11 or 14 or a family 2, 3, 4, 7, 9, 10, 11 or 14-like sequence.

A family 12 or family 12-like sequence includes the parent sequence and sequences that are derived from the parent (12.1, SEQ ID NO. 380) or a part thereof, for example a CDR3 sequence, and $V_H$ sequences or parts thereof that are derived from the parent 12.1 through a process of optimization, CDR sequences and full-length sequences of 12.1 in are numbered according to Table 12 as shown below.

TABLE 12

This shows SEQ ID NOs of family 12 CDR sequences and of family 12 full-length $V_H$ sequences that are within the scope of the invention. Corresponding sequences are shown in FIG. 12. Family 12-like sequences are variants that have certain percentage sequence identity with Family 12 sequences as set out herein.

| Name | CDR1 | CDR2 | CDR3 | $V_H$ Full length sequence |
|---|---|---|---|---|
| 12.1 | SEQ ID NO. 377 NFGMH | SEQ ID NO. 378 VISYDGNSKYYAD TVKG | SEQ ID NO. 379 GLWPPMDV | SEQ ID NO. 380 QVQLVESGGGVVQPG RSLRLSCAASGFTFSN FGMHWARQAPGKGLE WVAVISYDGNSKYYAD TVKGRFTISRDNSKNT LYLEMNSLRADDTAVY YCAKGLWPPMDVRGQ GTTVTVSS |

86%, 87%, 88%, 89%, 90%, 91%, 92%, 93%, 94%, 95%, 96%, 97%, 98% or 99% homology thereto. In one embodiment, the CDR sequences of the $V_H$ domain are as shown for sdAb 11.1 as in FIG. 11.

In one embodiment, the $V_H$ domain comprises or consists of SEQ ID NO. 376 or a sequence with at least 40%, 50%, 60%, 70%, 80%, 81%, 82%, 83%, 84%, 85%, 86%, 87%, 88%, 89%, 90%, 91%, 92%, 93%, 94%, 95%, 96%, 97%, 98% or 99% homology thereto.

In another embodiment, the $V_H$ domain is selected from one of the sequences above, but comprises one or more amino acid substitutions, for example 1, 2, 3, 4, 5, 6, 7, 8, 9 or 10 amino acid substitutions. In one embodiment, the one or more amino acid substitution is in one or more of the framework areas. In another embodiment, the one or more amino acid substitution is in one or more of the CDRs. In one embodiment, the amino acid substitutions are in the framework and CDR sequences.

The family 11 or family 11-like binding molecules have KD, Koff, KA, Kd, $EC_{50}$ and $IC_{50}$ values as further described herein and as shown in the examples.

In one aspect, the invention relates to a binding molecule capable of binding human PSMA comprising a human $V_H$ domain comprising a family 12 or family 12-like sequence. In one embodiment, two $V_H$ domains comprising a family 12 or a family-12 like sequence may be combined for a bivalent binding molecule. In another embodiment, one $V_H$ domain In one embodiment, the $V_H$ domain comprises at least one antigen binding site comprising a CDR3 sequence comprising SEQ ID NO. 379 or a sequence having at least 70%, at least 80%, at least 90%, or at least 95% homology to SEQ ID NO. 379. In one embodiment, homology is at least 90%. In one embodiment, the $V_H$ domain comprises a CDR3 of SEQ ID NO. 379.

In one embodiment, the single $V_H$ domain antibody comprises at least one antigen binding site comprising hypervariable region CDR3 said CDR3 having the amino acid sequence SEQ ID NO. 379 or a sequence having at least 70%, at least 80%, at least 90%, or at least 95% homology thereto. In one embodiment, the family 12 or family 12-like sequence comprises a binding molecule comprising or consisting of at least one immunoglobulin single domain antibody capable of binding PSMA wherein said domain is a human $V_H$ domain and wherein said PSMA binding molecule comprises at least one antigen binding site comprising hypervariable regions CDR1, CDR2 and CDR3, said CDR1 comprises or consists of the amino acid sequence SEQ ID NO. 377 or a sequence with at least 70%, at least 80%, at least 90%, or at least 95% homology thereto, said CDR2 comprises or consists of the amino acid sequence SEQ ID NO. 378 or a sequence with at least 70%, at least 80%, at least 90%, or at least 95% homology thereto, and said CDR3 comprises or consists of the amino acid sequence SEQ ID NO. 379 or a sequence with at least 70%, at least 80%, at least 90%, or at least 95% homology thereto.

In one embodiment, said CDR1 comprises or consists of the amino acid sequence SEQ ID NO. 377 or a sequence with at least 70%, 71%, 72%, 73%, 74%, 75%, 76%, 77%, 78%, 79%, 80%, 81%, 82%, 83%, 84%, 85%, 86%, 87%, 88%, 89%, 90%, 91%, 92%, 93%, 94%, 95%, 96%, 97%, 98% or 99% homology thereto. In one embodiment, said CDR2 comprises or consists of the amino acid sequence SEQ ID NO. 378 or a sequence with at least 70%, 71%, 72%, 73%, 74%, 75%, 76%, 77%, 78%, 79%, 80%, 81%, 82%, 83%, 84%, 85%, 86%, 87%, 88%, 89%, 90%, 91%, 92%, 93%, 94%, 95%, 96%, 97%, 98% or 99% homology thereto. In one embodiment, said CDR3 comprises or consists of the amino acid sequence SEQ ID NO. 379 or a sequence with at least 70%, 71%, 72%, 73%, 74%, 75%, 76%, 77%, 78%, 79%, 80%, 81%, 82%, 83%, 84%, 85%, 86%, 87%, 88%, 89%, 90%, 91%, 92%, 93%, 94%, 95%, 96%, 97%, 98% or 99% homology thereto. In one embodiment, the CDR sequences of the $V_H$ domain are as shown for clone 12.1 as in FIG. 12.

In one embodiment, the $V_H$ domain comprises or consists of SEQ ID NO. 380 or a sequence with at least 40%, 50%, 60%, 70%, 80%, 81%, 82%, 83%, 84%, 85%, 86%, 87%, 88%, 89%, 90%, 91%, 92%, 93%, 94%, 95%, 96%, 97%, 98% or 99% homology thereto.

In another embodiment, the $V_H$ domain is selected from one of the sequences above, but comprises one or more amino acid substitutions, for example 1, 2, 3, 4, 5, 6, 7, 8, 9 or 10 amino acid substitutions. In one embodiment, the one or more amino acid substitution is in one or more of the framework areas. In another embodiment, the one or more amino acid substitution is in one or more of the CDRs. In one embodiment, the amino acid substitutions are in the framework and CDR sequences.

The family 12 or family 12-like binding molecules have KD, Koff, KA, Kd, $EC_{50}$ and $IC_{50}$ values as further described herein and as shown in the examples In one aspect, the invention relates to a binding molecule capable of binding human PSMA comprising a human $V_H$ domain comprising a family 13 or family 13-like sequence. In one embodiment, two $V_H$ domains comprising a family 13 or a family-13 like sequence may be combined for a bivalent binding molecule. In another embodiment, one $V_H$ domain comprising a family 13 or a family-13 like sequence may be combined with a second $V_H$ domain as described herein that binds to the same a epitope, part, domain, subunit or confirmation of PSMA for a bivalent binding molecule. The second $V_H$ domain may be selected from family 1, 5, 6, 12 or 13 or family 1, 5, 6, 12 or 13-like sequence.

In one embodiment, one $V_H$ domain comprising a family 13 or a family-13 like sequence may be combined with a second $V_H$ domain as described herein that binds to a different epitope, part, domain, subunit or confirmation of PSMA for a biparatopic binding molecule. The second $V_H$ domain may be selected from a family 2, 3, 4, 7, 9, 10, 11 or 14 or a family 2, 3, 4, 7, 9, 10, 11 or 14-like sequence.

A family 13 or family-like 13 sequence includes the parent sequence and sequences that are derived from the parent (13.1, SEQ ID NO. 384) or a part thereof, for example a CDR3 sequence, and $V_H$ sequences of clones or parts thereof that are derived from the parent 13.1 through a process of optimization, CDR sequences and full-length sequences of 13.1 in are numbered according to Table 13 as shown below.

TABLE 13

This shows SEQ ID NOs of family 13 CDR sequences and of family 13 full-length $V_H$ sequences that are within the scope of the invention. Corresponding sequences are shown in FIG. 13. Family 13-like are variants sequences that have certain percentage sequence identity with Family 13 sequences as set out herein.

| Name | CDR1 | CDR2 | CDR3 | $V_H$ Full length sequence |
|---|---|---|---|---|
| 13.1 | SEQ ID NO. 381 DYWMT | SEQ ID NO. 382 NIKQDGSEKYY VDSVKG | SEQ ID NO. 383 DRGGAVALY HNGMDM | SEQ ID NO. 384 EVQLVESGGGSVQPGG SLRLSCAASGFTFSDYW MTWVRQVPGKGLEWV ANIKQDGSEKYYVDSVK GRFTISRDNAKNSLYLQ MNSLRAEDTAVYYCAR DRGGAVALYHNGMDM GGQGTTVTVSS |

In one embodiment, the $V_H$ domain comprises at least one antigen binding site comprising a CDR3 sequence comprising SEQ ID NO. 383 or a sequence having at least 70%, at least 80%, at least 90%, or at least 95% homology to SEQ ID NO. 383. In one embodiment, homology is at least 90%. In one embodiment, the $V_H$ domain comprises a CDR3 of SEQ ID NO. 383.

In one embodiment, the single $V_H$ domain antibody comprises at least one antigen binding site comprising hypervariable region CDR3 said CDR3 having the amino acid sequence SEQ ID NO. 383 or a sequence having at least 70%, at least 80%, at least 90%, or at least 95% homology thereto. In one embodiment, the family 13 or family 13-like sequence comprises a binding molecule comprising or consisting of at least one immunoglobulin single domain antibody capable of binding PSMA wherein said domain is a human $V_H$ domain and wherein said PSMA binding molecule comprises at least one antigen binding site comprising hypervariable regions CDR1, CDR2 and CDR3, said CDR1 comprises or consists of the amino acid sequence SEQ ID NO. 381 or a sequence with at least 70%, at least 80%, at least 90%, or at least 95% homology thereto, said CDR2 comprises or consists of the amino acid sequence SEQ ID NO. 382 or a sequence with at least 70%, at least 80%, at least 90%, or at least 95% homology thereto, and said CDR3 comprises or consists of the amino acid sequence SEQ ID NO. 383 or a sequence with at least 70%, at least 80%, at least 90%, or at least 95% homology thereto.

In one embodiment, said CDR1 comprises or consists of the amino acid sequence SEQ ID NO. 381 or a sequence with at least 70%, 71%, 72%, 73%, 74%, 75%, 76%, 77%, 78%, 79%, 80%, 81%, 82%, 83%, 84%, 85%, 86%, 87%, 88%, 89%, 90%, 91%, 92%, 93%, 94%, 95%, 96%, 97%, 98% or 99% homology thereto. In one embodiment, said CDR2 comprises or consists of the amino acid sequence SEQ ID NO. 382 or a sequence with at least 70%, 71%, 72%, 73%, 74%, 75%, 76%, 77%, 78%, 79%, 80%, 81%, 82%, 83%, 84%, 85%, 86%, 87%, 88%, 89%, 90%, 91%, 92%, 93%, 94%, 95%, 96%, 97%, 98% or 99% homology thereto. In one embodiment, said CDR3 comprises or consists of the amino acid sequence SEQ ID NO. 383 or a sequence with at least 70%, 71%, 72%, 73%, 74%, 75%, 76%, 77%, 78%, 79%, 80%, 81%, 82%, 83%, 84%, 85%, 86%, 87%, 88%, 89%, 90%, 91%, 92%, 93%, 94%, 95%, 96%, 97%, 98% or 99% homology thereto. In one embodiment, the CDR sequences of the $V_H$ domain are as shown for clone 13.1 as in FIG. 13.

In one embodiment, the $V_H$ domain comprises or consists of SEQ ID NO. 384 or a sequence with at least 40%, 50%, 60%, 70%, 80%, 81%, 82%, 83%, 84%, 85%, 86%, 87%, 88%, 89%, 90%, 91%, 92%, 93%, 94%, 95%, 96%, 97%, 98% or 99% homology thereto.

In another embodiment, the $V_H$ domain is selected from one of the sequences above, but comprises one or more amino acid substitutions, for example 1, 2, 3, 4, 5, 6, 7, 8, 9 or 10 amino acid substitutions. In one embodiment, the one or more amino acid substitution is in one or more of the framework areas. In another embodiment, the one or more amino acid substitution is in one or more of the CDRs. In one embodiment, the amino acid substitutions are in the framework and CDR sequences.

The family 13 or family 13-like binding molecules have KD, Koff, KA, Kd, $EC_{50}$ and $IC_{50}$ values as further described herein and as shown in the examples In one aspect, the invention relates to a binding molecule capable of binding human PSMA comprising a human $V_H$ domain comprising a family 14 or family 14-like sequence. In one embodiment, two $V_H$ domains comprising a family 14 or a family-14 like sequence may be combined for a bivalent binding molecule. In another embodiment, one $V_H$ domain comprising a family 14 or a family-14 like sequence may be combined with a second $V_H$ domain as described herein that binds to the same a epitope, part, domain, subunit or confirmation of PSMA for a bivalent binding molecule. The second $V_H$ domain may be selected from a family 2, 3, 4, 7, 9, 10, 11 or a family 2, 3, 4, 7, 9, 10, 11-like sequence.

In one embodiment, one $V_H$ domain comprising a family 14 or a family-14 like sequence may be combined with a second $V_H$ domain as described herein that binds to a different epitope, part, domain, subunit or confirmation of PSMA for a biparatopic binding molecule. The second $V_H$ domain may be selected from a family 1, 5, 6, 12 or 13 or a family 1, 5, 6, 12 or 13-like sequence.

A family 14 or family 14 sequence includes the parent sequence and sequences of clones that are derived from the parent (14.1) or a part thereof, for example a CDR3 sequence, and $V_H$ sequences or parts thereof that are derived from the parent 14.1 through a process of optimization, CDR sequences and full-length sequences of 14.1 in are numbered according to Table 14 as shown below.

TABLE 14

This shows SEQ ID NOs of family 14 CDR sequences and of family 14 full-length $V_H$ sequences that are within the scope of the invention. Corresponding sequences are shown in FIG. 14. Family 14-like sequences are variants that have certain percentage sequence identity with Family 14 sequences as set out herein.

| Name | CDR1 | CDR2 | CDR3 | $V_H$ Full length sequence |
|---|---|---|---|---|
| 14.1 | SEQ ID NO. 385 SYDIN | SEQ ID NO. 386 WMNPNSGNTG YAQKFQG | SEQ ID NO. 387 GNGPGITGTT DY | SEQ ID NO. 388 KCSWWSLGEVKKPGAS VKVSCKASGYTFTSYDI NWVRQATGQGLEWMG WMNPNSGNTGYAQKF QGRVTMTRNTSISTAYM ELSSLRSEDTAVYYCAR GNGPGITGTTDYWGQG TLVTVSS |

In one embodiment, the $V_H$ domain comprises at least one antigen binding site comprising a CDR3 sequence comprising SEQ ID NO. 387 or a sequence having at least 70%, at least 80%, at least 90%, or at least 95% homology to SEQ ID NO. 387. In one embodiment, homology is at least 90%. In one embodiment, the $V_H$ domain comprises a CDR3 of SEQ ID NO. 387.

In one embodiment, the single $V_H$ domain antibody comprises at least one antigen binding site comprising hypervariable region CDR3 said CDR3 having the amino acid sequence SEQ ID NO. 385 or a sequence having at least 70%, at least 80%, at least 90%, or at least 95% homology thereto. In one embodiment, the family 14 or family 14-like sequence comprises a binding molecule comprising or consisting of at least one immunoglobulin single domain antibody capable of binding PSMA wherein said domain is a human $V_H$ domain and wherein said PSMA binding molecule comprises at least one antigen binding site comprising hypervariable regions CDR1, CDR2 and CDR3, said CDR1 comprises or consists of the amino acid sequence SEQ ID NO. 385 or a sequence with at least 70%, at least 80%, at least 90%, or at least 95% homology thereto, said CDR2 comprises or consists of the amino acid sequence SEQ ID NO. 386 or a sequence with at least 70%, at least 80%, at least 90%, or at least 95% homology thereto, and said CDR3 comprises or consists of the amino acid sequence SEQ ID NO. 387 or a sequence with at least 70%, at least 80%, at least 90%, or at least 95% homology thereto.

In one embodiment, said CDR1 comprises or consists of the amino acid sequence SEQ ID NO. 385 or a sequence with at least 70%, 71%, 72%, 73%, 74%, 75%, 76%, 77%, 78%, 79%, 80%, 81%, 82%, 83%, 84%, 85%, 86%, 87%, 88%, 89%, 90%, 91%, 92%, 93%, 94%, 95%, 96%, 97%, 98% or 99% homology thereto. In one embodiment, said CDR2 comprises or consists of the amino acid sequence SEQ ID NO. 386 or a sequence with at least 70%, 71%, 72%, 73%, 74%, 75%, 76%, 77%, 78%, 79%, 80%, 81%, 82%, 83%, 84%, 85%, 86%, 87%, 88%, 89%, 90%, 91%, 92%, 93%, 94%, 95%, 96%, 97%, 98% or 99% homology thereto. In one embodiment, said CDR3 comprises or consists of the amino acid sequence SEQ ID NO. 387 or a sequence with at least 70%, 71%, 72%, 73%, 74%, 75%, 76%, 77%, 78%, 79%, 80%, 81%, 82%, 83%, 84%, 85%, 86%, 87%, 88%, 89%, 90%, 91%, 92%, 93%, 94%, 95%, 96%, 97%, 98% or 99% homology thereto. In one embodiment, the CDR sequences of the $V_H$ domain are as shown for clone 14.1 as in FIG. 14.

In one embodiment, the $V_H$ domain comprises or consists of SEQ ID NO. 388 or a sequence with at least 40%, 50%, 60%, 70%, 80%, 81%, 82%, 83%, 84%, 85%, 86%, 87%, 88%, 89%, 90%, 91%, 92%, 93%, 94%, 95%, 96%, 97%, 98% or 99% homology thereto.

In another embodiment, the $V_H$ domain is selected from one of the sequences above, but comprises one or more amino acid substitutions, for example 1, 2, 3, 4, 5, 6, 7, 8, 9 or 10 amino acid substitutions. In one embodiment, the one or more amino acid substitution is in one or more of the framework areas. In another embodiment, the one or more amino acid substitution is in one or more of the CDRs. In one embodiment, the amino acid substitutions are in the framework and CDR sequences.

The family 14 or family 14-like binding molecules have KD, Koff, KA, Kd, $EC_{50}$ and $IC_{50}$ values as further described herein and as shown in the examples In one aspect, the invention relates to a binding molecule capable of binding human PSMA comprising a human $V_H$ domain comprising a family 15 or family 15-like sequence. In one embodiment, the binding molecule comprises at least two one single $V_H$ domain antibodies capable of binding PSMA, preferably human PSMA, of family 15 or family 15 sequence.

Family 15 single $V_H$ domain antibodies include the parent sequence and sequences that are derived from the parent (15.1) or a part thereof, for example a CDR3 sequence, and $V_H$ sequences or parts thereof that are derived from the parent 15.1 through a process of optimization, CDR sequences and full-length sequences of 15.1 in are numbered according to Table 15 as shown below.

In one embodiment, the $V_H$ domain comprises a CDR3 of SEQ ID NO. 391.

In one embodiment, the single $V_H$ domain antibody comprises at least one antigen binding site comprising hypervariable region CDR3 said CDR3 having the amino acid sequence SEQ ID NO. 391 or a sequence having at least 70%, at least 80%, at least 90%, or at least 95% homology thereto. In one embodiment, the family 15 or family 15-like sequence comprises a binding molecule comprising or consisting of at least one immunoglobulin single domain antibody capable of binding PSMA wherein said domain is a human $V_H$ domain and wherein said PSMA binding molecule comprises at least one antigen binding site comprising hypervariable regions CDR1, CDR2 and CDR3, said CDR1 comprises or consists of the amino acid sequence SEQ ID NO. 389 or a sequence with at least 70%, at least 80%, at least 90%, or at least 95% homology thereto, said CDR2 comprises or consists of the amino acid sequence SEQ ID NO. 390 or a sequence with at least 70%, at least 80%, at least 90%, or at least 95% homology thereto, and said CDR3 comprises or consists of the amino acid sequence SEQ ID NO. 391 or a sequence with at least 70%, at least 80%, at least 90%, or at least 95% homology thereto.

In one embodiment, said CDR1 comprises or consists of the amino acid sequence SEQ ID NO. 389 or a sequence with at least 70%, 71%, 72%, 73%, 74%, 75%, 76%, 77%, 78%, 79%, 80%, 81%, 82%, 83%, 84%, 85%, 86%, 87%, 88%, 89%, 90%, 91%, 92%, 93%, 94%, 95%, 96%, 97%, 98% or 99% homology thereto. In one embodiment, said CDR2 comprises or consists of the amino acid sequence SEQ ID NO. 390 or a sequence with at least 70%, 71%, 72%, 73%, 74%, 75%, 76%, 77%, 78%, 79%, 80%, 81%, 82%, 83%, 84%, 85%, 86%, 87%, 88%, 89%, 90%, 91%, 92%, 93%, 94%, 95%, 96%, 97%, 98% or 99% homology thereto. In one embodiment, said CDR3 comprises or consists of the amino acid sequence SEQ ID NO. 391 or a sequence with at least 70%, 71%, 72%, 73%, 74%, 75%, 76%, 77%, 78%, 79%, 80%, 81%, 82%, 83%, 84%, 85%, 86%, 87%, 88%, 89%, 90%, 91%, 92%, 93%, 94%, 95%,

TABLE 15

This shows SEQ ID NOs of family 15 CDR sequences and of family 15 full length $V_H$ sequences that are within the scope of the invention. Corresponding sequences are shown in FIG. 15. Family 15-like sequences are variants that have certain percentage sequence identity with Family 15 sequences as set out herein.

| Name | CDR1 | CDR2 | CDR3 | $V_H$ Full length sequence |
|---|---|---|---|---|
| 15.1 | SEQ ID NO. 389 DYGMS | SEQ ID NO. 390 GINWNGDRTGY ADSVKG | SEQ ID NO. 391 ENVIVPAATY | SEQ ID NO. 392 EVQLVESGGGVV RPGGSLRLSCAA SGFTFDDYGMSW VRQAPGKGLEWV SGINWNGDRTGY ADSVKGRFTISRD NAKNSLYLQMNSL RAEDTALYYCGR ENVIVPAATYWGQ GTLVTVSS |

In one embodiment, the $V_H$ domain comprises at least one antigen binding site comprising a CDR3 sequence comprising SEQ ID NO. 391 or a sequence having at least 70%, at least 80%, at least 90%, or at least 95% homology to SEID NO. 391. In one embodiment, homology is at least 90%.

96%, 97%, 98% or 99% homology thereto. In one embodiment, the CDR sequences of the $V_H$ domain are as shown for clone 15.1 as in FIG. 15.

In one embodiment, the $V_H$ domain comprises or consists of SEQ ID NO. 392 or a sequence with at least 40%, 50%, 60%, 70%, 80%, 81%, 82%, 83%, 84%, 85%, 86%, 87%, 88%, 89%, 90%, 91%, 92%, 93%, 94%, 95%, 96%, 97%, 98% or 99% homology thereto.

In another embodiment, the $V_H$ domain is selected from one of the sequences above, but comprises one or more amino acid substitutions, for example 1, 2, 3, 4, 5, 6, 7, 8, 9 or 10 amino acid substitutions. In one embodiment, the one or more amino acid substitution is in one or more of the framework areas. In another embodiment, the one or more amino acid substitution is in one or more of the CDRs. In one embodiment, the amino acid substitutions are in the framework and CDR sequences.

The family 15 or family 15-like binding molecules have KD, Koff, KA, Kd, $EC_{50}$ and $IC_{50}$ values as further described herein and as shown in the examples In one aspect, the single $V_H$ domain antibody comprises a CDR3 sequence selected from a family 1 or family 1-like, family 2 or family 2-like, family 3 or family 3-like, family 4 or family 4-like, family 5 or family 5-like, family 6 or family 6-like, family 7 or family 7-like, family 8 or family 8-like, family 9 or family 9-like, family 10 or family 10-like, family 11 or family 11-like, family 12 or family 12-like, family 13 or family 13-like, family 14 or family 14-like or a family 15 or family 15-like CDR3 sequence combined with a CDR1 and CDR2 sequence from another family listed herein.

For example, the single $V_H$ domain antibody comprises a family 1 or family 1-like CDR3 sequence combined with a CDR1 and a CDR2 sequence from one or two other families as shown in any of Tables 2 to 15.

In another aspect, the single $V_H$ domain antibody comprises a family 2 or family 2-like CDR3 sequence combined with a CDR1 and a CDR2 sequence from one or two other families as shown in any of Tables 1, 3 to 15. Various combinations are possible as would be appreciated by a skilled person.

In another aspect, the single $V_H$ domain antibody comprises a family 3 or family 3-like CDR3 sequence combined with a CDR1 and a CDR2 sequence from one or two other families as shown in any of Tables 1, 2, 4 to 15. Various combinations are possible as would be appreciated by a skilled person.

In another aspect, the single $V_H$ domain antibody comprises a family 4 or family 4-like CDR3 sequence combined with a CDR1 and a CDR2 sequence from one or two other families as shown in Table 1 any of Tables 1 to 3, 5 to 15. Various combinations are possible as would be appreciated by a skilled person.

In another aspect, the single $V_H$ domain antibody comprises a family 5 or family 5-like CDR3 sequence combined with a CDR1 and a CDR2 sequence from one or two other families as shown in any of Tables 1 to 4, 6 to 15. Various combinations are possible as would be appreciated by a skilled person.

In another aspect, the single $V_H$ domain antibody comprises a family 6 or family 6-like CDR3 sequence combined with a CDR1 and a CDR2 sequence from one or two other families as shown in any of Tables 1 to 5, 7 to 15. Various combinations are possible as would be appreciated by a skilled person.

In another aspect, the single $V_H$ domain antibody comprises a family 7 or family 7-like CDR3 sequence combined with a CDR1 and a CDR2 sequence from one or two other families as shown in any of Tables 1 to 6, 8 to 15. Various combinations are possible as would be appreciated by a skilled person.

In another aspect, the single $V_H$ domain antibody comprises a family 8 or family 8-like CDR3 sequence combined with a CDR1 and a CDR2 sequence from one or two other families as shown in any of Tables 1 to 7, 9 to 15. Various combinations are possible as would be appreciated by a skilled person.

In another aspect, the single $V_H$ domain antibody comprises a family 9 or family 9-like CDR3 sequence combined with a CDR1 and a CDR2 sequence from one or two other families as shown in any of Tables 1 to 8, 10 to 15. Various combinations are possible as would be appreciated by a skilled person.

In another aspect, the single $V_H$ domain antibody comprises a family 10 family 10-like CDR3 sequence combined with a CDR1 and a CDR2 sequence from one or two other families as shown in any of Tables 1 to 4, 11 to 15. Various combinations are possible as would be appreciated by a skilled person.

In another aspect, the single $V_H$ domain antibody comprises a family 11 or family 11-like CDR3 sequence combined with a CDR1 and a CDR2 sequence from one or two other families as shown in any of Tables 1 to 10, 12 to 15. Various combinations are possible as would be appreciated by a skilled person.

In another aspect, the single $V_H$ domain antibody comprises a family 12 or family 12-like CDR3 sequence combined with a CDR1 and a CDR2 sequence from one or two other families as shown in any of Tables 1 to 11, 13 to 15. Various combinations are possible as would be appreciated by a skilled person.

In another aspect, the single $V_H$ domain antibody comprises a family 13 or family 13-like CDR3 sequence combined with a CDR1 and a CDR2 sequence from one or two other families as shown in any of Tables 1 to 12, 14 to 15. Various combinations are possible as would be appreciated by a skilled person.

In another aspect, the single $V_H$ domain antibody comprises a family 15 or family 15-like CDR3 sequence combined with a CDR1 and a CDR2 sequence from one or two other families as shown in any of Tables 1 to 14. Various combinations are possible as would be appreciated by a skilled person.

The invention also relates to a binding molecule comprising a first $V_H$ domain selected from one of the $V_H$ domains described above and listed in any of Tables 1 to 15 linked to a second $V_H$ domain selected from a described above and listed in any of Tables 1 to 15 wherein said first $V_H$ domain competes for binding to PSMA with the second $V_H$ domain in a competitive assay.

The invention also relates to a binding molecule comprising a first $V_H$ domain selected from one of the $V_H$ domains described above and listed in any of Tables 1 to 15 linked to a second $V_H$ domain selected from a described above and listed in any of Tables 1 to 15 wherein said first $V_H$ domain does not compete for binding to PSMA with the second $V_H$ domain in a competitive assay.

In preferred embodiment, the binding molecule is biparatopic or multiparatopic and comprises a first single $V_H$ domain antibody selected from single domain antibodies 1.1 to 1.20 as shown in Table 1, and a second single $V_H$ domain antibody selected from 2.1 to 2.25 as shown in Table 2. For example, the first single $V_H$ domain antibody is selected from single domain antibodies 1.1, 1.8-1.20 as shown in Table 1, and a second single $V_H$ domain antibody is selected from 2.1, 2.2, 2.11-2.19, 2.22-2.25 as shown in Table 2. In another embodiment, the binding molecule comprises a first single domain antibody selected from single domain antibodies 2.1 to 2.25 as shown in Table 2 and a second $V_H$ single domain antibody selected from 1.1 to 1.20 as shown in Table 1. For example, the first single $V_H$ domain antibody is selected from single domain antibodies 2.1, 2.2, 2.11-2.19, 2.22-2.25 as shown in Table 2, and the second single $V_H$ domain antibody is selected from 1.1, 1.8-1.20 as shown in Table 1. Single domain antibodies are linked with a $(G_4S)n$ linker, preferably a $(G_4S)n$. In further preferred embodiments, the binding molecules is selected from a binding molecule that comprises the following components: single $V_H$ domain antibody-linker-single $V_H$ domain antibody as follows:
1.1-6GS-2.1, 1.8-6GS-2.1, 1.1-6GS-2.17, 1.1-6GS-2.15, 1.1-6GS-2.22, 1.16-6GS-2.1, 1.16-6GS-2.17, 1.16-6GS-2.15, 1.16-6GS-2.22, 1.11-6GS-2.1, 1.11-6GS-2.17, 1.11-6GS-2.15, 1.11-6GS-2.22, 1.18-6GS-2.1, 1.18-6GS-2.17, 1.18-6GS-2.15, 1.18-6GS-2.22, 1.17-6GS-2.1, 1.17-6GS-2.17, 1.17-6GS-2.15 or 1.17-6GS-2.22.

In another embodiment, single $V_H$ domain antibodies as described above can be replaced with binding molecules, e.g. antibodies, antibody fragments or antibody mimetics, that bind to the same epitope on human PSMA as a single domain antibodies (i.e., antibodies that have the ability to cross-compete for binding to PSMA with any of the single domain antibodies described herein). The single domain antibodies described herein can thus be used as a reference antibody. In preferred embodiments, the reference antibody for cross-competition studies is single domain antibody 1.1, 2.1, 3.1, 4.1, 5.1, 6.1, 7.1, 8.1, 9.1, 10.1, 11.1, 12.1, 13.1, 14.1 or 15.1. Such cross-competing antibodies can be identified based on their ability to cross-compete with any of single domain antibodies described herein in standard PSMA binding assays. For example, BIAcore® analysis, ELISA assays or flow cytometry may be used to demonstrate cross-competition with the single domain antibodies of the current invention. In one embodiment, the invention provides a binding agent capable of binding human PSMA wherein any one of the single domain antibodies described above displaces the binding agent in a competitive assay.

A binding molecule described herein may be provided as a fusion protein with one or more additional protein moiety.

The second moiety may comprise a $V_H$ domain that is also specific for human PSMA thus providing a bivalent binding molecule. In one embodiment, the binding molecule is biparatopic. Biparatopic binding molecules comprise antigen-binding moieties that bind to different epitopes. Biparatopic binding molecules of the present invention can be constructed using methods known art.

Suitable linkers to connect the moieties of the binding molecule include peptide linker, for example linkers that include GS residues such as $(Gly_4Ser)_n$, where n=from 1 to 10, e.g., 1, 2, 3, 4, 5, 6, 7, 8, 9 or 10. As used herein, GS designates $Gly_4Ser$. $(Gly_4Ser)_n$ is also expressed as nGS herein.

In another embodiment, the binding molecule may comprise a further moiety that is specific for a different antigen to provide a bispecific binding molecule. As used herein, the term "bispecific binding molecule" thus refers to a polypeptide that comprises a binding molecule as described herein which has a binding site that has binding specificity for PSMA, and a second polypeptide domain which has a binding site that has binding specificity for a second target, i.e., the bispecific binding molecule has specificity for two targets. The first target and the second target are not the same, i.e. are different targets, e.g., proteins; both may be present on a cell surface. Accordingly, a bispecific binding molecule as described herein can selectively and specifically bind to a cell that expresses (or displays on its cell surface) the first target and the second target. In another embodiment, the binding molecule comprises more than two antigen-binding moieties.

In another embodiment, more than two moieties are joined together providing a multispecific binding molecule. A multispecific polypeptide agent as described herein can in addition to binding PSMA bind one or more additional targets, i.e., a multispecific polypeptide can bind at least two, at least three, at least four, at least five, at least six, or more targets, wherein the multispecific polypeptide agent has at least two, at least, at least three, at least four, at least five, at least six, or more target binding sites respectively.

As used herein, the term "target" refers to a biological molecule (e.g., antigen, peptide, polypeptide, protein, lipid, carbohydrate) to which a polypeptide domain which has a binding site can selectively bind. The target can be, for example, an intracellular target (such as an intracellular protein target) or a cell-surface target (such as a membrane protein, e.g., a receptor protein). Preferably, a target is a cell-surface target, such as a cell-surface protein. Preferably, the first cell-surface target and second cell-surface target are both present on a cell. In one embodiment, the target is an immunooncology target.

Multispecific antibodies of the present invention can be constructed using methods known art.

If desired, bispecific or multispecific binding molecules can be linked to an antibody Fc region or fragment thereof, comprising one or both of $C_H2$ and $C_H3$ domains, and optionally a hinge region. For example, vectors encoding bispecific or multispecific binding molecules linked as a single nucleotide sequence to an Fc region or fragment thereof can be used to prepare such polypeptides.

In one embodiment, the further moiety may serve to prolong the half-life of the binding molecule. The second moiety may comprise a protein, for example and antibody, or part thereof that binds a serum albumin, e.g., human serum albumin (HSA) or mouse serum albumin (MSA). The further moiety may comprise a $V_H$ domain that binds serum albumin, e.g., human serum albumin (HSA) or mouse serum albumin (MSA).

The further moiety may comprise a serum albumin, e.g. a human serum albumin (HSA) or a variant thereof such as HSA C34S. Further provided is binding molecule as described herein comprising a $V_H$ domain and an Fc domain, e.g., wherein the $V_H$ domain is fused to an Fc domain. Further provided is a binding molecule that comprises a second variable domain that specifically binds a second antigen, where the second antigen is an antigen other than human PSMA. The second antigen may be a cluster of differentiation (CD) molecule or a Major Histocompatibility Complex (MHC) Class II molecule.

In one embodiment, the binding molecule of the invention is labelled with a detectable or functional label. A label can be any molecule that produces or can be induced to produce a signal, including but not limited to fluorescers, radiolabels, enzymes, chemiluminescers, a nuclear magnetic resonance active label or photosensitizers. Thus, the binding may be detected and/or measured by detecting fluorescence or luminescence, radioactivity, enzyme activity or light absorbance.

In still other embodiments, the binding molecule of the invention is coupled to at least one therapeutic moiety, such as a drug, an enzyme or a toxin. In one embodiment, the therapeutic moiety is a toxin, for example a cytotoxic radionuclide, chemical toxin or protein toxin. For example, the PSMA binding molecule of the invention, can be coupled to a radioactive isotope such as an α-, β-, or γ-emitter, or a β- and γ-emitter.

The toxin may be selected from calicheamicin, esperamicin, methotrexate, doxorubicin, melphalan, chlorambucil, ARA-C, vindesine, mitomycin C, cis-platinum, etoposide, bleomycin, 5-fluorouracil, estramustine, vincristine, etoposide, doxorubicin, paclitaxel, docetaxel, dolastatin 10, auristatin E and auristatin PHE. In other embodiments, the therapeutic moiety is an immunostimulatory or immunomodulating agent.

In one aspect, the invention provides an immunoconjugate comprising more than one single $V_H$ domain antibody described herein.

Toxin-conjugated forms of the PSMA binding molecules of the present invention preferably mediate specific cell killing of PSMA-expressing cells at picomolar concentrations.

In another aspect, the PSMA binding molecules of the invention are modified to increase half-life, for example by a chemical modification, especially by PEGylation, or by incorporation in a liposome or using a serum albumin protein.

In one embodiment, the binding molecule of the invention is covalently modified. The term "covalently modified/covalent modification" includes modifications of a binding molecule according to the present invention, e.g., of a specified sequence herein; with an organic proteinaceous or non-proteinaceous derivatizing agent, fusions to heterologous polypeptide sequences, and post-translational modifications. Covalent modified polypeptides, e.g., of a specified sequence, still have the functional properties described herein, for example the ability to bind the human PSMA or, Covalent modifications are generally introduced by reacting targeted amino acid residues with an organic derivatizing agent that is capable of reacting with selected side chains or terminal residues, or by harnessing mechanisms of post-translational modifications that function in selected recombinant host cells. Certain post-translational modifications are the result of the action of recombinant host cells on the expressed polypeptide. Glutaminyl and asparaginyl residues are frequently post-translationally deamidated to the corresponding glutamyl and aspartyl residues. Alternatively, these residues are deaminated under mildly acidic conditions. Other post-translational modifications include hydroxylation of proline and lysine, phosphorylation of hydroxyl groups of seryl, tyrosine or threonyl residues, methylation of the [alpha]-amino groups of lysine, arginine, and histidine side chains. Covalent modifications, e.g., include fusion proteins comprising a PSMA binding molecule according to the present invention, e.g., of a specified sequence and their amino acid sequence variants, such as immunoadhesins, and N-terminal fusions to heterologous signal sequences.

The binding molecules of the invention have certain functional properties as further described below. These and other pharmacological activities of the binding molecules of the invention may be demonstrated in standard test methods for example as described in the art.

The binding molecules of the invention can be internalised into a cell along with the prostate-specific membrane antigen. Binding molecules of the invention bind specifically to epitopes on the extracellular domain of human PSMA. In embodiment, binding molecules of the invention specifically bind PSMA in its dimeric form. Binding molecules of the invention can be conjugated to a toxic moiety and used to ablate or kill PSMA-expressing prostatic or cancerous cells.

Binding molecules of the invention can bind live cells, such as a tumor cell or a prostate cell, such as human PSMA expressing CHO cells, LNCaP cells as shown in the examples and accompanying Tables. In a further aspect, the present invention provides single domain antibodies that bind to PSMA with an EC50 value of between 100 nM and 100 pM, such as at an average EC50 value of 100 nM or less, even more preferably at an average EC50 value of 90 nM or less, such as less than 80, 70, 60, 50, 40, 30, 20, 10, 5 nM or even less, such as less than 4, 3, 2, or 1 nM or even less, such as less than 500, 400, 300, 200, 100 pM, or even less, such as less than 4 pM, preferably as measured in a FMAT binding assay. In particular, EC50 values are shown in Table 19. In one embodiment, binding molecules of the invention are capable of binding specifically to human PSMA and to cynomolgus monkey PSMA.

Potency is normally expressed as an $IC_{50}$ value, in nM unless otherwise stated. In functional assays, $IC_{50}$ is the concentration of a binding member that reduces a biological response by 50% of its maximum. $IC_{50}$ may be calculated by plotting % of maximal biological response as a function of the log of the binding member concentration, and using a software program to fit a sigmoidal function to the data to generate $IC_{50}$ values. Methods for measuring $IC_{50}$ are well known in the art. For example, to determine the $IC_{50}$, a HIS ZAP Cell Killing assay may be employed to determine $IC_{50}$. $EC_{50}$ designates the half maximal effective concentration.

In another aspect, the invention relates to a binding molecule comprising or consisting of at least one immunoglobulin single domain antibody directed against PSMA, preferably human PSMA, wherein said domain is a human $V_H$ domain and has an $IC_{50}$ of about 0.2 to about 1000 nM or more, for example 0.2 to 900, 0.2 to 800, 0.2 to 700, 0.2 to 600, 0.2 to 500, 0.2 to 400, 0.2 to 300, 0.2 to 200, 0.2 to 100, 0.2 to 50, 0.2 to 40, 0.2 to 30, 0.2 to 20, 0.2 to 10, 0.2 to 9, 0.2 to 8, 0.2 to 7, 0.2 to 6, 0.2 to 5, 0.2 to 4, 0.2 to 3, 0.2 to 2 or 0.2 to 1 when tested as described in the examples.

Additionally, binding kinetics and affinity (expressed as the equilibrium dissociation constant, KD) of PSMA binding molecules of the invention for binding PSMA may be determined, e.g., using surface plasmon resonance such as BIAcore® or Octet, or KD may be estimated from pA2 analysis. In particular, the molecules of the invention are very potent (i.e., EC50 values as measured, e.g., in the experimental part in the pM range).

In a further aspect, the present invention provides a single domain antibody as described herein, wherein said sdAb binds to said PSMA with an average KD value of between 100 nM and 10 pM, such as at an average KD value of 90 nM or less, even more preferably at an average KD value of 80 nM or less, such as less than 70, 60, 50, 40, 30, 20, 10, 5 nM or even less, such as less than 4, 3, 2, or 1 nM, such as less than 500, 400, 300, 200, 100, 90, 80, 70, 60, 50, 40, 30, 20 pM, or even less such as, less than 10 pM. Preferably, the KD is determined as shown in the examples.

In one embodiment, a binding molecule according to the invention has a binding affinity to PSMA with an affinity constant of at least about $10^7$ $M^{-1}$, preferably about $10^9$ $M^{-1}$, and more preferably, about $10^{10}$ $M^{-1}$ to $10^{11}$ $M^{-1}$ or higher. In one embodiment, a binding molecule according to the invention has a Kon of 1.00E+04 to 1.00E+6 (1/Ms). In one embodiment, a binding molecule according to the invention has Koff of 1.00E-03 to 1.00E-05 (1/s).

Binding molecules of the invention have shown excellent stability, including heat and serum stability (see examples). Furthermore, binding molecules of the invention show rapid tumor targeting as shown in the examples. Furthermore, binding molecules of the invention also show high specificity for human PSMA and low uptake in non-target tissues (see examples).

In one embodiment, binding molecules of the invention show fast blood clearance. In one embodiment, binding molecules of the invention show low renal retention. In one embodiment, binding molecules can inhibit, e.g., competitively inhibit, the binding of another antibody e.g., J591, to human PSMA.

In one embodiment, a binding molecule of the invention may have one or more property select from the following non-limiting list:

a) high-affinity binding to human and/or cynomolgus prostate-specific membrane antigen in its native form occurring on the surface of tumor cells,
b) internalization by a tumor cell,
c) low uptake in non-target tissues,
d) rapid tumor targeting,
e) binding strongly to LNCaP cells, but not or only minimally to cells which lack expression of prostate-specific membrane antigen and/or
f) binding to a unique epitope on PSMA.

The present invention further provides an isolated nucleic acid encoding a binding molecule of the present invention. Nucleic acid may include DNA and/or RNA. In one aspect, the present invention provides a nucleic acid that codes for a CDR or set of CDRs or a $V_H$ domain as defined above.

The nucleic acid of the single domain antibodies described herein are set out below. These can be combined using linkers described herein to generate a nucleic acid construct for expression.

Sequences comprising or consisting of SEQ ID NOs. 393 to 410 as shown below which encode $V_H$ domains of family 1 comprising or consisting of SEQ ID NO. 4 to 80.

```
(encodes V_H domain 1.1)
                                                      SEQ ID NO. 393
GAGGTGCAGCTGTTGGAGTCTGGGGGAGGCTTGGTACAGCCTGGGGGGTCCCTGAGA

CTCTCCTGTGCAGCCTCTGGATTCAGTTTTAGCAGCTATGCCATGAGTTGGGTCCGCCA

GGCTCCAGGGAAGGGGCTGGAGTGGGTCTCAAGTATTGGTGAGAATGATGGTACCACA

GACTACGCAGACTCCGTGAAGGGCCGATTCACCATCTCCAGAGACAATTCCAAGAGTAT

GCTGTATCTGCAAATGAACAGCCTGAGAGTCGAGGACACGGCCGTCTATTACTGTGTGA

AAGATGGTGTCCACTGGGGCCAGGGAACCCTGGTCACCGTCTCCTCA (encodes V_H domain 1.2)
                                                      SEQ ID NO. 394
GAGGTGCAGCTGGTGGAGTCTGGGGGAGGCTTGGTACAGCCTGGGGGGTCCCTGAGA

CTCTCCTGTGCAGCCTCTGGATTCACCTTTAGCAGTTATGCCATGAGCTGGGTCCGCCA

GGCTCCAGGGAAGGGGCTGGAGTGGGTCTCAAGTATTGGTGATAATAATAATAGCACA

GAGTACGCAGACTCCGTGAAGGGCCGGTTCACCATCTCCAGAGACAATTCCAAGAGCA

CGCTGTATCTGCAAATGAACAGCCTGAGCGCCGAGGACACGGCCGTATATTACTGTGT

GAAAGATGGTGTCCACTGGGGCCAGGGAACCCTGGTCACTGTCTCTTCA (encodes V_H domain 1.3)
                                                      SEQ ID NO. 395
GAGGTGCAGCTGGTGGAGTCTGGGGGAGGCTTGGTACAGCCTGGGGGGTCCCTGAGA

CTCTCCTGTGCAGCCTCTGGATTCTCCTTTAGCAGTTATGCCATGAGCTGGGTCCGCCA

GGCTCCAGGGAAGGGACTGGAGTGGGTCTCAAGTATTGGTGATAATAATAATAGCACA

GACTACGCAGACTCCGTGAAGGGCCGGTTCACCATCTCCAGAGACAATTCCAAGAGTA

CGCTGTATCTGCAAATGAACAGCCTGAGAGCCGAGGACACGGCCGTATATTACTGTGT

GAAAGATGGTGTCCACTGGGGCCAGGGAACCCTGGTCACTGTCTCCTCA (encodes V_H domain 1.4)
                                                      SEQ ID NO. 396
GAGGTGCAGCTGGTGGAGTCTGGGGGAGGCTTGGTACAGCCTGGGGGGTCCCTGAGA

CTCTCCTGTGCAGCCTCTGGATTCACCTTTAGCAGTTATGCCATGAGCTGGGTCCGCCA

GGCTCCAGGGAAGGGGCTGGAGTGGGTCTCAAGTATTGGTGATGGAACCACATACTAC

GCAGACTCCGTGAAGGGCCGTTTCACCATCTCCAGAGACAATTCCAAGAGCACGCTGT

ATCTGCAAATGAACAGCCTGAGAGCCGAGGACACGGCCGTATATTACTGTGCGAAAGAT

GGTGTCCACTGGGGCCAGGGAACCCTGGTCACTGTCTCCTCA
```

(encodes V$_H$ domain 1.5)
SEQ ID NO. 397
GAAGTGCAGCTGGTGGAGTCTGGGGGAGGCTTGGTACAGCCTGGGGGGTCCCTGAGA

CTCTCCTGTGCAGCCTCTGGATTCACCTTTAGCACTTATGCCATGAGCTGGGTCCGCCA

GGCTCCAGGGAAGGGGCTGGAGTGGGTCTCAAGTATTGGTGAAAATGATCGAACCACA

TACTACGTAGACTCCGTGAAGGGCCGGTTCACCATCTCCAGAGACAATTCCAAGAGCAC

GCTGTATCTGCAAATGAACAGCCTGAGAGCCGAGGACACGGCCGTATATTACTGTGCG

AAAGATGGTGTCCACTGGGGCCAGGGAACCCTGGTCACTGTCTCTTCA (encodes V$_H$ domain 1.6)
SEQ ID NO. 398
CAGGTGCAGCTGGTGGAGTCTGGGGGAGGCTTGGTACAGCCTGGGGGGTCCCTGAGA

CTCTCCTGTGCAGCCTCTGGATTCACCTTTAGCAGTTATGCCATGAGCTGGGTCCGCCA

GGCTCCAGGGAAGGGGCTGGAGTGGGTCTCAAGTATTGGTGATAATAATAGAACCACA

TACTACGCAGACTCCGTGAAGGGCCGGTTCACCATCTCCAGAGACAATTCCAAGAGCA

CGCTGTATCTGCAAATGAACAGCCTGAGAGCCGAGGACACGGCCGTATATTACTGTGC

GAAAGATGGTGTCCACTGGGGCCAGGGAACCCTGGTCACCGTCTCCTCA (encodes V$_H$ domain 1.7)
SEQ ID NO. 399
GAGGTGCAGCTGGTGGAGTCTGGGGGAGGCTTGGTACAGCCTGGGGGGTCCCTGAGA

CTCTCCTGTGCAGCCTCTGGATTCACCTTTAGCAGTTATGCCATGAGCTGGGTCCGCCA

GGCTCCAGGGAAGGGGCTGGAGTGGGTCTCAAGTATTGGTGATGAACCACATACTAC

GCAGACTCCGTGAAGGGCCGGTTCACCATCTCCAGAGACAATTCCAAGAGCACGCTGT

ATCTGCAAATGAACAGCCTGAGAGCCGAGGACACGGCCGTATATTACTGTGCGAAAGAT

GGTGTCCACTGGGGCCAGGGAACCCTGGTCACCGTCTCCTCA (encodes V$_H$ domain 1.8)
SEQ ID NO. 400
GAGGTGCAGCTGTTGGAGTCTGGGGGAGGCTTGGTACAGCCTGGGGGGTCCCTGAGA

CTCTCCTGTGCAGCCTCTGGATTCAGTTTTAGCAGCTATGCCATGAGTTGGGTCCGCCA

GGCTCCAGGGAAGGGGCTGGAGTGGGTCTCAAGTATTGGTGAGAATGATGGTACCACA

GACTACGCAGACTCCGTGAAGGGCCGATTCACCATCTCCAGAGACAATTCCAAGAATAC

GCTGTATCTGCAAATGAACAGCCTGAGAGTCGAGGACACGGCCGTCTATTACTGTGTGA

AAGATGGTGTCCACTGGGGCCAGGGAACCCTGGTCACCGTCTCCTCA (encodes V$_H$ domain 1.9)
SEQ ID NO. 401
GAGGTGCAGCTGTTGGAGTCTGGGGGAGGCTTGGTACAGCCTGGGGGGTCCCTGAGA

CTCTCCTGTGCAGCCTCTGGATTCAGTTTTAGCAGCTATGCCCTCAGTTGGGTCCGCCA

GGCTCCAGGGAAGGGGCTGGAGTGGGTCTCAAGTATTGGTGAGAATAACGATACCACA

GACTACGCAGACAACGTGAAGGGCCGATTCACCATCTCCAGAGACAATTCCAAGAATAC

GCTGTATCTGCAAATGAACAGCCTGAGAGTCGAGGACACGGCCGTCTATTACTGTGTGA

AAGATGGTGTCCACTGGGGCCAGGGAACCCTGGTCACCGTCTCCTCA (encodes V$_H$ domain 1.10)
SEQ ID NO. 402
GAGGTGCAGCTGTTGGAGTCTGGGGGAGGCTTGGTACAGCCTGGGGGGTCCCTGAGA

CTCTCCTGTGCAGCCTCTGGATTCAGTTTTAGCAGCTATGCCCTCAGTTGGGTCCGCCA

GGCTCCAGGGAAGGGGCTGGAGTGGGTCTCAAGTATTGGTGAGAATAACGCTACCACA

GACTACGCAGACTTCGTGAAGGGCCGATTCACCATCTCCAGAGACAATTCCAAGAATAC

```
GCTGTATCTGCAAATGAACAGCCTGAGAGTCGAGGACACGGCCGTCTATTACTGTGTGA

AAGATGGTGTCCACTGGGGCCAGGGAACCCTGGTCACCGTCTCCTCA (encodes V_H domain 1.11)
                                                    SEQ ID NO. 403
GAGGTGCAGCTGTTGGAGTCTGGGGGAGGCTTGGTACAGCCTGGGGGGTCCCTGAGA

CTCTCCTGTGCAGCCTCTGGATTCAGTTTTAGCAGCTATGCCCTCAGTTGGGTCCGCCA

GGCTCCAGGGAAGGGGCTGGAGTGGGTCTCAAGTATTGGTGAGAATAACGCTACCACA

GACTACGCAGACGCCGTGAAGGGCCGATTCACCATCTCCAGAGACAATTCCAAGAATA

CGCTGTATCTGCAAATGAACAGCCTGAGAGTCGAGGACACGGCCGTCTATTACTGTGTG

AAAGATGGTGTCCACTGGGGCCAGGGAACCCTGGTCACCGTCTCCTCA (encodes V_H domain 1.12)
                                                    SEQ ID NO. 404
GAGGTGCAGCTGTTGGAGTCTGGGGGAGGCTTGGTACAGCCTGGGGGGTCCCTGAGA

CTCTCCTGTGCAGCCTCTGGATTCAGTTTTAGCAGCTATGCCCTCAGTTGGGTCCGCCA

GGCTCCAGGGAAGGGGCTGGAGTGGGTCTCAAGTATTGGTGAGAATAACGCTACCACA

GACTACGCAGACGCCGTGAAGGGCCGATTCACCATCTCCAGAGACAATTCCAAGAATA

CGCTGTATCTGCAAATGAACAGCCTGAGAGTCGAGGACACGGCCGTCTATTACTGTGTG

AAAGATGGTGTCCACTGGGGCCAGGGAACCCTGGTCACCGTCTCCTCA (encodes V_H domain 1.13)
                                                    SEQ ID NO. 405
GAGGTGCAGCTGTTGGAGTCTGGGGGAGGCTTGGTACAGCCTGGGGGGTCCCTGAGA

CTCTCCTGTGCAGCCTCTGGATTCAGTTTTAGCAGCTATGCCCTCAGTTGGGTCCGCCA

GGCTCCAGGGAAGGGGCTGGAGTGGGTCTCAAGTATTGGTGAGAATAACCATACCACA

GACTACGCAGCCGACGTGAAGGGCCGATTCACCATCTCCAGAGACAATTCCAAGAATA

CGCTGTATCTGCAAATGAACAGCCTGAGAGTCGAGGACACGGCCGTCTATTACTGTGTG

AAAGATGGTGTCCACTGGGGCCAGGGAACCCTGGTCACCGTCTCCTCA (encodes V_H domain 1.14)
                                                    SEQ ID NO. 406
GAGGTGCAGCTGTTGGAGTCTGGGGGAGGCTTGGTACAGCCTGGGGGGTCCCTGAGA

CTCTCCTGTGCAGCCTCTGGATTCAGTTTTAGCAGCTATGCCCTCAGTTGGGTCCGCCA

GGCTCCAGGGAAGGGGCTGGAGTGGGTCTCAAGTATTGGTGAGAATAACGCTACCACA

GACTACGCAGACGTCGTGAAGGGCCGATTCACCATCTCCAGAGACAATTCCAAGAATAC

GCTGTATCTGCAAATGAACAGCCTGAGAGTCGAGGACACGGCCGTCTATTACTGTGTGA

AAGATGGTGTCCACTGGGGCCAGGGAACCCTGGTCACCGTCTCCTCA (encodes V_H domain 1.15)
                                                    SEQ ID NO. 407
GAGGTGCAGCTGTTGGAGTCTGGGGGAGGCTTGGTACAGCCTGGGGGGTCCCTGAGA

CTCTCCTGTGCAGCCTCTGGATTCAGTTTTAGCAGCTATGCCCTCAGTTGGGTCCGCCA

GGCTCCAGGGAAGGGGCTGGAGTGGGTCTCAAGTATTGGTGAGAATAACCATACCACA

GACTACGCAGCCTTCGTGAAGGGCCGATTCACCATCTCCAGAGACAATTCCAAGAATAC

GCTGTATCTGCAAATGAACAGCCTGAGAGTCGAGGACACGGCCGTCTATTACTGTGTGA

AAGATGGTGTCCACTGGGGCCAGGGAACCCTGGTCACCGTCTCCTCA (encodes V_H domain 1.16)
                                                    SEQ ID NO. 408
GAGGTGCAGCTGTTGGAGTCTGGGGGAGGCTTGGTACAGCCTGGGGGGTCCCTGAGA

CTCTCCTGTGCAGCCTCTGGATTCAGTTTTAGCAGCTATGCCCTCAGTTGGGTCCGCCA
```

```
GGCTCCAGGGAAGGGGCTGGAGTGGGTCTCAAGTATTGGTGAGAATAACCATACCACA

GACTACGCAGACACCGTGAAGGGCCGATTCACCATCTCCAGAGACAATTCCAAGAATAC

GCTGTATCTGCAAATGAACAGCCTGAGAGTCGAGGACACGGCCGTCTATTACTGTGTGA

AAGATGGTGTCCACTGGGGCCAGGGAACCCTGGTCACCGTCTCCTCA (encodes V_H domain 1.17)
                                                 SEQ ID NO. 409
GAGGTGCAGCTGTTGGAGTCTGGGGGAGGCTTGGTACAGCCTGGGGGGTCCCTGAGA

CTCTCCTGTGCAGCCTCTGGATTCAGTTTTAGCAGCTATGCCCTCAGTTGGGTCCGCCA

GGCTCCAGGGAAGGGGCTGGAGTGGGTCTCAAGTATTGGTGAGAATAACGATACCACA

GACTACGCAGACGCCGTGAAGGGCCGATTCACCATCTCCAGAGACAATTCCAAGAATA

CGCTGTATCTGCAAATGAACAGCCTGAGAGTCGAGGACACGGCCGTCTATTACTGTGTG

AAAGATGGTGTCCACTGGGGCCAGGGAACCCTGGTCACCGTCTCCTCA (encodes V_H domain 1.18)
                                                 SEQ ID NO. 410
GAGGTGCAGCTGTTGGAGTCTGGGGGAGGCTTGGTACAGCCTGGGGGGTCCCTGAGA

CTCTCCTGTGCAGCCTCTGGATTCAGTTTTAGCAGCTATGCCCTCAGTTGGGTCCGCCA

GGCTCCAGGGAAGGGGCTGGAGTGGGTCTCAAGTATTGGTGAGAATAACGCTACCACA

GACTACGCAGCCTCCGTGAAGGGCCGATTCACCATCTCCAGAGACAATTCCAAGAATAC

GCTGTATCTGCAAATGAACAGCCTGAGAGTCGAGGACACGGCCGTCTATTACTGTGTGA

AAGATGGTGTCCACTGGGGCCAGGGAACCCTGGTCACCGTCTCCTCA (encodes V_H domain 1.19)
                                                 SEQ ID NO. 411
GAGGTGCAGCTGTTGGAGTCTGGGGGAGGCTTGGTACAGCCTGGGGGGTCCCTGAGA

CTCTCCTGTGCAGCCTCTGGATTCAGTTTTAGCAGCTATGCCCTCAGTTGGGTCCGCCA

GGCTCCAGGGAAGGGGCTGGAGTGGGTCTCAAGTATTGGTGAGAATAACGATACCACA

GACTACGCAGCCTACGTGAAGGGCCGATTCACCATCTCCAGAGACAATTCCAAGAATAC

GCTGTATCTGCAAATGAACAGCCTGAGAGTCGAGGACACGGCCGTCTATTACTGTGTGA

AAGATGGTGTCCACTGGGGCCAGGGAACCCTGGTCACCGTCTCCTCA (encodes V_H domain 1.20)
                                                 SEQ ID NO. 412
GAGGTGCAGCTGTTGGAGTCTGGGGGAGGCTTGGTACAGCCTGGGGGGTCCCTGAGA

CTCTCCTGTGCAGCCTCTGGATTCAGTTTTAGCAGCTATGCCCTCAGTTGGGTCCGCCA

GGCTCCAGGGAAGGGGCTGGAGTGGGTCTCAAGTATTGGTGAGAATAACCATACCACA

GACTACGCAGCCACCGTGAAGGGCCGATTCACCATCTCCAGAGACAATTCCAAGAATAC

GCTGTATCTGCAAATGAACAGCCTGAGAGTCGAGGACACGGCCGTCTATTACTGTGTGA

AAGATGGTGTCCACTGGGGCCAGGGAACCCTGGTCACCGTCTCCTCA

SEQ ID NOs. 413 to 437 as shown below encode V_H domains
of family 2 comprising or consisting of SEQ ID NO. 84 to 180.
(encodes V_H domain 2.1)
                                                 SEQ ID NO. 413
GAGGTGCAGCTGGTGGAGTCTGGGGGAGGCGTGGTCCAGCCTGGGAGGTCCCTGAGA

CTCTCCTGTGCAGCCTCTGGATTCTCCTTCAGTGGCTATGGCATGCACTGGGTCCGCCA

GGCTCCAGGCAAGGGACTGGAGTGGGTGGCATATATATCATATGATGGAAGTAATAAAT

ACTATGCAGACTCCGTGAAGGGCCGATTCACCATCTCCAGAGACAATTCCAAGAACACG

CTGTATCTGCAAATGAACAGCCTGAGAGCTGAGGACACGGCTGTGTATTACTGTGCGAA

AGATCCGGCCTGGGGATTACGTTTGGGGGAGTCATCGTCCTATGATTTTGATATCTGGG

GCCAAGGGACAATGGTCACTGTCTCTTCA
```

-continued (encodes V$_H$ domain 2.2)

SEQ ID NO. 414

GAGGTGCAGCTGGTGGAGTCTGGGGGAGGCGTGGTCCAGCCTGGGAGGTCCCTGAGA

CTCTCCTGTGCAGCCTCTGGATTCTCCTTCAGTGGCTATGGCATGCACTGGGTCCGCCA

GGCTCCAGGCAAGGGACTGGAGTGGGTGGCATATATATCATATGATGGAAGTAATAAAT

ACTATGCAGACTCCGTGAAGGGCCGATTCACCATCTCCAGAGACAATTCCAAGAACACG

CTGTATCTGCAAATGAACAGCCTGAGAGCTGAGGACACGGCTGTGTATTACTGTGCGAA

AGATCCGGCCTGGGGATTACGTTTGGGGGAGTCATCGTCCTATGATTTTGATATCTGGG

GCCAAGGGACAATGGTCACTGTCTCTTCA (encodes V$_H$ domain 2.3)

SEQ ID NO. 415

GAGGTGCAGCTGGTGGAGTCTGGGGGAGGCGTGGTCCAGCCTGGGAGGTCCCTGAGA

CTCTCCTGTGCAGCCTCTGGATTCAGCTTCAGTGGCTATGGCATGCACTGGGTCCGCC

AGGCTCCAGGCAAGGGGCTGGAGTGGGTGGCACATATATCATATGATGGAAGTAATAG

ATACTATGCAGAATCCGTGAAGGGCCGATTCACCATCTCCAGAGAGAATTCCAAGAACA

CGCTGTCTCTGCAAATGAACAGCCTGAGAGCTGAGGACACGGCTGTGTATTACTGTGC

GAAAGATCCGGCCTGGGGATTACGTTTGGGGGAGTTATCGTCCTATGATTTTGACATTT

GGGGCCAAGGGACAATGGTCACTGTCTCTTCA (encodes V$_H$ domain 2.4)

SEQ ID NO. 416

CAGGTCACCTTGAAGGAGTCTGGGGGAGGCGTGGTCCAGCCTGGGAGGTCCCTGAAA

CTCTCCTGTGCAGCCTCTGGATTCTCCTTCAGTGGCTATGGCATGCACTGGGTCCGCCA

GGCTCCAGGCAAGGGGCTGGAGTGGGTGGCAGTTATATCATATGATGGAAGTAATAGA

TACTATGCAGACTCCGTGAAGGGCCGATTCACCATCTCCAGAGACAATTCCAAGAACAC

GCTGTCTCTGCAAATGAACAGCCTGAGAGCTGAGGACACGGCTGTGTATTACTGTGCG

AGAGATCCGGCCTGGGGATTACGTTTGGGGAGTTATCGTCCTATGATTTTGAAATCTG

GGGCCAAGGGACAATGGTCACCGTCTCCTCA (encodes V$_H$ domain 2.5)

SEQ ID NO. 417

CAGGTGCAGCTGGTGGAGTCTGGGGGAGGCGTGGTCCAGCCTGGGAGGTCCCTGAGA

CTCTCCTGTGCAGCCTCTGGATTCTCCTTCAGTGGCTATGGCATGCACTGGGTCCGCCA

GGCTCCAGGCAAGGGGCTGGAGTGGGTGGCAGTTATATCATATGATGGAAGTAATAGA

TACTATGCAGACTCCGTGAAGGGCCGATTCACCATCTCCAGAGACAATTCCAAGAACAC

ACTGTCTCTGCAAATGAACAGCCTGAGAGCTGAGGACACGGCTGTGTATTACTGTGCGA

AAGATCCGGCCTGGGGATTACGTTTGGGGAGTTATCGTCCTATGATTTTGAAATTTGG

GGCCAAGGGACAATGGTCACCGTCTCTTCA (encodes V$_H$ domain 2.6)

SEQ ID NO. 418

GAAGTGCAGCTGGTGGAGTCTGGGGGAGGCGTGGTCCAGCCTGGGAGGTCCCTGAGA

CTCTCCTGTGCAGCCTCTGGATTCTCCTTCAGTGGCTATGGCATGCACTGGGTCCGCCA

GGCTCCAGGCAAGGGGCTGGAGTGGGTGGCAGTTATATCATATGATGGAAGTAATAAA

TACTATGCAGACTCCGTGAAGGGCCGATTCACCATCTCCAGAGACAATTCCAAGAACAC

GCTATATCTGCAAATGAACAGCCTGAGAGCTGAGGACACGGCTGTGTATTACTGTGCGA

AAGATCCGGCCTGGGGATTACGTTTGGGGAACTATCGTCCTATAAATTTGAAATCTGG

GGCCAAGGGACAATGGTCACCGTCTCTTCA

-continued (encodes V_H domain 2.7)

SEQ ID NO. 419

```
GAGGTGCAGCTGGTGGAGTCTGGGGGAGGCGTGGTCCAGCCTGGGAGGTCCCTGAGA
CTCTCCTGTGCAGCCTCTGGATTCTCCTTCAGTGGCTATGGCATGCACTGGGTCCGCCA
GGCTCCAGGCAAGGGGCTGGAGTGGGTGGCACTTATATCATATGATGGAAGTAATAAAT
ACTATGCAGACTCCGTGAAGGGCCGATTCACCATCTCCAGAGACAATTCCAAGAACACG
CTGTATCTGCAAATGAACAGCCTGAGAGCTGAGGACACGGCTGTGTATTACTGTGCGAA
AGATCCGGCCTGGGGATTACGTTTGGGGGAGCAATCGTCCTATGCTTTTGATATCTGGG
GCCAAGGGACAATGGTCACCGTCTCCTCA
```

(encodes V_H domain 2.8)

SEQ ID NO. 420

```
CAGGTGCAGCTGGTGGAGTCTGGGGGAGGCGTGGTCCAGCCTGGGAGGTCCCTGAGA
CTCTCCTGTGCAGCCTCTGGATTCTCCTTCAGTGGCTATGGCATGCACTGGGTCCGCCA
GGCTCCAGGCAAGGGGCTGGAGTGGGTGTCAGTTATATCATATGATGGAAGTAATAAAT
ACTATGCAGACTCCGTGAAGGGCCGATTCACCATCTCCAGAGACAATTCCAAGAACACG
CTGTATCTGCAAATGAACAGCCTGAGAACTGAGGACACGGCTGTGTATTACTGTGCGAA
AGATCCGGCCTGGGGATTACGTTTGGGGGAGCAATCGTCCTATGCTTTTGAAATCTGGG
GCCAAGGTACAATGGTCACCGTCTCCTCA
```

(encodes V_H domain 2.9)

SEQ ID NO. 421

```
GAGGTGCAGCTGTTGGAGTCTGGGGGAGGCGTGGTCCAGCCTGGGAGGTCCCTGAGA
CTCTCCTGTGCAGCCTCTGGATTCTCCTTCAGTGGCTATGGCATGCACTGGGTCCGCCA
GGCTCCAGGCAAGGGGCTGGAGTGGGTGGCAGTTATATCATATGATGGAAGTAATAAA
TACTATGCAGACTCCGTGAAGGGCCGATTCACCATCTCCAGAGACAATTCCAAGAACAC
GCTGTATCTGCAAATGAACAGCCTGAGAGTTGAGGACACGGCTGTGTATTACTGTGCGA
AAGATCCGGCCTGGGGATTACGTTTGGGGAGCAATCGTCCTATGCTTTTGAAATCCGG
GGCCAGGGGACAACGGTCACCGTCTCTTCA
```

(encodes V_H domain 2.10)

SEQ ID NO. 422

```
GAGGTGCAGCTGGTGGAGTCTGGGGGAGGCGTGGTCCAGCCTGGGAGGTCCCTGAGA
CTCTCCTGTGCAGCCTCTGGATTCACCTTTAGTGGCTATGGCATGCACTGGGTCCGCCA
GGCTCCAGGCAAGGGGCTGGAGTGGGTGGCATATATATCATATGATGGAAGTAATAGA
TACTATGCAGACTCCGTGAAGGGCCGATTCACCATCTCCAGAGACAATTCCAAGAAGAC
GCTGTCTCTGCAAATGAACAGCCTGAGAGCTGAGGACACGGCTGTGTATTACTGTGCG
AAAGATCCGGCCTGGGGATTACGTTTGGGGGAGTCATCGTCATATGATTTTGATATCTG
GGGCCAAGGGACAATGGTCACCGTCTCCTCA
```

(encodes V_H domain 2.11)

SEQ ID NO. 423

```
GAGGTGCAGCTGGTGGAGTCTGGGGGAGGCGTGGTCCAGCCTGGGAGGTCCCTGAGA
CTCTCCTGTGCAGCCTCTGGATTCTCCTTCAGTGGCTATGGCCTCCACTGGGTCCGCCA
GGCTCCAGGCAAGGGACTGGAGTGGGTGGCATATATATCATATGACGAGAGTAATAAAT
ACTATGCACCCAGCGTGAAGGGCCGATTCACCATCTCCAGAGACAATTCCAAGAACACG
CTGTATCTGCAAATGAACAGCCTGAGAGCTGAGGACACGGCTGTGTATTACTGTGCGAA
AGATCCGGCCTGGGGATTACGTTTGGGGAGTCATCGTCCTATGATTTTGATATCTGGG
GCCAAGGGACAATGGTCACCGTCTCCTCA
```

(encodes V<sub>H</sub> domain 2.12)

SEQ ID NO. 424

GAGGTGCAGCTGGTGGAGTCTGGGGGAGGCGTGGTCCAGCCTGGGAGGTCCCTGAGA

CTCTCCTGTGCAGCCTCTGGATTCTCCTTCAGTGGCTATGGCATGCACTGGGTCCGCCA

GGCTCCAGGCAAGGGACTGGAGTGGGTGGCATATATATCATATGATAAGAGTAATAAAT

ACTATGCAGACAAGGTGAAGGGCCGATTCACCATCTCCAGAGACAATTCCAAGAACACG

CTGTATCTGCAAATGAACAGCCTGAGAGCTGAGGACACGGCTGTGTATTACTGTGCGAA

AGATCCGGCCTGGGGATTACGTTTGGGGGAGTCATCGTCCTATGATTTTGATATCTGGG

GCCAAGGGACAATGGTCACTGTCTCTTCA (encodes V<sub>H</sub> domain 2.13)

SEQ ID NO. 425

GAGGTGCAGCTGGTGGAGTCTGGGGGAGGCGTGGTCCAGCCTGGGAGGTCCCTGAGA

CTCTCCTGTGCAGCCTCTGGATTCTCCTTCAGTGGCTATGGCCTCCACTGGGTCCGCCA

GGCTCCAGGCAAGGGACTGGAGTGGGTGGCATATATATCATATGATGCGAGTAATAAAT

ACTATGCAGACAACGTGAAGGGCCGATTCACCATCTCCAGAGACAATTCCAAGAACACG

CTGTATCTGCAAATGAACAGCCTGAGAGCTGAGGACACGGCTGTGTATTACTGTGCGAA

AGATCCGGCCTGGGGATTACGTTTGGGGGAGTCATCGTCCTATGATTTTGATATCTGGG

GCCAAGGGACAATGGTCACTGTCTCTTCA (encodes V<sub>H</sub> domain 2.14)

SEQ ID NO. 426

GAGGTGCAGCTGGTGGAGTCTGGGGGAGGCGTGGTCCAGCCTGGGAGGTCCCTGAGA

CTCTCCTGTGCAGCCTCTGGATTCTCCTTCAGTGGCTATGGCGTGCACTGGGTCCGCC

AGGCTCCAGGCAAGGGACTGGAGTGGGTGGCATATATATCATATGATGCGAGTAATAAA

TACTATGCAGACAACGTGAAGGGCCGATTCACCATCTCCAGAGACAATTCCAAGAACAC

GCTGTATCTGCAAATGAACAGCCTGAGAGCTGAGGACACGGCTGTGTATTACTGTGCGA

AAGATCCGGCCTGGGGATTACGTTTGGGGGAGTCATCGTCCTATGATTTTGATATCTGG

GGCCAAGGGACAATGGTCACTGTCTCTTCA (encodes V<sub>H</sub> domain 2.15)

SEQ ID NO. 427

GAGGTGCAGCTGGTGGAGTCTGGGGGAGGCGTGGTCCAGCCTGGGAGGTCCCTGAGA

CTCTCCTGTGCAGCCTCTGGATTCTCCTTCAGTGGCTATGGCCTCCACTGGGTCCGCCA

GGCTCCAGGCAAGGGACTGGAGTGGGTGGCATATATATCATATGATAAGAGTAATAAAT

ACTATGCAGACAAGGTGAAGGGCCGATTCACCATCTCCAGAGACAATTCCAAGAACACG

CTGTATCTGCAAATGAACAGCCTGAGAGCTGAGGACACGGCTGTGTATTACTGTGCGAA

AGATCCGGCCTGGGGATTACGTTTGGGGGAGTCATCGTCCTATGATTTTGATATCTGGG

GCCAAGGGACAATGGTCACTGTCTCTTCA (encodes V<sub>H</sub> domain 2.16)

SEQ ID NO. 428

GAGGTGCAGCTGGTGGAGTCTGGGGGAGGCGTGGTCCAGCCTGGGAGGTCCCTGAGA

CTCTCCTGTGCAGCCTCTGGATTCTCCTTCAGTGGCTATGGCGCGCACTGGGTCCGCC

AGGCTCCAGGCAAGGGACTGGAGTGGGTGGCATATATATCATATGATAAGAGTAATAAA

TACTATGCAGACAAGGTGAAGGGCCGATTCACCATCTCCAGAGACAATTCCAAGAACAC

GCTGTATCTGCAAATGAACAGCCTGAGAGCTGAGGACACGGCTGTGTATTACTGTGCGA

AAGATCCGGCCTGGGGATTACGTTTGGGGGAGTCATCGTCCTATGATTTTGATATCTGG

GGCCAAGGGACAATGGTCACTGTCTCTTCA

-continued (encodes V_H domain 2.17)

SEQ ID NO. 429

GAGGTGCAGCTGGTGGAGTCTGGGGGAGGCGTGGTCCAGCCTGGGAGGTCCCTGAGA
CTCTCCTGTGCAGCCTCTGGATTCTCCTTCAGTGGCTATGGCATGCACTGGGTCCGCCA
GGCTCCAGGCAAGGGACTGGAGTGGGTGGCATATATATCATATGATGCGAGTAATAAAT
ACTATGCAGACAACGTGAAGGGCCGATTCACCATCTCCAGAGACAATTCCAAGAACACG
CTGTATCTGCAAATGAACAGCCTGAGAGCTGAGGACACGGCTGTGTATTACTGTGCGAA
AGATCCGGCCTGGGGATTACGTTTGGGGGAGTCATCGTCCTATGATTTTGATATCTGGG
GCCAAGGGACAATGGTCACTGTCTCTTCA (encodes V_H domain 2.18)

SEQ ID NO. 430

GAGGTGCAGCTGGTGGAGTCTGGGGGAGGCGTGGTCCAGCCTGGGAGGTCCCTGAGA
CTCTCCTGTGCAGCCTCTGGATTCTCCTTCAGTGGCTATGGCCAGCACTGGGTCCGCC
AGGCTCCAGGCAAGGGACTGGAGTGGGTGGCATATATATCATATGATGCGAGTAATAAA
TACTATGCAGACAACGTGAAGGGCCGATTCACCATCTCCAGAGACAATTCCAAGAACAC
GCTGTATCTGCAAATGAACAGCCTGAGAGCTGAGGACACGGCTGTGTATTACTGTGCGA
AAGATCCGGCCTGGGGATTACGTTTGGGGGAGTCATCGTCCTATGATTTTGATATCTGG
GGCCAAGGGACAATGGTCACTGTCTCTTCA (encodes V_H domain 2.19)

SEQ ID NO. 431

GAGGTGCAGCTGGTGGAGTCTGGGGGAGGCGTGGTCCAGCCTGGGAGGTCCCTGAGA
CTCTCCTGTGCAGCCTCTGGATTCTCCTTCAGTGGCTATGGCTTCCACTGGGTCCGCCA
GGCTCCAGGCAAGGGACTGGAGTGGGTGGCATATATATCATATGATGCGAGTAATAAAT
ACTATGCAGACAACGTGAAGGGCCGATTCACCATCTCCAGAGACAATTCCAAGAACACG
CTGTATCTGCAAATGAACAGCCTGAGAGCTGAGGACACGGCTGTGTATTACTGTGCGAA
AGATCCGGCCTGGGGATTACGTTTGGGGGAGTCATCGTCCTATGATTTTGATATCTGGG
GCCAAGGGACAATGGTCACTGTCTCTTCA (encodes V_H domain 2.20)

SEQ ID NO. 432

GAGGTGCAGCTGGTGGAGTCTGGGGGAGGCGTGGTCCAGCCTGGGAGGTCCCTGAGA
CTCTCCTGTGCAGCCTCTGGATTCAGCTTCAGTGGCTATGGCATGCACTGGGTCCGCC
AGGCTCCAGGCAAGGGGCTGGAGTGGGTGGCAATTATATCATATGATGGAAGTAATAG
ATACTATGCAGACTCCGTGAAGGGCCGATTCACCATCTCCAGAGACAATTCCAAGAACA
CGCTGTCTCTGCAAATGAACAGCCTGAGAGCTGAGGACACGGCTGTGTATTACTGTGC
GAAAGATCCGGCCTGGGGATTACGTTTGGGGGAGTCATCGTCCTATGATTTTGAAATTT
GGGGCCAAGGGACAATGGTCACCGTCTCCTCA (encodes V_H domain 2.21)

SEQ ID NO. 433

CAGGTGCAGCTGGTGGAGTCTGGGGGAGGCGTGGTCCAGCCTGGGAGGTCCCTGAAA
CTCTCCTGTGCAGCCTCTGGATTCTCCTTCAGTGGCTATGGCATGCACTGGGTCCGCCA
GGCTCCAGGCAAGGGGCTGGAGTGGGTGGCAGTTATATCATATGATGGAAGTAATAGA
TACTATGCAGACTCCGTGAAGGGCCGATTCACCATCTCCAGAGACAATTCCAAGAACAC
GCTGTCTCTACAAATGAACAGCCTGAGAGCTGAGGACACGGCTGTGTATTACTGTGCGA
AAGATCCGGCCTGGGGATTACGTTTGGGGAAATTATCGTCCTATGATTTTGAAATCTGG
GGCCAAGGGACAATGGTCACTGTCTCTTCA (encodes V_H domain 2.22)

SEQ ID NO. 434

GAGGTGCAGCTGGTGGAGTCTGGGGGAGGCGTGGTCCAGCCTGGGAGGTCCCTGAGA

CTCTCCTGTGCAGCCTCTGGATTCTCCTTCAGTGGCTATGGCACGCACTGGGTCCGCC

AGGCTCCAGGCAAGGGACTGGAGTGGGTGGCATATATATCATATGACGGGAGTAATAA

ATACTATGCAGCCCCGGTGAAGGGCCGATTCACCATCTCCAGAGACAATTCCAAGAACA

CGCTGTATCTGCAAATGAACAGCCTGAGAGCTGAGGACACGGCTGTGTATTACTGTGC

GAAAGACGCGGCCTGGGGATTACGTTTGGGGGAGTCATCGTCCTATGATTTTGATATCT

GGGGCCAAGGGACAATGGTCACTGTCTCTTCA (encodes V_H domain 2.23)

SEQ ID NO. 435

GAGGTGCAGCTGGTGGAGTCTGGGGGAGGCGTGGTCCAGCCTGGGAGGTCCCTGAGA

CTCTCCTGTGCAGCCTCTGGATTCTCCTTCAGTGGCTATGGCACGCACTGGGTCCGCC

AGGCTCCAGGCAAGGGACTGGAGTGGGTGGCATATATATCATATGACGAGAGTAATAAA

TACTATGCATCCAGCGTGAAGGGCCGATTCACCATCTCCAGAGACAATTCCAAGAACAC

GCTGTATCTGCAAATGAACAGCCTGAGAGCTGAGGACACGGCTGTGTATTACTGTGCGA

AAGACCGGGCCTGGGGATTACGTTTGGGGGAGTCATCGTCCTATGATTTTGATATCTGG

GGCCAAGGGACAATGGTCACTGTCTCTTCA (encodes V_H domain 2.24)

SEQ ID NO. 436

GAGGTGCAGCTGGTGGAGTCTGGGGGAGGCGTGGTCCAGCCTGGGAGGTCCCTGAGA

CTCTCCTGTGCAGCCTCTGGATTCTCCTTCAGTGGCTATGGCATGCACTGGGTCCGCCA

GGCTCCAGGCAAGGGACTGGAGTGGGTGGCATATATATCATATGACGAGAGTAATAAAT

ACTATGCAAGGCTGGTGAAGGGCCGATTCACCATCTCCAGAGACAATTCCAAGAACACG

CTGTATCTGCAAATGAACAGCCTGAGAGCTGAGGACACGGCTGTGTATTACTGTGCGAA

AGACACGGCCTGGGGATTACGTTTGGGGGAGTCATCGTCCTATGATTTTGATATCTGGG

GCCAAGGGACAATGGTCACTGTCTCTTCA (encodes V_H domain 2.25)

SEQ ID NO. 437

GAGGTGCAGCTGGTGGAGTCTGGGGGAGGCGTGGTCCAGCCTGGGAGGTCCCTGAGA

CTCTCCTGTGCAGCCTCTGGATTCTCCTTCAGTGGCTATGGCCTCCACTGGGTCCGCCA

GGCTCCAGGCAAGGGACTGGAGTGGGTGGCATATATATCATATGACCTGAGTAATAAAT

ACTATGCAAGGGGGTGAAGGGCCGATTCACCATCTCCAGAGACAATTCCAAGAACAC

GCTGTATCTGCAAATGAACAGCCTGAGAGCTGAGGACACGGCTGTGTATTACTGTGCGA

AAGACGTGGCCTGGGGATTACGTTTGGGGGAGTCATCGTCCTATGATTTTGATATCTGG

GGCCAAGGGACAATGGTCACTGTCTCCTCA

In one aspect, the invention also relates to nucleic acid
sequences comprising or consisting of SEQ ID NOs. 438
to 461 as shown below which encode V_H domains of family 3
comprising or consisting of SEQ ID NO. 184 to 276.
(encodes V_H domain 3.1)

SEQ ID NO. 438

GAGGTGCAGCTGGTGGAGTCTGGGGGAGGCGTGGTCCAGCCTGGGAGGTCCCTGAGA

CTCTCCTGTGCAGCCTCTGGATTCCCCTTAATTAGCTATGGCATGCACTGGGTCCGCCA

GGCTCCAGGCAAGGGGCTGGAGTGGGTGGCATTTATGACATATGATGGAAGTAATAGA

TACTATGCAGACTCCGTGAAGGGCCGATTCACCATCTCCAGAGACAATTCCAAGAACAC

GCTGTATCTGCAAATGAACAGCCTGAGAGATGAGGACACGGCTCTATATTACTGTGCGA

GAGATCGTATAGTGGGAGGTAGGGTCCCTGATGCTTTTGATATCTGGGGCCAAGGGAC

AATGGTCACCGTCTCTTCA (encodes V<sub>H</sub> domain 3.2)

SEQ ID NO. 439

GAGGTGCAGCTGGTGGAGTCTGGGGGAGGCGTGGTCCAGCCTGGGAGGTCCCTGAGA

CTCTCCTGTGCAGCCTCTGGATTCCCCTTAATTAGCTATGGCATGAATTGGGTCCGCCA

GGCTCCAGGCAAGGGGCTGGACTGGGTGGCATTTATATCATATGATGGAAGTAATAAAT

ATTATGCAGACTCCGTGAAGGGCCGATTCACCATCTCCAAAGACAATTCCAAGAACACG

CTGTATCTGCAAATGAACAGCCTGAGAGCTGAGGACACGGCTGTGTATTACTGTGCGAA

AGATCGTATAGTGGGAGCCAGGGTCCCTGATGCTTTTGATATCTGGGGCCAAGGGACA

ATGGTCACCGTCTCCTCA (encodes V<sub>H</sub> domain 3.3)

SEQ ID NO. 440

GAGGTGCAGCTGGTGGAGTCTGGGGGAGGCGTGGTCCAGCCTGGGAGGTCCCTGAGA

CTCTCCTGTGCAGCCTCTGGATTCCCCCTCATTAGCTATGGCATGAACTGGGTCCGCCA

GGCTCCAGGCAAGGGGCTGGAGTGGGTGGCATTTATATCATATGATGGAAGTAATAGAT

ACTATGCAGACTCCGTGAAGGGCCGATTCACCATCTCCAGAGACAATTCCAAGAACACG

CTGTATCTGCAAATGAACAGCCTGAGAGCTGAGGACACGGCTGTATATTACTGTGCGAA

AGATCGTATAGTGGGAGCTAGGGTCCCTGATGCTTTTGATATCTGGGGCCAAGGGACA

ATGGTCACCGTCTCCTCA (encodes V<sub>H</sub> domain 3.4)

SEQ ID NO. 441

GAGGTGCAGCTGGTGGAGTCTGGGGGAGGCGCGGTCCAGCCTGGGAGGTCCCTGAG

ACTCTCCTGTGCAGCCTCTGGATTCCCCTTAATTAGCTATGGCATGAATTGGGTCCGCC

AGGCTCCAGGCAAGGGGCTGGACTGGGTGGCATTTATAACATATGATGGAAGTAATAG

ATATTATGCAGACTCTGTGAAGGGCCGATTCACCATCTCCAGAGACAATTCCAAGAACA

CGCTTTATCTGCAAATGAACAGCCTGAGACCTGAGGACACGGCTGTATATTACTGTGCG

AAAGATCGTATTGTGGGAGCTAGGGTCCCTGATGCTTATGATATCTGGGGCCAAGGGA

CAATGGTCACCGTCTCCTCA (encodes V<sub>H</sub> domain 3.5)

SEQ ID NO. 442

CAGGTGCAGCTGGTGGAGTCTGGGGGAGGCGTGGTCCAGCCTGGGAGGTCCCTGAGA

CTCTCCTGTGCAGCCTCTGGATTCCCCTTAATTAGCTATGGCATGAATTGGGTCCGCCA

GGCTCCAGGCAAGGGGCTGGACTGGGTGGCATTTATAACATATGATGGAAGTAATAGAT

ACTATGCAGACTCCGTGAAGGGCCGATTCACCATCTCCAGAGACAATTCCAAGAACACG

CTTTATCTGCAAATGAACAGCCTGAGACCTGAGGACACGGCTGTATATTACTGTGCGAA

AGATCGTATTGTGGGAGCTAGGGTCCCTGATGCTTATGATATCTGGGGCCAAGGGACA

ATGGTCACCGTCTCCTCA (encodes V<sub>H</sub> domain 3.6)

SEQ ID NO. 443

GAGGTGCAGCTGTTGGAGTCTGGGGGAGGCGTGGTCCAGCCTGGGAGGTCCCTGAGA

CTCTCCTGTGCAGCCTCTGGATTCCCCTTAATTAGCTATGGCATGAATTGGGTCCGCCA

GGCTCCAGGCAAGGGGCTGGACTGGGTGGCATTTATAACATATGATGGAAGTAATAGAT

ACTATGCAGACTCCGTGAAGGGCCGATTCACCATCTCCAGAGACAATTCCAAGAACACG

CTTTATCTGCAAATGAACAGCCTGAGACCTGAGGACACGGCTGTATATTACTGTGCGAA

-continued

AGATCGTATTGTGGGAGCTAGGGTCCCTGATGCTTATGATATCTGGGGCCAAGGGACA

ATGGTCACCGTCTCCTCA (encodes V<sub>H</sub> domain 3.7)

SEQ ID NO. 444
CAGGTGCAGCTGGTGGAGTCTGGGGGAGGCTTGGTACAGCCTGGGGGGTCCCTGAGA

CTCTCCTGTGCAGCCTCTGGATTCCCCTTAATTAGCTATGGCATGAATTGGGTCCGCCA

GGCTCCAGGCAAGGGGCTGGACTGGGTGGCATTTATAACATATGATGGAAGTAATAGAT

ACTATGCAGACTCCGTGAAGGGCCGATTCACCATCTCCAGAGACAATTCCAAGAACACG

CTTCATCTGCAAATGGACAGCCTGAGACCTGAGGACACGGCTGTATATTACTGTGCGAA

AGATCGTATTGTGGGAGCTAGGGTCCCTGATGCTTATGATATCTGGGGCCAAGGGACA

ATGGTCACTGTCTCTTCA (encodes V<sub>H</sub> domain 3.8)

SEQ ID NO. 445
GAAGTGCAGCTGGTGGAGTCTGGGGGAGGCGTGGTCCAGCCTGGGAGGTCCCTGAGA

CTCTCCTGTGCAGCCTCTGGATTCCCCTTAATTAGCTATGGCATGAATTGGGTCCGCCA

GGCTCCAGGCAAGGGGCTGGACTGGGTGGCATTTATAACATATGATGGAAGTAATAGAT

ACTATGCAGACTCCGTGAAGGGCCGATTCACCATCTCCAGAGACAATTCCAAGAACACG

CTTTATCTGCAAATGAACAGCCTGAGACCTGAGGACACGGCTGTATATTACTGTGCGAA

AGATCGTATTGTGGGAGCTAGGGTCCCTGATGCTTATGATATCTGGGGCCAGGGAACC

CTGGTCACTGTCTCCTCA (encodes V<sub>H</sub> domain 3.9)

SEQ ID NO. 446
CAGGTGCAGCTGGTGGAGTCTGGGGGAGGCGTGGTCCAGCCTGGGAGGTCCCTGAGA

CTCTCCTGTGCAGCCTCTGGATTCCCCTTAATTAGCTATGGCATGAATTGGGTCCGCCA

GGCTCCAGGCAAGGGGCTGGAGTGGGTGGCATTTATATCATATGATGGAAGTAATAGAT

ACTATGCAGACTCCGTGAAGGGCCGATTCACCATCTCCAGAGACAATTCCAAGAACACG

CTGTATCTGCAAATGAACAGCCTGAGACCTGAGGACACGGCTGTATATTACTGTGCGAA

AGATCGTATTGTGGGAGCTAGGGTCCCTGATGCTTATGATATCTGGGGCCAAGGGACA

ATGGTCACCGTCTCTTCA (encodes V<sub>H</sub> domain 3.10)

SEQ ID NO. 447
CAGGTGCAGCTGGTGGAGTCTGGGGGAGGCGTGGTCCAGCCTGGGAGGTCCCTGAGA

CTCTCCTGTGCAGCCTCTGGATTCCCCTTAATTAGCTATGGCATGAATTGGGTCCGCCA

GGCTCCAGGCAAGGGGCTGGACTGGGTGGCATTTATAACATATGATGGAAGTAATAGAT

ACTATGCAGACTCCGTGAAGGGCCGATTCACCATCTCCAGAGACAATTCCAAGAACACG

CTTCATCTGCAAATGAACAGCCTGAGACCTGAGGACACGGCTGTATATTACTGTGCGAA

AGATCGTATTGTGGGAGCTAGGGTCCCTGATGCTTATGATATCTGGGGCCAAGGGACA

ATGGTCACTGTCTCCTCA (encodes V<sub>H</sub> domain 3.11)

SEQ ID NO. 448
GAGGTGCAGCTGGTGGAGTCTGGGGGAGGCGTGGTCCAGCCTGGGAGGTCCCTGAGA

CTCTCCTGTGCAGCCTCTGGATTCCCCTTAATTAGCTATGGCATGAATTGGGTCCGCCA

GGCTCCAGGCAAGGGGCTGGACTGGGTGGCATTTATAACATATGATGGAAGTAATAGAT

ACTATGCAGACTCCGTGAAGGGCCGATTCACCATCTCCAGAGACAATTCCAAGAACACG

CTTCATCTGCAAATGAACAGCCTGAGACCTGAGGACACGGCTGTATATTACTGTGCGAA

AGATCGTATTGTGGGAGCTAGGGTCCCTGATGCTTATGATATCTGGGGCCAAGGGACA

ATGGTCACTGTCTCCTCA (encodes V$_H$ domain 3.12)

SEQ ID NO. 449

GAGGTGCAGCTGGTGGAGTCTGGGGGAGGCGTGGTCCAGCCTGGGAGGTCCCTGAGA

CTCTCCTGTGCAGCCTCTGGATTCCCCTTAATTAGCTATGGCATGAATTGGGTCCGCCA

GGCTCCAGGCAAGGGGCTGGACTGGGTGGCATTTATAACATATGATGGAAGTAATAGAT

ACTATGCAGACTCCGTGAAGGGCCGATTCACCATCTCCAGAGACAATTCCAAGAACACG

CTTTATCTGCAAATGAACAGCCTGAGACCTGAGGACACGGCTGTATATTACTGTGCGAA

AGATCGTATTGTGGGAGCTAGGGTCCCTGATGCTTATGATATCTGGGGCCAAGGGACA

ATGGTCACCGTCTCCTCA (encodes V$_H$ domain 3.13)

SEQ ID NO. 450

CAGGTGCAGCTGGTGGAGTCTGGGGGAGGCGTGGTCCAGCCTGGGAGGTCCCTGAGA

CTCTCCTGTGCAGCCTCTGGATTCCCCTTAATTAGCTATGGCATGAATTGGGTCCGCCA

GGCTCCAGGCAAGGGGCTGGACTGGGTGGCATTTATAACATATGATGGAAGTAATAGAT

ACTATGCAGACTCCGTGAAGGGCCGATTCACCATCTCCAGAGACAATTCCAAGAACACG

CTTTATCTGCAAATGAACAGCCTGAGACCTGAGGACACGGCTGTATATTACTGTGCGAA

AGATCGTATTGTGGGAGCTAGGGTCCCTGATGCTTATGATATCTGGGGCCAAGGGACA

ATGGTCACTGTCTCCTCA (encodes V$_H$ domain 3.14)

SEQ ID NO. 451

GAGGTGCAGCTGGTGGAGTCTGGGGGAGGTGTGGTACGGCCTGGGGGGTCCCTGAGA

CTCTCCTGTGCAGCCTCTGGATTCCCCTTAATTAGCTATGGCATGAATTGGGTCCGCCA

GGCTCCAGGCAAGGGGCTGGACTGGGTGGCATTTATAACATATGATGGAAGTAATAGAT

ACTATGCAGACTCCGTGAAGGGCCGATTCACCATCTCCAGAGACAATTCCAAGAACACG

CTTCATCTGCAAATGAACAGCCTGAGACCTGAGGACACGGCTGTATATTACTGTGCGAA

AGATCGTATTGTGGGAGCTAGGGTCCCTGATGCTTATGATATCTGGGGCCAAGGGACA

ATGGTCACTGTCTCCTCA (encodes V$_H$ domain 3.15)

SEQ ID NO. 452

GAAGTGCAGCTGGTGGAGTCTGGGGGAGGCTTGGTCCAGCCTGGGGGGTCCCTGAGA

CTCTCCTGTGCAGCCTCTGGATTCCCCTTAATTAGCTATGGCATGAATTGGGTCCGCCA

GGCTCCAGGCAAGGGGCTGGACTGGGTGGCATTTATAACATATGATGGAAGTAATAGAT

ACTATGCAGACTCCGTGAAGGGCCGATTCACCATCTCCAGAGACAATTCCAAGAACACG

CTTCATCTGCAAATGAACAGCCTGAGACCTGAGGACACGGCTGTATATTACTGTGCGAA

AGATCGTATTGTGGGAGCTAGGGTCCCTGATGCTTATGATATCTGGGGCCAAGGGACA

ATGGTCACCGTCTCCTCA (encodes V$_H$ domain 3.16)

SEQ ID NO. 453

GAGGTGCAGCTGTTGGAGTCTGGGGGAGGCGTGGTCCAGCCTGGGAGGTCCCTGAGA

CTCTCCTGTGCAGCCTCTGGATTCCCCTTAATTAGCTATGGCATGAATTGGGTCCGCCA

GGCTCCAGGCAAGGGGCTGGACTGGGTGGCATTTATAACATATGATGGAAGTAATAGAT

ACTATGCAGACTCCGTGAAGGGCCGATTCACCATCTCCAGAGACAATTCCAAGAACACG

CTTCATCTGCAAATGAACAGCCTGAGACCTGAGGACACGGCTGTATATTACTGTGCGAA

AGATCGTATTGTGGGAGCTAGGGTCCCTGATGCTTATGATATCTGGGGCCAAGGGACA

ATGGTCACCGTCTCCTCA (encodes V$_H$ domain 3.17)

SEQ ID NO. 454

GAGGTGCAGCTGTTGGAGTCTGGGGGAGGCGTGGTCCAGCCTGGGAGGTCCCTGAGA

CTCTCCTGTGCAGCCTCTGGATTCCCCTTAATTAGCTATGGCATGAATTGGGTCCGCCA

GGCTCCAGGCAAGGGGCTGGACTGGGTGGCATTTATAACATATGATGGAAGTAATAGAT

ACTATGCAGACTCCGTGAAGGGCCGATTCACCATCTCCAGAGACAATTCCAAGAACACG

CTTTATCTGCAAATGAACAGCCTGAAACCTGAGGACACGGCTGTATATTACTGTGCGAA

AGATCGTATTGTGGGAGCTAGGGTCCCTGATGCTTATGATATCTGGGGCCAAGGGACA

ATGGTCACCGTCTCCTCA (encodes V$_H$ domain 3.18)

SEQ ID NO. 455

GAGGTGCAGCTGGTGGAGTCTGGGGGAGGCGTGGTCCAGCCTGGGAGGTCCCTGAGA

CTCTCCTGTGCAGCCTCTGGATTCCCCTTAATTAGCTATGGCATGAATTGGGTCCGCCA

GGCTCCAGGCAAGGGGCTGGACTGGGTGGCATTTATAACATATGATGGAAGTAATAGAT

ACTATGCAGACTCCGTGAAGGGCCGATTCACCATCTCCAGAGACAATTCCAAGAACACG

CTTTATCTGCAAATGAACAGCCTGAAACCTGAGGACACGGCTGTATATTACTGTGCGAA

AGATCGTATTGTGGGAGCTAGGGTCCCTGATGCTTATGATATCTGGGGCCAAGGGACA

ATGGTCACCGTCTCCTCA (encodes V$_H$ domain 3.19)

SEQ ID NO. 456

CAGGTGCAGCTGGTGGAGTCTGGGGGAGGCGTGGTCCAGCCTGGGAGGTCCCTGAGA

CTCTCCTGTGCAGCCTCTGGATTCCCCTTAATTAGCTATGGCATGCACTGGGTCCGCCA

GGCTCCAGGCAAGGGGCTGGAGTGGGTGGCATTTATGACATATGATGGAAGTAATAGA

TACTATGCAGACGCCGTGAAGGGCCGATTCACCATCTCCAGAGACAATTCCAAGAACAC

GCTGTATCTGCAAATGAACAGCCTGAGAGCTGAGGACACGGCTGTGTATTACTGTGCGA

GAGATCGTATAGTGGGAGGTAGGGTCCCTGATGCTTTTGATATCTGGGGCCAAGGGAC

AATGGTCACCGTCTCTTCA (encodes V$_H$ domain 3.20)

SEQ ID NO. 457

CAGGTGCAGCTGGTGGAGTCTGGGGGAGGCGTGGTCCAGCCTGGGAGGTCCCTGAGA

CTCTCCTGTGCAGCCTCTGGATTCCCCTTAATTAGCTATGGCATGCACTGGGTCCGCCA

GGCTCCAGGCAAGGGGCTGGAGTGGGTGGCATTTCAGACATATGATGGCAGTAATAGA

TACTATGCAGACGCCGTGAAGGGCCGATTCACCATCTCCAGAGACAATTCCAAGAACAC

GCTGTATCTGCAAATGAACAGCCTGAGAGCTGAGGACACGGCTGTGTATTACTGTGCGA

GAGATCGTATAGTGGGAGGTAGGGTCCCTGATGCTTTTGATATCTGGGGCCAAGGGAC

AATGGTCACCGTCTCTTCA (encodes V$_H$ domain 3.21)

SEQ ID NO. 458

CAGGTGCAGCTGGTGGAGTCTGGGGGAGGCGTGGTCCAGCCTGGGAGGTCCCTGAGA

CTCTCCTGTGCAGCCTCTGGATTCCCCTTAATTAGCTATGGCATGCACTGGGTCCGCCA

GGCTCCAGGCAAGGGGCTGGAGTGGGTGGCATTTCAGACATATGATGGCAGTAATAGA

TACTATGCAGACTCCGTGAAGGGCCGATTCACCATCTCCAGAGACAATTCCAAGAACAC

GCTGTATCTGCAAATGAACAGCCTGAGAGCTGAGGACACGGCTGTGTATTACTGTGCGA

```
GAGATCGTATAGTGGGAGGTAGGGTCCCTGATGCTTTTGATATCTGGGGCCAAGGGAC

AATGGTCACCGTCTCTTCA (encodes V_H domain 3.22)
                                                    SEQ ID NO. 459
CAGGTGCAGCTGGTGGAGTCTGGGGGAGGCGTGGTCCAGCCTGGGAGGTCCCTGAGA

CTCTCCTGTGCAGCCTCTGGATTCCCCTTAATTAGCTATGGCATGCACTGGGTCCGCCA

GGCTCCAGGCAAGGGGCTGGAGTGGGTGGCATTTCAGACATATGATGCCAGTAATAGA

TACTATGCAGACGCCGTGAAGGGCCGATTCACCATCTCCAGAGACAATTCCAAGAACAC

GCTGTATCTGCAAATGAACAGCCTGAGAGCTGAGGACACGGCTGTGTATTACTGTGCGA

GAGATCGTATAGTGGGAGGTAGGGTCCCTGATGCTTTTGATATCTGGGGCCAAGGGAC

AATGGTCACCGTCTCTTCA (encodes V_H domain 3.23)
                                                    SEQ ID NO. 460
CAGGTGCAGCTGGTGGAGTCTGGGGGAGGCGTGGTCCAGCCTGGGAGGTCCCTGAGA

CTCTCCTGTGCAGCCTCTGGATTCCCCTTAATTAGCTATGGCATGAATTGGGTCCGCCA

GGCTCCAGGCAAGGGGCTGGAGTGGGTGGCATTTATAACATATGATGGAAGTAATAGA

TACTATGCAGACTCCGTGAAGGGCCGATTCACCATCTCCAGAGACAATTCCAAGAACAC

GCTTTATCTGCAAATGAACAGCCTGAGAGCTGAGGACACGGCTGTATATTACTGTGCGA

AAGATCGTATTGTGGGAGCTAGGGTCCCTGATGCTTATGATATCTGGGGCCAAGGGAC

AATGGTCACTGTCTCCTCA (encodes V_H domain 3.24)
                                                    SEQ ID NO. 461
AGGTGCAGCTGGTGGAGTCTGGGGGAGGCGTGGTCCAGCCTGGGAGGTCCCTGAGAC

TCTCCTGTGCAGCCTCTGGATTCCCCTTAATTAGCTATGGCATGAATTGGGTCCGCCAG

GCTCCAGGCAAGGGGCTGGAGTGGGTGGCATTTATAACATATGATGGAAGTAATAGATA

CTATGCAGACTCCGTGAAGGGCCGATTCACCATCTCCAGAGACAATTCCAAGAACACGC

TTTATCTGCAAATGAACAGCCTGAGAGCTGAGGACACGGCTGTATATTACTGTGCGAAA

GATCGTATTGTGGGAGCTAGGGTCCCTGATGCTTATGATATCTGGGGCCAAGGGACAAT

GGTCACTGTCTCCTCA

SEQ ID NOs. 4462, 463, 464 and 465 as shown below encode
V_H domains of family 4 comprising or consisting of
SEQ ID NO. 280 to 292.
(encodes V_H domain 4.1)
                                                    SEQ ID NO. 462
CAGGTGCAGCTGGTGGAGTCTGGGGGAGGCGTGGTCCAGCCTGGGAGGTCCTTGAGA

CTCTCCTGTGTAGCCTCTGGATTCCCCTTCATTAGCTATGGCATGCACTGGGTCCGCCA

GGCTCCAGGCAAGGGGCGGGAGTGGGTGGCAGTTATATCATATGATGGAAGTAATAGA

TACTATGCAGACTCCGTGAAGGGCCGATTCACCATCTCCAGAGACAATTCCAAGAACAC

GCTGTATCTGCAAATGAACAGCCTGAGACCTGAGGACACGGCTGTGTATTATTGTGCGA

AAGAGAGGATTTTTGGAGTGCTTACCCCTGATGATTTTGATATCTGGGGCCAAGGGACA

ACGGTCACCGTCTCCTCA (encodes V_H domain 4.2)
                                                    SEQ ID NO. 463
CAGGTGCAGCTGGTGGAGTCTGGGGGAGGCGTGGTCCAGCCTGGGAGGTCCCTGAGA

CTCTCCTGTGCAGCCTCTGGATTCCCCTTCATTAGCTATGGCATGCACTGGGTCCGCCA

GGCTCCAGGCAAGGGGCTGGAGTGGGTGGCAGTTATATCATATGATGGAAGTAATAGA

TACTATGCAGACTCCGTGAAGGGCCGATTCACCATCTCCAGAGACAATTCCAAGAACAC
```

-continued

GCTGTATCTGCAAATGAACAGCCTGAGACCTGAGGACACGGCTGTGTATTACTGTGCGA

AAGAGAGGATTTTTGGAGTGCTTACCCCTGATGATTTTGATATCTGGGGCCAAGGGACA

ACGGTCACTGTCTCCTCA (encodes V<sub>H</sub> domain 4.3)
SEQ ID NO. 464
GAGGTGCAGCTGTTGGAGTCTGGGGGAGGCGTGGTCCAGCCTGGGAGGTCCCTGAGA

CTCTCCTGTGCAGCCTCTGGATTCCCCTTCATTAGCTATGGCATGCACTGGGTCCGCCA

GGCTCCAGGCAAGGGGCTGGAGTGGGTGGCAGTTATATCATATGATGGAGCTAATAGA

TACTATGCAGACTCCGTGAAGGGCCGATTCACCATCTCCAGAGACAATTCCAAGAACAC

GCTGTATCTGCAAATGAACAGCCTGAGACCTGAGGACACGGCTGTGTATTATTGTGCGA

AAGAGAGGATTTTTGGCGTGCTTACCCCTGATGATTTTGAAATCTGGGGCCAAGGGACA

ACGGTCACCGTCTCCTCA (encodes V<sub>H</sub> domain 4.4)
SEQ ID NO. 465
GAGGTGCAGCTGGTGGAGTCTGGGGGAGGCGTGGTCCAGCCTGGGAGGTCCCTGAGA

CTCTCCTGTGCAGCCTCTGGATTCACCTTCACTAGCTATGGCATGCACTGGGTCCGCCA

GGCTCCAGGCAAGGGGCTGGAGTGGGTGGCAGTTATATCATATGATGGAAGTAATAGA

TACTATGCAGACTCCGTGAAGGGCCGATTCACCATCTCCAGAGACAATTCCAAGAACAC

GCTGTATCTGCAAATGAACAGCCTGAGACCTGAGGACACGGCTGTGTATTACTGTGCGA

AAGAGAGGATTTTTGGAGCGCTTACCCCTGATGATTTTGATATCTGGGGCCAAGGGACA

ACGGTCACCGTCTCTTCA

SEQ ID NOs. 466 or 467 as shown below encode V<sub>H</sub>
domains of family 5 comprising or consisting of SEQ ID NO.
296 and 300.
(encodes V<sub>H</sub> domain 5.1)
SEQ ID NO. 466
CAGGTGCAGCTGGTGGAGTCTGGGGGAGGCGTGGTCCAGCCTGGGAGGTCCCTGAGA

CTCTCCTGTGCAGCCTCTGGATTCACCTTCAATAACTATGGCATGCACTGGGTCCGCCA

GGCTCCAGGCAAGGGGCTGGAGTGGGTGGCAATTATATCATATGATGGAAATACTAAT

ATTATACAGACTCCGTGAAGGGCCGATTCACCATCTCCAGAGACAATTCCAAGAACACG

CTGTATCTGCAAATGAATAGCCTGAGAGTTGAGGACACGGCTGTGTATTACTGTGCGAA

AGGTTTATGGCCTTCGGACGTCTGGGGCCAAGGGACCACGGTCACTGTCTCTTCA (encodes V<sub>H</sub> domain 5.2)
SEQ ID NO. 467
GAGGTGCAGCTGGTGGAGTCTGGGGGAGGCGTGGTCCAGCCTGGGAGGTCCCTGAGA

CTCTCCTGTGCAGCCTCTGGATTCACCTTCAATAACTATGGCATGCACTGGGTCCGCCA

GGCTCCAGGCAAGGGGCTGGAGTGGGTGGCAATTATATCATATGATGGAAATAGTAAT

ATTATACAGACTCCGTGAAGGGCCGATTCACCATCTCCAGAGACAATTCCAAGAACACG

CTGTATCTGCAAATGAATAGCCTGAGAGTTGAGGACACGGCTGTGTATTACTGTGCGAA

AGGTTTATGGCCTTCGGACGTCTGGGGCCAAGGGACCACGGTCACCGTCTCCTCA

SEQ ID NOs. 468 to 474 as shown below encode V<sub>H</sub>
domains of family 6 comprising or consisting of SEQ ID NO.
304 to 328.
(encodes V<sub>H</sub> domain 6.1)
SEQ ID NO. 468
CAGGTGCAGCTACAGGAGTCGGGCCCAGGACTGGTGAAGCCTTCACAGACCCTGTCCC

TCACCTGCACTGTCTCTGGTGGCTCCATCAGCAATAGTGGTTATTACTGGAGCTGGGTC

CGCCAGCACCCAGGGAAGGACCTGGAGTGGATTGGGTTCATCTATTACAATGGGAGCA

TCCACTACAACCCGTCCCTCAAGAGTCGAGTTATCATATCAGTAGACACGTCTAAGAAC

```
CAGTTCTCCCTGAAAATGAACTCTGTGACTGCCGCGGACACGGCCGTGTATTACTGTGC

GAGAGACGGGGATGACTACGGTGACTACTTGAGGGGCCAGGGAACCCTGGTCACCGT

CTCCTCA
```

(encodes V<sub>H</sub> domain 6.2)

SEQ ID NO. 469
```
CAGGTGCAGCTGCAGGAGTCGGGCCCAGGACTGGTGAAGCCTTCACAGACCCTGTCC

CTCACCTGCACTGTCTCTGGTGGCTCCATCAGCAATAGTGGTTATTACTGGAGCTGGAT

CCGCCAGCACCCAGGGAAGGGCCTGGAGTGGATTGGGTTCATCTATTACAATGGGAGC

ATCCACTACAACCCGTCCCTCAAGAGTCGAGTTATCATATCAGTAGACACGTCTAAGAA

CCAGTTCTCCCTGAAAATGAGCTCTGTGACTGCCGCGGACACGGCCGTGTATTACTGTG

CGAGAGACGGGGATGACTACGGTGACTACTTGAGGGGCCAGGGAACCCTGGTCACCG

TCTCCTCA
```

(encodes V<sub>H</sub> domain 6.3)

SEQ ID NO. 470
```
CAGGTGCAGCTGCAGGAGTCGGGCCCAGGACTGGTGAAGCCTTCACAGACCCTGTCC

CTCACCTGCACTGTCTCTGGTGGCTCCATCAGCAATAGTGGTTATTACTGGAGCTGGGT

CCGCCAGCACCCAGGGAAGGGCCTGGAGTGGATTGGGTTCATCTATTACAATGGGAGC

ATCCACTACAACCCGTCCCTCAAGAGTCGAGTTATCATATCAGTAGACACGTCTAAGAA

CCAGTTCTCCCTGAAACTGAACTCTGTGACTGCCGCGGACACGGCCGTGTATTACTGTG

CGAGAGACGGGGATGACTACGGTGACTACTTGAGGGGCCAGGGAACCCTGGTCACCG

TCTCCTCA
```

(encodes V<sub>H</sub> domain 6.4)

SEQ ID NO. 471
```
CAGGTGCAGCTGCAGGAGTCGGGCCCAGGACTGGTGAAGCCTTCACAGACCCTGTCC

CTCACCTGCACTGTCTCTGGTGGCTCCATCAGCAATAGTGGTTATTACTGGAGCTGGAT

CCGCCAGCACCCAGGGAAGGGCCTGGAGTGGATTGGGTTCATCTATTACAATGGGAGC

ATCCACTACAACCCGTCCCTCAAGAGTCGAGTTATCATATCAGTAGACACGTCTAAGAA

CCAGTTCTCCCTGAAACTGAGCTCTGTGACTGCCGCGGACACGGCCGTGTATTACTGT

GCGAGAGACGGGGATGACTACGGTGACTACTTGAGGGGCCAGGGAACCCTGGTCACC

GTCTCCTCA
```

(encodes V<sub>H</sub> domain 6.5)

SEQ ID NO. 472
```
CAGGTGCAGCTGCAGGAGTCGGGCCCAGGACTGGTGAAGCCTTCACAGACCCTGTCC

CTCACCTGCACTGTCTCTGGTGGCTCCATCAGCAATAGTGGTTATTACTGGAGCTGGGT

CCGCCAGCACCCAGGGAAGGGCCTGGAGTGGATTGGGTTCATCTATTACAATGGGAGC

ATCCACTACAACCCGTCCCTCAAGAGTCGAGTTACCATATCAGTAGACACGTCTAAGAA

CCAGTTCTCCCTGAAAATGAGCTCTGTGACTGCCGCGGACACGGCCGTGTATTACTGTG

CGAGAGACGGGGATGACTACGGTGACTACTTGAGGGGCCAGGGAACCCTGGTCACCG

TCTCCTCA
```

(encodes V<sub>H</sub> domain 6.6)

SEQ ID NO. 473
```
CAGGTGCAGCTGCAGGAGTCGGGCCCAGGACTGGTGAAGCCTTCACAGACCCTGTCC

CTCACCTGCACTGTCTCTGGTGGCTCCATCAGCAATAGTGGTTATTACTGGAGCTGGGT

CCGCCAGCACCCAGGGAAGGGCCTGGAGTGGATTGGGTTCATCTATTACAATGGGAGC

ATCCACTACAACCCGTCCCTCAAGAGTCGAGTTACCATATCAGTAGACACGTCTAAGAA
```

```
CCAGTTCTCCCTGAAACTGAACTCTGTGACTGCCGCGGACACGGCCGTGTATTACTGTG

CGAGAGACGGGGATGACTACGGTGACTACTTGAGGGGCCAGGGAACCCTGGTCACCG

TCTCCTCA
```

(encodes V$_H$ domain 6.7)

SEQ ID NO. 474

```
CAGGTGCAGCTGCAGGAGTCGGGCCCAGGACTGGTGAAGCCTTCACAGACCCTGTCC

CTCACCTGCACTGTCTCTGGTGGCTCCATCAGCAATAGTGGTTATTACTGGAGCTGGGT

CCGCCAGCACCCAGGGAAGGGCCTGGAGTGGATTGGGTTCATCTATTACAATGGGAGC

ATCCACTACAACCCGTCCCTCAAGAGTCGAGTTACCATATCAGTAGACACGTCTAAGAA

CCAGTTCTCCCTGAAACTGAGCTCTGTGACTGCCGCGGACACGGCCGTGTATTACTGT

GCGAGAGACGGGGATGACTACGGTGACTACTTGAGGGGCCAGGGAACCCTGGTCACC

GTCTCCTCA
```

SEQ ID NOs. 475 to 482 as shown below w encode V$_H$
domains of family 7 comprising or consisting of SEQ ID NO.
332 to 360.

(encodes V$_H$ domain 7.1)

SEQ ID NO. 475

```
GAGGTGCAGCTGGTGGAGTCTGGGGGAGGCTTGGTCCAGCCTGGGGGGTCCCTGAGA

CTCTCCTGTGCAGCCTCTGGATTCACCTTTAGTAGCTATTGGATGTACTGGGTCCGCCA

GGCTCCAGGGAAGGGGCTGGAGTGGGTGGCCAACATAAATCACGATGGAAGTGAGAA

ATACTATGTGGACTCTGTGAAGGGCCGATTCACCATCTCCAGAGACAACGCCAAGAACT

CACTGTATCTGCAAATGAACAGCCTGAGAGCCGAGGACACGGCTGTGTATTACTGCGC

GAGAGATTCCCTTATAGTGGGAGAGAGGGGCTACTGGGGCCAGGGAACCCTGGTCAC

CGTCTCCTCA
```

(encodes V$_H$ domain 7.2)

SEQ ID NO. 476

```
GAGGTGCAGCTGGTGGAGTCTGGGGGAGGCTTGGTCCAGCCTGGGGGGTCCCTGAGA

CTCTCCTGTGCAGCCTCTGGATTCACCTTTAGTAGCTATTGGATGTACTGGGTCCGCCA

GGCTCCAGGGAAGGGGCTGGAGTGGGTGGCCAACATAAATCACGATGGAAGTGAGAA

ATACTATGTGGACTCTGTGAAGGGCCGATTCACCATCTCCAGAGACAACGCCAAGAACT

CACTGTATCTGCAAATGAACAGCCTGAGAGCCGAGGACACGGCTGTGTATTACTGCGC

GAGAGATAACCTTATAGTGGGAGAGAGGGGCTACTGGGGCCAGGGAACCCTGGTCAC

CGTCTCCTCA
```

(encodes V$_H$ domain 7.3)

SEQ ID NO. 477

```
GAGGTGCAGCTGGTGGAGTCTGGGGGAGGCTTGGTCCAGCCTGGGGGGTCCCTGAGA

CTCTCCTGTGCAGCCTCTGGATTCACCTTTAGTAGCTATTGGATGTACTGGGTCCGCCA

GGCTCCAGGGAAGGGGCTGGAGTGGGTGGCCAACATAAATCACGGGGGAAGTGAGAA

ATACTATGTGGACTCTGTGAAGGGCCGATTCACCATCTCCAGAGACAACGCCAAGAACT

CACTGTATCTGCAAATGAACAGCCTGAGAGCCGAGGACACGGCTGTGTATTACTGCGC

GAGAGATTCCCTTATAGTGGGAGAGAGGGGCTACT
```

(encodes V$_H$ domain 7.4)

SEQ ID NO. 478

```
GGGGCCAGGGAACCCTGGTCACCGTCTCCTCAGAGGTGCAGCTGGTGGAGTCTGGGGGAG

GCTTGGTCCAGCCTGGGGGGTCCCTGAGACTCTCCTGTGCAGCCTCTGGATTCACCTTTA

GTAGCTATTGGATGTACTGGGTCCGCCAGGCTCCAGGGAAGGGGCTGGAGTGGGTGGCCA

ACATAAATCACCAGGGAAGTGAGAAATACTATGTGGACTCTGTGAAGGGCCGATTCACCA
```

-continued

TCTCCAGAGACAACGCCAAGAACTCACTGTATCTGCAAATGAACAGCCTGAGAGCCGAGG

ACACGGCTGTGTATTACTGCGCGAGAGATTCCCTTATAGTGGGAGAGAGGGGCTACTGGG

GCCAGGGAACCCTGGTCACCGTCTCCTCA (encodes $V_H$ domain 7.5)

SEQ ID NO. 479

GAGGTGCAGCTGGTGGAGTCTGGGGGAGGCTTGGTCCAGCCTGGGGGGTCCCTGAGA

CTCTCCTGTGCAGCCTCTGGATTCACCTTTAGTAGCTATTGGATGTACTGGGTCCGCCA

GGCTCCAGGGAAGGGGCTGGAGTGGGTGGCCAACATAAATCACCCCGGAAGTGAGAA

ATACTATGTGGACTCTGTGAAGGGCCGATTCACCATCTCCAGAGACAACGCCAAGAACT

CACTGTATCTGCAAATGAACAGCCTGAGAGCCGAGGACACGGCTGTGTATTACTGCGC

GAGAGATTCCCTTATAGTGGGAGAGAGGGGCTACTGGGGCCAGGGAACCCTGGTCAC

CGTCTCCTCA (encodes $V_H$ domain 7.6)

SEQ ID NO. 480

GAGGTGCAGCTGGTGGAGTCTGGGGGAGGCTTGGTCCAGCCTGGGGGGTCCCTGAGA

CTCTCCTGTGCAGCCTCTGGATTCACCTTTAGTAGCTATTGGATGTACTGGGTCCGCCA

GGCTCCAGGGAAGGGGCTGGAGTGGGTGGCCAACATAAATCACGAGGGAAGTGAGAA

ATACTATGTGGACTCTGTGAAGGGCCGATTCACCATCTCCAGAGACAACGCCAAGAACT

CACTGTATCTGCAAATGAACAGCCTGAGAGCCGAGGACACGGCTGTGTATTACTGCGC

GAGAGATTCCCTTATAGTGGGAGAGAGGGGCTACTGGGGCCAGGGAACCCTGGTCAC

CGTCTCCTCA (encodes $V_H$ domain 7.7)

SEQ ID NO. 481

GAGGTGCAGCTGGTGGAGTCTGGGGGAGGCTTGGTCCAGCCTGGGGGGTCCCTGAGA

CTCTCCTGTGCAGCCTCTGGATTCACCTTTAGTAGCTATTGGATGTACTGGGTCCGCCA

GGCTCCAGGGAAGGGGCTGGAGTGGGTGGCCAACATAAATCACATCGGAAGTGAGAAA

TACTATGTGGACTCTGTGAAGGGCCGATTCACCATCTCCAGAGACAACGCCAAGAACTC

ACTGTATCTGCAAATGAACAGCCTGAGAGCCGAGGACACGGCTGTGTATTACTGCGCG

AGAGATTCCCTTATAGTGGGAGAGAGGGGCTACTGGGGCCAGGGAACCCTGGTCACC

GTCTCCTCA (encodes $V_H$ domain 7.8)

SEQ ID NO. 482

GAGGTGCAGCTGGTGGAGTCTGGGGGAGGCTTGGTCCAGCCTGGGGGGTCCCTGAGA

CTCTCCTGTGCAGCCTCTGGATTCACCTTTAGTAGCTATTGGATGTACTGGGTCCGCCA

GGCTCCAGGGAAGGGGCTGGAGTGGGTGGCCAACATAAATCACGATGGAAGTGAGAA

ATACTATGTGGACTCTGTGAAGGGCCGATTCACCATCTCCAGAGACAACGCCAAGAACT

CACTGTATCTGCAAATGAACAGCCTGAGAGCCGAGGACACGGCTGTGTATTACTGCGC

GAGAGATACCCTTATAGTGGGAGAGAGGGGCTACTGGGGCCAGGGAACCCTGGTCAC

CGTCTCCTCA

SEQ ID NO. 483 as shown below encodes a $V_H$ domain of
family 8 comprising or consisting of SEQ ID NO. 364.

SEQ ID NO. 483

CAGGTGCAGCTACAGCAGTGGGGCGCAGGACTGTTGAAGCCTTCGGAGACCCTGTCC

CTCACCTGCGCTGTCTATGGTGGGTCCTTCAGTGGTTACTACTGGAGCTGGATCCGCCA

GCCCCCAGGGAAGGGGCTGGAGTGGATTGGGGAAATCAATCATAGTGGAAGCACCAAC

TACAACCCGTCCCTCAAGAGTCGAGTCACCATATCAGTAGACACGTCCAAGAACCAGTT

-continued
CTCCCTGAAGCTGAGCTCTGTGACCGCCGCGGACACGGCTGTGTATTACTGTGCGAGA

GGCCCCATACCAGCCACTGCTATACCCGATGCTTTTGATATCTGGGGCCAAGGGACAAT

GGTCACTGTCTCCTCA

SEQ ID NO. 484 as shown below encodes a V$_H$ domain of
family 9 comprising or consisting of SEQ ID NO. 368.
SEQ ID NO. 484
GAGGTGCAGCTACAGCAGTGGGGCGCAGGACTGTTGAAGCCTTCGGAGACCCTGTCC

CTCACCTGCGCTGTCTATGGTGGGTCCTTCAGTGGTCACTACTGGAGCTGGATCCGCC

AGCCCCCAGGGAAGGGGCTGGAGTGGATTGGGGACATAAATCATAGTGGAAGCACCAA

CTACAACCCGTCCCTCAAGAGTCGAGTCACCATATCAGTAGACACGTCCAAGAATCAGT

TCTCCCTGAAGCTGAGCTCTGTGACCGCCGCGGACACGGCTGTGTATTACTGTGTGAG

AGACTACGGTGACTCCCGTAGCCTTTTTGACTACTGGGGCCAGGGAACCCTGGTCACC

GTCTCTTCA

SEQ ID NO. 485 as shown below encodes a V$_H$ domain of
family 10 comprising or consisting of SEQ ID NO. 372.
SEQ ID NO. 485
CAGGTGCAGCTGGTGGAGTCTGGGGGAGGCTTGGTACAGCCTGGGGGGTCCCTGAGA

CTCTCCTGTGCAGCCTCTGGATTCACCTTCAGTAGCTATGGCATGCACTGGGTCCGCCA

GGCTCCAGGCAAGGGGCTGGAGTGGGTGGCATTTATGTCATATGATGGCAGTAATAAA

TACTATGTAGACTCCGTGAAGGGCCGATTCACCATCTCCAGAGACAATTCCAAGAATAC

GCTGTATCTGCAAATGAACAGCCTGAGAGCTGAGGACACGGCTGTGTATTACTGTGCGA

AAGGCGATTACGATTTTTGGAGTGGTTACCCCGACTACGATATGGACGTCTGGGGCCAA

GGGACCACGGTCACCGTCTCCTCA

SEQ ID NO. 486 as shown below encode a V$_H$ domain of
family 11 comprising or consisting of SEQ ID NO. 376.
SEQ ID NO. 486
GAGGTGCAGCTGGTGGAGTCTGGGGGAGGCTTGGTCAAGCCTGGAGGGTCCCTGAGA

CTCTCCTGTGCAGCCTCTGGATTCAACTTGATTAGCTATGGCATGTACTGGGTCCGCCA

GGCTCCAGGCAAGGGGCTGGAGTGGGTGGCAGTTATATCATATGATGGAAGTAATAAA

AACTATGCAGACTCCGTGAAGGGCCGATTCACCATCTCCAGAGACAATTCCAAGAATAC

GCTGTTTCTGCAAATGAACAGCCTGAGAGTTGAGGACACGGCTGTGTATTACTGTGCGA

AAGGGGGGAATGCCTTGTATAGCAGTGGCTGGCCCGATGATGGTTTTGATATCAGGGG

CCAAGGGACAATGGTCACTGTCTCCTCA

SEQ ID NO. 487 as shown below encode a V$_H$ domain of
family 12 comprising or consisting of SEQ ID NO. 380.
SEQ ID NO. 487
CAGGTGCAGCTGGTGGAGTCTGGGGGAGGCGTGGTCCAGCCTGGGAGGTCCCTGAGA

CTCTCCTGTGCAGCCTCTGGATTCACCTTCAGTAACTTTGGCATGCACTGGGCCCGCCA

GGCTCCAGGCAAGGGACTGGAGTGGGTGGCAGTAATATCATATGATGGAAATAGTAAAT

ACTATGCAGACACCGTGAAGGGCCGATTCACCATCTCCAGAGACAATTCCAAGAACACG

CTGTATCTGGAAATGAACAGCCTGAGAGCTGATGACACGGCTGTGTATTACTGTGCGAA

AGGCCTATGGCCCCCAATGGACGTCAGGGGCCAAGGGACCACGGTCACCGTCTCCTCA

SEQ ID NO. 488 as shown below encode a V$_H$ domain of
family 13 comprising or consisting of SEQ ID NO. 384.
SEQ ID NO. 488
GAGGTGCAGCTGGTGGAGTCTGGGGGAGGCTCGGTCCAGCCTGGGGGGTCCCTGAGA

CTCTCCTGTGCAGCCTCTGGATTCACCTTTAGTGACTATTGGATGACCTGGGTCCGCCA

GGTTCCAGGGAAGGGGCTGGAGTGGGTGGCCAACATAAAGCAAGATGGAAGTGAGAA

-continued

ATACTATGTGGACTCTGTGAAGGGCCGATTCACCATCTCCAGAGACAACGCCAAGAACT

CACTATATCTGCAAATGAATAGCCTGAGAGCCGAGGACACGGCTGTGTATTACTGTGCG

AGAGATCGAGGAGGAGCAGTGGCCCTTTATCACAACGGTATGGACATGGGGGGCCAAG

GGACCACGGTCACTGTCTCTTCA

SEQ ID NO. 4899 as shown below encode a V$_H$ domain of
family 14 comprising or consisting of SEQ ID NO. 388.
SEQ ID NO. 489

GAAGTGCAGCTGGTGGAGTCTGGGGGAGGTGAAGAAGCCTGGGGCCTCAGTGAAGGT

CTCCTGCAAGGCTTCTGGATACACCTTCACCAGTTATGATATCAACTGGGTGCGACAGG

CCACTGGACAAGGGCTTGAGTGGATGGGATGGATGAACCCTAACAGTGGTAACACAGG

CTATGCACAGAAGTTCCAGGGCAGAGTCACCATGACCAGGAACACCTCCATAAGCACA

GCCTACATGGAGCTGAGCAGCCTGAGATCTGAGGACACGGCCGTGTATTACTGTGCGA

GAGGGAACGGGCCCGGTATAACTGGAACTACTGACTACTGGGGCCAGGGAACCCTGG

TCACTGTCTCTTCA

SEQ ID NO. 490 as shown below encodes a V$_H$ domain of
family 15 comprising or consisting of SEQ ID NO. 392.
SEQ ID NO. 490

GAGGTGCAGCTGGTGGAGTCTGGGGGAGGTGTGGTACGGCCTGGGGGGTCCCTGAGA

CTCTCCTGTGCAGCCTCTGGATTCACCTTTGATGATTATGGCATGAGCTGGGTCCGCCA

AGCTCCAGGGAAGGGGCTGGAGTGGGTCTCTGGTATTAATTGGAATGGTGATCGTACC

GGTTATGCAGACTCTGTGAAGGGCCGATTCACCATCTCCAGAGACAACGCCAAGAACTC

CCTGTATCTGCAAATGAACAGTCTGAGAGCCGAGGACACGGCCTTGTATTACTGTGGA

GAGAGAATGTTATAGTACCAGCTGCTACCTACTGGGGCCAGGGAACCCTGGTCACCGT

CTCCTCA

A nucleic acid according to the present invention may comprise DNA or RNA and may be wholly or partially synthetic or recombinantly produced. Reference to a nucleotide sequence as set out herein encompasses a DNA molecule with the specified sequence, and encompasses a RNA molecule with the specified sequence in which U is substituted for T, unless context requires otherwise.

The nucleic acid may be in the form of a construct, for example a plasmid, vector, transcription or expression cassette.

The invention also relates to an isolated recombinant host cell comprising one or more nucleic acid construct as described above. The host cell may be a bacterial, viral, mammalian or other suitable host cell. In one embodiment, the cell is an *E. coli* cell. In another embodiment, the cell is a yeast cell. In another embodiment, the cell is a Chinese Hamster Ovary (CHO) cell.

Methods for preparing or generating the polypeptides, nucleic acids, host cells, products and compositions described herein using in vitro expression libraries can comprise the steps of:
a) providing a set, collection or library of nucleic acid sequences encoding amino acid sequences; and
b) screening said set, collection or library for amino acid sequences that can bind to/have affinity for PSMA and
c) isolating the amino acid sequence(s) that can bind to/have affinity for PSMA.

In the above methods, the set, collection or library of amino acid sequences may be displayed on a phage, phagemid, ribosome or suitable micro-organism (such as yeast), such as to facilitate screening. Suitable methods, techniques and host organisms for displaying and screening (a set, collection or library of) amino acid sequences will be clear to the person skilled in the art (see for example Phage Display of Peptides and Proteins: A Laboratory Manual, Academic Press; 1st edition (Oct. 28, 1996) Brian K. Kay, Jill Winter, John McCafferty).

A binding molecule described herein, including a V$_H$ domain, can be expressed in a transgenic rodent. The transgenic rodent, for example a mouse, may have a reduced capacity to express endogenous antibody genes. Thus, in one embodiment, the rodent has a reduced capacity to express endogenous light and/or heavy chain antibody genes. The rodent may therefore comprise modifications to disrupt expression of endogenous light and/or heavy chain antibody genes so that no functional light and/or heavy chains are produced.

Human heavy chain only antibodies capable of binding human PSMA can be produced by a method comprising
a) immunising a transgenic rodent with an PSMA antigen wherein said rodent expresses a nucleic acid construct comprising unrearranged human heavy chain V genes and is not capable of making functional endogenous light or heavy chains,
b) isolating human heavy chain only antibodies.

V$_H$ domains can be produced by a method comprising
a) immunising a transgenic mouse with an PSMA antigen wherein said mouse expresses a nucleic acid construct comprising human heavy chain V genes and is not capable of making functional endogenous light or heavy chains,
b) generating a library of sequences comprising V$_H$ domain sequences from said mouse and c) isolating sequences comprising $V_H$ domain sequences from said libraries.

Further steps may include identifying a single $V_H$ domain antibody or heavy chain only antibody that binds to human PSMA, for example by using functional assays as shown in the examples.

In one embodiment, the rodent is a mouse. The mouse may comprise a non-functional endogenous lambda light chain locus. Thus, the mouse does not make a functional endogenous lambda light chain. In one embodiment, the lambda light chain locus is deleted in part or completely or rendered non-functional through insertion, inversion, a recombination event, gene editing or gene silencing. For example, at least the constant region genes C1, C2 and C3 may be deleted or rendered non-functional through insertion or other modification as described above. In one embodiment, the locus is functionally silenced so that the mouse does not make a functional lambda light chain.

Furthermore, the mouse may comprise a non-functional endogenous kappa light chain locus. Thus, the mouse does not make a functional endogenous kappa light chain. In one embodiment, the kappa light chain locus is deleted in part or completely or rendered non-functional through insertion, inversion, a recombination event, gene editing or gene silencing. In one embodiment, the locus is functionally silenced so that the mouse does not make a functional kappa light chain.

The mouse having functionally-silenced endogenous lambda and kappa L-chain loci may, for example, be made as disclosed in WO 2003/000737, which is hereby incorporated by reference in its entirety.

Furthermore, the mouse may comprise a non-functional endogenous heavy chain locus. Thus, the mouse does not make a functional endogenous heavy chain. In one embodiment, the heavy chain locus is deleted in part or completely or rendered non-functional through insertion, inversion, a recombination event, gene editing or gene silencing. In one embodiment, the locus is functionally silenced so that the mouse does not make a functional heavy chain.

For example, as described in WO 2004/076618 (hereby incorporated by reference in its entirety), all 8 endogenous heavy chain constant region immunoglobulin genes (μ, δ, γ3, γ1, γ2a, γ2b, ε and α) are absent in the mouse, or partially absent to the extent that they are non-functional, or genes δ, γ3, γ1, γ2a, γ2b and ε are absent and the flanking genes μ and α are partially absent to the extent that they are rendered non-functional, or genes μ, δ, γ3, γ1, γ2a, γ2b and ε are absent and a is partially absent to the extent that it is rendered non-functional, or δ, γ3, γ1, γ2a, γ2b, ε and α are absent and μ is partially absent to the extent that it is rendered non-functional. By deletion in part is meant that the endogenous locus gene sequence has been deleted or disrupted, for example by an insertion, to the extent that no functional endogenous gene product is encoded by the locus, i.e., that no functional product is expressed from the locus. In another embodiment, the locus is functionally silenced.

In one embodiment, the mouse comprises a non-functional endogenous heavy chain locus, a non-functional endogenous lambda light chain locus and a non-functional endogenous kappa light chain locus. The mouse therefore does not produce any functional endogenous light or heavy chains. Thus, the mouse is a triple knockout (TKO) mouse.

The transgenic mouse may comprise a vector, for example a Yeast Artificial Chromosome (YAC) for expressing a heterologous heavy chain locus. YACs are vectors that can be employed for the cloning of very large DNA inserts in yeast. As well as comprising all three cis-acting structural elements essential for behaving like natural yeast chromosomes (an autonomously replicating sequence (ARS), a centromere (CEN) and two telomeres (TEL)), their capacity to accept large DNA inserts enables them to reach the minimum size (150 kb) required for chromosome-like stability and for fidelity of transmission in yeast cells. The construction and use of YACs is well known in the art (e.g., Bruschi, C. V. and Gjuracic, K. Yeast Artificial Chromosomes, Encyclopedia of Life Sciences, 2002 Macmillan Publishers Ltd, Nature Publishing Group/www.els.net).

For example, the YAC may comprise a plethora of human $V_H$, D and J genes in combination with mouse immunoglobulin constant region genes lacking $C_H1$ domains, mouse enhancer and regulatory regions.

Alternative methods known in the art may be used for deletion or inactivation of endogenous mouse or rat immunoglobulin genes and introduction of human $V_H$, D and J genes in combination with mouse immunoglobulin constant region genes lacking $C_H1$ domains, mouse enhancer and regulatory regions.

Transgenic mice can be created according to standard techniques as illustrated in the examples. The two most characterised routes for creating transgenic mice are via pronuclear microinjection of genetic material into freshly fertilised oocytes or via the introduction of stably transfected embryonic stem cells into morula or blastocyst stage embryos. Regardless of how the genetic material is introduced, the manipulated embryos are transferred to pseudopregnant female recipients where pregnancy continues and candidate transgenic pups are born.

The main differences between these broad methods are that ES clones can be screened extensively before their use to create a transgenic animal. In contrast, pronuclear microinjection relies on the genetic material integrating to the host genome after its introduction and, generally speaking, the successful incorporation of the transgene cannot be confirmed until after pups are born.

There are many methods known in the art to both assist with and determine whether successful integration of transgenes occurs. Transgenic animals can be generated by multiple means including random integration of the construct into the genome, site-specific integration, or homologous recombination. There are various tools and techniques that can be used to both drive and select for transgene integration and subsequent modification including the use of drug resistance markers (positive selection), recombinases, recombination-mediated cassette exchange, negative selection techniques, and nucleases to improve the efficiency of recombination. Most of these methods are commonly used in the modification of ES cells. However, some of the techniques may have utility for enhancing transgenesis mediated via pronuclear injection.

Further refinements can be used to give more efficient generation of the transgenic line within the desired background. As described above, in preferred embodiments, the endogenous mouse immunoglobulin expression is silenced to permit sole use of the introduced transgene for the expression of the heavy-chain only repertoire that can be exploited for drug discovery. Genetically-manipulated mice, for example TKO mice that are silenced for all endogenous immunoglobulin loci (mouse heavy chain, mouse kappa chain and mouse lambda chain) can be used as described above. The transfer of any introduced transgene to this TKO background can be achieved via breeding, (either conventional or with the inclusion of an IVF step to give efficient scaling of the process). However, it is also possible to include the TKO background during the transgenesis procedure. For example, for microinjection, the oocytes may be derived from TKO donors. Similarly, ES cells from TKO embryos can be derived for use in transgenesis. Triple knock-out mice into which transgenes have been introduced are referred to herein as TKO/Tg. In one embodiment, the mouse is as described in WO2016/062990.

In another aspect of the present invention, there is provided a pharmaceutical composition comprising a PSMA binding molecule according to the present invention and optionally a pharmaceutically acceptable carrier. The binding molecule of the present invention or compositions can be administered by any convenient route. The compounds may be administered by any route, including oral and parenteral administration. Parenteral administration includes, for example, intravenous, intramuscular, intraarterial, intraperitoneal, intranasal, rectal, intravesical, intradermal, topical or subcutaneous administration. Compositions can take the form of one or more dosage units.

The composition of the invention can be in the form of a liquid, e.g., a solution, emulsion or suspension. The liquid can be useful for delivery by injection, infusion (e.g., IV infusion) or sub-cutaneously. The liquid compositions of the invention, whether they are solutions, suspensions or other like form, can also include one or more of the following: sterile diluents such as water, saline solution, preferably physiological saline, Ringer's solution, isotonic sodium chloride, fixed oils such as synthetic mono or diglycerides, polyethylene glycols, glycerin, or other solvents; antibacterial agents such as benzyl alcohol or methyl paraben; and agents for the adjustment of tonicity such as sodium chloride or dextrose. A composition can be enclosed in an ampoule, a disposable syringe or a multiple-dose vial made of glass, plastic or other material.

In specific embodiments, it can be desirable to administer one or more binding molecule of the present invention or compositions locally to the area in need of treatment, or by intravenous injection or infusion.

The amount of the binding molecule of the present invention that is effective/active in the treatment of a particular disorder or condition will depend on the nature of the disorder or condition, and can be determined by standard clinical techniques. In addition, in vitro or in vivo assays can optionally be employed to help identify optimal dosage ranges. The precise dose to be employed in the compositions will also depend on the route of administration, and the seriousness of the disease or disorder, and should be decided according to the judgment of the practitioner and each patient's circumstances.

The compositions of the invention comprise an effective amount of a binding molecule of the present invention such that a suitable dosage will be obtained. The correct dosage of the compounds will vary according to the particular formulation, the mode of application, and its particular site, host and the disease being treated. Other factors like age, body weight, sex, diet, time of administration, rate of excretion, condition of the host, drug combinations, reaction sensitivities and severity of the disease shall be taken into account. Administration can be carried out continuously or periodically within the maximum tolerated dose.

Typically, this amount is at least about 0.01% of a binding molecule of the present invention by weight of the composition.

Preferred compositions of the present invention are prepared so that a parenteral dosage unit contains from about 0.01% to about 2% by weight of the binding molecule of the present invention.

For intravenous administration, the composition can comprise from about typically about 0.1 mg/kg to about 250 mg/kg of the animal's body weight, preferably, between about 0.1 mg/kg and about 20 mg/kg of the animal's body weight, and more preferably about 1 mg/kg to about 10 mg/kg of the animal's body weight.

The present compositions can take the form of suitable carriers, such aerosols, sprays, suspensions, or any other form suitable for use. Other examples of suitable pharmaceutical carriers are described in "Remington's Pharmaceutical Sciences" by E. W. Martin.

The pharmaceutical compositions can be prepared using methodology well known in the pharmaceutical art. For example, a composition intended to be administered by injection can be prepared by combining a binding molecule of the present invention with water so as to form a solution. A surfactant can be added to facilitate the formation of a homogeneous solution or suspension.

The invention furthermore relates to a method for the prevention and/or treatment of cancer, in particular prostate cancer, comprising administering a binding molecule of the invention to a patient, said method comprising administering, to a subject in need thereof, a pharmaceutically active amount of a binding molecule and/or of a pharmaceutical composition of the invention. In particular, the invention relates to a method for the prevention and/or treatment of cancer, in particular prostate cancer, said method comprising administering, to a subject in need thereof, a pharmaceutically active amount of a binding molecule or a pharmaceutical composition of the invention.

The invention also relates to a binding molecule of the invention for use in the treatment of disease. The invention also relates to a binding molecule of the invention for use in the treatment of cancer, in particular prostate cancer or a prostatic disorder. "Prostate cancer" refers to all stages and all forms of cancer arising from the tissue of the prostate gland. The invention also relates to the treatment of a disease characterized by aberrant expression of PSMA.

In another aspect, the invention relates to the use of a binding molecule of the invention in the treatment of disease. In another aspect, the invention relates to the use of a binding molecule of the invention in the manufacture of a medicament for the treatment of cancer, in particular prostate cancer or a prostatic disorder.

The binding molecules of the invention are also useful for the treatment, prevention, or amelioration of cancer, in particular prostate cancer or a prostatic disorder. A prostatic disorder refers to any disease that afflicts the prostate gland in the male reproductive system. The prostate gland is dependent on the hormonal secretions of the testes. Expression of PSMA has been detected in other cancers, more specifically in the neovasculature associated with these cancers. A wide range of carcinomas, including conventional (clear cell) renal cell, transitional cell of the bladder, testicular-embryonal, neuroendocrine, colon, and breast, and the different types of malignancies were found consistently and strongly to express PSMA in their neovasculature.

The binding molecule of the invention may be administered as the sole active ingredient or in combination with one or more other therapeutic and/or cytotoxic moiety. In one embodiment, the binding molecule may be conjugated to a toxic moiety.

In therapies of prostatic disorders, e.g., prostate cancer, the anti-PSMA binding molecule can be used in combination with existing therapies. In one embodiment, the single domain antibody is used in combination with an existing therapy or therapeutic agent, for example an anti-cancer therapy. Thus, in another aspect, the invention also relates to a combination therapy comprising administration of a single domain antibody or pharmaceutical composition of the invention and an anti-cancer therapy. The anti-cancer therapy may include a therapeutic agent or radiation therapy and includes gene therapy, viral therapy, RNA therapy bone marrow transplantation, nanotherapy, targeted anti-cancer therapies or oncolytic drugs. Examples of other therapeutic agents include other checkpoint inhibitors, antineoplastic agents, immunogenic agents, attenuated cancerous cells, tumor antigens, antigen presenting cells such as dendritic cells pulsed with tumor-derived antigen or nucleic acids, immune stimulating cytokines (e.g., IL-2, IFNa2, GM-CSF), targeted small molecules and biological molecules (such as components of signal transduction pathways, e.g. modulators of tyrosine kinases and inhibitors of receptor tyrosine kinases, and agents that bind to tumor-specific antigens, including EGFR antagonists), an anti-inflammatory agent, a cytotoxic agent, a radiotoxic agent, or an immunosuppressive agent and cells transfected with a gene encoding an immune stimulating cytokine (e.g., GM-CSF), chemotherapy. In one embodiment, the single domain antibody is used in combination with surgery. The binding molecule of the invention may be administered at the same time or at a different time as the other therapy, e.g., simultaneously, separately or sequentially.

In another aspect, the invention provides a kit for detecting prostate cancer for diagnosis, treatment, prognosis or monitoring comprising a binding molecule of the invention. The kit may also comprise instructions for use. The kits may include a labeled binding molecule of the invention as described above and one or more compounds for detecting the label. The invention in another aspect provides a binding molecule of the invention packaged in lyophilized form, or packaged in an aqueous medium.

The invention also relates to detection methods using the binding molecule of the invention. Given their ability to bind to human PSMA, the human-PSMA-binding molecules, disclosed herein can be used to detect PSMA (e.g., in a biological sample, such as serum or plasma), using a conventional immunoassay, such as an enzyme linked immunosorbent assays (ELISA), an radioimmunoassay (RIA) or tissue immunohistochemistry. In particular, the invention also relates to in vitro or in vivo methods for diagnosing or monitoring progression of a cancer, in particular prostate cancer. In vitro methods comprise detecting the presence of a PSMA protein in a test sample and comparing this with control sample from a normal subject or with a standard value or standard value range for a normal subject. The sample may be selected from blood, plasma, serum, semen, urine or a tissue biopsy.

The method may include: (a) contacting the sample (and optionally, a reference, e.g., a positive and/or negative control sample) with a PSMA binding molecule of the invention and (b) detecting either the binding molecule bound to PSMA or unbound binding molecule in the sample, to thereby detect PSMA in the biological sample. The binding molecule can be directly or indirectly labeled with a detectable substance to facilitate detection of the bound or unbound antibody. Suitable detectable substances include various enzymes, prosthetic groups, fluorescent materials, luminescent materials and radioactive materials.

The invention also relates to an assay for assessing the internalization of PSMA binding molecule of the invention by labelling said binding molecule. Such an assay is described in the examples.

In vivo methods may comprise detecting the presence of PSMA in vivo, for example by imaging in a subject. In this method, a PSMA binding molecule of the invention is labeled to detect binding.

As an alternative to labeling the binding molecule of the invention, human PSMA can be assayed in biological fluids by a competition immunoassay utilizing PSMA standards labeled with a detectable substance and an unlabeled human PSMA binding molecule. In this assay, the biological sample, the labeled PSMA standards and the human PSMA binding molecule are combined and the amount of labeled PSMA standard bound to the unlabeled binding molecule is determined. The amount of human PSMA in the biological sample is inversely proportional to the amount of labeled PSMA standard bound to the PSMA binding molecule. Similarly, human PSMA can also be assayed in biological fluids by a competition immunoassay utilizing PSMA standards labeled with a detectable substance and an unlabeled human PSMA binding molecule.

Binding molecules disclosed herein can be used to inhibit PSMA activity, e.g., in a cell culture containing PSMA, in human subjects or in other mammalian subjects having PSMA with which a binding molecule disclosed herein cross-reacts. In one embodiment, a method for inhibiting or increasing PSMA activity is provided comprising contacting PSMA with a binding molecule disclosed herein such that PSMA activity is inhibited or increased. For example, in a cell culture containing, or suspected of containing PSMA, a binding molecule disclosed herein can be added to the culture medium to inhibit PSMA activity in the culture.

Therefore, in one embodiment, the invention also relates to a method of ablating or killing a cell that expresses PSMA, e.g., a cancerous or non-cancerous prostatic cell. Methods of the invention include contacting the cell, with PSMA binding molecule of the invention, in an amount sufficient to ablate or kill, the cell. The methods can be used on cells in culture, e.g., in vitro or ex vivo.

Unless otherwise defined herein, scientific and technical terms used in connection with the present disclosure shall have the meanings that are commonly understood by those of ordinary skill in the art. While the foregoing disclosure provides a general description of the subject matter encompassed within the scope of the present invention, including methods, as well as the best mode thereof, of making and using this invention, the following examples are provided to further enable those skilled in the art to practice this invention and to provide a complete written description thereof. However, those skilled in the art will appreciate that the specifics of these examples should not be read as limiting on the invention, the scope of which should be apprehended from the claims and equivalents thereof appended to this disclosure. Various further aspects and embodiments of the present invention will be apparent to those skilled in the art in view of the present disclosure.

All documents mentioned in this specification are incorporated herein by reference in their entirety, including references to gene accession numbers.

"and/or" where used herein is to be taken as specific disclosure of each of the two specified features or components with or without the other. For example "A and/or B" is to be taken as specific disclosure of each of (i) A, (ii) B and (iii) A and B, just as if each is set out individually herein. Unless context dictates otherwise, the descriptions and definitions of the features set out above are not limited to any particular aspect or embodiment of the invention and apply equally to all aspects and embodiments which are described.

The invention is further described in the non-limiting examples.

EXAMPLES

Example 1. Construction of Tg/TKO Mice

Mice carrying a heavy-chain antibody transgenic locus in germline configuration within a background that is silenced for endogenous heavy and light chain antibody expression (triple knock-out, or TKO) were created as previously described (WO2004/076618 and WO2003/000737, Ren et al., Genomics, 84, 686, 2004; Zou et al., J. Immunol., 170, 1354, 2003). Briefly, transgenic mice were derived following pronuclear microinjection of freshly fertilised oocytes with a yeast artificial chromosome (YAC) comprising a plethora of human $V_H$, D and J genes in combination with mouse immunoglobulin constant region genes lacking CH1 domains, mouse enhancer and regulatory regions. Yeast artificial chromosomes (YACs) are vectors that can be employed for the cloning of very large DNA inserts in yeast. As well as comprising all three cis-acting structural elements essential for behaving like natural yeast chromosomes (an autonomously replicating sequence (ARS), a centromere (CEN) and two telomeres (TEL)), their capacity to accept large DNA inserts enables them to reach the minimum size (150 kb) required for chromosome-like stability and for fidelity of transmission in yeast cells. The construction and use of YACs is well known in the art (e.g., Bruschi, C. V. and Gjuracic, K. Yeast Artificial Chromosomes, Encyclopedia of Life Sciences, 2002, Macmillan Publishers Ltd., Nature Publishing Group/www.els.net).

The transgenic founder mice were back crossed with animals that lacked endogenous immunoglobulin expression to create the Tg/TKO lines used in the immunisation studies described.

Example 2. Antigen for Immunisation

The immunisations used recombinant purified protein or Human Cell Line LNCap. Recombinant human PMSA was purchased from R&D, (cat. no. 4234-ZN), while the LNCap cells were from Sigma Aldrich (cat. no. 89110211-1VL).

Example 3. Immunisation Protocol

Briefly, Tg/TKO mice aged 8-12 weeks of age each received a total of 50 µg of recombinant purified human PSMA protein, emulsified in Complete Freund's Adjuvant and delivered subcutaneously, or 10 million LNCap cells in PBS delivered intraperitoneally, followed by boosts of 1-10 µg of the recombinant protein, emulsified in Incomplete Freund's Adjuvant, also administered subcutaneously, given at various intervals following the initial priming. A final dose of the recombinant purified human PSMA protein antigen was administered intraperitoneally, in phosphate buffered saline, in the absence of adjuvant.

Alternative immunisation routes and procedures can also be employed. For example, different adjuvants or immune potentiating procedures may be used instead of Freund's adjuvant. DNA immunisations are often delivered intramuscularly or via a Genegun. Transfected cells or membrane preparations from such cells are often, although not exclusively, administered intraperitoneally.

Example 4. Serum ELISA

During and following immunisation, serum was collected from mice and checked for the presence of heavy-chain antibody responses to the immunogen by ELISA. Nunc Maxisorp plates (Nunc cat. no. 443404) were coated overnight at 4° C. with 50 µl/well of a 1 µg recombinant antigen/ml of PBS solution. Following decanting of the antigen solution, plates were washed using PBS (prepared from PBS Tablets, Oxoid cat. no. BR0014G) supplemented with 0.05% (v/v) Tween® 20 (Sigma P1379), followed by washes with PBS without added Tween 20. To block non-specific protein interactions, a solution of 3% (w/v) skimmed milk powder (Marvel®) in PBS was added to the wells and the plate was incubated for at least one hour at room temperature. Dilutions of serum in 3% Marvel™/PBS were prepared in polypropylene tubes or plates and incubated for at least one hour at room temperature prior to transfer to the blocked ELISA plate where a further incubation of at least one hour took place. Unbound protein was then washed away using repetitive washes with PBS/Tween 20 followed by PBS. A solution of biotin-conjugated, goat anti-mouse IgG, Fcgamma subclass 1 specific antibody (Jackson cat. no. 115-065-205), prepared in PBS/3% Marvel was then added to each well and a further incubation at room temperature for at least one hour took place. Unbound detection antibody was removed by repeated washing using PBS/Tween 20 and PBS. Neutravidin-HRP solution (Pierce cat. no. 31030) in 3% Marvel/PBS was then added to the ELISA plates and allowed to bind for at least 30 minutes. Following further washing, the ELISA was developed using TMB substrate (Sigma cat. no. T0440) and the reaction was stopped after 10 minutes by the addition of 0.5M $H_2SO_4$ solution (Sigma cat. no. 320501). Absorbances were determined by reading at an optical density of 450 nm. Alternative assays, such as ELISPOT assays, may also be used to check for immunisation induced heavy-chain antibody responses.

Example 5. Generation of Libraries from Immunised Mice a) Processing Tissues, RNA Extraction and cDNA Manufacture Spleen, inguinal and brachial lymph nodes were collected into RNAlate® from each immunised animal. For each animal, ½ of the spleen and 4 lymph nodes were processed separately. Initially, the tissues were homogenised; following transfer of tissues to Lysing matrix D bead tubes (MP Bio. Cat. no. 116983001), 600 µl of RLT buffer containing β-mercaptoethanol (from Qiagen RNeas® kit cat. no. 74104) was added before homogenisation in a MP Bio Fastprep96 homogeniser (cat #116010500) at 1600 rpm for 60 seconds. The tubes containing the homogenised tissues were transferred to ice and debris was pelleted by centrifugation at 1200 rpm for 5 minutes. A 400 µl sample of the supernatant was removed and used for RT-PCR.

Initially, RNA was extracted using Qiagen RNeasy® kit (cat. no. 74104) following the manufacturer's protocol. Each RNA sample was then used to make cDNA using Superscript III RT-PCR high-fidelity kit (Invitrogen cat. no. 12574-035). For each spleen and lymph nodes RNA sample, 5 RT-PCR reactions were performed, each with $V_H$ J/F (long) primer in combination with a primer for $V_H1$, $V_H2$, $V_H3$, $V_H4$ or $V_H6$ family. Details of the primers are below.

TABLE 16

Primers for V10

| | |
|---|---|
| V1a/pelB (long) | GCCGCTGGATTGTTATTACTCGCGGCCCAGCCGGCCA TGGCCCAGGTBCAGCTGGTGCAGTCTGGGGCTGAGG SEQ ID No. 491 |
| V2/pelB (long) | GCCGCTGGATTGTTATTACTCGCGGCCCAGCCGGCCA TGGCCCAGATCACCTTGAAGGAGTCTGG SEQ ID No. 492 |
| V3/pelB (long) | GCCGCTGGATTGTTATTACTCGCGGCCCAGCCGGCCA TGGCCSAGGTGCAGCTGGTGGAGTCTGGGGGAGG SEQ ID No. 493 |
| V4-4/pelB (long) | GCCGCTGGATTGTTATTACTCGCGGCCCAGCCGGC CATGGCCCAGGTGCAGCTGCAGGAGTCGGG SEQ ID No. 494 |
| V6/pelB (long) | GCCGCTGGATTGTTATTACTCGCGGCCCAGCCGGCCA TGGCCCAGGTACAGCTGCAGCAGTCAGG SEQ ID No. 495 |
| VH_J/F (long) | CCGTGGTGATGGTGGTGATGGCTACCGCCACCCTC GAGTGARGAGACRGTGACC SEQ ID No. 496 |

Residues in bold have homology with pUCG3

TABLE 17

Primers for V23

| | |
|---|---|
| VH1-2 (long) | GCCGCTGGATTGTTATTACTCGCGGCCCAGCCGGCCATGGCC CAGGTGCAGCTGGTGCAGTCTGGGGCTGAGG SEQ ID No. 497 |
| VH1-3 (long) | GCCGCTGGATTGTTATTACTCGCGGCCCAGCCGGCCATGGCC CAGGTCCAGCTCGTGCAGTCTGGGGCTGAGG SEQ ID No. 498 |
| VH1-18 (long) | GCCGCTGGATTGTTATTACTCGCGGCCCAGCCGGCCATGGCC CAGGTTCAGCTGGTGCAGTCTGGAGCTGAGG SEQ ID No. 499 |
| VH1-24 (long) | GCCGCTGGATTGTTATTACTCGCGGCCCAGCCGGCCATGGCC CAGGTCCAGCTGGTACAGTCTGGGGCTGAGG SEQ ID No. 500 |
| VH2 (long) | GCCGCTGGATTGTTATTACTCGCGGCCCAGCCGGCCATGGCC CAGRTCACCTTGAAGGAGTCTGG SEQ ID No. 501 |
| VH3-7 (long) | GCCGCTGGATTGTTATTACTCGCGGCCCAGCCGGCCATGGCC CAGGTGCAGCTGGTGGAGTCTGGGGGAGG SEQ ID No. 502 |
| VH3-9 (long) | GCCGCTGGATTGTTATTACTCGCGGCCCAGCCGGCCATGGCC CAAGTGCAGCTGGTGGAGTCTGGGGGAGG SEQ ID No. 503 |
| VH3-11 (long) | GCCGCTGGATTGTTATTACTCGCGGCCCAGCCGGCCATGGCC CAGGTGCAGCTGGTGGAGTCTGGGGGAGG SEQ ID No. 504 |
| VH3-23 (long) | GCCGCTGGATTGTTATTACTCGCGGCCCAGCCGGCCATGGCC GAGGTGCAGCTGTTGGAGTCTGGGGGAGG SEQ ID No. 505 |
| VH3-23 (long) | GCCGCTGGATTGTTATTACTCGCGGCCCAGCCGGCCATGGCC GAGGTGCAGCTGTTGGAGTCTGGGGGAGG SEQ ID No. 506 |
| VH4-4 (long) | GCCGCTGGATTGTTATTACTCGCGGCCCAGCCGGCCATGGCC CAGGTGCAGCTGCAGGAGTCGGG SEQ ID No. 507 |
| VH4-34 (long) | GCCGCTGGATTGTTATTACTCGCGGCCCAGCCGGCCATGGCC CAGGTGCAGCTACAGCAGTGGGGC SEQ ID No. 508 |

TABLE 17-continued

Primers for V23

| | |
|---|---|
| VH6-1 (long) | GCCGCTGGATTGTTATTACTCGCGGCCCAGCCGGCCATGGCC CAGGTACAGCTGCAGCAGTCAGG SEQ ID No. 509 |
| VH_J/F (long) | CCGTGGTGATGGTGGTGATGGCTACCGCCACCCTCGAG TGARGAGACRGTGACC SEQ ID No. 510 |

Residues in bold have homology with pUCG3

The code for the choice of nucleotide for degenerate primer is shown below.

R A, G
Y C, T
M A, C
K G, T
S C, G
W A, T
B C, G, T
V A, C, G
D A, G, T
N A, C, G, T

Mastermixes were prepared for the RT-PCR reactions, based on the following tube reaction components:
12.5 μl 2× reaction mix
0.5 μl forward primer (10 μM)
0.5 μl reverse primer (10 μM)
0.5 μl enzyme mix
500 ng-1 μg RNA
Up to 25 μl with water The RT-PCR reactions were carried out in a thermal cycler using the following conditions:
55° C. 20 min
94° C. 2 min
35 cycles of 94° C. 15 sec
  58° C. 30 sec
  68° C. 30 sec
68° C. 5 min
Hold at 4° C.

Products in the range of 370 bp were confirmed by gel electrophoresis.

For each mouse, the $V_H$ products amplified for a given family from the ½ spleen and each of the 4 lymph nodes were then pooled for purification using Thermo/Fermentas GeneJet PCR purification kit (cat. no. K0702) which was used according to the manufacturer's instructions, with the products eluted in 50 μl of water.

a) Cloning into Phagemid Vector

The phagemid vector, pUCG3, was employed in these studies. A PCR-based method was used to construct the $V_H$ phagemid libraries from the amplified $V_H$ sequences. The following procedure was used:

A linearised version of pUCG3 was created using PCR; with the following primers:

pUCG3-pHENAPmut4
SEQ ID No. 511
GGCCATGGCCGGCTGGGCCGCGAG pUCG3-pHENAPmut5mycHis
SEQ ID No. 512
TCATCGAGGGTGGCGAGCGAACAAAAACTCATCTCAGAAGAATCTGAA

TCATCACACATCACACGGGAGCTAGACTGTTGAAAGTTGTTTAGCAAAA
CC

Phusion High fidelity PCR master mix with GC buffer (cat. no. F532L, NEB) was used for the PCR reactions which comprised the following reagents:
Phusion GC 2× mix 25 µl
pUCG3 5-10 ng
Primers (10 µM) 1.25 µl of each
DMSO 1.5 µl
Nuclease-free H$_2$O to final volume of 50 µl
The cycling conditions used were:
98° C. 30 seconds
10 cycles of
  98° C. 10 seconds
  58° C. 20 seconds
  68° C. 2 minutes, 30 seconds
20 cycles of
  98° C. 10 seconds
  58° C. 20 seconds
  68° C. 3 minutes
68° C. 5 minutes
4° C. hold The PCR product (3152 bp) was gel purified using Fermentas GeneJet Gel purification kit (cat. no. K0691), according to the manufacturer's instructions, with final elution in 40 µl of elution buffer.

The purified $V_H$ RT-PCR products were employed as megaprimers with the linearised pUCG3 to give phagemid products for transformation and library creation, based on the following reactions;
Phusion GC 2× mix 25 µl
Linearised pUCG3 800 ng
$V_H$ PCR product 200 ng
DMSO 1.5 µl
Nuclease-free H$_2$O to 50 µl final volume
PCR was performed as follows:

| | |
|---|---|
| 98° C. 30 sec | |
| 98° C. 10 sec | |
| 58° C. 20 sec | 10 cycles |
| 72° C. 2 min | |
| 72° C. 5 min | |
| Hold at 10° C. | |

The products of PCR were analysed on a 1% (w/v) agarose gel.

The various family $V_H$/phagemid products were purified using Fermentas PCR purification kit (cat. no. K0702) according to the manufacturer's instructions with the final elution being in 25 µl H$_2$O; this eluate was used for transformations of TG1 E. coli (Lucigen, cat. no. 60502-2) by electroporation using BioRad 2×0.2 cm cuvettes (BioRad cat. no. 165-2086) in a Bio-Rad GenePulser Xcell and pre-warmed recovery medium (Lucigen, proprietary mix). 22 µl of the purified products were added to 160 µl of cells for the electroporation, with 2 electroporations being performed for each $V_H$/phagemid product at 2000 v. Electroporated cells were pooled and recovered in 50 ml Falcon tubes incubated for 1 hour at 37° C. with shaking at 150 rpm. A 10-fold dilution series of an aliquot of the transformations was performed and plated in petri dishes containing 2×TY agar supplemented with 2% (w/v) glucose and 100 µg/ml ampicillin. Resulting colonies on these dishes were used to estimate the library size. The remainder of the transformation was plated on large format Bioassay dishes containing 2×TY agar supplemented with 2% (w/v) glucose and 100 µg/ml ampicillin. All agar plates were incubated overnight at 30° C. 10 ml of 2×TY broth was added to the large format bioassay dishes and colonies were scraped and OD$_{600}$ measured (OD of 1.0=5×10$^8$ cells/ml). Aliquots were stored at −80° C. in cryovials after addition of 50% (v/v) glycerol solution or used directly in a phage selection process.

Example 6. Selection Strategies for Isolation of PSMA Binders

Preparation of library phage stocks and phage display selections were performed according to published methods (Antibody Engineering, edited by Benny Lo, chapter 8, p 161-176, 2004). In most cases, phage display combined with a panning approach was used to isolate binding $V_H$ domains. However, a variety of different selection methods are well described in the art, including soluble selection and selections performed under stress (e.g. heat). Selections to promote internalising anti-PSMA $V_H$ were also conducted with monovalent and multivalent phage (patent US2009170792 (A1)—2009 Jul. 2). Briefly, blocked phage in ice-cold cell media were added to 4 ml ice-cold cell media containing 2.5×10$^6$ LnCAP cells. Phage and cells were incubated on ice for 2 hours, mixing occasionally to prevent cell clumping. Unbound or weakly bound phage were removed by washing five times in ice-cold PBS. The phage were then allowed to internalise by incubating the cells in media at 37° C. before removing phage bound to the outside of the cells with a 5 minutes wash step in a low pH cell-stripping buffer at 4° C. The cells were then lysed to harvest internalised phage using trimethylamine. Both the stripped and internalised fractions were neutralised with Tris buffer before being used to infect E. coli. The phage outputs were analysed as described for panning selections on recombinant proteins.

Example 7. Assays for Target Binding $V_H$ from the different selections were screened in one or more of the following assays to identify specific $V_H$ capable of binding PMSA.

a) Binding ELISA

Following selections of the libraries, specific $V_H$ antibodies were identified by phage ELISA following published methods (Antibody Engineering, edited by Benny Lo, chapter 8, p 161-176, 2004). Phage ELISAs were performed against target protein and an unrelated antigen as control. In some cases, purified or crude extracts of $V_H$ domains were assayed by ELISA instead of using a phage ELISA. In these cases, bacterial periplasmic extracts or purified $V_H$ were used.

Small-scale bacterial periplasmic extracts were prepared from 1 ml cultures, grown in deep well plates. Starter cultures were used to inoculate 96-well deep well plates (Fisher, cat. no. MPA-600-030X) containing 2×TY broth (Melford cat. no. M2130), supplemented with 0.1% (w/v) glucose+100 µg/ml ampicillin at 37° C. with 250 rpm shaking. When OD$_{600}$ had reached 0.6-1, $V_H$ production was induced by adding 100 µl of 2×TY, supplemented with IPTG (final concentration 1 mM) and ampicillin and the cultures were grown overnight at 30° C. with shaking at 250 rpm. E. coli were pelleted by centrifugation at 3200 rpm for 10 mins and supernatants discarded. Cell pellets were resuspended in 30-100 µl of ice cold extraction buffer (20% (w/v) sucrose, 1 mM EDTA & 50 mM Tris-HCl pH 8.0) by gently pipetting. Cells were incubated on ice for 30 minutes and then centrifuged at 4500 rpm for 15 mins at 4° C. Supernatants were transferred to polypropylene plates and used, following incubation in Marvel/PBS blocking solution, in the ELISA.

The purified V_H were obtained by using the V_H C-terminal 6×HIS tag for Ni-NTA affinity chromatographic purification of the periplasmic extracts. A starter culture of each V_H was grown overnight in 5 ml 2×TY broth (Melford cat. no. M2103) supplemented with 2% (w/v) glucose+100 µg/ml ampicillin at 30° C. with 250 rpm shaking. 50 µl of this overnight culture was then used to inoculate 50 ml 2×TY supplemented with 2% (w/v) glucose+100 µg/ml ampicillin and incubated at 37° C. with 250 rpm shaking for approximately 6-8 hours (until $OD_{600}$=0.6-1.0). Cultures were then centrifuged at 3200 rpm for 10 mins and the cell pellets resuspended in 50 ml fresh 2×TY broth containing 100 µg/ml ampicillin+1 mM IPTG. Shake flasks were then incubated overnight at 30° C. and 250 rpm. Cultures were again centrifuged at 3200 rpm for 10 mins and supernatants discarded. Cell pellets were resuspended in 1 ml ice cold extraction buffer (20% (w/v) sucrose, 1 mM EDTA & 50 mM Tris-HCl pH 8.0) by gently pipetting and then a further 1.5 ml of 1:5 diluted ice cold extraction buffer added. Cells were incubated on ice for 30 minutes and then centrifuged at 4500 rpm for 15 mins at 4° C. Supernatants were transferred to 50 ml Falcon tubes containing imidazole (Sigma cat. no. I2399-final concentration 10 mM) and 0.5 ml of nickel agarose beads (Qiagen, Ni-NTA 50% soln, cat. no. 30210) pre-equilibrated with PBS buffer. V_H binding to the nickel agarose beads was allowed to proceed for 2 hours at 4° C. with gentle shaking. The nickel agarose beads were then transferred to a polyprep column (BioRad cat. no. 731-1550) and the supernatant discarded by gravity flow. The columns were then washed 3 times with 5 ml of PBS+0.05% Tween® followed by 3 washes with 5 ml of PBS containing imidazole at a concentration of 20 mM. V_H were then eluted from the columns by the addition of 250 µl of PBS containing imidazole at a concentration of 250 mM. Imidazole was then removed from the purified V_H preparations by buffer exchange with NAP-5 columns (GE Healthcare, 17-0853-01) and then eluting with 1 ml of PBS. Yields of purified V_H were estimated spectrophotometrically and purity was assessed using SDS PAGE.

Alternatively anti-PSMA V_H were purified from the supernatants of W3110 E coli with pJExpress vector. For this procedure up to 400 ml cultures were grown at 37° C. with 250 rpm shaking in TB media before being induced overnight with 1 mM IPTG overnight. The resulting supernatants were harvested and V_H purified on AKTA Pure using a Ni-Sepharose excel column (HiScale 16, GE Healthcare). Yields of purified V_H were estimated spectrophotometrically and purity was assessed using SDS PAGE.

The binding ELISA for crude or purified V_H was similar to the serum ELISA and phage ELISA, previously described, mostly differing in the final detection steps. Briefly, antigen was immobilised on Maxisorb plates (Nunc 443404) by adding 50 µl volumes at 0.1-2 µg/ml in PBS and incubating at 4° C. overnight. Following coating, the antigen solution was aspirated and the plates were washed using PBS (prepared from PBS Tablets, Oxoid cat. no. BR0014G) supplemented with 0.05% Tween® 20 (Sigma cat. no. P1379), followed by washes with PBS without added Tween® 20. To block non-specific protein interactions, a solution of 3% skimmed milk powder (Marvel®) in PBS was added to the wells and the plate was incubated for at least one hour at room temperature. Dilutions of periplasmic extract or purified V_H in 3% Marvel®/PBS were prepared in polypropylene tubes or plates and incubated for at least one hour at room temperature prior to transfer to the blocked ELISA plate where a further incubation of at least one hour took place. Unbound protein was then washed away using repetitive washes with PBS/Tween followed by PBS. A solution of HRP-conjugated anti-Myc Ab (Santa Cruz cat. no. SC-40), prepared at 1:50 dilution in PBS/3% Marvel was then added to each well and a further incubation at room temperature for at least one hour took place. Unbound detection antibody was removed by repeated washing using PBS/Tween® and PBS. The ELISA was then developed using TMB substrate (Sigma cat. no. T0440) and the reaction was stopped after 10 minutes by the addition of 0.5M $H_2SO_4$ solution (Sigma cat. no. 320501). Absorbances were determined by reading at 450 nm.

b) FMAT Direct Cell Binding Assay

Periplasmic extracts from E. coli were screened for production of PSMA-binding-His-tagged V_H using Fluorescence Microvolume Assay Technology (FMAT), a fluorescence-based platform that detects fluorescence localized to beads or cells settled at the bottom of microwells (Dietz et al., Cytometry 23:177-186 (1996), Miraglia et al., J. Biomol. Screening 4:193-204 (1999). CHO TREX human and cynomolgus cell lines were generated in-house using full-length human and cynomolgus PSMA using standard procedures. LnCAP cells were purchased from Sigma Aldrich.

Peripreps were tested by single point screening for the presence of V_H that bound specifically to CHO human PSMA, CHO cyno PSMA and LnCAP cells with no binding to CHO parental cells in an FMAT Direct Binding Assay. Cells were resuspended at $0.1 \times 10^6$ cells/ml in FMAT assay buffer (pH 7.4) containing PBS, 0.1% Bovine Serum Albumin, 0.01% Sodium Azide and 120 nM DRAQ5 (Thermo Scientific cat. no. 62251) added to the cell suspension. Peripreps (10 µl) were transferred into 384 well black clear-bottomed assay plates (Costar cat. no. 3655) and 10 µl of 6 nM mouse Anti-His (Millipore cat. no. 05-949)/12 nM Goat Anti-Mouse Alexa Fluor-488 (Jackson Immunolabs cat. no. 115-545-071) mix added. The DRAQ5 stained cells (20 µl per well) were then added and the assay plates incubated for 2 hours at room temperature. Plates were read in the FL2 (502 nm-537 nm) and FL5 (677-800 nm) channels on the TIP Mirrorball plate reader following excitation at 488 nm and 640 nm. Data was gated on FL5 perimeter and peak intensity and the FL2 median mean fluorescence intensity of the gated data used for determination of V_H binding.

Figure 16C:
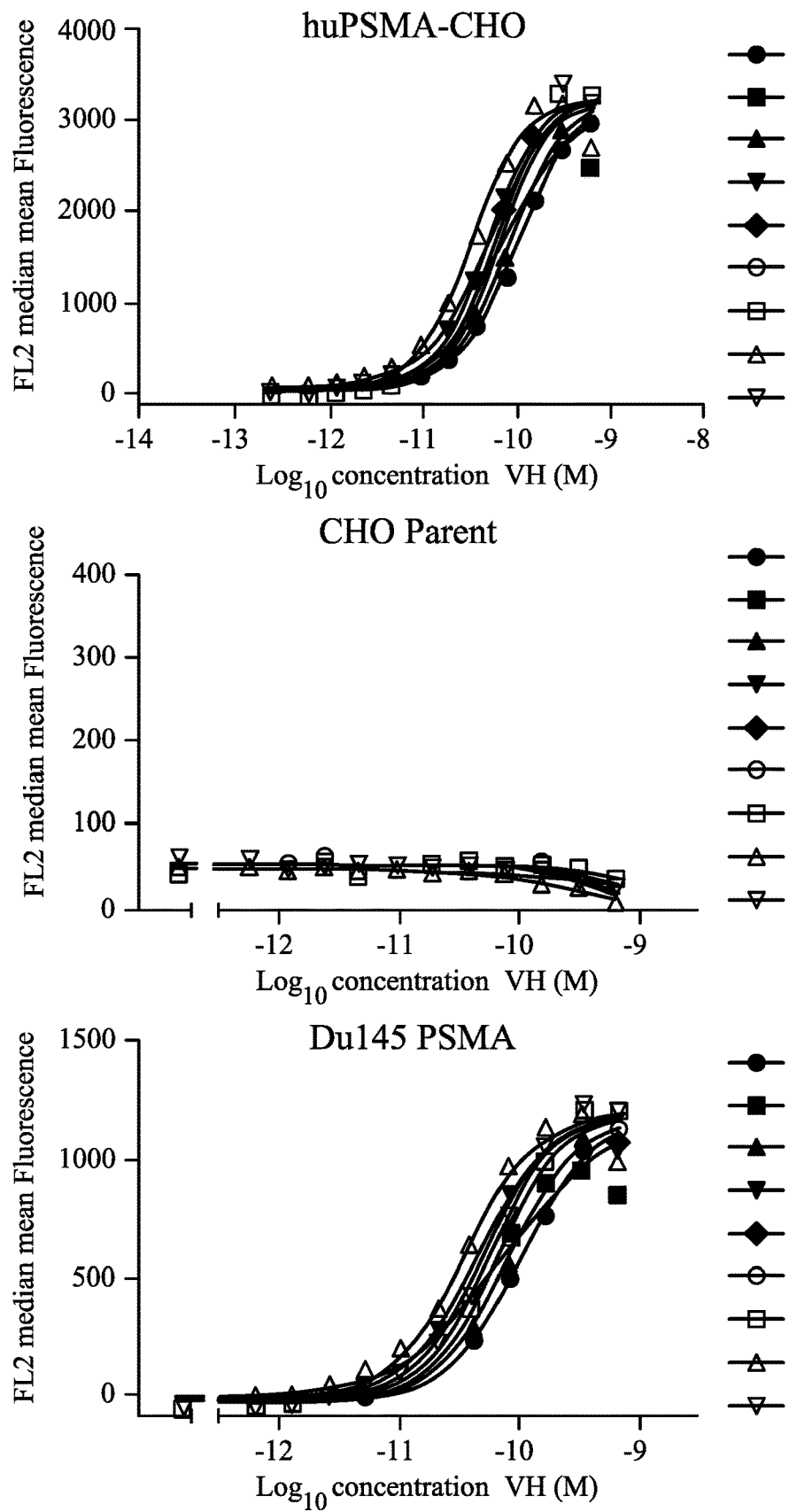
Figure 16C:
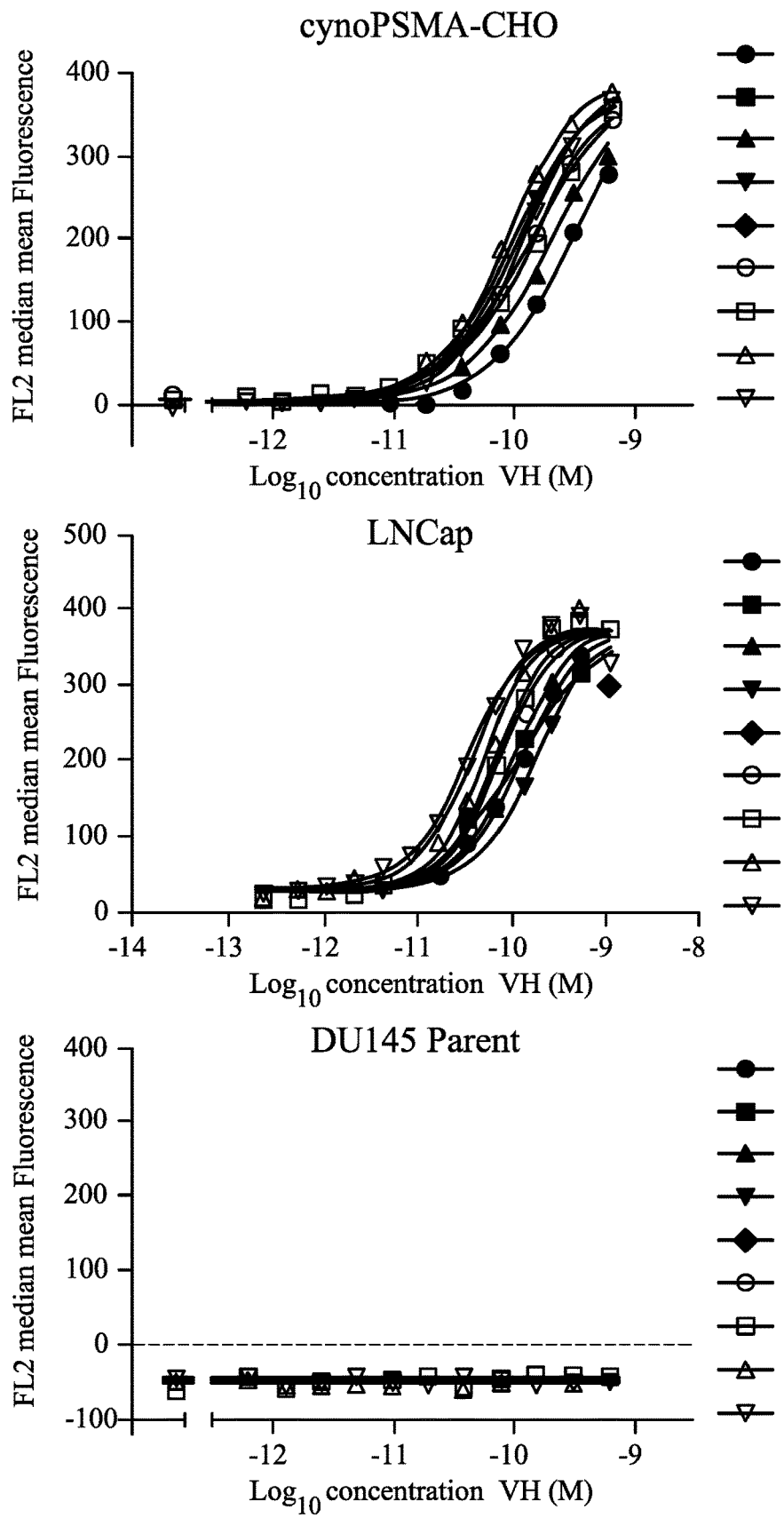
Figure 16D:
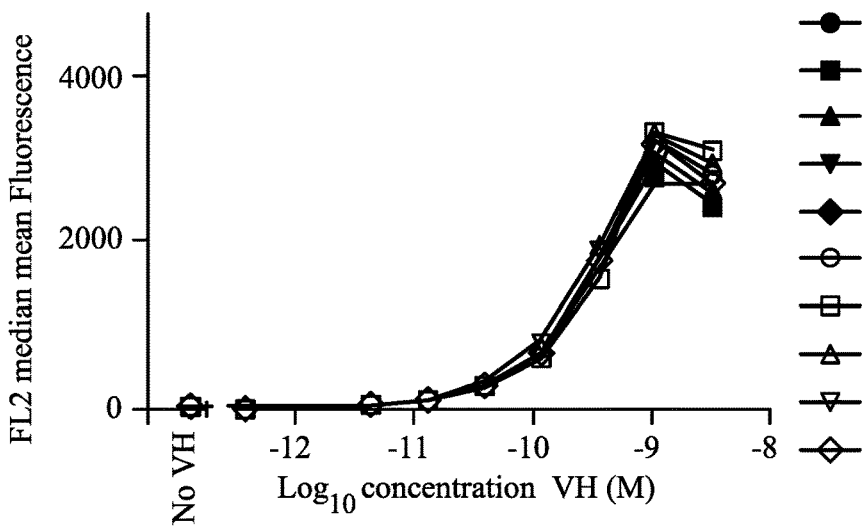
Figure 16E:
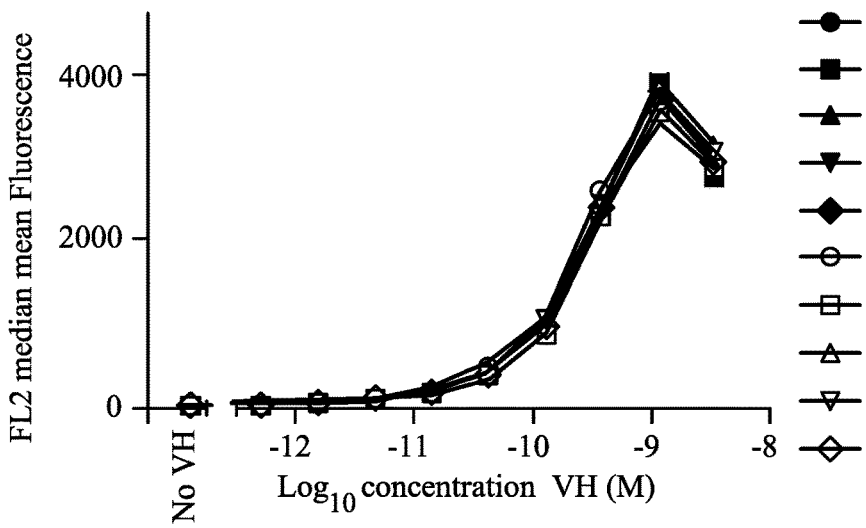

For titrations, V_H purified via the terminal His tag were serially diluted in FMAT assay buffer then binding was measured as described above (FIG. 16). Improved monovalent variants show similar properties to the parent V_H (FIGS. 16b and 16c). Biparatopic binding molecules were also tested (16d and e) and showed good binding to human PSMA CHO cells. The linker length used was $(G_4S)_6$. The Table below shows the different CDR3 sequences of the V_H families identified together with their binding characteristics.

TABLE 18

(prepared from phagemid and peripreps)

| CDR3 | VH family | rhPSMA | Cyno PSMA CHO | Human PSMA CHO | CHO parent | LnCAP |
|---|---|---|---|---|---|---|
| DPAWGLRLGESSSYDFDI SEQ ID No. 513 | VH3-30 | Y | Y | Y | N | Y |
| DRIVGGRVPDAFDI SEQ ID No. 514 | VH3-30 | Y | Y | Y | N | Y |
| ERIFGVLTPDDFDI SEQ ID No. 515 | VH3-30 | Y | Y | Y | N | Y |
| GLWPSDV 516 | VH3-30 | Y | Y | Y | N | Y |
| GLWPPMDV SEQ ID No. 517 | VH3-30 | Y | Y | Y | N | Y |
| GDYDFWSGYPDYDMDV SEQ ID No. 518 | VH3-30 | Y | Y | Y | N | Y |
| GGNALYSSGWPDD SEQ ID No. 519 | VH3-30 | Y | Y | Y | N | Y |
| DGVH SEQ ID No. 520 | VH3-23 | Y | Y (weak) | Y | N | Y |
| ENVIVPAATY SEQ ID No. 521 | VH3-20 | Y | Y | Y | N | Y |
| DSLIVGERGY SEQ ID No. 522 | VH3-07 | Y | Y (weak) | Y (weak) | N | Y (Weak) |
| DRGGAVALYHNGMDM SEQ ID No. 523 | VH3-07 | Y | N | Y | N | Y |
| DYGDSRSLFDY SEQ ID No. 524 | VH4-34 | N | Y | Y | N | Y |
| GPIPATAIPDAFDI SEQ ID No. 525 | VH4-34 | N | Y | Y | N | Y |
| DGDDYGDY SEQ ID No. 526 | VH4-41 | Y | Y (Very Weak) | Y | N | Y |
| GNGPGITGTTDY SEQ ID No. 527 | VH1-08 | Y/N | Y | Y | N | Y |

TABLE 19

EC50 values for anti-PSMA $V_H$ binding to PSMA expressing cell lines. (prepared from purified $V_H$)

| EC50 | huPSMA CHO | cynoPSMA CHO | DU145 PSMA | LNCap |
|---|---|---|---|---|
| 2.1 | 1.097E−10 | 3.667E−10 | 2.304E−10 | 6.07E−11 |
| 2.18 | 1.044E−10 | 3.370E−10 | 2.496E−10 | 3.54E−11 |
| 2.17 | 1.004E−10 | 3.082E−10 | 2.181E−10 | 1.13E−11 |
| 2.15 | 9.212E−11 | 3.335E−10 | 1.663E−10 | 8.41E−11 |
| 2.14 | 1.103E−10 | 4.269E−10 | 2.023E−10 | 3.32E−11 |
| 2.22 | 1.232E−10 | 6.129E−10 | 2.293E−10 | 1.53E−10 |
| 1.8 | 1.029E−10 | 3.099E−10 | 9.455E−11 | 1.473E−10 |
| 1.10 | 7.182E−11 | 1.518E−10 | 6.699E−11 | 1.328E−10 |
| 1.11 | 8.634E−11 | 2.168E−10 | 7.604E−11 | 1.189E−10 |
| 1.12 | 5.023E−11 | 1.097E−10 | 4.15E−11 | 1.992E−10 |
| 1.13 | 5.127E−11 | 1.154E−10 | 4.564E−11 | 3.862E−11 |
| 1.14 | 5.884E−11 | 1.45E−10 | 5.201E−11 | 8.329E−11 |
| 1.16 | 6.805E−11 | 1.458E−10 | 5.938E−11 | 7.539E−11 |
| 1.17 | 3.338E−11 | 9.127E−11 | 3.099E−11 | 5.853E−11 |
| 1.18 | 5.858E−11 | 1.237E−10 | 4.949E−11 | 4.239E−11 |

TABLE 20

$EC_{50}$ values for anti-PSMA $V_H$ binding to human PSMA-CHO. The linker length used was $(G_4S)_6$.

| No | Construct | EC50 |
|---|---|---|
| 1 | 1.1-2.1 | 3.616E−10 |
| 2 | 1.1-2.17 | 2.639E−10 |
| 3 | 1.1-2.15 | 1.948E−10 |
| 4 | 1.1-2.22 | 1.784E−10 |
| 5 | 1.16-2.1 | 3.057E−10 |
| 6 | 1.16-2.17 | 3.327E−10 |
| 7 | 1.16-2.15 | 1.967E−10 |
| 8 | 1.16-2.22 | 2.250E−10 |
| 9 | 1.11-2.1 | 2.871E−10 |
| 10 | 1.11-2.17 | 2.805E−10 |
| 11 | 1.11-2.15 | 2.100E−10 |
| 12 | 1.11-2.22 | 2.187E−10 |
| 13 | 1.18-2.1 | 2.938E−10 |
| 14 | 1.18-2.17 | 2.778E−10 |
| 15 | 1.18-2.15 | 1.921E−10 |
| 16 | 1.18-2.22 | 1.958E−10 |
| 17 | 1.17-2.1 | 3.252E−10 |
| 18 | 1.17-2.15 | 2.986E−10 |

TABLE 20-continued

EC$_{50}$ values for anti-PSMA V$_H$ binding to human
PSMA-CHO. The linker length used was (G$_4$S)$_6$.

| No | Construct | EC50 |
|---|---|---|
| 19 | 1.17-2.17 | 1.921E−10 |
| 20 | 1.17-2.22 | 1.989E−10 |

Each individual V$_H$ clone as identified above was sequenced from the phagemid and grouped based on V$_H$ germline and CDR3 amino acid similarity into separate families. Representative clones were further characterised. Variants, including germlined variants, were generated by standard methods of parent clones e.g 1.1 and 2.1. FIG. 1 shows the sequences of clones 1.1 to 1.20 isolated as described herein above and grouped into a single family. Clones 1.8-1.20 are variants of 1.1. FIG. 2 shows the sequences of clones 2.1 to 2.25 isolated as described herein above and grouped into a single family. Clones 2.2, 2.11-2.19, 2.22-2.25 are variants of 2.1. FIG. 3 shows the sequences of clones 3.1 to 3.24 isolated as described herein above and grouped into a single family. Clones 3.20-3.25 are variants of 3.1.

Example 8—Characterisation of V$_H$ a) Specificity of Anti-PMSA

The specificity of individual V$_H$ for target antigen was confirmed by ELISA, following the methods described in Example 7(a). V$_H$ were tested for binding to PMSA and shown not to cross react with irrelevant proteins.

b) Measurement of Binding Kinetics and Epitope Binding Using Octet

Binding kinetics of purified anti-PSMA V$_H$ antibodies were measured on a ForteBio Octet RED 384 instrument. Recombinant PMSA was diluted to 20 μg/ml in sodium acetate buffer, pH 5 (ForteBio, cat. no. 18-1069) and coupled to ARG2G biosensors (ForteBio cat. no. 18-5092) using amine-coupling chemistry (NHS-EDC amine-coupling, ForteBio cat. nos. 18-1067 and 18-1033), followed by quenching in ethanolamine (ForteBio cat. no. 18-1071). Binding kinetics of anti-PSMA V$_H$ antibodies were then determined by preparing each V$_H$ antibody in dilution series (typically 1:2 dilution series starting with 15 μg/ml, V$_H$ at the highest concentration), and then measuring binding of the different V$_H$ concentrations to the PSMA-coupled biosensors. V$_H$ binding kinetics were then determined from the (blank subtracted) sensorgram trace using 1:1 binding models and ForteBio Octet DataAnalysis software. Binding affinities from 1-150 nM and in the subnanomolar range were detected and examples of the binding parameters are shown in Table 21 below.

TABLE 21

| | KD (nM) | Kdis (1/s) |
|---|---|---|
| 2.1 | 1.64 | 4.56E−04 |
| 1.1 | 2.44 | 1.54E−03 |
| 3.1 | 3.78 | 4.52E−04 |

Further family members in particular variants of parent molecules were also tested as below using 1:2 dilution series starting with 0.375 μg/ml. Binding affinities in the nanomolar and picomolar range were detected as shown in Tables 22 and 23.

TABLE 22

Family 1

| Clone | KD (nM) | Kdis (1/s) |
|---|---|---|
| 1.8 | 1.95 | 1.04E−03 |
| 1.10 | 0.67 | 4.18E−04 |
| 1.11 | 0.80 | 4.95E−04 |
| 1.12 | 0.55 | 4.28E−04 |
| 1.14 | 0.46 | 3.35E−04 |
| 1.16 | 0.44 | 3.65E−04 |
| 1.17 | 0.61 | 5.51E−04 |
| 1.18 | 0.59 | 5.72E−04 |

TABLE 23

Family 2

| Clone | KD (nM) | Kdis (1/s) |
|---|---|---|
| 2.1 | 0.32 | 2.28E−04 |
| 2.13 | 0.99 | 7.43E−04 |
| 2.17 | 0.76 | 7.26E−04 |
| 2.15 | 4.72 | 3.44E−03 |
| 2.12 | 1.56 | 1.57E−03 |
| 2.22 | 2.62 | 2.44E−03 |

Single domain antibodies purified from periplasmic extracts using Ni-NTA chromatography (via the C-terminal His-tag) as in example 7a were also tested. Results are shown in the Table below. Binding affinities in the nanomolar range were detected.

TABLE 24

| clone number | KD (nM) | Kdiss (1/s) |
|---|---|---|
| 4.1 | 45 | 1.4 × 10−2 |
| 5.1 | 30 | 9.1 × 10−3 |
| 12.1 | 3.9 | 1.37E−03 |
| 10.1 | 95 | 1.85 × 10−3 |
| 11.1 | 26 | 0.00149 |
| 7.1 | 41 | 4.783 × 10−4 |
| 13.1 | 4.2 | 6 × 10−4 |
| 6.1 | 16 | 3.65 × 10−3 |
| 14.1 | 17 | 1.1 × 10−3 | c) Measurement of Internalization of Cynomolgus PSMA-Binding V$_H$ Using Fluorescence Microvolume Assay Technology Internalization of purified V$_H$ was measured using the pH-sensitive fluorescent dye pHrodo® green. Anti-His antibody (Millipore cat. no. 05-949) was labelled with pHrodo® Green STP ester (Molecular Probes cat. no. P35369) according to the manufacturer's instructions. All samples and reagents were prepared in internalization buffer (pH 7.4) containing PBS and 0.1% Bovine Serum Albumin. CHO cells expressing cynomolgus PSMA were resuspended at 0.1×10$^6$ cells/ml and 120 nM DRAQ5 added to the cell suspension. V$_H$ (10 μl) were transferred into 384-well black clear-bottomed assay plates (Costar cat. no. 3655) and 10 μl of 40 nM pHrodo® green labelled Anti-His antibody added followed by 20 μl DRAQ5 stained cells. Plates were incubated at 37° C. for 2 hr then equilibrated to room temperature. Fluorescence emission in the FL2 (502 nm-537 nm) and FL5 (677-800 nm) channels were measured on TTP Mirrorball plate reader following excitation at 488 nm and 640 nm. Data was gated on FL5 perimeter and peak intensity and the FL2 median mean fluorescence intensity of the gated data used for determination of V$_H$ internalization (FIG. 17).

Internalization of variants of single domain antibodies 1.1 and 1.2 was measured using the pH sensitive fluorescent dye pHrodo® green as described above except serially diluted $V_H$ were pre-incubated with pHrodo® green labelled Anti His antibody for 30 minutes at room temperature prior to addition of DRAQ5 stained CHO human PSMA clone 1A10 cells (20 µl). Plates were incubated for 2 hour at room temperature then fluorescent emission measured. Activity of the $V_H$ in the assay is shown in Table 25 below.

TABLE 25

| Name | pH ® RodoGreen Internalization Assay human PSMA Average $EC_{50}$ (M) |
|---|---|
| 1.8 | 5.0E−10 |
| 1.10 | 6.4E−10 |
| 1.11 | 3.7E−10 |
| 1.12 | 5.7E−10 |
| 1.14 | 4.4E−10 |
| 1.16 | 4.8E−10 |
| 1.17 | 2.9E−10 |
| 1.18 | 3.1E−10 |
| 2.1 | 8.0E−10 |
| 2.13 | 5.8E−10 |
| 2.17 | 8.0E−10 |
| 2.15 | 7.2E−10 |
| 2.12 | 5.3E−10 |
| 2.22 | 6.7E−10 | d) Measurement of Internalization of PSMA Binding $V_H$ Using the his-ZAP Assay

Internalization of His tagged PSMA binding $V_H$ was assessed using an anti-His antibody conjugated to saporin toxin (His-ZAP Advanced targeting Systems IT52). The His-ZAP reagent binds to the $V_H$ and is internalized through the $V_H$ interaction with PSMA on the cell surface. Saporin toxin is released from the complex in the endosome and inactivates ribosomes eventually resulting in cell death.

CHO cells expressing mouse or cynomolgus PSMA (400 cells per well in a 30 µl volume) were seeded into 384-well black clear-bottomed tissue culture-treated assay plates (Costar cat. no. 3712) in Hams F12 (Sigma cat. no. N6658) media containing 10% foetal bovine serum, 2 mM L-glutamine, 10 µg/ml blasticidin, 300 µg/ml Zeocin, penicillin/streptomycin, 1 µg/ml tetracycline and incubated overnight in a $CO_2$ incubator at 37° C. Purified $V_H$ were serially diluted in media then an equal volume of 40 nM His-ZAP added. Following incubation for 30 minutes at 37° C. the $V_H$/His-ZAP samples (10 µl) were transferred to the cell assay plates and incubated for 48 hours in a $CO_2$ incubator at 37° C. His-ZAP control wells (cells with His-ZAP reagent) and background controls (media only) were set up on each plate for data normalization. Cell viability was determined following the 48 hour incubation using the Cell Titer-Glo Cell Viability assay (Promega cat. no. G7571) according to the manufacturer's instructions. Relative luminescent signal (RLU) was measured using the BMG PHER-Astar plate reader. The data was normalized by subtraction of the RLU signal obtained in the absence of cells and expression as a percentage of the background-corrected signal of the His-ZAP control wells (FIG. 18).

For LnCAP assays, cells (2000 per well in a 100 µl volume) were seeded into 96-well TC-treated plates (Costar 3340) in RPMI 1640 media containing 10% foetal bovine serum, 2 mM L-glutamine and penicillin/streptomycin. Purified $V_H$ were serially diluted in media, then an equal volume of 60 nM His-ZAP was added. Following incubation for 30 minutes at 37° C. the $V_H$/His-ZAP samples (100 µl) were transferred to the cell assay plates and incubated for 96 hours in $CO_2$ incubator at 37° C. Cell viability was measured using the Cell Titer-Glo Cell Viability assay and data analysed as described above. Examples are given in FIG. 19.

The ability of variants of single domain antibodies 1.1 and 2.1 to internalize with a bound saporin conjugated anti His antibody, resulting in toxin mediated cell death, was determined. Assays were performed as described above except CHO human PSMA clone 1A10 cells were used for human PSMA assays and plates were incubated for 72 hours in a CO2 incubator at 37° C. prior to measurement of cell viability. Activity of the single domain antibodies tested in the assay is shown in Table 26 below.

TABLE 26

| | human PSMA Average $EC_{50}$ (M) | cyno PSMA $EC_{50}$ (M) |
|---|---|---|
| 1.8 | 2.6E−11 | 1.4E−09 |
| 1.10 | 2.1E−11 | 1.3E−09 |
| 1.11 | 1.4E−11 | 4.1E−10 |
| 1.12 | 1.8E−11 | 9.7E−10 |
| 1.14 | 1.7E−11 | 7.9E−10 |
| 1.16 | 1.7E−11 | 4.2E−10 |
| 1.17 | 1.5E−11 | 5.6E−10 |
| 1.18 | 2.3E−11 | 4.8E−10 |
| 2.1 | 1.4E−11 | 5.2E−11 |
| 2.13 | 2.7E−11 | 8.0E−11 |
| 2.17 | 3.5E−11 | 7.0E−11 |
| 2.15 | 6.9E−11 | 1.6E−10 |
| 2.12 | 1.6E−11 | 9.1E−11 |
| 2.22 | 6.9E−11 | 1.8E−10 |

Biparatopic molecules were tested and showed the following EC50 values.

TABLE 27

| | human PSMA Average $EC_{50}$ (M) | cyno PSMA Average $EC_{50}$ (M) |
|---|---|---|
| 1.1-6GS-2.1 | 1.4E−11 | 1.2E−11 |
| 1.1-6GS-2.17 | 1.2E−11 | 1.1E−11 |
| 1.1-6GS-2.15 | 1.3E−11 | 8.6E−12 |
| 1.1-6GS-2.22 | 8.8E−12 | 7.8E−12 |
| 1.16-6GS-2.1 | 1.4E−11 | 1.3E−11 |
| 1.16-6GS-2.17 | 1.5E−11 | 1.1E−11 |
| 1.16-6GS-2.15 | 1.8E−11 | 1.1E−11 |
| 1.16-6GS-2.22 | 2.0E−11 | 1.1E−11 |
| 1.11-6GS-2.1 | 1.7E−11 | 1.2E−11 |
| 1.11-6GS-2.17 | 7.9E−12 | 8.1E−12 |
| 1.11-6GS-2.15 | 1.1E−11 | 9.0E−12 |
| 1.11-6GS-2.22 | 1.0E−11 | 9.5E−12 |
| 1.18-6GS-2.1 | 5.7E−12 | 5.8E−12 |
| 1.18-6GS-2.17 | 1.2E−11 | 5.6E−12 |
| 1.18-6GS-2.15 | 1.4E−11 | 1.0E−11 |
| 1.18-6GS-2.22 | 1.5E−11 | 1.4E−11 |
| 1.17-6GS-2.1 | 1.3E−11 | 1.5E−11 |
| 1.17-6GS-2.17 | 1.4E−11 | 1.0E−11 |
| 1.17-6GS-2.15 | 1.5E−11 | 1.2E−11 |
| 1.17-6GS-2.22 | 1.8E−11 | 1.2E−11 |

Example 9—Stability of $V_H$ $V_H$ from the different CDR3 families were tested for developability characteristics.

a) Heat Stability: HPLC Size Exclusion Chromatography

Purified VH were subjected to size exclusion chromatography. Briefly, purified $V_H$ were stored in PBS buffer for 0-14 days at either 4° C. or 40° C., and then analysed at various time points using a Waters H-Class Bio UPLC containing a PDA detector (detection at 280 nm) with separation on a Waters ACQUITY BEH 125 Å SEC column.

Samples were injected in 10 µl volumes and were run in a mobile phase containing 200 mM NaCl, 100 mM sodium phosphate, pH 7.4+5% propan-1-ol at a flow rate of 0.4 ml/min. Data were collected for 6 minutes and the percentage of monomer remaining after storage as compared to that present at the start (T=0) was calculated. Parent molecules showed high stability. Variants were also tested.

It should be noted that these data were collected under non-optimised buffer conditions.

Concentration of samples varied: Monovalent 1.1 variants: 5.0 mg/ml
Monovalent 2.1 variants: 3.5 mg/ml
Results are shown in the Tables below.

Long term stability of monovalent single domain antibodies up to 35 days was also tested and showed a good profile.

b) Heat Stability: Mirror Ball

Purified $V_H$ samples were incubated for 0-8 days at 40° C. and then tested for binding to CHO cells expressing cynomolgus PSMA using the FMAT Direct Binding Assay as detailed in Examples 7(b). Molecules tested showed good stability.

c) Assessment of $V_H$ Serum Stability Using a Homogenous Time Resolved Fluorescence (HTRF) Assay.

Purified $V_H$ were mixed with cynomolgus monkey serum and incubated for 0-7 days at 37° C. Samples were then

TABLE 27

| Name | % Area T0 Monomer 4° C. | | | | % Area T0 Monomer 40° C. | | | | |
| --- | --- | --- | --- | --- | --- | --- | --- | --- | --- |
| | 0 | 4 | 7 | 14 | 0 | 1 | 4 | 7 | 14 |
| 1.8 | 100.00 | 100.47 | 99.06 | 102.71 | 100.00 | 98.65 | 97.70 | 90.78 | 88.64 |
| 1.10 | 100.00 | 100.75 | 99.74 | 101.47 | 100.00 | 97.73 | 94.35 | 82.99 | 85.89 |
| 1.11 | 100.00 | 101.34 | 100.41 | 103.26 | 100.00 | 98.34 | 97.92 | 90.95 | 100.75 |
| 1.12 | 100.00 | 100.97 | 103.69 | 110.61 | 100.00 | 97.62 | 97.03 | 87.86 | 100.99 |
| 1.14 | 100.00 | 101.44 | 101.09 | 109.51 | 100.00 | 97.55 | 95.03 | 83.69 | 88.01 |
| 1.16 | 100.00 | 101.44 | 100.84 | 107.00 | 100.00 | 97.24 | 93.57 | 82.10 | 88.46 |
| 1.17 | 100.00 | 101.06 | 100.29 | 108.35 | 100.00 | 98.44 | 100.56 | 93.92 | 108.68 |
| 1.18 | 100.00 | 100.36 | 101.41 | 106.39 | 100.00 | 98.38 | 98.70 | 88.09 | 95.31 |

TABLE 28

| Name | % Area T0 Monomer 4° C. | | | | % Area T0 Monomer 40° C. | | | | |
| --- | --- | --- | --- | --- | --- | --- | --- | --- | --- |
| | 0 | 4 | 7 | 14 | 0 | 1 | 4 | 7 | 14 |
| 2.1 | 100.00 | 100.85 | 98.69 | 101.05 | 100.00 | 99.75 | 100.07 | 100.59 | 100.55 |
| 2.13 | 100.00 | 103.11 | 100.91 | 99.78 | 100.00 | 99.80 | 99.92 | 100.30 | 100.34 |
| 2.17 | 100.00 | 101.89 | 99.62 | 99.64 | 100.00 | 100.10 | 101.00 | 101.17 | 101.50 |
| 2.15 | 100.00 | 102.20 | 99.85 | 99.20 | 100.00 | 99.46 | 100.23 | 100.28 | 101.03 |
| 2.12 | 100.00 | 100.06 | 99.56 | 99.66 | 100.00 | 99.51 | 99.92 | 100.84 | 101.71 |
| 2.22 | 100.00 | 100.76 | 99.91 | 100.48 | 100.00 | 99.12 | 99.88 | 100.23 | 102.02 |

TABLE 29

| Name | % Area T0 Monomer 4° C. | | | | % Area T0 Monomer 40° C. | | | | |
| --- | --- | --- | --- | --- | --- | --- | --- | --- | --- |
| | 0 | 4 | 7 | 14 | 0 | 1 | 4 | 7 | 14 |
| 1.1-6GS-2.1 | 100.00 | 109.56 | 68.16 | 68.02 | 100.00 | 105.79 | 94.77 | 64.98 | 64.58 |
| 1.1-6GS-2.17 | 100.00 | 116.15 | 75.23 | 75.20 | 100.00 | 111.31 | 101.98 | 68.73 | 63.67 |
| 1.1-6GS-2.15 | 100.00 | 111.01 | 72.93 | 73.21 | 100.00 | 106.51 | 95.09 | 70.50 | 58.28 |
| 1.1-6GS-2.22 | 100.00 | 116.88 | 80.88 | 80.66 | 100.00 | 110.00 | 105.22 | 74.44 | 75.37 |
| 1.16-6GS-2.1 | 100.00 | 135.96 | 110.01 | 110.26 | 100.00 | 101.92 | 116.20 | 106.53 | 106.74 |
| 1.16-6GS-2.17 | 100.00 | 125.26 | 106.57 | 106.10 | 100.00 | 117.55 | 110.34 | 100.59 | 96.83 |
| 1.16-6GS-2.15 | 100.00 | 136.57 | 117.42 | 118.25 | 100.00 | 121.10 | 117.79 | 107.33 | 106.12 |
| 1.16-6GS-2.22 | 100.00 | 122.20 | 105.46 | 104.15 | 100.00 | 100.32 | 104.92 | 97.31 | 93.30 |
| 1.11-6GS-2.1 | 100.00 | 76.33 | 98.05 | 97.37 | 100.00 | 96.51 | 95.53 | N/A | 98.38 |
| 1.11-6GS-2.17 | 100.00 | 45.23 | 98.17 | 97.40 | 100.00 | 96.51 | 94.72 | N/A | 90.52 |
| 1.11-6GS-2.15 | 100.00 | 101.17 | 98.87 | 98.68 | 100.00 | 97.23 | 94.78 | N/A | 87.98 |
| 1.11-6GS-2.22His | 100.00 | 102.38 | 100.84 | 99.07 | 100.00 | 98.45 | 100.47 | N/A | 82.62 |
| 1.18-6GS-2.1 | 100.00 | 102.42 | 98.53 | 97.83 | 100.00 | 92.81 | 90.11 | 85.86 | 85.82 |
| 1.18-6GS-2.17 | 100.00 | 101.18 | 97.79 | 97.30 | 100.00 | 92.66 | 87.07 | 84.42 | 79.49 |
| 1.18-6GS-2.15 | 100.00 | 100.57 | N/A | N/A | 100.00 | 88.40 | 93.87 | N/A | N/A |
| 1.18-6GS-2.22 | 100.00 | 102.69 | 97.73 | 97.54 | 100.00 | 94.07 | 91.87 | 86.53 | 100.98 |
| 1.17-6GS-2.1 | 100.00 | 101.15 | 98.97 | 97.85 | 100.00 | 97.08 | 96.59 | 95.85 | 97.40 |
| 1.17-6GS-2.17 | 100.00 | 98.88 | 98.94 | 99.34 | 100.00 | 96.16 | 95.61 | 98.86 | 92.37 |
| 1.17-6GS-2.15 | 100.00 | 97.67 | N/A | N/A | 100.00 | 99.14 | 99.77 | N/A | N/A |
| 1.17-6GS-2.22 | 100.00 | 100.20 | 97.98 | 98.47 | 100.00 | 101.00 | 102.12 | 102.52 | 100.19 | assessed for binding to PSMA using an HTRF assay. Briefly, PSMA (R&D Systems cat. no. 4234-ZN) was biotinylated using the Pierce EZ-Link Micro-Sulfo-NHS-LC-Biotinylation kit. (Thermo Scientific cat. no. 21935). For HTRF binding assays all samples and reagents were prepared in HTRF assay buffer containing PBS, 0.1% (w/v) BSA and 0.4M Potassium Fluoride. $V_H$ (C-terminally His-Myc tagged) were incubated with 3 nM biotinylated PSMA, 1.5 nM Streptavidin cryptate (Cisbio cat. no. 610SAKLA) and 10 nM Anti-Myc-Alexa Fluor-647 (AbD Serotec cat. no. MCA2200AF647) in a total assay volume of 10 µl in black 384-shallow-well plates (Costar cat. no. 3676) for a minimum of 3 hours at room temperature. Time-resolved fluorescent emission at 620 nm and 665 nm was measured following excitation at 337 nm on the BMG PHERAstar plate reader.

In another experiment, purified $V_H$ were mixed with human serum for 0-7 days at 37° C. and then assessed for binding to huPSMA CHO 1A10 cells as described in examples' 7(b) FMAT Direct cell Binding Assay. Data obtained is shown in and EC50 values are shown in Tables 29 and 30 below.

TABLE 29

| $V_H$ | EC50 |
| --- | --- |
| 2.1 Day 0 | 2.49E−10 |
| 2.1 Day 1 | 2.54E−10 |
| 2.1 Day 4 | 2.60E−10 |
| 2.1 Day 7 | 3.01E−10 |
| 2.17 Day 0 | 2.30E−10 |
| 2.17 Day 1 | 2.10E−10 |
| 2.17 Day 4 | 2.28E−10 |
| 2.17 Day 7 | 2.38E−10 |
| 2.15 Day 0 | 2.66E−10 |
| 2.15 Day 1 | 4.97E−10 |
| 2.15 Day 4 | 3.93E−10 |
| 2.15 Day 7 | 3.76E−10 |
| 2.22 Day 0 | 3.05E−10 |
| 2.22 Day 1 | 2.91E−10 |
| 2.22 Day 4 | 3.40E−10 |
| 2.22 Day 7 | 3.28E−10 |

TABLE 30

| $V_H$ | EC50 |
| --- | --- |
| 1.8 Day 0 | 4.09E−10 |
| 1.8 Day 1 | 4.86E−10 |
| 1.8 Day 4 | 4.96E−10 |
| 1.8 Day 7 | 5.42E−10 |
| 1.11 Day 0 | 2.34E−10 |
| 1.11 Day 1 | 2.08E−10 |
| 1.11 Day 4 | 2.27E−10 |
| 1.11 Day 7 | 2.78E−10 |
| 1.16 Day 0 | 1.65E−10 |
| 1.16 Day 1 | 2.43E−10 |
| 1.16 Day 4 | 2.42E−10 |
| 1.16 Day 7 | 2.36E−10 |
| 1.17 Day 0 | 2.73E−10 |
| 1.17 Day 1 | 2.53E−10 |
| 1.17 Day 4 | 2.59E−10 |
| 1.17 Day 7 | 2.74E−10 |
| 1.18 Day 0 | 3.04E−10 |
| 1.18 Day 1 | 3.11E−10 |
| 1.18 Day 4 | 3.19E−10 |
| 1.18 Day 7 | 3.13E−10 |

To assess the serum stability of the different biapartopic combinations the purified biparatopic $V_H$ were mixed with human serum for 0-7 days at 37° C. and then assessed for binding to huPSMA CHO cells as described in examples 7(b) FMAT Direct cell Binding Assay. Table 31 shows the EC50 values for the cell binding.

TABLE 31

EC50 values for biparatopic anti-PSMA $V_H$ binding to PSMA expressing cell line.

| Biparatopic binding molecule | Days | EC50 |
| --- | --- | --- |
| 1.1-6GS-2.1 | 0 | 8.02E−11 |
| | 1 | 1.03E−10 |
| | 4 | 7.86E−11 |
| | 7 | 7.88E−11 |
| 1.1-6GS-2.17 | 0 | 7.7E−11 |
| | 1 | 9.16E−11 |
| | 4 | 8.49E−11 |
| | 7 | 7.42E−11 |
| 1.11-6GS-2.1 | 0 | 8.92E−11 |
| | 1 | 6.05E−11 |
| | 4 | 7.36E−11 |
| | 7 | 8.65E−11 |
| 1.11-6GS-2.17 | 0 | 6.39E−11 |
| | 1 | 7.25E−11 |
| | 4 | 8.44E−11 |
| | 7 | 1.01E−10 |
| 1.16-6GS-2.1 | 0 | 9.02E−11 |
| | 1 | 8.60E−11 |
| | 4 | 1.00E−10 |
| | 7 | 1.07E−10 |
| 1.16-6GS-2.17 | 0 | 7.41E−11 |
| | 1 | 9.44E−11 |
| | 4 | 6.28E−11 |
| | 7 | 6.75E−11 |
| 1.17-6GS-2.1 | 0 | 5.69E−11 |
| | 1 | 4.77E−11 |
| | 4 | 4.58E−11 |
| | 7 | 5.44E−11 |
| 1.17-6GS-2.17 | 0 | 6.74E−11 |
| | 1 | 3.32E−11 |
| | 4 | 4.73E−11 |
| | 7 | 5.7E−11 | d) Assessment of $V_H$ Thermal Stability

Differential scanning calorimetry (DSC) was conducted using a MicroCal VP-Capillary DSC (Malvern). 300 µl of protein at 0.25 mg/ml in PBS was run using a scan rate of 60° C. per minute between 10 and 90° C. Data was analysed using the MicroCal software. Results are shown in Table 32 for monovalent single domain antibodies and in Table 33 for biparatopic binding molecules.

TABLE 32

| Name | $T_m$ (° C.) | $T_{onset}$ (° C.) | $T_{1/2}$ (° C.) |
| --- | --- | --- | --- |
| 2.1 | 73.91 | 70.12 | 2.5 |
| 2.17 | 72.55 | 59.96 | 7.04 |
| 2.15 | 63.62 | 46.37 | 11.75 |
| 2.22 | 71.18 | 56.74 | 8.05 |
| 1.1 | 63.92 | 54.86 | 4.02 |
| 1.11 | 61.51 | 52.62 | 3.25 |
| 1.16 | 60.02 | 48.77 | 5.19 |
| 1.17 | 62.15 | 53.59 | 3.69 |
| 1.18 | 60.34 | 51.44 | 3.69 |
| 1.1-6GS-2.1 | 67.63 | 57.06 | 6.37 |
| 1.1-6GS-2.17 | 65.60 | 58.39 | 3.52 |
| 1.1-6GS-2.15 | 61.28 | 50.36 | 3.69 |
| 1.1-6GS-2.22 | 64.39 | 57.01 | 3.53 |
| 1.16-6GS-2.1 | 64.18 | 54.28 | 9.07 |
| 1.16-6GS-2.17 | 62.98 | 53.08 | 5.37 |
| 1.16-6GS-2.15 | 58.97 | 48.07 | 4.03 |
| 1.16-6GS-2.22 | 61.54 | 51.97 | 4.86 |
| 1.11-6GS-2.1 | 65.75 | 54.00 | 7.56 |
| 1.11-6GS-2.17 | 64.36 | 55.80 | 4.03 |
| 1.11-6GS-2.15 | 60.05 | 50.81 | 3.52 |
| 1.11-6GS-2.22 | 63.07 | 54.00 | 4.02 |

TABLE 32-continued

| Name | $T_m$ (° C.) | $T_{onset}$ (° C.) | $T_{1/2}$ (° C.) |
|---|---|---|---|
| 1.18-6GS-2.1 | 63.89 | 53.15 | 9.57 |
| 1.18-6GS-2.17 | 62.98 | 52.92 | 5.70 |
| 1.18-6GS-2.15 | 60.75 | 48.67 | 7.38 |
| 1.18-6GS-2.22 | 61.75 | 51.68 | 5.04 |
| 1.17-6GS-2.1 | 66.58 | 54.49 | 7.22 |
| 1.17-6GS-2.17 | 64.84 | 56.45 | 4.20 |
| 1.17-6GS-2.15 | 60.69 | 51.29 | 3.86 |
| 1.17-6GS-2.22 | 63.23 | 53.83 | 4.53 |

Example 10 Imaging Studies in Mice $V_H$ were injected in mice ($V_H$1.1, $V_H$2.1 and $V_H$2.1 with half-life extension). The mice contain PSMA positive (+) and PSMA negative (−) tumours. Studies were carried out as follows:
- ~100 MBq of Tc-99m injected activity per mouse
- SPECT/CT at 5 min, 30 min, 60 min, 3 hrs, 6 hrs & 24 hrs.
- images produced for different time points
- Post imaging ex vivo biodistribution and autoradiography
- Negative control $V_H$(αHEL4)

The half-life extended $V_H$ comprises an anti-mouse serum albumin (anti-MSA) $V_H$ with the following sequence:

(SEQ ID NO: 528)
QVQLVESGGGLVQPGGSLRLSCAASGFTFSSYAMSWVRQAPGKGLEWVA

TISDSGSSADYADSVKGRFTISRDNSKNTLYLQMNSLRAEDTAVYYCAR

GRYNWNPRALGIWGQGTMVTVSS

The experiments showed high levels of specific tumor targeting, faster penetration and greater accumulation of the injected dose to PSMA+ tumor, in particular compared to a control monoclonal IgG anti-PSMA antibody. This can be further improved by extending the half life of the $V_H$. Furthermore, the data shows quick clearance of the naked Humabody® $V_H$.

Example 11 Epitope Mapping

In tandem epitope mapping of PSMA binding VH against each other was carried out using Octet RED 384. $V_H$ binding was then determined from the (reference sensor subtracted) sensorgram trace using 1:1 binding models and ForteBio Octet DataAnalysis software. See also example 8b. The epitope binning results are shown in Table 33. Some clones showed partial blocking.

TABLE 33

| Group 1 | Group 2 |
|---|---|
| 3.6 | 1.4 |
| 2.1 | 12.1 |
| 11.1 | 5.1 |
| 4.1 | 13.1 |
| 7.1 | 6.1 |
| 14.1 | |
| 10.1 | |
| 9.1 | |

In a further experiment, epitope competition between single domain antibodies 1.1 and 2.1 was further characterised. PSMA was coupled onto AR2G biosensors using the amine coupling second generation kit (ForteBio) and then used for epitope binning experiments conducted using the Octet RED384. In these experiments each $V_H$ was diluted to a concentration of 4 ug/ml. Biosensors were loaded with no $V_H$ or either 2.1 or 1.1 until binding to PSMA reached saturation level. These sensors were then briefly dipped into PBS/Tween before undergoing a second association step. The second association step involved dipping biosensors into wells containing the same $V_H$ only or both 2.1 and 1.1. The presence of the first $V_H$ in the later combination ensured that it continued to saturate its PSMA binding sites. The binding profiles were then studied using the ForteBio Analysis software. These data obtained demonstrate that single domain antibodies 2.1 and 1.2 bind distinct epitopes on PSMA.

Example 12 Imaging Studies

The following constructs were tested in these studies:

VH 2.1
VH 2.1-HIS, 1.2 mg/ml
Sequence:
(SEQ ID NO. 532)
EVQLVESGGGVVQPGRSLRLSCAASGFSFSGYGMHWVRQAPGKGLEWVA

YISYDGSNKYYADSVKGRFTISRDNSKNTLYLQMNSLRAEDTAVYYCAK

DPAWGLRLGESSSYDFDIWGQGTMVTVSSLEGGGSEQKLISEEDLNHHH

HHH

VH 1.1
VH 1.1-HIS
Sequence:
(SEQ ID NO. 533)
EVQLLESGGGLVQPGGSLRLSCAASGFSFSSYAMSWVRQAPGKGLEWVSS

IGENDGTTDYADSVKGRFTISRDNSKSMLYLQMNSLRVEDTAVYYCVKDG

VHWGQGTLVTVSSLEGGGSEQKLISEEDLNHHHHHH

Hel4
HEL-4-HIS
Sequence:
(SEQ ID NO. 534)
EVQLLESGGGLVQPGGSLRLSCAASGFRISDEDMGWVRQAPGKGLEWVS

SIYGPSGSTYYADSVKGRFTISRDNSKNTLYLQMNSLRAEDTAVYYCA

SALEPLSEPLGFWGQGTLVTVSSAAAHHHHHH

VH 2.1-VH 2.1
VH 2.1-6GS-VH 2.1
Sequence:
(SEQ ID NO. 535)
EVQLVESGGGVVQPGRSLRLSCAASGFSFSGYGMHWVRQAPGKGLEWV

AYISYDGSNKYYADSVKGRFTISRDNSKNTLYLQMNSLRAEDTAVYYCA

KDPAWGLRLGESSSYDFDIWGQGTMVTVSSGGGGSGGGGSGGGGSGG

GGSGGGGSGGGGSEVQLVESGGGVVQPGRSLRLSCAASGFSFSGYGM

HWVRQAPGKGLEWVAYISYDGSNKYYADSVKGRFTISRDNSKNTLYLQM

NSLRAEDTAVYYCAKDPAWGLRLGESSSYDFDIWGQGTMVTVSSAAAHH

HHHH

VH 2.1-VH 1.1
VH 2.1-6GS-VH 1.1
Sequence:
(SEQ ID NO. 536)
EVQLVESGGGVVQPGRSLRLSCAASGFSFSGYGMHWVRQAPGKGLEWVA

YISYDGSNKYYADSVKGRFTISRDNSKNTLYLQMNSLRAEDTAVYYCAK

-continued

DPAWGLRLGESSSYDFDIWGQGTMVTVSSGGGGSGGGGSGGGGSGGGG

SGGGGSGGGGSEVQLLESGGGLVQPGGSLRLSCAASGFSFSSYAMSVV

VRQAPGKGLEWVSSIGENDGTTDYADSVKGRFTISRDNSKSMLYLQMN

SLRVEDTAVYYCVKDGVHWGQGTLVTVSSAAAHHHHHH

All $V_H$ domains used in this study were expressed in *E. coli*. The proteins were purified from filtered supernatant using nickel affinity chromatography and size exclusion chromatography (SEC) as described in example 7a. After buffer exchange into storage buffer, the some proteins were concentrated using spin concentrators. The protein purity was analysed using SDS-PAGE and analytical SEC. Binding to PSMA was checked using recombinant protein and/or cells expressing PSMA. Stability was checked by heating the protein to 40° C. for an extended period of time (ranging from overnight to 4 weeks) and measuring the degree of protein degradation. Aliquots of the proteins were stored at −80° C. until use.

Confocal fluorescence microscopy method to test the occurrence of co-localization between the $V_H$ of interest (in a monovalent, bivalent and biparatopic format) and the markers of endocytosis LAMP-1 (staining lysosome) and EEA-1 (staining early endosome) in a PSMA expressing cell line. An IgG benchmark antibody that binds to PSMA was used as a positive control. The results are shown in FIGS. 20-24 and demonstrate improved internalisation of bivalent and biparatopic $V_H$ constructs.

Experimental Protocol

The cell line used was a CHO T-REx huPSMA cell line.
1) CHO T-REx huPSMA cells were induced with tetracycline for PSMA expression the day before the experiment and plated on coverslips.
2) On the following day cells were incubated with media comprising the test $V_H$ (either in their monovalent, bivalent or biparatopic format) at 500 nM or with the positive control.
3) Samples were first incubated on ice for 30 min to block endocytosis and then fixed with 4% PFA 10 min at RT, followed by 3 washes in PBS. Duplicate samples are further incubate at 37° C. for 2 hrs to trigger endocytosis, then fixed.
4) After fixation samples, were permeabilized with buffer.
5) Cells that were incubated with the positive control were stained using an anti-human-488 antibody diluted 1:2000 in 0.5% BSA/PBS+0.05% Tween for 1 hr, followed by three washes in PBS+0.05% Tween (5 min each).
6) Cells that were incubated with monovalent or bivalent/biparatopic test $V_H$ were stained using a primary anti-HIS antibody (mouse) for 1 hr, followed by washes, and then incubated with the secondary anti-mouse 488 antibody for 1 hr, followed by washes.
7) Lysosomes and endosomes are stained using a primary antibody against either the early endosome antigen 1 (EEA-1) or the lysosome membrane antigen 1 (LAMP-1) (both rabbit) for 1 hr. Cells are further incubated for 1 hr RT with anti-rabbit-647 secondary antibody, followed by washes.
8) All samples are also stained with HOECHST 1:1000 (0.5 ug/ml) for 5 min then washed.
9) Coverslips are mounted into frosty end slides and imaged using a NIKON A1R confocal system.

Pictures were taken using the program NIS-ELEMENTS AR.

Laser lines used were: 407.7 nm (HOECHST), 487.7 nm (VH/monoclonal benchmark), 639.7 (LAMP-1, EEA-1)

Objective: Apo 60× Oil λS DIC N2
For confocal mode: Pinhole Size (um): 39.6, Z step: 0.49 um.

Further imaging studies were conducted using CHO cells expressing human PSMA (15000/well) were seeded onto 96 well Poly-L-Lysine (Sigma P4707) coated plates (Perkin Elmer 6005550) in Hams F12 (Sigma N6658) media containing 10% Foetal Bovine Serum, 2 mM L-Glutamine, 10 µg/ml Blasticidin, 300 µg/ml Zeocin, penicillin/streptomycin, 1 µg/ml Tetracycline and incubated overnight in a $CO_2$ incubator at 37° C. VH were added to the plates and incubated at 4° C. for 30 minutes following by 37° C. for 2 hours. Plates were washed three times with PBS then the cells fixed in 4% paraformaldehyde and permeabilised with 0.5% saponin. Internalized VH were detected by staining with anti-His (Millipore 05-949) and anti-mouse AF488 (Jackson ImmunoResearch 115-545-098). Lysosomes were stained with LAMP-1 (Abcam Ab24170) and anti-rabbit AF647 (Jackson ImmunoResearch 111-605-008). Nuclei were stained using Hoescht stain (Life technologies H3570). Plates were imaged using the IN Cell Analyzer 6000 and Images processed using ImageJ software. The results are shown in FIG. 25.

Example 13 Potency of MMAE Toxin Conjugated to Binding Molecules In Vitro

The ability of MMAE-toxin-conjugated $V_H$ to internalize into PSMA-expressing cells resulting in cell killing was determined using an in vitro cytotoxicity assay.

Human cells (DU-145, ATCC HTB-81) stably expressing human PSMA or matched PSMA negative cells were seeded into 384-well black clear-bottomed tissue culture treated assay plates at 3000 cells per well in RPMI 1640 medium containing 10% foetal bovine serum, 2 mM L-Glutamine, 1× penicillin/streptomycin, and incubated overnight in a $CO_2$ incubator at 37° C. Cells were then incubated with serially-diluted MMAE-toxin-conjugated $V_H$ for 48 or 72 hours. Untreated control wells (cells in the absence of toxin-conjugated $V_H$) and background control wells (media only) were set up on each plate for data normalization. Cell killing was determined following the incubation using the Cell Titer-Glo Cell Viability assay (Promega G7571) according to the manufacturer's instructions. Relative luminescent signal (RLU) was measured using the BMG PHERAstar plate reader. The data was normalized by subtraction of the RLU signal obtained in the background control wells then expressed as a % of the untreated control wells (% survival). FIG. 26 illustrates dose response curves obtained using a human-PSMA-expressing human cell line and the matched parent (i.e. non-transfected) PSMA negative cell line in a representative experiment (48 hour incubation). $IC_{50}$ values and maximum % cell killing obtained for the MMAE-conjugated constructs are summarized in Table 20. Crescendo's Humabody® $V_H$ were conjugated to MMAE using HiPEG™ technology (WO 2009/047500; Cong et al., (2012) Bioconjugate Chem. 2012, 23, 248-263); the positive ADC control was generated using ThioBridge™ technology (\NO 2016063006; WO 2005/007197; Balan et al., (2007) Bioconjugate Chem., 18, 61-76). The anti-PSMA-MMAE-conjugated $V_H$ specifically killed PSMA positive cells with minimal cell killing observed for the PSMA negative control cell line. The biparatopics that consist of two $V_H$ targeting different epitopes of the PSMA were more potent than the monovalent or bivalent PSMA $V_H$ constructs. The DU145 assay was performed with a 48 h and with a 72 h HDC incubation. This had an impact on the $IC_{50}$ values measured and the % maximum kill, but was not expected to affect the ranking of the different HDC formats. For screening, a 48 h incubation was preferred for higher throughput. Using the 48 h incubation none of the constructs tested reached 100% cell kill (even at the highest concentrations tested). The maximum response leveled off at approx. 70-85% (see Table 34). Table 35 shows the $IC_{50}$ values and FIG. 27 illustrates the higher maximum % cell killing observed using a 72 hour incubation time (n=1 data).

TABLE 34

Summary of in vitro cytotoxicity data obtained with the human-PSMA-expressing human cell line following a 48 hour incubation.

| Construct | | | DAR | Mean $IC_{50}$ ± SD (nM), Mean Max % Cell kill, (n number) | $IC_{50}$ Toxin (nM) |
|---|---|---|---|---|---|
| HiPEG ™ A-His$_6$ val-cit-PAB-MMAE | Monovalent | 2.1-myc-his | 1 | 1.2 ± 0.7 nM Max cell kill 74% (n = 4) | 1.16 |
| HiPEG ™ B-His$_6$ val-cit-PAB-MMAE | Monovalent | 1.1-myc-his | 0.9 | 2.7 ± 2.5 nM Max cell kill 73% (n = 4) | 2.43 |
| HiPEG ™ C-His$_6$ val-cit-PAB-MMAE | Monovalent | 3.1-myc-his | 1 | 5.2 ± 2.6 nM Max cell kill 59% (n = 4) | 5.21 |
| HiPEG ™ D-His$_6$ val-cit-PAB-MMAE | Monovalent | HEL4-his | | >300 nM (n = 3) | |
| HiPEG ™ A-2-A-His$_6$ val-cit-PAB-MMAE | Bivalent | 2.1-(G4S)6-2.1 | 1 | 0.32 ± 0.2 nM Max cell kill 57% (n = 3) | 0.32 |
| HiPEG ™ B-2-B-His$_6$ val-cit-PAB-MMAE | Bivalent | 1.1-(G4S)6-1.1 | 0.7 | 18 ± 8 nM (n = 3) Max cell kill 80% (Estimated) | 12.6 |
| HiPEG ™ C-2-C-His$_6$ val-cit-PAB-MMAE | Bivalent | 3.1-(G4S)6-3.1 | 1 | 4.5 ± 2.4 nM Max cell kill 69% (n = 3) | 4.54 |
| HiPEG ™ A-1-B-His$_6$ val-cit-PAB-MMAE | Biparatopic | 2.1-(G4S)2-1.1 | 1 | 0.67 ± 0.3 nM Max cell kill 75% (n = 4) | 0.67 |
| HiPEG ™ A-2-B-His$_6$ val-cit-PAB-MMAE | Biparatopic | 2.1-(G4S)6-1.1 | 1 | 0.37 ± 0.1 nM Max cell kill 78% (n = 3) | 0.37 |
| HiPEG ™ B-1-A-His$_6$ val-cit-PAB-MMAE | Biparatopic | 1.1-(G4S)2-2.1 | 1 | 0.13 ± 0.1 nM Max cell kill 79% (n = 3) | 0.13 |
| HiPEG ™ B-2-A-His$_6$ val-cit-PAB-MMAE | Biparatopic | 1.1-(G4S)6-2.1 | 1 | 0.15 ± 0.1 nM Max cell kill 79% (n = 3) | 0.15 |
| ThioBridge ™ anti-PSMA val-cit-PAB-MMAE | Control ADC | control ADC | 4 | 0.03 ± 0.02 nM Max cell kill 82% (n = 3) | 0.13 |

TABLE 35

Summary of in vitro cytotoxicity data obtained with the human-PSMA-expressing human cell line following a 72 hour incubation.

| Construct | Format | $V_H$ | DAR | $IC_{50}$ (nM) | $IC_{50}$ (toxin) nM |
|---|---|---|---|---|---|
| HiPEG ™ A-His$_6$ val-cit-PAB-MMAE | monovalent | 2.1-myc-his | 1 | 0.55 | 0.55 |
| HiPEG ™ B-His$_6$ val-cit-PAB-MMAE | monovalent | 1.1-myc-his | 0.9 | 4.1 | 3.69 |
| HiPEG ™ A-2-A-His$_6$ val-cit-PAB-MMAE | bivalent | 2.1-(G4S)6-2.1 | 1 | 0.19 | 0.19 |
| HiPEG ™ B-2-B-His$_6$ val-cit-PAB-MMAE | bivalent | 1.1-(G4S)6-1.1 | 0.7 | 21 | 14.7 |
| HiPEG ™ A-2-B-His$_6$ val-cit-PAB-MMAE | biparatopic | 2.1-(G4S)6-1.1 | 1 | 0.29 | 0.29 |
| HiPEG ™ B-1-A-His$_6$ val-cit-PAB-MMAE | biparatopic | 1.1-(G4S)2-2.1 | 1 | 0.1 | 0.1 |
| ThioBridge ™ anti-PSMA val-cit-PAB-MMAE | mAb | Control ADC | 4 | 0.042 | 0.168 |

The order of potency observed for the monovalent constructs was $V_H2.1>V_H1.1>V_H3.1$.

The $V_H2.1$ bivalent construct was observed to be approximately 3-fold more potent than the $V_H2.1$ monovalent construct, however the max kill % was reduced when using the bivalent construct.

The $V_H1.1$ bivalent construct was observed to be approximately 6-fold less potent than the $V_H1.1$ monovalent construct.

The $V_H3.1$ bivalent construct had comparable activity to the $V_H3.1$ monovalent construct, with a slightly improved max kill % being observed.

The order of the VH in the biparatopic construct was found to impact on activity, with 2.5 to 4.6-fold differences being observed. The biparatopic construct in the orientation (N-C) $V_H2.1$-$V_H1.1$ was observed to be less active than when in the orientation $V_H1.1$-VH2.1.

The linker length was observed to have a minimal impact on activity (1.2 to 2.2 fold) in the experiments performed. However for some constructs tested the (G4S)6 linker version was slightly more active.

The biparatopic constructs showed improved activity over the monovalent constructs. The most active biparatopic was found to be approximately 7-fold more active than the most active monovalent.

The most active biparatopic was 4.7-fold less active than the control anti-PSMA mAb; however the DAR for the mAb was 4, whereas the DAR for the biparatopic construct was 1. All constructs showed the expected potency, with the biparatopic 1.1-2.1HDC being of comparable potency when compared to the control ADC, when calculating the $IC_{50}$ with respect to the toxin concentration.

Procedure for the Preparation of Humabody™ Drug Conjugates (HDCs)

A stock solution of conjugation reagent, HiPEG™ val-cit-PAB-MMAE (FIG. 28), was prepared in MeCN prior to performing conjugation reactions. A solution of Humabody™ (0.9 mg/mL in PBS; 20 mM EDTA, pH 7.5) was mixed gently with HiPEG™ val-cit-PAB-MMAE reagent (1.5 equiv. per Humabody™; 5% (v/v) final MeCN concentration) and incubated at 22° C. for 19 h. After 19 h, the conjugation reaction was mixed with an equal volume of 600 mM sodium phosphate buffer (150 mM NaCl; 20 mM EDTA), pH 7.5 and cooled to 4° C. A stock solution of 1 mg/mL $NaBH_4$ solution was prepared in 0.1 M NaOH. Two aliquots each of $NaBH_4$ solution, (10 equiv. per reagent), were added to the cooled conjugation reaction with a 30 min interval between additions. After a further 30 min interval, the crude mixture was purified by hydrophobic interaction chromatography (HIC) using a TOSOH ToyoPearl Phenyl-650S column. The sample was bound and washed onto the column using 50 mM sodium phosphate (2 M NaCl), pH 7 (buffer A) and eluted using a gradient of 50 mM sodium phosphate (20% v/v isopropanol), pH 7 (buffer B). Fractions containing the mono-loaded product were pooled and concentrated using Vivaspin20 concentrators fitted with 5 kDa MWCO PES membranes. The concentrated fractions were buffer exchanged into DPBS using PD10 columns and the buffer exchanged material sterile filtered using 0.2 μm PVDF syringe filtration unit.

The HiPEG val-cit-PAB-MMAE moiety is attached via a C terminal His6-tag on a $V_H$. Two histidines are needed for attachment of each "payload" toxin molecule. Humabody $V_H$, DAR=1 species were purified for use in cytotoxicity studies, in some instances an exact DAR of 1 was not achieved (see table below). In the examples herein a single MMAE moiety was attached, but multiple payloads are possible (DARs>1).

Procedure for the Preparation of Control ADC with Drug: Antibody Ratio (DAR) of 3.5

Positive control antibody Pro_006 is an anti-PSMA antibody composed of heavy and light chain sequences described within U.S. Pat. No. 8,470,330 and exemplified as antibody 006.

Conjugation 1:

A solution of mAb Pro_006 (5.07 mg/mL) in reaction buffer (20 mM sodium phosphate, 150 mM NaCl; 20 mM EDTA, pH 7.5), was warmed to 40° C. for 15 min. TCEP (5 mM, 2 equiv. per mAb) was added to the mAb solution, mixed gently and incubated at 40° C. for 1 h. A stock solution of conjugation reagent, mc-val-cit-PAB-MMAE (FIG. 29) was prepared in DMF at 2.8 mM. The reduced mAb was cooled to 22° C., diluted to 4.2 mg/mL with reaction buffer and mc-val-cit-PAB-MMAE (5.25 equiv. per mAb) was added. The conjugation mixture was incubated at 22° C. for 2 h. The crude conjugation mixture was treated with 50 mM N-acetyl-L-cysteine (20 equiv. over reagent) at 22° C. for 30 min. The reaction mixture was diafiltered against DPBS using a Vivaspin20 concentrator fitted with 30 kDa MWCO PES membranes. The diafiltered ADC solution was buffer exchanged into DPBS using a Centripure P50 column. The DAR of the sample was assessed by HIC (average DAR=3.21).

Conjugation 2:

A solution of mAb Pro_006 (5.07 mg/mL) in reaction buffer (20 mM sodium phosphate 150 mM NaCl; 20 mM EDTA), pH 7.5 was warmed to 40° C. for 15 min. TCEP (5 mM, 2.75 equiv. per mAb) was added to the mAb solution, mixed gently and incubated at 40° C. for 1 h. A stock solution of conjugation reagent, mc-val-cit-PAB-MMAE (FIG. 29) was prepared in DMF at 4.0 mM. The reduced mAb was cooled to 22° C., diluted to 4.2 mg/mL with reaction buffer and mc-val-cit-PAB-MMAE (7 equiv. per mAb) was added. The conjugation mixture was incubated at 22° C. for 2 h. The crude conjugation mixture was treated with 50 mM N-acetyl-L-cysteine (20 equiv. over reagent) at 22° C. for 30 min. The reaction mixture was diafiltered against DPBS using a Vivaspin20 concentrator fitted with 30 kDa MWCO PES membranes. The diafiltered ADC solution was buffer exchanged into DPBS using a Centripure P50 column. The DAR of the sample was assessed by HIC (average DAR=4.52).

Production of average DAR 3.5 ADC: ADC 1 (DAR 3.21) and ADC 2 (DAR 4.52) were mixed in a 4:1 mol ratio to prepare an ADC with intermediate DAR. The resulting sample was sterile filtered using 0.2 μm PVDF syringe filtration unit. The DAR of the sample was assessed by HIC (average DAR=3.45).

In Vitro Potency of Half-Life Extended HDCs

The in vitro potency of half-life extended HDCs was assessed using the DU145 cell killing assay (72 h).

This material described in Table 36 was generated to test the effect of adding a half-life extension moiety to the HDCs. Half-life-extended versions (HLE) were generated using the MSA-binding $V_H$ (SEQ ID No. 528). In vitro potency was assessed using the DU145 cell killing assay (72 h). FIGS. 30 A & B show $IC_{50}$ values observed in the PSMA-DU145 cytotoxicity assay (72 h) for: Control ADC mAB-MMAE (■), 2.1 6GS-1.1-MMAE biparatopic (▲), 2.1-6GS-1.1-MMAE-HLE half-life extended biparatopic (▼), HEL4-MMAE Monovalent (•) and HEL4-HLE-MMAE Monovalent half-life extended (I), for (A) DU145 expressing PSMA and (B) DU145 parental cells that have not been modified to express PSMA.

TABLE 36

| | | | | IC$_{50}$ | IC$_{50}$ (toxin) | Average Max Cell |
|---|---|---|---|---|---|---|
| Format | V$_H$ | Name | DAR | (nM) | (nM) | Kill % |
| Monovalent | HEL4 | HiPEG ™ HEL4-His val-cit-PAB-MMAE | 1 | >100 | >100 | |
| Biparatopic | 1.1-6GS-2.1 | HiPEG ™ 1.1-6GS-2.1-His val-cit-PAB-MMAE | 1 | 0.27 | 0.27 | 86 |
| Biparatopic-HLE | 1.1-6GS-2.1-6GS-half life extension | HiPEG ™ 1.1-6GS-2.1-6GS-half life extension-His val-cit-PAB-MMAE | 1 | 0.82 | 0.82 | 82 |
| Monovalent-HLE | HEL4-6GS-half life extension | HiPEG ™ HEL4-6GS-half life extension-His val-cit-PAB-MMAE | 1 | >100 | >100 | |
| mAb | Control PSMA mAb-MMAE | Pro_006-mc-val-cit-PAB-MMAE | 3.5 | 0.061 | 0.2135 | 89 |

The invention claimed is:

1. A binding molecule comprising a first single human heavy chain variable immunoglobulin ($V_H$) domain antibody capable of binding human PSMA and a second single $V_H$ domain antibody capable of binding human PSMA, wherein said first and said second single $V_H$ domain antibody comprise CDR1, CDR2 and CDR3 sequences selected from the following:

a. wherein said CDR1 sequence comprises SEQ ID NO. 1 or a sequence with at least 90%, or at least 95% homology thereto, said CDR2 sequence comprises SEQ ID NO. 2 or a sequence with at least 90%, or at least 95% homology thereto and wherein said CDR3 sequence comprises SEQ ID NO. 3 or a sequence with at least 90%, or at least 95% homology thereto;

b. wherein said CDR1 sequence comprises SEQ ID NO. 81 or a sequence with at least 90% or at least 95% homology thereto, said CDR2 sequence comprises SEQ ID NO. 82 or a sequence with at least 90%, or at least 95% homology thereto and wherein said CDR3 sequence comprises SEQ ID NO. 83 or a sequence with at least 90%, or at least 95% homology thereto;

c. wherein said CDR1 sequence comprises SEQ ID NO. 181 or a sequence with at least 90%, or at least 95% homology thereto and said CDR2 sequence comprises SEQ ID NO. 182 or a sequence with at least 90%, or at least 95% homology thereto and wherein said CDR3 sequence comprises SEQ ID NO. 183 or a sequence with at least 90%, or at least 95% homology thereto;

d. wherein said CDR1 sequence comprises SEQ ID NO. 277 or a sequence with at least 90%, or at least 95% homology thereto and a CDR2 sequence comprises SEQ ID NO. 278 or a sequence with at least 90%, or at least 95% homology thereto and wherein said CDR3 sequence comprises SEQ ID NO. 279 or a sequence with at least 90%, or at least 95% homology thereto;

e. wherein said CDR1 sequence comprises SEQ ID NO. 293 or a sequence with at least 90%, or at least 95% homology thereto and said CDR2 sequence comprises SEQ ID NO. 294 or a sequence with at least 90%, or at least 95% homology thereto and wherein said CDR3 sequence comprises SEQ ID NO. 295 or a sequence with at least 90%, or at least 95% homology thereto;

f. wherein said CDR1 sequence comprises SEQ ID NO. 301 or a sequence with at least 90%, or at least 95% homology thereto and said CDR2 sequence comprises SEQ ID NO. 302 or a sequence with at least 90%, or at least 95% homology thereto and wherein said CDR3 sequence comprises SEQ ID NO. 303 or a sequence with at least 90%, or at least 95% homology thereto;

g. wherein said CDR1 sequence comprises SEQ ID NO. 329 or a sequence with at least 90%, or at least 95% homology thereto, said CDR2 sequence comprises SEQ ID NO. 330 or a sequence with at least 90%, or at least 95% homology thereto and wherein said CDR3 sequence comprises SEQ ID NO. 331 or a sequence with at least 90%, or at least 95% homology thereto;

h. wherein said CDR1 sequence comprises SEQ ID NO. 361 or a sequence with at least 90%, or at least 95% homology thereto, said CDR2 sequence comprises SEQ ID NO. 362 or a sequence with at least 90%, or at least 95% homology thereto, and wherein said CDR3 sequence comprises SEQ ID NO. 363 or a sequence with at least 90%, or at least 95% homology thereto;

i. wherein said CDR1 sequence comprises SEQ ID NO. 365 or a sequence with at least 90%, or at least 95% homology thereto, said CDR2 sequence comprises SEQ ID NO. 366 or a sequence with at least 90%, or at least 95% homology thereto and wherein said CDR3 sequence comprises SEQ ID NO. 367 or a sequence with at least 90%, or at least 95% homology thereto;

j. wherein said CDR1 sequence comprises SEQ ID NO. 369 or a sequence with at least 90%, or at least 95% homology thereto, said CDR2 sequence comprises SEQ ID NO. 370 or a sequence with at least 90%, or at least 95% homology thereto and wherein said CDR3 sequence comprises SEQ ID NO. 371 or a sequence with at least 90%, or at least 95% homology thereto;

k. wherein said CDR1 sequence comprises SEQ ID NO. 373 or a sequence with at least 90%, or at least 95% homology thereto, said CDR2 sequence comprises SEQ ID NO. 374 or a sequence with at least 70%, at least 80%, at least 90%, or at least 95% homology thereto and wherein said CDR3 sequence comprises SEQ ID NO. 375 or a sequence with at least 90%, or at least 95% homology thereto;

l. wherein said CDR1 sequence comprises SEQ ID NO. 377 or a sequence with at least 90%, or at least 95% homology thereto, said CDR2 sequence comprises SEQ ID NO. 378 or a sequence with at least 90%, or at least 95% homology thereto and wherein said CDR3 sequence comprises SEQ ID NO. 379 or a sequence with at least 90%, or at least 95% homology thereto;

m. wherein said CDR1 sequence comprises SEQ ID NO. 381 or a sequence with at least 90%, or at least 95% homology thereto, said CDR2 sequence comprises SEQ ID NO. 382 or a sequence with at least 90%, or at least 95% homology thereto and wherein said CDR3 sequence comprises SEQ ID NO. 383 or a sequence with at least 90%, or at least 95% homology thereto;

n. wherein said CDR1 sequence comprises SEQ ID NO. 385 or a sequence with at least 90%, or at least 95% homology thereto, said CDR2 sequence comprises SEQ ID NO. 386 or a sequence with at least 90%, or at least 95% homology thereto and wherein said CDR3 sequence comprises SEQ ID NO. 387 or a sequence with at least 90%, or at least 95% homology thereto; or o. wherein said CDR1 sequence comprises SEQ ID NO. 389 or a sequence with at least 90%, or at least 95% homology thereto and said CDR2 sequence comprises SEQ ID NO. 390 or a sequence with at least 90%, or at least 95% homology thereto and wherein said CDR3 sequence comprises SEQ ID NO. 391 or a sequence with at least 90%, or at least 95% homology thereto.

2. The binding molecule according to claim 1 wherein said first $V_H$ domain antibody and said second $V_H$ domain antibody bind to the same epitope on human PSMA.

3. The binding molecule according to claim 1 wherein said first single VH domain antibody binds to a first epitope on PSMA and said second single VH domain antibody binds to a second epitope on PSMA wherein said first and said second epitope are not identical.

4. The binding molecule according to claim 1 wherein the binding molecule comprises a half-life extending moiety, wherein said half-life extending moiety is selected from the group consisting of an albumin binding moiety, a transferrin binding moiety, a polyethylene glycol molecule, a recombinant polyethylene glycol molecule, human serum albumin, a fragment of human serum albumin, and an albumin binding peptide.

5. The binding molecule according to claim 1, wherein said binding molecule is capable of being internalised by a cell.

6. The binding molecule according to claim 1, wherein said binding molecule is conjugated to a cytotoxic moiety or to a label.

7. The binding molecule according to claim 1, wherein said first and second $V_H$ domain antibody are obtained from a library obtained from a knock out mouse in which the light chain and heavy chain loci are functionally silenced and which expresses a transgene with one or more human heavy chain genes.

8. A pharmaceutical composition comprising a binding molecule according to claim 1 and a pharmaceutical carrier.

9. A method for treating prostate cancer or a prostatic disorder comprising administering a therapeutically-effective amount of a binding molecule according to claim 1.

10. A method for delivering a cytotoxic moiety into a tumor cell comprising exposing said cell to a binding molecule according to claim 1.

11. A method for imaging one or more PSMA tumors or cells, the method comprising contacting the one or more tumors or cells with an effective amount of binding molecule according to claim 1.

12. A method for determining the presence of PSMA in a test sample or detecting a tumor cell by an immunoassay comprising contacting said sample with binding molecule according to claim 1 and at least one detectable label.

13. An isolated nucleic acid molecule or a nucleic acid construct comprising a nucleotide sequence encoding a binding molecule according to claim 1.

14. A host cell comprising a nucleic acid molecule or construct according to claim 13.

15. A kit comprising a binding molecule according to claim 1.

16. A method for producing a binding molecule according to claim 1 comprising expressing a nucleic acid encoding said binding molecule in a host cell in culture and isolating the binding molecule from the host cell culture.

17. A method of determining if a subject has cancer comprising administering to the subject a composition comprising binding molecule according to claim 1 and obtaining an image of the subject; thereby determining if the subject has cancer.

* * * * *

UNITED STATES PATENT AND TRADEMARK OFFICE
CERTIFICATE OF CORRECTION

PATENT NO. : 10,975,161 B2
APPLICATION NO. : 16/069495
DATED : April 13, 2021
INVENTOR(S) : Balloi et al.

Page 1 of 1

It is certified that error appears in the above-identified patent and that said Letters Patent is hereby corrected as shown below:

On the Title Page

(30) Foreign Application Priority Data: Please correct "1600559" to read -- 1600559.7 --

(30) Foreign Application Priority Data: Please correct "1605763" to read -- 1605763.0 --

(30) Foreign Application Priority Data: Please correct "1605770" to read -- 1605770.5 --

In the Specification

Column 5, Line 25: Please insert:
-- The patent or application file contains at least one drawing executed in color. Copies of this patent or patent application publication with color drawing(s) will be provided by the Office upon request and payment of the necessary fee. --

Column 45, Line 35: Please correct "SEQ ID NO. 294 or 2984" to read -- SEQ ID NO. 294 or 298 --

Column 53, Line 55: Please correct "embodiment, n CDR1" to read -- embodiment, CDR1 --

Column 115, Line 47: Please correct "µ, 8, γ3," to read -- µ, δ, γ3, --

Column 115, Line 48: Please correct "and a is partially" to read -- and α is partially --

Signed and Sealed this
Twenty-seventh Day of July, 2021

Drew Hirshfeld
*Performing the Functions and Duties of the*
*Under Secretary of Commerce for Intellectual Property and*
*Director of the United States Patent and Trademark Office*

SEQUENCE LISTING

<160> NUMBER OF SEQ ID NOS: 536

<210> SEQ ID NO 1
<211> LENGTH: 5
<212> TYPE: PRT
<213> ORGANISM: Homo sapiens

<400> SEQUENCE: 1

Ser Tyr Ala Met Ser
1               5

<210> SEQ ID NO 2
<211> LENGTH: 17
<212> TYPE: PRT
<213> ORGANISM: Homo sapiens

<400> SEQUENCE: 2

Ser Ile Gly Glu Asn Asp Gly Thr Thr Asp Tyr Ala Asp Ser Val Lys
1               5                   10                  15

Gly

<210> SEQ ID NO 3
<211> LENGTH: 4
<212> TYPE: PRT
<213> ORGANISM: Homo sapiens

<400> SEQUENCE: 3

Asp Gly Val His
1

<210> SEQ ID NO 4
<211> LENGTH: 113
<212> TYPE: PRT
<213> ORGANISM: Homo sapiens

<400> SEQUENCE: 4

Glu Val Gln Leu Leu Glu Ser Gly Gly Gly Leu Val Gln Pro Gly Gly
1               5                   10                  15

Ser Leu Arg Leu Ser Cys Ala Ala Ser Gly Phe Ser Phe Ser Ser Tyr
            20                  25                  30

```
Ala Met Ser Trp Val Arg Gln Ala Pro Gly Lys Gly Leu Glu Trp Val
            35                  40                  45

Ser Ser Ile Gly Glu Asn Asp Gly Thr Thr Asp Tyr Ala Asp Ser Val
 50                  55                  60

Lys Gly Arg Phe Thr Ile Ser Arg Asp Asn Ser Lys Ser Met Leu Tyr
 65                  70                  75                  80

Leu Gln Met Asn Ser Leu Arg Val Glu Asp Thr Ala Val Tyr Tyr Cys
                 85                  90                  95

Val Lys Asp Gly Val His Trp Gly Gln Gly Thr Leu Val Thr Val Ser
            100                 105                 110

Ser

<210> SEQ ID NO 5
<211> LENGTH: 5
<212> TYPE: PRT
<213> ORGANISM: Homo sapiens

<400> SEQUENCE: 5

Ser Tyr Ala Met Ser
 1               5

<210> SEQ ID NO 6
<211> LENGTH: 17
<212> TYPE: PRT
<213> ORGANISM: Homo sapiens

<400> SEQUENCE: 6

Ser Ile Gly Asp Asn Asn Asn Ser Thr Glu Tyr Ala Asp Ser Val Lys
 1               5                  10                  15

Gly

<210> SEQ ID NO 7
<211> LENGTH: 4
<212> TYPE: PRT
<213> ORGANISM: Homo sapiens

<400> SEQUENCE: 7

Asp Gly Val His
 1

<210> SEQ ID NO 8
<211> LENGTH: 113
<212> TYPE: PRT
<213> ORGANISM: Homo sapiens

<400> SEQUENCE: 8

Glu Val Gln Leu Val Glu Ser Gly Gly Gly Leu Val Gln Pro Gly Gly
 1               5                  10                  15

Ser Leu Arg Leu Ser Cys Ala Ala Ser Gly Phe Thr Phe Ser Ser Tyr
             20                  25                  30

Ala Met Ser Trp Val Arg Gln Ala Pro Gly Lys Gly Leu Glu Trp Val
            35                  40                  45

Ser Ser Ile Gly Asp Asn Asn Asn Ser Thr Glu Tyr Ala Asp Ser Val
 50                  55                  60

Lys Gly Arg Phe Thr Ile Ser Arg Asp Asn Ser Lys Ser Thr Leu Tyr
 65                  70                  75                  80

Leu Gln Met Asn Ser Leu Ser Ala Glu Asp Thr Ala Val Tyr Tyr Cys
                 85                  90                  95

Val Lys Asp Gly Val His Trp Gly Gln Gly Thr Leu Val Thr Val Ser
```

-continued

```
                100                 105                 110
Ser

<210> SEQ ID NO 9
<211> LENGTH: 5
<212> TYPE: PRT
<213> ORGANISM: Homo sapiens

<400> SEQUENCE: 9

Ser Tyr Ala Met Ser
1               5

<210> SEQ ID NO 10
<211> LENGTH: 16
<212> TYPE: PRT
<213> ORGANISM: Homo sapiens

<400> SEQUENCE: 10

Ile Gly Asp Asn Asn Ser Thr Asp Tyr Ala Asp Ser Val Lys Gly
1               5                   10                  15

<210> SEQ ID NO 11
<211> LENGTH: 4
<212> TYPE: PRT
<213> ORGANISM: Homo sapiens

<400> SEQUENCE: 11

Asp Gly Val His
1

<210> SEQ ID NO 12
<211> LENGTH: 113
<212> TYPE: PRT
<213> ORGANISM: Homo sapiens

<400> SEQUENCE: 12

Glu Val Gln Leu Val Glu Ser Gly Gly Gly Leu Val Gln Pro Gly Gly
1               5                   10                  15

Ser Leu Arg Leu Ser Cys Ala Ala Ser Gly Phe Ser Phe Ser Ser Tyr
            20                  25                  30

Ala Met Ser Trp Val Arg Gln Ala Pro Gly Lys Gly Leu Glu Trp Val
        35                  40                  45

Ser Ser Ile Gly Asp Asn Asn Ser Thr Asp Tyr Ala Asp Ser Val
    50                  55                  60

Lys Gly Arg Phe Thr Ile Ser Arg Asp Asn Ser Lys Ser Thr Leu Tyr
65                  70                  75                  80

Leu Gln Met Asn Ser Leu Arg Ala Glu Asp Thr Ala Val Tyr Tyr Cys
                85                  90                  95

Val Lys Asp Gly Val His Trp Gly Gln Gly Thr Leu Val Thr Val Ser
                100                 105                 110

Ser

<210> SEQ ID NO 13
<211> LENGTH: 5
<212> TYPE: PRT
<213> ORGANISM: Homo sapiens

<400> SEQUENCE: 13

Ser Tyr Ala Met Ser
1               5
```

```
<210> SEQ ID NO 14
<211> LENGTH: 14
<212> TYPE: PRT
<213> ORGANISM: Homo sapiens

<400> SEQUENCE: 14

Ile Gly Asp Gly Thr Thr Tyr Tyr Ala Asp Ser Val Lys Gly
1               5                   10

<210> SEQ ID NO 15
<211> LENGTH: 4
<212> TYPE: PRT
<213> ORGANISM: Homo sapiens

<400> SEQUENCE: 15

Asp Gly Val His
1

<210> SEQ ID NO 16
<211> LENGTH: 111
<212> TYPE: PRT
<213> ORGANISM: Homo sapiens

<400> SEQUENCE: 16

Glu Val Gln Leu Val Glu Ser Gly Gly Gly Leu Val Gln Pro Gly Gly
1               5                   10                  15

Ser Leu Arg Leu Ser Cys Ala Ala Ser Gly Phe Thr Phe Ser Ser Tyr
            20                  25                  30

Ala Met Ser Trp Val Arg Gln Ala Pro Gly Lys Gly Leu Glu Trp Val
        35                  40                  45

Ser Ser Ile Gly Asp Gly Thr Thr Tyr Tyr Ala Asp Ser Val Lys Gly
    50                  55                  60

Arg Phe Thr Ile Ser Arg Asp Asn Ser Lys Ser Thr Leu Tyr Leu Gln
65              70                  75                  80

Met Asn Ser Leu Arg Ala Glu Asp Thr Ala Val Tyr Tyr Cys Ala Lys
            85                  90                  95

Asp Gly Val His Trp Gly Gln Gly Thr Leu Val Thr Val Ser Ser
            100                 105                 110

<210> SEQ ID NO 17
<211> LENGTH: 5
<212> TYPE: PRT
<213> ORGANISM: Homo sapiens

<400> SEQUENCE: 17

Thr Tyr Ala Met Ser
1               5

<210> SEQ ID NO 18
<211> LENGTH: 17
<212> TYPE: PRT
<213> ORGANISM: Homo sapiens

<400> SEQUENCE: 18

Ser Ile Gly Glu Asn Asp Arg Thr Thr Tyr Tyr Val Asp Ser Val Lys
1               5                   10                  15

Gly

<210> SEQ ID NO 19
<211> LENGTH: 4
<212> TYPE: PRT
```

```
<213> ORGANISM: Homo sapiens

<400> SEQUENCE: 19

Asp Gly Val His
1

<210> SEQ ID NO 20
<211> LENGTH: 113
<212> TYPE: PRT
<213> ORGANISM: Homo sapiens

<400> SEQUENCE: 20

Glu Val Gln Leu Val Glu Ser Gly Gly Gly Leu Val Gln Pro Gly Gly
1               5                   10                  15

Ser Leu Arg Leu Ser Cys Ala Ala Ser Gly Phe Thr Phe Ser Thr Tyr
            20                  25                  30

Ala Met Ser Trp Val Arg Gln Ala Pro Gly Lys Gly Leu Glu Trp Val
        35                  40                  45

Ser Ser Ile Gly Glu Asn Asp Arg Thr Thr Tyr Tyr Val Asp Ser Val
    50                  55                  60

Lys Gly Arg Phe Thr Ile Ser Arg Asp Asn Ser Lys Ser Thr Leu Tyr
65                  70                  75                  80

Leu Gln Met Asn Ser Leu Arg Ala Glu Asp Thr Ala Val Tyr Tyr Cys
                85                  90                  95

Ala Lys Asp Gly Val His Trp Gly Gln Gly Thr Leu Val Thr Val Ser
            100                 105                 110

Ser

<210> SEQ ID NO 21
<211> LENGTH: 5
<212> TYPE: PRT
<213> ORGANISM: Homo sapiens

<400> SEQUENCE: 21

Ser Tyr Ala Met Ser
1               5

<210> SEQ ID NO 22
<211> LENGTH: 17
<212> TYPE: PRT
<213> ORGANISM: Homo sapiens

<400> SEQUENCE: 22

Ser Ile Gly Asp Asn Asn Arg Thr Thr Tyr Tyr Ala Asp Ser Val Lys
1               5                   10                  15

Gly

<210> SEQ ID NO 23
<211> LENGTH: 4
<212> TYPE: PRT
<213> ORGANISM: Homo sapiens

<400> SEQUENCE: 23

Asp Gly Val His
1

<210> SEQ ID NO 24
<211> LENGTH: 113
<212> TYPE: PRT
<213> ORGANISM: Homo sapiens
```

```
<400> SEQUENCE: 24

Gln Val Gln Leu Val Glu Ser Gly Gly Gly Leu Val Gln Pro Gly Gly
1               5                   10                  15

Ser Leu Arg Leu Ser Cys Ala Ala Ser Gly Phe Thr Phe Ser Ser Tyr
            20                  25                  30

Ala Met Ser Trp Val Arg Gln Ala Pro Gly Lys Gly Leu Glu Trp Val
        35                  40                  45

Ser Ser Ile Gly Asp Asn Asn Arg Thr Thr Tyr Tyr Ala Asp Ser Val
    50                  55                  60

Lys Gly Arg Phe Thr Ile Ser Arg Asp Asn Ser Lys Ser Thr Leu Tyr
65                  70                  75                  80

Leu Gln Met Asn Ser Leu Arg Ala Glu Asp Thr Ala Val Tyr Tyr Cys
                85                  90                  95

Ala Lys Asp Gly Val His Trp Gly Gln Gly Thr Leu Val Thr Val Ser
            100                 105                 110

Ser

<210> SEQ ID NO 25
<211> LENGTH: 5
<212> TYPE: PRT
<213> ORGANISM: Homo sapiens

<400> SEQUENCE: 25

Ser Tyr Ala Met Ser
1               5

<210> SEQ ID NO 26
<211> LENGTH: 15
<212> TYPE: PRT
<213> ORGANISM: Homo sapiens

<400> SEQUENCE: 26

Ser Ile Gly Asp Gly Thr Thr Tyr Tyr Ala Asp Ser Val Lys Gly
1               5                   10                  15

<210> SEQ ID NO 27
<211> LENGTH: 4
<212> TYPE: PRT
<213> ORGANISM: Homo sapiens

<400> SEQUENCE: 27

Asp Gly Val His
1

<210> SEQ ID NO 28
<211> LENGTH: 111
<212> TYPE: PRT
<213> ORGANISM: Homo sapiens

<400> SEQUENCE: 28

Glu Val Gln Leu Val Glu Ser Gly Gly Gly Leu Val Gln Pro Gly Gly
1               5                   10                  15

Ser Leu Arg Leu Ser Cys Ala Ala Ser Gly Phe Thr Phe Ser Ser Tyr
            20                  25                  30

Ala Met Ser Trp Val Arg Gln Ala Pro Gly Lys Gly Leu Glu Trp Val
        35                  40                  45

Ser Ser Ile Gly Asp Gly Thr Thr Tyr Tyr Ala Asp Ser Val Lys Gly
    50                  55                  60

Arg Phe Thr Ile Ser Arg Asp Asn Ser Lys Ser Thr Leu Tyr Leu Gln
```

```
                65                  70                  75                  80
Met Asn Ser Leu Arg Ala Glu Asp Thr Ala Val Tyr Tyr Cys Ala Lys
                    85                  90                  95

Asp Gly Val His Trp Gly Gln Gly Thr Leu Val Thr Val Ser Ser
                100                 105                 110

<210> SEQ ID NO 29
<211> LENGTH: 5
<212> TYPE: PRT
<213> ORGANISM: Homo sapiens

<400> SEQUENCE: 29

Ser Tyr Ala Met Ser
1               5

<210> SEQ ID NO 30
<211> LENGTH: 17
<212> TYPE: PRT
<213> ORGANISM: Homo sapiens

<400> SEQUENCE: 30

Ser Ile Gly Glu Asn Asp Gly Thr Thr Asp Tyr Ala Asp Ser Val Lys
1               5                   10                  15

Gly

<210> SEQ ID NO 31
<211> LENGTH: 4
<212> TYPE: PRT
<213> ORGANISM: Homo sapiens

<400> SEQUENCE: 31

Asp Gly Val His
1

<210> SEQ ID NO 32
<211> LENGTH: 113
<212> TYPE: PRT
<213> ORGANISM: Homo sapiens

<400> SEQUENCE: 32

Glu Val Gln Leu Leu Glu Ser Gly Gly Gly Leu Val Gln Pro Gly Gly
1               5                   10                  15

Ser Leu Arg Leu Ser Cys Ala Ala Ser Gly Phe Ser Phe Ser Ser Tyr
                20                  25                  30

Ala Met Ser Trp Val Arg Gln Ala Pro Gly Lys Gly Leu Glu Trp Val
            35                  40                  45

Ser Ser Ile Gly Glu Asn Asp Gly Thr Thr Asp Tyr Ala Asp Ser Val
        50                  55                  60

Lys Gly Arg Phe Thr Ile Ser Arg Asp Asn Ser Lys Asn Thr Leu Tyr
65                  70                  75                  80

Leu Gln Met Asn Ser Leu Arg Val Glu Asp Thr Ala Val Tyr Tyr Cys
                85                  90                  95

Val Lys Asp Gly Val His Trp Gly Gln Gly Thr Leu Val Thr Val Ser
                100                 105                 110

Ser

<210> SEQ ID NO 33
<211> LENGTH: 5
<212> TYPE: PRT
<213> ORGANISM: Homo sapiens
```

<400> SEQUENCE: 33

Ser Tyr Ala Leu Ser
1               5

<210> SEQ ID NO 34
<211> LENGTH: 17
<212> TYPE: PRT
<213> ORGANISM: Homo sapiens

<400> SEQUENCE: 34

Ser Ile Gly Glu Asn Asp Gly Thr Thr Asp Tyr Ala Asp Ser Val Lys
1               5                   10                  15

Gly

<210> SEQ ID NO 35
<211> LENGTH: 4
<212> TYPE: PRT
<213> ORGANISM: Homo sapiens

<400> SEQUENCE: 35

Asp Gly Val His
1

<210> SEQ ID NO 36
<211> LENGTH: 113
<212> TYPE: PRT
<213> ORGANISM: Homo sapiens

<400> SEQUENCE: 36

Glu Val Gln Leu Leu Glu Ser Gly Gly Gly Leu Val Gln Pro Gly Gly
1               5                   10                  15

Ser Leu Arg Leu Ser Cys Ala Ala Ser Gly Phe Ser Phe Ser Ser Tyr
            20                  25                  30

Ala Leu Ser Trp Val Arg Gln Ala Pro Gly Lys Gly Leu Glu Trp Val
        35                  40                  45

Ser Ser Ile Gly Glu Asn Asp Gly Thr Thr Asp Tyr Ala Asp Ser Val
    50                  55                  60

Lys Gly Arg Phe Thr Ile Ser Arg Asp Asn Ser Lys Asn Thr Leu Tyr
65                  70                  75                  80

Leu Gln Met Asn Ser Leu Arg Val Glu Asp Thr Ala Val Tyr Tyr Cys
                85                  90                  95

Val Lys Asp Gly Val His Trp Gly Gln Gly Thr Leu Val Thr Val Ser
            100                 105                 110

Ser

<210> SEQ ID NO 37
<211> LENGTH: 5
<212> TYPE: PRT
<213> ORGANISM: Homo sapiens

<400> SEQUENCE: 37

Ser Tyr Ala Leu Ser
1               5

<210> SEQ ID NO 38
<211> LENGTH: 17
<212> TYPE: PRT
<213> ORGANISM: Homo sapiens

<400> SEQUENCE: 38

```
Ser Ile Gly Glu Asn Asn Ala Thr Thr Asp Tyr Ala Asp Phe Val Lys
1               5                   10                  15
Gly

<210> SEQ ID NO 39
<211> LENGTH: 4
<212> TYPE: PRT
<213> ORGANISM: Homo sapiens

<400> SEQUENCE: 39

Asp Gly Val His
1

<210> SEQ ID NO 40
<211> LENGTH: 113
<212> TYPE: PRT
<213> ORGANISM: Homo sapiens

<400> SEQUENCE: 40

Glu Val Gln Leu Leu Glu Ser Gly Gly Gly Leu Val Gln Pro Gly Gly
1               5                   10                  15

Ser Leu Arg Leu Ser Cys Ala Ala Ser Gly Phe Ser Phe Ser Ser Tyr
            20                  25                  30

Ala Leu Ser Trp Val Arg Gln Ala Pro Gly Lys Gly Leu Glu Trp Val
        35                  40                  45

Ser Ser Ile Gly Glu Asn Asn Ala Thr Thr Asp Tyr Ala Asp Phe Val
    50                  55                  60

Lys Gly Arg Phe Thr Ile Ser Arg Asp Asn Lys Asn Thr Leu Tyr
65                  70                  75                  80

Leu Gln Met Asn Ser Leu Arg Val Glu Asp Thr Ala Val Tyr Tyr Cys
                85                  90                  95

Val Lys Asp Gly Val His Trp Gly Gln Gly Thr Leu Val Thr Val Ser
            100                 105                 110

Ser

<210> SEQ ID NO 41
<211> LENGTH: 5
<212> TYPE: PRT
<213> ORGANISM: Homo sapiens

<400> SEQUENCE: 41

Ser Tyr Ala Leu Ser
1               5

<210> SEQ ID NO 42
<211> LENGTH: 17
<212> TYPE: PRT
<213> ORGANISM: Homo sapiens

<400> SEQUENCE: 42

Ser Ile Gly Glu Asn Asn Asp Thr Thr Asp Tyr Ala Asp Asn Val Lys
1               5                   10                  15

Gly

<210> SEQ ID NO 43
<211> LENGTH: 4
<212> TYPE: PRT
<213> ORGANISM: Homo sapiens

<400> SEQUENCE: 43
```

Asp Gly Val His
1

<210> SEQ ID NO 44
<211> LENGTH: 113
<212> TYPE: PRT
<213> ORGANISM: Homo sapiens

<400> SEQUENCE: 44

Glu Val Gln Leu Leu Glu Ser Gly Gly Gly Leu Val Gln Pro Gly Gly
1               5                   10                  15

Ser Leu Arg Leu Ser Cys Ala Ala Ser Gly Phe Ser Phe Ser Ser Tyr
            20                  25                  30

Ala Leu Ser Trp Val Arg Gln Ala Pro Gly Lys Gly Leu Glu Trp Val
        35                  40                  45

Ser Ser Ile Gly Glu Asn Asn Asp Thr Thr Asp Tyr Ala Asp Asn Val
    50                  55                  60

Lys Gly Arg Phe Thr Ile Ser Arg Asp Asn Ser Lys Asn Thr Leu Tyr
65                  70                  75                  80

Leu Gln Met Asn Ser Leu Arg Val Glu Asp Thr Ala Val Tyr Tyr Cys
                85                  90                  95

Val Lys Asp Gly Val His Trp Gly Gln Gly Thr Leu Val Thr Val Ser
            100                 105                 110

Ser

<210> SEQ ID NO 45
<211> LENGTH: 5
<212> TYPE: PRT
<213> ORGANISM: Homo sapiens

<400> SEQUENCE: 45

Ser Tyr Ala Leu Ser
1               5

<210> SEQ ID NO 46
<211> LENGTH: 17
<212> TYPE: PRT
<213> ORGANISM: Homo sapiens

<400> SEQUENCE: 46

Ser Ile Gly Glu Asn Asn Ala Thr Thr Asp Tyr Ala Asp Ala Val Lys
1               5                   10                  15

Gly

<210> SEQ ID NO 47
<211> LENGTH: 4
<212> TYPE: PRT
<213> ORGANISM: Homo sapiens

<400> SEQUENCE: 47

Asp Gly Val His
1

<210> SEQ ID NO 48
<211> LENGTH: 113
<212> TYPE: PRT
<213> ORGANISM: Homo sapiens

<400> SEQUENCE: 48

Glu Val Gln Leu Leu Glu Ser Gly Gly Gly Leu Val Gln Pro Gly Gly

```
                1               5                   10                  15
Ser Leu Arg Leu Ser Cys Ala Ala Ser Gly Phe Ser Phe Ser Ser Tyr
                20                  25                  30

Ala Leu Ser Trp Val Arg Gln Ala Pro Gly Lys Gly Leu Glu Trp Val
                35                  40                  45

Ser Ser Ile Gly Glu Asn Asn Ala Thr Thr Asp Tyr Ala Asp Ala Val
                50                  55                  60

Lys Gly Arg Phe Thr Ile Ser Arg Asp Asn Ser Lys Asn Thr Leu Tyr
 65                  70                  75                  80

Leu Gln Met Asn Ser Leu Arg Val Glu Asp Thr Ala Val Tyr Tyr Cys
                85                  90                  95

Val Lys Asp Gly Val His Trp Gly Gln Gly Thr Leu Val Thr Val Ser
                100                 105                 110

Ser
```

<210> SEQ ID NO 49
<211> LENGTH: 5
<212> TYPE: PRT
<213> ORGANISM: Homo sapiens

<400> SEQUENCE: 49

```
Ser Tyr Ala Leu Ser
 1               5
```

<210> SEQ ID NO 50
<211> LENGTH: 17
<212> TYPE: PRT
<213> ORGANISM: Homo sapiens

<400> SEQUENCE: 50

```
Ser Ile Gly Glu Asn Asn His Thr Thr Asp Tyr Ala Ala Asp Val Lys
 1               5                   10                  15

Gly
```

<210> SEQ ID NO 51
<211> LENGTH: 4
<212> TYPE: PRT
<213> ORGANISM: Homo sapiens

<400> SEQUENCE: 51

```
Asp Gly Val His
 1
```

<210> SEQ ID NO 52
<211> LENGTH: 113
<212> TYPE: PRT
<213> ORGANISM: Homo sapiens

<400> SEQUENCE: 52

```
Glu Val Gln Leu Leu Glu Ser Gly Gly Gly Leu Val Gln Pro Gly Gly
 1               5                   10                  15

Ser Leu Arg Leu Ser Cys Ala Ala Ser Gly Phe Ser Phe Ser Ser Tyr
                20                  25                  30

Ala Leu Ser Trp Val Arg Gln Ala Pro Gly Lys Gly Leu Glu Trp Val
                35                  40                  45

Ser Ser Ile Gly Glu Asn Asn His Thr Thr Asp Tyr Ala Ala Asp Val
                50                  55                  60

Lys Gly Arg Phe Thr Ile Ser Arg Asp Asn Ser Lys Asn Thr Leu Tyr
 65                  70                  75                  80
```

```
Leu Gln Met Asn Ser Leu Arg Val Glu Asp Thr Ala Val Tyr Tyr Cys
                85                  90                  95

Val Lys Asp Gly Val His Trp Gly Gln Gly Thr Leu Val Thr Val Ser
            100                 105                 110

Ser

<210> SEQ ID NO 53
<211> LENGTH: 5
<212> TYPE: PRT
<213> ORGANISM: Homo sapiens

<400> SEQUENCE: 53

Ser Tyr Ala Leu Ser
1               5

<210> SEQ ID NO 54
<211> LENGTH: 17
<212> TYPE: PRT
<213> ORGANISM: Homo sapiens

<400> SEQUENCE: 54

Ser Ile Gly Glu Asn Asn Ala Thr Thr Asp Tyr Ala Asp Val Val Lys
1               5                   10                  15

Gly

<210> SEQ ID NO 55
<211> LENGTH: 4
<212> TYPE: PRT
<213> ORGANISM: Homo sapiens

<400> SEQUENCE: 55

Asp Gly Val His
1

<210> SEQ ID NO 56
<211> LENGTH: 113
<212> TYPE: PRT
<213> ORGANISM: Homo sapiens

<400> SEQUENCE: 56

Glu Val Gln Leu Leu Glu Ser Gly Gly Gly Leu Val Gln Pro Gly Gly
1               5                   10                  15

Ser Leu Arg Leu Ser Cys Ala Ala Ser Gly Phe Ser Phe Ser Ser Tyr
            20                  25                  30

Ala Leu Ser Trp Val Arg Gln Ala Pro Gly Lys Gly Leu Glu Trp Val
        35                  40                  45

Ser Ser Ile Gly Glu Asn Asn Ala Thr Thr Asp Tyr Ala Asp Val Val
    50                  55                  60

Lys Gly Arg Phe Thr Ile Ser Arg Asp Asn Ser Lys Asn Thr Leu Tyr
65                  70                  75                  80

Leu Gln Met Asn Ser Leu Arg Val Glu Asp Thr Ala Val Tyr Tyr Cys
                85                  90                  95

Val Lys Asp Gly Val His Trp Gly Gln Gly Thr Leu Val Thr Val Ser
            100                 105                 110

Ser

<210> SEQ ID NO 57
<211> LENGTH: 5
<212> TYPE: PRT
```

```
<213> ORGANISM: Homo sapiens

<400> SEQUENCE: 57

Ser Tyr Ala Leu Ser
1               5

<210> SEQ ID NO 58
<211> LENGTH: 17
<212> TYPE: PRT
<213> ORGANISM: Homo sapiens

<400> SEQUENCE: 58

Ser Ile Gly Glu Asn Asn His Thr Thr Asp Tyr Ala Ala Phe Val Lys
1               5                   10                  15

Gly

<210> SEQ ID NO 59
<211> LENGTH: 4
<212> TYPE: PRT
<213> ORGANISM: Homo sapiens

<400> SEQUENCE: 59

Asp Gly Val His
1

<210> SEQ ID NO 60
<211> LENGTH: 113
<212> TYPE: PRT
<213> ORGANISM: Homo sapiens

<400> SEQUENCE: 60

Glu Val Gln Leu Leu Glu Ser Gly Gly Gly Leu Val Gln Pro Gly Gly
1               5                   10                  15

Ser Leu Arg Leu Ser Cys Ala Ala Ser Gly Phe Ser Phe Ser Ser Tyr
            20                  25                  30

Ala Leu Ser Trp Val Arg Gln Ala Pro Gly Lys Gly Leu Glu Trp Val
        35                  40                  45

Ser Ser Ile Gly Glu Asn Asn His Thr Thr Asp Tyr Ala Ala Phe Val
    50                  55                  60

Lys Gly Arg Phe Thr Ile Ser Arg Asp Asn Ser Lys Asn Thr Leu Tyr
65                  70                  75                  80

Leu Gln Met Asn Ser Leu Arg Val Glu Asp Thr Ala Val Tyr Tyr Cys
                85                  90                  95

Val Lys Asp Gly Val His Trp Gly Gln Gly Thr Leu Val Thr Val Ser
            100                 105                 110

Ser

<210> SEQ ID NO 61
<211> LENGTH: 5
<212> TYPE: PRT
<213> ORGANISM: Homo sapiens

<400> SEQUENCE: 61

Ser Tyr Ala Leu Ser
1               5

<210> SEQ ID NO 62
<211> LENGTH: 17
<212> TYPE: PRT
<213> ORGANISM: Homo sapiens
```

<400> SEQUENCE: 62

Ser Ile Gly Glu Asn Asn His Thr Thr Asp Tyr Ala Asp Thr Val Lys
1               5                   10                  15

Gly

<210> SEQ ID NO 63
<211> LENGTH: 4
<212> TYPE: PRT
<213> ORGANISM: Homo sapiens

<400> SEQUENCE: 63

Asp Gly Val His
1

<210> SEQ ID NO 64
<211> LENGTH: 113
<212> TYPE: PRT
<213> ORGANISM: Homo sapiens

<400> SEQUENCE: 64

Glu Val Gln Leu Leu Glu Ser Gly Gly Gly Leu Val Gln Pro Gly Gly
1               5                   10                  15

Ser Leu Arg Leu Ser Cys Ala Ala Ser Gly Phe Ser Phe Ser Ser Tyr
            20                  25                  30

Ala Leu Ser Trp Val Arg Gln Ala Pro Gly Lys Gly Leu Glu Trp Val
        35                  40                  45

Ser Ser Ile Gly Glu Asn Asn His Thr Thr Asp Tyr Ala Asp Thr Val
    50                  55                  60

Lys Gly Arg Phe Thr Ile Ser Arg Asp Asn Ser Lys Asn Thr Leu Tyr
65                  70                  75                  80

Leu Gln Met Asn Ser Leu Arg Val Glu Asp Thr Ala Val Tyr Tyr Cys
                85                  90                  95

Val Lys Asp Gly Val His Trp Gly Gln Gly Thr Leu Val Thr Val Ser
            100                 105                 110

Ser

<210> SEQ ID NO 65
<211> LENGTH: 5
<212> TYPE: PRT
<213> ORGANISM: Homo sapiens

<400> SEQUENCE: 65

Ser Tyr Ala Leu Ser
1               5

<210> SEQ ID NO 66
<211> LENGTH: 17
<212> TYPE: PRT
<213> ORGANISM: Homo sapiens

<400> SEQUENCE: 66

Ser Ile Gly Glu Asn Asn Asp Thr Thr Asp Tyr Ala Asp Ala Val Lys
1               5                   10                  15

Gly

<210> SEQ ID NO 67
<211> LENGTH: 4
<212> TYPE: PRT
<213> ORGANISM: Homo sapiens

```
<400> SEQUENCE: 67

Asp Gly Val His
1

<210> SEQ ID NO 68
<211> LENGTH: 113
<212> TYPE: PRT
<213> ORGANISM: Homo sapiens

<400> SEQUENCE: 68

Glu Val Gln Leu Leu Glu Ser Gly Gly Gly Leu Val Gln Pro Gly Gly
1               5                   10                  15

Ser Leu Arg Leu Ser Cys Ala Ala Ser Gly Phe Ser Phe Ser Ser Tyr
            20                  25                  30

Ala Leu Ser Trp Val Arg Gln Ala Pro Gly Lys Gly Leu Glu Trp Val
        35                  40                  45

Ser Ser Ile Gly Glu Asn Asn Asp Thr Thr Asp Tyr Ala Asp Ala Val
    50                  55                  60

Lys Gly Arg Phe Thr Ile Ser Arg Asp Asn Ser Lys Asn Thr Leu Tyr
65                  70                  75                  80

Leu Gln Met Asn Ser Leu Arg Val Glu Asp Thr Ala Val Tyr Tyr Cys
                85                  90                  95

Val Lys Asp Gly Val His Trp Gly Gln Gly Thr Leu Val Thr Val Ser
            100                 105                 110

Ser

<210> SEQ ID NO 69
<211> LENGTH: 5
<212> TYPE: PRT
<213> ORGANISM: Homo sapiens

<400> SEQUENCE: 69

Ser Tyr Ala Leu Ser
1               5

<210> SEQ ID NO 70
<211> LENGTH: 17
<212> TYPE: PRT
<213> ORGANISM: Homo sapiens

<400> SEQUENCE: 70

Ser Ile Gly Glu Asn Asn Ala Thr Thr Asp Tyr Ala Ala Ser Val Lys
1               5                   10                  15

Gly

<210> SEQ ID NO 71
<211> LENGTH: 4
<212> TYPE: PRT
<213> ORGANISM: Homo sapiens

<400> SEQUENCE: 71

Asp Gly Val His
1

<210> SEQ ID NO 72
<211> LENGTH: 113
<212> TYPE: PRT
<213> ORGANISM: Homo sapiens

<400> SEQUENCE: 72
```

```
Glu Val Gln Leu Leu Glu Ser Gly Gly Gly Leu Val Gln Pro Gly Gly
1               5                   10                  15

Ser Leu Arg Leu Ser Cys Ala Ala Ser Gly Phe Ser Phe Ser Ser Tyr
            20                  25                  30

Ala Leu Ser Trp Val Arg Gln Ala Pro Gly Lys Gly Leu Glu Trp Val
        35                  40                  45

Ser Ser Ile Gly Glu Asn Asn Ala Thr Thr Asp Tyr Ala Ala Ser Val
    50                  55                  60

Lys Gly Arg Phe Thr Ile Ser Arg Asp Asn Ser Lys Asn Thr Leu Tyr
65                  70                  75                  80

Leu Gln Met Asn Ser Leu Arg Val Glu Asp Thr Ala Val Tyr Tyr Cys
                85                  90                  95

Val Lys Asp Gly Val His Trp Gly Gln Gly Thr Leu Val Thr Val Ser
            100                 105                 110

Ser
```

<210> SEQ ID NO 73
<211> LENGTH: 5
<212> TYPE: PRT
<213> ORGANISM: Homo sapiens

<400> SEQUENCE: 73

```
Ser Tyr Ala Leu Ser
1               5
```

<210> SEQ ID NO 74
<211> LENGTH: 17
<212> TYPE: PRT
<213> ORGANISM: Homo sapiens

<400> SEQUENCE: 74

```
Ser Ile Gly Glu Asn Asn Asp Thr Thr Asp Tyr Ala Ala Tyr Val Lys
1               5                   10                  15

Gly
```

<210> SEQ ID NO 75
<211> LENGTH: 4
<212> TYPE: PRT
<213> ORGANISM: Homo sapiens

<400> SEQUENCE: 75

```
Asp Gly Val His
1
```

<210> SEQ ID NO 76
<211> LENGTH: 113
<212> TYPE: PRT
<213> ORGANISM: Homo sapiens

<400> SEQUENCE: 76

```
Glu Val Gln Leu Leu Glu Ser Gly Gly Gly Leu Val Gln Pro Gly Gly
1               5                   10                  15

Ser Leu Arg Leu Ser Cys Ala Ala Ser Gly Phe Ser Phe Ser Ser Tyr
            20                  25                  30

Ala Leu Ser Trp Val Arg Gln Ala Pro Gly Lys Gly Leu Glu Trp Val
        35                  40                  45

Ser Ser Ile Gly Glu Asn Asn Asp Thr Thr Asp Tyr Ala Ala Tyr Val
    50                  55                  60

Lys Gly Arg Phe Thr Ile Ser Arg Asp Asn Ser Lys Asn Thr Leu Tyr
```

```
                65                  70                  75                  80
Leu Gln Met Asn Ser Leu Arg Val Glu Asp Thr Ala Val Tyr Tyr Cys
                    85                  90                  95

Val Lys Asp Gly Val His Trp Gly Gln Gly Thr Leu Val Thr Val Ser
                100                 105                 110

Ser

<210> SEQ ID NO 77
<211> LENGTH: 5
<212> TYPE: PRT
<213> ORGANISM: Homo sapiens

<400> SEQUENCE: 77

Ser Tyr Ala Leu Ser
1               5

<210> SEQ ID NO 78
<211> LENGTH: 17
<212> TYPE: PRT
<213> ORGANISM: Homo sapiens

<400> SEQUENCE: 78

Ser Ile Gly Glu Asn Asn His Thr Thr Asp Tyr Ala Ala Thr Val Lys
1               5                   10                  15

Gly

<210> SEQ ID NO 79
<211> LENGTH: 4
<212> TYPE: PRT
<213> ORGANISM: Homo sapiens

<400> SEQUENCE: 79

Asp Gly Val His
1

<210> SEQ ID NO 80
<211> LENGTH: 113
<212> TYPE: PRT
<213> ORGANISM: Homo sapiens

<400> SEQUENCE: 80

Glu Val Gln Leu Leu Glu Ser Gly Gly Gly Leu Val Gln Pro Gly Gly
1               5                   10                  15

Ser Leu Arg Leu Ser Cys Ala Ala Ser Gly Phe Ser Phe Ser Ser Tyr
                20                  25                  30

Ala Leu Ser Trp Val Arg Gln Ala Pro Gly Lys Gly Leu Glu Trp Val
            35                  40                  45

Ser Ser Ile Gly Glu Asn Asn His Thr Thr Asp Tyr Ala Ala Thr Val
        50                  55                  60

Lys Gly Arg Phe Thr Ile Ser Arg Asp Asn Ser Lys Asn Thr Leu Tyr
65                  70                  75                  80

Leu Gln Met Asn Ser Leu Arg Val Glu Asp Thr Ala Val Tyr Tyr Cys
                    85                  90                  95

Val Lys Asp Gly Val His Trp Gly Gln Gly Thr Leu Val Thr Val Ser
                100                 105                 110

Ser

<210> SEQ ID NO 81
<211> LENGTH: 5
```

```
<212> TYPE: PRT
<213> ORGANISM: Homo sapiens

<400> SEQUENCE: 81

Gly Tyr Gly Met His
1               5

<210> SEQ ID NO 82
<211> LENGTH: 17
<212> TYPE: PRT
<213> ORGANISM: Homo sapiens

<400> SEQUENCE: 82

Tyr Ile Ser Tyr Asp Gly Ser Asn Lys Tyr Tyr Ala Asp Ser Val Lys
1               5                   10                  15

Gly

<210> SEQ ID NO 83
<211> LENGTH: 18
<212> TYPE: PRT
<213> ORGANISM: Homo sapiens

<400> SEQUENCE: 83

Asp Pro Ala Trp Gly Leu Arg Leu Gly Glu Ser Ser Tyr Asp Phe
1               5                   10                  15

Asp Ile

<210> SEQ ID NO 84
<211> LENGTH: 127
<212> TYPE: PRT
<213> ORGANISM: Homo sapiens

<400> SEQUENCE: 84

Glu Val Gln Leu Val Glu Ser Gly Gly Gly Val Val Gln Pro Gly Arg
1               5                   10                  15

Ser Leu Arg Leu Ser Cys Ala Ala Ser Gly Phe Ser Phe Ser Gly Tyr
                20                  25                  30

Gly Met His Trp Val Arg Gln Ala Pro Gly Lys Gly Leu Glu Trp Val
            35                  40                  45

Ala Tyr Ile Ser Tyr Asp Gly Ser Asn Lys Tyr Tyr Ala Asp Ser Val
        50                  55                  60

Lys Gly Arg Phe Thr Ile Ser Arg Asp Asn Ser Lys Asn Thr Leu Tyr
65                  70                  75                  80

Leu Gln Met Asn Ser Leu Arg Ala Glu Asp Thr Ala Val Tyr Tyr Cys
                85                  90                  95

Ala Lys Asp Pro Ala Trp Gly Leu Arg Leu Gly Glu Ser Ser Tyr
            100                 105                 110

Asp Phe Asp Ile Trp Gly Gln Gly Thr Met Val Thr Val Ser Ser
        115                 120                 125

<210> SEQ ID NO 85
<211> LENGTH: 5
<212> TYPE: PRT
<213> ORGANISM: Homo sapiens

<400> SEQUENCE: 85

Gly Tyr Gly Met His
1               5

<210> SEQ ID NO 86
```

-continued

```
<211> LENGTH: 17
<212> TYPE: PRT
<213> ORGANISM: Homo sapiens

<400> SEQUENCE: 86

Tyr Ile Ser Tyr Asp Gly Ser Asn Lys Tyr Tyr Ala Asp Ser Val Lys
1               5                   10                  15
Gly

<210> SEQ ID NO 87
<211> LENGTH: 18
<212> TYPE: PRT
<213> ORGANISM: Homo sapiens

<400> SEQUENCE: 87

Asp Pro Ala Trp Gly Leu Arg Leu Gly Glu Ser Ser Ser Tyr Asp Phe
1               5                   10                  15
Asp Ile

<210> SEQ ID NO 88
<211> LENGTH: 127
<212> TYPE: PRT
<213> ORGANISM: Homo sapiens

<400> SEQUENCE: 88

Glu Val Gln Leu Val Glu Ser Gly Gly Val Val Gln Pro Gly Arg
1               5                   10                  15

Ser Leu Arg Leu Ser Cys Ala Ala Ser Gly Phe Ser Phe Ser Gly Tyr
                20                  25                  30

Gly Met His Trp Val Arg Gln Ala Pro Gly Lys Gly Leu Glu Trp Val
            35                  40                  45

Ala Tyr Ile Ser Tyr Asp Gly Ser Asn Lys Tyr Tyr Ala Asp Ser Val
        50                  55                  60

Lys Gly Arg Phe Thr Ile Ser Arg Asp Asn Ser Lys Asn Thr Leu Tyr
65                  70                  75                  80

Leu Gln Met Asn Ser Leu Arg Ala Glu Asp Thr Ala Val Tyr Tyr Cys
                85                  90                  95

Ala Lys Asp Pro Ala Trp Gly Leu Arg Leu Gly Glu Ser Ser Ser Tyr
            100                 105                 110

Asp Phe Asp Ile Trp Gly Gln Gly Thr Met Val Thr Val Ser Ser
        115                 120                 125

<210> SEQ ID NO 89
<211> LENGTH: 5
<212> TYPE: PRT
<213> ORGANISM: Homo sapiens

<400> SEQUENCE: 89

Gly Tyr Gly Met His
1               5

<210> SEQ ID NO 90
<211> LENGTH: 17
<212> TYPE: PRT
<213> ORGANISM: Homo sapiens

<400> SEQUENCE: 90

His Ile Ser Tyr Asp Gly Ser Asn Arg Tyr Tyr Ala Glu Ser Val Lys
1               5                   10                  15
Gly
```

```
<210> SEQ ID NO 91
<211> LENGTH: 18
<212> TYPE: PRT
<213> ORGANISM: Homo sapiens

<400> SEQUENCE: 91
```

Asp Pro Ala Trp Gly Leu Arg Leu Gly Glu Leu Ser Ser Tyr Asp Phe
1               5                   10                  15

Asp Ile

```
<210> SEQ ID NO 92
<211> LENGTH: 127
<212> TYPE: PRT
<213> ORGANISM: Homo sapiens

<400> SEQUENCE: 92
```

Glu Val Gln Leu Val Glu Ser Gly Gly Val Val Gln Pro Gly Arg
1               5                   10                  15

Ser Leu Arg Leu Ser Cys Ala Ala Ser Gly Phe Ser Phe Ser Gly Tyr
                20                  25                  30

Gly Met His Trp Val Arg Gln Ala Pro Gly Lys Gly Leu Glu Trp Val
            35                  40                  45

Ala His Ile Ser Tyr Asp Gly Ser Asn Arg Tyr Tyr Ala Glu Ser Val
        50                  55                  60

Lys Gly Arg Phe Thr Ile Ser Arg Glu Asn Ser Lys Asn Thr Leu Ser
65                  70                  75                  80

Leu Gln Met Asn Ser Leu Arg Ala Glu Asp Thr Ala Val Tyr Tyr Cys
                85                  90                  95

Ala Lys Asp Pro Ala Trp Gly Leu Arg Leu Gly Glu Leu Ser Ser Tyr
            100                 105                 110

Asp Phe Asp Ile Trp Gly Gln Gly Thr Met Val Thr Val Ser Ser
        115                 120                 125

```
<210> SEQ ID NO 93
<211> LENGTH: 5
<212> TYPE: PRT
<213> ORGANISM: Homo sapiens

<400> SEQUENCE: 93
```

Gly Tyr Gly Met His
1               5

```
<210> SEQ ID NO 94
<211> LENGTH: 17
<212> TYPE: PRT
<213> ORGANISM: Homo sapiens

<400> SEQUENCE: 94
```

Val Ile Ser Tyr Asp Gly Ser Asn Arg Tyr Tyr Ala Asp Ser Val Lys
1               5                   10                  15

Gly

```
<210> SEQ ID NO 95
<211> LENGTH: 18
<212> TYPE: PRT
<213> ORGANISM: Homo sapiens

<400> SEQUENCE: 95
```

Asp Pro Ala Trp Gly Leu Arg Leu Gly Glu Leu Ser Ser Tyr Asp Phe

<210> SEQ ID NO 96
<211> LENGTH: 127
<212> TYPE: PRT
<213> ORGANISM: Homo sapiens

<400> SEQUENCE: 96

Gln Val Thr Leu Lys Glu Ser Gly Gly Val Val Gln Pro Gly Arg
1               5                   10                  15

Ser Leu Lys Leu Ser Cys Ala Ala Ser Gly Phe Ser Phe Ser Gly Tyr
                20                  25                  30

Gly Met His Trp Val Arg Gln Ala Pro Gly Lys Gly Leu Glu Trp Val
            35                  40                  45

Ala Val Ile Ser Tyr Asp Gly Ser Asn Arg Tyr Tyr Ala Asp Ser Val
        50                  55                  60

Lys Gly Arg Phe Thr Ile Ser Arg Asp Asn Ser Lys Asn Thr Leu Ser
65                  70                  75                  80

Leu Gln Met Asn Ser Leu Arg Ala Glu Asp Thr Ala Val Tyr Tyr Cys
                85                  90                  95

Ala Arg Asp Pro Ala Trp Gly Leu Arg Leu Gly Glu Leu Ser Ser Tyr
            100                 105                 110

Asp Phe Glu Ile Trp Gly Gln Gly Thr Met Val Thr Val Ser Ser
        115                 120                 125

<210> SEQ ID NO 97
<211> LENGTH: 5
<212> TYPE: PRT
<213> ORGANISM: Homo sapiens

<400> SEQUENCE: 97

Gly Tyr Gly Met His
1               5

<210> SEQ ID NO 98
<211> LENGTH: 17
<212> TYPE: PRT
<213> ORGANISM: Homo sapiens

<400> SEQUENCE: 98

Val Ile Ser Tyr Asp Gly Ser Asn Arg Tyr Tyr Ala Asp Ser Val Lys
1               5                   10                  15

Gly

<210> SEQ ID NO 99
<211> LENGTH: 18
<212> TYPE: PRT
<213> ORGANISM: Homo sapiens

<400> SEQUENCE: 99

Asp Pro Ala Trp Gly Leu Arg Leu Gly Glu Leu Ser Ser Tyr Asp Phe
1               5                   10                  15

Glu Ile

<210> SEQ ID NO 100
<211> LENGTH: 127
<212> TYPE: PRT
<213> ORGANISM: Homo sapiens

<400> SEQUENCE: 100

Gln Val Gln Leu Val Glu Ser Gly Gly Val Val Gln Pro Gly Arg
1               5                   10                  15

Ser Leu Arg Leu Ser Cys Ala Ala Ser Gly Phe Ser Phe Ser Gly Tyr
            20                  25                  30

Gly Met His Trp Val Arg Gln Ala Pro Gly Lys Gly Leu Glu Trp Val
        35                  40                  45

Ala Val Ile Ser Tyr Asp Gly Ser Asn Arg Tyr Tyr Ala Asp Ser Val
    50                  55                  60

Lys Gly Arg Phe Thr Ile Ser Arg Asp Asn Ser Lys Asn Thr Leu Ser
65                  70                  75                  80

Leu Gln Met Asn Ser Leu Arg Ala Glu Asp Thr Ala Val Tyr Tyr Cys
                85                  90                  95

Ala Lys Asp Pro Ala Trp Gly Leu Arg Leu Gly Glu Leu Ser Ser Tyr
            100                 105                 110

Asp Phe Glu Ile Trp Gly Gln Gly Thr Met Val Thr Val Ser Ser
        115                 120                 125

<210> SEQ ID NO 101
<211> LENGTH: 5
<212> TYPE: PRT
<213> ORGANISM: Homo sapiens

<400> SEQUENCE: 101

Gly Tyr Gly Met His
1               5

<210> SEQ ID NO 102
<211> LENGTH: 17
<212> TYPE: PRT
<213> ORGANISM: Homo sapiens

<400> SEQUENCE: 102

Val Ile Ser Tyr Asp Gly Ser Asn Lys Tyr Tyr Ala Asp Ser Val Lys
1               5                   10                  15

Gly

<210> SEQ ID NO 103
<211> LENGTH: 18
<212> TYPE: PRT
<213> ORGANISM: Homo sapiens

<400> SEQUENCE: 103

Asp Pro Ala Trp Gly Leu Arg Leu Gly Glu Leu Ser Ser Tyr Lys Phe
1               5                   10                  15

Glu Ile

<210> SEQ ID NO 104
<211> LENGTH: 127
<212> TYPE: PRT
<213> ORGANISM: Homo sapiens

<400> SEQUENCE: 104

Glu Val Gln Leu Val Glu Ser Gly Gly Gly Val Val Gln Pro Gly Arg
1               5                   10                  15

Ser Leu Arg Leu Ser Cys Ala Ala Ser Gly Phe Ser Phe Ser Gly Tyr
            20                  25                  30

Gly Met His Trp Val Arg Gln Ala Pro Gly Lys Gly Leu Glu Trp Val
        35                  40                  45

```
Ala Val Ile Ser Tyr Asp Gly Ser Asn Lys Tyr Tyr Ala Asp Ser Val
    50                  55                  60
Lys Gly Arg Phe Thr Ile Ser Arg Asp Asn Ser Lys Asn Thr Leu Tyr
 65                  70                  75                  80
Leu Gln Met Asn Ser Leu Arg Ala Glu Asp Thr Ala Val Tyr Tyr Cys
                 85                  90                  95
Ala Lys Asp Pro Ala Trp Gly Leu Arg Leu Gly Glu Leu Ser Ser Tyr
            100                 105                 110
Lys Phe Glu Ile Trp Gly Gln Gly Thr Met Val Thr Val Ser Ser
            115                 120                 125
```

<210> SEQ ID NO 105
<211> LENGTH: 5
<212> TYPE: PRT
<213> ORGANISM: Homo sapiens

<400> SEQUENCE: 105

```
Gly Tyr Gly Met His
 1               5
```

<210> SEQ ID NO 106
<211> LENGTH: 17
<212> TYPE: PRT
<213> ORGANISM: Homo sapiens

<400> SEQUENCE: 106

```
Leu Ile Ser Tyr Asp Gly Ser Asn Lys Tyr Tyr Ala Asp Ser Val Lys
 1               5                  10                  15
Gly
```

<210> SEQ ID NO 107
<211> LENGTH: 18
<212> TYPE: PRT
<213> ORGANISM: Homo sapiens

<400> SEQUENCE: 107

```
Asp Pro Ala Trp Gly Leu Arg Leu Gly Glu Gln Ser Ser Tyr Ala Phe
 1               5                  10                  15
Asp Ile
```

<210> SEQ ID NO 108
<211> LENGTH: 127
<212> TYPE: PRT
<213> ORGANISM: Homo sapiens

<400> SEQUENCE: 108

```
Glu Val Gln Leu Val Glu Ser Gly Gly Gly Val Val Gln Pro Gly Arg
 1               5                  10                  15
Ser Leu Arg Leu Ser Cys Ala Ala Ser Gly Phe Ser Phe Ser Gly Tyr
             20                  25                  30
Gly Met His Trp Val Arg Gln Ala Pro Gly Lys Gly Leu Glu Trp Val
         35                  40                  45
Ala Leu Ile Ser Tyr Asp Gly Ser Asn Lys Tyr Tyr Ala Asp Ser Val
    50                  55                  60
Lys Gly Arg Phe Thr Ile Ser Arg Asp Asn Ser Lys Asn Thr Leu Tyr
 65                  70                  75                  80
Leu Gln Met Asn Ser Leu Arg Ala Glu Asp Thr Ala Val Tyr Tyr Cys
                 85                  90                  95
```

Ala Lys Asp Pro Ala Trp Gly Leu Arg Leu Gly Glu Gln Ser Ser Tyr
            100                 105                 110

Ala Phe Asp Ile Trp Gly Gln Gly Thr Met Val Thr Val Ser Ser
        115                 120                 125

<210> SEQ ID NO 109
<211> LENGTH: 5
<212> TYPE: PRT
<213> ORGANISM: Homo sapiens

<400> SEQUENCE: 109

Gly Tyr Gly Met His
1               5

<210> SEQ ID NO 110
<211> LENGTH: 17
<212> TYPE: PRT
<213> ORGANISM: Homo sapiens

<400> SEQUENCE: 110

Val Ile Ser Tyr Asp Gly Ser Asn Lys Tyr Tyr Ala Asp Ser Val Lys
1               5                   10                  15

Gly

<210> SEQ ID NO 111
<211> LENGTH: 17
<212> TYPE: PRT
<213> ORGANISM: Homo sapiens

<400> SEQUENCE: 111

Asp Pro Ala Trp Gly Leu Arg Leu Gly Glu Gln Ser Ser Tyr Ala Phe
1               5                   10                  15

Glu

<210> SEQ ID NO 112
<211> LENGTH: 127
<212> TYPE: PRT
<213> ORGANISM: Homo sapiens

<400> SEQUENCE: 112

Gln Val Gln Leu Val Glu Ser Gly Gly Val Val Gln Pro Gly Arg
1               5                   10                  15

Ser Leu Arg Leu Ser Cys Ala Ala Ser Gly Phe Ser Phe Ser Gly Tyr
            20                  25                  30

Gly Met His Trp Val Arg Gln Ala Pro Gly Lys Gly Leu Glu Trp Val
        35                  40                  45

Ser Val Ile Ser Tyr Asp Gly Ser Asn Lys Tyr Tyr Ala Asp Ser Val
    50                  55                  60

Lys Gly Arg Phe Thr Ile Ser Arg Asp Asn Ser Lys Asn Thr Leu Tyr
65                  70                  75                  80

Leu Gln Met Asn Ser Leu Arg Thr Glu Asp Thr Ala Val Tyr Tyr Cys
                85                  90                  95

Ala Lys Asp Pro Ala Trp Gly Leu Arg Leu Gly Glu Gln Ser Ser Tyr
            100                 105                 110

Ala Phe Glu Ile Trp Gly Gln Gly Thr Met Val Thr Val Ser Ser
        115                 120                 125

<210> SEQ ID NO 113
<211> LENGTH: 5
<212> TYPE: PRT

-continued

```
<213> ORGANISM: Homo sapiens

<400> SEQUENCE: 113

Gly Tyr Gly Met His
1               5

<210> SEQ ID NO 114
<211> LENGTH: 17
<212> TYPE: PRT
<213> ORGANISM: Homo sapiens

<400> SEQUENCE: 114

Val Ile Ser Tyr Asp Gly Ser Asn Lys Tyr Tyr Ala Asp Ser Val Lys
1               5                   10                  15

Gly

<210> SEQ ID NO 115
<211> LENGTH: 18
<212> TYPE: PRT
<213> ORGANISM: Homo sapiens

<400> SEQUENCE: 115

Asp Pro Ala Trp Gly Leu Arg Leu Gly Glu Gln Ser Ser Tyr Ala Phe
1               5                   10                  15

Glu Ile

<210> SEQ ID NO 116
<211> LENGTH: 127
<212> TYPE: PRT
<213> ORGANISM: Homo sapiens

<400> SEQUENCE: 116

Glu Val Gln Leu Leu Glu Ser Gly Gly Val Val Gln Pro Gly Arg
1               5                   10                  15

Ser Leu Arg Leu Ser Cys Ala Ala Ser Gly Phe Ser Phe Ser Gly Tyr
                20                  25                  30

Gly Met His Trp Val Arg Gln Ala Pro Gly Lys Gly Leu Glu Trp Val
            35                  40                  45

Ala Val Ile Ser Tyr Asp Gly Ser Asn Lys Tyr Tyr Ala Asp Ser Val
        50                  55                  60

Lys Gly Arg Phe Thr Ile Ser Arg Asp Asn Ser Lys Asn Thr Leu Tyr
65                  70                  75                  80

Leu Gln Met Asn Ser Leu Arg Val Glu Asp Thr Ala Val Tyr Tyr Cys
                85                  90                  95

Ala Lys Asp Pro Ala Trp Gly Leu Arg Leu Gly Glu Gln Ser Ser Tyr
            100                 105                 110

Ala Phe Glu Ile Arg Gly Gln Gly Thr Thr Val Thr Val Ser Ser
        115                 120                 125

<210> SEQ ID NO 117
<211> LENGTH: 5
<212> TYPE: PRT
<213> ORGANISM: Homo sapiens

<400> SEQUENCE: 117

Gly Tyr Gly Met His
1               5

<210> SEQ ID NO 118
<211> LENGTH: 17
```

<212> TYPE: PRT
<213> ORGANISM: Homo sapiens

<400> SEQUENCE: 118

Tyr Ile Ser Tyr Asp Gly Ser Asn Arg Tyr Tyr Ala Asp Ser Val Lys
1               5                   10                  15

Gly

<210> SEQ ID NO 119
<211> LENGTH: 18
<212> TYPE: PRT
<213> ORGANISM: Homo sapiens

<400> SEQUENCE: 119

Asp Pro Ala Trp Gly Leu Arg Leu Gly Glu Ser Ser Ser Tyr Asp Phe
1               5                   10                  15

Asp Ile

<210> SEQ ID NO 120
<211> LENGTH: 127
<212> TYPE: PRT
<213> ORGANISM: Homo sapiens

<400> SEQUENCE: 120

Glu Val Gln Leu Val Glu Ser Gly Gly Val Val Gln Pro Gly Arg
1               5                   10                  15

Ser Leu Arg Leu Ser Cys Ala Ala Ser Gly Phe Thr Phe Ser Gly Tyr
                20                  25                  30

Gly Met His Trp Val Arg Gln Ala Pro Gly Lys Gly Leu Glu Trp Val
            35                  40                  45

Ala Tyr Ile Ser Tyr Asp Gly Ser Asn Arg Tyr Tyr Ala Asp Ser Val
        50                  55                  60

Lys Gly Arg Phe Thr Ile Ser Arg Asp Asn Ser Lys Lys Thr Leu Ser
65                  70                  75                  80

Leu Gln Met Asn Ser Leu Arg Ala Glu Asp Thr Ala Val Tyr Tyr Cys
                85                  90                  95

Ala Lys Asp Pro Ala Trp Gly Leu Arg Leu Gly Glu Ser Ser Ser Tyr
            100                 105                 110

Asp Phe Asp Ile Trp Gly Gln Gly Thr Met Val Thr Val Ser Ser
        115                 120                 125

<210> SEQ ID NO 121
<211> LENGTH: 5
<212> TYPE: PRT
<213> ORGANISM: Homo sapiens

<400> SEQUENCE: 121

Gly Tyr Gly Leu His
1               5

<210> SEQ ID NO 122
<211> LENGTH: 17
<212> TYPE: PRT
<213> ORGANISM: Homo sapiens

<400> SEQUENCE: 122

Tyr Ile Ser Tyr Asp Glu Ser Asn Lys Tyr Tyr Ala Pro Ser Val Lys
1               5                   10                  15

Gly

<210> SEQ ID NO 123
<211> LENGTH: 18
<212> TYPE: PRT
<213> ORGANISM: Homo sapiens

<400> SEQUENCE: 123

Asp Pro Ala Trp Gly Leu Arg Leu Gly Glu Ser Ser Tyr Asp Phe
1               5                   10                  15
Asp Ile

<210> SEQ ID NO 124
<211> LENGTH: 127
<212> TYPE: PRT
<213> ORGANISM: Homo sapiens

<400> SEQUENCE: 124

Glu Val Gln Leu Val Glu Ser Gly Gly Val Val Gln Pro Gly Arg
1               5                   10                  15

Ser Leu Arg Leu Ser Cys Ala Ala Ser Gly Phe Ser Phe Ser Gly Tyr
                20                  25                  30

Gly Leu His Trp Val Arg Gln Ala Pro Gly Lys Gly Leu Glu Trp Val
            35                  40                  45

Ala Tyr Ile Ser Tyr Asp Glu Ser Asn Lys Tyr Tyr Ala Pro Ser Val
        50                  55                  60

Lys Gly Arg Phe Thr Ile Ser Arg Asp Asn Ser Lys Asn Thr Leu Tyr
65                  70                  75                  80

Leu Gln Met Asn Ser Leu Arg Ala Glu Asp Thr Ala Val Tyr Tyr Cys
                85                  90                  95

Ala Lys Asp Pro Ala Trp Gly Leu Arg Leu Gly Glu Ser Ser Tyr
            100                 105                 110

Asp Phe Asp Ile Trp Gly Gln Gly Thr Met Val Thr Val Ser Ser
        115                 120                 125

<210> SEQ ID NO 125
<211> LENGTH: 5
<212> TYPE: PRT
<213> ORGANISM: Homo sapiens

<400> SEQUENCE: 125

Gly Tyr Gly Met His
1               5

<210> SEQ ID NO 126
<211> LENGTH: 17
<212> TYPE: PRT
<213> ORGANISM: Homo sapiens

<400> SEQUENCE: 126

Tyr Ile Ser Tyr Asp Lys Ser Asn Lys Tyr Tyr Ala Asp Lys Val Lys
1               5                   10                  15
Gly

<210> SEQ ID NO 127
<211> LENGTH: 18
<212> TYPE: PRT
<213> ORGANISM: Homo sapiens

<400> SEQUENCE: 127

Asp Pro Ala Trp Gly Leu Arg Leu Gly Glu Ser Ser Tyr Asp Phe
1               5                   10                  15

Asp Ile

<210> SEQ ID NO 128
<211> LENGTH: 127
<212> TYPE: PRT
<213> ORGANISM: Homo sapiens

<400> SEQUENCE: 128

Glu Val Gln Leu Val Glu Ser Gly Gly Gly Val Val Gln Pro Gly Arg
1               5                   10                  15

Ser Leu Arg Leu Ser Cys Ala Ala Ser Gly Phe Ser Phe Ser Gly Tyr
            20                  25                  30

Gly Met His Trp Val Arg Gln Ala Pro Gly Lys Gly Leu Glu Trp Val
        35                  40                  45

Ala Tyr Ile Ser Tyr Asp Lys Ser Asn Lys Tyr Tyr Ala Asp Lys Val
    50                  55                  60

Lys Gly Arg Phe Thr Ile Ser Arg Asp Asn Ser Lys Asn Thr Leu Tyr
65                  70                  75                  80

Leu Gln Met Asn Ser Leu Arg Ala Glu Asp Thr Ala Val Tyr Tyr Cys
                85                  90                  95

Ala Lys Asp Pro Ala Trp Gly Leu Arg Leu Gly Glu Ser Ser Ser Tyr
            100                 105                 110

Asp Phe Asp Ile Trp Gly Gln Gly Thr Met Val Thr Val Ser Ser
        115                 120                 125

<210> SEQ ID NO 129
<211> LENGTH: 5
<212> TYPE: PRT
<213> ORGANISM: Homo sapiens

<400> SEQUENCE: 129

Gly Tyr Gly Leu His
1               5

<210> SEQ ID NO 130
<211> LENGTH: 17
<212> TYPE: PRT
<213> ORGANISM: Homo sapiens

<400> SEQUENCE: 130

Tyr Ile Ser Tyr Asp Ala Ser Asn Lys Tyr Tyr Ala Asp Asn Val Lys
1               5                   10                  15

Gly

<210> SEQ ID NO 131
<211> LENGTH: 18
<212> TYPE: PRT
<213> ORGANISM: Homo sapiens

<400> SEQUENCE: 131

Asp Pro Ala Trp Gly Leu Arg Leu Gly Glu Ser Ser Tyr Asp Phe
1               5                   10                  15

Asp Ile

<210> SEQ ID NO 132
<211> LENGTH: 127
<212> TYPE: PRT
<213> ORGANISM: Homo sapiens

<400> SEQUENCE: 132

Glu Val Gln Leu Val Glu Ser Gly Gly Gly Val Val Gln Pro Gly Arg
1               5                   10                  15

Ser Leu Arg Leu Ser Cys Ala Ala Ser Gly Phe Ser Phe Ser Gly Tyr
            20                  25                  30

Gly Leu His Trp Val Arg Gln Ala Pro Gly Lys Gly Leu Glu Trp Val
            35                  40                  45

Ala Tyr Ile Ser Tyr Asp Ala Ser Asn Lys Tyr Tyr Ala Asp Asn Val
50                  55                  60

Lys Gly Arg Phe Thr Ile Ser Arg Asp Asn Ser Lys Asn Thr Leu Tyr
65                  70                  75                  80

Leu Gln Met Asn Ser Leu Arg Ala Glu Asp Thr Ala Val Tyr Tyr Cys
            85                  90                  95

Ala Lys Asp Pro Ala Trp Gly Leu Arg Leu Gly Glu Ser Ser Ser Tyr
            100                 105                 110

Asp Phe Asp Ile Trp Gly Gln Gly Thr Met Val Thr Val Ser Ser
            115                 120                 125

<210> SEQ ID NO 133
<211> LENGTH: 5
<212> TYPE: PRT
<213> ORGANISM: Homo sapiens

<400> SEQUENCE: 133

Gly Tyr Gly Val His
1               5

<210> SEQ ID NO 134
<211> LENGTH: 17
<212> TYPE: PRT
<213> ORGANISM: Homo sapiens

<400> SEQUENCE: 134

Tyr Ile Ser Tyr Asp Ala Ser Asn Lys Tyr Tyr Ala Asp Asn Val Lys
1               5                   10                  15

Gly

<210> SEQ ID NO 135
<211> LENGTH: 18
<212> TYPE: PRT
<213> ORGANISM: Homo sapiens

<400> SEQUENCE: 135

Asp Pro Ala Trp Gly Leu Arg Leu Gly Glu Ser Ser Ser Tyr Asp Phe
1               5                   10                  15

Asp Ile

<210> SEQ ID NO 136
<211> LENGTH: 127
<212> TYPE: PRT
<213> ORGANISM: Homo sapiens

<400> SEQUENCE: 136

Glu Val Gln Leu Val Glu Ser Gly Gly Gly Val Val Gln Pro Gly Arg
1               5                   10                  15

Ser Leu Arg Leu Ser Cys Ala Ala Ser Gly Phe Ser Phe Ser Gly Tyr
            20                  25                  30

Gly Val His Trp Val Arg Gln Ala Pro Gly Lys Gly Leu Glu Trp Val
            35                  40                  45

```
Ala Tyr Ile Ser Tyr Asp Ala Ser Asn Lys Tyr Tyr Ala Asp Asn Val
         50                  55                  60

Lys Gly Arg Phe Thr Ile Ser Arg Asp Asn Ser Lys Asn Thr Leu Tyr
 65                  70                  75                  80

Leu Gln Met Asn Ser Leu Arg Ala Glu Asp Thr Ala Val Tyr Tyr Cys
                 85                  90                  95

Ala Lys Asp Pro Ala Trp Gly Leu Arg Leu Gly Glu Ser Ser Ser Tyr
                100                 105                 110

Asp Phe Asp Ile Trp Gly Gln Gly Thr Met Val Thr Val Ser Ser
                115                 120                 125
```

<210> SEQ ID NO 137
<211> LENGTH: 5
<212> TYPE: PRT
<213> ORGANISM: Homo sapiens

<400> SEQUENCE: 137

```
Gly Tyr Gly Leu His
 1               5
```

<210> SEQ ID NO 138
<211> LENGTH: 17
<212> TYPE: PRT
<213> ORGANISM: Homo sapiens

<400> SEQUENCE: 138

```
Tyr Ile Ser Tyr Asp Lys Ser Asn Lys Tyr Tyr Ala Asp Lys Val Lys
 1               5                  10                  15

Gly
```

<210> SEQ ID NO 139
<211> LENGTH: 18
<212> TYPE: PRT
<213> ORGANISM: Homo sapiens

<400> SEQUENCE: 139

```
Asp Pro Ala Trp Gly Leu Arg Leu Gly Glu Ser Ser Ser Tyr Asp Phe
 1               5                  10                  15

Asp Ile
```

<210> SEQ ID NO 140
<211> LENGTH: 127
<212> TYPE: PRT
<213> ORGANISM: Homo sapiens

<400> SEQUENCE: 140

```
Glu Val Gln Leu Val Glu Ser Gly Gly Val Val Gln Pro Gly Arg
 1               5                  10                  15

Ser Leu Arg Leu Ser Cys Ala Ala Ser Gly Phe Ser Phe Ser Gly Tyr
                 20                  25                  30

Gly Leu His Trp Val Arg Gln Ala Pro Gly Lys Gly Leu Glu Trp Val
             35                  40                  45

Ala Tyr Ile Ser Tyr Asp Lys Ser Asn Lys Tyr Tyr Ala Asp Lys Val
         50                  55                  60

Lys Gly Arg Phe Thr Ile Ser Arg Asp Asn Ser Lys Asn Thr Leu Tyr
 65                  70                  75                  80

Leu Gln Met Asn Ser Leu Arg Ala Glu Asp Thr Ala Val Tyr Tyr Cys
                 85                  90                  95

Ala Lys Asp Pro Ala Trp Gly Leu Arg Leu Gly Glu Ser Ser Ser Tyr
```

```
                100                 105                 110
Asp Phe Asp Ile Trp Gly Gln Gly Thr Met Val Thr Val Ser Ser
        115                 120                 125
```

<210> SEQ ID NO 141
<211> LENGTH: 5
<212> TYPE: PRT
<213> ORGANISM: Homo sapiens

<400> SEQUENCE: 141

```
Gly Tyr Gly Ala His
1               5
```

<210> SEQ ID NO 142
<211> LENGTH: 17
<212> TYPE: PRT
<213> ORGANISM: Homo sapiens

<400> SEQUENCE: 142

```
Tyr Ile Ser Tyr Asp Lys Ser Asn Lys Tyr Tyr Ala Asp Lys Val Lys
1               5                   10                  15

Gly
```

<210> SEQ ID NO 143
<211> LENGTH: 18
<212> TYPE: PRT
<213> ORGANISM: Homo sapiens

<400> SEQUENCE: 143

```
Asp Pro Ala Trp Gly Leu Arg Leu Gly Glu Ser Ser Tyr Asp Phe
1               5                   10                  15

Asp Ile
```

<210> SEQ ID NO 144
<211> LENGTH: 127
<212> TYPE: PRT
<213> ORGANISM: Homo sapiens

<400> SEQUENCE: 144

```
Glu Val Gln Leu Val Glu Ser Gly Gly Val Val Gln Pro Gly Arg
1               5                   10                  15

Ser Leu Arg Leu Ser Cys Ala Ala Ser Gly Phe Ser Phe Ser Gly Tyr
                20                  25                  30

Gly Ala His Trp Val Arg Gln Ala Pro Gly Lys Gly Leu Glu Trp Val
        35                  40                  45

Ala Tyr Ile Ser Tyr Asp Lys Ser Asn Lys Tyr Tyr Ala Asp Lys Val
    50                  55                  60

Lys Gly Arg Phe Thr Ile Ser Arg Asp Asn Ser Lys Asn Thr Leu Tyr
65                  70                  75                  80

Leu Gln Met Asn Ser Leu Arg Ala Glu Asp Thr Ala Val Tyr Tyr Cys
                85                  90                  95

Ala Lys Asp Pro Ala Trp Gly Leu Arg Leu Gly Glu Ser Ser Tyr
                100                 105                 110

Asp Phe Asp Ile Trp Gly Gln Gly Thr Met Val Thr Val Ser Ser
        115                 120                 125
```

<210> SEQ ID NO 145
<211> LENGTH: 5
<212> TYPE: PRT
<213> ORGANISM: Homo sapiens

```
<400> SEQUENCE: 145

Gly Tyr Gly Met His
1               5

<210> SEQ ID NO 146
<211> LENGTH: 17
<212> TYPE: PRT
<213> ORGANISM: Homo sapiens

<400> SEQUENCE: 146

Tyr Ile Ser Tyr Asp Ala Ser Asn Lys Tyr Tyr Ala Asp Asn Val Lys
1               5                   10                  15

Gly

<210> SEQ ID NO 147
<211> LENGTH: 18
<212> TYPE: PRT
<213> ORGANISM: Homo sapiens

<400> SEQUENCE: 147

Asp Pro Ala Trp Gly Leu Arg Leu Gly Glu Ser Ser Ser Tyr Asp Phe
1               5                   10                  15

Asp Ile

<210> SEQ ID NO 148
<211> LENGTH: 127
<212> TYPE: PRT
<213> ORGANISM: Homo sapiens

<400> SEQUENCE: 148

Glu Val Gln Leu Val Glu Ser Gly Gly Val Val Gln Pro Gly Arg
1               5                   10                  15

Ser Leu Arg Leu Ser Cys Ala Ala Ser Gly Phe Ser Phe Ser Gly Tyr
                20                  25                  30

Gly Met His Trp Val Arg Gln Ala Pro Gly Lys Gly Leu Glu Trp Val
            35                  40                  45

Ala Tyr Ile Ser Tyr Asp Ala Ser Asn Lys Tyr Tyr Ala Asp Asn Val
        50                  55                  60

Lys Gly Arg Phe Thr Ile Ser Arg Asp Asn Ser Lys Asn Thr Leu Tyr
65                  70                  75                  80

Leu Gln Met Asn Ser Leu Arg Ala Glu Asp Thr Ala Val Tyr Tyr Cys
                85                  90                  95

Ala Lys Asp Pro Ala Trp Gly Leu Arg Leu Gly Glu Ser Ser Ser Tyr
                100                 105                 110

Asp Phe Asp Ile Trp Gly Gln Gly Thr Met Val Thr Val Ser Ser
            115                 120                 125

<210> SEQ ID NO 149
<211> LENGTH: 5
<212> TYPE: PRT
<213> ORGANISM: Homo sapiens

<400> SEQUENCE: 149

Gly Tyr Gly Gln His
1               5

<210> SEQ ID NO 150
<211> LENGTH: 17
<212> TYPE: PRT
```

<213> ORGANISM: Homo sapiens

<400> SEQUENCE: 150

Tyr Ile Ser Tyr Asp Ala Ser Asn Lys Tyr Tyr Ala Asp Asn Val Lys
1               5                   10                  15
Gly

<210> SEQ ID NO 151
<211> LENGTH: 17
<212> TYPE: PRT
<213> ORGANISM: Homo sapiens

<400> SEQUENCE: 151

Asp Pro Ala Trp Gly Leu Arg Leu Gly Glu Ser Ser Tyr Asp Phe
1               5                   10                  15
Asp

<210> SEQ ID NO 152
<211> LENGTH: 127
<212> TYPE: PRT
<213> ORGANISM: Homo sapiens

<400> SEQUENCE: 152

Glu Val Gln Leu Val Glu Ser Gly Gly Val Val Gln Pro Gly Arg
1               5                   10                  15

Ser Leu Arg Leu Ser Cys Ala Ala Ser Gly Phe Ser Phe Ser Gly Tyr
            20                  25                  30

Gly Gln His Trp Val Arg Gln Ala Pro Gly Lys Gly Leu Glu Trp Val
        35                  40                  45

Ala Tyr Ile Ser Tyr Asp Ala Ser Asn Lys Tyr Tyr Ala Asp Asn Val
    50                  55                  60

Lys Gly Arg Phe Thr Ile Ser Arg Asp Asn Ser Lys Asn Thr Leu Tyr
65                  70                  75                  80

Leu Gln Met Asn Ser Leu Arg Ala Glu Asp Thr Ala Val Tyr Tyr Cys
                85                  90                  95

Ala Lys Asp Pro Ala Trp Gly Leu Arg Leu Gly Glu Ser Ser Ser Tyr
            100                 105                 110

Asp Phe Asp Ile Trp Gly Gln Gly Thr Met Val Thr Val Ser Ser
        115                 120                 125

<210> SEQ ID NO 153
<211> LENGTH: 5
<212> TYPE: PRT
<213> ORGANISM: Homo sapiens

<400> SEQUENCE: 153

Gly Tyr Gly Phe His
1               5

<210> SEQ ID NO 154
<211> LENGTH: 17
<212> TYPE: PRT
<213> ORGANISM: Homo sapiens

<400> SEQUENCE: 154

Tyr Ile Ser Tyr Asp Ala Ser Asn Lys Tyr Tyr Ala Asp Asn Val Lys
1               5                   10                  15
Gly

```
<210> SEQ ID NO 155
<211> LENGTH: 18
<212> TYPE: PRT
<213> ORGANISM: Homo sapiens

<400> SEQUENCE: 155

Asp Pro Ala Trp Gly Leu Arg Leu Gly Glu Ser Ser Tyr Asp Phe
1               5                   10                  15

Asp Ile

<210> SEQ ID NO 156
<211> LENGTH: 127
<212> TYPE: PRT
<213> ORGANISM: Homo sapiens

<400> SEQUENCE: 156

Glu Val Gln Leu Val Glu Ser Gly Gly Val Val Gln Pro Gly Arg
1               5                   10                  15

Ser Leu Arg Leu Ser Cys Ala Ala Ser Gly Phe Ser Phe Ser Gly Tyr
            20                  25                  30

Gly Phe His Trp Val Arg Gln Ala Pro Gly Lys Gly Leu Glu Trp Val
        35                  40                  45

Ala Tyr Ile Ser Tyr Asp Ala Ser Asn Lys Tyr Tyr Ala Asp Asn Val
    50                  55                  60

Lys Gly Arg Phe Thr Ile Ser Arg Asp Asn Ser Lys Asn Thr Leu Tyr
65                  70                  75                  80

Leu Gln Met Asn Ser Leu Arg Ala Glu Asp Thr Ala Val Tyr Tyr Cys
                85                  90                  95

Ala Lys Asp Pro Ala Trp Gly Leu Arg Leu Gly Glu Ser Ser Tyr
            100                 105                 110

Asp Phe Asp Ile Trp Gly Gln Gly Thr Met Val Thr Val Ser Ser
            115                 120                 125

<210> SEQ ID NO 157
<211> LENGTH: 5
<212> TYPE: PRT
<213> ORGANISM: Homo sapiens

<400> SEQUENCE: 157

Gly Tyr Gly Met His
1               5

<210> SEQ ID NO 158
<211> LENGTH: 17
<212> TYPE: PRT
<213> ORGANISM: Homo sapiens

<400> SEQUENCE: 158

Ile Ile Ser Tyr Asp Gly Ser Asn Arg Tyr Tyr Ala Asp Ser Val Lys
1               5                   10                  15

Gly

<210> SEQ ID NO 159
<211> LENGTH: 18
<212> TYPE: PRT
<213> ORGANISM: Homo sapiens

<400> SEQUENCE: 159

Asp Pro Ala Trp Gly Leu Arg Leu Gly Glu Ser Ser Tyr Asp Phe
1               5                   10                  15
```

Glu Ile

<210> SEQ ID NO 160
<211> LENGTH: 127
<212> TYPE: PRT
<213> ORGANISM: Homo sapiens

<400> SEQUENCE: 160

Glu Val Gln Leu Val Glu Ser Gly Gly Gly Val Val Gln Pro Gly Arg
1               5                   10                  15

Ser Leu Arg Leu Ser Cys Ala Ala Ser Gly Phe Ser Phe Ser Gly Tyr
            20                  25                  30

Gly Met His Trp Val Arg Gln Ala Pro Gly Lys Gly Leu Glu Trp Val
        35                  40                  45

Ala Ile Ile Ser Tyr Asp Gly Ser Asn Arg Tyr Tyr Ala Asp Ser Val
    50                  55                  60

Lys Gly Arg Phe Thr Ile Ser Arg Asp Asn Ser Lys Asn Thr Leu Ser
65                  70                  75                  80

Leu Gln Met Asn Ser Leu Arg Ala Glu Asp Thr Ala Val Tyr Tyr Cys
                85                  90                  95

Ala Lys Asp Pro Ala Trp Gly Leu Arg Leu Gly Lys Leu Ser Ser Tyr
            100                 105                 110

Asp Phe Glu Ile Trp Gly Gln Gly Thr Met Val Thr Val Ser Ser
        115                 120                 125

<210> SEQ ID NO 161
<211> LENGTH: 5
<212> TYPE: PRT
<213> ORGANISM: Homo sapiens

<400> SEQUENCE: 161

Gly Tyr Gly Met His
1               5

<210> SEQ ID NO 162
<211> LENGTH: 17
<212> TYPE: PRT
<213> ORGANISM: Homo sapiens

<400> SEQUENCE: 162

Val Ile Ser Tyr Asp Gly Ser Asn Arg Tyr Tyr Ala Asp Ser Val Lys
1               5                   10                  15

Gly

<210> SEQ ID NO 163
<211> LENGTH: 18
<212> TYPE: PRT
<213> ORGANISM: Homo sapiens

<400> SEQUENCE: 163

Asp Pro Ala Trp Gly Leu Arg Leu Gly Lys Leu Ser Ser Tyr Asp Phe
1               5                   10                  15

Glu Ile

<210> SEQ ID NO 164
<211> LENGTH: 127
<212> TYPE: PRT
<213> ORGANISM: Homo sapiens

<400> SEQUENCE: 164

```
Gln Val Gln Leu Val Glu Ser Gly Gly Gly Val Val Gln Pro Gly Arg
1               5                   10                  15

Ser Leu Lys Leu Ser Cys Ala Ala Ser Gly Phe Ser Phe Ser Gly Tyr
            20                  25                  30

Gly Met His Trp Val Arg Gln Ala Pro Gly Lys Gly Leu Glu Trp Val
        35                  40                  45

Ala Val Ile Ser Tyr Asp Gly Ser Asn Arg Tyr Tyr Ala Asp Ser Val
    50                  55                  60

Lys Gly Arg Phe Thr Ile Ser Arg Asp Asn Lys Asn Thr Leu Ser
65                  70                  75                  80

Leu Gln Met Asn Ser Leu Arg Ala Glu Asp Thr Ala Val Tyr Tyr Cys
                85                  90                  95

Ala Lys Asp Pro Ala Trp Gly Leu Arg Leu Gly Lys Leu Ser Ser Tyr
                100                 105                 110

Asp Phe Glu Ile Trp Gly Gln Gly Thr Met Val Thr Val Ser Ser
                115                 120                 125
```

<210> SEQ ID NO 165
<211> LENGTH: 5
<212> TYPE: PRT
<213> ORGANISM: Homo sapiens

<400> SEQUENCE: 165

```
Gly Tyr Gly Thr His
1               5
```

<210> SEQ ID NO 166
<211> LENGTH: 17
<212> TYPE: PRT
<213> ORGANISM: Homo sapiens

<400> SEQUENCE: 166

```
Tyr Ile Ser Tyr Asp Gly Ser Asn Lys Tyr Tyr Ala Ala Pro Val Lys
1               5                   10                  15

Gly
```

<210> SEQ ID NO 167
<211> LENGTH: 18
<212> TYPE: PRT
<213> ORGANISM: Homo sapiens

<400> SEQUENCE: 167

```
Asp Ala Ala Trp Gly Leu Arg Leu Gly Glu Ser Ser Tyr Asp Phe
1               5                   10                  15

Asp Ile
```

<210> SEQ ID NO 168
<211> LENGTH: 127
<212> TYPE: PRT
<213> ORGANISM: Homo sapiens

<400> SEQUENCE: 168

```
Glu Val Gln Leu Val Glu Ser Gly Gly Gly Val Val Gln Pro Gly Arg
1               5                   10                  15

Ser Leu Arg Leu Ser Cys Ala Ala Ser Gly Phe Ser Phe Ser Gly Tyr
            20                  25                  30

Gly Thr His Trp Val Arg Gln Ala Pro Gly Lys Gly Leu Glu Trp Val
        35                  40                  45

Ala Tyr Ile Ser Tyr Asp Gly Ser Asn Lys Tyr Tyr Ala Ala Pro Val
```

```
                 50                  55                  60
Lys Gly Arg Phe Thr Ile Ser Arg Asp Asn Ser Lys Asn Thr Leu Tyr
 65                  70                  75                  80

Leu Gln Met Asn Ser Leu Arg Ala Glu Asp Thr Ala Val Tyr Tyr Cys
                 85                  90                  95

Ala Lys Asp Ala Ala Trp Gly Leu Arg Leu Gly Glu Ser Ser Ser Tyr
                100                 105                 110

Asp Phe Asp Ile Trp Gly Gln Gly Thr Met Val Thr Val Ser Ser
            115                 120                 125
```

<210> SEQ ID NO 169
<211> LENGTH: 5
<212> TYPE: PRT
<213> ORGANISM: Homo sapiens

<400> SEQUENCE: 169

```
Gly Tyr Gly Thr His
 1               5
```

<210> SEQ ID NO 170
<211> LENGTH: 17
<212> TYPE: PRT
<213> ORGANISM: Homo sapiens

<400> SEQUENCE: 170

```
Tyr Ile Ser Tyr Asp Glu Ser Asn Lys Tyr Tyr Ala Ser Ser Val Lys
 1               5                  10                  15

Gly
```

<210> SEQ ID NO 171
<211> LENGTH: 18
<212> TYPE: PRT
<213> ORGANISM: Homo sapiens

<400> SEQUENCE: 171

```
Asp Arg Ala Trp Gly Leu Arg Leu Gly Glu Ser Ser Ser Tyr Asp Phe
 1               5                  10                  15

Asp Ile
```

<210> SEQ ID NO 172
<211> LENGTH: 127
<212> TYPE: PRT
<213> ORGANISM: Homo sapiens

<400> SEQUENCE: 172

```
Glu Val Gln Leu Val Glu Ser Gly Gly Val Val Gln Pro Gly Arg
 1               5                  10                  15

Ser Leu Arg Leu Ser Cys Ala Ala Ser Gly Phe Ser Phe Ser Gly Tyr
                 20                  25                  30

Gly Thr His Trp Val Arg Gln Ala Pro Gly Lys Gly Leu Glu Trp Val
             35                  40                  45

Ala Tyr Ile Ser Tyr Asp Glu Ser Asn Lys Tyr Tyr Ala Ser Ser Val
         50                  55                  60

Lys Gly Arg Phe Thr Ile Ser Arg Asp Asn Ser Lys Asn Thr Leu Tyr
 65                  70                  75                  80

Leu Gln Met Asn Ser Leu Arg Ala Glu Asp Thr Ala Val Tyr Tyr Cys
                 85                  90                  95

Ala Lys Asp Arg Ala Trp Gly Leu Arg Leu Gly Glu Ser Ser Ser Tyr
                100                 105                 110
```

Asp Phe Asp Ile Trp Gly Gln Gly Thr Met Val Thr Val Ser Ser
            115                 120                 125

<210> SEQ ID NO 173
<211> LENGTH: 5
<212> TYPE: PRT
<213> ORGANISM: Homo sapiens

<400> SEQUENCE: 173

Gly Tyr Gly Met His
1               5

<210> SEQ ID NO 174
<211> LENGTH: 17
<212> TYPE: PRT
<213> ORGANISM: Homo sapiens

<400> SEQUENCE: 174

Tyr Ile Ser Tyr Asp Glu Ser Asn Lys Tyr Tyr Ala Arg Leu Val Lys
1               5                   10                  15

Gly

<210> SEQ ID NO 175
<211> LENGTH: 18
<212> TYPE: PRT
<213> ORGANISM: Homo sapiens

<400> SEQUENCE: 175

Asp Thr Ala Trp Gly Leu Arg Leu Gly Glu Ser Ser Tyr Asp Phe
1               5                   10                  15

Asp Ile

<210> SEQ ID NO 176
<211> LENGTH: 127
<212> TYPE: PRT
<213> ORGANISM: Homo sapiens

<400> SEQUENCE: 176

Glu Val Gln Leu Val Glu Ser Gly Gly Val Val Gln Pro Gly Arg
1               5                   10                  15

Ser Leu Arg Leu Ser Cys Ala Ala Ser Gly Phe Ser Phe Ser Gly Tyr
            20                  25                  30

Gly Met His Trp Val Arg Gln Ala Pro Gly Lys Gly Leu Glu Trp Val
        35                  40                  45

Ala Tyr Ile Ser Tyr Asp Glu Ser Asn Lys Tyr Tyr Ala Arg Leu Val
    50                  55                  60

Lys Gly Arg Phe Thr Ile Ser Arg Asp Asn Ser Lys Asn Thr Leu Tyr
65                  70                  75                  80

Leu Gln Met Asn Ser Leu Arg Ala Glu Asp Thr Ala Val Tyr Tyr Cys
                85                  90                  95

Ala Lys Asp Thr Ala Trp Gly Leu Arg Leu Gly Glu Ser Ser Tyr
            100                 105                 110

Asp Phe Asp Ile Trp Gly Gln Gly Thr Met Val Thr Val Ser Ser
            115                 120                 125

<210> SEQ ID NO 177
<211> LENGTH: 5
<212> TYPE: PRT
<213> ORGANISM: Homo sapiens

```
<400> SEQUENCE: 177

Gly Tyr Gly Leu His
1               5

<210> SEQ ID NO 178
<211> LENGTH: 17
<212> TYPE: PRT
<213> ORGANISM: Homo sapiens

<400> SEQUENCE: 178

Tyr Ile Ser Tyr Asp Leu Ser Asn Lys Tyr Tyr Ala Arg Gly Val Lys
1               5                   10                  15

Gly

<210> SEQ ID NO 179
<211> LENGTH: 18
<212> TYPE: PRT
<213> ORGANISM: Homo sapiens

<400> SEQUENCE: 179

Asp Val Ala Trp Gly Leu Arg Leu Gly Glu Ser Ser Ser Tyr Asp Phe
1               5                   10                  15

Asp Ile

<210> SEQ ID NO 180
<211> LENGTH: 127
<212> TYPE: PRT
<213> ORGANISM: Homo sapiens

<400> SEQUENCE: 180

Glu Val Gln Leu Val Glu Ser Gly Gly Val Val Gln Pro Gly Arg
1               5                   10                  15

Ser Leu Arg Leu Ser Cys Ala Ala Ser Gly Phe Ser Phe Ser Gly Tyr
                20                  25                  30

Gly Leu His Trp Val Arg Gln Ala Pro Gly Lys Gly Leu Glu Trp Val
            35                  40                  45

Ala Tyr Ile Ser Tyr Asp Leu Ser Asn Lys Tyr Tyr Ala Arg Gly Val
        50                  55                  60

Lys Gly Arg Phe Thr Ile Ser Arg Asp Asn Ser Lys Asn Thr Leu Tyr
65                  70                  75                  80

Leu Gln Met Asn Ser Leu Arg Ala Glu Asp Thr Ala Val Tyr Tyr Cys
                85                  90                  95

Ala Lys Asp Val Ala Trp Gly Leu Arg Leu Gly Glu Ser Ser Ser Tyr
            100                 105                 110

Asp Phe Asp Ile Trp Gly Gln Gly Thr Met Val Thr Val Ser Ser
        115                 120                 125

<210> SEQ ID NO 181
<211> LENGTH: 5
<212> TYPE: PRT
<213> ORGANISM: Homo sapiens

<400> SEQUENCE: 181

Ser Tyr Gly Met His
1               5

<210> SEQ ID NO 182
<211> LENGTH: 17
<212> TYPE: PRT
<213> ORGANISM: Homo sapiens
```

<400> SEQUENCE: 182

Phe Met Thr Tyr Asp Gly Ser Asn Arg Tyr Tyr Ala Asp Ser Val Lys
1               5                   10                  15

Gly

<210> SEQ ID NO 183
<211> LENGTH: 14
<212> TYPE: PRT
<213> ORGANISM: Homo sapiens

<400> SEQUENCE: 183

Asp Arg Ile Val Gly Gly Arg Val Pro Asp Ala Phe Asp Ile
1               5                   10

<210> SEQ ID NO 184
<211> LENGTH: 123
<212> TYPE: PRT
<213> ORGANISM: Homo sapiens

<400> SEQUENCE: 184

Glu Val Gln Leu Val Glu Ser Gly Gly Val Val Gln Pro Gly Arg
1               5                   10                  15

Ser Leu Arg Leu Ser Cys Ala Ala Ser Gly Phe Pro Leu Ile Ser Tyr
                20                  25                  30

Gly Met His Trp Val Arg Gln Ala Pro Gly Lys Gly Leu Glu Trp Val
            35                  40                  45

Ala Phe Met Thr Tyr Asp Gly Ser Asn Arg Tyr Tyr Ala Asp Ser Val
        50                  55                  60

Lys Gly Arg Phe Thr Ile Ser Arg Asp Asn Ser Lys Asn Thr Leu Tyr
65                  70                  75                  80

Leu Gln Met Asn Ser Leu Arg Asp Glu Asp Thr Ala Leu Tyr Tyr Cys
                85                  90                  95

Ala Arg Asp Arg Ile Val Gly Gly Arg Val Pro Asp Ala Phe Asp Ile
            100                 105                 110

Trp Gly Gln Gly Thr Met Val Thr Val Ser Ser
        115                 120

<210> SEQ ID NO 185
<211> LENGTH: 5
<212> TYPE: PRT
<213> ORGANISM: Homo sapiens

<400> SEQUENCE: 185

Ser Tyr Gly Met Asn
1               5

<210> SEQ ID NO 186
<211> LENGTH: 17
<212> TYPE: PRT
<213> ORGANISM: Homo sapiens

<400> SEQUENCE: 186

Phe Ile Ser Tyr Asp Gly Ser Asn Lys Tyr Tyr Ala Asp Ser Val Lys
1               5                   10                  15

Gly

<210> SEQ ID NO 187
<211> LENGTH: 14
<212> TYPE: PRT

<213> ORGANISM: Homo sapiens

<400> SEQUENCE: 187

Asp Arg Ile Val Gly Ala Arg Val Pro Asp Ala Phe Asp Ile
1               5                   10

<210> SEQ ID NO 188
<211> LENGTH: 123
<212> TYPE: PRT
<213> ORGANISM: Homo sapiens

<400> SEQUENCE: 188

Glu Val Gln Leu Val Glu Ser Gly Gly Val Val Gln Pro Gly Arg
1               5                   10                  15

Ser Leu Arg Leu Ser Cys Ala Ala Ser Gly Phe Pro Leu Ile Ser Tyr
                20                  25                  30

Gly Met Asn Trp Val Arg Gln Ala Pro Gly Lys Gly Leu Asp Trp Val
            35                  40                  45

Ala Phe Ile Ser Tyr Asp Gly Ser Asn Lys Tyr Tyr Ala Asp Ser Val
        50                  55                  60

Lys Gly Arg Phe Thr Ile Ser Lys Asp Asn Ser Lys Asn Thr Leu Tyr
65                  70                  75                  80

Leu Gln Met Asn Ser Leu Arg Ala Glu Asp Thr Ala Val Tyr Tyr Cys
                85                  90                  95

Ala Lys Asp Arg Ile Val Gly Ala Arg Val Pro Asp Ala Phe Asp Ile
                100                 105                 110

Trp Gly Gln Gly Thr Met Val Thr Val Ser Ser
            115                 120

<210> SEQ ID NO 189
<211> LENGTH: 5
<212> TYPE: PRT
<213> ORGANISM: Homo sapiens

<400> SEQUENCE: 189

Ser Tyr Gly Met Asn
1               5

<210> SEQ ID NO 190
<211> LENGTH: 17
<212> TYPE: PRT
<213> ORGANISM: Homo sapiens

<400> SEQUENCE: 190

Phe Ile Ser Tyr Asp Gly Ser Asn Arg Tyr Tyr Ala Asp Ser Val Lys
1               5                   10                  15
Gly

<210> SEQ ID NO 191
<211> LENGTH: 14
<212> TYPE: PRT
<213> ORGANISM: Homo sapiens

<400> SEQUENCE: 191

Asp Arg Ile Val Gly Ala Arg Val Pro Asp Ala Phe Asp Ile
1               5                   10

<210> SEQ ID NO 192
<211> LENGTH: 123
<212> TYPE: PRT
<213> ORGANISM: Homo sapiens

<400> SEQUENCE: 192

```
Glu Val Gln Leu Val Glu Ser Gly Gly Val Val Gln Pro Gly Arg
1               5                   10                  15

Ser Leu Arg Leu Ser Cys Ala Ala Ser Gly Phe Pro Leu Ile Ser Tyr
            20                  25                  30

Gly Met Asn Trp Val Arg Gln Ala Pro Gly Lys Gly Leu Glu Trp Val
            35                  40                  45

Ala Phe Ile Ser Tyr Asp Gly Ser Asn Arg Tyr Tyr Ala Asp Ser Val
        50                  55                  60

Lys Gly Arg Phe Thr Ile Ser Arg Asp Asn Ser Lys Asn Thr Leu Tyr
65                  70                  75                  80

Leu Gln Met Asn Ser Leu Arg Ala Glu Asp Thr Ala Val Tyr Tyr Cys
                85                  90                  95

Ala Lys Asp Arg Ile Val Gly Ala Arg Val Pro Asp Ala Phe Asp Ile
                100                 105                 110

Trp Gly Gln Gly Thr Met Val Thr Val Ser Ser
            115                 120
```

<210> SEQ ID NO 193
<211> LENGTH: 5
<212> TYPE: PRT
<213> ORGANISM: Homo sapiens

<400> SEQUENCE: 193

```
Ser Tyr Gly Met Asn
1               5
```

<210> SEQ ID NO 194
<211> LENGTH: 17
<212> TYPE: PRT
<213> ORGANISM: Homo sapiens

<400> SEQUENCE: 194

```
Phe Ile Thr Tyr Asp Gly Ser Asn Arg Tyr Tyr Ala Asp Ser Val Lys
1               5                   10                  15

Gly
```

<210> SEQ ID NO 195
<211> LENGTH: 14
<212> TYPE: PRT
<213> ORGANISM: Homo sapiens

<400> SEQUENCE: 195

```
Asp Arg Ile Val Gly Ala Arg Val Pro Asp Ala Tyr Asp Ile
1               5                   10
```

<210> SEQ ID NO 196
<211> LENGTH: 123
<212> TYPE: PRT
<213> ORGANISM: Homo sapiens

<400> SEQUENCE: 196

```
Glu Val Gln Leu Val Glu Ser Gly Gly Ala Val Gln Pro Gly Arg
1               5                   10                  15

Ser Leu Arg Leu Ser Cys Ala Ala Ser Gly Phe Pro Leu Ile Ser Tyr
            20                  25                  30

Gly Met Asn Trp Val Arg Gln Ala Pro Gly Lys Gly Leu Asp Trp Val
            35                  40                  45
```

```
Ala Phe Ile Thr Tyr Asp Gly Ser Asn Arg Tyr Tyr Ala Asp Ser Val
    50                  55                  60

Lys Gly Arg Phe Thr Ile Ser Arg Asp Asn Ser Lys Asn Thr Leu Tyr
65                  70                  75                  80

Leu Gln Met Asn Ser Leu Arg Pro Glu Asp Thr Ala Val Tyr Tyr Cys
                85                  90                  95

Ala Lys Asp Arg Ile Val Gly Ala Arg Val Pro Asp Ala Tyr Asp Ile
            100                 105                 110

Trp Gly Gln Gly Thr Met Val Thr Val Ser Ser
        115                 120

<210> SEQ ID NO 197
<211> LENGTH: 5
<212> TYPE: PRT
<213> ORGANISM: Homo sapiens

<400> SEQUENCE: 197

Ser Tyr Gly Met Asn
1               5

<210> SEQ ID NO 198
<211> LENGTH: 17
<212> TYPE: PRT
<213> ORGANISM: Homo sapiens

<400> SEQUENCE: 198

Phe Ile Thr Tyr Asp Gly Ser Asn Arg Tyr Tyr Ala Asp Ser Val Lys
1               5                   10                  15

Gly

<210> SEQ ID NO 199
<211> LENGTH: 14
<212> TYPE: PRT
<213> ORGANISM: Homo sapiens

<400> SEQUENCE: 199

Asp Arg Ile Val Gly Ala Arg Val Pro Asp Ala Tyr Asp Ile
1               5                   10

<210> SEQ ID NO 200
<211> LENGTH: 123
<212> TYPE: PRT
<213> ORGANISM: Homo sapiens

<400> SEQUENCE: 200

Gln Val Gln Leu Val Glu Ser Gly Gly Gly Val Val Gln Pro Gly Arg
1               5                   10                  15

Ser Leu Arg Leu Ser Cys Ala Ala Ser Gly Phe Pro Leu Ile Ser Tyr
            20                  25                  30

Gly Met Asn Trp Val Arg Gln Ala Pro Gly Lys Gly Leu Asp Trp Val
        35                  40                  45

Ala Phe Ile Thr Tyr Asp Gly Ser Asn Arg Tyr Tyr Ala Asp Ser Val
    50                  55                  60

Lys Gly Arg Phe Thr Ile Ser Arg Asp Asn Ser Lys Asn Thr Leu Tyr
65                  70                  75                  80

Leu Gln Met Asn Ser Leu Arg Pro Glu Asp Thr Ala Val Tyr Tyr Cys
                85                  90                  95

Ala Lys Asp Arg Ile Val Gly Ala Arg Val Pro Asp Ala Tyr Asp Ile
            100                 105                 110
```

Trp Gly Gln Gly Thr Met Val Thr Val Ser Ser
            115                 120

<210> SEQ ID NO 201
<211> LENGTH: 5
<212> TYPE: PRT
<213> ORGANISM: Homo sapiens

<400> SEQUENCE: 201

Ser Tyr Gly Met Asn
1               5

<210> SEQ ID NO 202
<211> LENGTH: 17
<212> TYPE: PRT
<213> ORGANISM: Homo sapiens

<400> SEQUENCE: 202

Phe Ile Thr Tyr Asp Gly Ser Asn Arg Tyr Tyr Ala Asp Ser Val Lys
1               5                   10                  15

Gly

<210> SEQ ID NO 203
<211> LENGTH: 14
<212> TYPE: PRT
<213> ORGANISM: Homo sapiens

<400> SEQUENCE: 203

Asp Arg Ile Val Gly Ala Arg Val Pro Asp Ala Tyr Asp Ile
1               5                   10

<210> SEQ ID NO 204
<211> LENGTH: 123
<212> TYPE: PRT
<213> ORGANISM: Homo sapiens

<400> SEQUENCE: 204

Glu Val Gln Leu Leu Glu Ser Gly Gly Val Val Gln Pro Gly Arg
1               5                   10                  15

Ser Leu Arg Leu Ser Cys Ala Ala Ser Gly Phe Pro Leu Ile Ser Tyr
            20                  25                  30

Gly Met Asn Trp Val Arg Gln Ala Pro Gly Lys Gly Leu Asp Trp Val
            35                  40                  45

Ala Phe Ile Thr Tyr Asp Gly Ser Asn Arg Tyr Tyr Ala Asp Ser Val
        50                  55                  60

Lys Gly Arg Phe Thr Ile Ser Arg Asp Asn Ser Lys Asn Thr Leu Tyr
65                  70                  75                  80

Leu Gln Met Asn Ser Leu Arg Pro Glu Asp Thr Ala Val Tyr Tyr Cys
            85                  90                  95

Ala Lys Asp Arg Ile Val Gly Ala Arg Val Pro Asp Ala Tyr Asp Ile
            100                 105                 110

Trp Gly Gln Gly Thr Met Val Thr Val Ser Ser
            115                 120

<210> SEQ ID NO 205
<211> LENGTH: 5
<212> TYPE: PRT
<213> ORGANISM: Homo sapiens

<400> SEQUENCE: 205

Ser Tyr Gly Met Asn

```
<210> SEQ ID NO 206
<211> LENGTH: 17
<212> TYPE: PRT
<213> ORGANISM: Homo sapiens

<400> SEQUENCE: 206

Phe Ile Thr Tyr Asp Gly Ser Asn Arg Tyr Tyr Ala Asp Ser Val Lys
1               5                   10                  15
Gly

<210> SEQ ID NO 207
<211> LENGTH: 14
<212> TYPE: PRT
<213> ORGANISM: Homo sapiens

<400> SEQUENCE: 207

Asp Arg Ile Val Gly Ala Arg Val Pro Asp Ala Tyr Asp Ile
1               5                   10

<210> SEQ ID NO 208
<211> LENGTH: 123
<212> TYPE: PRT
<213> ORGANISM: Homo sapiens

<400> SEQUENCE: 208

Gln Val Gln Leu Val Glu Ser Gly Gly Gly Leu Val Gln Pro Gly Gly
1               5                   10                  15

Ser Leu Arg Leu Ser Cys Ala Ala Ser Gly Phe Pro Leu Ile Ser Tyr
            20                  25                  30

Gly Met Asn Trp Val Arg Gln Ala Pro Gly Lys Gly Leu Asp Trp Val
        35                  40                  45

Ala Phe Ile Thr Tyr Asp Gly Ser Asn Arg Tyr Tyr Ala Asp Ser Val
    50                  55                  60

Lys Gly Arg Phe Thr Ile Ser Arg Asp Asn Ser Lys Asn Thr Leu His
65                  70                  75                  80

Leu Gln Met Asp Ser Leu Arg Pro Glu Asp Thr Ala Val Tyr Tyr Cys
                85                  90                  95

Ala Lys Asp Arg Ile Val Gly Ala Arg Val Pro Asp Ala Tyr Asp Ile
            100                 105                 110

Trp Gly Gln Gly Thr Met Val Thr Val Ser Ser
        115                 120

<210> SEQ ID NO 209
<211> LENGTH: 5
<212> TYPE: PRT
<213> ORGANISM: Homo sapiens

<400> SEQUENCE: 209

Ser Tyr Gly Met Asn
1               5

<210> SEQ ID NO 210
<211> LENGTH: 17
<212> TYPE: PRT
<213> ORGANISM: Homo sapiens

<400> SEQUENCE: 210

Phe Ile Thr Tyr Asp Gly Ser Asn Arg Tyr Tyr Ala Asp Ser Val Lys
1               5                   10                  15
```

Gly

<210> SEQ ID NO 211
<211> LENGTH: 14
<212> TYPE: PRT
<213> ORGANISM: Homo sapiens

<400> SEQUENCE: 211

Asp Arg Ile Val Gly Ala Arg Val Pro Asp Ala Tyr Asp Ile
1               5                   10

<210> SEQ ID NO 212
<211> LENGTH: 123
<212> TYPE: PRT
<213> ORGANISM: Homo sapiens

<400> SEQUENCE: 212

Glu Val Gln Leu Val Glu Ser Gly Gly Val Val Gln Pro Gly Arg
1               5                   10                  15

Ser Leu Arg Leu Ser Cys Ala Ala Ser Gly Phe Pro Leu Ile Ser Tyr
            20                  25                  30

Gly Met Asn Trp Val Arg Gln Ala Pro Gly Lys Gly Leu Asp Trp Val
        35                  40                  45

Ala Phe Ile Thr Tyr Asp Gly Ser Asn Arg Tyr Tyr Ala Asp Ser Val
    50                  55                  60

Lys Gly Arg Phe Thr Ile Ser Arg Asp Asn Ser Lys Asn Thr Leu Tyr
65                  70                  75                  80

Leu Gln Met Asn Ser Leu Arg Pro Glu Asp Thr Ala Val Tyr Tyr Cys
                85                  90                  95

Ala Lys Asp Arg Ile Val Gly Ala Arg Val Pro Asp Ala Tyr Asp Ile
            100                 105                 110

Trp Gly Gln Gly Thr Leu Val Thr Val Ser Ser
        115                 120

<210> SEQ ID NO 213
<211> LENGTH: 5
<212> TYPE: PRT
<213> ORGANISM: Homo sapiens

<400> SEQUENCE: 213

Ser Tyr Gly Met Asn
1               5

<210> SEQ ID NO 214
<211> LENGTH: 17
<212> TYPE: PRT
<213> ORGANISM: Homo sapiens

<400> SEQUENCE: 214

Phe Ile Ser Tyr Asp Gly Ser Asn Arg Tyr Tyr Ala Asp Ser Val Lys
1               5                   10                  15

Gly

<210> SEQ ID NO 215
<211> LENGTH: 14
<212> TYPE: PRT
<213> ORGANISM: Homo sapiens

<400> SEQUENCE: 215

Asp Arg Ile Val Gly Ala Arg Val Pro Asp Ala Tyr Asp Ile

-continued

```
1               5                   10
```

<210> SEQ ID NO 216
<211> LENGTH: 123
<212> TYPE: PRT
<213> ORGANISM: Homo sapiens

<400> SEQUENCE: 216

```
Gln Val Gln Leu Val Glu Ser Gly Gly Val Val Gln Pro Gly Arg
1               5                   10                  15

Ser Leu Arg Leu Ser Cys Ala Ala Ser Gly Phe Pro Leu Ile Ser Tyr
            20                  25                  30

Gly Met Asn Trp Val Arg Gln Ala Pro Gly Lys Gly Leu Glu Trp Val
        35                  40                  45

Ala Phe Ile Ser Tyr Asp Gly Ser Asn Arg Tyr Tyr Ala Asp Ser Val
    50                  55                  60

Lys Gly Arg Phe Thr Ile Ser Arg Asp Asn Ser Lys Asn Thr Leu Tyr
65                  70                  75                  80

Leu Gln Met Asn Ser Leu Arg Pro Glu Asp Thr Ala Val Tyr Tyr Cys
                85                  90                  95

Ala Lys Asp Arg Ile Val Gly Ala Arg Val Pro Asp Ala Tyr Asp Ile
            100                 105                 110

Trp Gly Gln Gly Thr Met Val Thr Val Ser Ser
        115                 120
```

<210> SEQ ID NO 217
<211> LENGTH: 5
<212> TYPE: PRT
<213> ORGANISM: Homo sapiens

<400> SEQUENCE: 217

```
Ser Tyr Gly Met Asn
1               5
```

<210> SEQ ID NO 218
<211> LENGTH: 17
<212> TYPE: PRT
<213> ORGANISM: Homo sapiens

<400> SEQUENCE: 218

```
Phe Ile Thr Tyr Asp Gly Ser Asn Arg Tyr Tyr Ala Asp Ser Val Lys
1               5                   10                  15

Gly
```

<210> SEQ ID NO 219
<211> LENGTH: 14
<212> TYPE: PRT
<213> ORGANISM: Homo sapiens

<400> SEQUENCE: 219

```
Asp Arg Ile Val Gly Ala Arg Val Pro Asp Ala Tyr Asp Ile
1               5                   10
```

<210> SEQ ID NO 220
<211> LENGTH: 123
<212> TYPE: PRT
<213> ORGANISM: Homo sapiens

<400> SEQUENCE: 220

```
Gln Val Gln Leu Val Glu Ser Gly Gly Val Val Gln Pro Gly Arg
1               5                   10                  15
```

Ser Leu Arg Leu Ser Cys Ala Ala Ser Gly Phe Pro Leu Ile Ser Tyr
            20                  25                  30

Gly Met Asn Trp Val Arg Gln Ala Pro Gly Lys Gly Leu Asp Trp Val
            35                  40                  45

Ala Phe Ile Thr Tyr Asp Gly Ser Asn Arg Tyr Tyr Ala Asp Ser Val
        50                  55                  60

Lys Gly Arg Phe Thr Ile Ser Arg Asp Asn Ser Lys Asn Thr Leu His
65                  70                  75                  80

Leu Gln Met Asn Ser Leu Arg Pro Glu Asp Thr Ala Val Tyr Tyr Cys
                85                  90                  95

Ala Lys Asp Arg Ile Val Gly Ala Arg Val Pro Asp Ala Tyr Asp Ile
            100                 105                 110

Trp Gly Gln Gly Thr Met Val Thr Val Ser Ser
        115                 120

<210> SEQ ID NO 221
<211> LENGTH: 5
<212> TYPE: PRT
<213> ORGANISM: Homo sapiens

<400> SEQUENCE: 221

Ser Tyr Gly Met Asn
1               5

<210> SEQ ID NO 222
<211> LENGTH: 17
<212> TYPE: PRT
<213> ORGANISM: Homo sapiens

<400> SEQUENCE: 222

Phe Ile Thr Tyr Asp Gly Ser Asn Arg Tyr Tyr Ala Asp Ser Val Lys
1               5                   10                  15

Gly

<210> SEQ ID NO 223
<211> LENGTH: 14
<212> TYPE: PRT
<213> ORGANISM: Homo sapiens

<400> SEQUENCE: 223

Asp Arg Ile Val Gly Ala Arg Val Pro Asp Ala Tyr Asp Ile
1               5                   10

<210> SEQ ID NO 224
<211> LENGTH: 123
<212> TYPE: PRT
<213> ORGANISM: Homo sapiens

<400> SEQUENCE: 224

Glu Val Gln Leu Val Glu Ser Gly Gly Gly Val Val Gln Pro Gly Arg
1               5                   10                  15

Ser Leu Arg Leu Ser Cys Ala Ala Ser Gly Phe Pro Leu Ile Ser Tyr
            20                  25                  30

Gly Met Asn Trp Val Arg Gln Ala Pro Gly Lys Gly Leu Asp Trp Val
            35                  40                  45

Ala Phe Ile Thr Tyr Asp Gly Ser Asn Arg Tyr Tyr Ala Asp Ser Val
        50                  55                  60

Lys Gly Arg Phe Thr Ile Ser Arg Asp Asn Ser Lys Asn Thr Leu His
65                  70                  75                  80

-continued

Leu Gln Met Asn Ser Leu Arg Pro Glu Asp Thr Ala Val Tyr Tyr Cys
                85                  90                  95

Ala Lys Asp Arg Ile Val Gly Ala Arg Val Pro Asp Ala Tyr Asp Ile
            100                 105                 110

Trp Gly Gln Gly Thr Met Val Thr Val Ser Ser
        115                 120

<210> SEQ ID NO 225
<211> LENGTH: 5
<212> TYPE: PRT
<213> ORGANISM: Homo sapiens

<400> SEQUENCE: 225

Ser Tyr Gly Met Asn
1               5

<210> SEQ ID NO 226
<211> LENGTH: 17
<212> TYPE: PRT
<213> ORGANISM: Homo sapiens

<400> SEQUENCE: 226

Phe Ile Thr Tyr Asp Gly Ser Asn Arg Tyr Tyr Ala Asp Ser Val Lys
1               5                   10                  15

Gly

<210> SEQ ID NO 227
<211> LENGTH: 14
<212> TYPE: PRT
<213> ORGANISM: Homo sapiens

<400> SEQUENCE: 227

Asp Arg Ile Val Gly Ala Arg Val Pro Asp Ala Tyr Asp Ile
1               5                   10

<210> SEQ ID NO 228
<211> LENGTH: 123
<212> TYPE: PRT
<213> ORGANISM: Homo sapiens

<400> SEQUENCE: 228

Glu Val Gln Leu Val Glu Ser Gly Gly Gly Val Val Gln Pro Gly Arg
1               5                   10                  15

Ser Leu Arg Leu Ser Cys Ala Ala Ser Gly Phe Pro Leu Ile Ser Tyr
            20                  25                  30

Gly Met Asn Trp Val Arg Gln Ala Pro Gly Lys Gly Leu Asp Trp Val
        35                  40                  45

Ala Phe Ile Thr Tyr Asp Gly Ser Asn Arg Tyr Tyr Ala Asp Ser Val
    50                  55                  60

Lys Gly Arg Phe Thr Ile Ser Arg Asp Asn Ser Lys Asn Thr Leu Tyr
65                  70                  75                  80

Leu Gln Met Asn Ser Leu Arg Pro Glu Asp Thr Ala Val Tyr Tyr Cys
                85                  90                  95

Ala Lys Asp Arg Ile Val Gly Ala Arg Val Pro Asp Ala Tyr Asp Ile
            100                 105                 110

Trp Gly Gln Gly Thr Met Val Thr Val Ser Ser
        115                 120

<210> SEQ ID NO 229

```
<211> LENGTH: 5
<212> TYPE: PRT
<213> ORGANISM: Homo sapiens

<400> SEQUENCE: 229

Ser Tyr Gly Met Asn
1               5

<210> SEQ ID NO 230
<211> LENGTH: 17
<212> TYPE: PRT
<213> ORGANISM: Homo sapiens

<400> SEQUENCE: 230

Phe Ile Thr Tyr Asp Gly Ser Asn Arg Tyr Tyr Ala Asp Ser Val Lys
1               5                   10                  15

Gly

<210> SEQ ID NO 231
<211> LENGTH: 14
<212> TYPE: PRT
<213> ORGANISM: Homo sapiens

<400> SEQUENCE: 231

Asp Arg Ile Val Gly Ala Arg Val Pro Asp Ala Tyr Asp Ile
1               5                   10

<210> SEQ ID NO 232
<211> LENGTH: 123
<212> TYPE: PRT
<213> ORGANISM: Homo sapiens

<400> SEQUENCE: 232

Gln Val Gln Leu Val Glu Ser Gly Gly Val Val Gln Pro Gly Arg
1               5                   10                  15

Ser Leu Arg Leu Ser Cys Ala Ala Ser Gly Phe Pro Leu Ile Ser Tyr
                20                  25                  30

Gly Met Asn Trp Val Arg Gln Ala Pro Gly Lys Gly Leu Asp Trp Val
            35                  40                  45

Ala Phe Ile Thr Tyr Asp Gly Ser Asn Arg Tyr Tyr Ala Asp Ser Val
        50                  55                  60

Lys Gly Arg Phe Thr Ile Ser Arg Asp Asn Ser Lys Asn Thr Leu Tyr
65                  70                  75                  80

Leu Gln Met Asn Ser Leu Arg Pro Glu Asp Thr Ala Val Tyr Tyr Cys
                85                  90                  95

Ala Lys Asp Arg Ile Val Gly Ala Arg Val Pro Asp Ala Tyr Asp Ile
            100                 105                 110

Trp Gly Gln Gly Thr Met Val Thr Val Ser Ser
        115                 120

<210> SEQ ID NO 233
<211> LENGTH: 5
<212> TYPE: PRT
<213> ORGANISM: Homo sapiens

<400> SEQUENCE: 233

Ser Tyr Gly Met Asn
1               5

<210> SEQ ID NO 234
<211> LENGTH: 17
```

```
<212> TYPE: PRT
<213> ORGANISM: Homo sapiens

<400> SEQUENCE: 234

Phe Ile Thr Tyr Asp Gly Ser Asn Arg Tyr Tyr Ala Asp Ser Val Lys
1               5                   10                  15

Gly

<210> SEQ ID NO 235
<211> LENGTH: 14
<212> TYPE: PRT
<213> ORGANISM: Homo sapiens

<400> SEQUENCE: 235

Asp Arg Ile Val Gly Ala Arg Val Pro Asp Ala Tyr Asp Ile
1               5                   10

<210> SEQ ID NO 236
<211> LENGTH: 123
<212> TYPE: PRT
<213> ORGANISM: Homo sapiens

<400> SEQUENCE: 236

Glu Val Gln Leu Val Glu Ser Gly Gly Val Val Arg Pro Gly Gly
1               5                   10                  15

Ser Leu Arg Leu Ser Cys Ala Ala Ser Gly Phe Pro Leu Ile Ser Tyr
            20                  25                  30

Gly Met Asn Trp Val Arg Gln Ala Pro Gly Lys Gly Leu Asp Trp Val
        35                  40                  45

Ala Phe Ile Thr Tyr Asp Gly Ser Asn Arg Tyr Tyr Ala Asp Ser Val
    50                  55                  60

Lys Gly Arg Phe Thr Ile Ser Arg Asp Asn Ser Lys Asn Thr Leu His
65                  70                  75                  80

Leu Gln Met Asn Ser Leu Arg Pro Glu Asp Thr Ala Val Tyr Tyr Cys
                85                  90                  95

Ala Lys Asp Arg Ile Val Gly Ala Arg Val Pro Asp Ala Tyr Asp Ile
            100                 105                 110

Trp Gly Gln Gly Thr Met Val Thr Val Ser Ser
        115                 120

<210> SEQ ID NO 237
<211> LENGTH: 5
<212> TYPE: PRT
<213> ORGANISM: Homo sapiens

<400> SEQUENCE: 237

Ser Tyr Gly Met Asn
1               5

<210> SEQ ID NO 238
<211> LENGTH: 17
<212> TYPE: PRT
<213> ORGANISM: Homo sapiens

<400> SEQUENCE: 238

Phe Ile Thr Tyr Asp Gly Ser Asn Arg Tyr Tyr Ala Asp Ser Val Lys
1               5                   10                  15

Gly

<210> SEQ ID NO 239
```

```
<211> LENGTH: 14
<212> TYPE: PRT
<213> ORGANISM: Homo sapiens

<400> SEQUENCE: 239

Asp Arg Ile Val Gly Ala Arg Val Pro Asp Ala Tyr Asp Ile
1               5                   10

<210> SEQ ID NO 240
<211> LENGTH: 123
<212> TYPE: PRT
<213> ORGANISM: Homo sapiens

<400> SEQUENCE: 240

Glu Val Gln Leu Val Glu Ser Gly Gly Gly Leu Val Gln Pro Gly Gly
1               5                   10                  15

Ser Leu Arg Leu Ser Cys Ala Ala Ser Gly Phe Pro Leu Ile Ser Tyr
            20                  25                  30

Gly Met Asn Trp Val Arg Gln Ala Pro Gly Lys Gly Leu Asp Trp Val
        35                  40                  45

Ala Phe Ile Thr Tyr Asp Gly Ser Asn Arg Tyr Tyr Ala Asp Ser Val
    50                  55                  60

Lys Gly Arg Phe Thr Ile Ser Arg Asp Asn Ser Lys Asn Thr Leu His
65                  70                  75                  80

Leu Gln Met Asn Ser Leu Arg Pro Glu Asp Thr Ala Val Tyr Tyr Cys
                85                  90                  95

Ala Lys Asp Arg Ile Val Gly Ala Arg Val Pro Asp Ala Tyr Asp Ile
            100                 105                 110

Trp Gly Gln Gly Thr Met Val Thr Val Ser Ser
        115                 120

<210> SEQ ID NO 241
<211> LENGTH: 5
<212> TYPE: PRT
<213> ORGANISM: Homo sapiens

<400> SEQUENCE: 241

Ser Tyr Gly Met Asn
1               5

<210> SEQ ID NO 242
<211> LENGTH: 17
<212> TYPE: PRT
<213> ORGANISM: Homo sapiens

<400> SEQUENCE: 242

Phe Ile Thr Tyr Asp Gly Ser Asn Arg Tyr Tyr Ala Asp Ser Val Lys
1               5                   10                  15

Gly

<210> SEQ ID NO 243
<211> LENGTH: 14
<212> TYPE: PRT
<213> ORGANISM: Homo sapiens

<400> SEQUENCE: 243

Asp Arg Ile Val Gly Ala Arg Val Pro Asp Ala Tyr Asp Ile
1               5                   10

<210> SEQ ID NO 244
<211> LENGTH: 123
```

```
<212> TYPE: PRT
<213> ORGANISM: Homo sapiens

<400> SEQUENCE: 244

Glu Val Gln Leu Leu Glu Ser Gly Gly Gly Val Val Gln Pro Gly Arg
 1               5                  10                  15

Ser Leu Arg Leu Ser Cys Ala Ala Ser Gly Phe Pro Leu Ile Ser Tyr
             20                  25                  30

Gly Met Asn Trp Val Arg Gln Ala Pro Gly Lys Gly Leu Asp Trp Val
         35                  40                  45

Ala Phe Ile Thr Tyr Asp Gly Ser Asn Arg Tyr Tyr Ala Asp Ser Val
     50                  55                  60

Lys Gly Arg Phe Thr Ile Ser Arg Asp Asn Ser Lys Asn Thr Leu His
 65                  70                  75                  80

Leu Gln Met Asn Ser Leu Arg Pro Glu Asp Thr Ala Val Tyr Tyr Cys
                 85                  90                  95

Ala Lys Asp Arg Ile Val Gly Ala Arg Val Pro Asp Ala Tyr Asp Ile
            100                 105                 110

Trp Gly Gln Gly Thr Met Val Thr Val Ser Ser
        115                 120

<210> SEQ ID NO 245
<211> LENGTH: 5
<212> TYPE: PRT
<213> ORGANISM: Homo sapiens

<400> SEQUENCE: 245

Ser Tyr Gly Met Asn
 1               5

<210> SEQ ID NO 246
<211> LENGTH: 17
<212> TYPE: PRT
<213> ORGANISM: Homo sapiens

<400> SEQUENCE: 246

Phe Ile Thr Tyr Asp Gly Ser Asn Arg Tyr Tyr Ala Asp Ser Val Lys
 1               5                  10                  15

Gly

<210> SEQ ID NO 247
<211> LENGTH: 14
<212> TYPE: PRT
<213> ORGANISM: Homo sapiens

<400> SEQUENCE: 247

Asp Arg Ile Val Gly Ala Arg Val Pro Asp Ala Tyr Asp Ile
 1               5                  10

<210> SEQ ID NO 248
<211> LENGTH: 123
<212> TYPE: PRT
<213> ORGANISM: Homo sapiens

<400> SEQUENCE: 248

Glu Val Gln Leu Leu Glu Ser Gly Gly Gly Val Val Gln Pro Gly Arg
 1               5                  10                  15

Ser Leu Arg Leu Ser Cys Ala Ala Ser Gly Phe Pro Leu Ile Ser Tyr
             20                  25                  30

Gly Met Asn Trp Val Arg Gln Ala Pro Gly Lys Gly Leu Asp Trp Val
```

```
            35                  40                  45

Ala Phe Ile Thr Tyr Asp Gly Ser Asn Arg Tyr Tyr Ala Asp Ser Val
    50                  55                  60

Lys Gly Arg Phe Thr Ile Ser Arg Asp Asn Ser Lys Asn Thr Leu Tyr
65                  70                  75                  80

Leu Gln Met Asn Ser Leu Lys Pro Glu Asp Thr Ala Val Tyr Tyr Cys
                85                  90                  95

Ala Lys Asp Arg Ile Val Gly Ala Arg Val Pro Asp Ala Tyr Asp Ile
            100                 105                 110

Trp Gly Gln Gly Thr Met Val Thr Val Ser Ser
            115                 120

<210> SEQ ID NO 249
<211> LENGTH: 5
<212> TYPE: PRT
<213> ORGANISM: Homo sapiens

<400> SEQUENCE: 249

Ser Tyr Gly Met Asn
1               5

<210> SEQ ID NO 250
<211> LENGTH: 17
<212> TYPE: PRT
<213> ORGANISM: Homo sapiens

<400> SEQUENCE: 250

Phe Ile Thr Tyr Asp Gly Ser Asn Arg Tyr Tyr Ala Asp Ser Val Lys
1               5                   10                  15

Gly

<210> SEQ ID NO 251
<211> LENGTH: 14
<212> TYPE: PRT
<213> ORGANISM: Homo sapiens

<400> SEQUENCE: 251

Asp Arg Ile Val Gly Ala Arg Val Pro Asp Ala Tyr Asp Ile
1               5                   10

<210> SEQ ID NO 252
<211> LENGTH: 123
<212> TYPE: PRT
<213> ORGANISM: Homo sapiens

<400> SEQUENCE: 252

Glu Val Gln Leu Val Glu Ser Gly Gly Val Val Gln Pro Gly Arg
1               5                   10                  15

Ser Leu Arg Leu Ser Cys Ala Ala Ser Gly Phe Pro Leu Ile Ser Tyr
                20                  25                  30

Gly Met Asn Trp Val Arg Gln Ala Pro Gly Lys Gly Leu Asp Trp Val
            35                  40                  45

Ala Phe Ile Thr Tyr Asp Gly Ser Asn Arg Tyr Tyr Ala Asp Ser Val
    50                  55                  60

Lys Gly Arg Phe Thr Ile Ser Arg Asp Asn Ser Lys Asn Thr Leu Tyr
65                  70                  75                  80

Leu Gln Met Asn Ser Leu Lys Pro Glu Asp Thr Ala Val Tyr Tyr Cys
                85                  90                  95

Ala Lys Asp Arg Ile Val Gly Ala Arg Val Pro Asp Ala Tyr Asp Ile
```

-continued

```
                    100                 105                 110
Trp Gly Gln Gly Thr Met Val Thr Val Ser Ser
            115                 120

<210> SEQ ID NO 253
<211> LENGTH: 5
<212> TYPE: PRT
<213> ORGANISM: Homo sapiens

<400> SEQUENCE: 253

Ser Tyr Gly Met His
1               5

<210> SEQ ID NO 254
<211> LENGTH: 17
<212> TYPE: PRT
<213> ORGANISM: Homo sapiens

<400> SEQUENCE: 254

Phe Met Thr Tyr Asp Gly Ser Asn Arg Tyr Tyr Ala Asp Ala Val Lys
1               5                   10                  15
Gly

<210> SEQ ID NO 255
<211> LENGTH: 14
<212> TYPE: PRT
<213> ORGANISM: Homo sapiens

<400> SEQUENCE: 255

Asp Arg Ile Val Gly Gly Arg Val Pro Asp Ala Phe Asp Ile
1               5                   10

<210> SEQ ID NO 256
<211> LENGTH: 123
<212> TYPE: PRT
<213> ORGANISM: Homo sapiens

<400> SEQUENCE: 256

Gln Val Gln Leu Val Glu Ser Gly Gly Val Val Gln Pro Gly Arg
1               5                   10                  15

Ser Leu Arg Leu Ser Cys Ala Ala Ser Gly Phe Pro Leu Ile Ser Tyr
            20                  25                  30

Gly Met His Trp Val Arg Gln Ala Pro Gly Lys Gly Leu Glu Trp Val
        35                  40                  45

Ala Phe Met Thr Tyr Asp Gly Ser Asn Arg Tyr Tyr Ala Asp Ala Val
    50                  55                  60

Lys Gly Arg Phe Thr Ile Ser Arg Asp Asn Ser Lys Asn Thr Leu Tyr
65                  70                  75                  80

Leu Gln Met Asn Ser Leu Arg Ala Glu Asp Thr Ala Val Tyr Tyr Cys
                85                  90                  95

Ala Arg Asp Arg Ile Val Gly Gly Arg Val Pro Asp Ala Phe Asp Ile
            100                 105                 110

Trp Gly Gln Gly Thr Met Val Thr Val Ser Ser
        115                 120

<210> SEQ ID NO 257
<211> LENGTH: 5
<212> TYPE: PRT
<213> ORGANISM: Homo sapiens

<400> SEQUENCE: 257
```

```
Ser Tyr Gly Met His
1               5

<210> SEQ ID NO 258
<211> LENGTH: 17
<212> TYPE: PRT
<213> ORGANISM: Homo sapiens

<400> SEQUENCE: 258

Phe Gln Thr Tyr Asp Gly Ser Asn Arg Tyr Tyr Ala Asp Ala Val Lys
1               5                   10                  15

Gly

<210> SEQ ID NO 259
<211> LENGTH: 14
<212> TYPE: PRT
<213> ORGANISM: Homo sapiens

<400> SEQUENCE: 259

Asp Arg Ile Val Gly Gly Arg Val Pro Asp Ala Phe Asp Ile
1               5                   10

<210> SEQ ID NO 260
<211> LENGTH: 123
<212> TYPE: PRT
<213> ORGANISM: Homo sapiens

<400> SEQUENCE: 260

Gln Val Gln Leu Val Glu Ser Gly Gly Val Val Gln Pro Gly Arg
1               5                   10                  15

Ser Leu Arg Leu Ser Cys Ala Ala Ser Gly Phe Pro Leu Ile Ser Tyr
                20                  25                  30

Gly Met His Trp Val Arg Gln Ala Pro Gly Lys Gly Leu Glu Trp Val
            35                  40                  45

Ala Phe Gln Thr Tyr Asp Gly Ser Asn Arg Tyr Tyr Ala Asp Ala Val
        50                  55                  60

Lys Gly Arg Phe Thr Ile Ser Arg Asp Asn Ser Lys Asn Thr Leu Tyr
65                  70                  75                  80

Leu Gln Met Asn Ser Leu Arg Ala Glu Asp Thr Ala Val Tyr Tyr Cys
                85                  90                  95

Ala Arg Asp Arg Ile Val Gly Gly Arg Val Pro Asp Ala Phe Asp Ile
            100                 105                 110

Trp Gly Gln Gly Thr Met Val Thr Val Ser Ser
        115                 120

<210> SEQ ID NO 261
<211> LENGTH: 5
<212> TYPE: PRT
<213> ORGANISM: Homo sapiens

<400> SEQUENCE: 261

Ser Tyr Gly Met His
1               5

<210> SEQ ID NO 262
<211> LENGTH: 17
<212> TYPE: PRT
<213> ORGANISM: Homo sapiens

<400> SEQUENCE: 262
```

```
Phe Gln Thr Tyr Asp Gly Ser Asn Arg Tyr Tyr Ala Asp Ser Val Lys
1               5                   10                  15

Gly

<210> SEQ ID NO 263
<211> LENGTH: 14
<212> TYPE: PRT
<213> ORGANISM: Homo sapiens

<400> SEQUENCE: 263

Asp Arg Ile Val Gly Gly Arg Val Pro Asp Ala Phe Asp Ile
1               5                   10

<210> SEQ ID NO 264
<211> LENGTH: 123
<212> TYPE: PRT
<213> ORGANISM: Homo sapiens

<400> SEQUENCE: 264

Gln Val Gln Leu Val Glu Ser Gly Gly Val Val Gln Pro Gly Arg
1               5                   10                  15

Ser Leu Arg Leu Ser Cys Ala Ala Ser Gly Phe Pro Leu Ile Ser Tyr
            20                  25                  30

Gly Met His Trp Val Arg Gln Ala Pro Gly Lys Gly Leu Glu Trp Val
        35                  40                  45

Ala Phe Gln Thr Tyr Asp Gly Ser Asn Arg Tyr Tyr Ala Asp Ser Val
    50                  55                  60

Lys Gly Arg Phe Thr Ile Ser Arg Asp Asn Ser Lys Asn Thr Leu Tyr
65                  70                  75                  80

Leu Gln Met Asn Ser Leu Arg Ala Glu Asp Thr Ala Val Tyr Tyr Cys
                85                  90                  95

Ala Arg Asp Arg Ile Val Gly Gly Arg Val Pro Asp Ala Phe Asp Ile
            100                 105                 110

Trp Gly Gln Gly Thr Met Val Thr Val Ser Ser
        115                 120

<210> SEQ ID NO 265
<211> LENGTH: 5
<212> TYPE: PRT
<213> ORGANISM: Homo sapiens

<400> SEQUENCE: 265

Ser Tyr Gly Met His
1               5

<210> SEQ ID NO 266
<211> LENGTH: 17
<212> TYPE: PRT
<213> ORGANISM: Homo sapiens

<400> SEQUENCE: 266

Phe Gln Thr Tyr Asp Ala Ser Asn Arg Tyr Tyr Ala Asp Ser Val Lys
1               5                   10                  15

Gly

<210> SEQ ID NO 267
<211> LENGTH: 14
<212> TYPE: PRT
<213> ORGANISM: Homo sapiens

<400> SEQUENCE: 267
```

Asp Arg Ile Val Gly Gly Arg Val Pro Asp Ala Phe Asp Ile
1               5                   10

<210> SEQ ID NO 268
<211> LENGTH: 123
<212> TYPE: PRT
<213> ORGANISM: Homo sapiens

<400> SEQUENCE: 268

Gln Val Gln Leu Val Glu Ser Gly Gly Val Val Gln Pro Gly Arg
1               5                   10                  15

Ser Leu Arg Leu Ser Cys Ala Ala Ser Gly Phe Pro Leu Ile Ser Tyr
            20                  25                  30

Gly Met His Trp Val Arg Gln Ala Pro Gly Lys Gly Leu Glu Trp Val
        35                  40                  45

Ala Phe Gln Thr Tyr Asp Ala Ser Asn Arg Tyr Tyr Ala Asp Ser Val
    50                  55                  60

Lys Gly Arg Phe Thr Ile Ser Arg Asp Asn Ser Lys Asn Thr Leu Tyr
65                  70                  75                  80

Leu Gln Met Asn Ser Leu Arg Ala Glu Asp Thr Ala Val Tyr Tyr Cys
                85                  90                  95

Ala Arg Asp Arg Ile Val Gly Gly Arg Val Pro Asp Ala Phe Asp Ile
            100                 105                 110

Trp Gly Gln Gly Thr Met Val Thr Val Ser Ser
        115                 120

<210> SEQ ID NO 269
<211> LENGTH: 5
<212> TYPE: PRT
<213> ORGANISM: Homo sapiens

<400> SEQUENCE: 269

Ser Tyr Gly Met His
1               5

<210> SEQ ID NO 270
<211> LENGTH: 17
<212> TYPE: PRT
<213> ORGANISM: Homo sapiens

<400> SEQUENCE: 270

Phe Gln Thr Tyr Asp Ala Ser Asn Arg Tyr Tyr Ala Asp Ala Val Lys
1               5                   10                  15

Gly

<210> SEQ ID NO 271
<211> LENGTH: 14
<212> TYPE: PRT
<213> ORGANISM: Homo sapiens

<400> SEQUENCE: 271

Asp Arg Ile Val Gly Gly Arg Val Pro Asp Ala Phe Asp Ile
1               5                   10

<210> SEQ ID NO 272
<211> LENGTH: 123
<212> TYPE: PRT
<213> ORGANISM: Homo sapiens

<400> SEQUENCE: 272

```
Gln Val Gln Leu Val Glu Ser Gly Gly Gly Val Val Gln Pro Gly Arg
1               5                   10                  15

Ser Leu Arg Leu Ser Cys Ala Ala Ser Gly Phe Pro Leu Ile Ser Tyr
            20                  25                  30

Gly Met His Trp Val Arg Gln Ala Pro Gly Lys Gly Leu Glu Trp Val
        35                  40                  45

Ala Phe Gln Thr Tyr Asp Ala Ser Asn Arg Tyr Tyr Ala Asp Ala Val
    50                  55                  60

Lys Gly Arg Phe Thr Ile Ser Arg Asp Asn Ser Lys Asn Thr Leu Tyr
65                  70                  75                  80

Leu Gln Met Asn Ser Leu Arg Ala Glu Asp Thr Ala Val Tyr Tyr Cys
                85                  90                  95

Ala Arg Asp Arg Ile Val Gly Gly Arg Val Pro Asp Ala Phe Asp Ile
            100                 105                 110

Trp Gly Gln Gly Thr Met Val Thr Val Ser Ser
            115                 120
```

<210> SEQ ID NO 273
<211> LENGTH: 5
<212> TYPE: PRT
<213> ORGANISM: Homo sapiens

<400> SEQUENCE: 273

```
Ser Tyr Gly Met Asn
1               5
```

<210> SEQ ID NO 274
<211> LENGTH: 17
<212> TYPE: PRT
<213> ORGANISM: Homo sapiens

<400> SEQUENCE: 274

```
Phe Ile Thr Tyr Asp Gly Ser Asn Arg Tyr Tyr Ala Asp Ser Val Lys
1               5                   10                  15

Gly
```

<210> SEQ ID NO 275
<211> LENGTH: 14
<212> TYPE: PRT
<213> ORGANISM: Homo sapiens

<400> SEQUENCE: 275

```
Asp Arg Ile Val Gly Ala Arg Val Pro Asp Ala Tyr Asp Ile
1               5                   10
```

<210> SEQ ID NO 276
<211> LENGTH: 123
<212> TYPE: PRT
<213> ORGANISM: Homo sapiens

<400> SEQUENCE: 276

```
Gln Val Gln Leu Val Glu Ser Gly Gly Gly Val Val Gln Pro Gly Arg
1               5                   10                  15

Ser Leu Arg Leu Ser Cys Ala Ala Ser Gly Phe Pro Leu Ile Ser Tyr
            20                  25                  30

Gly Met Asn Trp Val Arg Gln Ala Pro Gly Lys Gly Leu Glu Trp Val
        35                  40                  45

Ala Phe Ile Thr Tyr Asp Gly Ser Asn Arg Tyr Tyr Ala Asp Ser Val
    50                  55                  60
```

```
Lys Gly Arg Phe Thr Ile Ser Arg Asp Asn Ser Lys Asn Thr Leu Tyr
 65                  70                  75                  80

Leu Gln Met Asn Ser Leu Arg Ala Glu Asp Thr Ala Val Tyr Tyr Cys
                 85                  90                  95

Ala Lys Asp Arg Ile Val Gly Ala Arg Val Pro Asp Ala Tyr Asp Ile
            100                 105                 110

Trp Gly Gln Gly Thr Met Val Thr Val Ser Ser
        115                 120
```

<210> SEQ ID NO 277
<211> LENGTH: 5
<212> TYPE: PRT
<213> ORGANISM: Homo sapiens

<400> SEQUENCE: 277

```
Ser Tyr Gly Met His
 1               5
```

<210> SEQ ID NO 278
<211> LENGTH: 17
<212> TYPE: PRT
<213> ORGANISM: Homo sapiens

<400> SEQUENCE: 278

```
Val Ile Ser Tyr Asp Gly Ser Asn Arg Tyr Tyr Ala Asp Ser Val Lys
 1               5                  10                  15

Gly
```

<210> SEQ ID NO 279
<211> LENGTH: 14
<212> TYPE: PRT
<213> ORGANISM: Homo sapiens

<400> SEQUENCE: 279

```
Glu Arg Ile Phe Gly Val Leu Thr Pro Asp Phe Asp Ile
 1               5                  10
```

<210> SEQ ID NO 280
<211> LENGTH: 123
<212> TYPE: PRT
<213> ORGANISM: Homo sapiens

<400> SEQUENCE: 280

```
Gln Val Gln Leu Val Glu Ser Gly Gly Val Val Gln Pro Gly Arg
 1               5                  10                  15

Ser Leu Arg Leu Ser Cys Val Ala Ser Gly Phe Pro Phe Ile Ser Tyr
            20                  25                  30

Gly Met His Trp Val Arg Gln Ala Pro Gly Lys Gly Arg Glu Trp Val
        35                  40                  45

Ala Val Ile Ser Tyr Asp Gly Ser Asn Arg Tyr Tyr Ala Asp Ser Val
    50                  55                  60

Lys Gly Arg Phe Thr Ile Ser Arg Asp Asn Ser Lys Asn Thr Leu Tyr
 65                  70                  75                  80

Leu Gln Met Asn Ser Leu Arg Pro Glu Asp Thr Ala Val Tyr Tyr Cys
                 85                  90                  95

Ala Lys Glu Arg Ile Phe Gly Val Leu Thr Pro Asp Phe Asp Ile
            100                 105                 110

Trp Gly Gln Gly Thr Thr Val Thr Val Ser Ser
        115                 120
```

```
<210> SEQ ID NO 281
<211> LENGTH: 5
<212> TYPE: PRT
<213> ORGANISM: Homo sapiens

<400> SEQUENCE: 281

Ser Tyr Gly Met His
1               5

<210> SEQ ID NO 282
<211> LENGTH: 17
<212> TYPE: PRT
<213> ORGANISM: Homo sapiens

<400> SEQUENCE: 282

Val Ile Ser Tyr Asp Gly Ser Asn Arg Tyr Tyr Ala Asp Ser Val Lys
1               5                   10                  15

Gly

<210> SEQ ID NO 283
<211> LENGTH: 14
<212> TYPE: PRT
<213> ORGANISM: Homo sapiens

<400> SEQUENCE: 283

Glu Arg Ile Phe Gly Val Leu Thr Pro Asp Asp Phe Asp Ile
1               5                   10

<210> SEQ ID NO 284
<211> LENGTH: 123
<212> TYPE: PRT
<213> ORGANISM: Homo sapiens

<400> SEQUENCE: 284

Gln Val Gln Leu Val Glu Ser Gly Gly Gly Val Val Gln Pro Gly Arg
1               5                   10                  15

Ser Leu Arg Leu Ser Cys Ala Ala Ser Gly Phe Pro Phe Ile Ser Tyr
            20                  25                  30

Gly Met His Trp Val Arg Gln Ala Pro Gly Lys Gly Leu Glu Trp Val
        35                  40                  45

Ala Val Ile Ser Tyr Asp Gly Ser Asn Arg Tyr Tyr Ala Asp Ser Val
    50                  55                  60

Lys Gly Arg Phe Thr Ile Ser Arg Asp Asn Ser Lys Asn Thr Leu Tyr
65                  70                  75                  80

Leu Gln Met Asn Ser Leu Arg Pro Glu Asp Thr Ala Val Tyr Tyr Cys
                85                  90                  95

Ala Lys Glu Arg Ile Phe Gly Val Leu Thr Pro Asp Asp Phe Asp Ile
            100                 105                 110

Trp Gly Gln Gly Thr Thr Val Thr Val Ser Ser
        115                 120

<210> SEQ ID NO 285
<211> LENGTH: 5
<212> TYPE: PRT
<213> ORGANISM: Homo sapiens

<400> SEQUENCE: 285

Ser Tyr Gly Met His
1               5
```

```
<210> SEQ ID NO 286
<211> LENGTH: 17
<212> TYPE: PRT
<213> ORGANISM: Homo sapiens

<400> SEQUENCE: 286

Val Ile Ser Tyr Asp Gly Ala Asn Arg Tyr Tyr Ala Asp Ser Val Lys
1               5                   10                  15

Gly

<210> SEQ ID NO 287
<211> LENGTH: 14
<212> TYPE: PRT
<213> ORGANISM: Homo sapiens

<400> SEQUENCE: 287

Glu Arg Ile Phe Gly Val Leu Thr Pro Asp Asp Phe Glu Ile
1               5                   10

<210> SEQ ID NO 288
<211> LENGTH: 123
<212> TYPE: PRT
<213> ORGANISM: Homo sapiens

<400> SEQUENCE: 288

Glu Val Gln Leu Leu Glu Ser Gly Gly Val Val Gln Pro Gly Arg
1               5                   10                  15

Ser Leu Arg Leu Ser Cys Ala Ala Ser Gly Phe Pro Phe Ile Ser Tyr
                20                  25                  30

Gly Met His Trp Val Arg Gln Ala Pro Gly Lys Gly Leu Glu Trp Val
            35                  40                  45

Ala Val Ile Ser Tyr Asp Gly Ala Asn Arg Tyr Tyr Ala Asp Ser Val
        50                  55                  60

Lys Gly Arg Phe Thr Ile Ser Arg Asp Asn Ser Lys Asn Thr Leu Tyr
65                  70                  75                  80

Leu Gln Met Asn Ser Leu Arg Pro Glu Asp Thr Ala Val Tyr Tyr Cys
                85                  90                  95

Ala Lys Glu Arg Ile Phe Gly Val Leu Thr Pro Asp Asp Phe Glu Ile
            100                 105                 110

Trp Gly Gln Gly Thr Thr Val Thr Val Ser Ser
        115                 120

<210> SEQ ID NO 289
<211> LENGTH: 5
<212> TYPE: PRT
<213> ORGANISM: Homo sapiens

<400> SEQUENCE: 289

Ser Tyr Gly Met His
1               5

<210> SEQ ID NO 290
<211> LENGTH: 17
<212> TYPE: PRT
<213> ORGANISM: Homo sapiens

<400> SEQUENCE: 290

Val Ile Ser Tyr Asp Gly Ser Asn Arg Tyr Tyr Ala Asp Ser Val Lys
1               5                   10                  15

Gly
```

```
<210> SEQ ID NO 291
<211> LENGTH: 14
<212> TYPE: PRT
<213> ORGANISM: Homo sapiens

<400> SEQUENCE: 291

Glu Arg Ile Phe Gly Ala Leu Thr Pro Asp Asp Phe Asp Ile
1               5                   10

<210> SEQ ID NO 292
<211> LENGTH: 123
<212> TYPE: PRT
<213> ORGANISM: Homo sapiens

<400> SEQUENCE: 292

Glu Val Gln Leu Val Glu Ser Gly Gly Val Val Gln Pro Gly Arg
1               5                   10                  15

Ser Leu Arg Leu Ser Cys Ala Ala Ser Gly Phe Thr Phe Thr Ser Tyr
            20                  25                  30

Gly Met His Trp Val Arg Gln Ala Pro Gly Lys Gly Leu Glu Trp Val
        35                  40                  45

Ala Val Ile Ser Tyr Asp Gly Ser Asn Arg Tyr Tyr Ala Asp Ser Val
    50                  55                  60

Lys Gly Arg Phe Thr Ile Ser Arg Asp Asn Ser Lys Asn Thr Leu Tyr
65                  70                  75                  80

Leu Gln Met Asn Ser Leu Arg Pro Glu Asp Thr Ala Val Tyr Tyr Cys
                85                  90                  95

Ala Lys Glu Arg Ile Phe Gly Ala Leu Thr Pro Asp Asp Phe Asp Ile
            100                 105                 110

Trp Gly Gln Gly Thr Thr Val Thr Val Ser Ser
        115                 120

<210> SEQ ID NO 293
<211> LENGTH: 5
<212> TYPE: PRT
<213> ORGANISM: Homo sapiens

<400> SEQUENCE: 293

Asn Tyr Gly Met His
1               5

<210> SEQ ID NO 294
<211> LENGTH: 17
<212> TYPE: PRT
<213> ORGANISM: Homo sapiens

<400> SEQUENCE: 294

Ile Ile Ser Tyr Asp Gly Asn Thr Lys Tyr Tyr Thr Asp Ser Val Lys
1               5                   10                  15

Gly

<210> SEQ ID NO 295
<211> LENGTH: 7
<212> TYPE: PRT
<213> ORGANISM: Homo sapiens

<400> SEQUENCE: 295

Gly Leu Trp Pro Ser Asp Val
1               5
```

-continued

```
<210> SEQ ID NO 296
<211> LENGTH: 116
<212> TYPE: PRT
<213> ORGANISM: Homo sapiens

<400> SEQUENCE: 296
```

Gln Val Gln Leu Val Glu Ser Gly Gly Gly Val Val Gln Pro Gly Arg
1               5                   10                  15

Ser Leu Arg Leu Ser Cys Ala Ala Ser Gly Phe Thr Phe Asn Asn Tyr
            20                  25                  30

Gly Met His Trp Val Arg Gln Ala Pro Gly Lys Gly Leu Glu Trp Val
        35                  40                  45

Ala Ile Ile Ser Tyr Asp Gly Asn Thr Lys Tyr Tyr Thr Asp Ser Val
    50                  55                  60

Lys Gly Arg Phe Thr Ile Ser Arg Asp Asn Ser Lys Asn Thr Leu Tyr
65                  70                  75                  80

Leu Gln Met Asn Ser Leu Arg Val Glu Asp Thr Ala Val Tyr Tyr Cys
                85                  90                  95

Ala Lys Gly Leu Trp Pro Ser Asp Val Trp Gly Gln Gly Thr Thr Val
            100                 105                 110

Thr Val Ser Ser
        115

```
<210> SEQ ID NO 297
<211> LENGTH: 5
<212> TYPE: PRT
<213> ORGANISM: Homo sapiens

<400> SEQUENCE: 297
```

Asn Tyr Gly Met His
1               5

```
<210> SEQ ID NO 298
<211> LENGTH: 17
<212> TYPE: PRT
<213> ORGANISM: Homo sapiens

<400> SEQUENCE: 298
```

Ile Ile Ser Tyr Asp Gly Asn Ser Lys Tyr Tyr Thr Asp Ser Val Lys
1               5                   10                  15

Gly

```
<210> SEQ ID NO 299
<211> LENGTH: 7
<212> TYPE: PRT
<213> ORGANISM: Homo sapiens

<400> SEQUENCE: 299
```

Gly Leu Trp Pro Ser Asp Val
1               5

```
<210> SEQ ID NO 300
<211> LENGTH: 116
<212> TYPE: PRT
<213> ORGANISM: Homo sapiens

<400> SEQUENCE: 300
```

Glu Val Gln Leu Val Glu Ser Gly Gly Gly Val Val Gln Pro Gly Arg
1               5                   10                  15

Ser Leu Arg Leu Ser Cys Ala Ala Ser Gly Phe Thr Phe Asn Asn Tyr
            20                  25                  30

```
Gly Met His Trp Val Arg Gln Ala Pro Gly Lys Gly Leu Glu Trp Val
            35                  40                  45

Ala Ile Ile Ser Tyr Asp Gly Asn Ser Lys Tyr Tyr Thr Asp Ser Val
 50                  55                  60

Lys Gly Arg Phe Thr Ile Ser Arg Asp Asn Ser Lys Asn Thr Leu Tyr
 65                  70                  75                  80

Leu Gln Met Asn Ser Leu Arg Val Glu Asp Thr Ala Val Tyr Tyr Cys
                85                  90                  95

Ala Lys Gly Leu Trp Pro Ser Asp Val Trp Gly Gln Gly Thr Thr Val
            100                 105                 110

Thr Val Ser Ser
        115
```

<210> SEQ ID NO 301
<211> LENGTH: 7
<212> TYPE: PRT
<213> ORGANISM: Homo sapiens

<400> SEQUENCE: 301

```
Asn Ser Gly Tyr Tyr Trp Ser
 1               5
```

<210> SEQ ID NO 302
<211> LENGTH: 16
<212> TYPE: PRT
<213> ORGANISM: Homo sapiens

<400> SEQUENCE: 302

```
Phe Ile Tyr Tyr Asn Gly Ser Ile His Tyr Asn Pro Ser Leu Lys Ser
 1               5                  10                  15
```

<210> SEQ ID NO 303
<211> LENGTH: 8
<212> TYPE: PRT
<213> ORGANISM: Homo sapiens

<400> SEQUENCE: 303

```
Asp Gly Asp Asp Tyr Gly Asp Tyr
 1               5
```

<210> SEQ ID NO 304
<211> LENGTH: 119
<212> TYPE: PRT
<213> ORGANISM: Homo sapiens

<400> SEQUENCE: 304

```
Gln Val Gln Leu Gln Glu Ser Gly Pro Gly Leu Val Lys Pro Ser Gln
 1               5                  10                  15

Thr Leu Ser Leu Thr Cys Thr Val Ser Gly Gly Ser Ile Ser Asn Ser
            20                  25                  30

Gly Tyr Tyr Trp Ser Trp Val Arg Gln His Pro Gly Lys Asp Leu Glu
        35                  40                  45

Trp Ile Gly Phe Ile Tyr Tyr Asn Gly Ser Ile His Tyr Asn Pro Ser
 50                  55                  60

Leu Lys Ser Arg Val Ile Ile Ser Val Asp Thr Ser Lys Asn Gln Phe
 65                  70                  75                  80

Ser Leu Lys Met Asn Ser Val Thr Ala Ala Asp Thr Ala Val Tyr Tyr
                85                  90                  95

Cys Ala Arg Asp Gly Asp Asp Tyr Gly Asp Tyr Leu Arg Gly Gln Gly
```

```
                    100                 105                 110

Thr Leu Val Thr Val Ser Ser
            115

<210> SEQ ID NO 305
<211> LENGTH: 7
<212> TYPE: PRT
<213> ORGANISM: Homo sapiens

<400> SEQUENCE: 305

Asn Ser Gly Tyr Tyr Trp Ser
1               5

<210> SEQ ID NO 306
<211> LENGTH: 16
<212> TYPE: PRT
<213> ORGANISM: Homo sapiens

<400> SEQUENCE: 306

Phe Ile Tyr Tyr Asn Gly Ser Ile His Tyr Asn Pro Ser Leu Lys Ser
1               5                   10                  15

<210> SEQ ID NO 307
<211> LENGTH: 8
<212> TYPE: PRT
<213> ORGANISM: Homo sapiens

<400> SEQUENCE: 307

Asp Gly Asp Asp Tyr Gly Asp Tyr
1               5

<210> SEQ ID NO 308
<211> LENGTH: 119
<212> TYPE: PRT
<213> ORGANISM: Homo sapiens

<400> SEQUENCE: 308

Gln Val Gln Leu Gln Glu Ser Gly Pro Gly Leu Val Lys Pro Ser Gln
1               5                   10                  15

Thr Leu Ser Leu Thr Cys Thr Val Ser Gly Gly Ser Ile Ser Asn Ser
            20                  25                  30

Gly Tyr Tyr Trp Ser Trp Ile Arg Gln His Pro Gly Lys Gly Leu Glu
        35                  40                  45

Trp Ile Gly Phe Ile Tyr Tyr Asn Gly Ser Ile His Tyr Asn Pro Ser
    50                  55                  60

Leu Lys Ser Arg Val Ile Ile Ser Val Asp Thr Ser Lys Asn Gln Phe
65                  70                  75                  80

Ser Leu Lys Met Ser Ser Val Thr Ala Ala Asp Thr Ala Val Tyr Tyr
                85                  90                  95

Cys Ala Arg Asp Gly Asp Asp Tyr Gly Asp Tyr Leu Arg Gly Gln Gly
            100                 105                 110

Thr Leu Val Thr Val Ser Ser
            115

<210> SEQ ID NO 309
<211> LENGTH: 7
<212> TYPE: PRT
<213> ORGANISM: Homo sapiens

<400> SEQUENCE: 309

Asn Ser Gly Tyr Tyr Trp Ser
```

<210> SEQ ID NO 310
<211> LENGTH: 16
<212> TYPE: PRT
<213> ORGANISM: Homo sapiens

<400> SEQUENCE: 310

Phe Ile Tyr Tyr Asn Gly Ser Ile His Tyr Asn Pro Ser Leu Lys Ser
1               5                   10                  15

<210> SEQ ID NO 311
<211> LENGTH: 8
<212> TYPE: PRT
<213> ORGANISM: Homo sapiens

<400> SEQUENCE: 311

Asp Gly Asp Asp Tyr Gly Asp Tyr
1               5

<210> SEQ ID NO 312
<211> LENGTH: 119
<212> TYPE: PRT
<213> ORGANISM: Homo sapiens

<400> SEQUENCE: 312

Gln Val Gln Leu Gln Glu Ser Gly Pro Gly Leu Val Lys Pro Ser Gln
1               5                   10                  15

Thr Leu Ser Leu Thr Cys Thr Val Ser Gly Gly Ser Ile Ser Asn Ser
            20                  25                  30

Gly Tyr Tyr Trp Ser Trp Val Arg Gln His Pro Gly Lys Gly Leu Glu
        35                  40                  45

Trp Ile Gly Phe Ile Tyr Tyr Asn Gly Ser Ile His Tyr Asn Pro Ser
    50                  55                  60

Leu Lys Ser Arg Val Ile Ile Ser Val Asp Thr Ser Lys Asn Gln Phe
65                  70                  75                  80

Ser Leu Lys Leu Asn Ser Val Thr Ala Ala Asp Thr Ala Val Tyr Tyr
                85                  90                  95

Cys Ala Arg Asp Gly Asp Asp Tyr Gly Asp Tyr Leu Arg Gly Gln Gly
            100                 105                 110

Thr Leu Val Thr Val Ser Ser
        115

<210> SEQ ID NO 313
<211> LENGTH: 7
<212> TYPE: PRT
<213> ORGANISM: Homo sapiens

<400> SEQUENCE: 313

Asn Ser Gly Tyr Tyr Trp Ser
1               5

<210> SEQ ID NO 314
<211> LENGTH: 16
<212> TYPE: PRT
<213> ORGANISM: Homo sapiens

<400> SEQUENCE: 314

Phe Ile Tyr Tyr Asn Gly Ser Ile His Tyr Asn Pro Ser Leu Lys Ser
1               5                   10                  15

```
<210> SEQ ID NO 315
<211> LENGTH: 8
<212> TYPE: PRT
<213> ORGANISM: Homo sapiens

<400> SEQUENCE: 315

Asp Gly Asp Asp Tyr Gly Asp Tyr
1               5

<210> SEQ ID NO 316
<211> LENGTH: 119
<212> TYPE: PRT
<213> ORGANISM: Homo sapiens

<400> SEQUENCE: 316

Gln Val Gln Leu Gln Glu Ser Gly Pro Gly Leu Val Lys Pro Ser Gln
1               5                   10                  15

Thr Leu Ser Leu Thr Cys Thr Val Ser Gly Gly Ser Ile Ser Asn Ser
            20                  25                  30

Gly Tyr Tyr Trp Ser Trp Ile Arg Gln His Pro Gly Lys Gly Leu Glu
        35                  40                  45

Trp Ile Gly Phe Ile Tyr Tyr Asn Gly Ser Ile His Tyr Asn Pro Ser
    50                  55                  60

Leu Lys Ser Arg Val Ile Ile Ser Val Asp Thr Ser Lys Asn Gln Phe
65                  70                  75                  80

Ser Leu Lys Leu Ser Ser Val Thr Ala Ala Asp Thr Ala Val Tyr Tyr
                85                  90                  95

Cys Ala Arg Asp Gly Asp Asp Tyr Gly Asp Tyr Leu Arg Gly Gln Gly
            100                 105                 110

Thr Leu Val Thr Val Ser Ser
        115

<210> SEQ ID NO 317
<211> LENGTH: 7
<212> TYPE: PRT
<213> ORGANISM: Homo sapiens

<400> SEQUENCE: 317

Asn Ser Gly Tyr Tyr Trp Ser
1               5

<210> SEQ ID NO 318
<211> LENGTH: 16
<212> TYPE: PRT
<213> ORGANISM: Homo sapiens

<400> SEQUENCE: 318

Phe Ile Tyr Tyr Asn Gly Ser Ile His Tyr Asn Pro Ser Leu Lys Ser
1               5                   10                  15

<210> SEQ ID NO 319
<211> LENGTH: 8
<212> TYPE: PRT
<213> ORGANISM: Homo sapiens

<400> SEQUENCE: 319

Asp Gly Asp Asp Tyr Gly Asp Tyr
1               5

<210> SEQ ID NO 320
<211> LENGTH: 119
<212> TYPE: PRT
```

<213> ORGANISM: Homo sapiens

<400> SEQUENCE: 320

Gln Val Gln Leu Gln Glu Ser Gly Pro Gly Leu Val Lys Pro Ser Gln
1               5                   10                  15

Thr Leu Ser Leu Thr Cys Thr Val Ser Gly Gly Ser Ile Ser Asn Ser
            20                  25                  30

Gly Tyr Tyr Trp Ser Trp Val Arg Gln His Pro Gly Lys Gly Leu Glu
        35                  40                  45

Trp Ile Gly Phe Ile Tyr Tyr Asn Gly Ser Ile His Tyr Asn Pro Ser
    50                  55                  60

Leu Lys Ser Arg Val Thr Ile Ser Val Asp Thr Ser Lys Asn Gln Phe
65                  70                  75                  80

Ser Leu Lys Met Ser Ser Val Thr Ala Ala Asp Thr Ala Val Tyr Tyr
            85                  90                  95

Cys Ala Arg Asp Gly Asp Asp Tyr Gly Asp Tyr Leu Arg Gly Gln Gly
            100                 105                 110

Thr Leu Val Thr Val Ser Ser
        115

<210> SEQ ID NO 321
<211> LENGTH: 7
<212> TYPE: PRT
<213> ORGANISM: Homo sapiens

<400> SEQUENCE: 321

Asn Ser Gly Tyr Tyr Trp Ser
1               5

<210> SEQ ID NO 322
<211> LENGTH: 16
<212> TYPE: PRT
<213> ORGANISM: Homo sapiens

<400> SEQUENCE: 322

Phe Ile Tyr Tyr Asn Gly Ser Ile His Tyr Asn Pro Ser Leu Lys Ser
1               5                   10                  15

<210> SEQ ID NO 323
<211> LENGTH: 8
<212> TYPE: PRT
<213> ORGANISM: Homo sapiens

<400> SEQUENCE: 323

Asp Gly Asp Asp Tyr Gly Asp Tyr
1               5

<210> SEQ ID NO 324
<211> LENGTH: 119
<212> TYPE: PRT
<213> ORGANISM: Homo sapiens

<400> SEQUENCE: 324

Gln Val Gln Leu Gln Glu Ser Gly Pro Gly Leu Val Lys Pro Ser Gln
1               5                   10                  15

Thr Leu Ser Leu Thr Cys Thr Val Ser Gly Gly Ser Ile Ser Asn Ser
            20                  25                  30

Gly Tyr Tyr Trp Ser Trp Val Arg Gln His Pro Gly Lys Gly Leu Glu
        35                  40                  45

Trp Ile Gly Phe Ile Tyr Tyr Asn Gly Ser Ile His Tyr Asn Pro Ser

```
            50                  55                  60
Leu Lys Ser Arg Val Thr Ile Ser Val Asp Thr Ser Lys Asn Gln Phe
 65                  70                  75                  80

Ser Leu Lys Leu Asn Ser Val Thr Ala Ala Asp Thr Ala Val Tyr Tyr
                 85                  90                  95

Cys Ala Arg Asp Gly Asp Tyr Gly Asp Tyr Leu Arg Gly Gln Gly
                100                 105                 110

Thr Leu Val Thr Val Ser Ser
            115

<210> SEQ ID NO 325
<211> LENGTH: 7
<212> TYPE: PRT
<213> ORGANISM: Homo sapiens

<400> SEQUENCE: 325

Asn Ser Gly Tyr Tyr Trp Ser
1               5

<210> SEQ ID NO 326
<211> LENGTH: 16
<212> TYPE: PRT
<213> ORGANISM: Homo sapiens

<400> SEQUENCE: 326

Phe Ile Tyr Tyr Asn Gly Ser Ile His Tyr Asn Pro Ser Leu Lys Ser
1               5                   10                  15

<210> SEQ ID NO 327
<211> LENGTH: 8
<212> TYPE: PRT
<213> ORGANISM: Homo sapiens

<400> SEQUENCE: 327

Asp Gly Asp Asp Tyr Gly Asp Tyr
1               5

<210> SEQ ID NO 328
<211> LENGTH: 119
<212> TYPE: PRT
<213> ORGANISM: Homo sapiens

<400> SEQUENCE: 328

Gln Val Gln Leu Gln Glu Ser Gly Pro Gly Leu Val Lys Pro Ser Gln
1               5                   10                  15

Thr Leu Ser Leu Thr Cys Thr Val Ser Gly Gly Ser Ile Ser Asn Ser
                20                  25                  30

Gly Tyr Tyr Trp Ser Trp Val Arg Gln His Pro Gly Lys Gly Leu Glu
            35                  40                  45

Trp Ile Gly Phe Ile Tyr Tyr Asn Gly Ser Ile His Tyr Asn Pro Ser
 50                  55                  60

Leu Lys Ser Arg Val Thr Ile Ser Val Asp Thr Ser Lys Asn Gln Phe
 65                  70                  75                  80

Ser Leu Lys Leu Ser Ser Val Thr Ala Ala Asp Thr Ala Val Tyr Tyr
                 85                  90                  95

Cys Ala Arg Asp Gly Asp Asp Tyr Gly Asp Tyr Leu Arg Gly Gln Gly
                100                 105                 110

Thr Leu Val Thr Val Ser Ser
            115
```

<210> SEQ ID NO 329
<211> LENGTH: 5
<212> TYPE: PRT
<213> ORGANISM: Homo sapiens

<400> SEQUENCE: 329

Ser Tyr Trp Met Tyr
1               5

<210> SEQ ID NO 330
<211> LENGTH: 17
<212> TYPE: PRT
<213> ORGANISM: Homo sapiens

<400> SEQUENCE: 330

Asn Ile Asn His Asp Gly Ser Glu Lys Tyr Tyr Val Asp Ser Val Lys
1               5                   10                  15

Gly

<210> SEQ ID NO 331
<211> LENGTH: 10
<212> TYPE: PRT
<213> ORGANISM: Homo sapiens

<400> SEQUENCE: 331

Asp Ser Leu Ile Val Gly Glu Arg Gly Tyr
1               5                   10

<210> SEQ ID NO 332
<211> LENGTH: 119
<212> TYPE: PRT
<213> ORGANISM: Homo sapiens

<400> SEQUENCE: 332

Glu Val Gln Leu Val Glu Ser Gly Gly Leu Val Gln Pro Gly Gly
1               5                   10                  15

Ser Leu Arg Leu Ser Cys Ala Ala Ser Gly Phe Thr Phe Ser Ser Tyr
                20                  25                  30

Trp Met Tyr Trp Val Arg Gln Ala Pro Gly Lys Gly Leu Glu Trp Val
            35                  40                  45

Ala Asn Ile Asn His Asp Gly Ser Glu Lys Tyr Tyr Val Asp Ser Val
        50                  55                  60

Lys Gly Arg Phe Thr Ile Ser Arg Asp Asn Ala Lys Asn Ser Leu Tyr
65                  70                  75                  80

Leu Gln Met Asn Ser Leu Arg Ala Glu Asp Thr Ala Val Tyr Tyr Cys
                85                  90                  95

Ala Arg Asp Ser Leu Ile Val Gly Glu Arg Gly Tyr Trp Gly Gln Gly
            100                 105                 110

Thr Leu Val Thr Val Ser Ser
        115

<210> SEQ ID NO 333
<211> LENGTH: 5
<212> TYPE: PRT
<213> ORGANISM: Homo sapiens

<400> SEQUENCE: 333

Ser Tyr Trp Met Tyr
1               5

```
<210> SEQ ID NO 334
<211> LENGTH: 17
<212> TYPE: PRT
<213> ORGANISM: Homo sapiens

<400> SEQUENCE: 334

Asn Ile Asn His Asp Gly Ser Glu Lys Tyr Tyr Val Asp Ser Val Lys
1               5                   10                  15

Gly

<210> SEQ ID NO 335
<211> LENGTH: 10
<212> TYPE: PRT
<213> ORGANISM: Homo sapiens

<400> SEQUENCE: 335

Asp Asn Leu Ile Val Gly Glu Arg Gly Tyr
1               5                   10

<210> SEQ ID NO 336
<211> LENGTH: 119
<212> TYPE: PRT
<213> ORGANISM: Homo sapiens

<400> SEQUENCE: 336

Glu Val Gln Leu Val Glu Ser Gly Gly Leu Val Gln Pro Gly Gly
1               5                   10                  15

Ser Leu Arg Leu Ser Cys Ala Ala Ser Gly Phe Thr Phe Ser Ser Tyr
                20                  25                  30

Trp Met Tyr Trp Val Arg Gln Ala Pro Gly Lys Gly Leu Glu Trp Val
            35                  40                  45

Ala Asn Ile Asn His Asp Gly Ser Glu Lys Tyr Tyr Val Asp Ser Val
        50                  55                  60

Lys Gly Arg Phe Thr Ile Ser Arg Asp Asn Ala Lys Asn Ser Leu Tyr
65                  70                  75                  80

Leu Gln Met Asn Ser Leu Arg Ala Glu Asp Thr Ala Val Tyr Tyr Cys
                85                  90                  95

Ala Arg Asp Asn Leu Ile Val Gly Glu Arg Gly Tyr Trp Gly Gln Gly
            100                 105                 110

Thr Leu Val Thr Val Ser Ser
        115

<210> SEQ ID NO 337
<211> LENGTH: 5
<212> TYPE: PRT
<213> ORGANISM: Homo sapiens

<400> SEQUENCE: 337

Ser Tyr Trp Met Tyr
1               5

<210> SEQ ID NO 338
<211> LENGTH: 17
<212> TYPE: PRT
<213> ORGANISM: Homo sapiens

<400> SEQUENCE: 338

Asn Ile Asn His Gly Gly Ser Glu Lys Tyr Tyr Val Asp Ser Val Lys
1               5                   10                  15

Gly
```

<210> SEQ ID NO 339
<211> LENGTH: 10
<212> TYPE: PRT
<213> ORGANISM: Homo sapiens

<400> SEQUENCE: 339

Asp Ser Leu Ile Val Gly Glu Arg Gly Tyr
1               5                   10

<210> SEQ ID NO 340
<211> LENGTH: 119
<212> TYPE: PRT
<213> ORGANISM: Homo sapiens

<400> SEQUENCE: 340

Glu Val Gln Leu Val Glu Ser Gly Gly Gly Leu Val Gln Pro Gly Gly
1               5                   10                  15

Ser Leu Arg Leu Ser Cys Ala Ala Ser Gly Phe Thr Phe Ser Ser Tyr
            20                  25                  30

Trp Met Tyr Trp Val Arg Gln Ala Pro Gly Lys Gly Leu Glu Trp Val
        35                  40                  45

Ala Asn Ile Asn His Gly Gly Ser Glu Lys Tyr Tyr Val Asp Ser Val
    50                  55                  60

Lys Gly Arg Phe Thr Ile Ser Arg Asp Asn Ala Lys Asn Ser Leu Tyr
65                  70                  75                  80

Leu Gln Met Asn Ser Leu Arg Ala Glu Asp Thr Ala Val Tyr Tyr Cys
                85                  90                  95

Ala Arg Asp Ser Leu Ile Val Gly Glu Arg Gly Tyr Trp Gly Gln Gly
            100                 105                 110

Thr Leu Val Thr Val Ser Ser
        115

<210> SEQ ID NO 341
<211> LENGTH: 5
<212> TYPE: PRT
<213> ORGANISM: Homo sapiens

<400> SEQUENCE: 341

Ser Tyr Trp Met Tyr
1               5

<210> SEQ ID NO 342
<211> LENGTH: 17
<212> TYPE: PRT
<213> ORGANISM: Homo sapiens

<400> SEQUENCE: 342

Asn Ile Asn His Gln Gly Ser Glu Lys Tyr Tyr Val Asp Ser Val Lys
1               5                   10                  15

Gly

<210> SEQ ID NO 343
<211> LENGTH: 10
<212> TYPE: PRT
<213> ORGANISM: Homo sapiens

<400> SEQUENCE: 343

Asp Ser Leu Ile Val Gly Glu Arg Gly Tyr
1               5                   10

<210> SEQ ID NO 344
<211> LENGTH: 119
<212> TYPE: PRT
<213> ORGANISM: Homo sapiens

<400> SEQUENCE: 344

Glu Val Gln Leu Val Glu Ser Gly Gly Gly Leu Val Gln Pro Gly Gly
1               5                   10                  15

Ser Leu Arg Leu Ser Cys Ala Ala Ser Gly Phe Thr Phe Ser Ser Tyr
            20                  25                  30

Trp Met Tyr Trp Val Arg Gln Ala Pro Gly Lys Gly Leu Glu Trp Val
        35                  40                  45

Ala Asn Ile Asn His Gln Gly Ser Glu Lys Tyr Tyr Val Asp Ser Val
    50                  55                  60

Lys Gly Arg Phe Thr Ile Ser Arg Asp Asn Ala Lys Asn Ser Leu Tyr
65                  70                  75                  80

Leu Gln Met Asn Ser Leu Arg Ala Glu Asp Thr Ala Val Tyr Tyr Cys
                85                  90                  95

Ala Arg Asp Ser Leu Ile Val Gly Glu Arg Gly Tyr Trp Gly Gln Gly
            100                 105                 110

Thr Leu Val Thr Val Ser Ser
        115

<210> SEQ ID NO 345
<211> LENGTH: 5
<212> TYPE: PRT
<213> ORGANISM: Homo sapiens

<400> SEQUENCE: 345

Ser Tyr Trp Met Tyr
1               5

<210> SEQ ID NO 346
<211> LENGTH: 17
<212> TYPE: PRT
<213> ORGANISM: Homo sapiens

<400> SEQUENCE: 346

Asn Ile Asn His Pro Gly Ser Glu Lys Tyr Tyr Val Asp Ser Val Lys
1               5                   10                  15

Gly

<210> SEQ ID NO 347
<211> LENGTH: 10
<212> TYPE: PRT
<213> ORGANISM: Homo sapiens

<400> SEQUENCE: 347

Asp Ser Leu Ile Val Gly Glu Arg Gly Tyr
1               5                   10

<210> SEQ ID NO 348
<211> LENGTH: 119
<212> TYPE: PRT
<213> ORGANISM: Homo sapiens

<400> SEQUENCE: 348

Glu Val Gln Leu Val Glu Ser Gly Gly Gly Leu Val Gln Pro Gly Gly
1               5                   10                  15

Ser Leu Arg Leu Ser Cys Ala Ala Ser Gly Phe Thr Phe Ser Ser Tyr
            20                  25                  30

Trp Met Tyr Trp Val Arg Gln Ala Pro Gly Lys Gly Leu Glu Trp Val
            35                  40                  45

Ala Asn Ile Asn His Pro Gly Ser Glu Lys Tyr Tyr Val Asp Ser Val
    50                  55                  60

Lys Gly Arg Phe Thr Ile Ser Arg Asp Asn Ala Lys Asn Ser Leu Tyr
65                  70                  75                  80

Leu Gln Met Asn Ser Leu Arg Ala Glu Asp Thr Ala Val Tyr Tyr Cys
                85                  90                  95

Ala Arg Asp Ser Leu Ile Val Gly Glu Arg Gly Tyr Trp Gly Gln Gly
                100                 105                 110

Thr Leu Val Thr Val Ser Ser
            115

<210> SEQ ID NO 349
<211> LENGTH: 5
<212> TYPE: PRT
<213> ORGANISM: Homo sapiens

<400> SEQUENCE: 349

Ser Tyr Trp Met Tyr
1               5

<210> SEQ ID NO 350
<211> LENGTH: 17
<212> TYPE: PRT
<213> ORGANISM: Homo sapiens

<400> SEQUENCE: 350

Asn Ile Asn His Glu Gly Ser Glu Lys Tyr Tyr Val Asp Ser Val Lys
1               5                   10                  15

Gly

<210> SEQ ID NO 351
<211> LENGTH: 10
<212> TYPE: PRT
<213> ORGANISM: Homo sapiens

<400> SEQUENCE: 351

Asp Ser Leu Ile Val Gly Glu Arg Gly Tyr
1               5                   10

<210> SEQ ID NO 352
<211> LENGTH: 119
<212> TYPE: PRT
<213> ORGANISM: Homo sapiens

<400> SEQUENCE: 352

Glu Val Gln Leu Val Glu Ser Gly Gly Gly Leu Val Gln Pro Gly Gly
1               5                   10                  15

Ser Leu Arg Leu Ser Cys Ala Ala Ser Gly Phe Thr Phe Ser Ser Tyr
            20                  25                  30

Trp Met Tyr Trp Val Arg Gln Ala Pro Gly Lys Gly Leu Glu Trp Val
            35                  40                  45

Ala Asn Ile Asn His Glu Gly Ser Glu Lys Tyr Tyr Val Asp Ser Val
    50                  55                  60

Lys Gly Arg Phe Thr Ile Ser Arg Asp Asn Ala Lys Asn Ser Leu Tyr
65                  70                  75                  80

Leu Gln Met Asn Ser Leu Arg Ala Glu Asp Thr Ala Val Tyr Tyr Cys
                85                  90                  95

Ala Arg Asp Ser Leu Ile Val Gly Glu Arg Gly Tyr Trp Gly Gln Gly
            100                 105                 110

Thr Leu Val Thr Val Ser Ser
        115

<210> SEQ ID NO 353
<211> LENGTH: 5
<212> TYPE: PRT
<213> ORGANISM: Homo sapiens

<400> SEQUENCE: 353

Ser Tyr Trp Met Tyr
1               5

<210> SEQ ID NO 354
<211> LENGTH: 17
<212> TYPE: PRT
<213> ORGANISM: Homo sapiens

<400> SEQUENCE: 354

Asn Ile Asn His Ile Gly Ser Glu Lys Tyr Tyr Val Asp Ser Val Lys
1               5                   10                  15

Gly

<210> SEQ ID NO 355
<211> LENGTH: 10
<212> TYPE: PRT
<213> ORGANISM: Homo sapiens

<400> SEQUENCE: 355

Asp Ser Leu Ile Val Gly Glu Arg Gly Tyr
1               5                   10

<210> SEQ ID NO 356
<211> LENGTH: 119
<212> TYPE: PRT
<213> ORGANISM: Homo sapiens

<400> SEQUENCE: 356

Glu Val Gln Leu Val Glu Ser Gly Gly Gly Leu Val Gln Pro Gly Gly
1               5                   10                  15

Ser Leu Arg Leu Ser Cys Ala Ala Ser Gly Phe Thr Phe Ser Ser Tyr
            20                  25                  30

Trp Met Tyr Trp Val Arg Gln Ala Pro Gly Lys Gly Leu Glu Trp Val
        35                  40                  45

Ala Asn Ile Asn His Ile Gly Ser Glu Lys Tyr Tyr Val Asp Ser Val
    50                  55                  60

Lys Gly Arg Phe Thr Ile Ser Arg Asp Asn Ala Lys Asn Ser Leu Tyr
65                  70                  75                  80

Leu Gln Met Asn Ser Leu Arg Ala Glu Asp Thr Ala Val Tyr Tyr Cys
                85                  90                  95

Ala Arg Asp Ser Leu Ile Val Gly Glu Arg Gly Tyr Trp Gly Gln Gly
            100                 105                 110

Thr Leu Val Thr Val Ser Ser
        115

<210> SEQ ID NO 357
<211> LENGTH: 5
<212> TYPE: PRT
<213> ORGANISM: Homo sapiens

<400> SEQUENCE: 357

Ser Tyr Trp Met Tyr
1               5

<210> SEQ ID NO 358
<211> LENGTH: 17
<212> TYPE: PRT
<213> ORGANISM: Homo sapiens

<400> SEQUENCE: 358

Asn Ile Asn His Asp Gly Ser Glu Lys Tyr Tyr Val Asp Ser Val Lys
1               5                   10                  15

Gly

<210> SEQ ID NO 359
<211> LENGTH: 10
<212> TYPE: PRT
<213> ORGANISM: Homo sapiens

<400> SEQUENCE: 359

Asp Thr Leu Ile Val Gly Glu Arg Gly Tyr
1               5                   10

<210> SEQ ID NO 360
<211> LENGTH: 119
<212> TYPE: PRT
<213> ORGANISM: Homo sapiens

<400> SEQUENCE: 360

Glu Val Gln Leu Val Glu Ser Gly Gly Gly Leu Val Gln Pro Gly Gly
1               5                   10                  15

Ser Leu Arg Leu Ser Cys Ala Ala Ser Gly Phe Thr Phe Ser Ser Tyr
            20                  25                  30

Trp Met Tyr Trp Val Arg Gln Ala Pro Gly Lys Gly Leu Glu Trp Val
        35                  40                  45

Ala Asn Ile Asn His Asp Gly Ser Glu Lys Tyr Tyr Val Asp Ser Val
    50                  55                  60

Lys Gly Arg Phe Thr Ile Ser Arg Asp Asn Ala Lys Asn Ser Leu Tyr
65                  70                  75                  80

Leu Gln Met Asn Ser Leu Arg Ala Glu Asp Thr Ala Val Tyr Tyr Cys
                85                  90                  95

Ala Arg Asp Thr Leu Ile Val Gly Glu Arg Gly Tyr Trp Gly Gln Gly
            100                 105                 110

Thr Leu Val Thr Val Ser Ser
        115

<210> SEQ ID NO 361
<211> LENGTH: 5
<212> TYPE: PRT
<213> ORGANISM: Homo sapiens

<400> SEQUENCE: 361

Gly Tyr Tyr Trp Ser
1               5

<210> SEQ ID NO 362
<211> LENGTH: 16
<212> TYPE: PRT
<213> ORGANISM: Homo sapiens

<400> SEQUENCE: 362

Glu Ile Asn His Ser Gly Ser Thr Asn Tyr Asn Pro Ser Leu Lys Ser
1               5                   10                  15

<210> SEQ ID NO 363
<211> LENGTH: 13
<212> TYPE: PRT
<213> ORGANISM: Homo sapiens

<400> SEQUENCE: 363

Gly Pro Ile Pro Ala Thr Ala Ile Pro Asp Ala Phe Asp
1               5                   10

<210> SEQ ID NO 364
<211> LENGTH: 122
<212> TYPE: PRT
<213> ORGANISM: Homo sapiens

<400> SEQUENCE: 364

Gln Val Gln Leu Gln Gln Trp Gly Ala Gly Leu Leu Lys Pro Ser Glu
1               5                   10                  15

Thr Leu Ser Leu Thr Cys Ala Val Tyr Gly Gly Ser Phe Ser Gly Tyr
            20                  25                  30

Tyr Trp Ser Trp Ile Arg Gln Pro Pro Gly Lys Gly Leu Glu Trp Ile
        35                  40                  45

Gly Glu Ile Asn His Ser Gly Ser Thr Asn Tyr Asn Pro Ser Leu Lys
    50                  55                  60

Ser Arg Val Thr Ile Ser Val Asp Thr Ser Lys Asn Gln Phe Ser Leu
65                  70                  75                  80

Lys Leu Ser Ser Val Thr Ala Ala Asp Thr Ala Val Tyr Tyr Cys Ala
                85                  90                  95

Arg Gly Pro Ile Pro Ala Thr Ala Ile Pro Asp Ala Phe Asp Ile Trp
            100                 105                 110

Gly Gln Gly Thr Met Val Thr Val Ser Ser
        115                 120

<210> SEQ ID NO 365
<211> LENGTH: 5
<212> TYPE: PRT
<213> ORGANISM: Homo sapiens

<400> SEQUENCE: 365

Gly His Tyr Trp Ser
1               5

<210> SEQ ID NO 366
<211> LENGTH: 16
<212> TYPE: PRT
<213> ORGANISM: Homo sapiens

<400> SEQUENCE: 366

Asp Ile Asn His Ser Gly Ser Thr Asn Tyr Asn Pro Ser Leu Lys Ser
1               5                   10                  15

<210> SEQ ID NO 367
<211> LENGTH: 11
<212> TYPE: PRT
<213> ORGANISM: Homo sapiens

<400> SEQUENCE: 367

Asp Tyr Gly Asp Ser Arg Ser Leu Phe Asp Tyr

<210> SEQ ID NO 368
<211> LENGTH: 119
<212> TYPE: PRT
<213> ORGANISM: Homo sapiens

<400> SEQUENCE: 368

Gln Val Gln Leu Gln Gln Trp Gly Ala Gly Leu Leu Lys Pro Ser Glu
1               5                   10                  15
Thr Leu Ser Leu Thr Cys Ala Val Tyr Gly Gly Ser Phe Ser Gly His
            20                  25                  30
Tyr Trp Ser Trp Ile Arg Gln Pro Pro Gly Lys Gly Leu Glu Trp Ile
        35                  40                  45
Gly Asp Ile Asn His Ser Gly Ser Thr Asn Tyr Asn Pro Ser Leu Lys
    50                  55                  60
Ser Arg Val Thr Ile Ser Val Asp Thr Ser Lys Asn Gln Phe Ser Leu
65                  70                  75                  80
Lys Leu Ser Ser Val Thr Ala Ala Asp Thr Ala Val Tyr Tyr Cys Val
                85                  90                  95
Arg Asp Tyr Gly Asp Ser Arg Ser Leu Phe Asp Tyr Trp Gly Gln Gly
            100                 105                 110
Thr Leu Val Thr Val Ser Ser
        115

<210> SEQ ID NO 369
<211> LENGTH: 5
<212> TYPE: PRT
<213> ORGANISM: Homo sapiens

<400> SEQUENCE: 369

Ser Tyr Gly Met Tyr
1               5

<210> SEQ ID NO 370
<211> LENGTH: 17
<212> TYPE: PRT
<213> ORGANISM: Homo sapiens

<400> SEQUENCE: 370

Phe Met Ser Tyr Asp Gly Ser Asn Lys Tyr Tyr Val Asp Ser Val Lys
1               5                   10                  15
Gly

<210> SEQ ID NO 371
<211> LENGTH: 13
<212> TYPE: PRT
<213> ORGANISM: Homo sapiens

<400> SEQUENCE: 371

Gly Asp Tyr Asp Phe Trp Ser Gly Tyr Pro Asp Tyr Asp
1               5                   10

<210> SEQ ID NO 372
<211> LENGTH: 125
<212> TYPE: PRT
<213> ORGANISM: Homo sapiens

<400> SEQUENCE: 372

Gln Val Gln Leu Val Glu Ser Gly Gly Gly Leu Val Gln Pro Gly Gly
1               5                   10                  15

```
Ser Leu Arg Leu Ser Cys Ala Ala Ser Gly Phe Thr Phe Ser Ser Tyr
            20                  25                  30

Gly Met His Trp Val Arg Gln Ala Pro Gly Lys Gly Leu Glu Trp Val
            35                  40                  45

Ala Phe Met Ser Tyr Asp Gly Ser Asn Lys Tyr Tyr Val Asp Ser Val
 50                  55                  60

Lys Gly Arg Phe Thr Ile Ser Arg Asp Asn Ser Lys Asn Thr Leu Tyr
 65                  70                  75                  80

Leu Gln Met Asn Ser Leu Arg Ala Glu Asp Thr Ala Val Tyr Tyr Cys
                85                  90                  95

Ala Lys Gly Asp Tyr Asp Phe Trp Ser Gly Tyr Pro Asp Tyr Asp Met
               100                 105                 110

Asp Val Trp Gly Gln Gly Thr Thr Val Thr Val Ser Ser
           115                 120                 125

<210> SEQ ID NO 373
<211> LENGTH: 5
<212> TYPE: PRT
<213> ORGANISM: Homo sapiens

<400> SEQUENCE: 373

Ser Tyr Gly Met Tyr
 1               5

<210> SEQ ID NO 374
<211> LENGTH: 17
<212> TYPE: PRT
<213> ORGANISM: Homo sapiens

<400> SEQUENCE: 374

Val Ile Ser Tyr Asp Gly Ser Asn Lys Asn Tyr Ala Asp Ser Val Lys
 1               5                  10                  15

Gly

<210> SEQ ID NO 375
<211> LENGTH: 13
<212> TYPE: PRT
<213> ORGANISM: Homo sapiens

<400> SEQUENCE: 375

Gly Gly Asn Ala Leu Tyr Ser Ser Gly Trp Pro Asp Asp
 1               5                  10

<210> SEQ ID NO 376
<211> LENGTH: 126
<212> TYPE: PRT
<213> ORGANISM: Homo sapiens

<400> SEQUENCE: 376

Glu Val Gln Leu Val Glu Ser Gly Gly Gly Leu Val Lys Pro Gly Gly
 1               5                  10                  15

Ser Leu Arg Leu Ser Cys Ala Ala Ser Gly Phe Asn Leu Ile Ser Tyr
            20                  25                  30

Gly Met Tyr Trp Val Arg Gln Ala Pro Gly Lys Gly Leu Glu Trp Val
            35                  40                  45

Ala Val Ile Ser Tyr Asp Gly Ser Asn Lys Asn Tyr Ala Asp Ser Val
 50                  55                  60

Lys Gly Arg Phe Thr Ile Ser Arg Asp Asn Ser Lys Asn Thr Leu Phe
 65                  70                  75                  80
```

```
Leu Gln Met Asn Ser Leu Arg Val Glu Asp Thr Ala Val Tyr Tyr Cys
                85                  90                  95

Ala Lys Gly Gly Asn Ala Leu Tyr Ser Ser Gly Trp Pro Asp Asp Gly
            100                 105                 110

Phe Asp Ile Arg Gly Gln Gly Thr Met Val Thr Val Ser Ser
        115                 120                 125
```

<210> SEQ ID NO 377
<211> LENGTH: 5
<212> TYPE: PRT
<213> ORGANISM: Homo sapiens

<400> SEQUENCE: 377

```
Asn Phe Gly Met His
1               5
```

<210> SEQ ID NO 378
<211> LENGTH: 17
<212> TYPE: PRT
<213> ORGANISM: Homo sapiens

<400> SEQUENCE: 378

```
Val Ile Ser Tyr Asp Gly Asn Ser Lys Tyr Tyr Ala Asp Thr Val Lys
1               5                   10                  15

Gly
```

<210> SEQ ID NO 379
<211> LENGTH: 8
<212> TYPE: PRT
<213> ORGANISM: Homo sapiens

<400> SEQUENCE: 379

```
Gly Leu Trp Pro Pro Met Asp Val
1               5
```

<210> SEQ ID NO 380
<211> LENGTH: 117
<212> TYPE: PRT
<213> ORGANISM: Homo sapiens

<400> SEQUENCE: 380

```
Gln Val Gln Leu Val Glu Ser Gly Gly Gly Val Val Gln Pro Gly Arg
1               5                   10                  15

Ser Leu Arg Leu Ser Cys Ala Ala Ser Gly Phe Thr Phe Ser Asn Phe
            20                  25                  30

Gly Met His Trp Ala Arg Gln Ala Pro Gly Lys Gly Leu Glu Trp Val
        35                  40                  45

Ala Val Ile Ser Tyr Asp Gly Asn Ser Lys Tyr Tyr Ala Asp Thr Val
    50                  55                  60

Lys Gly Arg Phe Thr Ile Ser Arg Asp Asn Ser Lys Asn Thr Leu Tyr
65                  70                  75                  80

Leu Glu Met Asn Ser Leu Arg Ala Asp Asp Thr Ala Val Tyr Tyr Cys
                85                  90                  95

Ala Lys Gly Leu Trp Pro Pro Met Asp Val Arg Gly Gln Gly Thr Thr
            100                 105                 110

Val Thr Val Ser Ser
        115
```

<210> SEQ ID NO 381

```
<211> LENGTH: 5
<212> TYPE: PRT
<213> ORGANISM: Homo sapiens

<400> SEQUENCE: 381

Asp Tyr Trp Met Thr
1               5

<210> SEQ ID NO 382
<211> LENGTH: 17
<212> TYPE: PRT
<213> ORGANISM: Homo sapiens

<400> SEQUENCE: 382

Asn Ile Lys Gln Asp Gly Ser Glu Lys Tyr Tyr Val Asp Ser Val Lys
1               5                  10                  15

Gly

<210> SEQ ID NO 383
<211> LENGTH: 15
<212> TYPE: PRT
<213> ORGANISM: Homo sapiens

<400> SEQUENCE: 383

Asp Arg Gly Gly Ala Val Ala Leu Tyr His Asn Gly Met Asp Met
1               5                   10                  15

<210> SEQ ID NO 384
<211> LENGTH: 124
<212> TYPE: PRT
<213> ORGANISM: Homo sapiens

<400> SEQUENCE: 384

Glu Val Gln Leu Val Glu Ser Gly Gly Gly Ser Val Gln Pro Gly Gly
1               5                   10                  15

Ser Leu Arg Leu Ser Cys Ala Ala Ser Gly Phe Thr Phe Ser Asp Tyr
            20                  25                  30

Trp Met Thr Trp Val Arg Gln Val Pro Gly Lys Gly Leu Glu Trp Val
        35                  40                  45

Ala Asn Ile Lys Gln Asp Gly Ser Glu Lys Tyr Tyr Val Asp Ser Val
    50                  55                  60

Lys Gly Arg Phe Thr Ile Ser Arg Asp Asn Ala Lys Asn Ser Leu Tyr
65                  70                  75                  80

Leu Gln Met Asn Ser Leu Arg Ala Glu Asp Thr Ala Val Tyr Tyr Cys
                85                  90                  95

Ala Arg Asp Arg Gly Gly Ala Val Ala Leu Tyr His Asn Gly Met Asp
            100                 105                 110

Met Gly Gly Gln Gly Thr Thr Val Thr Val Ser Ser
        115                 120

<210> SEQ ID NO 385
<211> LENGTH: 5
<212> TYPE: PRT
<213> ORGANISM: Homo sapiens

<400> SEQUENCE: 385

Ser Tyr Asp Ile Asn
1               5

<210> SEQ ID NO 386
<211> LENGTH: 17
```

```
<212> TYPE: PRT
<213> ORGANISM: Homo sapiens

<400> SEQUENCE: 386

Trp Met Asn Pro Asn Ser Gly Asn Thr Gly Tyr Ala Gln Lys Phe Gln
1               5                   10                  15

Gly

<210> SEQ ID NO 387
<211> LENGTH: 12
<212> TYPE: PRT
<213> ORGANISM: Homo sapiens

<400> SEQUENCE: 387

Gly Asn Gly Pro Gly Ile Thr Gly Thr Thr Asp Tyr
1               5                   10

<210> SEQ ID NO 388
<211> LENGTH: 120
<212> TYPE: PRT
<213> ORGANISM: Homo sapiens

<400> SEQUENCE: 388

Lys Cys Ser Trp Trp Ser Leu Gly Glu Val Lys Lys Pro Gly Ala Ser
1               5                   10                  15

Val Lys Val Ser Cys Lys Ala Ser Gly Tyr Thr Phe Thr Ser Tyr Asp
            20                  25                  30

Ile Asn Trp Val Arg Gln Ala Thr Gly Gln Gly Leu Glu Trp Met Gly
        35                  40                  45

Trp Met Asn Pro Asn Ser Gly Asn Thr Gly Tyr Ala Gln Lys Phe Gln
    50                  55                  60

Gly Arg Val Thr Met Thr Arg Asn Thr Ser Ile Ser Thr Ala Tyr Met
65                  70                  75                  80

Glu Leu Ser Ser Leu Arg Ser Glu Asp Thr Ala Val Tyr Tyr Cys Ala
                85                  90                  95

Arg Gly Asn Gly Pro Gly Ile Thr Gly Thr Thr Asp Tyr Trp Gly Gln
            100                 105                 110

Gly Thr Leu Val Thr Val Ser Ser
        115                 120

<210> SEQ ID NO 389
<211> LENGTH: 5
<212> TYPE: PRT
<213> ORGANISM: Homo sapiens

<400> SEQUENCE: 389

Asp Tyr Gly Met Ser
1               5

<210> SEQ ID NO 390
<211> LENGTH: 17
<212> TYPE: PRT
<213> ORGANISM: Homo sapiens

<400> SEQUENCE: 390

Gly Ile Asn Trp Asn Gly Asp Arg Thr Gly Tyr Ala Asp Ser Val Lys
1               5                   10                  15

Gly

<210> SEQ ID NO 391
```

```
<211> LENGTH: 10
<212> TYPE: PRT
<213> ORGANISM: Homo sapiens

<400> SEQUENCE: 391

Glu Asn Val Ile Val Pro Ala Ala Thr Tyr
1               5                   10

<210> SEQ ID NO 392
<211> LENGTH: 119
<212> TYPE: PRT
<213> ORGANISM: Homo sapiens

<400> SEQUENCE: 392

Glu Val Gln Leu Val Glu Ser Gly Gly Gly Val Val Arg Pro Gly Gly
1               5                   10                  15

Ser Leu Arg Leu Ser Cys Ala Ala Ser Gly Phe Thr Phe Asp Asp Tyr
            20                  25                  30

Gly Met Ser Trp Val Arg Gln Ala Pro Gly Lys Gly Leu Glu Trp Val
        35                  40                  45

Ser Gly Ile Asn Trp Asn Gly Asp Arg Thr Gly Tyr Ala Asp Ser Val
    50                  55                  60

Lys Gly Arg Phe Thr Ile Ser Arg Asp Asn Ala Lys Asn Ser Leu Tyr
65                  70                  75                  80

Leu Gln Met Asn Ser Leu Arg Ala Glu Asp Thr Ala Leu Tyr Tyr Cys
                85                  90                  95

Gly Arg Glu Asn Val Ile Val Pro Ala Ala Thr Tyr Trp Gly Gln Gly
            100                 105                 110

Thr Leu Val Thr Val Ser Ser
        115

<210> SEQ ID NO 393
<211> LENGTH: 339
<212> TYPE: DNA
<213> ORGANISM: Homo sapiens

<400> SEQUENCE: 393
gaggtgcagc tgttggagtc tgggggaggc ttggtacagc ctgggggtc cctgagactc      60 tcctgtgcag cctctggatt cagttttagc agctatgcca tgagttgggt ccgccaggct    120
ccagggaagg ggctggagtg ggtctcaagt attggtgaga atgatggtac cacagactac    180
gcagactccg tgaagggccg attcaccatc tccagagaca attccaagag tatgctgtat    240
ctgcaaatga acagcctgag agtcgaggac acggccgtct attactgtgt gaaagatggt    300
gtccactggg gccagggaac cctggtcacc gtctcctca                           339

<210> SEQ ID NO 394
<211> LENGTH: 339
<212> TYPE: DNA
<213> ORGANISM: Homo sapiens

<400> SEQUENCE: 394
gaggtgcagc tggtggagtc tgggggaggc ttggtacagc ctgggggtc cctgagactc      60 tcctgtgcag cctctggatt cacctttagc agttatgcca tgagctgggt ccgccaggct    120
ccagggaagg ggctggagtg ggtctcaagt attggtgata ataataatag cacagagtac    180
gcagactccg tgaagggccg gttcaccatc tccagagaca attccaagag cacgctgtat    240
ctgcaaatga acagcctgag cgccgaggac acggccgtat attactgtgt gaaagatggt    300
```

```
gtccactggg gccagggaac cctggtcact gtctcttca                              339
```

<210> SEQ ID NO 395
<211> LENGTH: 339
<212> TYPE: DNA
<213> ORGANISM: Homo sapiens

<400> SEQUENCE: 395

```
gaggtgcagc tggtggagtc tggggggaggc ttggtacagc ctgggggtc cctgagactc         60
tcctgtgcag cctctggatt ctcctttagc agttatgcca tgagctgggt ccgccaggct        120
ccagggaagg gactggagtg ggtctcaagt attggtgata taataatag cacagactac         180
gcagactccg tgaagggccg gttcaccatc tccagagaca attccaagag tacgctgtat        240
ctgcaaatga acagcctgag agccgaggac acggccgtat attactgtgt gaaagatggt        300
gtccactggg gccagggaac cctggtcact gtctcctca                               339
```

<210> SEQ ID NO 396
<211> LENGTH: 333
<212> TYPE: DNA
<213> ORGANISM: Homo sapiens

<400> SEQUENCE: 396

```
gaggtgcagc tggtggagtc tggggggaggc ttggtacagc ctgggggtc cctgagactc         60
tcctgtgcag cctctggatt caccttagc agttatgcca tgagctgggt ccgccaggct         120
ccagggaagg ggctggagtg ggtctcaagt attggtgatg gaaccacata ctacgcagac        180
tccgtgaagg gccgtttcac catctccaga gacaattcca agagcacgct gtatctgcaa        240
atgaacagcc tgagagccga ggacacggcc gtatattact gtgcgaaaga tggtgtccac        300
tggggccagg gaaccctggt cactgtctcc tca                                     333
```

<210> SEQ ID NO 397
<211> LENGTH: 339
<212> TYPE: DNA
<213> ORGANISM: Homo sapiens

<400> SEQUENCE: 397

```
gaagtgcagc tggtggagtc tggggggaggc ttggtacagc ctgggggtc cctgagactc         60
tcctgtgcag cctctggatt caccttagc acttatgcca tgagctgggt ccgccaggct         120
ccagggaagg ggctggagtg ggtctcaagt attggtgaaa atgatcgaac cacatactac        180
gtagactccg tgaagggccg gttcaccatc tccagagaca attccaagag cacgctgtat        240
ctgcaaatga acagcctgag agccgaggac acggccgtat attactgtgc gaaagatggt        300
gtccactggg gccagggaac cctggtcact gtctcttca                               339
```

<210> SEQ ID NO 398
<211> LENGTH: 339
<212> TYPE: DNA
<213> ORGANISM: Homo sapiens

<400> SEQUENCE: 398

```
caggtgcagc tggtggagtc tggggggaggc ttggtacagc ctgggggtc cctgagactc         60
tcctgtgcag cctctggatt caccttagc agttatgcca tgagctgggt ccgccaggct         120
ccagggaagg ggctggagtg ggtctcaagt attggtgata ataatagaac cacatactac        180
gcagactccg tgaagggccg gttcaccatc tccagagaca attccaagag cacgctgtat        240
ctgcaaatga acagcctgag agccgaggac acggccgtat attactgtgc gaaagatggt        300
```

```
gtccactggg gccagggaac cctggtcacc gtctcctca                    339
```

<210> SEQ ID NO 399
<211> LENGTH: 333
<212> TYPE: DNA
<213> ORGANISM: Homo sapiens

<400> SEQUENCE: 399

```
gaggtgcagc tggtggagtc tgggggaggc ttggtacagc ctgggggtc cctgagactc   60 tcctgtgcag cctctggatt cacctttagc agttatgcca tgagctgggt ccgccaggct  120
ccagggaagg ggctggagtg ggtctcaagt attggtgatg gaaccacata ctacgcagac  180
tccgtgaagg gccggttcac catctccaga gacaattcca agagcacgct gtatctgcaa  240
atgaacagcc tgagagccga ggacacggcc gtatattact gtgcgaaaga tggtgtccac  300
tggggccagg gaaccctggt caccgtctcc tca                              333
```

<210> SEQ ID NO 400
<211> LENGTH: 339
<212> TYPE: DNA
<213> ORGANISM: Homo sapiens

<400> SEQUENCE: 400

```
gaggtgcagc tgttggagtc tgggggaggc ttggtacagc ctgggggtc cctgagactc    60 tcctgtgcag cctctggatt cagttttagc agctatgcca tgagttgggt ccgccaggct  120
ccagggaagg ggctggagtg ggtctcaagt attggtgaga atgatggtac cacagactac  180
gcagactccg tgaagggccg attcaccatc tccagagaca attccaagaa tacgctgtat  240
ctgcaaatga acagcctgag agtcgaggac acggccgtct attactgtgt gaaagatggt  300
gtccactggg gccagggaac cctggtcacc gtctcctca                         339
```

<210> SEQ ID NO 401
<211> LENGTH: 339
<212> TYPE: DNA
<213> ORGANISM: Homo sapiens

<400> SEQUENCE: 401

```
gaggtgcagc tgttggagtc tgggggaggc ttggtacagc ctgggggtc cctgagactc    60 tcctgtgcag cctctggatt cagttttagc agctatgcca tgagttgggt ccgccaggct  120
ccagggaagg ggctggagtg ggtctcaagt attggtgaga atgatggtac cacagactac  180
gcagactccg tgaagggccg attcaccatc tccagagaca attccaagaa tacgctgtat  240
ctgcaaatga acagcctgag agtcgaggac acggccgtct attactgtgt gaaagatggt  300
gtccactggg gccagggaac cctggtcacc gtctcctca                         339
```

<210> SEQ ID NO 402
<211> LENGTH: 339
<212> TYPE: DNA
<213> ORGANISM: Homo sapiens

<400> SEQUENCE: 402

```
gaggtgcagc tgttggagtc tgggggaggc ttggtacagc ctgggggtc cctgagactc    60 tcctgtgcag cctctggatt cagttttagc agctatgccc tcagttgggt ccgccaggct  120
ccagggaagg ggctggagtg ggtctcaagt attggtgaga atgatggtac cacagactac  180
gcagactccg tgaagggccg attcaccatc tccagagaca attccaagaa tacgctgtat  240
```
ctgcaaatga acagcctgag agccgaggac acggccgtct attactgtgt gaaagatggt    300
gtccactggg gccagggaac cctggtcacc gtctcctca    339

<210> SEQ ID NO 403
<211> LENGTH: 339
<212> TYPE: DNA
<213> ORGANISM: Homo sapiens

<400> SEQUENCE: 403
gaggtgcagc tgttggagtc tgggggaggc ttggtacagc ctgggggtc cctgagactc    60 tcctgtgcag cctctggatt cagttttagc agctatgccc tcagttgggt ccgccaggct    120
ccagggaagg ggctggagtg ggtctcaagt attggtgaga ataacgctac cacagactac    180
gcagacttcg tgaagggccg attcaccatc tccagagaca attccaagaa tacgctgtat    240
ctgcaaatga acagcctgag agccgaggac acggccgtct attactgtgt gaaagatggt    300
gtccactggg gccagggaac cctggtcacc gtctcctca    339

<210> SEQ ID NO 404
<211> LENGTH: 331
<212> TYPE: DNA
<213> ORGANISM: Homo sapiens

<400> SEQUENCE: 404
gctgttggag tctgggggag gcttggtaca gcctgggggg tccctgagac tctcctgtgc    60
agcctctgga ttcagttttta gcagctatgc cctcagttgg gtccgccagg ctccagggaa    120
ggggctggag tgggtctcaa gtattggtga gaataacgat accacagact acgcagacaa    180
cgtgaagggc cgattcacca tctccagaga caattccaag aatacgctgt atctgcaaat    240
gaacagcctg agagccgagg acacggccgt ctattactgt gtgaaagatg gtgtccactg    300
gggccaggga accctggtca ccgtctcctc a    331

<210> SEQ ID NO 405
<211> LENGTH: 339
<212> TYPE: DNA
<213> ORGANISM: Homo sapiens

<400> SEQUENCE: 405
gaggtgcagc tgttggagtc tgggggaggc ttggtacagc ctgggggtc cctgagactc    60 tcctgtgcag cctctggatt cagttttagc agctatgccc tcagttgggt ccgccaggct    120
ccagggaagg ggctggagtg ggtctcaagt attggtgaga ataacgctac cacagactac    180
gcagacgccg tgaagggccg attcaccatc tccagagaca attccaagaa tacgctgtat    240
ctgcaaatga acagcctgag agccgaggac acggccgtct attactgtgt gaaagatggt    300
gtccactggg gccagggaac cctggtcacc gtctcctca    339

<210> SEQ ID NO 406
<211> LENGTH: 339
<212> TYPE: DNA
<213> ORGANISM: Homo sapiens

<400> SEQUENCE: 406
gaggtgcagc tgttggagtc tgggggaggc ttggtacagc ctgggggtc cctgagactc    60 tcctgtgcag cctctggatt cagttttagc agctatgccc tcagttgggt ccgccaggct    120
ccagggaagg ggctggagtg ggtctcaagt attggtgaga ataaccatac cacagactac    180
gcagccgacg tgaagggccg attcaccatc tccagagaca attccaagaa tacgctgtat    240

```
ctgcaaatga acagcctgag agccgaggac acggccgtct attactgtgt gaaagatggt    300
gtccactggg gccagggaac cctggtcacc gtctcctca                          339

<210> SEQ ID NO 407
<211> LENGTH: 339
<212> TYPE: DNA
<213> ORGANISM: Homo sapiens

<400> SEQUENCE: 407
gaggtgcagc tgttggagtc tgggggaggc ttggtacagc ctggggggtc cctgagactc    60
tcctgtgcag cctctggatt cagttttagc agctatgccc tcagttgggt ccgccaggct   120
ccagggaagg ggctggagtg ggtctcaagt attggtgaga ataacgctac cacagactac   180
gcagacgtcg tgaagggccg attcaccatc tccagagaca attccaagaa tacgctgtat   240
ctgcaaatga acagcctgag agccgaggac acggccgtct attactgtgt gaaagatggt   300
gtccactggg gccagggaac cctggtcacc gtctcctca                          339

<210> SEQ ID NO 408
<211> LENGTH: 339
<212> TYPE: DNA
<213> ORGANISM: Homo sapiens

<400> SEQUENCE: 408
gaggtgcagc tgttggagtc tgggggaggc ttggtacagc ctggggggtc cctgagactc    60
tcctgtgcag cctctggatt cagttttagc agctatgccc tcagttgggt ccgccaggct   120
ccagggaagg ggctggagtg ggtctcaagt attggtgaga ataaccatac cacagactac   180
gcagccttcg tgaagggccg attcaccatc tccagagaca attccaagaa tacgctgtat   240
ctgcaaatga acagcctgag agccgaggac acggccgtct attactgtgt gaaagatggt   300
gtccactggg gccagggaac cctggtcacc gtctcctca                          339

<210> SEQ ID NO 409
<211> LENGTH: 339
<212> TYPE: DNA
<213> ORGANISM: Homo sapiens

<400> SEQUENCE: 409
gaggtgcagc tgttggagtc tgggggaggc ttggtacagc ctggggggtc cctgagactc    60
tcctgtgcag cctctggatt cagttttagc agctatgccc tcagttgggt ccgccaggct   120
ccagggaagg ggctggagtg ggtctcaagt attggtgaga ataaccatac cacagactac   180
gcagacaccg tgaagggccg attcaccatc tccagagaca attccaagaa tacgctgtat   240
ctgcaaatga acagcctgag agccgaggac acggccgtct attactgtgt gaaagatggt   300
gtccactggg gccagggaac cctggtcacc gtctcctca                          339

<210> SEQ ID NO 410
<211> LENGTH: 339
<212> TYPE: DNA
<213> ORGANISM: Homo sapiens

<400> SEQUENCE: 410
gaggtgcagc tgttggagtc tgggggaggc ttggtacagc ctggggggtc cctgagactc    60
tcctgtgcag cctctggatt cagttttagc agctatgccc tcagttgggt ccgccaggct   120
ccagggaagg ggctggagtg ggtctcaagt attggtgaga ataacgatac cacagactac   180
```

```
gcagacgccg tgaagggccg attcaccatc tccagagaca attccaagaa tacgctgtat    240
ctgcaaatga acagcctgag agccgaggac acggccgtct attactgtgt gaaagatggt    300
gtccactggg gccagggaac cctggtcacc gtctcctca                           339
```

<210> SEQ ID NO 411
<211> LENGTH: 339
<212> TYPE: DNA
<213> ORGANISM: Homo sapiens

<400> SEQUENCE: 411

```
gaggtgcagc tgttggagtc tggggggaggc ttggtacagc ctgggggggtc cctgagactc    60 tcctgtgcag cctctggatt cagttttagc agctatgccc tcagttgggt ccgccaggct   120
ccagggaagg ggctggagtg ggtctcaagt attggtgaga ataacgctac cacagactac   180
gcagcctccg tgaagggccg attcaccatc tccagagaca attccaagaa tacgctgtat   240
ctgcaaatga acagcctgag agccgaggac acggccgtct attactgtgt gaaagatggt   300
gtccactggg gccagggaac cctggtcacc gtctcctca                           339
```

<210> SEQ ID NO 412
<211> LENGTH: 339
<212> TYPE: DNA
<213> ORGANISM: Homo sapiens

<400> SEQUENCE: 412

```
gaggtgcagc tgttggagtc tggggggaggc ttggtacagc ctgggggggtc cctgagactc    60 tcctgtgcag cctctggatt cagttttagc agctatgccc tcagttgggt ccgccaggct   120
ccagggaagg ggctggagtg ggtctcaagt attggtgaga ataaccatac cacagactac   180
gcagccaccg tgaagggccg attcaccatc tccagagaca attccaagaa tacgctgtat   240
ctgcaaatga acagcctgag agtcgaggac acggccgtct attactgtgt gaaagatggt   300
gtccactggg gccagggaac cctggtcacc gtctcctca                           339
```

<210> SEQ ID NO 413
<211> LENGTH: 339
<212> TYPE: DNA
<213> ORGANISM: Homo sapiens

<400> SEQUENCE: 413

```
gaggtgcagc tgttggagtc tggggggaggc ttggtacagc ctgggggggtc cctgagactc    60 tcctgtgcag cctctggatt cagttttagc agctatgccc tcagttgggt ccgccaggct   120
ccagggaagg ggctggagtg ggtctcaagt attggtgaga ataacgatac cacagactac   180
gcagcctacg tgaagggccg attcaccatc tccagagaca attccaagaa tacgctgtat   240
ctgcaaatga acagcctgag agccgaggac acggccgtct attactgtgt gaaagatggt   300
gtccactggg gccagggaac cctggtcacc gtctcctca                           339
```

<210> SEQ ID NO 414
<211> LENGTH: 339
<212> TYPE: DNA
<213> ORGANISM: Homo sapiens

<400> SEQUENCE: 414

```
gaggtgcagc tgttggagtc tggggggaggc ttggtacagc ctgggggggtc cctgagactc    60 tcctgtgcag cctctggatt cagttttagc agctatgccc tcagttgggt ccgccaggct   120
ccagggaagg ggctggagtg ggtctcaagt attggtgaga ataaccatac cacagactac   180
```

```
gcagccaccg tgaagggccg attcaccatc tccagagaca attccaagaa tacgctgtat    240
ctgcaaatga acagcctgag agtcgaggac acggccgtct attactgtgt gaaagatggt    300
gtccactggg gccagggaac cctggtcacc gtctcctca                           339
```

<210> SEQ ID NO 415
<211> LENGTH: 381
<212> TYPE: DNA
<213> ORGANISM: Homo sapiens

<400> SEQUENCE: 415

```
gaggtgcagc tggtggagtc tgggggaggc gtggtccagc ctgggaggtc cctgagactc     60
tcctgtgcag cctctggatt ctccttcagt ggctatggca tgcactgggt ccgccaggct    120
ccaggcaagg gactggagtg ggtggcatat atatcatatg atggaagtaa taaatactat    180
gcagactccg tgaagggccg attcaccatc tccagagaca attccaagaa cacgctgtat    240
ctgcaaatga acagcctgag agctgaggac acggctgtgt attactgtgc gaaagatccg    300
gcctggggat tacgtttggg ggagtcatcg tcctatgatt ttgatatctg gggccaaggg    360
acaatggtca ctgtctcttc a                                              381
```

<210> SEQ ID NO 416
<211> LENGTH: 381
<212> TYPE: DNA
<213> ORGANISM: Homo sapiens

<400> SEQUENCE: 416

```
caggtgcagc tggtggagtc tgggggaggc gtggtccagc ctgggaggtc cctgagactc     60
tcctgtgcag cctctggatt ctccttcagt ggctatggca tgcactgggt ccgccaggct    120
ccaggcaagg gactggagtg ggtggcatat atatcatatg atggaagtaa taaatactat    180
gcagactccg tgaagggccg attcaccatc tccagagaca attccaagaa cacgctgtat    240
ctgcaaatga acagcctgag agctgaggac acggctgtgt attactgtgc gaaagatccg    300
gcctggggat tacgtttggg ggagtcatcg tcctatgatt ttgatatctg gggccaaggg    360
acaatggtca ctgtctcttc a                                              381
```

<210> SEQ ID NO 417
<211> LENGTH: 381
<212> TYPE: DNA
<213> ORGANISM: Homo sapiens

<400> SEQUENCE: 417

```
gaggtgcagc tggtggagtc tgggggaggc gtggtccagc ctgggaggtc cctgagactc     60
tcctgtgcag cctctggatt cagcttcagt ggctatggca tgcactgggt ccgccaggct    120
ccaggcaagg ggctggagtg ggtggcacat atatcatatg atggaagtaa tagatactat    180
gcagaatccg tgaagggccg attcaccatc tccagagaga attccaagaa cacgctgtct    240
ctgcaaatga acagcctgag agctgaggac acggctgtgt attactgtgc gaaagatccg    300
gcctggggat tacgtttggg ggagttatcg tcctatgatt ttgacatttg gggccaaggg    360
acaatggtca ctgtctcttc a                                              381
```

<210> SEQ ID NO 418
<211> LENGTH: 381
<212> TYPE: DNA
<213> ORGANISM: Homo sapiens

```
<400> SEQUENCE: 418
caggtcacct tgaaggagtc tgggggaggc gtggtccagc ctgggaggtc cctgaaactc      60
tcctgtgcag cctctggatt ctccttcagt ggctatggca tgcactgggt ccgccaggct     120
ccaggcaagg ggctggagtg ggtggcagtt atatcatatg atggaagtaa tagatactat     180
gcagactccg tgaagggccg attcaccatc tccagagaca attccaagaa cacgctgtct     240
ctgcaaatga acagcctgag agctgaggac acggctgtgt attactgtgc gagagatccg     300
gcctggggat tacgtttggg ggagttatcg tcctatgatt ttgaaatctg gggccaaggg     360
acaatggtca ccgtctcctc a                                              381

<210> SEQ ID NO 419
<211> LENGTH: 381
<212> TYPE: DNA
<213> ORGANISM: Homo sapiens

<400> SEQUENCE: 419
caggtgcagc tggtggagtc tgggggaggc gtggtccagc ctgggaggtc cctgagactc      60
tcctgtgcag cctctggatt ctccttcagt ggctatggca tgcactgggt ccgccaggct     120
ccaggcaagg ggctggagtg ggtggcagtt atatcatatg atggaagtaa tagatactat     180
gcagactccg tgaagggccg attcaccatc tccagagaca attccaagaa cacactgtct     240
ctgcaaatga acagcctgag agctgaggac acggctgtgt attactgtgc gaaagatccg     300
gcctggggat tacgtttggg ggagttatcg tcctatgatt ttgaaatttg gggccaaggg     360
acaatggtca ccgtctcttc a                                              381

<210> SEQ ID NO 420
<211> LENGTH: 381
<212> TYPE: DNA
<213> ORGANISM: Homo sapiens

<400> SEQUENCE: 420
gaagtgcagc tggtggagtc tgggggaggc gtggtccagc ctgggaggtc cctgagactc      60
tcctgtgcag cctctggatt ctccttcagt ggctatggca tgcactgggt ccgccaggct     120
ccaggcaagg ggctggagtg ggtggcagtt atatcatatg atggaagtaa taaatactat     180
gcagactccg tgaagggccg attcaccatc tccagagaca attccaagaa cacgctatat     240
ctgcaaatga acagcctgag agctgaggac acggctgtgt attactgtgc gaaagatccg     300
gcctggggat tacgtttggg ggaactatcg tcctataaat ttgaaatctg gggccaaggg     360
acaatggtca ccgtctcttc a                                              381

<210> SEQ ID NO 421
<211> LENGTH: 381
<212> TYPE: DNA
<213> ORGANISM: Homo sapiens

<400> SEQUENCE: 421
gaggtgcagc tggtggagtc tgggggaggc gtggtccagc ctgggaggtc cctgagactc      60
tcctgtgcag cctctggatt ctccttcagt ggctatggca tgcactgggt ccgccaggct     120
ccaggcaagg ggctggagtg ggtggcactt atatcatatg atggaagtaa taaatactat     180
gcagactccg tgaagggccg attcaccatc tccagagaca attccaagaa cacgctgtat     240
ctgcaaatga acagcctgag agctgaggac acggctgtgt attactgtgc gaaagatccg     300
gcctggggat tacgtttggg ggagcaatcg tcctatgctt ttgatatctg gggccaaggg     360
```

```
acaatggtca ccgtctcctc a                                              381

<210> SEQ ID NO 422
<211> LENGTH: 381
<212> TYPE: DNA
<213> ORGANISM: Homo sapiens

<400> SEQUENCE: 422
caggtgcagc tggtggagtc tgggggaggc gtggtccagc ctgggaggtc cctgagactc    60
tcctgtgcag cctctggatt ctccttcagt ggctatggca tgcactgggt ccgccaggct   120
ccaggcaagg ggctggagtg ggtgtcagtt atatcatatg atggaagtaa taaatactat   180
gcagactccg tgaagggccg attcaccatc tccagagaca attccaagaa cacgctgtat   240
ctgcaaatga acagcctgag aactgaggac acggctgtgt attactgtgc gaaagatccg   300
gcctggggat tacgtttggg ggagcaatcg tcctatgctt ttgaaatctg gggccaaggt   360
acaatggtca ccgtctcctc a                                              381

<210> SEQ ID NO 423
<211> LENGTH: 381
<212> TYPE: DNA
<213> ORGANISM: Homo sapiens

<400> SEQUENCE: 423
gaggtgcagc tgttggagtc tgggggaggc gtggtccagc ctgggaggtc cctgagactc    60
tcctgtgcag cctctggatt ctccttcagt ggctatggca tgcactgggt ccgccaggct   120
ccaggcaagg ggctggagtg ggtggcagtt atatcatatg atggaagtaa taaatactat   180
gcagactccg tgaagggccg attcaccatc tccagagaca attccaagaa cacgctgtat   240
ctgcaaatga acagcctgag agttgaggac acggctgtgt attactgtgc gaaagatccg   300
gcctggggat tacgtttggg ggagcaatcg tcctatgctt ttgaaatccg gggccagggg   360
acaacggtca ccgtctcttc a                                              381

<210> SEQ ID NO 424
<211> LENGTH: 381
<212> TYPE: DNA
<213> ORGANISM: Homo sapiens

<400> SEQUENCE: 424
gaggtgcagc tggtggagtc tgggggaggc gtggtccagc ctgggaggtc cctgagactc    60
tcctgtgcag cctctggatt caccttagt ggctatggca tgcactgggt ccgccaggct    120
ccaggcaagg ggctggagtg ggtggcatat atatcatatg atggaagtaa tagatactat   180
gcagactccg tgaagggccg attcaccatc tccagagaca attccaagaa gacgctgtct   240
ctgcaaatga acagcctgag agctgaggac acggctgtgt attactgtgc gaaagatccg   300
gcctggggat tacgtttggg ggagtcatcg tcatatgatt ttgatatctg gggccaaggg   360
acaatggtca ccgtctcctc a                                              381

<210> SEQ ID NO 425
<211> LENGTH: 381
<212> TYPE: DNA
<213> ORGANISM: Homo sapiens

<400> SEQUENCE: 425
gaggtgcagc tggtggagtc tgggggaggc gtggtccagc ctgggaggtc cctgagactc    60
```

```
tcctgtgcag cctctggatt ctccttcagt ggctatggcc tccactgggt ccgccaggct      120
ccaggcaagg gactggagtg ggtggcatat atatcatatg acgagagtaa taaatactat      180
gcacccagcg tgaagggccg attcaccatc tccagagaca attccaagaa cacgctgtat      240
ctgcaaatga acagcctgag agctgaggac acggctgtgt attactgtgc gaaagatccg      300
gcctggggat tacgtttggg ggagtcatcg tcctatgatt ttgatatctg gggccaaggg      360
acaatggtca ccgtctcctc a                                                381

<210> SEQ ID NO 426
<211> LENGTH: 381
<212> TYPE: DNA
<213> ORGANISM: Homo sapiens

<400> SEQUENCE: 426
caggtgcagc tggtggagtc tgggggaggc gtggtccagc ctgggaggtc cctgagactc       60
tcctgtgcag cctctggatt ctccttcagt ggctatggca tgcactgggt ccgccaggct      120
ccaggcaagg gactggagtg ggtggcatat atatcatatg ataagagtaa taaatactat      180
gcagacaagg tgaagggccg attcaccatc tccagagaca attccaagaa cacgctgtat      240
ctgcaaatga acagcctgag agctgaggac acggctgtgt attactgtgc gaaagatccg      300
gcctggggat tacgtttggg ggagtcatcg tcctatgatt ttgatatctg gggccaaggg      360
acaatggtca ctgtctcttc a                                                381

<210> SEQ ID NO 427
<211> LENGTH: 381
<212> TYPE: DNA
<213> ORGANISM: Homo sapiens

<400> SEQUENCE: 427
gaggtgcagc tggtggagtc tgggggaggc gtggtccagc ctgggaggtc cctgagactc       60
tcctgtgcag cctctggatt ctccttcagt ggctatggcc tccactgggt ccgccaggct      120
ccaggcaagg gactggagtg ggtggcatat atatcatatg atgcgagtaa taaatactat      180
gcagacaacg tgaagggccg attcaccatc tccagagaca attccaagaa cacgctgtat      240
ctgcaaatga acagcctgag agctgaggac acggctgtgt attactgtgc gaaagatccg      300
gcctggggat tacgtttggg ggagtcatcg tcctatgatt ttgatatctg gggccaaggg      360
acaatggtca ctgtctcttc a                                                381

<210> SEQ ID NO 428
<211> LENGTH: 381
<212> TYPE: DNA
<213> ORGANISM: Homo sapiens

<400> SEQUENCE: 428
gaggtgcagc tggtggagtc tgggggaggc gtggtccagc ctgggaggtc cctgagactc       60
tcctgtgcag cctctggatt ctccttcagt ggctatggcg tgcactgggt ccgccaggct      120
ccaggcaagg gactggagtg ggtggcatat atatcatatg atgcgagtaa taaatactat      180
gcagacaacg tgaagggccg attcaccatc tccagagaca attccaagaa cacgctgtat      240
ctgcaaatga acagcctgag agctgaggac acggctgtgt attactgtgc gaaagatccg      300
gcctggggat tacgtttggg ggagtcatcg tcctatgatt ttgatatctg gggccaaggg      360
acaatggtca ctgtctcttc a                                                381
```

<210> SEQ ID NO 429
<211> LENGTH: 381
<212> TYPE: DNA
<213> ORGANISM: Homo sapiens

<400> SEQUENCE: 429

```
gaggtgcagc tggtggagtc tgggggaggc gtggtccagc ctgggaggtc cctgagactc    60
tcctgtgcag cctctggatt ctccttcagt ggctatggcc tccactgggt ccgccaggct   120
ccaggcaagg gactggagtg ggtggcatat atatcatatg ataagagtaa taaatactat   180
gcagacaagg tgaagggccg attcaccatc tccagagaca attccaagaa cacgctgtat   240
ctgcaaatga acagcctgag agctgaggac acggctgtgt attactgtgc gaaagatccg   300
gcctggggat tacgtttggg ggagtcatcg tcctatgatt ttgatatctg gggccaaggg   360
acaatggtca ctgtctcttc a                                             381
```

<210> SEQ ID NO 430
<211> LENGTH: 381
<212> TYPE: DNA
<213> ORGANISM: Homo sapiens

<400> SEQUENCE: 430

```
gaggtgcagc tggtggagtc tgggggaggc gtggtccagc ctgggaggtc cctgagactc    60
tcctgtgcag cctctggatt ctccttcagt ggctatggcg cgcactgggt ccgccaggct   120
ccaggcaagg gactggagtg ggtggcatat atatcatatg ataagagtaa taaatactat   180
gcagacaagg tgaagggccg attcaccatc tccagagaca attccaagaa cacgctgtat   240
ctgcaaatga acagcctgag agctgaggac acggctgtgt attactgtgc gaaagatccg   300
gcctggggat tacgtttggg ggagtcatcg tcctatgatt ttgatatctg gggccaaggg   360
acaatggtca ctgtctcttc a                                             381
```

<210> SEQ ID NO 431
<211> LENGTH: 381
<212> TYPE: DNA
<213> ORGANISM: Homo sapiens

<400> SEQUENCE: 431

```
gaggtgcagc tggtggagtc tgggggaggc gtggtccagc ctgggaggtc cctgagactc    60
tcctgtgcag cctctggatt ctccttcagt ggctatggca tgcactgggt ccgccaggct   120
ccaggcaagg gactggagtg ggtggcatat atatcatatg atgcgagtaa taaatactat   180
gcagacaacg tgaagggccg attcaccatc tccagagaca attccaagaa cacgctgtat   240
ctgcaaatga acagcctgag agctgaggac acggctgtgt attactgtgc gaaagatccg   300
gcctggggat tacgtttggg ggagtcatcg tcctatgatt ttgatatctg gggccaaggg   360
acaatggtca ctgtctcttc a                                             381
```

<210> SEQ ID NO 432
<211> LENGTH: 381
<212> TYPE: DNA
<213> ORGANISM: Homo sapiens

<400> SEQUENCE: 432

```
caggtgcagc tggtggagtc tgggggaggc gtggtccagc ctgggaggtc cctgagactc    60
tcctgtgcag cctctggatt ctccttcagt ggctatggcc agcactgggt ccgccaggct   120
ccaggcaagg gactggagtg ggtggcatat atatcatatg atgcgagtaa taaatactat   180
```

```
gcagacaacg tgaagggccg attcaccatc tccagagaca attccaagaa cacgctgtat    240
ctgcaaatga acagcctgag agctgaggac acggctgtgt attactgtgc gaaagatccg    300
gcctggggat tacgtttggg ggagtcatcg tcctatgatt ttgatatctg gggccaaggg    360
acaatggtca ctgtctcttc a                                              381

<210> SEQ ID NO 433
<211> LENGTH: 381
<212> TYPE: DNA
<213> ORGANISM: Homo sapiens

<400> SEQUENCE: 433
caggtgcagc tggtggagtc tgggggaggc gtggtccagc ctgggaggtc cctgagactc    60
tcctgtgcag cctctggatt ctccttcagt ggctatggct tccactgggt ccgccaggct    120
ccaggcaagg gactggagtg ggtggcatat atatcatatg atgcgagtaa taaatactat    180
gcagacaacg tgaagggccg attcaccatc tccagagaca attccaagaa cacgctgtat    240
ctgcaaatga acagcctgag agctgaggac acggctgtgt attactgtgc gaaagatccg    300
gcctggggat tacgtttggg ggagtcatcg tcctatgatt ttgatatctg gggccaaggg    360
acaatggtca ctgtctcttc a                                              381

<210> SEQ ID NO 434
<211> LENGTH: 381
<212> TYPE: DNA
<213> ORGANISM: Homo sapiens

<400> SEQUENCE: 434
gaggtgcagc tggtggagtc tgggggaggc gtggtccagc ctgggaggtc cctgagactc    60
tcctgtgcag cctctggatt cagcttcagt ggctatggca tgcactgggt ccgccaggct    120
ccaggcaagg ggctggagtg ggtggcaatt atatcatatg atggaagtaa tagatactat    180
gcagactccg tgaagggccg attcaccatc tccagagaca attccaagaa cacgctgtct    240
ctgcaaatga acagcctgag agctgaggac acggctgtgt attactgtgc gaaagatccg    300
gcctggggat tacgtttggg ggagtcatcg tcctatgatt ttgaaatttg gggccaaggg    360
acaatggtca ccgtctcctc a                                              381

<210> SEQ ID NO 435
<211> LENGTH: 381
<212> TYPE: DNA
<213> ORGANISM: Homo sapiens

<400> SEQUENCE: 435
gaggtgcagc tggtggagtc tgggggaggc gtggtccagc ctgggaggtc cctgaaactc    60
tcctgtgcag cctctggatt ctccttcagt ggctatggca tgcactgggt ccgccaggct    120
ccaggcaagg ggctggagtg ggtggcagtt atatcatatg atggaagtaa tagatactat    180
gcagactccg tgaagggccg attcaccatc tccagagaca attccaagaa cacgctgtct    240
ctacaaatga acagcctgag agctgaggac acggctgtgt attactgtgc gaaagatccg    300
gcctggggat tacgtttggg gaaattatcg tcctatgatt ttgaaatctg gggccaaggg    360
acaatggtca ctgtctcttc a                                              381

<210> SEQ ID NO 436
<211> LENGTH: 381
<212> TYPE: DNA
<213> ORGANISM: Homo sapiens
```

<400> SEQUENCE: 436

| | | |
|---|---|---|
| gaggtgcagc tggtggagtc tgggggaggc gtggtccagc ctgggaggtc cctgagactc | 60 |
| tcctgtgcag cctctggatt ctccttcagt ggctatggca cgcactgggt ccgccaggct | 120 |
| ccaggcaagg gactggagtg gtggcatat atatcatatg acgggagtaa taaatactat | 180 |
| gcagccccgg tgaagggccg attcaccatc tccagagaca attccaagaa cacgctgtat | 240 |
| ctgcaaatga acagcctgag agctgaggac acggctgtgt attactgtgc gaaagacgcg | 300 |
| gcctggggat tacgtttggg ggagtcatcg tcctatgatt ttgatatctg gggccaaggg | 360 |
| acaatggtca ctgtctcttc a | 381 |

<210> SEQ ID NO 437
<211> LENGTH: 381
<212> TYPE: DNA
<213> ORGANISM: Homo sapiens

<400> SEQUENCE: 437

| | | |
|---|---|---|
| gaggtgcagc tggtggagtc tgggggaggc gtggtccagc ctgggaggtc cctgagactc | 60 |
| tcctgtgcag cctctggatt ctccttcagt ggctatggca cgcactgggt ccgccaggct | 120 |
| ccaggcaagg gactggagtg gtggcatat atatcatatg acgagagtaa taaatactat | 180 |
| gcatccagcg tgaagggccg attcaccatc tccagagaca attccaagaa cacgctgtat | 240 |
| ctgcaaatga acagcctgag agctgaggac acggctgtgt attactgtgc gaaagaccgg | 300 |
| gcctggggat tacgtttggg ggagtcatcg tcctatgatt ttgatatctg gggccaaggg | 360 |
| acaatggtca ctgtctcttc a | 381 |

<210> SEQ ID NO 438
<211> LENGTH: 381
<212> TYPE: DNA
<213> ORGANISM: Homo sapiens

<400> SEQUENCE: 438

| | | |
|---|---|---|
| caggtgcagc tggtggagtc tgggggaggc gtggtccagc ctgggaggtc cctgagactc | 60 |
| tcctgtgcag cctctggatt ctccttcagt ggctatggcc tccactgggt ccgccaggct | 120 |
| ccaggcaagg gactggagtg gtggcatat atatcatatg acctgagtaa taaatactat | 180 |
| gcaaggggg tgaagggccg attcaccatc tccagagaca attccaagaa cacgctgtat | 240 |
| ctgcaaatga acagcctgag agctgaggac acggctgtgt attactgtgc gaaagacgtg | 300 |
| gcctggggat tacgtttggg ggagtcatcg tcctatgatt ttgatatctg gggccaaggg | 360 |
| acaatggtca ctgtctcctc a | 381 |

<210> SEQ ID NO 439
<211> LENGTH: 369
<212> TYPE: DNA
<213> ORGANISM: Homo sapiens

<400> SEQUENCE: 439

| | | |
|---|---|---|
| gaggtgcagc tggtggagtc tgggggaggc gtggtccagc ctgggaggtc cctgagactc | 60 |
| tcctgtgcag cctctggatt ccccttaatt agctatggca tgcactgggt ccgccaggct | 120 |
| ccaggcaagg ggctggagtg gtggcatttt atgacatatg atggaagtaa tagatactat | 180 |
| gcagactccg tgaagggccg attcaccatc tccagagaca attccaagaa cacgctgtat | 240 |
| ctgcaaatga acagcctgag agatgaggac acggctctat attactgtgc gagagatcgt | 300 |

```
atagtgggag gtagggtccc tgatgctttt gatatctggg gccaagggac aatggtcacc    360
gtctcttca                                                            369
```

<210> SEQ ID NO 440
<211> LENGTH: 369
<212> TYPE: DNA
<213> ORGANISM: Homo sapiens

<400> SEQUENCE: 440

```
gaggtgcagc tggtggagtc tggggaggc gtggtccagc ctggaggtc cctgagactc     60 tcctgtgcag cctctggatt cccttaatt agctatggca tgaattgggt ccgccaggct    120
ccaggcaagg ggctggactg ggtggcattt atatcatatg atggaagtaa taaatattat    180
gcagactccg tgaagggccg attcaccatc tccaaagaca attccaagaa cacgctgtat    240
ctgcaaatga acagcctgag agctgaggac acggctgtgt attactgtgc gaaagatcgt    300
atagtgggag ccagggtccc tgatgctttt gatatctggg gccaagggac aatggtcacc    360
gtctcctca                                                            369
```

<210> SEQ ID NO 441
<211> LENGTH: 369
<212> TYPE: DNA
<213> ORGANISM: Homo sapiens

<400> SEQUENCE: 441

```
gaggtgcagc tggtggagtc tggggaggc gtggtccagc ctggaggtc cctgagactc     60 tcctgtgcag cctctggatt cccctcatt agctatggca tgaactgggt ccgccaggct    120
ccaggcaagg ggctggagtg ggtggcattt atatcatatg atggaagtaa tagatactat    180
gcagactccg tgaagggccg attcaccatc tccagagaca attccaagaa cacgctgtat    240
ctgcaaatga acagcctgag agctgaggac acggctgtat attactgtgc gaaagatcgt    300
atagtgggag ctagggtccc tgatgctttt gatatctggg gccaagggac aatggtcacc    360
gtctcctca                                                            369
```

<210> SEQ ID NO 442
<211> LENGTH: 369
<212> TYPE: DNA
<213> ORGANISM: Homo sapiens

<400> SEQUENCE: 442

```
gaggtgcagc tggtggagtc tggggaggc gcggtccagc ctggaggtc cctgagactc     60 tcctgtgcag cctctggatt cccttaatt agctatggca tgaattgggt ccgccaggct    120
ccaggcaagg ggctggactg ggtggcattt ataacatatg atggaagtaa tagatattat    180
gcagactctg tgaagggccg attcaccatc tccagagaca attccaagaa cacgctttat    240
ctgcaaatga acagcctgag acctgaggac acggctgtat attactgtgc gaaagatcgt    300
attgtgggag ctagggtccc tgatgcttat gatatctggg gccaagggac aatggtcacc    360
gtctcctca                                                            369
```

<210> SEQ ID NO 443
<211> LENGTH: 369
<212> TYPE: DNA
<213> ORGANISM: Homo sapiens

<400> SEQUENCE: 443

```
caggtgcagc tggtggagtc tggggaggc gtggtccagc ctggaggtc cctgagactc     60
```

```
tcctgtgcag cctctggatt ccccttaatt agctatggca tgaattgggt ccgccaggct      120
ccaggcaagg ggctggactg ggtggcattt ataacatatg atggaagtaa tagatactat      180
gcagactccg tgaagggccg attcaccatc tccagagaca attccaagaa cacgctttat      240
ctgcaaatga acagcctgag acctgaggac acggctgtat attactgtgc gaaagatcgt      300
attgtgggag ctagggtccc tgatgcttat gatatctggg gccaagggac aatggtcacc      360
gtctcctca                                                              369
```

<210> SEQ ID NO 444
<211> LENGTH: 369
<212> TYPE: DNA
<213> ORGANISM: Homo sapiens

<400> SEQUENCE: 444

```
gaggtgcagc tgttggagtc tgggggaggc gtggtccagc ctggagggtc cctgagactc       60
tcctgtgcag cctctggatt ccccttaatt agctatggca tgaattgggt ccgccaggct      120
ccaggcaagg ggctggactg ggtggcattt ataacatatg atggaagtaa tagatactat      180
gcagactccg tgaagggccg attcaccatc tccagagaca attccaagaa cacgctttat      240
ctgcaaatga acagcctgag acctgaggac acggctgtat attactgtgc gaaagatcgt      300
attgtgggag ctagggtccc tgatgcttat gatatctggg gccaagggac aatggtcacc      360
gtctcctca                                                              369
```

<210> SEQ ID NO 445
<211> LENGTH: 369
<212> TYPE: DNA
<213> ORGANISM: Homo sapiens

<400> SEQUENCE: 445

```
caggtgcagc tggtggagtc tgggggaggc ttggtacagc ctgggggtc cctgagactc        60 tcctgtgcag cctctggatt ccccttaatt agctatggca tgaattgggt ccgccaggct      120
ccaggcaagg ggctggactg ggtggcattt ataacatatg atggaagtaa tagatactat      180
gcagactccg tgaagggccg attcaccatc tccagagaca attccaagaa cacgcttcat      240
ctgcaaatgg acagcctgag acctgaggac acggctgtat attactgtgc gaaagatcgt      300
attgtgggag ctagggtccc tgatgcttat gatatctggg gccaagggac aatggtcact      360
gtctcttca                                                              369
```

<210> SEQ ID NO 446
<211> LENGTH: 369
<212> TYPE: DNA
<213> ORGANISM: Homo sapiens

<400> SEQUENCE: 446

```
gaagtgcagc tggtggagtc tgggggaggc gtggtccagc ctggagggtc cctgagactc       60
tcctgtgcag cctctggatt ccccttaatt agctatggca tgaattgggt ccgccaggct      120
ccaggcaagg ggctggactg ggtggcattt ataacatatg atggaagtaa tagatactat      180
gcagactccg tgaagggccg attcaccatc tccagagaca attccaagaa cacgctttat      240
ctgcaaatga acagcctgag acctgaggac acggctgtat attactgtgc gaaagatcgt      300
attgtgggag ctagggtccc tgatgcttat gatatctggg gccagggaac cctggtcact      360
gtctcctca                                                              369
```

<210> SEQ ID NO 447
<211> LENGTH: 369
<212> TYPE: DNA
<213> ORGANISM: Homo sapiens

<400> SEQUENCE: 447

```
caggtgcagc tggtggagtc tgggggaggc gtggtccagc ctgggaggtc cctgagactc      60
tcctgtgcag cctctggatt ccccttaatt agctatggca tgaattgggt ccgccaggct     120
ccaggcaagg ggctggagtg ggtggcattt atatcatatg atggaagtaa tagatactat     180
gcagactccg tgaagggccg attcaccatc tccagagaca attccaagaa cacgctgtat     240
ctgcaaatga acagcctgag acctgaggac acggctgtat attactgtgc gaaagatcgt     300
attgtgggag ctagggtccc tgatgcttat gatatctggg gccaagggac aatggtcacc     360
gtctcttca                                                             369
```

<210> SEQ ID NO 448
<211> LENGTH: 369
<212> TYPE: DNA
<213> ORGANISM: Homo sapiens

<400> SEQUENCE: 448

```
caggtgcagc tggtggagtc tgggggaggc gtggtccagc ctgggaggtc cctgagactc      60
tcctgtgcag cctctggatt ccccttaatt agctatggca tgaattgggt ccgccaggct     120
ccaggcaagg ggctggactg ggtggcattt ataacatatg atggaagtaa tagatactat     180
gcagactccg tgaagggccg attcaccatc tccagagaca attccaagaa cacgcttcat     240
ctgcaaatga acagcctgag acctgaggac acggctgtat attactgtgc gaaagatcgt     300
attgtgggag ctagggtccc tgatgcttat gatatctggg gccaagggac aatggtcact     360
gtctcctca                                                             369
```

<210> SEQ ID NO 449
<211> LENGTH: 369
<212> TYPE: DNA
<213> ORGANISM: Homo sapiens

<400> SEQUENCE: 449

```
gaggtgcagc tggtggagtc tgggggaggc gtggtccagc ctgggaggtc cctgagactc      60
tcctgtgcag cctctggatt ccccttaatt agctatggca tgaattgggt ccgccaggct     120
ccaggcaagg ggctggactg ggtggcattt ataacatatg atggaagtaa tagatactat     180
gcagactccg tgaagggccg attcaccatc tccagagaca attccaagaa cacgcttcat     240
ctgcaaatga acagcctgag acctgaggac acggctgtat attactgtgc gaaagatcgt     300
attgtgggag ctagggtccc tgatgcttat gatatctggg gccaagggac aatggtcact     360
gtctcctca                                                             369
```

<210> SEQ ID NO 450
<211> LENGTH: 369
<212> TYPE: DNA
<213> ORGANISM: Homo sapiens

<400> SEQUENCE: 450

```
gaggtgcagc tggtggagtc tgggggaggc gtggtccagc ctgggaggtc cctgagactc      60
tcctgtgcag cctctggatt ccccttaatt agctatggca tgaattgggt ccgccaggct     120
ccaggcaagg ggctggactg ggtggcattt ataacatatg atggaagtaa tagatactat     180
```

```
gcagactccg tgaagggccg attcaccatc tccagagaca attccaagaa cacgctttat    240
ctgcaaatga acagcctgag acctgaggac acggctgtat attactgtgc gaaagatcgt    300
attgtgggag ctagggtccc tgatgcttat gatatctggg gccaagggac aatggtcacc    360
gtctcctca                                                           369

<210> SEQ ID NO 451
<211> LENGTH: 369
<212> TYPE: DNA
<213> ORGANISM: Homo sapiens

<400> SEQUENCE: 451
caggtgcagc tggtggagtc tgggggaggc gtggtccagc ctggggaggtc cctgagactc    60 tcctgtgcag cctctggatt ccccttaatt agctatggca tgaattgggt ccgccaggct   120
ccaggcaagg ggctggactg ggtggcattt ataacatatg atggaagtaa tagatactat   180
gcagactccg tgaagggccg attcaccatc tccagagaca attccaagaa cacgctttat   240
ctgcaaatga acagcctgag acctgaggac acggctgtat attactgtgc gaaagatcgt   300
attgtgggag ctagggtccc tgatgcttat gatatctggg gccaagggac aatggtcact   360
gtctcctca                                                           369

<210> SEQ ID NO 452
<211> LENGTH: 369
<212> TYPE: DNA
<213> ORGANISM: Homo sapiens

<400> SEQUENCE: 452
gaggtgcagc tggtggagtc tgggggaggt gtggtacggc ctggggggtc cctgagactc    60
tcctgtgcag cctctggatt ccccttaatt agctatggca tgaattgggt ccgccaggct   120
ccaggcaagg ggctggactg ggtggcattt ataacatatg atggaagtaa tagatactat   180
gcagactccg tgaagggccg attcaccatc tccagagaca attccaagaa cacgcttcat   240
ctgcaaatga acagcctgag acctgaggac acggctgtat attactgtgc gaaagatcgt   300
attgtgggag ctagggtccc tgatgcttat gatatctggg gccaagggac aatggtcact   360
gtctcctca                                                           369

<210> SEQ ID NO 453
<211> LENGTH: 369
<212> TYPE: DNA
<213> ORGANISM: Homo sapiens

<400> SEQUENCE: 453
gaagtgcagc tggtggagtc tgggggaggc ttggtccagc ctggggggtc cctgagactc    60
tcctgtgcag cctctggatt ccccttaatt agctatggca tgaattgggt ccgccaggct   120
ccaggcaagg ggctggactg ggtggcattt ataacatatg atggaagtaa tagatactat   180
gcagactccg tgaagggccg attcaccatc tccagagaca attccaagaa cacgcttcat   240
ctgcaaatga acagcctgag acctgaggac acggctgtat attactgtgc gaaagatcgt   300
attgtgggag ctagggtccc tgatgcttat gatatctggg gccaagggac aatggtcacc   360
gtctcctca                                                           369

<210> SEQ ID NO 454
<211> LENGTH: 369
<212> TYPE: DNA
```

<213> ORGANISM: Homo sapiens

<400> SEQUENCE: 454

| gaggtgcagc tgttggagtc tgggggaggc gtggtccagc ctggaggtc cctgagactc | 60 |
| tcctgtgcag cctctggatt cccccttaatt agctatggca tgaattgggt ccgccaggct | 120 |
| ccaggcaagg ggctggactg ggtggcattt ataacatatg atggaagtaa tagatactat | 180 |
| gcagactccg tgaagggccg attcaccatc tccagagaca attccaagaa cacgcttcat | 240 |
| ctgcaaatga acagcctgag acctgaggac acggctgtat attactgtgc gaaagatcgt | 300 |
| attgtgggag ctagggtccc tgatgcttat gatatctggg gccaagggac aatggtcacc | 360 |
| gtctcctca | 369 |

<210> SEQ ID NO 455
<211> LENGTH: 369
<212> TYPE: DNA
<213> ORGANISM: Homo sapiens

<400> SEQUENCE: 455

| gaggtgcagc tgttggagtc tgggggaggc gtggtccagc ctggaggtc cctgagactc | 60 |
| tcctgtgcag cctctggatt cccccttaatt agctatggca tgaattgggt ccgccaggct | 120 |
| ccaggcaagg ggctggactg ggtggcattt ataacatatg atggaagtaa tagatactat | 180 |
| gcagactccg tgaagggccg attcaccatc tccagagaca attccaagaa cacgctttat | 240 |
| ctgcaaatga acagcctgaa acctgaggac acggctgtat attactgtgc gaaagatcgt | 300 |
| attgtgggag ctagggtccc tgatgcttat gatatctggg gccaagggac aatggtcacc | 360 |
| gtctcctca | 369 |

<210> SEQ ID NO 456
<211> LENGTH: 369
<212> TYPE: DNA
<213> ORGANISM: Homo sapiens

<400> SEQUENCE: 456

| gaggtgcagc tggtggagtc tgggggaggc gtggtccagc ctggaggtc cctgagactc | 60 |
| tcctgtgcag cctctggatt cccccttaatt agctatggca tgaattgggt ccgccaggct | 120 |
| ccaggcaagg ggctggactg ggtggcattt ataacatatg atggaagtaa tagatactat | 180 |
| gcagactccg tgaagggccg attcaccatc tccagagaca attccaagaa cacgctttat | 240 |
| ctgcaaatga acagcctgaa acctgaggac acggctgtat attactgtgc gaaagatcgt | 300 |
| attgtgggag ctagggtccc tgatgcttat gatatctggg gccaagggac aatggtcacc | 360 |
| gtctcctca | 369 |

<210> SEQ ID NO 457
<211> LENGTH: 369
<212> TYPE: DNA
<213> ORGANISM: Homo sapiens

<400> SEQUENCE: 457

| caggtgcagc tggtggagtc tgggggaggc gtggtccagc ctggaggtc cctgagactc | 60 |
| tcctgtgcag cctctggatt cccccttaatt agctatggca tgcactgggt ccgccaggct | 120 |
| ccaggcaagg ggctggagtg ggtggcattt atgacatatg atggaagtaa tagatactat | 180 |
| gcagacgccg tgaagggccg attcaccatc tccagagaca attccaagaa cacgctgtat | 240 |
| ctgcaaatga acagcctgag agctgaggac acggctgtgt attactgtgc gagagatcgt | 300 |

```
atagtgggag gtagggtccc tgatgctttt gatatctggg gccaagggac aatggtcacc    360
gtctcttca                                                            369

<210> SEQ ID NO 458
<211> LENGTH: 369
<212> TYPE: DNA
<213> ORGANISM: Homo sapiens

<400> SEQUENCE: 458
caggtgcagc tggtggagtc tgggggaggc gtggtccagc ctgggaggtc cctgagactc    60
tcctgtgcag cctctggatt cccctttaatt agctatggca tgcactgggt ccgccaggct  120
ccaggcaagg ggctggagtg ggtggcattt cagacatatg atggcagtaa tagatactat   180
gcagacgccg tgaagggccg attcaccatc tccagagaca attccaagaa cacgctgtat   240
ctgcaaatga acagcctgag agctgaggac acggctgtgt attactgtgc gagagatcgt   300
atagtgggag gtagggtccc tgatgctttt gatatctggg gccaagggac aatggtcacc   360
gtctcttca                                                            369

<210> SEQ ID NO 459
<211> LENGTH: 369
<212> TYPE: DNA
<213> ORGANISM: Homo sapiens

<400> SEQUENCE: 459
caggtgcagc tggtggagtc tgggggaggc gtggtccagc ctgggaggtc cctgagactc    60
tcctgtgcag cctctggatt cccctttaatt agctatggca tgcactgggt ccgccaggct  120
ccaggcaagg ggctggagtg ggtggcattt cagacatatg atggcagtaa tagatactat   180
gcagactccg tgaagggccg attcaccatc tccagagaca attccaagaa cacgctgtat   240
ctgcaaatga acagcctgag agctgaggac acggctgtgt attactgtgc gagagatcgt   300
atagtgggag gtagggtccc tgatgctttt gatatctggg gccaagggac aatggtcacc   360
gtctcttca                                                            369

<210> SEQ ID NO 460
<211> LENGTH: 369
<212> TYPE: DNA
<213> ORGANISM: Homo sapiens

<400> SEQUENCE: 460
caggtgcagc tggtggagtc tgggggaggc gtggtccagc ctgggaggtc cctgagactc    60
tcctgtgcag cctctggatt cccctttaatt agctatggca tgcactgggt ccgccaggct  120
ccaggcaagg ggctggagtg ggtggcattt cagacatatg atgccagtaa tagatactat   180
gcagacgccg tgaagggccg attcaccatc tccagagaca attccaagaa cacgctgtat   240
ctgcaaatga acagcctgag agctgaggac acggctgtgt attactgtgc gagagatcgt   300
atagtgggag gtagggtccc tgatgctttt gatatctggg gccaagggac aatggtcacc   360
gtctcttca                                                            369

<210> SEQ ID NO 461
<211> LENGTH: 369
<212> TYPE: DNA
<213> ORGANISM: Homo sapiens

<400> SEQUENCE: 461
```

```
caggtgcagc tggtggagtc tggggagggc gtggtccagc ctgggaggtc cctgagactc      60
tcctgtgcag cctctggatt cccctttaatt agctatggca tgaattgggt ccgccaggct    120
ccaggcaagg ggctggagtg ggtggcattt ataacatatg atggaagtaa tagatactat    180
gcagactccg tgaagggccg attcaccatc tccagagaca attccaagaa cacgctttat    240
ctgcaaatga acagcctgag agctgaggac acggctgtat attactgtgc gaaagatcgt    300
attgtgggag ctagggtccc tgatgcttat gatatctggg gccaagggac aatggtcact    360
gtctcctca                                                              369

<210> SEQ ID NO 462
<211> LENGTH: 369
<212> TYPE: DNA
<213> ORGANISM: Homo sapiens

<400> SEQUENCE: 462
caggtgcagc tggtggagtc tggggagggc gtggtccagc ctgggaggtc cttgagactc      60
tcctgtgtag cctctggatt cccccttcatt agctatggca tgcactgggt ccgccaggct   120
ccaggcaagg ggcgggagtg ggtggcagtt atatcatatg atggaagtaa tagatactat    180
gcagactccg tgaagggccg attcaccatc tccagagaca attccaagaa cacgctgtat    240
ctgcaaatga acagcctgag acctgaggac acggctgtgt attattgtgc gaaagagagg    300 attttttggag tgcttacccc tgatgatttt gatatctggg gccaagggac aacggtcacc    360
gtctcctca                                                              369

<210> SEQ ID NO 463
<211> LENGTH: 369
<212> TYPE: DNA
<213> ORGANISM: Homo sapiens

<400> SEQUENCE: 463
caggtgcagc tggtggagtc tggggagggc gtggtccagc ctgggaggtc cctgagactc      60
tcctgtgcag cctctggatt cccccttcatt agctatggca tgcactgggt ccgccaggct   120
ccaggcaagg ggctggagtg ggtggcagtt atatcatatg atggaagtaa tagatactat    180
gcagactccg tgaagggccg attcaccatc tccagagaca attccaagaa cacgctgtat    240
ctgcaaatga acagcctgag acctgaggac acggctgtgt attactgtgc gaaagagagg    300 attttttggag tgcttacccc tgatgatttt gatatctggg gccaagggac aacggtcact    360
gtctcctca                                                              369

<210> SEQ ID NO 464
<211> LENGTH: 369
<212> TYPE: DNA
<213> ORGANISM: Homo sapiens

<400> SEQUENCE: 464
gaggtgcagc tgttggagtc tggggagggc gtggtccagc ctgggaggtc cctgagactc      60
tcctgtgcag cctctggatt cccccttcatt agctatggca tgcactgggt ccgccaggct   120
ccaggcaagg ggctggagtg ggtggcagtt atatcatatg atggagctaa tagatactat    180
gcagactccg tgaagggccg attcaccatc tccagagaca attccaagaa cacgctgtat    240
ctgcaaatga acagcctgag acctgaggac acggctgtgt attattgtgc gaaagagagg    300 attttttggcg tgcttacccc tgatgatttt gaaatctggg gccaagggac aacggtcacc    360
gtctcctca                                                              369
```

<210> SEQ ID NO 465
<211> LENGTH: 369
<212> TYPE: DNA
<213> ORGANISM: Homo sapiens

<400> SEQUENCE: 465
gaggtgcagc tggtggagtc tggggggaggc gtggtccagc ctggggaggtc cctgagactc      60 tcctgtgcag cctctggatt caccttcact agctatggca tgcactgggt ccgccaggct     120
ccaggcaagg ggctggagtg ggtggcagtt atatcatatg atggaagtaa tagatactat     180
gcagactccg tgaagggccg attcaccatc tccagagaca attccaagaa cacgctgtat     240
ctgcaaatga acagcctgag acctgaggac acggctgtgt attactgtgc gaaagagagg     300
atttttggag cgcttaccccc tgatgatttt gatatctggg gccaagggac aacggtcacc     360
gtctcttca                                                             369

<210> SEQ ID NO 466
<211> LENGTH: 348
<212> TYPE: DNA
<213> ORGANISM: Homo sapiens

<400> SEQUENCE: 466
caggtgcagc tggtggagtc tggggggaggc gtggtccagc ctggggaggtc cctgagactc      60 tcctgtgcag cctctggatt caccttcaat aactatggca tgcactgggt ccgccaggct     120
ccaggcaagg ggctggagtg ggtggcaatt atatcatatg atggaaatac taaatattat     180
acagactccg tgaagggccg attcaccatc tccagagaca attccaagaa cacgctgtat     240
ctgcaaatga atagcctgag agttgaggac acggctgtgt attactgtgc gaaaggttta     300
tggccttcgg acgtctgggg ccaagggacc acggtcactg tctcttca                   348

<210> SEQ ID NO 467
<211> LENGTH: 348
<212> TYPE: DNA
<213> ORGANISM: Homo sapiens

<400> SEQUENCE: 467
gaggtgcagc tggtggagtc tggggggaggc gtggtccagc ctggggaggtc cctgagactc      60 tcctgtgcag cctctggatt caccttcaat aactatggca tgcactgggt ccgccaggct     120
ccaggcaagg ggctggagtg ggtggcaatt atatcatatg atggaaatag taaatattat     180
acagactccg tgaagggccg attcaccatc tccagagaca attccaagaa cacgctgtat     240
ctgcaaatga atagcctgag agttgaggac acggctgtgt attactgtgc gaaaggttta     300
tggccttcgg acgtctgggg ccaagggacc acggtcaccg tctcctca                   348

<210> SEQ ID NO 468
<211> LENGTH: 357
<212> TYPE: DNA
<213> ORGANISM: Homo sapiens

<400> SEQUENCE: 468
caggtgcagc tacaggagtc gggcccagga ctggtgaagc cttcacagac cctgtccctc      60
acctgcactg tctctggtgg ctccatcagc aatagtggtt attactggag ctgggtccgc     120
cagcacccag ggaaggacct ggagtggatt gggttcatct attacaatgg gagcatccac     180
tacaacccgt ccctcaagag tcgagttatc atatcagtag acacgtctaa gaaccagttc     240

```
tccctgaaaa tgaactctgt gactgccgcg gacacggccg tgtattactg tgcgagagac      300
ggggatgact acggtgacta cttgaggggc cagggaaccc tggtcaccgt ctcctca         357
```

<210> SEQ ID NO 469
<211> LENGTH: 357
<212> TYPE: DNA
<213> ORGANISM: Homo sapiens

<400> SEQUENCE: 469

```
caggtgcagc tgcaggagtc gggcccagga ctggtgaagc cttcacagac cctgtccctc      60
acctgcactg tctctggtgg ctccatcagc aatagtggtt attactggag ctggatccgc     120
cagcacccag ggaagggcct ggagtggatt gggttcatct attacaatgg gagcatccac     180
tacaacccgt ccctcaagag tcgagttatc atatcagtag acacgtctaa gaaccagttc     240
tccctgaaaa tgagctctgt gactgccgcg gacacggccg tgtattactg tgcgagagac     300
ggggatgact acggtgacta cttgaggggc cagggaaccc tggtcaccgt ctcctca        357
```

<210> SEQ ID NO 470
<211> LENGTH: 357
<212> TYPE: DNA
<213> ORGANISM: Homo sapiens

<400> SEQUENCE: 470

```
caggtgcagc tgcaggagtc gggcccagga ctggtgaagc cttcacagac cctgtccctc      60
acctgcactg tctctggtgg ctccatcagc aatagtggtt attactggag ctgggtccgc     120
cagcacccag ggaagggcct ggagtggatt gggttcatct attacaatgg gagcatccac     180
tacaacccgt ccctcaagag tcgagttatc atatcagtag acacgtctaa gaaccagttc     240
tccctgaaac tgaactctgt gactgccgcg gacacggccg tgtattactg tgcgagagac     300
ggggatgact acggtgacta cttgaggggc cagggaaccc tggtcaccgt ctcctca        357
```

<210> SEQ ID NO 471
<211> LENGTH: 357
<212> TYPE: DNA
<213> ORGANISM: Homo sapiens

<400> SEQUENCE: 471

```
caggtgcagc tgcaggagtc gggcccagga ctggtgaagc cttcacagac cctgtccctc      60
acctgcactg tctctggtgg ctccatcagc aatagtggtt attactggag ctggatccgc     120
cagcacccag ggaagggcct ggagtggatt gggttcatct attacaatgg gagcatccac     180
tacaacccgt ccctcaagag tcgagttatc atatcagtag acacgtctaa gaaccagttc     240
tccctgaaac tgagctctgt gactgccgcg gacacggccg tgtattactg tgcgagagac     300
ggggatgact acggtgacta cttgaggggc cagggaaccc tggtcaccgt ctcctca        357
```

<210> SEQ ID NO 472
<211> LENGTH: 357
<212> TYPE: DNA
<213> ORGANISM: Homo sapiens

<400> SEQUENCE: 472

```
caggtgcagc tgcaggagtc gggcccagga ctggtgaagc cttcacagac cctgtccctc      60
acctgcactg tctctggtgg ctccatcagc aatagtggtt attactggag ctgggtccgc     120
cagcacccag ggaagggcct ggagtggatt gggttcatct attacaatgg gagcatccac     180
tacaacccgt ccctcaagag tcgagttacc atatcagtag acacgtctaa gaaccagttc     240
```

| | |
|---|---|
| tccctgaaaa tgagctctgt gactgccgcg acacggccg tgtattactg tgcgagagac | 300 |
| ggggatgact acggtgacta cttgagggc cagggaaccc tggtcaccgt ctcctca | 357 |

<210> SEQ ID NO 473
<211> LENGTH: 357
<212> TYPE: DNA
<213> ORGANISM: Homo sapiens

<400> SEQUENCE: 473

| | |
|---|---|
| caggtgcagc tgcaggagtc gggcccagga ctggtgaagc cttcacagac cctgtccctc | 60 |
| acctgcactg tctctggtgg ctccatcagc aatagtggtt attactggag ctgggtccgc | 120 |
| cagcacccag ggaagggcct ggagtggatt gggttcatct attacaatgg gagcatccac | 180 |
| tacaacccgt ccctcaagag tcgagttacc atatcagtag acacgtctaa gaaccagttc | 240 |
| tccctgaaac tgaactctgt gactgccgcg acacggccg tgtattactg tgcgagagac | 300 |
| ggggatgact acggtgacta cttgagggc cagggaaccc tggtcaccgt ctcctca | 357 |

<210> SEQ ID NO 474
<211> LENGTH: 357
<212> TYPE: DNA
<213> ORGANISM: Homo sapiens

<400> SEQUENCE: 474

| | |
|---|---|
| caggtgcagc tgcaggagtc gggcccagga ctggtgaagc cttcacagac cctgtccctc | 60 |
| acctgcactg tctctggtgg ctccatcagc aatagtggtt attactggag ctgggtccgc | 120 |
| cagcacccag ggaagggcct ggagtggatt gggttcatct attacaatgg gagcatccac | 180 |
| tacaacccgt ccctcaagag tcgagttacc atatcagtag acacgtctaa gaaccagttc | 240 |
| tccctgaaac tgagctctgt gactgccgcg acacggccg tgtattactg tgcgagagac | 300 |
| ggggatgact acggtgacta cttgagggc cagggaaccc tggtcaccgt ctcctca | 357 |

<210> SEQ ID NO 475
<211> LENGTH: 357
<212> TYPE: DNA
<213> ORGANISM: Homo sapiens

<400> SEQUENCE: 475

| | |
|---|---|
| gaggtgcagc tggtggagtc tgggggaggc ttggtccagc ctgggggtc cctgagactc | 60 |
| tcctgtgcag cctctggatt cacctttagt agctattgga tgtactgggt ccgccaggct | 120 |
| ccagggaagg ggctggagtg ggtggccaac ataaatcacg atggaagtga gaaatactat | 180 |
| gtggactctg tgaagggccg attcaccatc tccagagaca acgccaagaa ctcactgtat | 240 |
| ctgcaaatga acagcctgag agccgaggac acggctgtgt attactgcgc gagagattcc | 300 |
| cttatagtgg gagagagggg ctactgggc cagggaaccc tggtcaccgt ctcctca | 357 |

<210> SEQ ID NO 476
<211> LENGTH: 357
<212> TYPE: DNA
<213> ORGANISM: Homo sapiens

<400> SEQUENCE: 476

| | |
|---|---|
| gaggtgcagc tggtggagtc tgggggaggc ttggtccagc ctgggggtc cctgagactc | 60 |
| tcctgtgcag cctctggatt cacctttagt agctattgga tgtactgggt ccgccaggct | 120 |
| ccagggaagg ggctggagtg ggtggccaac ataaatcacg atggaagtga gaaatactat | 180 |

```
gtggactctg tgaagggccg attcaccatc tccagagaca acgccaagaa ctcactgtat    240
ctgcaaatga acagcctgag agccgaggac acggctgtgt attactgcgc gagagataac    300
cttatagtgg gagagagggg ctactggggc cagggaaccc tggtcaccgt ctcctca      357
```

<210> SEQ ID NO 477
<211> LENGTH: 325
<212> TYPE: DNA
<213> ORGANISM: Homo sapiens

<400> SEQUENCE: 477

```
gaggtgcagc tggtggagtc tgggggaggc ttggtccagc ctgggggtc cctgagactc     60 tcctgtgcag cctctggatt cacctttagt agctattgga tgtactgggt ccgccaggct   120
ccagggaagg ggctggagtg ggtggccaac ataaatcacg ggggaagtga aaatactat    180 gtggactctg tgaagggccg attcaccatc tccagagaca acgccaagaa ctcactgtat   240
ctgcaaatga acagcctgag agccgaggac acggctgtgt attactgcgc gagagattcc   300
cttatagtgg gagagagggg ctact                                         325
```

<210> SEQ ID NO 478
<211> LENGTH: 389
<212> TYPE: DNA
<213> ORGANISM: Homo sapiens

<400> SEQUENCE: 478

```
ggggccaggg aaccctggtc accgtctcct cagaggtgca gctggtggag tctgggggag     60
gcttggtcca gcctgggggg tccctgagac tctcctgtgc agcctctgga ttcaccttta   120
gtagctattg gatgtactgg gtccgccagg ctccagggaa ggggctggag tgggtggcca   180
acataaatca ccggggaagt gagaaatact atgtggactc tgtgaagggc cgattcacca   240
tctccagaga caacgccaag aactcactgt atctgcaaat gaacagcctg agagccgagg   300
acacggctgt gtattactgc gcgagagatt cccttatagt gggagagagg ggctactggg   360
gccagggaac cctggtcacc gtctcctca                                     389
```

<210> SEQ ID NO 479
<211> LENGTH: 357
<212> TYPE: DNA
<213> ORGANISM: Homo sapiens

<400> SEQUENCE: 479

```
gaggtgcagc tggtggagtc tgggggaggc ttggtccagc ctgggggtc cctgagactc     60 tcctgtgcag cctctggatt cacctttagt agctattgga tgtactgggt ccgccaggct   120
ccagggaagg ggctggagtg ggtggccaac ataaatcacc ccggaagtga aaatactat    180 gtggactctg tgaagggccg attcaccatc tccagagaca acgccaagaa ctcactgtat   240
ctgcaaatga acagcctgag agccgaggac acggctgtgt attactgcgc gagagattcc   300
cttatagtgg gagagagggg ctactggggc cagggaaccc tggtcaccgt ctcctca      357
```

<210> SEQ ID NO 480
<211> LENGTH: 357
<212> TYPE: DNA
<213> ORGANISM: Homo sapiens

<400> SEQUENCE: 480

```
gaggtgcagc tggtggagtc tgggggaggc ttggtccagc ctgggggtc cctgagactc     60 tcctgtgcag cctctggatt cacctttagt agctattgga tgtactgggt ccgccaggct   120
```

```
ccagggaagg ggctggagtg ggtggccaac ataaatcacg agggaagtga gaaatactat      180
gtggactctg tgaagggccg attcaccatc tccagagaca acgccaagaa ctcactgtat      240
ctgcaaatga acagcctgag agccgaggac acggctgtgt attactgcgc gagagattcc      300
cttatagtgg gagagagggg ctactggggc cagggaaccc tggtcaccgt ctcctca        357
```

<210> SEQ ID NO 481
<211> LENGTH: 357
<212> TYPE: DNA
<213> ORGANISM: Homo sapiens

<400> SEQUENCE: 481

```
gaggtgcagc tggtggagtc tggggggaggc ttggtccagc ctgggggggtc cctgagactc     60 tcctgtgcag cctctggatt cacctttagt agctattgga tgtactgggt ccgccaggct     120
ccagggaagg ggctggagtg ggtggccaac ataaatcaca tcggaagtga gaaatactat     180
gtggactctg tgaagggccg attcaccatc tccagagaca acgccaagaa ctcactgtat     240
ctgcaaatga acagcctgag agccgaggac acggctgtgt attactgcgc gagagattcc     300
cttatagtgg gagagagggg ctactggggc cagggaaccc tggtcaccgt ctcctca       357
```

<210> SEQ ID NO 482
<211> LENGTH: 357
<212> TYPE: DNA
<213> ORGANISM: Homo sapiens

<400> SEQUENCE: 482

```
gaggtgcagc tggtggagtc tggggggaggc ttggtccagc ctgggggggtc cctgagactc     60 tcctgtgcag cctctggatt cacctttagt agctattgga tgtactgggt ccgccaggct    120
ccagggaagg ggctggagtg ggtggccaac ataaatcacg atggaagtga gaaatactat    180
gtggactctg tgaagggccg attcaccatc tccagagaca acgccaagaa ctcactgtat    240
ctgcaaatga acagcctgag agccgaggac acggctgtgt attactgcgc gagagatacc    300
cttatagtgg gagagagggg ctactggggc cagggaaccc tggtcaccgt ctcctca       357
```

<210> SEQ ID NO 483
<211> LENGTH: 366
<212> TYPE: DNA
<213> ORGANISM: Homo sapiens

<400> SEQUENCE: 483

```
caggtgcagc tacagcagtg gggcgcagga ctgttgaagc cttcggagac cctgtccctc      60
acctgcgctg tctatggtgg gtccttcagt ggttactact ggagctggat ccgccagccc    120
ccagggaagg ggctggagtg gattggggaa atcaatcata gtggaagcac caactacaac    180
ccgtccctca agagtcgagt caccatatca gtagacacgt ccaagaacca gttctccctg    240
aagctgagct ctgtgaccgc cgcggacacg gctgtgtatt actgtgcgag aggccccata    300
ccagccactg ctatacccga tgcttttgat atctggggcc aagggacaat ggtcactgtc    360
tcctca                                                              366
```

<210> SEQ ID NO 484
<211> LENGTH: 357
<212> TYPE: DNA
<213> ORGANISM: Homo sapiens

<400> SEQUENCE: 484

```
gaggtgcagc tacagcagtg gggcgcagga ctgttgaagc cttcggagac cctgtccctc      60
acctgcgctg tctatggtgg gtccttcagt ggtcactact ggagctggat ccgccagccc     120
ccagggaagg ggctggagtg gattggggac ataaatcata gtggaagcac caactacaac     180
ccgtccctca agagtcgagt caccatatca gtagacacgt ccaagaatca gttctccctg     240
aagctgagct ctgtgaccgc cgcggacacg gctgtgtatt actgtgtgag agactacggt     300
gactcccgta gccttttga  ctactggggc cagggaaccc tggtcaccgt ctcttca       357

<210> SEQ ID NO 485
<211> LENGTH: 375
<212> TYPE: DNA
<213> ORGANISM: Homo sapiens

<400> SEQUENCE: 485
caggtgcagc tggtggagtc tgggggaggc ttggtacagc ctgggggtc cctgagactc       60 tcctgtgcag cctctggatt caccttcagt agctatggca tgcactgggt ccgccaggct     120
ccaggcaagg ggctggagtg ggtggcattt atgtcatatg atggcagtaa taatactat      180 gtagactccg tgaagggccg attcaccatc tccagagaca attccaagaa tacgctgtat     240
ctgcaaatga acagcctgag agctgaggac acggctgtgt attactgtgc gaaaggcgat     300
tacgattttt ggagtggtta ccccgactac gatatggacg tctggggcca agggaccacg     360
gtcaccgtct cctca                                                      375

<210> SEQ ID NO 486
<211> LENGTH: 378
<212> TYPE: DNA
<213> ORGANISM: Homo sapiens

<400> SEQUENCE: 486
gaggtgcagc tggtggagtc tgggggaggc ttggtcaagc ctggagggtc cctgagactc       60
tcctgtgcag cctctggatt caacttgatt agctatggca tgtactgggt ccgccaggct     120
ccaggcaagg ggctggagtg ggtggcagtt atatcatatg atggaagtaa taaaaactat     180
gcagactccg tgaagggccg attcaccatc tccagagaca attccaagaa tacgctgttt     240
ctgcaaatga acagcctgag agttgaggac acggctgtgt attactgtgc gaaggggggg     300 aatgcctttgt atagcagtgg ctggcccgat gatggttttg atatcagggg ccaagggaca     360
atggtcactg tctcctca                                                   378

<210> SEQ ID NO 487
<211> LENGTH: 351
<212> TYPE: DNA
<213> ORGANISM: Homo sapiens

<400> SEQUENCE: 487
caggtgcagc tggtggagtc tgggggaggc gtggtccagc ctggagggtc cctgagactc       60
tcctgtgcag cctctggatt caccttcagt aactttggca tgcactgggc ccgccaggct     120
ccaggcaagg gactggagtg ggtggcagta atatcatatg atggaaatag taaatactat     180
gcagacaccg tgaagggccg attcaccatc tccagagaca attccaagaa cacgctgtat     240
ctggaaatga acagcctgag agctgatgac acggctgtgt attactgtgc gaaaggccta     300 tggccccaa tggacgtcag gggccaaggg accacggtca ccgtctcctc a                351

<210> SEQ ID NO 488
<211> LENGTH: 372
```

<212> TYPE: DNA
<213> ORGANISM: Homo sapiens

<400> SEQUENCE: 488

```
gaggtgcagc tggtggagtc tgggggaggc tcggtccagc ctgggggtc cctgagactc    60
tcctgtgcag cctctggatt cacctttagt gactattgga tgacctgggt ccgccaggtt   120
ccagggaagg ggctggagtg ggtggccaac ataaagcaag atggaagtga gaaatactat   180
gtggactctg tgaagggccg attcaccatc tccagagaca cgccaagaa ctcactatat    240
ctgcaaatga atagcctgag agccgaggac acggctgtgt attactgtgc gagagatcga   300
ggaggagcag tggccctta tcacaacggt atggacatgg ggggccaagg gaccacggtc    360
actgtctctt ca                                                       372
```

<210> SEQ ID NO 489
<211> LENGTH: 361
<212> TYPE: DNA
<213> ORGANISM: Homo sapiens

<400> SEQUENCE: 489

```
gaagtgcagc tggtggagtc tgggggaggt gaagaagcct ggggcctcag tgaaggtctc    60
ctgcaaggct tctggataca ccttcaccag ttatgatatc aactgggtgc gacaggccac   120
tggacaaggg cttgagtgga tgggatggat gaaccctaac agtggtaaca caggctatgc   180
acagaagttc cagggcagag tcaccatgac caggaacacc tccataagca gcctacat     240
ggagctgagc agcctgagat ctgaggacac ggccgtgtat tactgtgcga gagggaacgg   300
gcccggtata actggaacta ctgactactg gggccaggga accctggtca ctgtctcttc   360
a                                                                   361
```

<210> SEQ ID NO 490
<211> LENGTH: 357
<212> TYPE: DNA
<213> ORGANISM: Homo sapiens

<400> SEQUENCE: 490

```
gaggtgcagc tggtggagtc tgggggaggt gtggtacggc ctgggggtc cctgagactc     60
tcctgtgcag cctctggatt cacctttgat gattatggca tgagctgggt ccgccaagct   120
ccagggaagg ggctggagtg ggtctctggt attaattgga tggtgatcg taccggttat    180
gcagactctg tgaagggccg attcaccatc tccagagaca cgccaagaa ctccctgtat    240
ctgcaaatga acagtctgag agccgaggac acggccttgt attactgtgg gagagagaat   300
gttatagtac cagctgctac ctactggggc cagggaaccc tggtcaccgt ctcctca      357
```

<210> SEQ ID NO 491
<211> LENGTH: 73
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic primer" B= C or G or T

<400> SEQUENCE: 491

```
gccgctggat tgttattact cgcggcccag ccggccatgg cccaggtbca gctggtgcag    60
tctggggctg agg                                                      73
```

<210> SEQ ID NO 492

```
<211> LENGTH: 65
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic primer"

<400> SEQUENCE: 492
gccgctggat tgttattact cgcggcccag ccggccatgg cccagatcac cttgaaggag     60
tctgg                                                                 65

<210> SEQ ID NO 493
<211> LENGTH: 71
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic primer" s=c or g

<400> SEQUENCE: 493
gccgctggat tgttattact cgcggcccag ccggccatgg ccsaggtgca gctggtggag     60 tctggggag g                                                           71

<210> SEQ ID NO 494
<211> LENGTH: 65
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic primer"

<400> SEQUENCE: 494
gccgctggat tgttattact cgcggcccag ccggccatgg cccaggtgca gctgcaggag     60
tcggg                                                                 65

<210> SEQ ID NO 495
<211> LENGTH: 65
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic primer"

<400> SEQUENCE: 495
gccgctggat tgttattact cgcggcccag ccggccatgg cccaggtaca gctgcagcag     60
tcagg                                                                 65

<210> SEQ ID NO 496
<211> LENGTH: 54
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic primer" r=a or g

<400> SEQUENCE: 496
ccgtggtgat ggtggtgatg gctaccgcca ccctcgagtg argagacrgt gacc            54

<210> SEQ ID NO 497
<211> LENGTH: 73
```

<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic primer"

<400> SEQUENCE: 497
gccgctggat tgttattact cgcggcccag ccggccatgg cccaggtgca gctggtgcag    60
tctggggctg agg                                                        73

<210> SEQ ID NO 498
<211> LENGTH: 73
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic primer"

<400> SEQUENCE: 498
gccgctggat tgttattact cgcggcccag ccggccatgg cccaggtcca gctcgtgcag    60
tctggggctg agg                                                        73

<210> SEQ ID NO 499
<211> LENGTH: 73
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic primer"

<400> SEQUENCE: 499
gccgctggat tgttattact cgcggcccag ccggccatgg cccaggttca gctggtgcag    60
tctggagctg agg                                                        73

<210> SEQ ID NO 500
<211> LENGTH: 73
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic primer"

<400> SEQUENCE: 500
gccgctggat tgttattact cgcggcccag ccggccatgg cccaggtcca gctggtacag    60
tctggggctg agg                                                        73

<210> SEQ ID NO 501
<211> LENGTH: 65
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic primer" r=a or g

<400> SEQUENCE: 501
gccgctggat tgttattact cgcggcccag ccggccatgg cccagrtcac cttgaaggag    60
tctgg                                                                 65

<210> SEQ ID NO 502

```
<211> LENGTH: 71
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic primer"

<400> SEQUENCE: 502
gccgctggat tgttattact cgcggcccag ccggccatgg ccgaggtgca gctggtggag      60
tctgggggag g                                                          71

<210> SEQ ID NO 503
<211> LENGTH: 71
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic primer"

<400> SEQUENCE: 503
gccgctggat tgttattact cgcggcccag ccggccatgg ccgaagtgca gctggtggag      60
tctgggggag g                                                          71

<210> SEQ ID NO 504
<211> LENGTH: 71
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic primer"

<400> SEQUENCE: 504
gccgctggat tgttattact cgcggcccag ccggccatgg cccaggtgca gctggtggag      60
tctgggggag g                                                          71

<210> SEQ ID NO 505
<211> LENGTH: 71
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic primer"

<400> SEQUENCE: 505
gccgctggat tgttattact cgcggcccag ccggccatgg ccgaggtgca gctgttggag      60
tctgggggag g                                                          71

<210> SEQ ID NO 506
<211> LENGTH: 71
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic primer"

<400> SEQUENCE: 506
gccgctggat tgttattact cgcggcccag ccggccatgg ccgaggtgca gctgttggag      60
tctgggggag g                                                          71
```

-continued

```
<210> SEQ ID NO 507
<211> LENGTH: 65
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic primer"

<400> SEQUENCE: 507
gccgctggat tgttattact cgcggcccag ccggccatgg cccaggtgca gctgcaggag      60
tcggg                                                                 65

<210> SEQ ID NO 508
<211> LENGTH: 66
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic primer"

<400> SEQUENCE: 508
gccgctggat tgttattact cgcggcccag ccggccatgg cccaggtgca gctacagcag      60
tggggc                                                                66

<210> SEQ ID NO 509
<211> LENGTH: 65
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic primer"

<400> SEQUENCE: 509
gccgctggat tgttattact cgcggcccag ccggccatgg cccaggtaca gctgcagcag      60
tcagg                                                                 65

<210> SEQ ID NO 510
<211> LENGTH: 54
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic primer" r=a or g

<400> SEQUENCE: 510
ccgtggtgat ggtggtgatg gctaccgcca ccctcgagtg argagacrgt gacc            54

<210> SEQ ID NO 511
<211> LENGTH: 24
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic primer"

<400> SEQUENCE: 511
ggccatggcc ggctgggccg cgag                                            24

<210> SEQ ID NO 512
<211> LENGTH: 99
<212> TYPE: DNA
```

<213> ORGANISM: Artificial Sequence
<220> FEATURE:
<221> NAME/KEY: source
<223> OTHER INFORMATION: /note="Description of Artificial Sequence: Synthetic primer"

<400> SEQUENCE: 512
tcatcgaggg tggcgagcga acaaaaactc atctcagaag aatctgaatc atcacacatc    60
acacgggagc tagactgttg aaagttgttt agcaaaacc    99

<210> SEQ ID NO 513
<211> LENGTH: 18
<212> TYPE: PRT
<213> ORGANISM: Homo sapiens

<400> SEQUENCE: 513

Asp Pro Ala Trp Gly Leu Arg Leu Gly Glu Ser Ser Ser Tyr Asp Phe
1               5                   10                  15

Asp Ile

<210> SEQ ID NO 514
<211> LENGTH: 14
<212> TYPE: PRT
<213> ORGANISM: Homo sapiens

<400> SEQUENCE: 514

Asp Arg Ile Val Gly Gly Arg Val Pro Asp Ala Phe Asp Ile
1               5                   10

<210> SEQ ID NO 515
<211> LENGTH: 14
<212> TYPE: PRT
<213> ORGANISM: Homo sapiens

<400> SEQUENCE: 515

Glu Arg Ile Phe Gly Val Leu Thr Pro Asp Asp Phe Asp Ile
1               5                   10

<210> SEQ ID NO 516
<211> LENGTH: 7
<212> TYPE: PRT
<213> ORGANISM: Homo sapiens

<400> SEQUENCE: 516

Gly Leu Trp Pro Ser Asp Val
1               5

<210> SEQ ID NO 517
<211> LENGTH: 8
<212> TYPE: PRT
<213> ORGANISM: Homo sapiens

<400> SEQUENCE: 517

Gly Leu Trp Pro Pro Met Asp Val
1               5

<210> SEQ ID NO 518
<211> LENGTH: 16
<212> TYPE: PRT
<213> ORGANISM: Homo sapiens

<400> SEQUENCE: 518

Gly Asp Tyr Asp Phe Trp Ser Gly Tyr Pro Asp Tyr Asp Met Asp Val
1               5                   10                  15

```
<210> SEQ ID NO 519
<211> LENGTH: 13
<212> TYPE: PRT
<213> ORGANISM: Homo sapiens

<400> SEQUENCE: 519

Gly Gly Asn Ala Leu Tyr Ser Ser Gly Trp Pro Asp Asp
1               5                   10

<210> SEQ ID NO 520
<211> LENGTH: 4
<212> TYPE: PRT
<213> ORGANISM: Homo sapiens

<400> SEQUENCE: 520

Asp Gly Val His
1

<210> SEQ ID NO 521
<211> LENGTH: 10
<212> TYPE: PRT
<213> ORGANISM: Homo sapiens

<400> SEQUENCE: 521

Glu Asn Val Ile Val Pro Ala Ala Thr Tyr
1               5                   10

<210> SEQ ID NO 522
<211> LENGTH: 10
<212> TYPE: PRT
<213> ORGANISM: Homo sapiens

<400> SEQUENCE: 522

Asp Ser Leu Ile Val Gly Glu Arg Gly Tyr
1               5                   10

<210> SEQ ID NO 523
<211> LENGTH: 15
<212> TYPE: PRT
<213> ORGANISM: Homo sapiens

<400> SEQUENCE: 523

Asp Arg Gly Gly Ala Val Ala Leu Tyr His Asn Gly Met Asp Met
1               5                   10                  15

<210> SEQ ID NO 524
<211> LENGTH: 11
<212> TYPE: PRT
<213> ORGANISM: Homo sapiens

<400> SEQUENCE: 524

Asp Tyr Gly Asp Ser Arg Ser Leu Phe Asp Tyr
1               5                   10

<210> SEQ ID NO 525
<211> LENGTH: 14
<212> TYPE: PRT
<213> ORGANISM: Homo sapiens

<400> SEQUENCE: 525

Gly Pro Ile Pro Ala Thr Ala Ile Pro Asp Ala Phe Asp Ile
1               5                   10
```

<210> SEQ ID NO 526
<211> LENGTH: 8
<212> TYPE: PRT
<213> ORGANISM: Homo sapiens

<400> SEQUENCE: 526

Asp Gly Asp Asp Tyr Gly Asp Tyr
1               5

<210> SEQ ID NO 527
<211> LENGTH: 12
<212> TYPE: PRT
<213> ORGANISM: Homo sapiens

<400> SEQUENCE: 527

Gly Asn Gly Pro Gly Ile Thr Gly Thr Thr Asp Tyr
1               5                   10

<210> SEQ ID NO 528
<211> LENGTH: 121
<212> TYPE: PRT
<213> ORGANISM: Mus sp.

<400> SEQUENCE: 528

Gln Val Gln Leu Val Glu Ser Gly Gly Gly Leu Val Gln Pro Gly Gly
1               5                   10                  15

Ser Leu Arg Leu Ser Cys Ala Ala Ser Gly Phe Thr Phe Ser Ser Tyr
            20                  25                  30

Ala Met Ser Trp Val Arg Gln Ala Pro Gly Lys Gly Leu Glu Trp Val
        35                  40                  45

Ala Thr Ile Ser Asp Ser Gly Ser Ala Asp Tyr Ala Asp Ser Val
    50                  55                  60

Lys Gly Arg Phe Thr Ile Ser Arg Asp Asn Ser Lys Asn Thr Leu Tyr
65                  70                  75                  80

Leu Gln Met Asn Ser Leu Arg Ala Glu Asp Thr Ala Val Tyr Tyr Cys
                85                  90                  95

Ala Arg Gly Arg Tyr Asn Trp Asn Pro Arg Ala Leu Gly Ile Trp Gly
            100                 105                 110

Gln Gly Thr Met Val Thr Val Ser Ser
        115                 120

<210> SEQ ID NO 529
<211> LENGTH: 749
<212> TYPE: PRT
<213> ORGANISM: Homo sapiens

<400> SEQUENCE: 529

Met Trp Asn Leu Leu His Glu Thr Asp Ser Ala Val Ala Thr Ala Arg
1               5                   10                  15

Arg Pro Arg Trp Leu Cys Ala Gly Ala Leu Val Leu Ala Gly Gly Phe
            20                  25                  30

Phe Leu Leu Gly Phe Leu Phe Gly Trp Phe Ile Lys Ser Ser Asn Glu
        35                  40                  45

Ala Thr Asn Ile Thr Pro Lys His Asn Met Lys Ala Phe Leu Asp Glu
    50                  55                  60

Leu Lys Ala Glu Asn Ile Lys Lys Phe Leu Tyr Asn Phe Thr Gln Ile
65                  70                  75                  80

Pro His Leu Ala Gly Thr Glu Gln Asn Phe Gln Leu Ala Lys Gln Ile
                85                  90                  95

```
Gln Ser Gln Trp Lys Glu Phe Gly Leu Asp Ser Val Glu Leu Ala His
                100                 105                 110

Tyr Asp Val Leu Leu Ser Tyr Pro Asn Lys Thr His Pro Asn Tyr Ile
            115                 120                 125

Ser Ile Ile Asn Glu Asp Gly Asn Glu Ile Phe Asn Thr Ser Leu Phe
        130                 135                 140

Glu Pro Pro Pro Gly Tyr Glu Asn Val Ser Asp Ile Val Pro Pro
145                 150                 155                 160

Phe Ser Ala Phe Ser Pro Gln Gly Met Pro Glu Gly Asp Leu Val Tyr
                165                 170                 175

Val Asn Tyr Ala Arg Thr Glu Asp Phe Phe Lys Leu Glu Arg Asp Met
            180                 185                 190

Lys Ile Asn Cys Ser Gly Lys Ile Val Ile Ala Arg Tyr Gly Lys Val
        195                 200                 205

Phe Arg Gly Asn Lys Val Lys Asn Ala Gln Leu Ala Gly Ala Lys Gly
    210                 215                 220

Val Ile Leu Tyr Ser Asp Pro Ala Asp Tyr Phe Ala Pro Gly Val Lys
225                 230                 235                 240

Ser Tyr Pro Asp Gly Trp Asn Leu Pro Gly Gly Val Gln Arg Gly
                245                 250                 255

Asn Ile Leu Asn Leu Asn Gly Ala Gly Asp Pro Leu Thr Pro Gly Tyr
            260                 265                 270

Pro Ala Asn Glu Tyr Ala Tyr Arg Arg Gly Ile Ala Glu Ala Val Gly
        275                 280                 285

Leu Pro Ser Ile Pro Val His Pro Ile Gly Tyr Asp Ala Gln Lys Leu
    290                 295                 300

Leu Glu Lys Met Gly Gly Ser Ala Pro Pro Asp Ser Ser Trp Arg Gly
305                 310                 315                 320

Ser Leu Lys Val Pro Tyr Asn Val Gly Pro Gly Phe Thr Gly Asn Phe
                325                 330                 335

Ser Thr Gln Lys Val Lys Met His Ile His Ser Thr Asn Glu Val Thr
            340                 345                 350

Arg Ile Tyr Asn Val Ile Gly Thr Leu Arg Gly Ala Val Glu Pro Asp
        355                 360                 365

Arg Tyr Val Ile Leu Gly Gly His Arg Asp Ser Trp Val Phe Gly Gly
    370                 375                 380

Ile Asp Pro Gln Ser Gly Ala Ala Val Val His Glu Ile Val Arg Ser
385                 390                 395                 400

Phe Gly Thr Leu Lys Lys Glu Gly Trp Arg Pro Arg Thr Ile Leu
                405                 410                 415

Phe Ala Ser Trp Asp Ala Glu Glu Phe Gly Leu Leu Gly Ser Thr Glu
            420                 425                 430

Trp Ala Glu Glu Asn Ser Arg Leu Leu Gln Glu Arg Gly Val Ala Tyr
        435                 440                 445

Ile Asn Ala Asp Ser Ser Ile Glu Gly Asn Tyr Thr Leu Arg Val Asp
    450                 455                 460

Cys Thr Pro Leu Met Tyr Ser Leu Val His Asn Leu Thr Lys Glu Leu
465                 470                 475                 480

Lys Ser Pro Asp Glu Gly Phe Glu Gly Lys Ser Leu Tyr Glu Ser Trp
                485                 490                 495

Thr Lys Lys Ser Pro Ser Pro Glu Phe Ser Gly Met Pro Arg Ile Ser
            500                 505                 510

Lys Leu Gly Ser Gly Asn Asp Phe Glu Val Phe Phe Gln Arg Leu Gly
```

```
              515                 520                 525
Ile Ala Ser Gly Arg Ala Arg Tyr Thr Lys Asn Trp Glu Thr Asn Lys
    530                 535                 540

Phe Ser Gly Tyr Pro Leu Tyr His Ser Val Tyr Glu Thr Tyr Glu Leu
545                 550                 555                 560

Val Glu Lys Phe Tyr Asp Pro Met Phe Lys Tyr His Leu Thr Val Ala
                565                 570                 575

Gln Val Arg Gly Gly Met Val Phe Glu Leu Ala Asn Ser Ile Val Leu
            580                 585                 590

Pro Phe Asp Cys Arg Asp Tyr Ala Val Val Leu Arg Lys Tyr Ala Asp
        595                 600                 605

Lys Ile Tyr Ser Ile Ser Met Lys His Pro Gln Glu Met Lys Thr Tyr
    610                 615                 620

Ser Val Ser Phe Asp Ser Leu Phe Ser Ala Val Lys Asn Phe Thr Glu
625                 630                 635                 640

Ile Ala Ser Lys Phe Ser Glu Arg Leu Gln Asp Phe Asp Lys Ser Asn
                645                 650                 655

Pro Ile Val Leu Arg Met Met Asn Asp Gln Leu Met Phe Leu Glu Arg
            660                 665                 670

Ala Phe Ile Asp Pro Leu Gly Leu Pro Asp Arg Pro Phe Tyr Arg His
        675                 680                 685

Val Ile Tyr Ala Pro Ser Ser His Asn Lys Tyr Ala Gly Glu Ser Phe
    690                 695                 700

Pro Gly Ile Tyr Asp Ala Leu Phe Asp Ile Glu Ser Lys Val Asp Pro
705                 710                 715                 720

Ser Lys Ala Trp Gly Glu Val Lys Arg Gln Ile Tyr Val Ala Ala Phe
                725                 730                 735

Thr Val Gln Ala Ala Ala Glu Thr Leu Ser Glu Val Ala
            740                 745

<210> SEQ ID NO 530
<211> LENGTH: 6
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic 6xHis tag"

<400> SEQUENCE: 530

His His His His His His
1               5

<210> SEQ ID NO 531
<211> LENGTH: 25
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic peptide"

<400> SEQUENCE: 531

Leu Glu Gly Gly Gly Ser Glu Gln Lys Leu Ile Ser Glu Glu Asp Leu
1               5                   10                  15

Asn His His His His His His Gly Ser
            20                  25

<210> SEQ ID NO 532
```

-continued

```
<211> LENGTH: 150
<212> TYPE: PRT
<213> ORGANISM: Artificial Sequence
<220> FEATURE:
<221> NAME/KEY: source
<223> OTHER INFORMATION: /note="combination of two human single domain
      antibodies"

<400> SEQUENCE: 532

Glu Val Gln Leu Val Glu Ser Gly Gly Val Val Gln Pro Gly Arg
1               5                   10                  15

Ser Leu Arg Leu Ser Cys Ala Ala Ser Gly Phe Ser Phe Ser Gly Tyr
            20                  25                  30

Gly Met His Trp Val Arg Gln Ala Pro Gly Lys Gly Leu Glu Trp Val
        35                  40                  45

Ala Tyr Ile Ser Tyr Asp Gly Ser Asn Lys Tyr Tyr Ala Asp Ser Val
50                  55                  60

Lys Gly Arg Phe Thr Ile Ser Arg Asp Asn Ser Lys Asn Thr Leu Tyr
65                  70                  75                  80

Leu Gln Met Asn Ser Leu Arg Ala Glu Asp Thr Ala Val Tyr Tyr Cys
                85                  90                  95

Ala Lys Asp Pro Ala Trp Gly Leu Arg Leu Gly Glu Ser Ser Ser Tyr
            100                 105                 110

Asp Phe Asp Ile Trp Gly Gln Gly Thr Met Val Thr Val Ser Ser Leu
        115                 120                 125

Glu Gly Gly Gly Ser Glu Gln Lys Leu Ile Ser Glu Glu Asp Leu Asn
    130                 135                 140

His His His His His His
145                 150

<210> SEQ ID NO 533
<211> LENGTH: 136
<212> TYPE: PRT
<213> ORGANISM: Artificial Sequence
<220> FEATURE:
<221> NAME/KEY: source
<223> OTHER INFORMATION: /note="combination of two human single domain
      antibodies"

<400> SEQUENCE: 533

Glu Val Gln Leu Leu Glu Ser Gly Gly Leu Val Gln Pro Gly Gly
1               5                   10                  15

Ser Leu Arg Leu Ser Cys Ala Ala Ser Gly Phe Ser Phe Ser Ser Tyr
            20                  25                  30

Ala Met Ser Trp Val Arg Gln Ala Pro Gly Lys Gly Leu Glu Trp Val
        35                  40                  45

Ser Ser Ile Gly Glu Asn Asp Gly Thr Thr Asp Tyr Ala Asp Ser Val
50                  55                  60

Lys Gly Arg Phe Thr Ile Ser Arg Asp Asn Ser Lys Ser Met Leu Tyr
65                  70                  75                  80

Leu Gln Met Asn Ser Leu Arg Val Glu Asp Thr Ala Val Tyr Tyr Cys
                85                  90                  95

Val Lys Asp Gly Val His Trp Gly Gln Gly Thr Leu Val Thr Val Ser
            100                 105                 110

Ser Leu Glu Gly Gly Gly Ser Glu Gln Lys Leu Ile Ser Glu Glu Asp
        115                 120                 125

Leu Asn His His His His His His
    130                 135
```

```
<210> SEQ ID NO 534
<211> LENGTH: 129
<212> TYPE: PRT
<213> ORGANISM: Artificial Sequence
<220> FEATURE:
<221> NAME/KEY: source
<223> OTHER INFORMATION: /note="combination of two human single domain
      antibodies"

<400> SEQUENCE: 534

Glu Val Gln Leu Leu Glu Ser Gly Gly Gly Leu Val Gln Pro Gly Gly
1               5                   10                  15

Ser Leu Arg Leu Ser Cys Ala Ala Ser Gly Phe Arg Ile Ser Asp Glu
            20                  25                  30

Asp Met Gly Trp Val Arg Gln Ala Pro Gly Lys Gly Leu Glu Trp Val
        35                  40                  45

Ser Ser Ile Tyr Gly Pro Ser Gly Ser Thr Tyr Tyr Ala Asp Ser Val
    50                  55                  60

Lys Gly Arg Phe Thr Ile Ser Arg Asp Asn Ser Lys Asn Thr Leu Tyr
65                  70                  75                  80

Leu Gln Met Asn Ser Leu Arg Ala Glu Asp Thr Ala Val Tyr Tyr Cys
                85                  90                  95

Ala Ser Ala Leu Glu Pro Leu Ser Glu Pro Leu Gly Phe Trp Gly Gln
            100                 105                 110

Gly Thr Leu Val Thr Val Ser Ser Ala Ala Ala His His His His His
        115                 120                 125

His

<210> SEQ ID NO 535
<211> LENGTH: 293
<212> TYPE: PRT
<213> ORGANISM: Artificial Sequence
<220> FEATURE:
<221> NAME/KEY: source
<223> OTHER INFORMATION: /note="combination of two human single domain
      antibodies"

<400> SEQUENCE: 535

Glu Val Gln Leu Val Glu Ser Gly Gly Gly Val Val Gln Pro Gly Arg
1               5                   10                  15

Ser Leu Arg Leu Ser Cys Ala Ala Ser Gly Phe Ser Phe Ser Gly Tyr
            20                  25                  30

Gly Met His Trp Val Arg Gln Ala Pro Gly Lys Gly Leu Glu Trp Val
        35                  40                  45

Ala Tyr Ile Ser Tyr Asp Gly Ser Asn Lys Tyr Tyr Ala Asp Ser Val
    50                  55                  60

Lys Gly Arg Phe Thr Ile Ser Arg Asp Asn Ser Lys Asn Thr Leu Tyr
65                  70                  75                  80

Leu Gln Met Asn Ser Leu Arg Ala Glu Asp Thr Ala Val Tyr Tyr Cys
                85                  90                  95

Ala Lys Asp Pro Ala Trp Gly Leu Arg Leu Gly Glu Ser Ser Tyr
            100                 105                 110

Asp Phe Asp Ile Trp Gly Gln Gly Thr Met Val Thr Val Ser Ser Gly
        115                 120                 125

Gly Gly Gly Ser Gly Gly Gly Gly Ser Gly Gly Gly Gly Ser Gly Gly
    130                 135                 140

Gly Gly Ser Gly Gly Gly Gly Ser Gly Gly Gly Gly Ser Glu Val Gln
145                 150                 155                 160
```

```
Leu Val Glu Ser Gly Gly Val Val Gln Pro Gly Arg Ser Leu Arg
                165                 170                 175

Leu Ser Cys Ala Ala Ser Gly Phe Ser Phe Ser Gly Tyr Gly Met His
                180                 185                 190

Trp Val Arg Gln Ala Pro Gly Lys Gly Leu Glu Trp Val Ala Tyr Ile
            195                 200                 205

Ser Tyr Asp Gly Ser Asn Lys Tyr Tyr Ala Asp Ser Val Lys Gly Arg
210                 215                 220

Phe Thr Ile Ser Arg Asp Asn Ser Lys Asn Thr Leu Tyr Leu Gln Met
225                 230                 235                 240

Asn Ser Leu Arg Ala Glu Asp Thr Ala Val Tyr Tyr Cys Ala Lys Asp
                245                 250                 255

Pro Ala Trp Gly Leu Arg Leu Gly Glu Ser Ser Ser Tyr Asp Phe Asp
                260                 265                 270

Ile Trp Gly Gln Gly Thr Met Val Thr Val Ser Ser Ala Ala Ala His
            275                 280                 285

His His His His His
            290

<210> SEQ ID NO 536
<211> LENGTH: 279
<212> TYPE: PRT
<213> ORGANISM: Artificial Sequence
<220> FEATURE:
<221> NAME/KEY: source
<223> OTHER INFORMATION: /note="combination of two human single domain
      antibodies"

<400> SEQUENCE: 536

Glu Val Gln Leu Val Glu Ser Gly Gly Val Val Gln Pro Gly Arg
1               5                   10                  15

Ser Leu Arg Leu Ser Cys Ala Ala Ser Gly Phe Ser Phe Ser Gly Tyr
                20                  25                  30

Gly Met His Trp Val Arg Gln Ala Pro Gly Lys Gly Leu Glu Trp Val
            35                  40                  45

Ala Tyr Ile Ser Tyr Asp Gly Ser Asn Lys Tyr Tyr Ala Asp Ser Val
        50                  55                  60

Lys Gly Arg Phe Thr Ile Ser Arg Asp Asn Ser Lys Asn Thr Leu Tyr
65                  70                  75                  80

Leu Gln Met Asn Ser Leu Arg Ala Glu Asp Thr Ala Val Tyr Tyr Cys
                85                  90                  95

Ala Lys Asp Pro Ala Trp Gly Leu Arg Leu Gly Glu Ser Ser Ser Tyr
            100                 105                 110

Asp Phe Asp Ile Trp Gly Gln Gly Thr Met Val Thr Val Ser Ser Gly
        115                 120                 125

Gly Gly Gly Ser Gly Gly Gly Gly Ser Gly Gly Gly Gly Ser Gly Gly
    130                 135                 140

Gly Gly Ser Gly Gly Gly Gly Ser Gly Gly Gly Gly Ser Glu Val Gln
145                 150                 155                 160

Leu Leu Glu Ser Gly Gly Gly Leu Val Gln Pro Gly Gly Ser Leu Arg
                165                 170                 175

Leu Ser Cys Ala Ala Ser Gly Phe Ser Phe Ser Ser Tyr Ala Met Ser
                180                 185                 190

Trp Val Arg Gln Ala Pro Gly Lys Gly Leu Glu Trp Val Ser Ser Ile
            195                 200                 205
```

```
Gly Glu Asn Asp Gly Thr Thr Asp Tyr Ala Asp Ser Val Lys Gly Arg
    210             215                 220

Phe Thr Ile Ser Arg Asp Asn Ser Lys Ser Met Leu Tyr Leu Gln Met
225             230                 235                 240

Asn Ser Leu Arg Val Glu Asp Thr Ala Val Tyr Tyr Cys Val Lys Asp
                245             250                 255

Gly Val His Trp Gly Gln Gly Thr Leu Val Thr Val Ser Ser Ala Ala
            260             265                 270

Ala His His His His His His
        275
```